US012453279B2

(12) United States Patent
Boudreault et al.

(10) Patent No.: US 12,453,279 B2
(45) Date of Patent: Oct. 21, 2025

(54) ORGANIC ELECTROLUMINESCENT MATERIALS AND DEVICES

(71) Applicant: Universal Display Corporation, Ewing, NJ (US)

(72) Inventors: Pierre-Luc T. Boudreault, Pennington, NJ (US); Bert Alleyne, Newtown, PA (US)

(73) Assignee: Universal Display Corporation, Ewing, NJ (US)

( * ) Notice: Subject to any disclaimer, the term of this patent is extended or adjusted under 35 U.S.C. 154(b) by 619 days.

(21) Appl. No.: 16/519,287

(22) Filed: Jul. 23, 2019

(65) Prior Publication Data

US 2020/0075870 A1 Mar. 5, 2020

Related U.S. Application Data

(60) Provisional application No. 62/720,983, filed on Aug. 22, 2018.

(51) Int. Cl.

| | |
|---|---|
| ***H10K 85/30*** | (2023.01) |
| ***C07D 209/82*** | (2006.01) |
| ***H10K 85/60*** | (2023.01) |

(52) U.S. Cl.

CPC ......... *H10K 85/342* (2023.02); *C07D 209/82* (2013.01); *H10K 85/346* (2023.02); (Continued)

(58) Field of Classification Search

CPC ............. H01L 51/0085; H01L 51/0061; H01L 51/0072; H01L 51/0071; C07F 15/0033; (Continued)

(56) References Cited

U.S. PATENT DOCUMENTS 4,769,292 A 9/1988 Tang et al.
5,061,569 A 10/1991 VanSlyke et al.

(Continued)

FOREIGN PATENT DOCUMENTS

CN 104370968 2/2015
EP 0650955 5/1995

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Jenna N Chandhok
(74) *Attorney, Agent, or Firm* — DUANE MORRIS LLP

(57) ABSTRACT

A compound that can be useful as emitters in an OLED that includes a ligand $L_A$ of Formula I

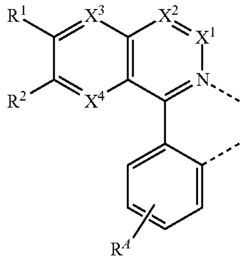

is disclosed.

20 Claims, 2 Drawing Sheets

(52) U.S. Cl.
CPC ......... *H10K 85/622* (2023.02); *H10K 85/636* (2023.02); *H10K 85/6572* (2023.02); *H10K 85/6574* (2023.02); *H10K 85/6576* (2023.02); *C07B 2200/05* (2013.01)

(58) Field of Classification Search
CPC ........... C09K 2211/185; H10K 85/657; H10K 85/6572; H10K 85/342; H10K 85/636
See application file for complete search history.

(56) References Cited

U.S. PATENT DOCUMENTS

| | | | | |
|---|---|---|---|---|
| 5,247,190 | A | 9/1993 | Friend et al. | |
| 5,703,436 | A | 12/1997 | Forrest et al. | |
| 5,707,745 | A | 1/1998 | Forrest et al. | |
| 5,834,893 | A | 11/1998 | Bulovic et al. | |
| 5,844,363 | A | 12/1998 | Gu et al. | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A | 8/2000 | Baldo et al. | |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 9,397,302 | B2 * | 7/2016 | Boudreault | C07F 15/0033 |
| 9,512,355 | B2 | 12/2016 | Ma et al. | |
| 2002/0034656 | A1 | 3/2002 | Thompson et al. | |
| 2002/0134984 | A1 | 9/2002 | Igarashi | |
| 2002/0158242 | A1 | 10/2002 | Son et al. | |
| 2003/0138657 | A1 | 7/2003 | Li et al. | |
| 2003/0152802 | A1 | 8/2003 | Tsuboyama et al. | |
| 2003/0162053 | A1 | 8/2003 | Marks et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0137267 | A1 | 7/2004 | Igarashi et al. | |
| 2004/0137268 | A1 | 7/2004 | Igarashi et al. | |
| 2004/0174116 | A1 | 9/2004 | Lu et al. | |
| 2005/0025993 | A1 | 2/2005 | Thompson et al. | |
| 2005/0112407 | A1 | 5/2005 | Ogasawara et al. | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong et al. | |
| 2007/0190359 | A1 | 8/2007 | Knowles et al. | |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0261076 | A1 | 10/2008 | Kwong et al. | |
| 2008/0297033 | A1 | 12/2008 | Knowles et al. | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0101870 | A1 | 4/2009 | Prakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2012/0153816 | A1 * | 6/2012 | Takizawa | C07D 405/14 313/504 |
| 2013/0146848 | A1 | 6/2013 | Ma et al. | |
| 2015/0243913 | A1 | 8/2015 | Takizawa et al. | |
| 2015/0295199 | A1 | 10/2015 | Yamamoto et al. | |
| 2016/0104848 | A1 * | 4/2016 | Boudreault | C09K 11/06 546/4 |
| 2017/0229663 | A1 * | 8/2017 | Tsai | C07F 15/0033 |
| 2019/0077818 | A1 * | 3/2019 | Xia | H01L 51/0085 |
| 2021/0083203 | A1 * | 3/2021 | Leung | C07F 15/0033 |

FOREIGN PATENT DOCUMENTS

| | | |
|---|---|---|
| EP | 1725079 | 11/2006 |
| EP | 2034538 | 3/2009 |
| EP | 2907820 | 8/2015 |
| EP | 3492528 | 6/2019 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

(56) References Cited

FOREIGN PATENT DOCUMENTS

| | | |
|---|---|---|
| WO | 2018124697 | 7/2018 |
| WO | 2019/114668 | 6/2019 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N∧C∧N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).

(56) References Cited

OTHER PUBLICATIONS

Wong, Wai-Yeung, "Multifunctional Iridium Complexes Based on Carbazole Modules as Highly Efficient Electrophosphors," Angew. Chem. Int. Ed., 45:7800-7803 (2006).
Extended European Search Report and Search Opinion issued on Dec. 19, 2019 for corresponding European Application No. EP19193072.6.

* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/720,983, filed Aug. 22, 2018, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

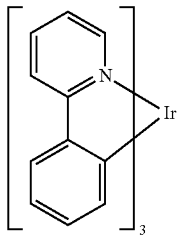

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

A series of new phosphorescent metal complexes based on ligands containing phenylisoquinoline or phenyl quinazoline that can function as emitters in OLEDs are disclosed. Further functionalization of these moieties allows fine tuning of the properties of the final complexes in OLED application, such as the color of the emission, emission efficiency, lifetime, etc.).

According to an embodiment, a compound comprising a ligand $L_A$ of Formula I

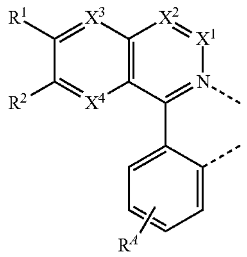

is disclosed. In Formula I, $R^A$ represents mono to the maximum allowable number of substitutions; $X^1$ to $X^4$ are each independently CR or N; $R^A$, R, $R^1$, and $R^2$ are each independently selected from the group consisting of hydrogen or the general substituents defined above; at least one of $R^1$ and $R^2$ has the formula of $-L^1-G^1$; $L^1$ is an organic linker or a direct bond, $G^1$ is a substituted cycloalkyl group, or a substituted or unsubstituted multicyclic group; at least one $R^A$ is not hydrogen; $L_A$ is coordinated to Ir; Ir can be coordinated to other ligands; $L_A$ can be linked with other ligands to comprise a tridentate, tetradentate, pentadentate, or hexadentate ligand; and any two substituents can be joined or fused together to form a ring, with the proviso that $R^1$ and $R^2$ are not joined to form a ring.

An OLED comprising the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
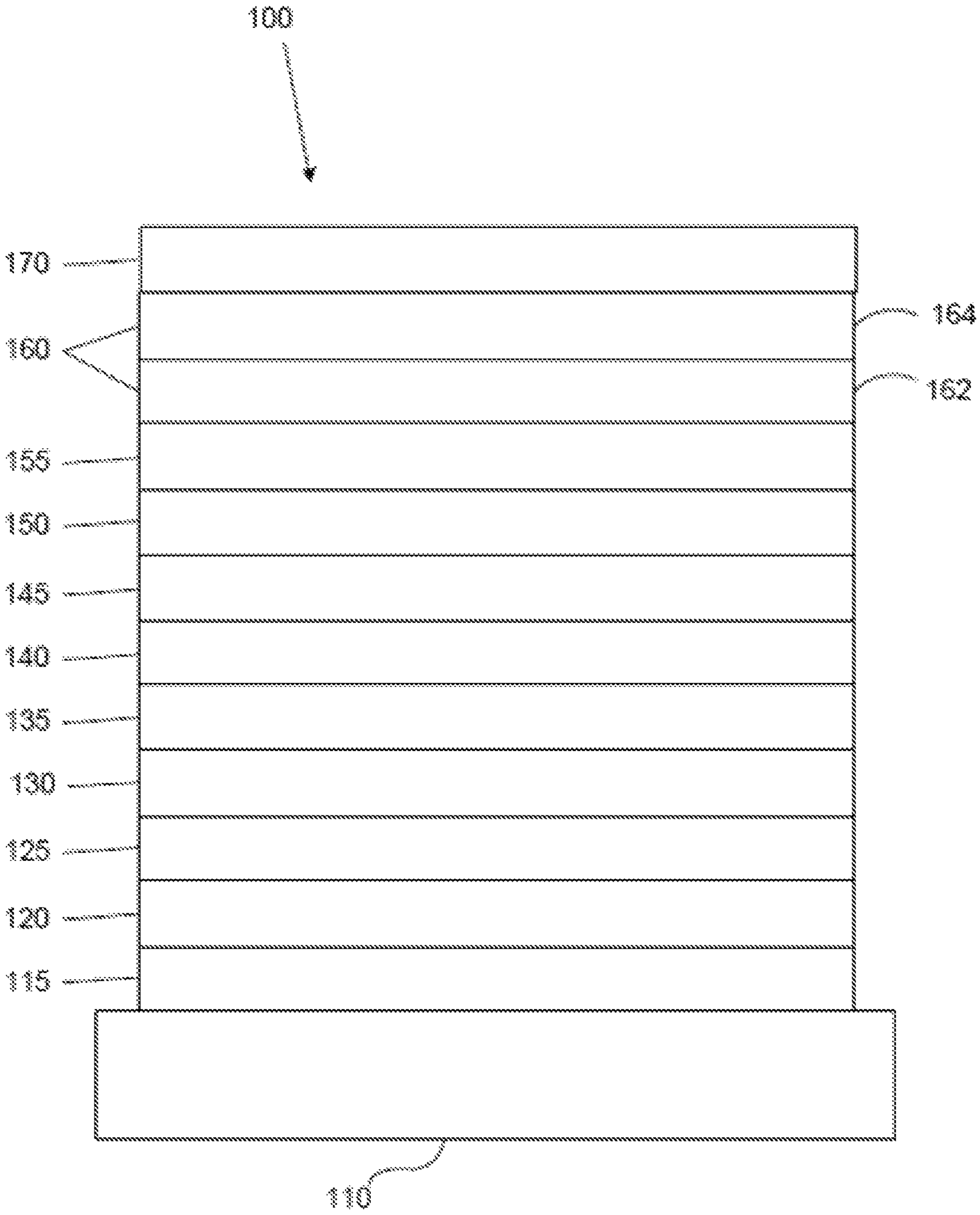
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
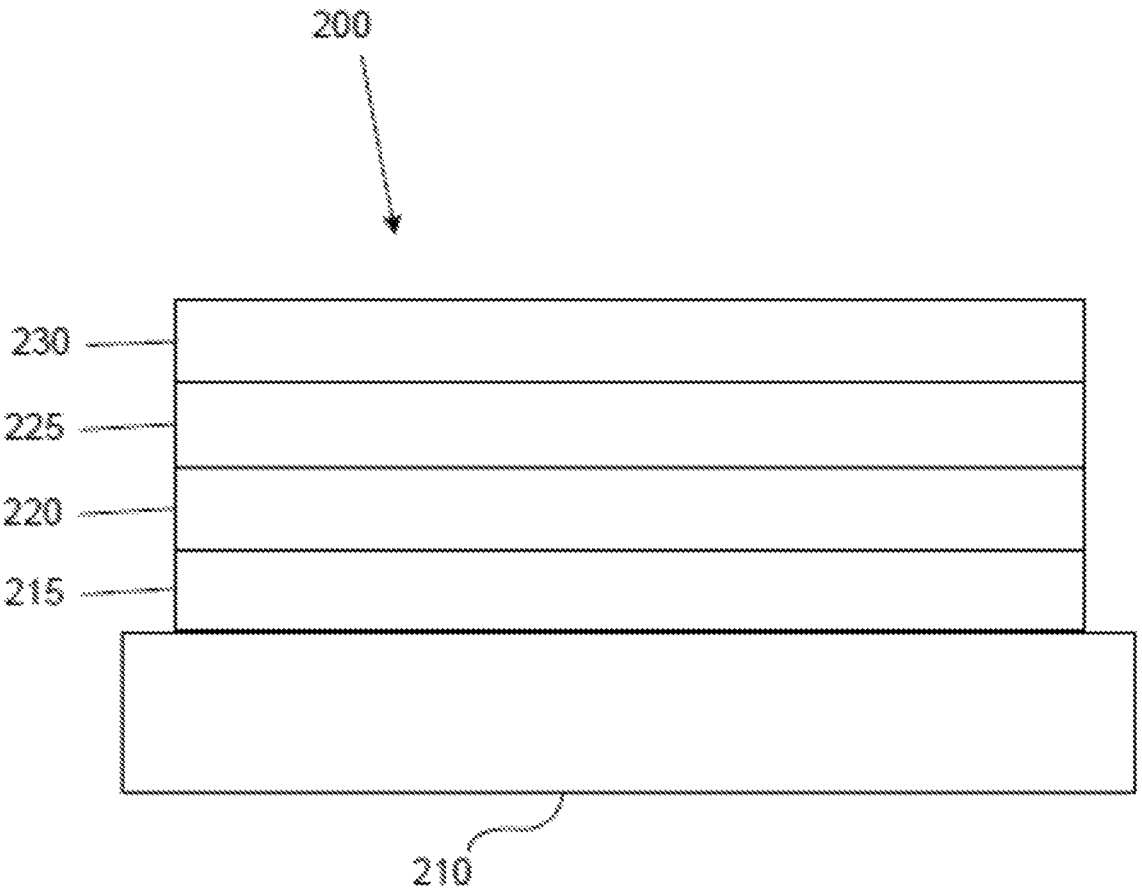
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order.

Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

The novelty of the inventive compounds disclosed herein comes from the new side used on the core of the ligand. The use of substituted cycloalkyl side chains on the isoquinoline and quinazoline cores allows to further increase the external quantum efficiencies (EQEs) when used as the emitter in a phosphorescent device. The color of the compound's emission ($\lambda_{MAX}$) can be fine tuned depending on the position on the isoquinoline or the quinazoline cores the substituted cycloalkyl side chain is added. Furthermore, the substitution on the cycloalkyl side chains enable much better thermal properties for the compound such as better (i.e., lower) sublimation temperature ($T_{SUB}$) which is beneficial in OLED fabrication process.

This invention describes novel side chains that enables very high EQEs in PhOLEDs application. From a commercial standpoint, the main request is to keep providing phosphorescent emitters that show better efficiency. These new side chains have been added to well-known cores such as isoquinoline but still provided EQE that had not been observed before.

According to an embodiment, a compound comprising a ligand $L_A$ of Formula I

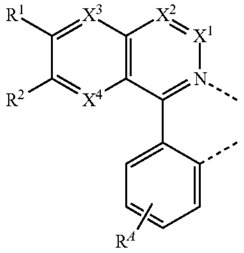

is disclosed. In Formula I, $R^A$ represents mono to the maximum allowable number of substitutions; $X^1$ to $X^4$ are each independently CR or N; $R^A$, R, $R^1$, and $R^2$ are each independently selected from the group consisting of hydrogen or the general substituents defined above; at least one of $R^1$ and $R^2$ has the formula of $-L^1-G^1$; $L^1$ is an organic linker or a direct bond, $G^1$ is a substituted cycloalkyl group, or a substituted or unsubstituted multicyclic group; at least one $R^A$ is not hydrogen; $L_A$ is coordinated to Ir; Ir can be coordinated to other ligands; $L_A$ can be linked with other ligands to comprise a tridentate, tetradentate, pentadentate, or hexadentate ligand; and any two substituents can be joined or fused together to form a ring, with the proviso that $R^1$ and $R^2$ are not joined to form a ring.

In some embodiments of the compound, $R^A$, R, $R^1$, and $R^2$ are each independently selected from the group consisting of hydrogen or the preferred general substituents defined above.

In some embodiments, $G^1$ is selected from the group consisting of alkyl substituted cycloalkyl, a partially or fully fluorinated cycloalkyl or alkyl substituted cycloalkyl, partially or fully deuterated variants thereof, and combination thereof.

In some embodiments, the compound can be heteroleptic. In some embodiments, the compound can be homoleptic.

In some embodiments, $L^1$ is a direct bond. In some embodiments, $L^1$ is alkyl.

In some embodiments, $R^1$ comprises more C atoms than $R^2$. In some embodiments, $R^2$ comprises more C atoms than $R^1$. In some embodiments, one of $R^1$ and $R^2$ is a substituted cyclohexyl or substituted cyclopentyl group, and the other one is hydrogen.

In some embodiments, $R^1$ is a substituted cyclohexyl group, and $R^2$ is hydrogen.

In some embodiments, the first ligand $L_A$ is

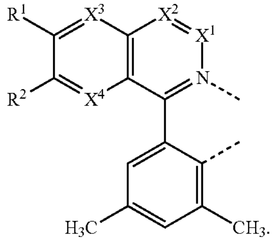

In some embodiments, the compound further comprises a substituted or unsubstituted acetylacetonate ligand.

In some embodiments, $R^1$ is a cyclohexyl group that is substituted by at least one alkyl group.

In some embodiments, $X^1$ to $X^4$ are each CH. In some embodiments, one of $X^1$ to $X^4$ is N, and the remainder are CH.

In some embodiments, two $R^A$ substituents are joined together to form a ring.

In some embodiments, the first ligand $L_A$ is selected from the group consisting of:

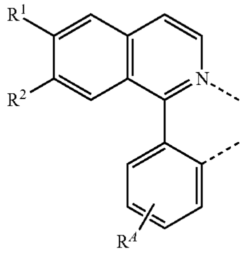

,

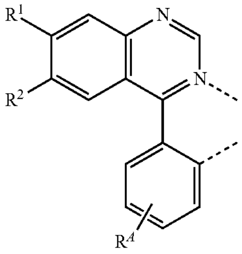

,

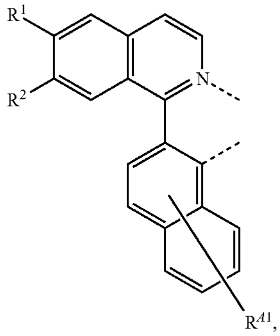

,

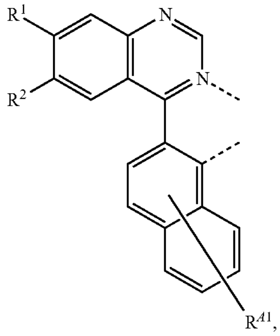

,

-continued
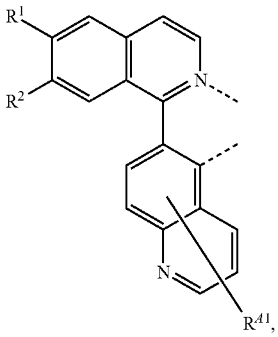
,
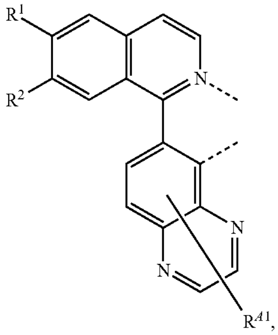
,
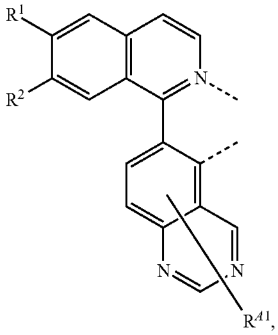
,
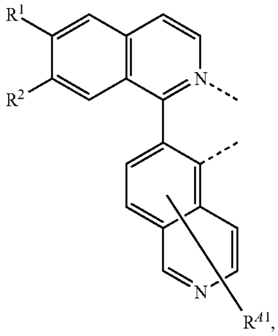
,
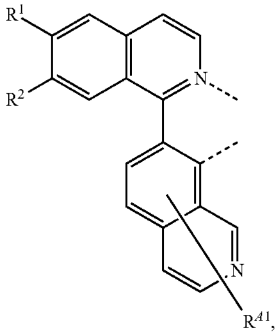
,
-continued
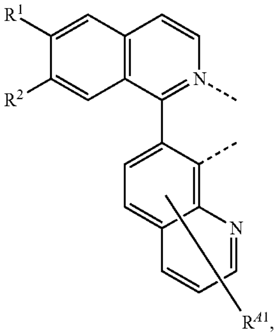
,
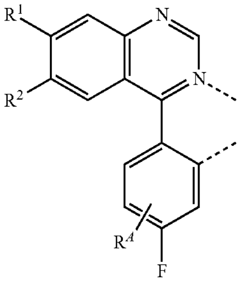
,
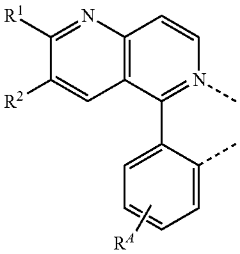
,
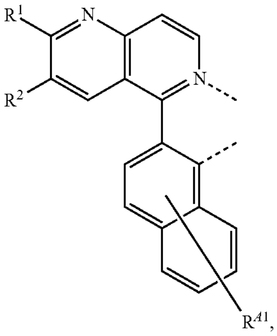
,
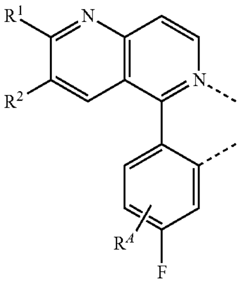
, -continued

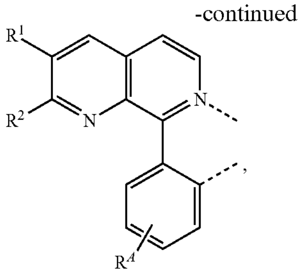

,

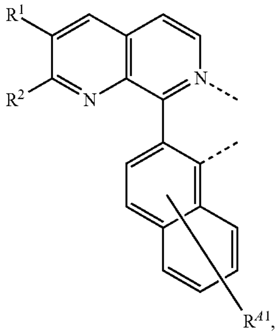

, and

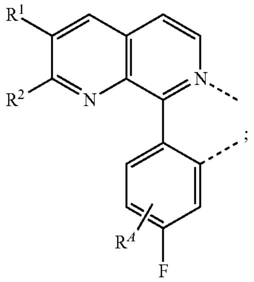

;

and wherein $R^{A1}$ has the same definition as $R^A$.

In some embodiments of the compound, the first ligand $L_A$ is selected from the group consisting of:

$L_{A1}$ through $L_{A416}$ based on a structure of Formula II,

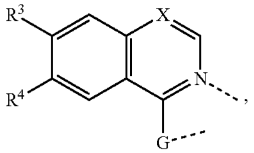

, in which $R^3$, $R^4$, G, and X are defined as:

| Ligand | $R^3$ | $R^4$ | G | X |
|---|---|---|---|---|
| $L_{A1}$ | $R^{C11}$ | H | $R^{D1}$ | C |
| $L_{A2}$ | $R^{C14}$ | H | $R^{D1}$ | C |
| $L_{A3}$ | $R^{C18}$ | H | $R^{D1}$ | C |
| $L_{A4}$ | $R^{C19}$ | H | $R^{D1}$ | C |
| $L_{A5}$ | $R^{C23}$ | H | $R^{D1}$ | C |
| $L_{A6}$ | $R^{C33}$ | H | $R^{D1}$ | C |
| $L_{A7}$ | $R^{C38}$ | H | $R^{D1}$ | C |
| $L_{A8}$ | $R^{C40}$ | H | $R^{D1}$ | C |
| $L_{A9}$ | $R^{C41}$ | H | $R^{D1}$ | C |
| $L_{A10}$ | $R^{C48}$ | H | $R^{D1}$ | C |
| $L_{A11}$ | $R^{C54}$ | H | $R^{D1}$ | C |
| $L_{A12}$ | $R^{C55}$ | H | $R^{D1}$ | C |
| $L_{A13}$ | $R^{C57}$ | H | $R^{D1}$ | C |
| $L_{A14}$ | $R^{C11}$ | H | $R^{D2}$ | C |
| $L_{A15}$ | $R^{C14}$ | H | $R^{D2}$ | C |
| $L_{A16}$ | $R^{C18}$ | H | $R^{D2}$ | C |
| $L_{A17}$ | $R^{C19}$ | H | $R^{D2}$ | C |

-continued

| Ligand | $R^3$ | $R^4$ | G | X |
|---|---|---|---|---|
| $L_{A418}$ | $R^{C23}$ | H | $R^{D2}$ | C |
| $L_{A419}$ | $R^{C33}$ | H | $R^{D2}$ | C |
| $L_{A420}$ | $R^{C38}$ | H | $R^{D2}$ | C |
| $L_{A421}$ | $R^{C40}$ | H | $R^{D2}$ | C |
| $L_{A422}$ | $R^{C41}$ | H | $R^{D2}$ | C |
| $L_{A423}$ | $R^{C48}$ | H | $R^{D2}$ | C |
| $L_{A424}$ | $R^{C54}$ | H | $R^{D2}$ | C |
| $L_{A425}$ | $R^{C55}$ | H | $R^{D2}$ | C |
| $L_{A426}$ | $R^{C57}$ | H | $R^{D2}$ | C |
| $L_{A427}$ | $R^{C11}$ | H | $R^{D4}$ | C |
| $L_{A428}$ | $R^{C14}$ | H | $R^{D4}$ | C |
| $L_{A429}$ | $R^{C18}$ | H | $R^{D4}$ | C |
| $L_{A430}$ | $R^{C19}$ | H | $R^{D4}$ | C |
| $L_{A431}$ | $R^{C23}$ | H | $R^{D4}$ | C |
| $L_{A432}$ | $R^{C33}$ | H | $R^{D4}$ | C |
| $L_{A433}$ | $R^{C38}$ | H | $R^{D4}$ | C |
| $L_{A434}$ | $R^{C40}$ | H | $R^{D4}$ | C |
| $L_{A435}$ | $R^{C41}$ | H | $R^{D4}$ | C |
| $L_{A436}$ | $R^{C48}$ | H | $R^{D4}$ | C |
| $L_{A437}$ | $R^{C54}$ | H | $R^{D4}$ | C |
| $L_{A438}$ | $R^{C55}$ | H | $R^{D4}$ | C |
| $L_{A439}$ | $R^{C57}$ | H | $R^{D4}$ | C |
| $L_{A440}$ | $R^{C11}$ | H | $R^{D8}$ | C |
| $L_{A441}$ | $R^{C14}$ | H | $R^{D8}$ | C |
| $L_{A442}$ | $R^{C18}$ | H | $R^{D8}$ | C |
| $L_{A443}$ | $R^{C19}$ | H | $R^{D8}$ | C |
| $L_{A444}$ | $R^{C23}$ | H | $R^{D8}$ | C |
| $L_{A445}$ | $R^{C33}$ | H | $R^{D8}$ | C |
| $L_{A446}$ | $R^{C38}$ | H | $R^{D8}$ | C |
| $L_{A447}$ | $R^{C40}$ | H | $R^{D8}$ | C |
| $L_{A448}$ | $R^{C41}$ | H | $R^{D8}$ | C |
| $L_{A449}$ | $R^{C48}$ | H | $R^{D8}$ | C |
| $L_{A450}$ | $R^{C54}$ | H | $R^{D8}$ | C |
| $L_{A451}$ | $R^{C55}$ | H | $R^{D8}$ | C |
| $L_{A452}$ | $R^{C57}$ | H | $R^{D8}$ | C |
| $L_{A453}$ | $R^{C11}$ | H | $R^{D9}$ | C |
| $L_{A454}$ | $R^{C14}$ | H | $R^{D9}$ | C |
| $L_{A455}$ | $R^{C18}$ | H | $R^{D9}$ | C |
| $L_{A456}$ | $R^{C19}$ | H | $R^{D9}$ | C |
| $L_{A457}$ | $R^{C23}$ | H | $R^{D9}$ | C |
| $L_{A458}$ | $R^{C33}$ | H | $R^{D9}$ | C |
| $L_{A459}$ | $R^{C38}$ | H | $R^{D9}$ | C |
| $L_{A460}$ | $R^{C40}$ | H | $R^{D9}$ | C |
| $L_{A461}$ | $R^{C41}$ | H | $R^{D9}$ | C |
| $L_{A462}$ | $R^{C48}$ | H | $R^{D9}$ | C |
| $L_{A463}$ | $R^{C54}$ | H | $R^{D9}$ | C |
| $L_{A464}$ | $R^{C55}$ | H | $R^{D9}$ | C |
| $L_{A465}$ | $R^{C57}$ | H | $R^{D9}$ | C |
| $L_{A466}$ | $R^{C11}$ | H | $R^{D14}$ | C |
| $L_{A467}$ | $R^{C14}$ | H | $R^{D14}$ | C |
| $L_{A468}$ | $R^{C18}$ | H | $R^{D14}$ | C |
| $L_{A469}$ | $R^{C19}$ | H | $R^{D14}$ | C |
| $L_{A470}$ | $R^{C23}$ | H | $R^{D14}$ | C |
| $L_{A471}$ | $R^{C33}$ | H | $R^{D14}$ | C |
| $L_{A472}$ | $R^{C38}$ | H | $R^{D14}$ | C |
| $L_{A473}$ | $R^{C40}$ | H | $R^{D14}$ | C |
| $L_{A474}$ | $R^{C41}$ | H | $R^{D14}$ | C |
| $L_{A475}$ | $R^{C48}$ | H | $R^{D14}$ | C |
| $L_{A476}$ | $R^{C54}$ | H | $R^{D14}$ | C |
| $L_{A477}$ | $R^{C55}$ | H | $R^{D14}$ | C |
| $L_{A478}$ | $R^{C57}$ | H | $R^{D14}$ | C |
| $L_{A479}$ | $R^{C11}$ | H | $R^{D22}$ | C |
| $L_{A480}$ | $R^{C14}$ | H | $R^{D22}$ | C |
| $L_{A481}$ | $R^{C18}$ | H | $R^{D22}$ | C |
| $L_{A482}$ | $R^{C19}$ | H | $R^{D22}$ | C |
| $L_{A483}$ | $R^{C23}$ | H | $R^{D22}$ | C |
| $L_{A484}$ | $R^{C33}$ | H | $R^{D22}$ | C |
| $L_{A485}$ | $R^{C38}$ | H | $R^{D22}$ | C |
| $L_{A486}$ | $R^{C40}$ | H | $R^{D22}$ | C |
| $L_{A487}$ | $R^{C41}$ | H | $R^{D22}$ | C |
| $L_{A488}$ | $R^{C48}$ | H | $R^{D22}$ | C |
| $L_{A489}$ | $R^{C54}$ | H | $R^{D22}$ | C |
| $L_{A490}$ | $R^{C55}$ | H | $R^{D22}$ | C |
| $L_{A491}$ | $R^{C57}$ | H | $R^{D22}$ | C |
| $L_{A492}$ | $R^{C11}$ | H | $R^{D28}$ | C |
| $L_{A493}$ | $R^{C14}$ | H | $R^{D28}$ | C |
| $L_{A494}$ | $R^{C18}$ | H | $R^{D28}$ | C |

-continued

| Ligand | $R^3$ | $R^4$ | G | X |
|---|---|---|---|---|
| $L_{A95}$ | $R^{C19}$ | H | $R^{D28}$ | C |
| $L_{A96}$ | $R^{C23}$ | H | $R^{D28}$ | C |
| $L_{A97}$ | $R^{C33}$ | H | $R^{D28}$ | C |
| $L_{A98}$ | $R^{C38}$ | H | $R^{D28}$ | C |
| $L_{A99}$ | $R^{C40}$ | H | $R^{D28}$ | C |
| $L_{A100}$ | $R^{C41}$ | H | $R^{D28}$ | C |
| $L_{A101}$ | $R^{C48}$ | H | $R^{D28}$ | C |
| $L_{A102}$ | $R^{C54}$ | H | $R^{D28}$ | C |
| $L_{A103}$ | $R^{C55}$ | H | $R^{D28}$ | C |
| $L_{A104}$ | $R^{C57}$ | H | $R^{D28}$ | C |
| $L_{A105}$ | H | $R^{C11}$ | $R^{D1}$ | C |
| $L_{A106}$ | H | $R^{C14}$ | $R^{D1}$ | C |
| $L_{A107}$ | H | $R^{C18}$ | $R^{D1}$ | C |
| $L_{A108}$ | H | $R^{C19}$ | $R^{D1}$ | C |
| $L_{A109}$ | H | $R^{C23}$ | $R^{D1}$ | C |
| $L_{A110}$ | H | $R^{C33}$ | $R^{D1}$ | C |
| $L_{A111}$ | H | $R^{C38}$ | $R^{D1}$ | C |
| $L_{A112}$ | H | $R^{C40}$ | $R^{D1}$ | C |
| $L_{A113}$ | H | $R^{C41}$ | $R^{D1}$ | C |
| $L_{A114}$ | H | $R^{C48}$ | $R^{D1}$ | C |
| $L_{A115}$ | H | $R^{C54}$ | $R^{D1}$ | C |
| $L_{A116}$ | H | $R^{C55}$ | $R^{D1}$ | C |
| $L_{A117}$ | H | $R^{C57}$ | $R^{D1}$ | C |
| $L_{A118}$ | H | $R^{C11}$ | $R^{D2}$ | C |
| $L_{A119}$ | H | $R^{C14}$ | $R^{D2}$ | C |
| $L_{A120}$ | H | $R^{C18}$ | $R^{D2}$ | C |
| $L_{A121}$ | H | $R^{C19}$ | $R^{D2}$ | C |
| $L_{A122}$ | H | $R^{C23}$ | $R^{D2}$ | C |
| $L_{A123}$ | H | $R^{C33}$ | $R^{D2}$ | C |
| $L_{A124}$ | H | $R^{C38}$ | $R^{D2}$ | C |
| $L_{A125}$ | H | $R^{C40}$ | $R^{D2}$ | C |
| $L_{A126}$ | H | $R^{C41}$ | $R^{D2}$ | C |
| $L_{A127}$ | H | $R^{C48}$ | $R^{D2}$ | C |
| $L_{A128}$ | H | $R^{C54}$ | $R^{D2}$ | C |
| $L_{A129}$ | H | $R^{C55}$ | $R^{D2}$ | C |
| $L_{A130}$ | H | $R^{C57}$ | $R^{D2}$ | C |
| $L_{A131}$ | H | $R^{C11}$ | $R^{D4}$ | C |
| $L_{A132}$ | H | $R^{C14}$ | $R^{D4}$ | C |
| $L_{A133}$ | H | $R^{C18}$ | $R^{D4}$ | C |
| $L_{A134}$ | H | $R^{C19}$ | $R^{D4}$ | C |
| $L_{A135}$ | H | $R^{C23}$ | $R^{D4}$ | C |
| $L_{A136}$ | H | $R^{C33}$ | $R^{D4}$ | C |
| $L_{A137}$ | H | $R^{C38}$ | $R^{D4}$ | C |
| $L_{A138}$ | H | $R^{C40}$ | $R^{D4}$ | C |
| $L_{A139}$ | H | $R^{C41}$ | $R^{D4}$ | C |
| $L_{A140}$ | H | $R^{C48}$ | $R^{D4}$ | C |
| $L_{A141}$ | H | $R^{C54}$ | $R^{D4}$ | C |
| $L_{A142}$ | H | $R^{C55}$ | $R^{D4}$ | C |
| $L_{A143}$ | H | $R^{C57}$ | $R^{D4}$ | C |
| $L_{A144}$ | H | $R^{C11}$ | $R^{D8}$ | C |
| $L_{A145}$ | H | $R^{C14}$ | $R^{D8}$ | C |
| $L_{A146}$ | H | $R^{C18}$ | $R^{D8}$ | C |
| $L_{A147}$ | H | $R^{C19}$ | $R^{D8}$ | C |
| $L_{A148}$ | H | $R^{C23}$ | $R^{D8}$ | C |
| $L_{A149}$ | H | $R^{C33}$ | $R^{D8}$ | C |
| $L_{A150}$ | H | $R^{C38}$ | $R^{D8}$ | C |
| $L_{A151}$ | H | $R^{C40}$ | $R^{D8}$ | C |
| $L_{A152}$ | H | $R^{C41}$ | $R^{D8}$ | C |
| $L_{A153}$ | H | $R^{C48}$ | $R^{D8}$ | C |
| $L_{A154}$ | H | $R^{C54}$ | $R^{D8}$ | C |
| $L_{A155}$ | H | $R^{C55}$ | $R^{D8}$ | C |
| $L_{A156}$ | H | $R^{C57}$ | $R^{D8}$ | C |
| $L_{A157}$ | H | $R^{C11}$ | $R^{D9}$ | C |
| $L_{A158}$ | H | $R^{C14}$ | $R^{D9}$ | C |
| $L_{A159}$ | H | $R^{C18}$ | $R^{D9}$ | C |
| $L_{A160}$ | H | $R^{C19}$ | $R^{D9}$ | C |
| $L_{A161}$ | H | $R^{C23}$ | $R^{D9}$ | C |
| $L_{A162}$ | H | $R^{C33}$ | $R^{D9}$ | C |
| $L_{A163}$ | H | $R^{C38}$ | $R^{D9}$ | C |
| $L_{A164}$ | H | $R^{C40}$ | $R^{D9}$ | C |
| $L_{A165}$ | H | $R^{C41}$ | $R^{D9}$ | C |
| $L_{A166}$ | H | $R^{C48}$ | $R^{D9}$ | C |
| $L_{A167}$ | H | $R^{C54}$ | $R^{D9}$ | C |
| $L_{A168}$ | H | $R^{C55}$ | $R^{D9}$ | C |
| $L_{A169}$ | H | $R^{C57}$ | $R^{D9}$ | C |
| $L_{A170}$ | H | $R^{C11}$ | $R^{D14}$ | C |
| $L_{A171}$ | H | $R^{C14}$ | $R^{D14}$ | C |

-continued

| Ligand | $R^3$ | $R^4$ | G | X |
|---|---|---|---|---|
| $L_{A172}$ | H | $R^{C18}$ | $R^{D14}$ | C |
| $L_{A173}$ | H | $R^{C19}$ | $R^{D14}$ | C |
| $L_{A174}$ | H | $R^{C23}$ | $R^{D14}$ | C |
| $L_{A175}$ | H | $R^{C33}$ | $R^{D14}$ | C |
| $L_{A176}$ | H | $R^{C38}$ | $R^{D14}$ | C |
| $L_{A177}$ | H | $R^{C40}$ | $R^{D14}$ | C |
| $L_{A178}$ | H | $R^{C41}$ | $R^{D14}$ | C |
| $L_{A179}$ | H | $R^{C48}$ | $R^{D14}$ | C |
| $L_{A180}$ | H | $R^{C54}$ | $R^{D14}$ | C |
| $L_{A181}$ | H | $R^{C55}$ | $R^{D14}$ | C |
| $L_{A182}$ | H | $R^{C57}$ | $R^{D14}$ | C |
| $L_{A183}$ | H | $R^{C11}$ | $R^{D22}$ | C |
| $L_{A184}$ | H | $R^{C14}$ | $R^{D22}$ | C |
| $L_{A185}$ | H | $R^{C18}$ | $R^{D22}$ | C |
| $L_{A186}$ | H | $R^{C19}$ | $R^{D22}$ | C |
| $L_{A187}$ | H | $R^{C23}$ | $R^{D22}$ | C |
| $L_{A188}$ | H | $R^{C33}$ | $R^{D22}$ | C |
| $L_{A189}$ | H | $R^{C38}$ | $R^{D22}$ | C |
| $L_{A190}$ | H | $R^{C40}$ | $R^{D22}$ | C |
| $L_{A191}$ | H | $R^{C41}$ | $R^{D22}$ | C |
| $L_{A192}$ | H | $R^{C48}$ | $R^{D22}$ | C |
| $L_{A193}$ | H | $R^{C54}$ | $R^{D22}$ | C |
| $L_{A194}$ | H | $R^{C55}$ | $R^{D22}$ | C |
| $L_{A195}$ | H | $R^{C57}$ | $R^{D22}$ | C |
| $L_{A196}$ | H | $R^{C11}$ | $R^{D28}$ | C |
| $L_{A197}$ | H | $R^{C14}$ | $R^{D28}$ | C |
| $L_{A198}$ | H | $R^{C18}$ | $R^{D28}$ | C |
| $L_{A199}$ | H | $R^{C19}$ | $R^{D28}$ | C |
| $L_{A200}$ | H | $R^{C23}$ | $R^{D28}$ | C |
| $L_{A201}$ | H | $R^{C33}$ | $R^{D28}$ | C |
| $L_{A202}$ | H | $R^{C38}$ | $R^{D28}$ | C |
| $L_{A203}$ | H | $R^{C40}$ | $R^{D28}$ | C |
| $L_{A204}$ | H | $R^{C41}$ | $R^{D28}$ | C |
| $L_{A205}$ | H | $R^{C48}$ | $R^{D28}$ | C |
| $L_{A206}$ | H | $R^{C54}$ | $R^{D28}$ | C |
| $L_{A207}$ | H | $R^{C55}$ | $R^{D28}$ | C |
| $L_{A208}$ | H | $R^{C57}$ | $R^{D28}$ | C |
| $L_{A209}$ | $R^{C11}$ | H | $R^{D1}$ | N |
| $L_{A210}$ | $R^{C14}$ | H | $R^{D1}$ | N |
| $L_{A211}$ | $R^{C18}$ | H | $R^{D1}$ | N |
| $L_{A212}$ | $R^{C19}$ | H | $R^{D1}$ | N |
| $L_{A213}$ | $R^{C23}$ | H | $R^{D1}$ | N |
| $L_{A214}$ | $R^{C33}$ | H | $R^{D1}$ | N |
| $L_{A215}$ | $R^{C38}$ | H | $R^{D1}$ | N |
| $L_{A216}$ | $R^{C40}$ | H | $R^{D1}$ | N |
| $L_{A217}$ | $R^{C41}$ | H | $R^{D1}$ | N |
| $L_{A218}$ | $R^{C48}$ | H | $R^{D1}$ | N |
| $L_{A219}$ | $R^{C54}$ | H | $R^{D1}$ | N |
| $L_{A220}$ | $R^{C55}$ | H | $R^{D1}$ | N |
| $L_{A221}$ | $R^{C57}$ | H | $R^{D1}$ | N |
| $L_{A222}$ | $R^{C11}$ | H | $R^{D2}$ | N |
| $L_{A223}$ | $R^{C14}$ | H | $R^{D2}$ | N |
| $L_{A224}$ | $R^{C18}$ | H | $R^{D2}$ | N |
| $L_{A225}$ | $R^{C19}$ | H | $R^{D2}$ | N |
| $L_{A226}$ | $R^{C23}$ | H | $R^{D2}$ | N |
| $L_{A227}$ | $R^{C33}$ | H | $R^{D2}$ | N |
| $L_{A228}$ | $R^{C38}$ | H | $R^{D2}$ | N |
| $L_{A229}$ | $R^{C40}$ | H | $R^{D2}$ | N |
| $L_{A230}$ | $R^{C41}$ | H | $R^{D2}$ | N |
| $L_{A231}$ | $R^{C48}$ | H | $R^{D2}$ | N |
| $L_{A232}$ | $R^{C54}$ | H | $R^{D2}$ | N |
| $L_{A233}$ | $R^{C55}$ | H | $R^{D2}$ | N |
| $L_{A234}$ | $R^{C57}$ | H | $R^{D2}$ | N |
| $L_{A235}$ | $R^{C11}$ | H | $R^{D4}$ | N |
| $L_{A236}$ | $R^{C14}$ | H | $R^{D4}$ | N |
| $L_{A237}$ | $R^{C18}$ | H | $R^{D4}$ | N |
| $L_{A238}$ | $R^{C19}$ | H | $R^{D4}$ | N |
| $L_{A239}$ | $R^{C23}$ | H | $R^{D4}$ | N |
| $L_{A240}$ | $R^{C33}$ | H | $R^{D4}$ | N |
| $L_{A241}$ | $R^{C38}$ | H | $R^{D4}$ | N |
| $L_{A242}$ | $R^{C40}$ | H | $R^{D4}$ | N |
| $L_{A243}$ | $R^{C41}$ | H | $R^{D4}$ | N |
| $L_{A244}$ | $R^{C48}$ | H | $R^{D4}$ | N |
| $L_{A245}$ | $R^{C54}$ | H | $R^{D4}$ | N |
| $L_{A246}$ | $R^{C55}$ | H | $R^{D4}$ | N |
| $L_{A247}$ | $R^{C57}$ | H | $R^{D4}$ | N |
| $L_{A248}$ | $R^{C11}$ | H | $R^{D8}$ | N |

-continued

| Ligand | $R^3$ | $R^4$ | G | X |
|---|---|---|---|---|
| $L_{A249}$ | $R^{C14}$ | H | $R^{D8}$ | N |
| $L_{A250}$ | $R^{C18}$ | H | $R^{D8}$ | N |
| $L_{A251}$ | $R^{C19}$ | H | $R^{D8}$ | N |
| $L_{A252}$ | $R^{C23}$ | H | $R^{D8}$ | N |
| $L_{A253}$ | $R^{C33}$ | H | $R^{D8}$ | N |
| $L_{A254}$ | $R^{C38}$ | H | $R^{D8}$ | N |
| $L_{A255}$ | $R^{C40}$ | H | $R^{D8}$ | N |
| $L_{A256}$ | $R^{C41}$ | H | $R^{D8}$ | N |
| $L_{A257}$ | $R^{C48}$ | H | $R^{D8}$ | N |
| $L_{A258}$ | $R^{C54}$ | H | $R^{D8}$ | N |
| $L_{A259}$ | $R^{C55}$ | H | $R^{D8}$ | N |
| $L_{A260}$ | $R^{C57}$ | H | $R^{D8}$ | N |
| $L_{A261}$ | $R^{C11}$ | H | $R^{D9}$ | N |
| $L_{A262}$ | $R^{C14}$ | H | $R^{D9}$ | N |
| $L_{A263}$ | $R^{C18}$ | H | $R^{D9}$ | N |
| $L_{A264}$ | $R^{C19}$ | H | $R^{D9}$ | N |
| $L_{A265}$ | $R^{C23}$ | H | $R^{D9}$ | N |
| $L_{A266}$ | $R^{C33}$ | H | $R^{D9}$ | N |
| $L_{A267}$ | $R^{C38}$ | H | $R^{D9}$ | N |
| $L_{A268}$ | $R^{C40}$ | H | $R^{D9}$ | N |
| $L_{A269}$ | $R^{C41}$ | H | $R^{D9}$ | N |
| $L_{A270}$ | $R^{C48}$ | H | $R^{D9}$ | N |
| $L_{A271}$ | $R^{C54}$ | H | $R^{D9}$ | N |
| $L_{A272}$ | $R^{C55}$ | H | $R^{D9}$ | N |
| $L_{A273}$ | $R^{C57}$ | H | $R^{D9}$ | N |
| $L_{A274}$ | $R^{C11}$ | H | $R^{D14}$ | N |
| $L_{A275}$ | $R^{C14}$ | H | $R^{D14}$ | N |
| $L_{A276}$ | $R^{C18}$ | H | $R^{D14}$ | N |
| $L_{A277}$ | $R^{C19}$ | H | $R^{D14}$ | N |
| $L_{A278}$ | $R^{C23}$ | H | $R^{D14}$ | N |
| $L_{A279}$ | $R^{C33}$ | H | $R^{D14}$ | N |
| $L_{A280}$ | $R^{C38}$ | H | $R^{D14}$ | N |
| $L_{A281}$ | $R^{C40}$ | H | $R^{D14}$ | N |
| $L_{A282}$ | $R^{C41}$ | H | $R^{D14}$ | N |
| $L_{A283}$ | $R^{C48}$ | H | $R^{D14}$ | N |
| $L_{A284}$ | $R^{C54}$ | H | $R^{D14}$ | N |
| $L_{A285}$ | $R^{C55}$ | H | $R^{D14}$ | N |
| $L_{A286}$ | $R^{C57}$ | H | $R^{D14}$ | N |
| $L_{A287}$ | $R^{C11}$ | H | $R^{D22}$ | N |
| $L_{A288}$ | $R^{C14}$ | H | $R^{D22}$ | N |
| $L_{A289}$ | $R^{C18}$ | H | $R^{D22}$ | N |
| $L_{A290}$ | $R^{C19}$ | H | $R^{D22}$ | N |
| $L_{A291}$ | $R^{C23}$ | H | $R^{D22}$ | N |
| $L_{A292}$ | $R^{C33}$ | H | $R^{D22}$ | N |
| $L_{A293}$ | $R^{C38}$ | H | $R^{D22}$ | N |
| $L_{A294}$ | $R^{C40}$ | H | $R^{D22}$ | N |
| $L_{A295}$ | $R^{C41}$ | H | $R^{D22}$ | N |
| $L_{A296}$ | $R^{C48}$ | H | $R^{D22}$ | N |
| $L_{A297}$ | $R^{C54}$ | H | $R^{D22}$ | N |
| $L_{A298}$ | $R^{C55}$ | H | $R^{D22}$ | N |
| $L_{A299}$ | $R^{C57}$ | H | $R^{D22}$ | N |
| $L_{A300}$ | $R^{C11}$ | H | $R^{D28}$ | N |
| $L_{A301}$ | $R^{C14}$ | H | $R^{D28}$ | N |
| $L_{A302}$ | $R^{C18}$ | H | $R^{D28}$ | N |
| $L_{A303}$ | $R^{C19}$ | H | $R^{D28}$ | N |
| $L_{A304}$ | $R^{C23}$ | H | $R^{D28}$ | N |
| $L_{A305}$ | $R^{C33}$ | H | $R^{D28}$ | N |
| $L_{A306}$ | $R^{C38}$ | H | $R^{D28}$ | N |
| $L_{A307}$ | $R^{C40}$ | H | $R^{D28}$ | N |
| $L_{A308}$ | $R^{C41}$ | H | $R^{D28}$ | N |
| $L_{A309}$ | $R^{C48}$ | H | $R^{D28}$ | N |
| $L_{A310}$ | $R^{C54}$ | H | $R^{D28}$ | N |
| $L_{A311}$ | $R^{C55}$ | H | $R^{D28}$ | N |
| $L_{A312}$ | $R^{C57}$ | H | $R^{D28}$ | N |
| $L_{A313}$ | H | $R^{C11}$ | $R^{D1}$ | N |
| $L_{A314}$ | H | $R^{C14}$ | $R^{D1}$ | N |
| $L_{A315}$ | H | $R^{C18}$ | $R^{D1}$ | N |
| $L_{A316}$ | H | $R^{C19}$ | $R^{D1}$ | N |
| $L_{A317}$ | H | $R^{C23}$ | $R^{D1}$ | N |
| $L_{A318}$ | H | $R^{C33}$ | $R^{D1}$ | N |
| $L_{A319}$ | H | $R^{C38}$ | $R^{D1}$ | N |
| $L_{A320}$ | H | $R^{C40}$ | $R^{D1}$ | N |
| $L_{A321}$ | H | $R^{C41}$ | $R^{D1}$ | N |
| $L_{A322}$ | H | $R^{C48}$ | $R^{D1}$ | N |
| $L_{A323}$ | H | $R^{C54}$ | $R^{D1}$ | N |
| $L_{A324}$ | H | $R^{C55}$ | $R^{D1}$ | N |
| $L_{A325}$ | H | $R^{C57}$ | $R^{D1}$ | N |

-continued

| Ligand | $R^3$ | $R^4$ | G | X |
|---|---|---|---|---|
| $L_{A326}$ | H | $R^{C11}$ | $R^{D2}$ | N |
| $L_{A327}$ | H | $R^{C14}$ | $R^{D2}$ | N |
| $L_{A328}$ | H | $R^{C18}$ | $R^{D2}$ | N |
| $L_{A329}$ | H | $R^{C19}$ | $R^{D2}$ | N |
| $L_{A330}$ | H | $R^{C23}$ | $R^{D2}$ | N |
| $L_{A331}$ | H | $R^{C33}$ | $R^{D2}$ | N |
| $L_{A332}$ | H | $R^{C38}$ | $R^{D2}$ | N |
| $L_{A333}$ | H | $R^{C40}$ | $R^{D2}$ | N |
| $L_{A334}$ | H | $R^{C41}$ | $R^{D2}$ | N |
| $L_{A335}$ | H | $R^{C48}$ | $R^{D2}$ | N |
| $L_{A336}$ | H | $R^{C54}$ | $R^{D2}$ | N |
| $L_{A337}$ | H | $R^{C55}$ | $R^{D2}$ | N |
| $L_{A338}$ | H | $R^{C57}$ | $R^{D2}$ | N |
| $L_{A339}$ | H | $R^{C11}$ | $R^{D4}$ | N |
| $L_{A340}$ | H | $R^{C14}$ | $R^{D4}$ | N |
| $L_{A341}$ | H | $R^{C18}$ | $R^{D4}$ | N |
| $L_{A342}$ | H | $R^{C19}$ | $R^{D4}$ | N |
| $L_{A343}$ | H | $R^{C23}$ | $R^{D4}$ | N |
| $L_{A344}$ | H | $R^{C33}$ | $R^{D4}$ | N |
| $L_{A345}$ | H | $R^{C38}$ | $R^{D4}$ | N |
| $L_{A346}$ | H | $R^{C40}$ | $R^{D4}$ | N |
| $L_{A347}$ | H | $R^{C41}$ | $R^{D4}$ | N |
| $L_{A348}$ | H | $R^{C48}$ | $R^{D4}$ | N |
| $L_{A349}$ | H | $R^{C54}$ | $R^{D4}$ | N |
| $L_{A350}$ | H | $R^{C55}$ | $R^{D4}$ | N |
| $L_{A351}$ | H | $R^{C57}$ | $R^{D4}$ | N |
| $L_{A352}$ | H | $R^{C11}$ | $R^{D8}$ | N |
| $L_{A353}$ | H | $R^{C14}$ | $R^{D8}$ | N |
| $L_{A354}$ | H | $R^{C18}$ | $R^{D8}$ | N |
| $L_{A355}$ | H | $R^{C19}$ | $R^{D8}$ | N |
| $L_{A356}$ | H | $R^{C23}$ | $R^{D8}$ | N |
| $L_{A357}$ | H | $R^{C33}$ | $R^{D8}$ | N |
| $L_{A358}$ | H | $R^{C38}$ | $R^{D8}$ | N |
| $L_{A359}$ | H | $R^{C40}$ | $R^{D8}$ | N |
| $L_{A360}$ | H | $R^{C41}$ | $R^{D8}$ | N |
| $L_{A361}$ | H | $R^{C48}$ | $R^{D8}$ | N |
| $L_{A362}$ | H | $R^{C54}$ | $R^{D8}$ | N |
| $L_{A363}$ | H | $R^{C55}$ | $R^{D8}$ | N |
| $L_{A364}$ | H | $R^{C57}$ | $R^{D8}$ | N |
| $L_{A365}$ | H | $R^{C11}$ | $R^{D9}$ | N |
| $L_{A366}$ | H | $R^{C14}$ | $R^{D9}$ | N |
| $L_{A367}$ | H | $R^{C18}$ | $R^{D9}$ | N |
| $L_{A368}$ | H | $R^{C19}$ | $R^{D9}$ | N |
| $L_{A369}$ | H | $R^{C23}$ | $R^{D9}$ | N |
| $L_{A370}$ | H | $R^{C33}$ | $R^{D9}$ | N |
| $L_{A371}$ | H | $R^{C38}$ | $R^{D9}$ | N |
| $L_{A372}$ | H | $R^{C40}$ | $R^{D9}$ | N |
| $L_{A373}$ | H | $R^{C41}$ | $R^{D9}$ | N |
| $L_{A374}$ | H | $R^{C48}$ | $R^{D9}$ | N |
| $L_{A375}$ | H | $R^{C54}$ | $R^{D9}$ | N |
| $L_{A376}$ | H | $R^{C55}$ | $R^{D9}$ | N |
| $L_{A377}$ | H | $R^{C57}$ | $R^{D9}$ | N |
| $L_{A378}$ | H | $R^{C11}$ | $R^{D14}$ | N |
| $L_{A379}$ | H | $R^{C14}$ | $R^{D14}$ | N |
| $L_{A380}$ | H | $R^{C18}$ | $R^{D14}$ | N |
| $L_{A381}$ | H | $R^{C19}$ | $R^{D14}$ | N |
| $L_{A382}$ | H | $R^{C23}$ | $R^{D14}$ | N |
| $L_{A383}$ | H | $R^{C33}$ | $R^{D14}$ | N |
| $L_{A384}$ | H | $R^{C38}$ | $R^{D14}$ | N |
| $L_{A385}$ | H | $R^{C40}$ | $R^{D14}$ | N |
| $L_{A386}$ | H | $R^{C41}$ | $R^{D14}$ | N |
| $L_{A387}$ | H | $R^{C48}$ | $R^{D14}$ | N |
| $L_{A388}$ | H | $R^{C54}$ | $R^{D14}$ | N |
| $L_{A389}$ | H | $R^{C55}$ | $R^{D14}$ | N |
| $L_{A390}$ | H | $R^{C57}$ | $R^{D14}$ | N |
| $L_{A391}$ | H | $R^{C11}$ | $R^{D22}$ | N |
| $L_{A392}$ | H | $R^{C14}$ | $R^{D22}$ | N |
| $L_{A393}$ | H | $R^{C18}$ | $R^{D22}$ | N |
| $L_{A394}$ | H | $R^{C19}$ | $R^{D22}$ | N |
| $L_{A395}$ | H | $R^{C23}$ | $R^{D22}$ | N |
| $L_{A396}$ | H | $R^{C33}$ | $R^{D22}$ | N |
| $L_{A397}$ | H | $R^{C38}$ | $R^{D22}$ | N |
| $L_{A398}$ | H | $R^{C40}$ | $R^{D22}$ | N |
| $L_{A399}$ | H | $R^{C41}$ | $R^{D22}$ | N |
| $L_{A400}$ | H | $R^{C48}$ | $R^{D22}$ | N |
| $L_{A401}$ | H | $R^{C54}$ | $R^{D22}$ | N |
| $L_{A402}$ | H | $R^{C55}$ | $R^{D22}$ | N |

-continued

| Ligand | $R^3$ | $R^4$ | G | X |
|---|---|---|---|---|
| $L_{A403}$ | H | $R^{C57}$ | $R^{D22}$ | N |
| $L_{A404}$ | H | $R^{C11}$ | $R^{D28}$ | N |
| $L_{A405}$ | H | $R^{C14}$ | $R^{D28}$ | N |
| $L_{A406}$ | H | $R^{C18}$ | $R^{D28}$ | N |
| $L_{A407}$ | H | $R^{C19}$ | $R^{D28}$ | N |
| $L_{A408}$ | H | $R^{C23}$ | $R^{D28}$ | N |
| $L_{A409}$ | H | $R^{C33}$ | $R^{D28}$ | N |
| $L_{A410}$ | H | $R^{C38}$ | $R^{D28}$ | N |
| $L_{A411}$ | H | $R^{C40}$ | $R^{D28}$ | N |
| $L_{A412}$ | H | $R^{C41}$ | $R^{D28}$ | N |
| $L_{A413}$ | H | $R^{C48}$ | $R^{D28}$ | N |
| $L_{A414}$ | H | $R^{C54}$ | $R^{D28}$ | N |
| $L_{A415}$ | H | $R^{C55}$ | $R^{D28}$ | N |
| $L_{A416}$ | H | $R^{C57}$ | $R^{D28}$ | N, |

$L_{A417}$ through $L_{A832}$ based on a structure of Formula III,

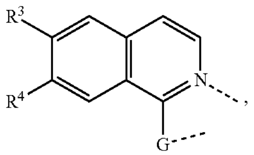

in which $R^3$, $R^4$, and G are defined as:

| Ligand | $R^3$ | $R^4$ | G |
|---|---|---|---|
| $L_{A417}$ | $R^{C11}$ | $R^{C11}$ | $R^{D1}$ |
| $L_{A418}$ | $R^{C14}$ | $R^{C14}$ | $R^{D1}$ |
| $L_{A419}$ | $R^{C18}$ | $R^{C18}$ | $R^{D1}$ |
| $L_{A420}$ | $R^{C19}$ | $R^{C19}$ | $R^{D1}$ |
| $L_{A421}$ | $R^{C23}$ | $R^{C23}$ | $R^{D1}$ |
| $L_{A422}$ | $R^{C33}$ | $R^{C33}$ | $R^{D1}$ |
| $L_{A423}$ | $R^{C38}$ | $R^{C38}$ | $R^{D1}$ |
| $L_{A424}$ | $R^{C40}$ | $R^{C40}$ | $R^{D1}$ |
| $L_{A425}$ | $R^{C41}$ | $R^{C41}$ | $R^{D1}$ |
| $L_{A426}$ | $R^{C48}$ | $R^{C48}$ | $R^{D1}$ |
| $L_{A427}$ | $R^{C54}$ | $R^{C54}$ | $R^{D1}$ |
| $L_{A428}$ | $R^{C55}$ | $R^{C55}$ | $R^{D1}$ |
| $L_{A429}$ | $R^{C57}$ | $R^{C57}$ | $R^{D1}$ |
| $L_{A430}$ | $R^{C11}$ | $R^{B1}$ | $R^{D1}$ |
| $L_{A431}$ | $R^{C14}$ | $R^{B1}$ | $R^{D1}$ |
| $L_{A432}$ | $R^{C18}$ | $R^{B1}$ | $R^{D1}$ |
| $L_{A433}$ | $R^{C19}$ | $R^{B1}$ | $R^{D1}$ |
| $L_{A434}$ | $R^{C23}$ | $R^{B1}$ | $R^{D1}$ |
| $L_{A435}$ | $R^{C33}$ | $R^{B1}$ | $R^{D1}$ |
| $L_{A436}$ | $R^{C38}$ | $R^{B1}$ | $R^{D1}$ |
| $L_{A437}$ | $R^{C40}$ | $R^{B1}$ | $R^{D1}$ |
| $L_{A438}$ | $R^{C41}$ | $R^{B1}$ | $R^{D1}$ |
| $L_{A439}$ | $R^{C48}$ | $R^{B1}$ | $R^{D1}$ |
| $L_{A440}$ | $R^{C54}$ | $R^{B1}$ | $R^{D1}$ |
| $L_{A441}$ | $R^{C55}$ | $R^{B1}$ | $R^{D1}$ |
| $L_{A442}$ | $R^{C57}$ | $R^{B1}$ | $R^{D1}$ |
| $L_{A443}$ | $R^{C11}$ | $R^{B3}$ | $R^{D1}$ |
| $L_{A444}$ | $R^{C14}$ | $R^{B3}$ | $R^{D1}$ |
| $L_{A445}$ | $R^{C18}$ | $R^{B3}$ | $R^{D1}$ |
| $L_{A446}$ | $R^{C19}$ | $R^{B3}$ | $R^{D1}$ |
| $L_{A447}$ | $R^{C23}$ | $R^{B3}$ | $R^{D1}$ |
| $L_{A448}$ | $R^{C33}$ | $R^{B3}$ | $R^{D1}$ |
| $L_{A449}$ | $R^{C38}$ | $R^{B3}$ | $R^{D1}$ |
| $L_{A450}$ | $R^{C40}$ | $R^{B3}$ | $R^{D1}$ |
| $L_{A451}$ | $R^{C41}$ | $R^{B3}$ | $R^{D1}$ |
| $L_{A452}$ | $R^{C48}$ | $R^{B3}$ | $R^{D1}$ |
| $L_{A453}$ | $R^{C54}$ | $R^{B3}$ | $R^{D1}$ |
| $L_{A454}$ | $R^{C55}$ | $R^{B3}$ | $R^{D1}$ |
| $L_{A455}$ | $R^{C57}$ | $R^{B3}$ | $R^{D1}$ |
| $L_{A456}$ | $R^{C11}$ | $R^{B4}$ | $R^{D1}$ |
| $L_{A457}$ | $R^{C14}$ | $R^{B4}$ | $R^{D1}$ |
| $L_{A458}$ | $R^{C18}$ | $R^{B4}$ | $R^{D1}$ |
| $L_{A459}$ | $R^{C19}$ | $R^{B4}$ | $R^{D1}$ |

-continued

| Ligand | $R^3$ | $R^4$ | G |
|---|---|---|---|
| $L_{A460}$ | $R^{C23}$ | $R^{B4}$ | $R^{D1}$ |
| $L_{A461}$ | $R^{C33}$ | $R^{B4}$ | $R^{D1}$ |
| $L_{A462}$ | $R^{C38}$ | $R^{B4}$ | $R^{D1}$ |
| $L_{A463}$ | $R^{C40}$ | $R^{B4}$ | $R^{D1}$ |
| $L_{A464}$ | $R^{C41}$ | $R^{B4}$ | $R^{D1}$ |
| $L_{A465}$ | $R^{C48}$ | $R^{B4}$ | $R^{D1}$ |
| $L_{A466}$ | $R^{C54}$ | $R^{B4}$ | $R^{D1}$ |
| $L_{A467}$ | $R^{C55}$ | $R^{B4}$ | $R^{D1}$ |
| $L_{A468}$ | $R^{C57}$ | $R^{B4}$ | $R^{D1}$ |
| $L_{A469}$ | $R^{C11}$ | $R^{C11}$ | $R^{D2}$ |
| $L_{A470}$ | $R^{C14}$ | $R^{C14}$ | $R^{D2}$ |
| $L_{A471}$ | $R^{C18}$ | $R^{C18}$ | $R^{D2}$ |
| $L_{A472}$ | $R^{C19}$ | $R^{C19}$ | $R^{D2}$ |
| $L_{A473}$ | $R^{C23}$ | $R^{C23}$ | $R^{D2}$ |
| $L_{A474}$ | $R^{C33}$ | $R^{C33}$ | $R^{D2}$ |
| $L_{A475}$ | $R^{C38}$ | $R^{C38}$ | $R^{D2}$ |
| $L_{A476}$ | $R^{C40}$ | $R^{C40}$ | $R^{D2}$ |
| $L_{A477}$ | $R^{C41}$ | $R^{C41}$ | $R^{D2}$ |
| $L_{A478}$ | $R^{C48}$ | $R^{C48}$ | $R^{D2}$ |
| $L_{A479}$ | $R^{C54}$ | $R^{C54}$ | $R^{D2}$ |
| $L_{A480}$ | $R^{C55}$ | $R^{C55}$ | $R^{D2}$ |
| $L_{A481}$ | $R^{C57}$ | $R^{C57}$ | $R^{D2}$ |
| $L_{A482}$ | $R^{C11}$ | $R^{B1}$ | $R^{D2}$ |
| $L_{A483}$ | $R^{C14}$ | $R^{B1}$ | $R^{D2}$ |
| $L_{A484}$ | $R^{C18}$ | $R^{B1}$ | $R^{D2}$ |
| $L_{A485}$ | $R^{C19}$ | $R^{B1}$ | $R^{D2}$ |
| $L_{A486}$ | $R^{C23}$ | $R^{B1}$ | $R^{D2}$ |
| $L_{A487}$ | $R^{C33}$ | $R^{B1}$ | $R^{D2}$ |
| $L_{A488}$ | $R^{C38}$ | $R^{B1}$ | $R^{D2}$ |
| $L_{A489}$ | $R^{C40}$ | $R^{B1}$ | $R^{D2}$ |
| $L_{A490}$ | $R^{C41}$ | $R^{B1}$ | $R^{D2}$ |
| $L_{A491}$ | $R^{C48}$ | $R^{B1}$ | $R^{D2}$ |
| $L_{A492}$ | $R^{C54}$ | $R^{B1}$ | $R^{D2}$ |
| $L_{A493}$ | $R^{C55}$ | $R^{B1}$ | $R^{D2}$ |
| $L_{A494}$ | $R^{C57}$ | $R^{B1}$ | $R^{D2}$ |
| $L_{A495}$ | $R^{C11}$ | $R^{B3}$ | $R^{D2}$ |
| $L_{A496}$ | $R^{C14}$ | $R^{B3}$ | $R^{D2}$ |
| $L_{A497}$ | $R^{C18}$ | $R^{B3}$ | $R^{D2}$ |
| $L_{A498}$ | $R^{C19}$ | $R^{B3}$ | $R^{D2}$ |
| $L_{A499}$ | $R^{C23}$ | $R^{B3}$ | $R^{D2}$ |
| $L_{A500}$ | $R^{C33}$ | $R^{B3}$ | $R^{D2}$ |
| $L_{A501}$ | $R^{C38}$ | $R^{B3}$ | $R^{D2}$ |
| $L_{A502}$ | $R^{C40}$ | $R^{B3}$ | $R^{D2}$ |
| $L_{A503}$ | $R^{C41}$ | $R^{B3}$ | $R^{D2}$ |
| $L_{A504}$ | $R^{C48}$ | $R^{B3}$ | $R^{D2}$ |
| $L_{A505}$ | $R^{C54}$ | $R^{B3}$ | $R^{D2}$ |
| $L_{A506}$ | $R^{C55}$ | $R^{B3}$ | $R^{D2}$ |
| $L_{A507}$ | $R^{C57}$ | $R^{B3}$ | $R^{D2}$ |
| $L_{A508}$ | $R^{C11}$ | $R^{B4}$ | $R^{D2}$ |
| $L_{A509}$ | $R^{C14}$ | $R^{B4}$ | $R^{D2}$ |
| $L_{A510}$ | $R^{C18}$ | $R^{B4}$ | $R^{D2}$ |
| $L_{A511}$ | $R^{C19}$ | $R^{B4}$ | $R^{D2}$ |
| $L_{A512}$ | $R^{C23}$ | $R^{B4}$ | $R^{D2}$ |
| $L_{A513}$ | $R^{C33}$ | $R^{B4}$ | $R^{D2}$ |
| $L_{A514}$ | $R^{C38}$ | $R^{B4}$ | $R^{D2}$ |
| $L_{A515}$ | $R^{C40}$ | $R^{B4}$ | $R^{D2}$ |
| $L_{A516}$ | $R^{C41}$ | $R^{B4}$ | $R^{D2}$ |
| $L_{A517}$ | $R^{C48}$ | $R^{B4}$ | $R^{D2}$ |
| $L_{A518}$ | $R^{C54}$ | $R^{B4}$ | $R^{D2}$ |
| $L_{A519}$ | $R^{C55}$ | $R^{B4}$ | $R^{D2}$ |
| $L_{A520}$ | $R^{C57}$ | $R^{B4}$ | $R^{D2}$ |
| $L_{A521}$ | $R^{C11}$ | $R^{C11}$ | $R^{D4}$ |
| $L_{A522}$ | $R^{C14}$ | $R^{C14}$ | $R^{D4}$ |
| $L_{A523}$ | $R^{C18}$ | $R^{C18}$ | $R^{D4}$ |
| $L_{A524}$ | $R^{C19}$ | $R^{C19}$ | $R^{D4}$ |
| $L_{A525}$ | $R^{C23}$ | $R^{C23}$ | $R^{D4}$ |
| $L_{A526}$ | $R^{C33}$ | $R^{C33}$ | $R^{D4}$ |
| $L_{A527}$ | $R^{C38}$ | $R^{C38}$ | $R^{D4}$ |
| $L_{A528}$ | $R^{C40}$ | $R^{C40}$ | $R^{D4}$ |
| $L_{A529}$ | $R^{C41}$ | $R^{C41}$ | $R^{D4}$ |
| $L_{A530}$ | $R^{C48}$ | $R^{C48}$ | $R^{D4}$ |
| $L_{A531}$ | $R^{C54}$ | $R^{C54}$ | $R^{D4}$ |
| $L_{A532}$ | $R^{C55}$ | $R^{C55}$ | $R^{D4}$ |
| $L_{A533}$ | $R^{C57}$ | $R^{C57}$ | $R^{D4}$ |
| $L_{A534}$ | $R^{C11}$ | $R^{B1}$ | $R^{D4}$ |
| $L_{A535}$ | $R^{C14}$ | $R^{B1}$ | $R^{D4}$ |
| $L_{A536}$ | $R^{C18}$ | $R^{B1}$ | $R^{D4}$ |

-continued

| Ligand | $R^3$ | $R^4$ | G |
|---|---|---|---|
| $L_{A4537}$ | $R^{C19}$ | $R^{B1}$ | $R^{D4}$ |
| $L_{A4538}$ | $R^{C23}$ | $R^{B1}$ | $R^{D4}$ |
| $L_{A4539}$ | $R^{C33}$ | $R^{B1}$ | $R^{D4}$ |
| $L_{A4540}$ | $R^{C38}$ | $R^{B1}$ | $R^{D4}$ |
| $L_{A4541}$ | $R^{C40}$ | $R^{B1}$ | $R^{D4}$ |
| $L_{A4542}$ | $R^{C41}$ | $R^{B1}$ | $R^{D4}$ |
| $L_{A4543}$ | $R^{C48}$ | $R^{B1}$ | $R^{D4}$ |
| $L_{A4544}$ | $R^{C54}$ | $R^{B1}$ | $R^{D4}$ |
| $L_{A4545}$ | $R^{C55}$ | $R^{B1}$ | $R^{D4}$ |
| $L_{A4546}$ | $R^{C57}$ | $R^{B1}$ | $R^{D4}$ |
| $L_{A4547}$ | $R^{C11}$ | $R^{B3}$ | $R^{D4}$ |
| $L_{A4548}$ | $R^{C14}$ | $R^{B3}$ | $R^{D4}$ |
| $L_{A4549}$ | $R^{C18}$ | $R^{B3}$ | $R^{D4}$ |
| $L_{A4550}$ | $R^{C19}$ | $R^{B3}$ | $R^{D4}$ |
| $L_{A4551}$ | $R^{C23}$ | $R^{B3}$ | $R^{D4}$ |
| $L_{A4552}$ | $R^{C33}$ | $R^{B3}$ | $R^{D4}$ |
| $L_{A4553}$ | $R^{C38}$ | $R^{B3}$ | $R^{D4}$ |
| $L_{A4554}$ | $R^{C40}$ | $R^{B3}$ | $R^{D4}$ |
| $L_{A4555}$ | $R^{C41}$ | $R^{B3}$ | $R^{D4}$ |
| $L_{A4556}$ | $R^{C48}$ | $R^{B3}$ | $R^{D4}$ |
| $L_{A4557}$ | $R^{C54}$ | $R^{B3}$ | $R^{D4}$ |
| $L_{A4558}$ | $R^{C55}$ | $R^{B3}$ | $R^{D4}$ |
| $L_{A4559}$ | $R^{C57}$ | $R^{B3}$ | $R^{D4}$ |
| $L_{A4560}$ | $R^{C11}$ | $R^{B4}$ | $R^{D4}$ |
| $L_{A4561}$ | $R^{C14}$ | $R^{B4}$ | $R^{D4}$ |
| $L_{A4562}$ | $R^{C18}$ | $R^{B4}$ | $R^{D4}$ |
| $L_{A4563}$ | $R^{C19}$ | $R^{B4}$ | $R^{D4}$ |
| $L_{A4564}$ | $R^{C23}$ | $R^{B4}$ | $R^{D4}$ |
| $L_{A4565}$ | $R^{C33}$ | $R^{B4}$ | $R^{D4}$ |
| $L_{A4566}$ | $R^{C38}$ | $R^{B4}$ | $R^{D4}$ |
| $L_{A4567}$ | $R^{C40}$ | $R^{B4}$ | $R^{D4}$ |
| $L_{A4568}$ | $R^{C41}$ | $R^{B4}$ | $R^{D4}$ |
| $L_{A4569}$ | $R^{C48}$ | $R^{B4}$ | $R^{D4}$ |
| $L_{A4570}$ | $R^{C54}$ | $R^{B4}$ | $R^{D4}$ |
| $L_{A4571}$ | $R^{C55}$ | $R^{B4}$ | $R^{D4}$ |
| $L_{A4572}$ | $R^{C57}$ | $R^{B4}$ | $R^{D4}$ |
| $L_{A4573}$ | $R^{C11}$ | $R^{C11}$ | $R^{D8}$ |
| $L_{A4574}$ | $R^{C14}$ | $R^{C14}$ | $R^{D8}$ |
| $L_{A4575}$ | $R^{C18}$ | $R^{C18}$ | $R^{D8}$ |
| $L_{A4576}$ | $R^{C19}$ | $R^{C19}$ | $R^{D8}$ |
| $L_{A4577}$ | $R^{C23}$ | $R^{C23}$ | $R^{D8}$ |
| $L_{A4578}$ | $R^{C33}$ | $R^{C33}$ | $R^{D8}$ |
| $L_{A4579}$ | $R^{C38}$ | $R^{C38}$ | $R^{D8}$ |
| $L_{A4580}$ | $R^{C40}$ | $R^{C40}$ | $R^{D8}$ |
| $L_{A4581}$ | $R^{C41}$ | $R^{C41}$ | $R^{D8}$ |
| $L_{A4582}$ | $R^{C48}$ | $R^{C48}$ | $R^{D8}$ |
| $L_{A4583}$ | $R^{C54}$ | $R^{C54}$ | $R^{D8}$ |
| $L_{A4584}$ | $R^{C55}$ | $R^{C55}$ | $R^{D8}$ |
| $L_{A4585}$ | $R^{C57}$ | $R^{C57}$ | $R^{D8}$ |
| $L_{A4586}$ | $R^{C11}$ | $R^{B1}$ | $R^{D8}$ |
| $L_{A4587}$ | $R^{C14}$ | $R^{B1}$ | $R^{D8}$ |
| $L_{A4588}$ | $R^{C18}$ | $R^{B1}$ | $R^{D8}$ |
| $L_{A4589}$ | $R^{C19}$ | $R^{B1}$ | $R^{D8}$ |
| $L_{A4590}$ | $R^{C23}$ | $R^{B1}$ | $R^{D8}$ |
| $L_{A4591}$ | $R^{C33}$ | $R^{B1}$ | $R^{D8}$ |
| $L_{A4592}$ | $R^{C38}$ | $R^{B1}$ | $R^{D8}$ |
| $L_{A4593}$ | $R^{C40}$ | $R^{B1}$ | $R^{D8}$ |
| $L_{A4594}$ | $R^{C41}$ | $R^{B1}$ | $R^{D8}$ |
| $L_{A4595}$ | $R^{C48}$ | $R^{B1}$ | $R^{D8}$ |
| $L_{A4596}$ | $R^{C54}$ | $R^{B1}$ | $R^{D8}$ |
| $L_{A4597}$ | $R^{C55}$ | $R^{B1}$ | $R^{D8}$ |
| $L_{A4598}$ | $R^{C57}$ | $R^{B1}$ | $R^{D8}$ |
| $L_{A4599}$ | $R^{C11}$ | $R^{B3}$ | $R^{D8}$ |
| $L_{A4600}$ | $R^{C14}$ | $R^{B3}$ | $R^{D8}$ |
| $L_{A4601}$ | $R^{C18}$ | $R^{B3}$ | $R^{D8}$ |
| $L_{A4602}$ | $R^{C19}$ | $R^{B3}$ | $R^{D8}$ |
| $L_{A4603}$ | $R^{C23}$ | $R^{B3}$ | $R^{D8}$ |
| $L_{A4604}$ | $R^{C33}$ | $R^{B3}$ | $R^{D8}$ |
| $L_{A4605}$ | $R^{C38}$ | $R^{B3}$ | $R^{D8}$ |
| $L_{A4606}$ | $R^{C40}$ | $R^{B3}$ | $R^{D8}$ |
| $L_{A4607}$ | $R^{C41}$ | $R^{B3}$ | $R^{D8}$ |
| $L_{A4608}$ | $R^{C48}$ | $R^{B3}$ | $R^{D8}$ |
| $L_{A4609}$ | $R^{C54}$ | $R^{B3}$ | $R^{D8}$ |
| $L_{A4610}$ | $R^{C55}$ | $R^{B3}$ | $R^{D8}$ |
| $L_{A4611}$ | $R^{C57}$ | $R^{B3}$ | $R^{D8}$ |
| $L_{A4612}$ | $R^{C11}$ | $R^{B4}$ | $R^{D8}$ |
| $L_{A4613}$ | $R^{C14}$ | $R^{B4}$ | $R^{D8}$ |
| $L_{A4614}$ | $R^{C18}$ | $R^{B4}$ | $R^{D8}$ |
| $L_{A4615}$ | $R^{C19}$ | $R^{B4}$ | $R^{D8}$ |
| $L_{A4616}$ | $R^{C23}$ | $R^{B4}$ | $R^{D8}$ |
| $L_{A4617}$ | $R^{C33}$ | $R^{B4}$ | $R^{D8}$ |
| $L_{A4618}$ | $R^{C38}$ | $R^{B4}$ | $R^{D8}$ |
| $L_{A4619}$ | $R^{C40}$ | $R^{B4}$ | $R^{D8}$ |
| $L_{A4620}$ | $R^{C41}$ | $R^{B4}$ | $R^{D8}$ |
| $L_{A4621}$ | $R^{C48}$ | $R^{B4}$ | $R^{D8}$ |
| $L_{A4622}$ | $R^{C54}$ | $R^{B4}$ | $R^{D8}$ |
| $L_{A4623}$ | $R^{C55}$ | $R^{B4}$ | $R^{D8}$ |
| $L_{A4624}$ | $R^{C57}$ | $R^{B4}$ | $R^{D8}$ |
| $L_{A4625}$ | $R^{C11}$ | $R^{C11}$ | $R^{D9}$ |
| $L_{A4626}$ | $R^{C14}$ | $R^{C14}$ | $R^{D9}$ |
| $L_{A4627}$ | $R^{C18}$ | $R^{C18}$ | $R^{D9}$ |
| $L_{A4628}$ | $R^{C19}$ | $R^{C19}$ | $R^{D9}$ |
| $L_{A4629}$ | $R^{C23}$ | $R^{C23}$ | $R^{D9}$ |
| $L_{A4630}$ | $R^{C33}$ | $R^{C33}$ | $R^{D9}$ |
| $L_{A4631}$ | $R^{C38}$ | $R^{C38}$ | $R^{D9}$ |
| $L_{A4632}$ | $R^{C40}$ | $R^{C40}$ | $R^{D9}$ |
| $L_{A4633}$ | $R^{C41}$ | $R^{C41}$ | $R^{D9}$ |
| $L_{A4634}$ | $R^{C48}$ | $R^{C48}$ | $R^{D9}$ |
| $L_{A4635}$ | $R^{C54}$ | $R^{C54}$ | $R^{D9}$ |
| $L_{A4636}$ | $R^{C55}$ | $R^{C55}$ | $R^{D9}$ |
| $L_{A4637}$ | $R^{C57}$ | $R^{C57}$ | $R^{D9}$ |
| $L_{A4638}$ | $R^{C11}$ | $R^{B1}$ | $R^{D9}$ |
| $L_{A4639}$ | $R^{C14}$ | $R^{B1}$ | $R^{D9}$ |
| $L_{A4640}$ | $R^{C18}$ | $R^{B1}$ | $R^{D9}$ |
| $L_{A4641}$ | $R^{C19}$ | $R^{B1}$ | $R^{D9}$ |
| $L_{A4642}$ | $R^{C23}$ | $R^{B1}$ | $R^{D9}$ |
| $L_{A4643}$ | $R^{C33}$ | $R^{B1}$ | $R^{D9}$ |
| $L_{A4644}$ | $R^{C38}$ | $R^{B1}$ | $R^{D9}$ |
| $L_{A4645}$ | $R^{C40}$ | $R^{B1}$ | $R^{D9}$ |
| $L_{A4646}$ | $R^{C41}$ | $R^{B1}$ | $R^{D9}$ |
| $L_{A4647}$ | $R^{C48}$ | $R^{B1}$ | $R^{D9}$ |
| $L_{A4648}$ | $R^{C54}$ | $R^{B1}$ | $R^{D9}$ |
| $L_{A4649}$ | $R^{C55}$ | $R^{B1}$ | $R^{D9}$ |
| $L_{A4650}$ | $R^{C57}$ | $R^{B1}$ | $R^{D9}$ |
| $L_{A4651}$ | $R^{C11}$ | $R^{B3}$ | $R^{D9}$ |
| $L_{A4652}$ | $R^{C14}$ | $R^{B3}$ | $R^{D9}$ |
| $L_{A4653}$ | $R^{C18}$ | $R^{B3}$ | $R^{D9}$ |
| $L_{A4654}$ | $R^{C19}$ | $R^{B3}$ | $R^{D9}$ |
| $L_{A4655}$ | $R^{C23}$ | $R^{B3}$ | $R^{D9}$ |
| $L_{A4656}$ | $R^{C33}$ | $R^{B3}$ | $R^{D9}$ |
| $L_{A4657}$ | $R^{C38}$ | $R^{B3}$ | $R^{D9}$ |
| $L_{A4658}$ | $R^{C40}$ | $R^{B3}$ | $R^{D9}$ |
| $L_{A4659}$ | $R^{C41}$ | $R^{B3}$ | $R^{D9}$ |
| $L_{A4660}$ | $R^{C48}$ | $R^{B3}$ | $R^{D9}$ |
| $L_{A4661}$ | $R^{C54}$ | $R^{B3}$ | $R^{D9}$ |
| $L_{A4662}$ | $R^{C55}$ | $R^{B3}$ | $R^{D9}$ |
| $L_{A4663}$ | $R^{C57}$ | $R^{B3}$ | $R^{D9}$ |
| $L_{A4664}$ | $R^{C11}$ | $R^{B4}$ | $R^{D9}$ |
| $L_{A4665}$ | $R^{C14}$ | $R^{B4}$ | $R^{D9}$ |
| $L_{A4666}$ | $R^{C18}$ | $R^{B4}$ | $R^{D9}$ |
| $L_{A4667}$ | $R^{C19}$ | $R^{B4}$ | $R^{D9}$ |
| $L_{A4668}$ | $R^{C23}$ | $R^{B4}$ | $R^{D9}$ |
| $L_{A4669}$ | $R^{C33}$ | $R^{B4}$ | $R^{D9}$ |
| $L_{A4670}$ | $R^{C38}$ | $R^{B4}$ | $R^{D9}$ |
| $L_{A4671}$ | $R^{C40}$ | $R^{B4}$ | $R^{D9}$ |
| $L_{A4672}$ | $R^{C41}$ | $R^{B4}$ | $R^{D9}$ |
| $L_{A4673}$ | $R^{C48}$ | $R^{B4}$ | $R^{D9}$ |
| $L_{A4674}$ | $R^{C54}$ | $R^{B4}$ | $R^{D9}$ |
| $L_{A4675}$ | $R^{C55}$ | $R^{B4}$ | $R^{D9}$ |
| $L_{A4676}$ | $R^{C57}$ | $R^{B4}$ | $R^{D9}$ |
| $L_{A4677}$ | $R^{C11}$ | $R^{C11}$ | $R^{D14}$ |
| $L_{A4678}$ | $R^{C14}$ | $R^{C14}$ | $R^{D14}$ |
| $L_{A4679}$ | $R^{C18}$ | $R^{C18}$ | $R^{D14}$ |
| $L_{A4680}$ | $R^{C19}$ | $R^{C19}$ | $R^{D14}$ |
| $L_{A4681}$ | $R^{C23}$ | $R^{C23}$ | $R^{D14}$ |
| $L_{A4682}$ | $R^{C33}$ | $R^{C33}$ | $R^{D14}$ |
| $L_{A4683}$ | $R^{C38}$ | $R^{C38}$ | $R^{D14}$ |
| $L_{A4684}$ | $R^{C40}$ | $R^{C40}$ | $R^{D14}$ |
| $L_{A4685}$ | $R^{C41}$ | $R^{C41}$ | $R^{D14}$ |
| $L_{A4686}$ | $R^{C48}$ | $R^{C48}$ | $R^{D14}$ |
| $L_{A4687}$ | $R^{C54}$ | $R^{C54}$ | $R^{D14}$ |
| $L_{A4688}$ | $R^{C55}$ | $R^{C55}$ | $R^{D14}$ |
| $L_{A4689}$ | $R^{C57}$ | $R^{C57}$ | $R^{D14}$ |
| $L_{A4690}$ | $R^{C11}$ | $R^{B1}$ | $R^{D14}$ |

-continued

| Ligand | $R^3$ | $R^4$ | G |
|---|---|---|---|
| $L_{4691}$ | $R^{C14}$ | $R^{B1}$ | $R^{D14}$ |
| $L_{4692}$ | $R^{C18}$ | $R^{B1}$ | $R^{D14}$ |
| $L_{4693}$ | $R^{C19}$ | $R^{B1}$ | $R^{D14}$ |
| $L_{4694}$ | $R^{C23}$ | $R^{B1}$ | $R^{D14}$ |
| $L_{4695}$ | $R^{C33}$ | $R^{B1}$ | $R^{D14}$ |
| $L_{4696}$ | $R^{C38}$ | $R^{B1}$ | $R^{D14}$ |
| $L_{4697}$ | $R^{C40}$ | $R^{B1}$ | $R^{D14}$ |
| $L_{4698}$ | $R^{C41}$ | $R^{B1}$ | $R^{D14}$ |
| $L_{4699}$ | $R^{C48}$ | $R^{B1}$ | $R^{D14}$ |
| $L_{4700}$ | $R^{C54}$ | $R^{B1}$ | $R^{D14}$ |
| $L_{4701}$ | $R^{C55}$ | $R^{B1}$ | $R^{D14}$ |
| $L_{4702}$ | $R^{C57}$ | $R^{B1}$ | $R^{D14}$ |
| $L_{4703}$ | $R^{C11}$ | $R^{B3}$ | $R^{D14}$ |
| $L_{4704}$ | $R^{C14}$ | $R^{B3}$ | $R^{D14}$ |
| $L_{4705}$ | $R^{C18}$ | $R^{B3}$ | $R^{D14}$ |
| $L_{4706}$ | $R^{C19}$ | $R^{B3}$ | $R^{D14}$ |
| $L_{4707}$ | $R^{C23}$ | $R^{B3}$ | $R^{D14}$ |
| $L_{4708}$ | $R^{C33}$ | $R^{B3}$ | $R^{D14}$ |
| $L_{4709}$ | $R^{C38}$ | $R^{B3}$ | $R^{D14}$ |
| $L_{4710}$ | $R^{C40}$ | $R^{B3}$ | $R^{D14}$ |
| $L_{4711}$ | $R^{C41}$ | $R^{B3}$ | $R^{D14}$ |
| $L_{4712}$ | $R^{C48}$ | $R^{B3}$ | $R^{D14}$ |
| $L_{4713}$ | $R^{C54}$ | $R^{B3}$ | $R^{D14}$ |
| $L_{4714}$ | $R^{C55}$ | $R^{B3}$ | $R^{D14}$ |
| $L_{4715}$ | $R^{C57}$ | $R^{B3}$ | $R^{D14}$ |
| $L_{4716}$ | $R^{C11}$ | $R^{B4}$ | $R^{D14}$ |
| $L_{4717}$ | $R^{C14}$ | $R^{B4}$ | $R^{D14}$ |
| $L_{4718}$ | $R^{C18}$ | $R^{B4}$ | $R^{D14}$ |
| $L_{4719}$ | $R^{C19}$ | $R^{B4}$ | $R^{D14}$ |
| $L_{4720}$ | $R^{C23}$ | $R^{B4}$ | $R^{D14}$ |
| $L_{4721}$ | $R^{C33}$ | $R^{B4}$ | $R^{D14}$ |
| $L_{4722}$ | $R^{C38}$ | $R^{B4}$ | $R^{D14}$ |
| $L_{4723}$ | $R^{C40}$ | $R^{B4}$ | $R^{D14}$ |
| $L_{4724}$ | $R^{C41}$ | $R^{B4}$ | $R^{D14}$ |
| $L_{4725}$ | $R^{C48}$ | $R^{B4}$ | $R^{D14}$ |
| $L_{4726}$ | $R^{C54}$ | $R^{B4}$ | $R^{D14}$ |
| $L_{4727}$ | $R^{C55}$ | $R^{B4}$ | $R^{D14}$ |
| $L_{4728}$ | $R^{C57}$ | $R^{B4}$ | $R^{D14}$ |
| $L_{4729}$ | $R^{C11}$ | $R^{C11}$ | $R^{D22}$ |
| $L_{4730}$ | $R^{C14}$ | $R^{C14}$ | $R^{D22}$ |
| $L_{4731}$ | $R^{C18}$ | $R^{C18}$ | $R^{D22}$ |
| $L_{4732}$ | $R^{C19}$ | $R^{C19}$ | $R^{D22}$ |
| $L_{4733}$ | $R^{C23}$ | $R^{C23}$ | $R^{D22}$ |
| $L_{4734}$ | $R^{C33}$ | $R^{C33}$ | $R^{D22}$ |
| $L_{4735}$ | $R^{C38}$ | $R^{C38}$ | $R^{D22}$ |
| $L_{4736}$ | $R^{C40}$ | $R^{C40}$ | $R^{D22}$ |
| $L_{4737}$ | $R^{C41}$ | $R^{C41}$ | $R^{D22}$ |
| $L_{4738}$ | $R^{C48}$ | $R^{C48}$ | $R^{D22}$ |
| $L_{4739}$ | $R^{C54}$ | $R^{C54}$ | $R^{D22}$ |
| $L_{4740}$ | $R^{C55}$ | $R^{C55}$ | $R^{D22}$ |
| $L_{4741}$ | $R^{C57}$ | $R^{C57}$ | $R^{D22}$ |
| $L_{4742}$ | $R^{C11}$ | $R^{B1}$ | $R^{D22}$ |
| $L_{4743}$ | $R^{C14}$ | $R^{B1}$ | $R^{D22}$ |
| $L_{4744}$ | $R^{C18}$ | $R^{B1}$ | $R^{D22}$ |
| $L_{4745}$ | $R^{C19}$ | $R^{B1}$ | $R^{D22}$ |
| $L_{4746}$ | $R^{C23}$ | $R^{B1}$ | $R^{D22}$ |
| $L_{4747}$ | $R^{C33}$ | $R^{B1}$ | $R^{D22}$ |
| $L_{4748}$ | $R^{C38}$ | $R^{B1}$ | $R^{D22}$ |
| $L_{4749}$ | $R^{C40}$ | $R^{B1}$ | $R^{D22}$ |
| $L_{4750}$ | $R^{C41}$ | $R^{B1}$ | $R^{D22}$ |
| $L_{4751}$ | $R^{C48}$ | $R^{B1}$ | $R^{D22}$ |
| $L_{4752}$ | $R^{C54}$ | $R^{B1}$ | $R^{D22}$ |
| $L_{4753}$ | $R^{C55}$ | $R^{B1}$ | $R^{D22}$ |
| $L_{4754}$ | $R^{C57}$ | $R^{B1}$ | $R^{D22}$ |
| $L_{4755}$ | $R^{C11}$ | $R^{B3}$ | $R^{D22}$ |
| $L_{4756}$ | $R^{C14}$ | $R^{B3}$ | $R^{D22}$ |
| $L_{4757}$ | $R^{C18}$ | $R^{B3}$ | $R^{D22}$ |
| $L_{4758}$ | $R^{C19}$ | $R^{B3}$ | $R^{D22}$ |
| $L_{4759}$ | $R^{C23}$ | $R^{B3}$ | $R^{D22}$ |
| $L_{4760}$ | $R^{C33}$ | $R^{B3}$ | $R^{D22}$ |
| $L_{4761}$ | $R^{C38}$ | $R^{B3}$ | $R^{D22}$ |
| $L_{4762}$ | $R^{C40}$ | $R^{B3}$ | $R^{D22}$ |
| $L_{4763}$ | $R^{C41}$ | $R^{B3}$ | $R^{D22}$ |
| $L_{4764}$ | $R^{C48}$ | $R^{B3}$ | $R^{D22}$ |
| $L_{4765}$ | $R^{C54}$ | $R^{B3}$ | $R^{D22}$ |
| $L_{4766}$ | $R^{C55}$ | $R^{B3}$ | $R^{D22}$ |
| $L_{4767}$ | $R^{C57}$ | $R^{B3}$ | $R^{D22}$ |
| $L_{4768}$ | $R^{C11}$ | $R^{B4}$ | $R^{D22}$ |
| $L_{4769}$ | $R^{C14}$ | $R^{B4}$ | $R^{D22}$ |
| $L_{4770}$ | $R^{C18}$ | $R^{B4}$ | $R^{D22}$ |
| $L_{4771}$ | $R^{C19}$ | $R^{B4}$ | $R^{D22}$ |
| $L_{4772}$ | $R^{C23}$ | $R^{B4}$ | $R^{D22}$ |
| $L_{4773}$ | $R^{C33}$ | $R^{B4}$ | $R^{D22}$ |
| $L_{4774}$ | $R^{C38}$ | $R^{B4}$ | $R^{D22}$ |
| $L_{4775}$ | $R^{C40}$ | $R^{B4}$ | $R^{D22}$ |
| $L_{4776}$ | $R^{C41}$ | $R^{B4}$ | $R^{D22}$ |
| $L_{4777}$ | $R^{C48}$ | $R^{B4}$ | $R^{D22}$ |
| $L_{4778}$ | $R^{C54}$ | $R^{B4}$ | $R^{D22}$ |
| $L_{4779}$ | $R^{C55}$ | $R^{B4}$ | $R^{D22}$ |
| $L_{4780}$ | $R^{C57}$ | $R^{B4}$ | $R^{D22}$ |
| $L_{4781}$ | $R^{C11}$ | $R^{C11}$ | $R^{D28}$ |
| $L_{4782}$ | $R^{C14}$ | $R^{C14}$ | $R^{D28}$ |
| $L_{4783}$ | $R^{C18}$ | $R^{C18}$ | $R^{D28}$ |
| $L_{4784}$ | $R^{C19}$ | $R^{C19}$ | $R^{D28}$ |
| $L_{4785}$ | $R^{C23}$ | $R^{C23}$ | $R^{D28}$ |
| $L_{4786}$ | $R^{C33}$ | $R^{C33}$ | $R^{D28}$ |
| $L_{4787}$ | $R^{C38}$ | $R^{C38}$ | $R^{D28}$ |
| $L_{4788}$ | $R^{C40}$ | $R^{C40}$ | $R^{D28}$ |
| $L_{4789}$ | $R^{C41}$ | $R^{C41}$ | $R^{D28}$ |
| $L_{4790}$ | $R^{C48}$ | $R^{C48}$ | $R^{D28}$ |
| $L_{4791}$ | $R^{C54}$ | $R^{C54}$ | $R^{D28}$ |
| $L_{4792}$ | $R^{C55}$ | $R^{C55}$ | $R^{D28}$ |
| $L_{4793}$ | $R^{C57}$ | $R^{C57}$ | $R^{D28}$ |
| $L_{4794}$ | $R^{C11}$ | $R^{B1}$ | $R^{D28}$ |
| $L_{4795}$ | $R^{C14}$ | $R^{B1}$ | $R^{D28}$ |
| $L_{4796}$ | $R^{C18}$ | $R^{B1}$ | $R^{D28}$ |
| $L_{4797}$ | $R^{C19}$ | $R^{B1}$ | $R^{D28}$ |
| $L_{4798}$ | $R^{C23}$ | $R^{B1}$ | $R^{D28}$ |
| $L_{4799}$ | $R^{C33}$ | $R^{B1}$ | $R^{D28}$ |
| $L_{4800}$ | $R^{C38}$ | $R^{B1}$ | $R^{D28}$ |
| $L_{4801}$ | $R^{C40}$ | $R^{B1}$ | $R^{D28}$ |
| $L_{4802}$ | $R^{C41}$ | $R^{B1}$ | $R^{D28}$ |
| $L_{4803}$ | $R^{C48}$ | $R^{B1}$ | $R^{D28}$ |
| $L_{4804}$ | $R^{C54}$ | $R^{B1}$ | $R^{D28}$ |
| $L_{4805}$ | $R^{C55}$ | $R^{B1}$ | $R^{D28}$ |
| $L_{4806}$ | $R^{C57}$ | $R^{B1}$ | $R^{D28}$ |
| $L_{4807}$ | $R^{C11}$ | $R^{B3}$ | $R^{D28}$ |
| $L_{4808}$ | $R^{C14}$ | $R^{B3}$ | $R^{D28}$ |
| $L_{4809}$ | $R^{C18}$ | $R^{B3}$ | $R^{D28}$ |
| $L_{4810}$ | $R^{C19}$ | $R^{B3}$ | $R^{D28}$ |
| $L_{4811}$ | $R^{C23}$ | $R^{B3}$ | $R^{D28}$ |
| $L_{4812}$ | $R^{C33}$ | $R^{B3}$ | $R^{D28}$ |
| $L_{4813}$ | $R^{C38}$ | $R^{B3}$ | $R^{D28}$ |
| $L_{4814}$ | $R^{C40}$ | $R^{B3}$ | $R^{D28}$ |
| $L_{4815}$ | $R^{C41}$ | $R^{B3}$ | $R^{D28}$ |
| $L_{4816}$ | $R^{C48}$ | $R^{B3}$ | $R^{D28}$ |
| $L_{4817}$ | $R^{C54}$ | $R^{B3}$ | $R^{D28}$ |
| $L_{4818}$ | $R^{C55}$ | $R^{B3}$ | $R^{D28}$ |
| $L_{4819}$ | $R^{C57}$ | $R^{B3}$ | $R^{D28}$ |
| $L_{4820}$ | $R^{C11}$ | $R^{B4}$ | $R^{D28}$ |
| $L_{4821}$ | $R^{C14}$ | $R^{B4}$ | $R^{D28}$ |
| $L_{4822}$ | $R^{C18}$ | $R^{B4}$ | $R^{D28}$ |
| $L_{4823}$ | $R^{C19}$ | $R^{B4}$ | $R^{D28}$ |
| $L_{4824}$ | $R^{C23}$ | $R^{B4}$ | $R^{D28}$ |
| $L_{4825}$ | $R^{C33}$ | $R^{B4}$ | $R^{D28}$ |
| $L_{4826}$ | $R^{C38}$ | $R^{B4}$ | $R^{D28}$ |
| $L_{4827}$ | $R^{C40}$ | $R^{B4}$ | $R^{D28}$ |
| $L_{4828}$ | $R^{C41}$ | $R^{B4}$ | $R^{D28}$ |
| $L_{4829}$ | $R^{C48}$ | $R^{B4}$ | $R^{D28}$ |
| $L_{4830}$ | $R^{C54}$ | $R^{B4}$ | $R^{D28}$ |
| $L_{4831}$ | $R^{C55}$ | $R^{B4}$ | $R^{D28}$ |
| $L_{4832}$ | $R^{C57}$ | $R^{B4}$ | $R^{D28}$, |

$L_{4833}$ through $L_{41144}$ based on a structure of Formula III,

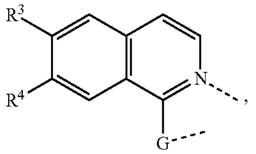

in which $R^3$, $R^4$, and G are defined as:

| Ligand | $R^3$ | $R^4$ | G |
|---|---|---|---|
| $L_{4833}$ | $R^{C11}$ | $R^{B1}$ | $R^{D1}$ |
| $L_{4834}$ | $R^{C14}$ | $R^{B1}$ | $R^{D1}$ |
| $L_{4835}$ | $R^{C18}$ | $R^{B1}$ | $R^{D1}$ |
| $L_{4836}$ | $R^{C19}$ | $R^{B1}$ | $R^{D1}$ |
| $L_{4837}$ | $R^{C23}$ | $R^{B1}$ | $R^{D1}$ |
| $L_{4838}$ | $R^{C33}$ | $R^{B1}$ | $R^{D1}$ |
| $L_{4839}$ | $R^{C38}$ | $R^{B1}$ | $R^{D1}$ |
| $L_{4840}$ | $R^{C40}$ | $R^{B1}$ | $R^{D1}$ |
| $L_{4841}$ | $R^{C41}$ | $R^{B1}$ | $R^{D1}$ |
| $L_{4842}$ | $R^{C48}$ | $R^{B1}$ | $R^{D1}$ |
| $L_{4843}$ | $R^{C54}$ | $R^{B1}$ | $R^{D1}$ |
| $L_{4844}$ | $R^{C55}$ | $R^{B1}$ | $R^{D1}$ |
| $L_{4845}$ | $R^{C57}$ | $R^{B1}$ | $R^{D1}$ |
| $L_{4846}$ | $R^{C11}$ | $R^{B3}$ | $R^{D1}$ |
| $L_{4847}$ | $R^{C14}$ | $R^{B3}$ | $R^{D1}$ |
| $L_{4848}$ | $R^{C18}$ | $R^{B3}$ | $R^{D1}$ |
| $L_{4849}$ | $R^{C19}$ | $R^{B3}$ | $R^{D1}$ |
| $L_{4850}$ | $R^{C23}$ | $R^{B3}$ | $R^{D1}$ |
| $L_{4851}$ | $R^{C33}$ | $R^{B3}$ | $R^{D1}$ |
| $L_{4852}$ | $R^{C38}$ | $R^{B3}$ | $R^{D1}$ |
| $L_{4853}$ | $R^{C40}$ | $R^{B3}$ | $R^{D1}$ |
| $L_{4854}$ | $R^{C41}$ | $R^{B3}$ | $R^{D1}$ |
| $L_{4855}$ | $R^{C48}$ | $R^{B3}$ | $R^{D1}$ |
| $L_{4856}$ | $R^{C54}$ | $R^{B3}$ | $R^{D1}$ |
| $L_{4857}$ | $R^{C55}$ | $R^{B3}$ | $R^{D1}$ |
| $L_{4858}$ | $R^{C57}$ | $R^{B3}$ | $R^{D1}$ |
| $L_{4859}$ | $R^{C11}$ | $R^{B4}$ | $R^{D1}$ |
| $L_{4860}$ | $R^{C14}$ | $R^{B4}$ | $R^{D1}$ |
| $L_{4861}$ | $R^{C18}$ | $R^{B4}$ | $R^{D1}$ |
| $L_{4862}$ | $R^{C19}$ | $R^{B4}$ | $R^{D1}$ |
| $L_{4863}$ | $R^{C23}$ | $R^{B4}$ | $R^{D1}$ |
| $L_{4864}$ | $R^{C33}$ | $R^{B4}$ | $R^{D1}$ |
| $L_{4865}$ | $R^{C38}$ | $R^{B4}$ | $R^{D1}$ |
| $L_{4866}$ | $R^{C40}$ | $R^{B4}$ | $R^{D1}$ |
| $L_{4867}$ | $R^{C41}$ | $R^{B4}$ | $R^{D1}$ |
| $L_{4868}$ | $R^{C48}$ | $R^{B4}$ | $R^{D1}$ |
| $L_{4869}$ | $R^{C54}$ | $R^{B4}$ | $R^{D1}$ |
| $L_{4870}$ | $R^{C55}$ | $R^{B4}$ | $R^{D1}$ |
| $L_{4871}$ | $R^{C57}$ | $R^{B4}$ | $R^{D1}$ |
| $L_{4872}$ | $R^{C11}$ | $R^{B1}$ | $R^{D2}$ |
| $L_{4873}$ | $R^{C14}$ | $R^{B1}$ | $R^{D2}$ |
| $L_{4874}$ | $R^{C18}$ | $R^{B1}$ | $R^{D2}$ |
| $L_{4875}$ | $R^{C19}$ | $R^{B1}$ | $R^{D2}$ |
| $L_{4876}$ | $R^{C23}$ | $R^{B1}$ | $R^{D2}$ |
| $L_{4877}$ | $R^{C33}$ | $R^{B1}$ | $R^{D2}$ |
| $L_{4878}$ | $R^{C38}$ | $R^{B1}$ | $R^{D2}$ |
| $L_{4879}$ | $R^{C40}$ | $R^{B1}$ | $R^{D2}$ |
| $L_{4880}$ | $R^{C41}$ | $R^{B1}$ | $R^{D2}$ |
| $L_{4881}$ | $R^{C48}$ | $R^{B1}$ | $R^{D2}$ |
| $L_{4882}$ | $R^{C54}$ | $R^{B1}$ | $R^{D2}$ |
| $L_{4883}$ | $R^{C55}$ | $R^{B1}$ | $R^{D2}$ |
| $L_{4884}$ | $R^{C57}$ | $R^{B1}$ | $R^{D2}$ |
| $L_{4885}$ | $R^{C11}$ | $R^{B3}$ | $R^{D2}$ |
| $L_{4886}$ | $R^{C14}$ | $R^{B3}$ | $R^{D2}$ |
| $L_{4887}$ | $R^{C18}$ | $R^{B3}$ | $R^{D2}$ |
| $L_{4888}$ | $R^{C19}$ | $R^{B3}$ | $R^{D2}$ |
| $L_{4889}$ | $R^{C23}$ | $R^{B3}$ | $R^{D2}$ |
| $L_{4890}$ | $R^{C33}$ | $R^{B3}$ | $R^{D2}$ |
| $L_{4891}$ | $R^{C38}$ | $R^{B3}$ | $R^{D2}$ |
| $L_{4892}$ | $R^{C40}$ | $R^{B3}$ | $R^{D2}$ |
| $L_{4893}$ | $R^{C41}$ | $R^{B3}$ | $R^{D2}$ |
| $L_{4894}$ | $R^{C48}$ | $R^{B3}$ | $R^{D2}$ |
| $L_{4895}$ | $R^{C54}$ | $R^{B3}$ | $R^{D2}$ |
| $L_{4896}$ | $R^{C55}$ | $R^{B3}$ | $R^{D2}$ |

-continued

| Ligand | $R^3$ | $R^4$ | G |
|---|---|---|---|
| $L_{4897}$ | $R^{C57}$ | $R^{B3}$ | $R^{D2}$ |
| $L_{4898}$ | $R^{C11}$ | $R^{B4}$ | $R^{D2}$ |
| $L_{4899}$ | $R^{C14}$ | $R^{B4}$ | $R^{D2}$ |
| $L_{4900}$ | $R^{C18}$ | $R^{B4}$ | $R^{D2}$ |
| $L_{4901}$ | $R^{C19}$ | $R^{B4}$ | $R^{D2}$ |
| $L_{4902}$ | $R^{C23}$ | $R^{B4}$ | $R^{D2}$ |
| $L_{4903}$ | $R^{C33}$ | $R^{B4}$ | $R^{D2}$ |
| $L_{4904}$ | $R^{C38}$ | $R^{B4}$ | $R^{D2}$ |
| $L_{4905}$ | $R^{C40}$ | $R^{B4}$ | $R^{D2}$ |
| $L_{4906}$ | $R^{C41}$ | $R^{B4}$ | $R^{D2}$ |
| $L_{4907}$ | $R^{C48}$ | $R^{B4}$ | $R^{D2}$ |
| $L_{4908}$ | $R^{C54}$ | $R^{B4}$ | $R^{D2}$ |
| $L_{4909}$ | $R^{C55}$ | $R^{B4}$ | $R^{D2}$ |
| $L_{4910}$ | $R^{C57}$ | $R^{B4}$ | $R^{D2}$ |
| $L_{4911}$ | $R^{C11}$ | $R^{B1}$ | $R^{D4}$ |
| $L_{4912}$ | $R^{C14}$ | $R^{B1}$ | $R^{D4}$ |
| $L_{4913}$ | $R^{C18}$ | $R^{B1}$ | $R^{D4}$ |
| $L_{4914}$ | $R^{C19}$ | $R^{B1}$ | $R^{D4}$ |
| $L_{4915}$ | $R^{C23}$ | $R^{B1}$ | $R^{D4}$ |
| $L_{4916}$ | $R^{C33}$ | $R^{B1}$ | $R^{D4}$ |
| $L_{4917}$ | $R^{C38}$ | $R^{B1}$ | $R^{D4}$ |
| $L_{4918}$ | $R^{C40}$ | $R^{B1}$ | $R^{D4}$ |
| $L_{4919}$ | $R^{C41}$ | $R^{B1}$ | $R^{D4}$ |
| $L_{4920}$ | $R^{C48}$ | $R^{B1}$ | $R^{D4}$ |
| $L_{4921}$ | $R^{C54}$ | $R^{B1}$ | $R^{D4}$ |
| $L_{4922}$ | $R^{C55}$ | $R^{B1}$ | $R^{D4}$ |
| $L_{4923}$ | $R^{C57}$ | $R^{B1}$ | $R^{D4}$ |
| $L_{4924}$ | $R^{C11}$ | $R^{B3}$ | $R^{D4}$ |
| $L_{4925}$ | $R^{C14}$ | $R^{B3}$ | $R^{D4}$ |
| $L_{4926}$ | $R^{C18}$ | $R^{B3}$ | $R^{D4}$ |
| $L_{4927}$ | $R^{C19}$ | $R^{B3}$ | $R^{D4}$ |
| $L_{4928}$ | $R^{C23}$ | $R^{B3}$ | $R^{D4}$ |
| $L_{4929}$ | $R^{C33}$ | $R^{B3}$ | $R^{D4}$ |
| $L_{4930}$ | $R^{C38}$ | $R^{B3}$ | $R^{D4}$ |
| $L_{4931}$ | $R^{C40}$ | $R^{B3}$ | $R^{D4}$ |
| $L_{4932}$ | $R^{C41}$ | $R^{B3}$ | $R^{D4}$ |
| $L_{4933}$ | $R^{C48}$ | $R^{B3}$ | $R^{D4}$ |
| $L_{4934}$ | $R^{C54}$ | $R^{B3}$ | $R^{D4}$ |
| $L_{4935}$ | $R^{C55}$ | $R^{B3}$ | $R^{D4}$ |
| $L_{4936}$ | $R^{C57}$ | $R^{B3}$ | $R^{D4}$ |
| $L_{4937}$ | $R^{C11}$ | $R^{B4}$ | $R^{D4}$ |
| $L_{4938}$ | $R^{C14}$ | $R^{B4}$ | $R^{D4}$ |
| $L_{4939}$ | $R^{C18}$ | $R^{B4}$ | $R^{D4}$ |
| $L_{4940}$ | $R^{C19}$ | $R^{B4}$ | $R^{D4}$ |
| $L_{4941}$ | $R^{C23}$ | $R^{B4}$ | $R^{D4}$ |
| $L_{4942}$ | $R^{C33}$ | $R^{B4}$ | $R^{D4}$ |
| $L_{4943}$ | $R^{C38}$ | $R^{B4}$ | $R^{D4}$ |
| $L_{4944}$ | $R^{C40}$ | $R^{B4}$ | $R^{D4}$ |
| $L_{4945}$ | $R^{C41}$ | $R^{B4}$ | $R^{D4}$ |
| $L_{4946}$ | $R^{C48}$ | $R^{B4}$ | $R^{D4}$ |
| $L_{4947}$ | $R^{C54}$ | $R^{B4}$ | $R^{D4}$ |
| $L_{4948}$ | $R^{C55}$ | $R^{B4}$ | $R^{D4}$ |
| $L_{4949}$ | $R^{C57}$ | $R^{B4}$ | $R^{D4}$ |
| $L_{4950}$ | $R^{C11}$ | $R^{B1}$ | $R^{D8}$ |
| $L_{4951}$ | $R^{C14}$ | $R^{B1}$ | $R^{D8}$ |
| $L_{4952}$ | $R^{C18}$ | $R^{B1}$ | $R^{D8}$ |
| $L_{4953}$ | $R^{C19}$ | $R^{B1}$ | $R^{D8}$ |
| $L_{4954}$ | $R^{C23}$ | $R^{B1}$ | $R^{D8}$ |
| $L_{4955}$ | $R^{C33}$ | $R^{B1}$ | $R^{D8}$ |
| $L_{4956}$ | $R^{C38}$ | $R^{B1}$ | $R^{D8}$ |
| $L_{4957}$ | $R^{C40}$ | $R^{B1}$ | $R^{D8}$ |
| $L_{4958}$ | $R^{C41}$ | $R^{B1}$ | $R^{D8}$ |
| $L_{4959}$ | $R^{C48}$ | $R^{B1}$ | $R^{D8}$ |
| $L_{4960}$ | $R^{C54}$ | $R^{B1}$ | $R^{D8}$ |
| $L_{4961}$ | $R^{C55}$ | $R^{B1}$ | $R^{D8}$ |
| $L_{4962}$ | $R^{C57}$ | $R^{B1}$ | $R^{D8}$ |
| $L_{4963}$ | $R^{C11}$ | $R^{B3}$ | $R^{D8}$ |
| $L_{4964}$ | $R^{C14}$ | $R^{B3}$ | $R^{D8}$ |
| $L_{4965}$ | $R^{C18}$ | $R^{B3}$ | $R^{D8}$ |
| $L_{4966}$ | $R^{C19}$ | $R^{B3}$ | $R^{D8}$ |
| $L_{4967}$ | $R^{C23}$ | $R^{B3}$ | $R^{D8}$ |
| $L_{4968}$ | $R^{C33}$ | $R^{B3}$ | $R^{D8}$ |
| $L_{4969}$ | $R^{C38}$ | $R^{B3}$ | $R^{D8}$ |
| $L_{4970}$ | $R^{C40}$ | $R^{B3}$ | $R^{D8}$ |
| $L_{4971}$ | $R^{C41}$ | $R^{B3}$ | $R^{D8}$ |
| $L_{4972}$ | $R^{C48}$ | $R^{B3}$ | $R^{D8}$ |
| $L_{4973}$ | $R^{C54}$ | $R^{B3}$ | $R^{D8}$ |

-continued

| Ligand | $R^3$ | $R^4$ | G |
|---|---|---|---|
| $L_{A974}$ | $R^{C55}$ | $R^{B3}$ | $R^{D8}$ |
| $L_{A975}$ | $R^{C57}$ | $R^{B3}$ | $R^{D8}$ |
| $L_{A976}$ | $R^{C11}$ | $R^{B4}$ | $R^{D8}$ |
| $L_{A977}$ | $R^{C14}$ | $R^{B4}$ | $R^{D8}$ |
| $L_{A978}$ | $R^{C18}$ | $R^{B4}$ | $R^{D8}$ |
| $L_{A979}$ | $R^{C19}$ | $R^{B4}$ | $R^{D8}$ |
| $L_{A980}$ | $R^{C23}$ | $R^{B4}$ | $R^{D8}$ |
| $L_{A981}$ | $R^{C33}$ | $R^{B4}$ | $R^{D8}$ |
| $L_{A982}$ | $R^{C38}$ | $R^{B4}$ | $R^{D8}$ |
| $L_{A983}$ | $R^{C40}$ | $R^{B4}$ | $R^{D8}$ |
| $L_{A984}$ | $R^{C41}$ | $R^{B4}$ | $R^{D8}$ |
| $L_{A985}$ | $R^{C48}$ | $R^{B4}$ | $R^{D8}$ |
| $L_{A986}$ | $R^{C54}$ | $R^{B4}$ | $R^{D8}$ |
| $L_{A987}$ | $R^{C55}$ | $R^{B4}$ | $R^{D8}$ |
| $L_{A988}$ | $R^{C57}$ | $R^{B4}$ | $R^{D8}$ |
| $L_{A989}$ | $R^{C11}$ | $R^{B1}$ | $R^{D9}$ |
| $L_{A990}$ | $R^{C14}$ | $R^{B1}$ | $R^{D9}$ |
| $L_{A991}$ | $R^{C18}$ | $R^{B1}$ | $R^{D9}$ |
| $L_{A992}$ | $R^{C19}$ | $R^{B1}$ | $R^{D9}$ |
| $L_{A993}$ | $R^{C23}$ | $R^{B1}$ | $R^{D9}$ |
| $L_{A994}$ | $R^{C33}$ | $R^{B1}$ | $R^{D9}$ |
| $L_{A995}$ | $R^{C38}$ | $R^{B1}$ | $R^{D9}$ |
| $L_{A996}$ | $R^{C40}$ | $R^{B1}$ | $R^{D9}$ |
| $L_{A997}$ | $R^{C41}$ | $R^{B1}$ | $R^{D9}$ |
| $L_{A998}$ | $R^{C48}$ | $R^{B1}$ | $R^{D9}$ |
| $L_{A999}$ | $R^{C54}$ | $R^{B1}$ | $R^{D9}$ |
| $L_{A1000}$ | $R^{C55}$ | $R^{B1}$ | $R^{D9}$ |
| $L_{A1001}$ | $R^{C57}$ | $R^{B1}$ | $R^{D9}$ |
| $L_{A1002}$ | $R^{C11}$ | $R^{B3}$ | $R^{D9}$ |
| $L_{A1003}$ | $R^{C14}$ | $R^{B3}$ | $R^{D9}$ |
| $L_{A1004}$ | $R^{C18}$ | $R^{B3}$ | $R^{D9}$ |
| $L_{A1005}$ | $R^{C19}$ | $R^{B3}$ | $R^{D9}$ |
| $L_{A1006}$ | $R^{C23}$ | $R^{B3}$ | $R^{D9}$ |
| $L_{A1007}$ | $R^{C33}$ | $R^{B3}$ | $R^{D9}$ |
| $L_{A1008}$ | $R^{C38}$ | $R^{B3}$ | $R^{D9}$ |
| $L_{A1009}$ | $R^{C40}$ | $R^{B3}$ | $R^{D9}$ |
| $L_{A1010}$ | $R^{C41}$ | $R^{B3}$ | $R^{D9}$ |
| $L_{A1011}$ | $R^{C48}$ | $R^{B3}$ | $R^{D9}$ |
| $L_{A1012}$ | $R^{C54}$ | $R^{B3}$ | $R^{D9}$ |
| $L_{A1013}$ | $R^{C55}$ | $R^{B3}$ | $R^{D9}$ |
| $L_{A1014}$ | $R^{C57}$ | $R^{B3}$ | $R^{D9}$ |
| $L_{A1015}$ | $R^{C11}$ | $R^{B4}$ | $R^{D9}$ |
| $L_{A1016}$ | $R^{C14}$ | $R^{B4}$ | $R^{D9}$ |
| $L_{A1017}$ | $R^{C18}$ | $R^{B4}$ | $R^{D9}$ |
| $L_{A1018}$ | $R^{C19}$ | $R^{B4}$ | $R^{D9}$ |
| $L_{A1019}$ | $R^{C23}$ | $R^{B4}$ | $R^{D9}$ |
| $L_{A1020}$ | $R^{C33}$ | $R^{B4}$ | $R^{D9}$ |
| $L_{A1021}$ | $R^{C38}$ | $R^{B4}$ | $R^{D9}$ |
| $L_{A1022}$ | $R^{C40}$ | $R^{B4}$ | $R^{D9}$ |
| $L_{A1023}$ | $R^{C41}$ | $R^{B4}$ | $R^{D9}$ |
| $L_{A1024}$ | $R^{C48}$ | $R^{B4}$ | $R^{D9}$ |
| $L_{A1025}$ | $R^{C54}$ | $R^{B4}$ | $R^{D9}$ |
| $L_{A1026}$ | $R^{C55}$ | $R^{B4}$ | $R^{D9}$ |
| $L_{A1027}$ | $R^{C57}$ | $R^{B4}$ | $R^{D9}$ |
| $L_{A1028}$ | $R^{C11}$ | $R^{B1}$ | $R^{D14}$ |
| $L_{A1029}$ | $R^{C14}$ | $R^{B1}$ | $R^{D14}$ |
| $L_{A1030}$ | $R^{C18}$ | $R^{B1}$ | $R^{D14}$ |
| $L_{A1031}$ | $R^{C19}$ | $R^{B1}$ | $R^{D14}$ |
| $L_{A1032}$ | $R^{C23}$ | $R^{B1}$ | $R^{D14}$ |
| $L_{A1033}$ | $R^{C33}$ | $R^{B1}$ | $R^{D14}$ |
| $L_{A1034}$ | $R^{C38}$ | $R^{B1}$ | $R^{D14}$ |
| $L_{A1035}$ | $R^{C40}$ | $R^{B1}$ | $R^{D14}$ |
| $L_{A1036}$ | $R^{C41}$ | $R^{B1}$ | $R^{D14}$ |
| $L_{A1037}$ | $R^{C48}$ | $R^{B1}$ | $R^{D14}$ |
| $L_{A1038}$ | $R^{C54}$ | $R^{B1}$ | $R^{D14}$ |
| $L_{A1039}$ | $R^{C55}$ | $R^{B1}$ | $R^{D14}$ |
| $L_{A1040}$ | $R^{C57}$ | $R^{B1}$ | $R^{D14}$ |
| $L_{A1041}$ | $R^{C11}$ | $R^{B3}$ | $R^{D14}$ |
| $L_{A1042}$ | $R^{C14}$ | $R^{B3}$ | $R^{D14}$ |
| $L_{A1043}$ | $R^{C18}$ | $R^{B3}$ | $R^{D14}$ |
| $L_{A1044}$ | $R^{C19}$ | $R^{B3}$ | $R^{D14}$ |
| $L_{A1045}$ | $R^{C23}$ | $R^{B3}$ | $R^{D14}$ |
| $L_{A1046}$ | $R^{C33}$ | $R^{B3}$ | $R^{D14}$ |
| $L_{A1047}$ | $R^{C38}$ | $R^{B3}$ | $R^{D14}$ |
| $L_{A1048}$ | $R^{C40}$ | $R^{B3}$ | $R^{D14}$ |
| $L_{A1049}$ | $R^{C41}$ | $R^{B3}$ | $R^{D14}$ |
| $L_{A1050}$ | $R^{C48}$ | $R^{B3}$ | $R^{D14}$ |

-continued

| Ligand | $R^3$ | $R^4$ | G |
|---|---|---|---|
| $L_{A1051}$ | $R^{C54}$ | $R^{B3}$ | $R^{D14}$ |
| $L_{A1052}$ | $R^{C55}$ | $R^{B3}$ | $R^{D14}$ |
| $L_{A1053}$ | $R^{C57}$ | $R^{B3}$ | $R^{D14}$ |
| $L_{A1054}$ | $R^{C11}$ | $R^{B4}$ | $R^{D14}$ |
| $L_{A1055}$ | $R^{C14}$ | $R^{B4}$ | $R^{D14}$ |
| $L_{A1056}$ | $R^{C18}$ | $R^{B4}$ | $R^{D14}$ |
| $L_{A1057}$ | $R^{C19}$ | $R^{B4}$ | $R^{D14}$ |
| $L_{A1058}$ | $R^{C23}$ | $R^{B4}$ | $R^{D14}$ |
| $L_{A1059}$ | $R^{C33}$ | $R^{B4}$ | $R^{D14}$ |
| $L_{A1060}$ | $R^{C38}$ | $R^{B4}$ | $R^{D14}$ |
| $L_{A1061}$ | $R^{C40}$ | $R^{B4}$ | $R^{D14}$ |
| $L_{A1062}$ | $R^{C41}$ | $R^{B4}$ | $R^{D14}$ |
| $L_{A1063}$ | $R^{C48}$ | $R^{B4}$ | $R^{D14}$ |
| $L_{A1064}$ | $R^{C54}$ | $R^{B4}$ | $R^{D14}$ |
| $L_{A1065}$ | $R^{C55}$ | $R^{B4}$ | $R^{D14}$ |
| $L_{A1066}$ | $R^{C57}$ | $R^{B4}$ | $R^{D14}$ |
| $L_{A1067}$ | $R^{C11}$ | $R^{B1}$ | $R^{D22}$ |
| $L_{A1068}$ | $R^{C14}$ | $R^{B1}$ | $R^{D22}$ |
| $L_{A1069}$ | $R^{C18}$ | $R^{B1}$ | $R^{D22}$ |
| $L_{A1070}$ | $R^{C19}$ | $R^{B1}$ | $R^{D22}$ |
| $L_{A1071}$ | $R^{C23}$ | $R^{B1}$ | $R^{D22}$ |
| $L_{A1072}$ | $R^{C33}$ | $R^{B1}$ | $R^{D22}$ |
| $L_{A1073}$ | $R^{C38}$ | $R^{B1}$ | $R^{D22}$ |
| $L_{A1074}$ | $R^{C40}$ | $R^{B1}$ | $R^{D22}$ |
| $L_{A1075}$ | $R^{C41}$ | $R^{B1}$ | $R^{D22}$ |
| $L_{A1076}$ | $R^{C48}$ | $R^{B1}$ | $R^{D22}$ |
| $L_{A1077}$ | $R^{C54}$ | $R^{B1}$ | $R^{D22}$ |
| $L_{A1078}$ | $R^{C55}$ | $R^{B1}$ | $R^{D22}$ |
| $L_{A1079}$ | $R^{C57}$ | $R^{B1}$ | $R^{D22}$ |
| $L_{A1080}$ | $R^{C11}$ | $R^{B3}$ | $R^{D22}$ |
| $L_{A1081}$ | $R^{C14}$ | $R^{B3}$ | $R^{D22}$ |
| $L_{A1082}$ | $R^{C18}$ | $R^{B3}$ | $R^{D22}$ |
| $L_{A1083}$ | $R^{C19}$ | $R^{B3}$ | $R^{D22}$ |
| $L_{A1084}$ | $R^{C23}$ | $R^{B3}$ | $R^{D22}$ |
| $L_{A1085}$ | $R^{C33}$ | $R^{B3}$ | $R^{D22}$ |
| $L_{A1086}$ | $R^{C38}$ | $R^{B3}$ | $R^{D22}$ |
| $L_{A1087}$ | $R^{C40}$ | $R^{B3}$ | $R^{D22}$ |
| $L_{A1088}$ | $R^{C41}$ | $R^{B3}$ | $R^{D22}$ |
| $L_{A1089}$ | $R^{C48}$ | $R^{B3}$ | $R^{D22}$ |
| $L_{A1090}$ | $R^{C54}$ | $R^{B3}$ | $R^{D22}$ |
| $L_{A1091}$ | $R^{C55}$ | $R^{B3}$ | $R^{D22}$ |
| $L_{A1092}$ | $R^{C57}$ | $R^{B3}$ | $R^{D22}$ |
| $L_{A1093}$ | $R^{C11}$ | $R^{B4}$ | $R^{D22}$ |
| $L_{A1094}$ | $R^{C14}$ | $R^{B4}$ | $R^{D22}$ |
| $L_{A1095}$ | $R^{C18}$ | $R^{B4}$ | $R^{D22}$ |
| $L_{A1096}$ | $R^{C19}$ | $R^{B4}$ | $R^{D22}$ |
| $L_{A1097}$ | $R^{C23}$ | $R^{B4}$ | $R^{D22}$ |
| $L_{A1098}$ | $R^{C33}$ | $R^{B4}$ | $R^{D22}$ |
| $L_{A1099}$ | $R^{C38}$ | $R^{B4}$ | $R^{D22}$ |
| $L_{A1100}$ | $R^{C40}$ | $R^{B4}$ | $R^{D22}$ |
| $L_{A1101}$ | $R^{C41}$ | $R^{B4}$ | $R^{D22}$ |
| $L_{A1102}$ | $R^{C48}$ | $R^{B4}$ | $R^{D22}$ |
| $L_{A1103}$ | $R^{C54}$ | $R^{B4}$ | $R^{D22}$ |
| $L_{A1104}$ | $R^{C55}$ | $R^{B4}$ | $R^{D22}$ |
| $L_{A1105}$ | $R^{C57}$ | $R^{B4}$ | $R^{D22}$ |
| $L_{A1106}$ | $R^{C11}$ | $R^{B1}$ | $R^{D28}$ |
| $L_{A1107}$ | $R^{C14}$ | $R^{B1}$ | $R^{D28}$ |
| $L_{A1108}$ | $R^{C18}$ | $R^{B1}$ | $R^{D28}$ |
| $L_{A1109}$ | $R^{C19}$ | $R^{B1}$ | $R^{D28}$ |
| $L_{A1110}$ | $R^{C23}$ | $R^{B1}$ | $R^{D28}$ |
| $L_{A1111}$ | $R^{C33}$ | $R^{B1}$ | $R^{D28}$ |
| $L_{A1112}$ | $R^{C38}$ | $R^{B1}$ | $R^{D28}$ |
| $L_{A1113}$ | $R^{C40}$ | $R^{B1}$ | $R^{D28}$ |
| $L_{A1114}$ | $R^{C41}$ | $R^{B1}$ | $R^{D28}$ |
| $L_{A1115}$ | $R^{C48}$ | $R^{B1}$ | $R^{D28}$ |
| $L_{A1116}$ | $R^{C54}$ | $R^{B1}$ | $R^{D28}$ |
| $L_{A1117}$ | $R^{C55}$ | $R^{B1}$ | $R^{D28}$ |
| $L_{A1118}$ | $R^{C57}$ | $R^{B1}$ | $R^{D28}$ |
| $L_{A1119}$ | $R^{C11}$ | $R^{B3}$ | $R^{D28}$ |
| $L_{A1120}$ | $R^{C14}$ | $R^{B3}$ | $R^{D28}$ |
| $L_{A1121}$ | $R^{C18}$ | $R^{B3}$ | $R^{D28}$ |
| $L_{A1122}$ | $R^{C19}$ | $R^{B3}$ | $R^{D28}$ |
| $L_{A1123}$ | $R^{C23}$ | $R^{B3}$ | $R^{D28}$ |
| $L_{A1124}$ | $R^{C33}$ | $R^{B3}$ | $R^{D28}$ |
| $L_{A1125}$ | $R^{C38}$ | $R^{B3}$ | $R^{D28}$ |
| $L_{A1126}$ | $R^{C40}$ | $R^{B3}$ | $R^{D28}$ |
| $L_{A1127}$ | $R^{C41}$ | $R^{B3}$ | $R^{D28}$ |

-continued

| Ligand | $R^3$ | $R^4$ | G |
|---|---|---|---|
| $L_{A1128}$ | $R^{C48}$ | $R^{B3}$ | $R^{D28}$ |
| $L_{A1129}$ | $R^{C54}$ | $R^{B3}$ | $R^{D28}$ |
| $L_{A1130}$ | $R^{C55}$ | $R^{B3}$ | $R^{D28}$ |
| $L_{A1131}$ | $R^{C57}$ | $R^{B3}$ | $R^{D28}$ |
| $L_{A1132}$ | $R^{C11}$ | $R^{B4}$ | $R^{D28}$ |
| $L_{A1133}$ | $R^{C14}$ | $R^{B4}$ | $R^{D28}$ |
| $L_{A1134}$ | $R^{C18}$ | $R^{B4}$ | $R^{D28}$ |
| $L_{A1135}$ | $R^{C19}$ | $R^{B4}$ | $R^{D28}$ |
| $L_{A1136}$ | $R^{C23}$ | $R^{B4}$ | $R^{D28}$ |
| $L_{A1137}$ | $R^{C33}$ | $R^{B4}$ | $R^{D28}$ |
| $L_{A1138}$ | $R^{C38}$ | $R^{B4}$ | $R^{D28}$ |
| $L_{A1139}$ | $R^{C40}$ | $R^{B4}$ | $R^{D28}$ |
| $L_{A1140}$ | $R^{C41}$ | $R^{B4}$ | $R^{D28}$ |
| $L_{A1141}$ | $R^{C48}$ | $R^{B4}$ | $R^{D28}$ |
| $L_{A1142}$ | $R^{C54}$ | $R^{B4}$ | $R^{D28}$ |
| $L_{A1143}$ | $R^{C55}$ | $R^{B4}$ | $R^{D28}$ |
| $L_{A1144}$ | $R^{C57}$ | $R^{B4}$ | $R^{D28}$, |

wherein $R^{A1}$ to $R^{A54}$ have the following structures:

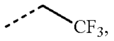
$R^{A1}$

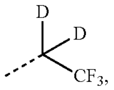
$R^{A2}$

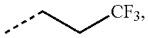
$R^{A3}$

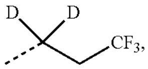
$R^{A4}$

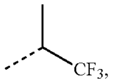
$R^{A5}$

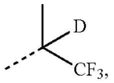
$R^{A6}$

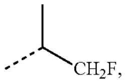
$R^{A7}$

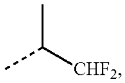
$R^{A8}$

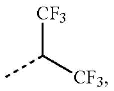
$R^{A9}$

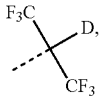
$R^{A10}$

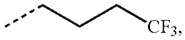
$R^{A11}$

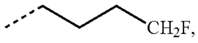
$R^{A12}$

-continued

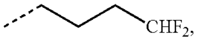
$R^{A13}$

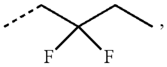
$R^{A14}$

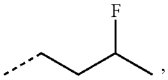
$R^{A15}$

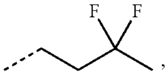
$R^{A16}$

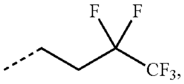
$R^{A17}$

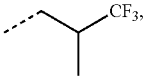
$R^{A18}$

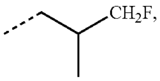
$R^{A19}$

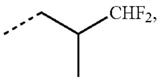
$R^{A20}$

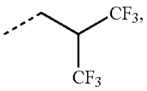
$R^{A21}$

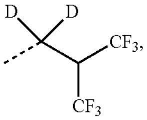
$R^{A22}$

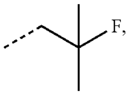
$R^{A23}$

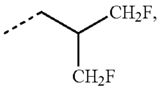
$R^{A24}$

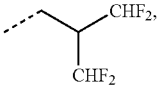
$R^{A25}$

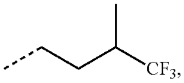
$R^{A26}$

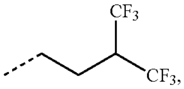
$R^{A27}$

-continued
$R^{A428}$
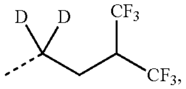
$R^{A429}$
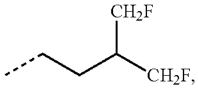
$R^{A430}$
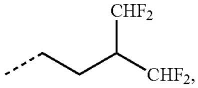
$R^{A431}$
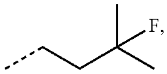
$R^{A432}$
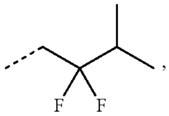
$R^{A433}$
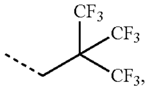
$R^{A434}$
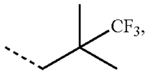
$R^{A435}$
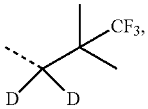
$R^{A436}$
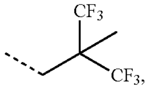
$R^{A437}$
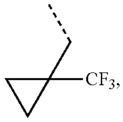
$R^{A438}$
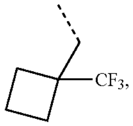
$R^{A439}$
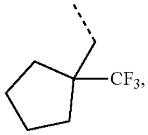
$R^{A440}$
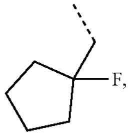
-continued
$R^{A441}$
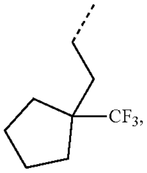
$R^{A442}$
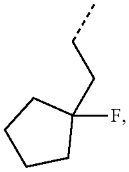
$R^{A443}$
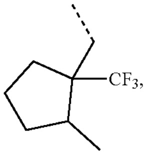
$R^{A444}$
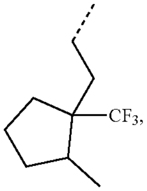
$R^{A445}$
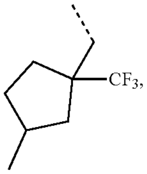
$R^{A446}$
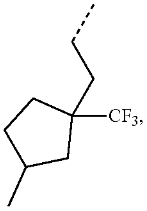
$R^{A447}$
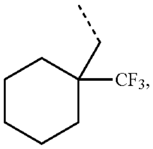
$R^{A448}$
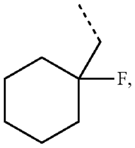

-continued
$R^{A49}$
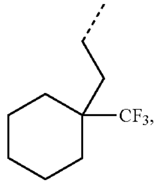
$R^{A50}$
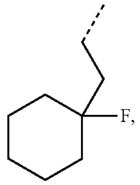
$R^{A51}$
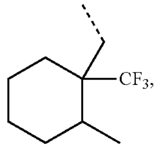
$R^{A52}$
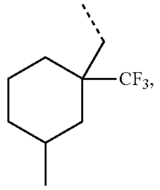
$R^{A53}$
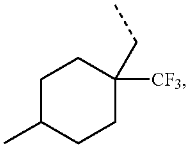
and
$R^{A54}$
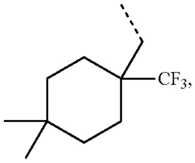
wherein $R^{B1}$ to $R^{B22}$ have the following structures:
$R^{B1}$
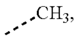
$R^{B2}$
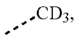
$R^{B3}$
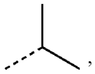
$R^{B4}$
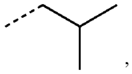
$R^{B5}$
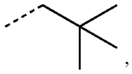
-continued
$R^{B6}$
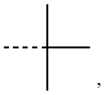
$R^{B7}$
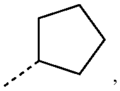
$R^{B8}$
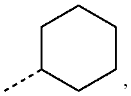
$R^{B9}$
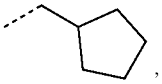
$R^{B10}$
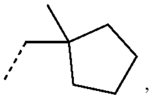
$R^{B11}$
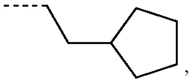
$R^{B12}$
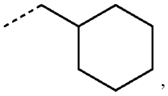
$R^{B13}$
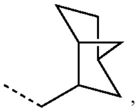
$R^{B14}$
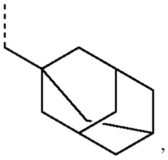
$R^{B15}$
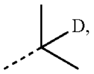
$R^{B16}$
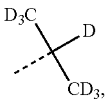
$R^{B17}$
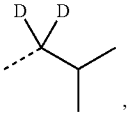
$R^{B18}$
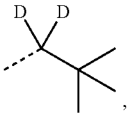

-continued
$R^{B19}$
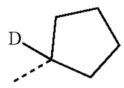
,
$R^{B20}$
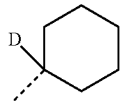
,
$R^{B21}$
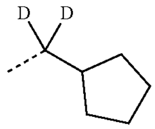
, and
$R^{B22}$
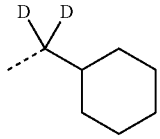
,
wherein $R^{C1}$ to $R^{C95}$ have the following structures:
$R^{C1}$
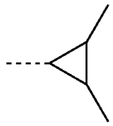
,
$R^{C2}$
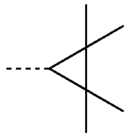
,
$R^{C3}$
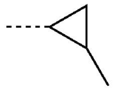
,
$R^{C4}$
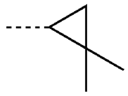
,
$R^{C5}$
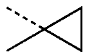
,
$R^{C6}$
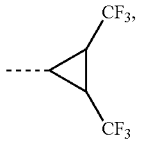
$R^{C7}$
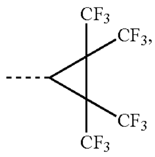
-continued
$R^{C8}$
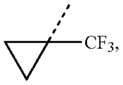
$R^{C9}$
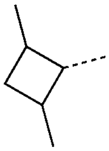
,
$R^{C10}$
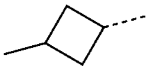
,
$R^{C11}$
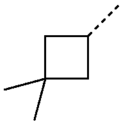
,
$R^{C12}$
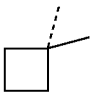
,
$R^{C13}$
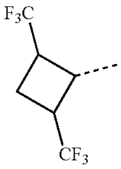
,
$R^{C14}$
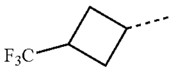
,
$R^{C15}$
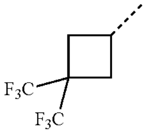
,
$R^{C16}$
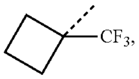
$R^{C17}$
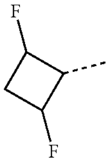
,
$R^{C18}$
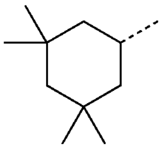
,
$R^{C19}$
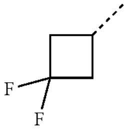
, -continued
$R^{C20}$
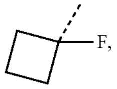
$R^{C21}$
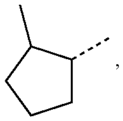
$R^{C22}$
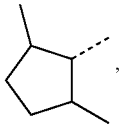
$R^{C23}$
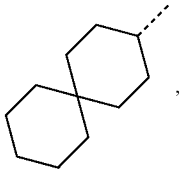
$R^{C24}$
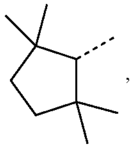
$R^{C25}$
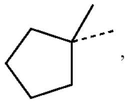
$R^{C26}$
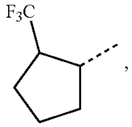
$R^{C27}$
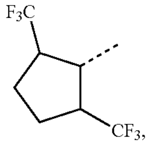
$R^{C28}$
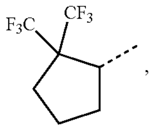
$R^{C29}$
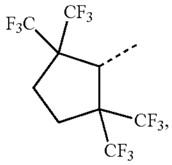
$R^{C30}$
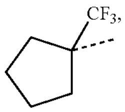
-continued
$R^{C31}$
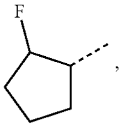
$R^{C32}$
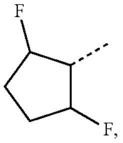
$R^{C33}$
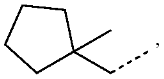
$R^{C34}$
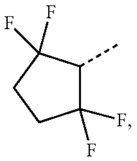
$R^{C35}$
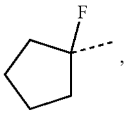
$R^{C36}$
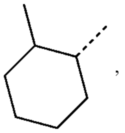
$R^{C37}$
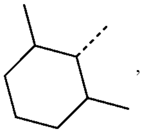
$R^{C38}$
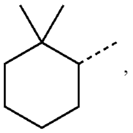
$R^{C39}$
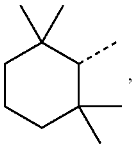
$R^{C40}$
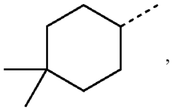
$R^{C41}$
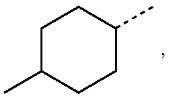

-continued
$R^{C42}$
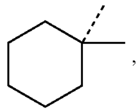
$R^{C43}$
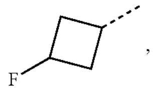
$R^{C44}$
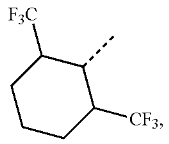
$R^{C45}$
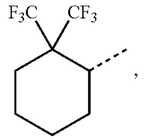
$R^{C46}$
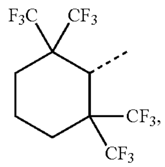
$R^{C47}$
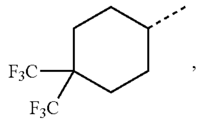
$R^{C48}$
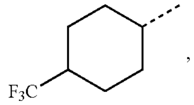
$R^{C49}$
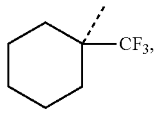
$R^{C50}$
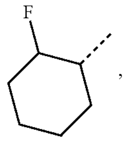
$R^{C51}$
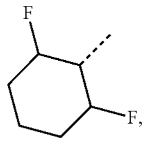
$R^{C52}$
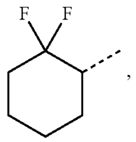
-continued
$R^{C53}$
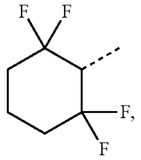
$R^{C54}$
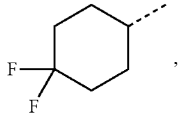
$R^{C55}$
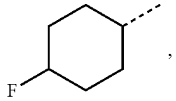
$R^{C56}$
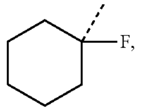
$R^{C57}$
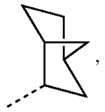
$R^{C58}$
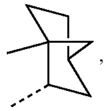
$R^{C59}$
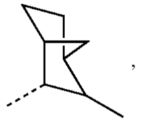
$R^{C60}$
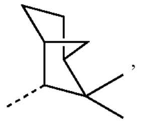
$R^{C61}$
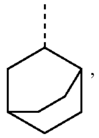
$R^{C62}$
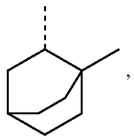
$R^{C63}$
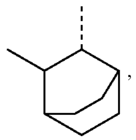

-continued
$R^{C64}$
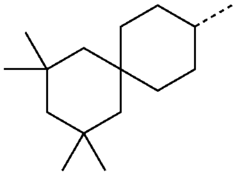
,
$R^{C65}$
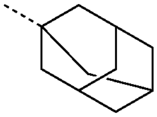
,
$R^{C66}$
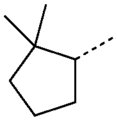
,
$R^{C67}$
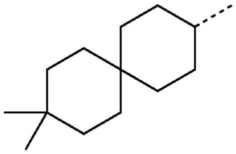
,
$R^{C68}$
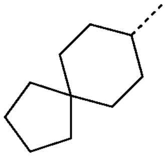
,
$R^{C69}$
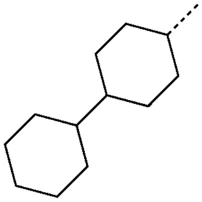
,
$R^{C70}$
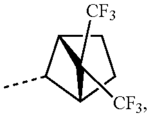
$R^{C71}$
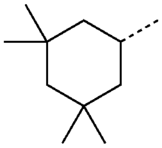
,
$R^{C72}$
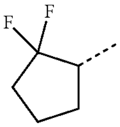
,
$R^{C73}$
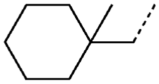
-continued
$R^{C74}$
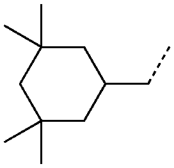
,
$R^{C75}$
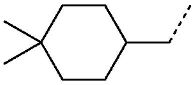
,
$R^{C76}$
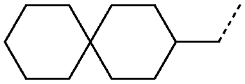
,
$R^{C77}$
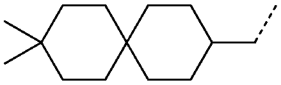
,
$R^{C78}$
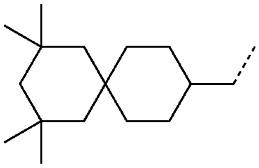
,
$R^{C79}$
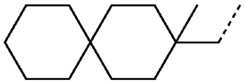
,
$R^{C80}$
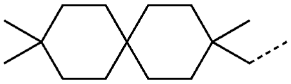
,
$R^{C81}$
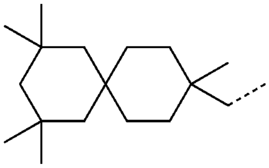
,
$R^{C82}$
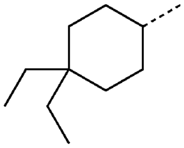
,
$R^{C83}$
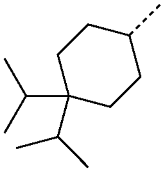
,
$R^{C84}$
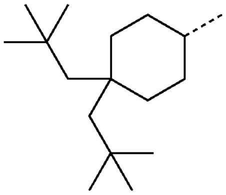
, -continued
$R^{C85}$
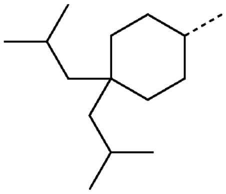
,
$R^{C86}$
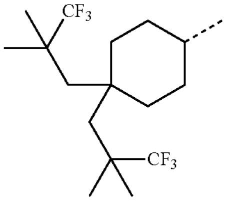
,
$R^{C87}$
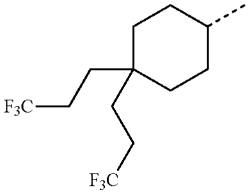
,
$R^{C88}$
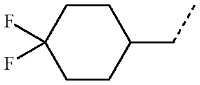
,
$R^{C89}$
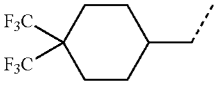
,
$R^{C90}$
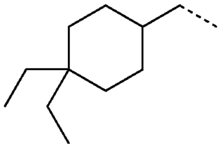
,
$R^{C91}$
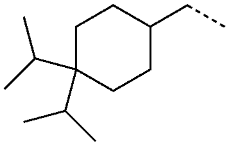
,
$R^{C92}$
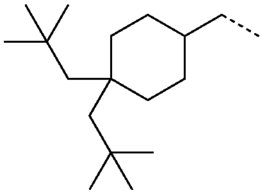
,
$R^{C93}$
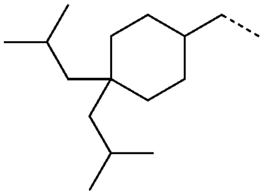
,
-continued
$R^{C94}$
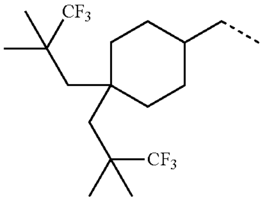
,
$R^{C95}$
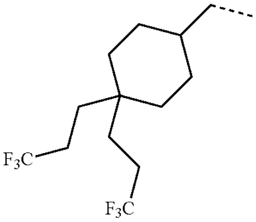
,
wherein $R^{D1}$ to $R^{D37}$ have the following structures:
$R^{D1}$
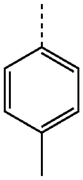
,
$R^{D2}$
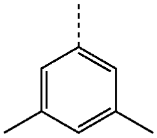
,
$R^{D3}$
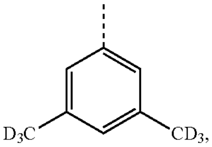
$R^{D4}$
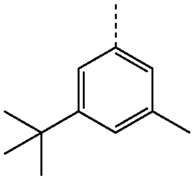
,
$R^{D5}$
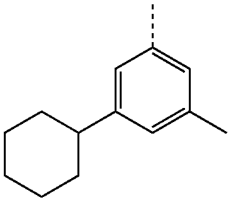
, -continued
$R^{D6}$
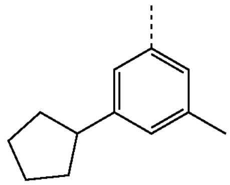
,
$R^{D7}$
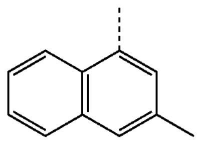
,
$R^{D8}$
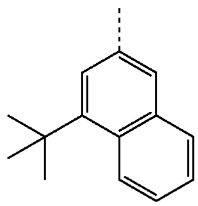
,
$R^{D9}$
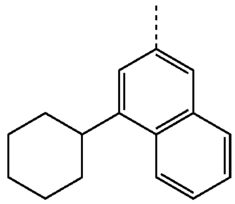
,
$R^{D10}$
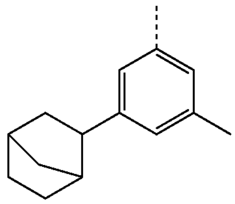
,
$R^{D11}$
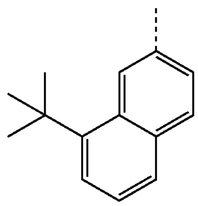
,
$R^{D12}$
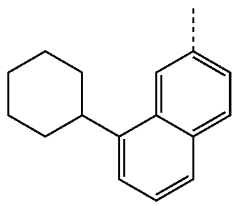
,
-continued
$R^{D13}$
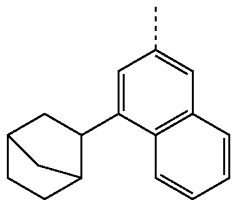
,
$R^{D14}$
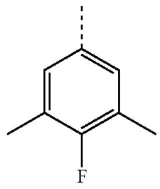
,
$R^{D15}$
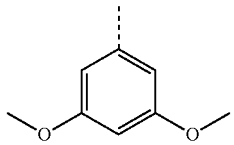
,
$R^{D16}$
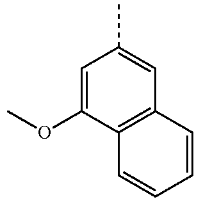
,
$R^{D17}$
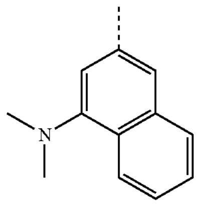
,
$R^{D18}$
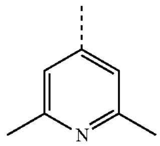
,
$R^{D19}$
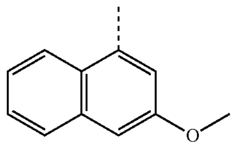
,
$R^{D20}$
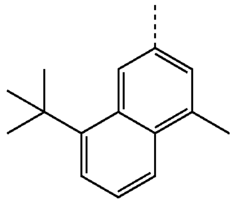
, -continued
$R^{D21}$
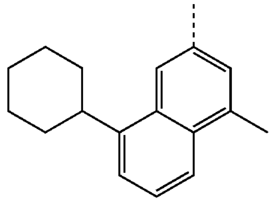
,
$R^{D22}$
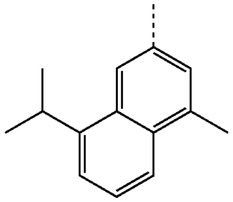
,
$R^{D23}$
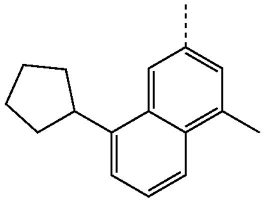
,
$R^{D24}$
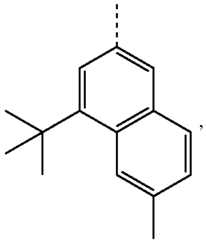
,
$R^{D25}$
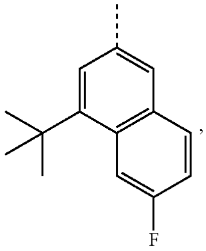
,
$R^{D26}$
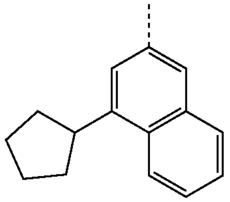
,
$R^{D27}$
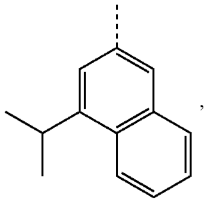
,
-continued
$R^{D28}$
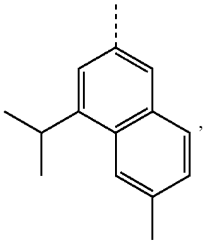
,
$R^{D29}$
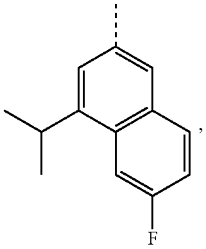
,
$R^{D30}$
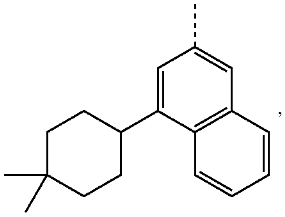
,
$R^{D31}$
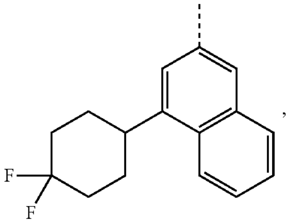
,
$R^{D32}$
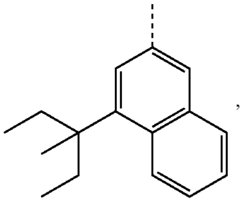
,
$R^{D33}$
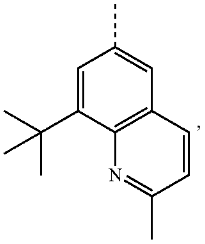
, -continued $R^{D34}$

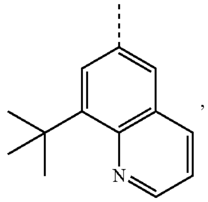
, $R^{D35}$

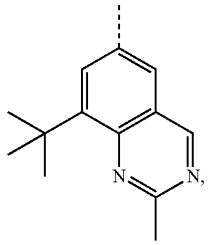

$R^{D36}$

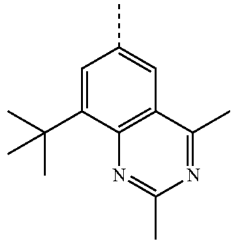
, and $R^{D37}$

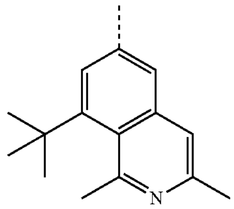
.

In some embodiments, the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$, where $L_B$ and $L_C$ are each a bidentate ligand, and $L_A$, $L_B$, and $L_C$ are different from each other. In some embodiments, $L_B$ and $L_C$ are each independently selected from Group A ligands consisting of:

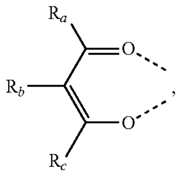

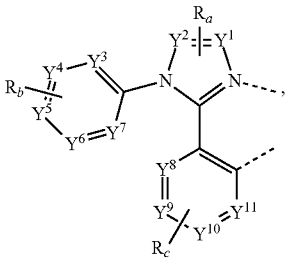

-continued

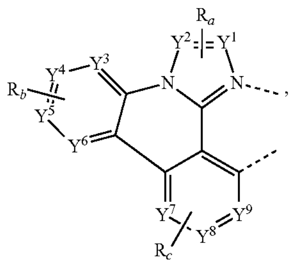

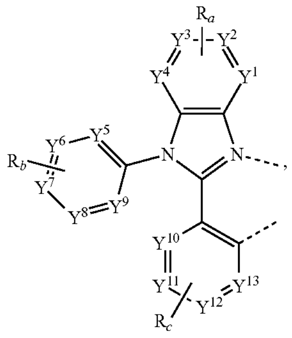

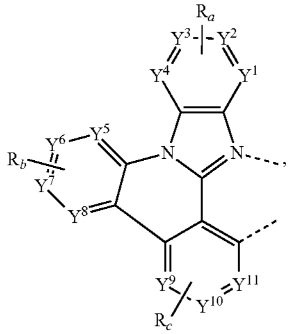

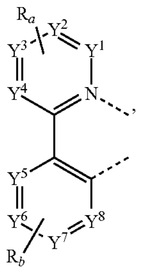

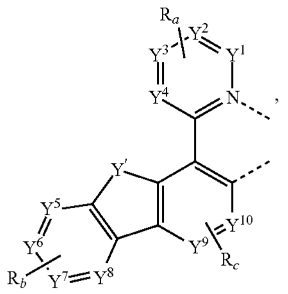

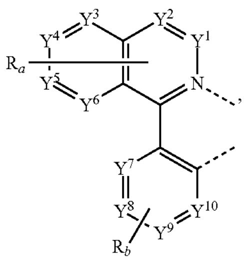

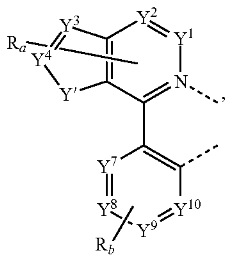

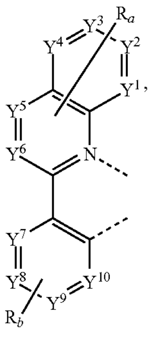

-continued

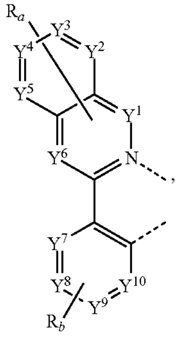

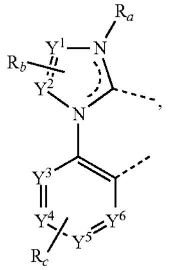

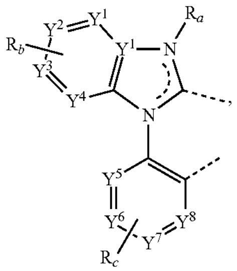

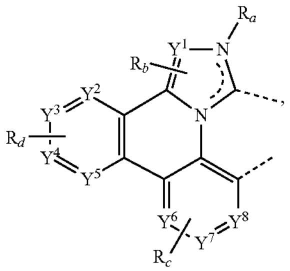

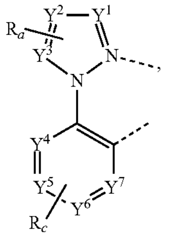

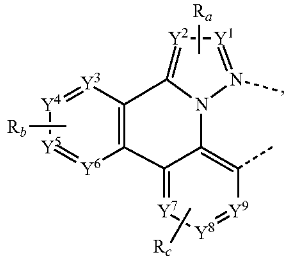

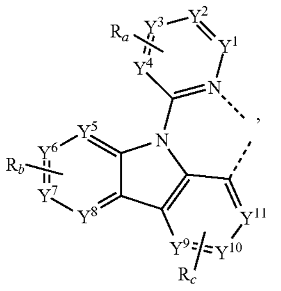

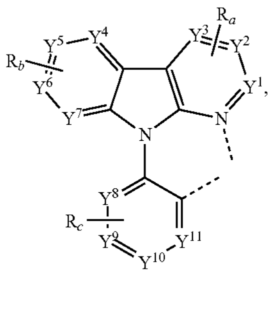

and

-continued

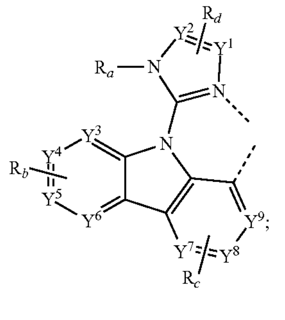

where $Y^1$ to $Y^{13}$ are each independently selected from the group consisting of carbon and nitrogen; Y' is selected from the group consisting of $BR_e$, $NR_e$, $PR_e$, O, S, Se, C═O, S═O, $SO_2$, $CR_eR_f$, $SiR_eR_f$, and $GeR_eR_f$; $R_e$ and $R_f$ are optionally fused or joined to form a ring; each $R_a$, $R_b$, $R_c$, and $R_d$ can independently represent from mono substitution to the maximum possible number of substitutions, or no substitution; $R_a$, $R_b$, R, $R_d$, $R_e$ and $R_f$ are each independently selected from the group consisting of hydrogen, or a substituent selected from the group consisting of the general substituents defined above; and any two adjacent substituents of $R_a$, $R_b$, $R_c$, and $R_d$ are optionally fused or joined to form a ring or form a multidentate ligand.

In some embodiments of the compound, where $L_B$ and $L_C$ are each independently selected from the Group A ligands, $L_B$ and $L_C$ can each be independently selected from the group consisting of:

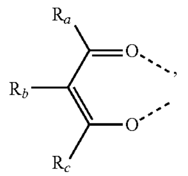

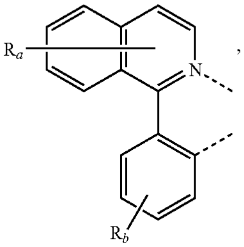

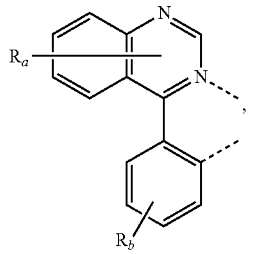

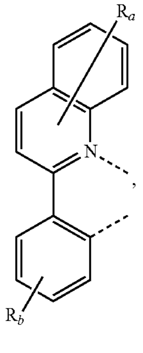

-continued
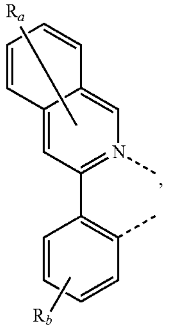
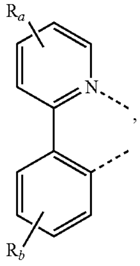
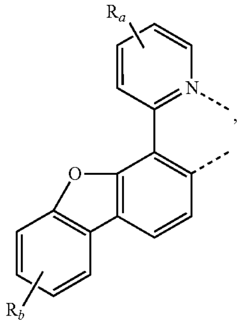
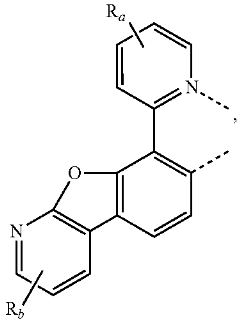
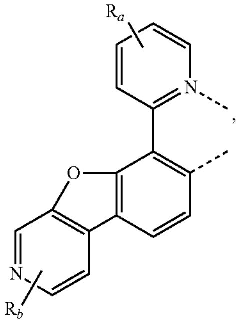
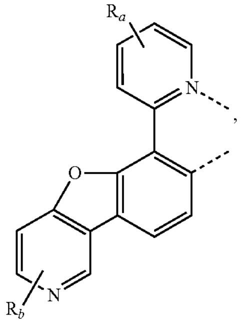
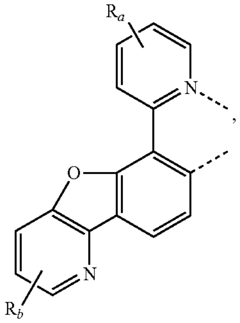
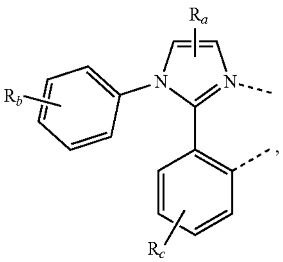
-continued
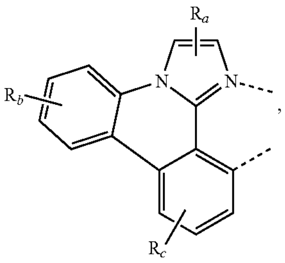
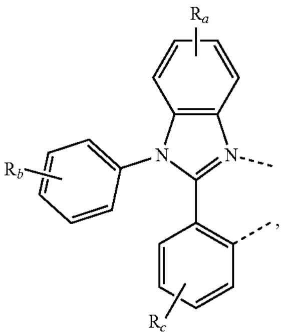
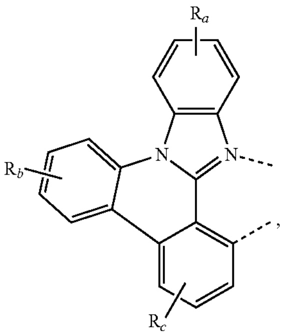
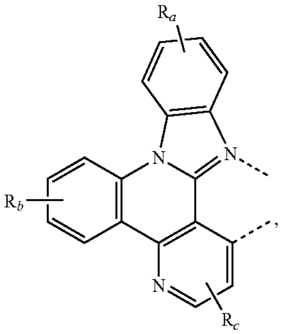
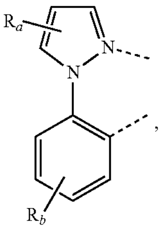
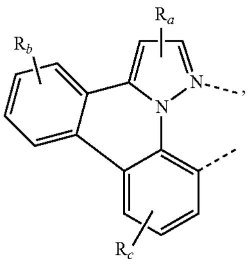
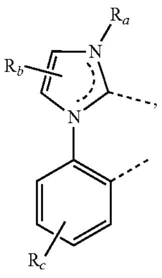

-continued
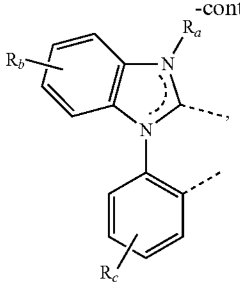
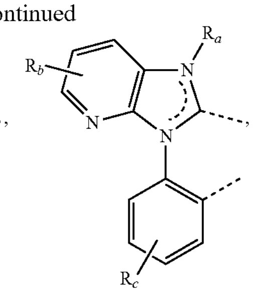
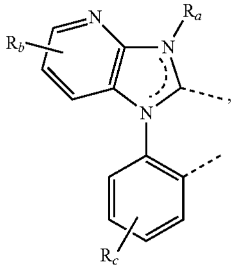
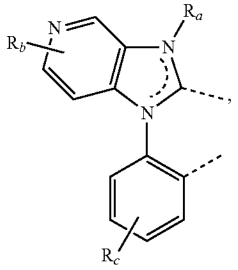
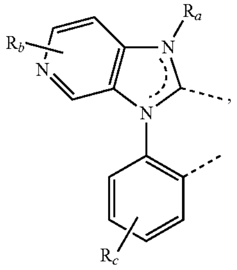
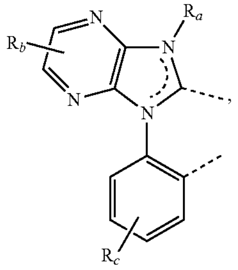
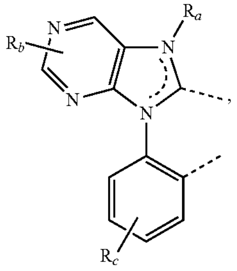
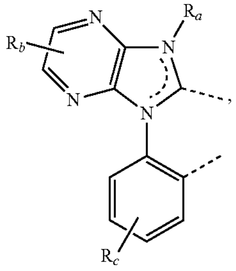
and
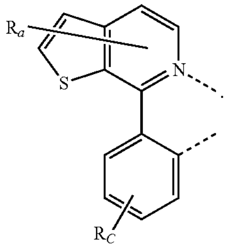
In some embodiments where the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$, where $L_B$ and $L_C$ are each a bidentate ligand, and $L_A$, $L_B$, and $L_C$ are different from each other, $L_B$ can be selected from the group consisting of the following structures:
$L_{B1}$
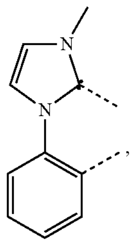
$L_{B2}$
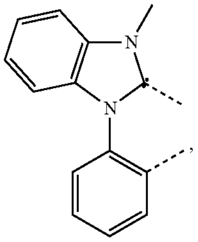
$L_{B3}$
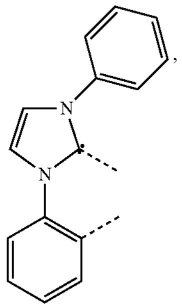
$L_{B4}$
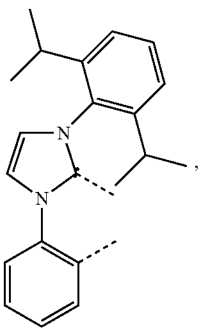
$L_{B5}$
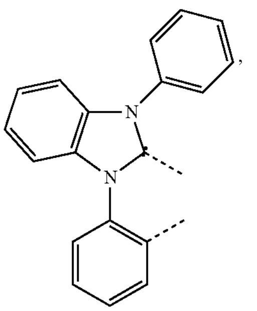

-continued
$L_{B6}$
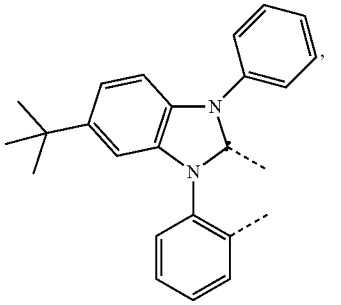
$L_{B7}$
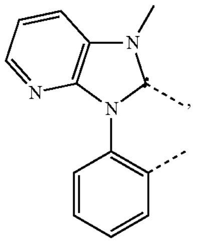
$L_{B8}$
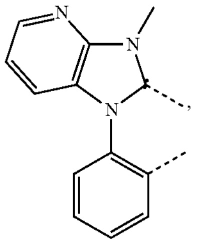
$L_{B9}$
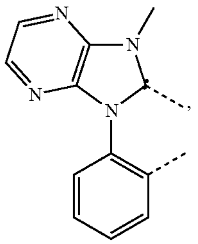
$L_{B10}$
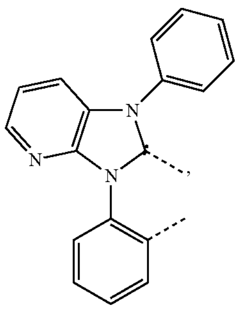
-continued
$L_{B11}$
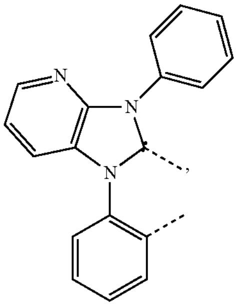
$L_{B12}$
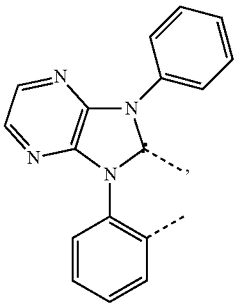
$L_{B13}$
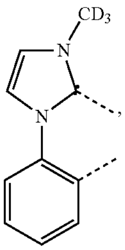
$L_{B14}$
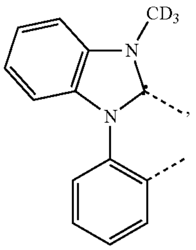
$L_{B15}$
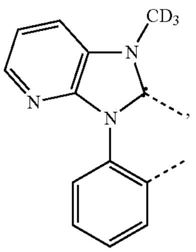

-continued
$L_{B16}$
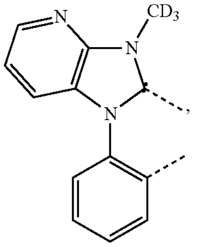
$L_{B17}$
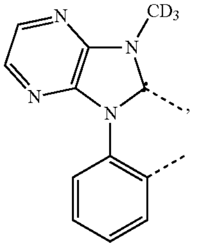
$L_{B18}$
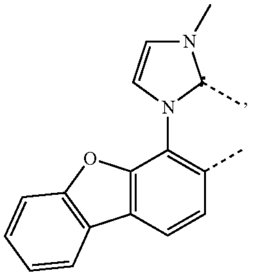
$L_{B19}$
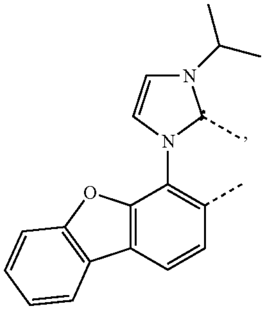
$L_{B20}$
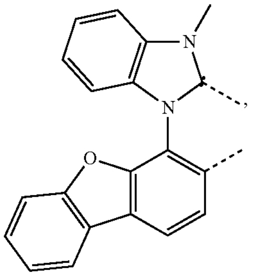
-continued
$L_{B21}$
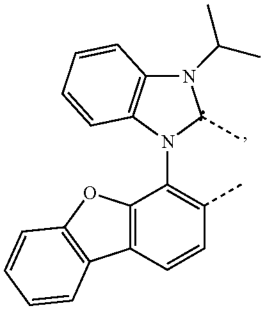
$L_{B22}$
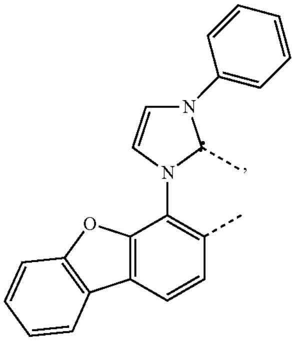
$L_{B23}$
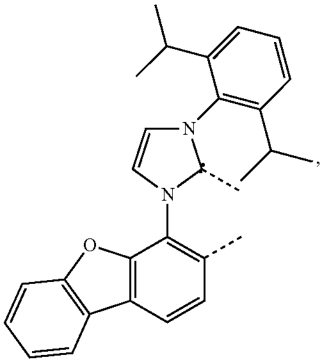
$L_{B24}$
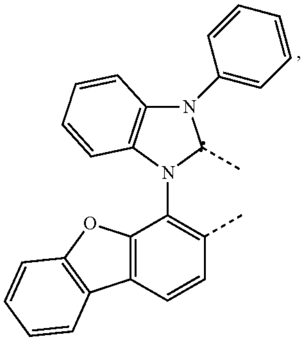

-continued
$L_{B25}$
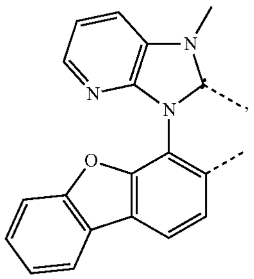
$L_{B26}$
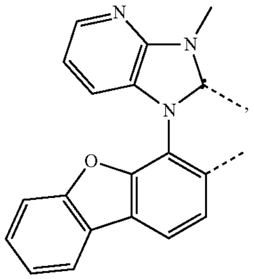
$L_{B27}$
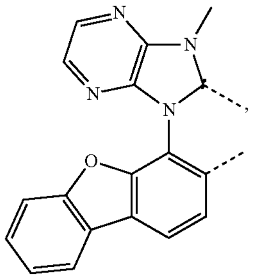
$L_{B28}$
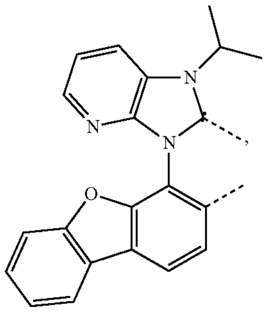
$L_{B29}$
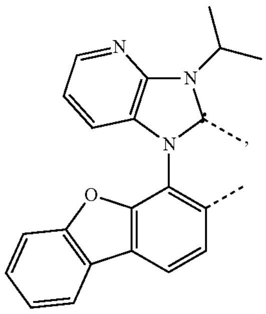
-continued
$L_{B30}$
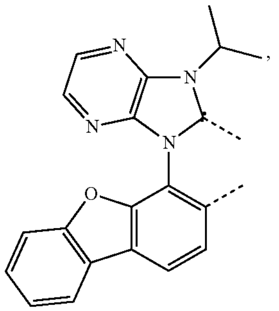
$L_{B31}$
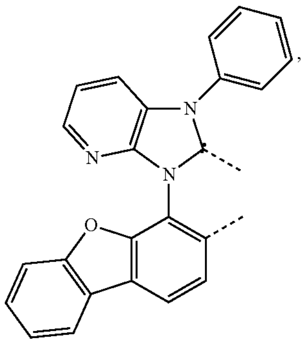
$L_{B32}$
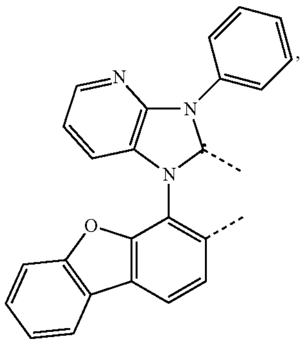
$L_{B33}$
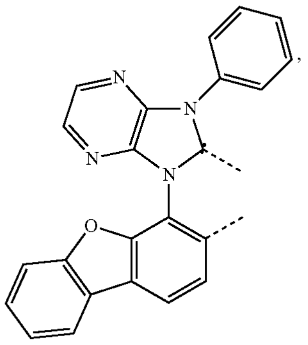

-continued
$L_{B34}$
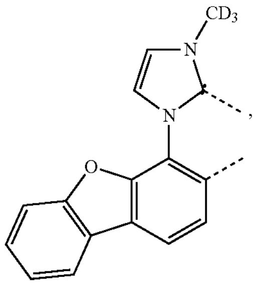
$L_{B35}$
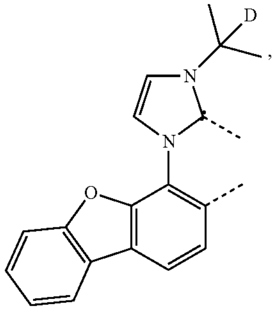
$L_{B36}$
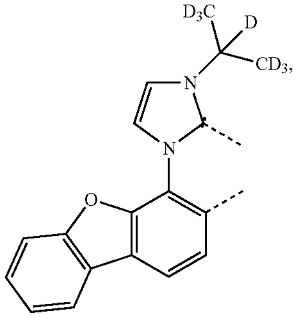
$L_{B37}$
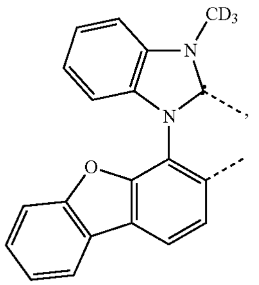
$L_{B38}$
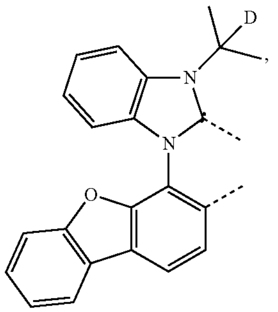
-continued
$L_{B39}$
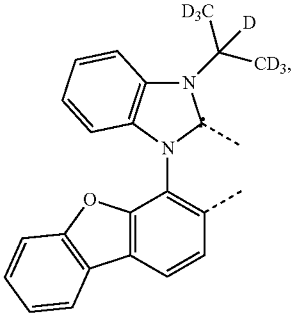
$L_{B40}$
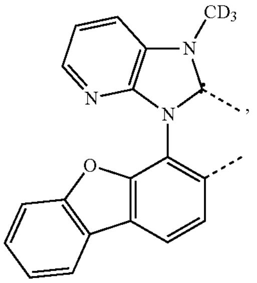
$L_{B41}$
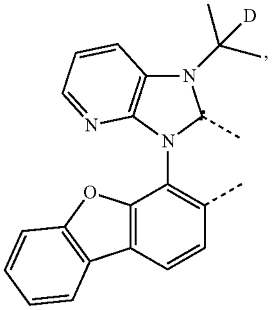
$L_{B42}$
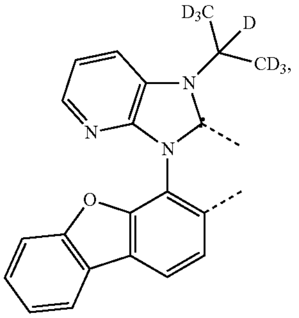
$L_{B43}$
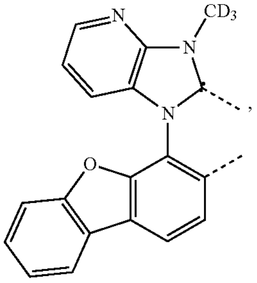

-continued
$L_{B44}$
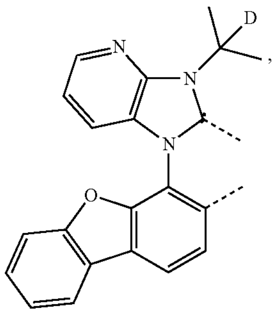
$L_{B45}$
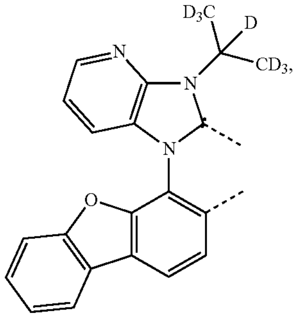
$L_{B46}$
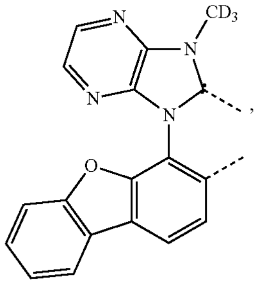
$L_{B47}$
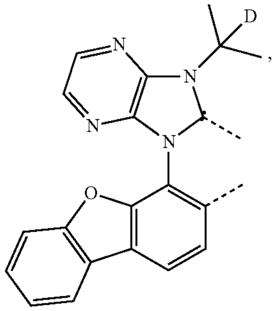
$L_{B48}$
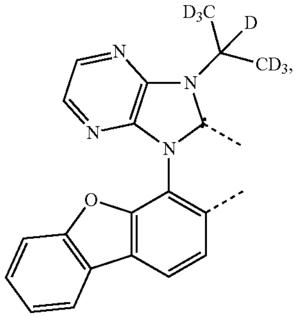
-continued
$L_{B49}$
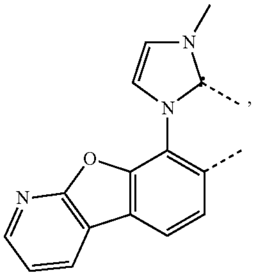
$L_{B50}$
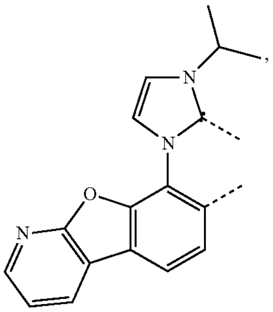
$L_{B51}$
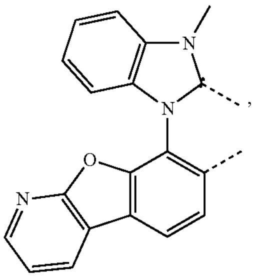
$L_{B52}$
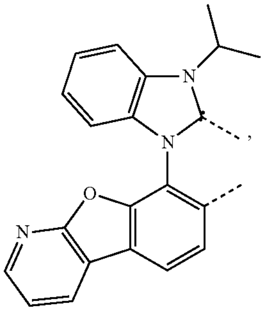
$L_{B53}$
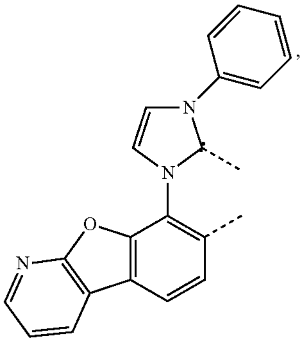

-continued
$L_{B54}$
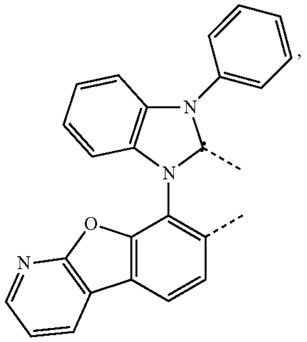
$L_{B55}$
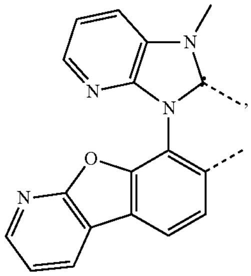
$L_{B56}$
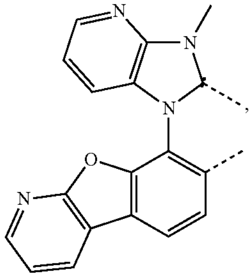
$L_{B57}$
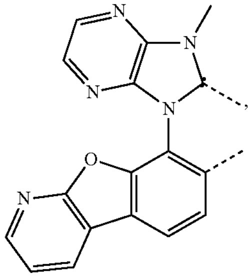
$L_{B58}$
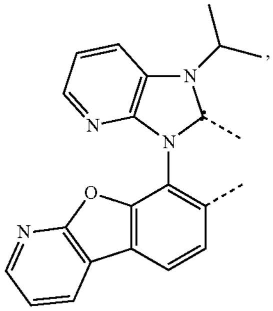
-continued
$L_{B59}$
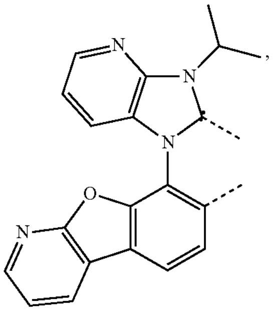
$L_{B60}$
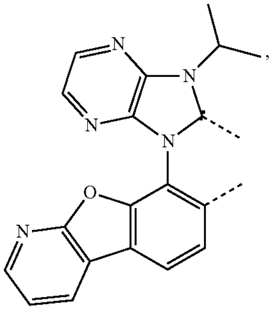
$L_{B61}$
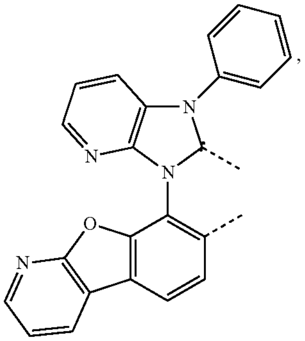
$L_{B62}$
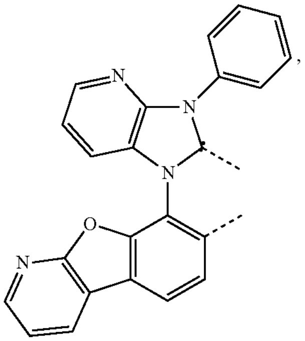

-continued
$L_{B63}$
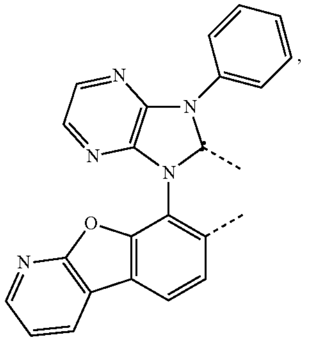
$L_{B64}$
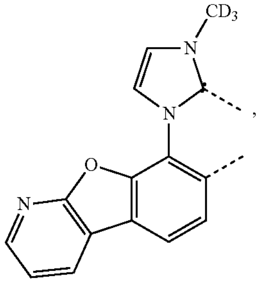
$L_{B65}$
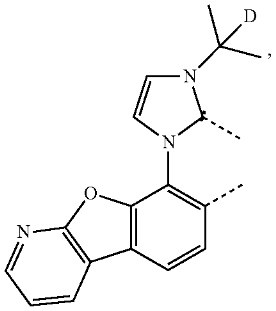
$L_{B66}$
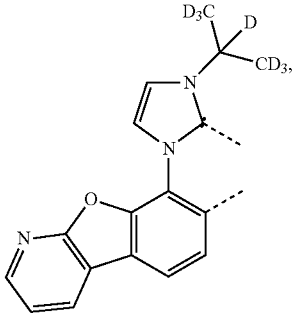
$L_{B67}$
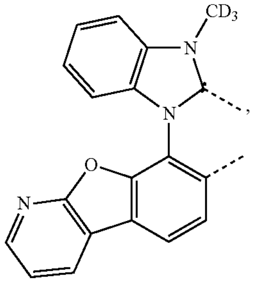
-continued
$L_{B68}$
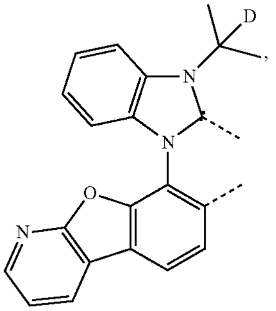
$L_{B69}$
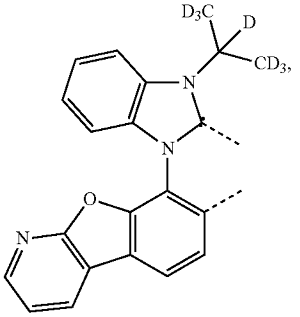
$L_{B70}$
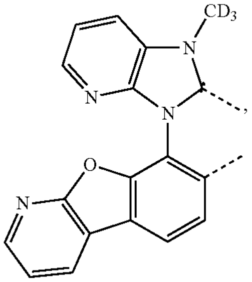
$L_{B71}$
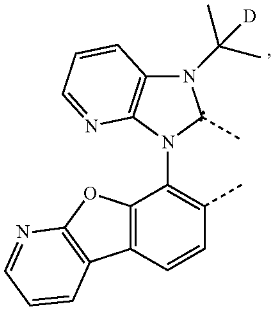
$L_{B72}$
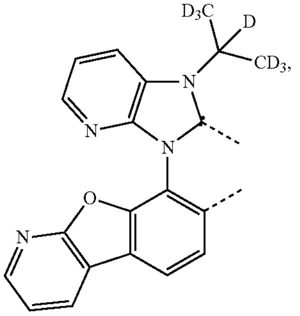

-continued
$L_{B73}$
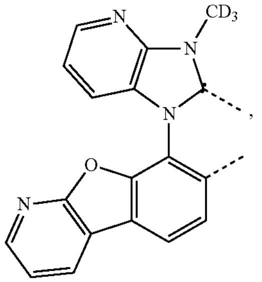
$L_{B74}$
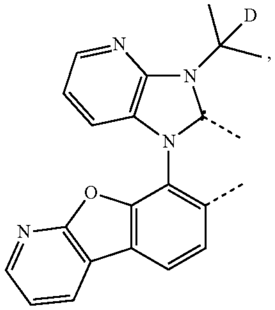
$L_{B75}$
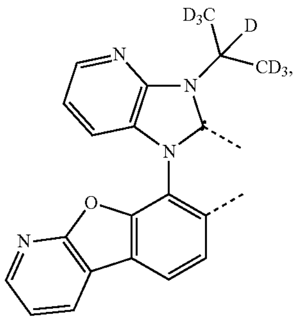
$L_{B76}$
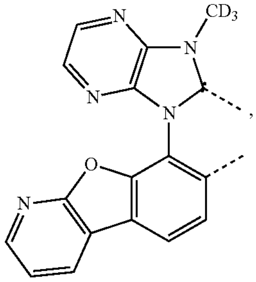
$L_{B77}$
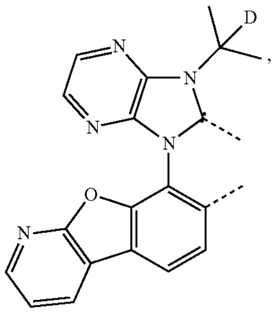
-continued
$L_{B78}$
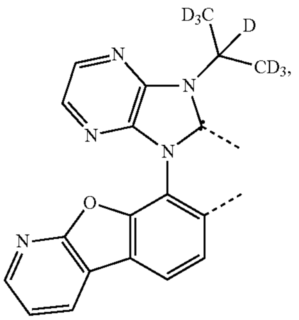
$L_{B79}$
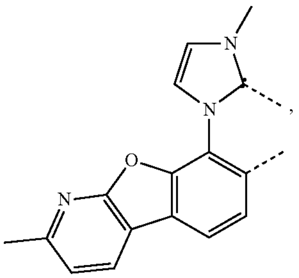
$L_{B80}$
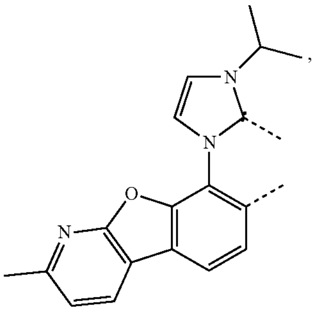
$L_{B81}$
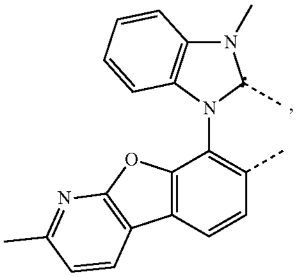
$L_{B82}$
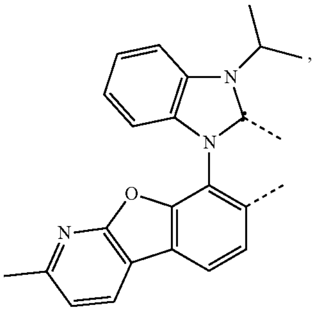

-continued
$L_{B83}$
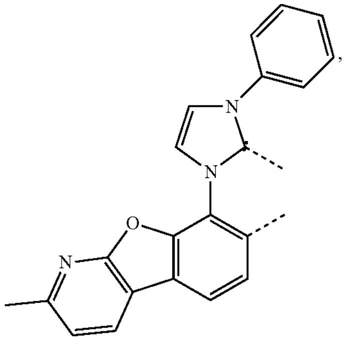
$L_{B84}$
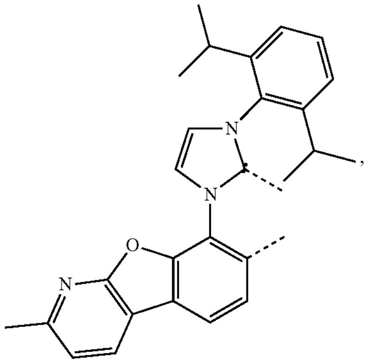
$L_{B85}$
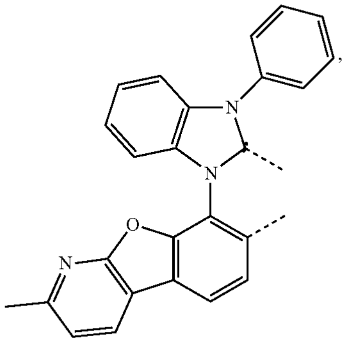
$L_{B86}$
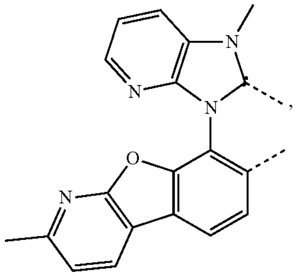
$L_{B87}$
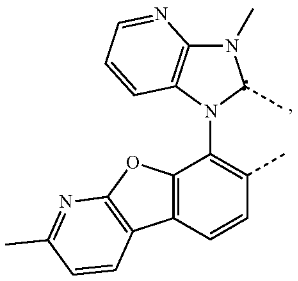
-continued
$L_{B88}$
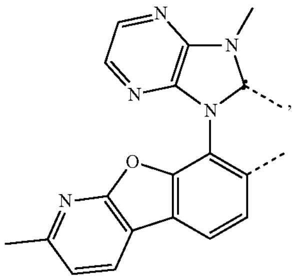
$L_{B89}$
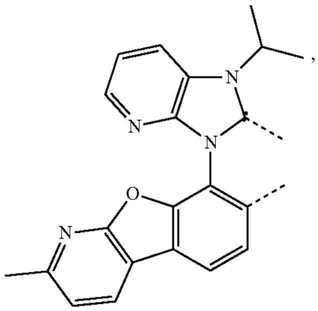
$L_{B90}$
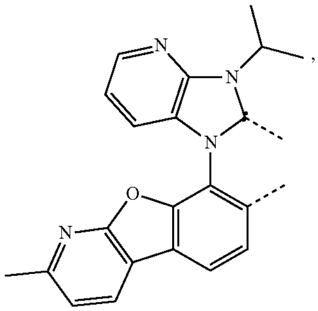
$L_{B91}$
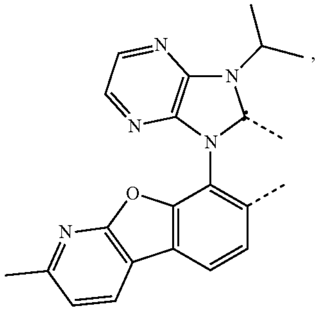
$L_{B92}$
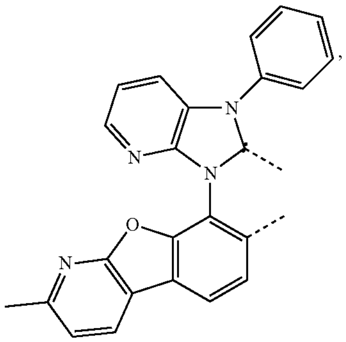

-continued
$L_{B93}$
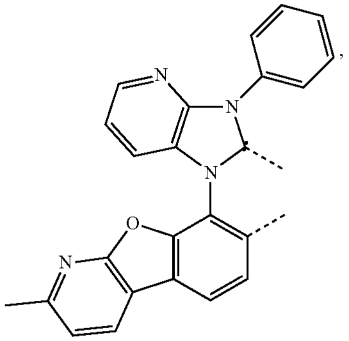
$L_{B94}$
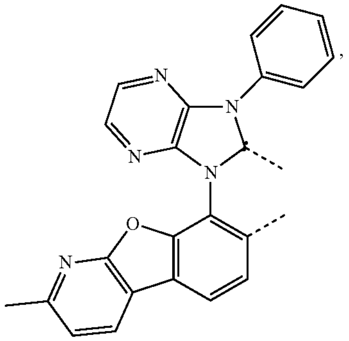
$L_{B95}$
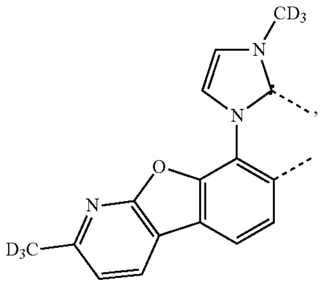
$L_{B96}$
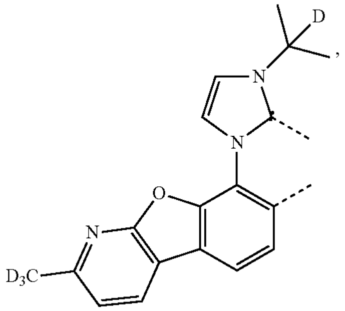
$L_{B97}$
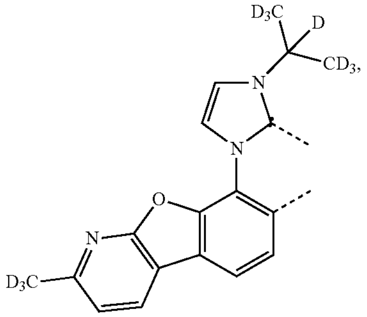
-continued
$L_{B98}$
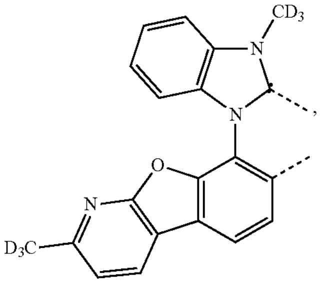
$L_{B99}$
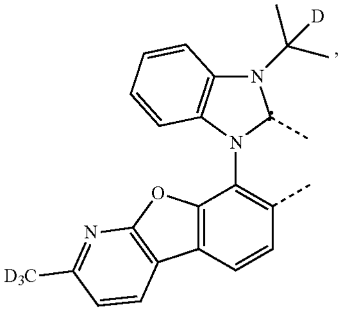
$L_{B100}$
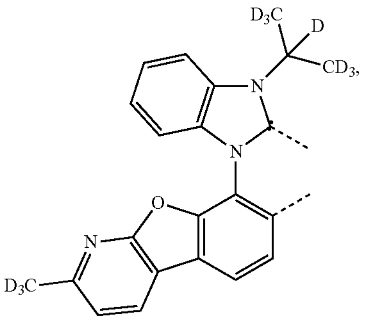
$L_{B101}$
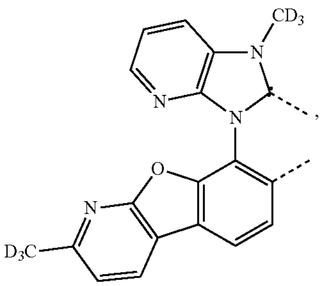
$L_{B102}$
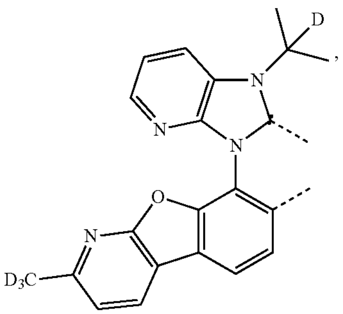

-continued
L$_{B103}$
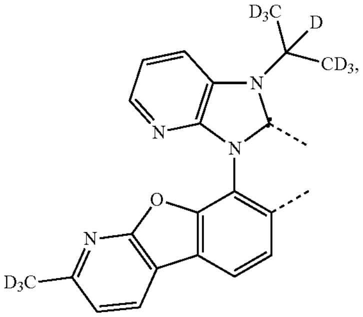
L$_{B104}$
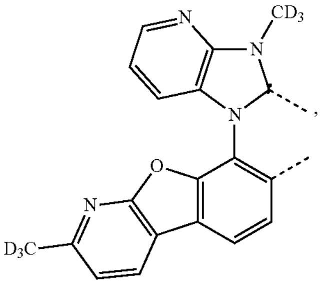
L$_{B105}$
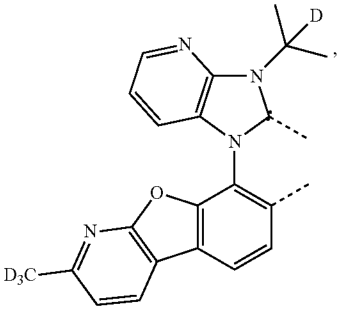
L$_{B106}$
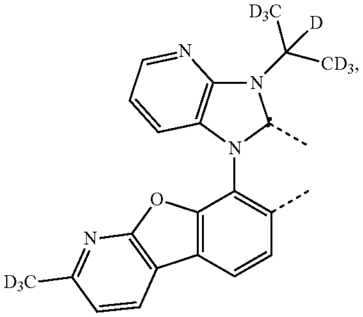
L$_{B107}$
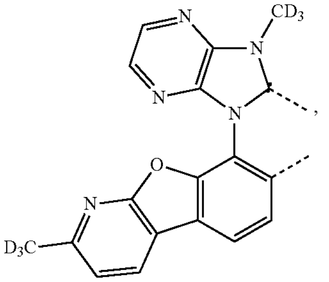
-continued
L$_{B108}$
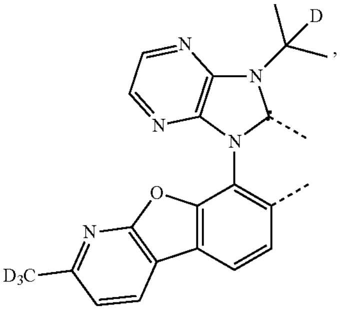
L$_{B109}$
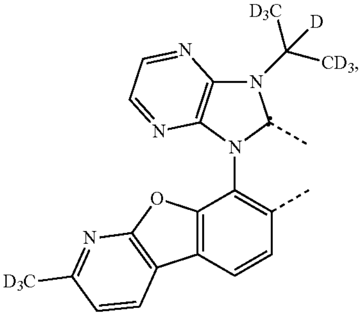
L$_{B110}$
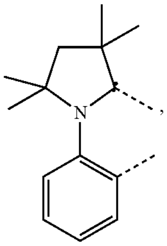
L$_{B111}$
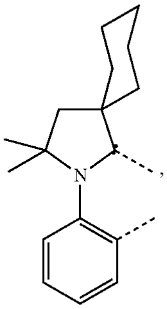
L$_{B112}$
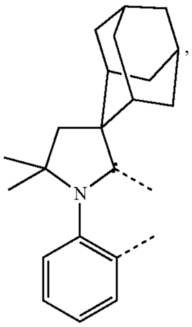

-continued
$L_{B113}$
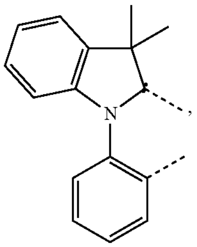
$L_{B114}$
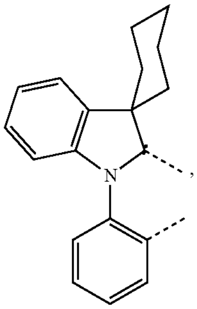
$L_{B115}$
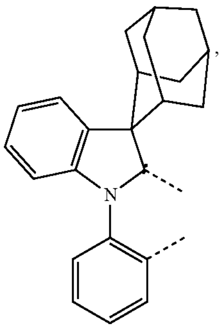
$L_{B116}$
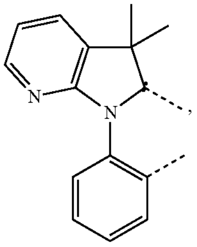
$L_{B117}$
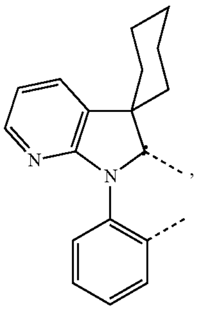
-continued
$L_{B118}$
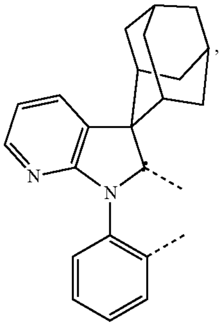
$L_{B119}$
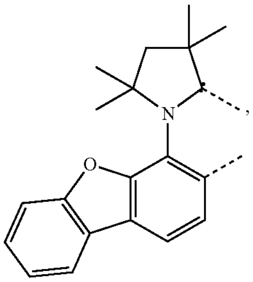
$L_{B120}$
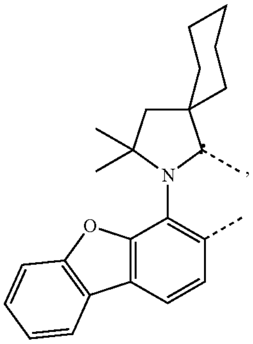
$L_{B121}$
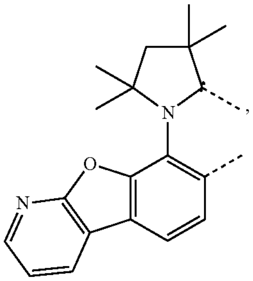
$L_{B122}$
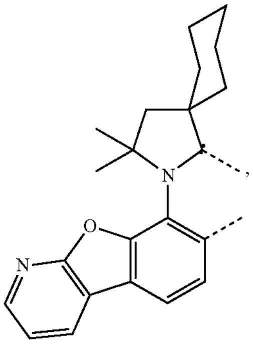

-continued
$L_{B123}$
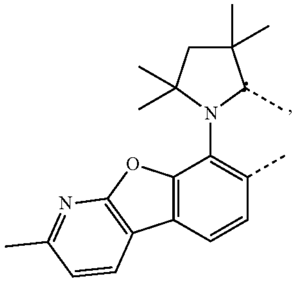
$L_{B124}$
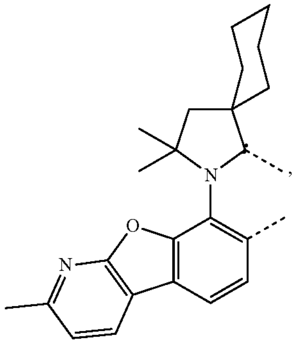
$L_{B125}$
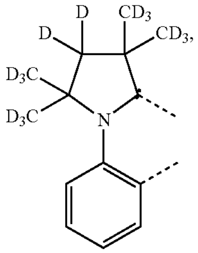
$L_{B126}$
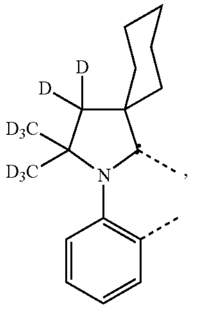
$L_{B127}$
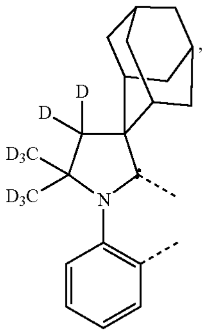
-continued
$L_{B128}$
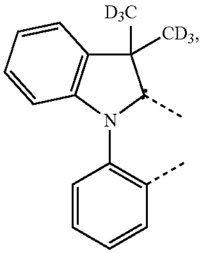
$L_{B129}$
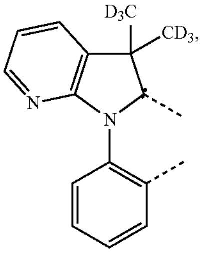
$L_{B130}$
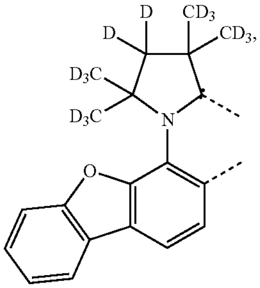
$L_{B131}$
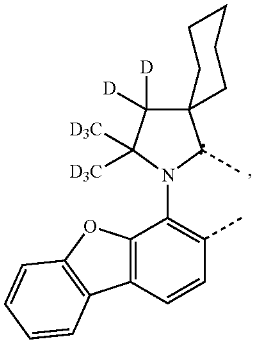
$L_{B132}$
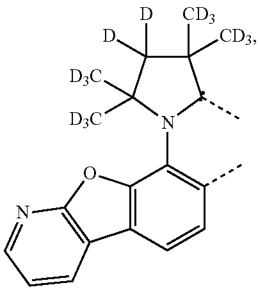

-continued
$L_{B133}$
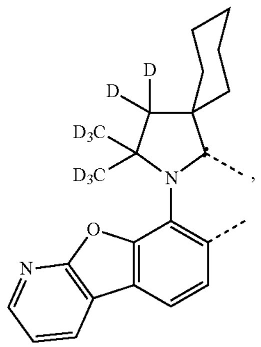
$L_{B134}$
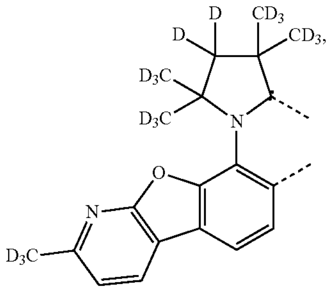
$L_{B135}$
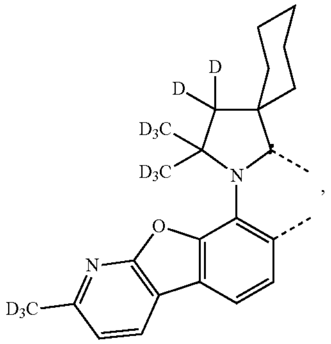
$L_{B136}$
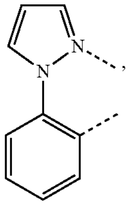
$L_{B137}$
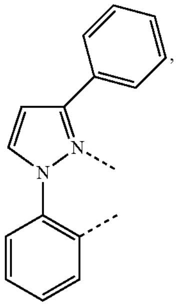
-continued
$L_{B138}$
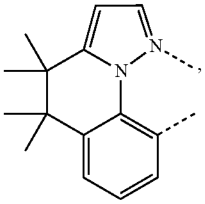
$L_{B139}$
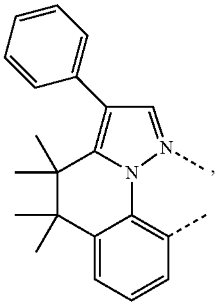
$L_{B140}$
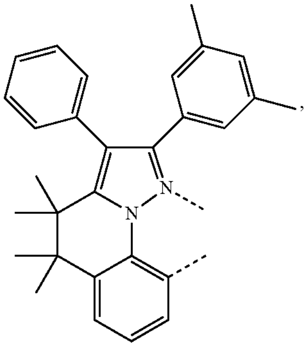
$L_{B141}$
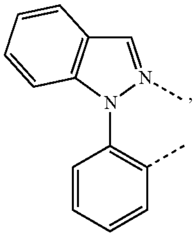
$L_{B142}$
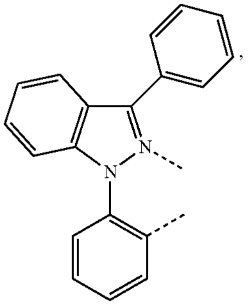

$L_{B143}$
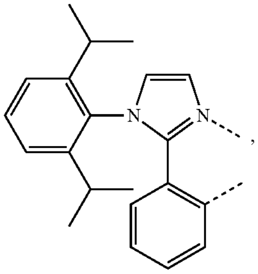
$L_{B144}$
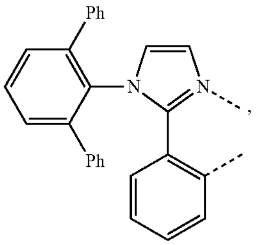
$L_{B145}$
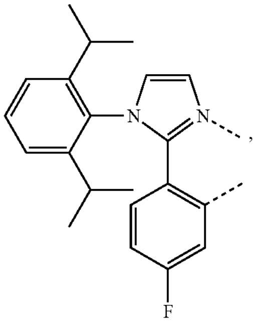
$L_{B146}$
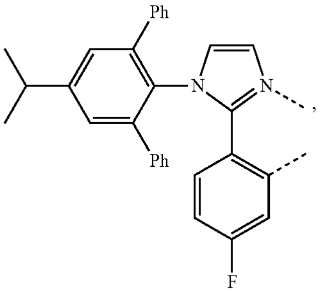
$L_{B147}$
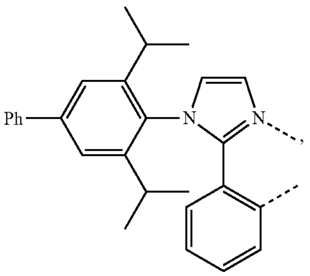
$L_{B148}$
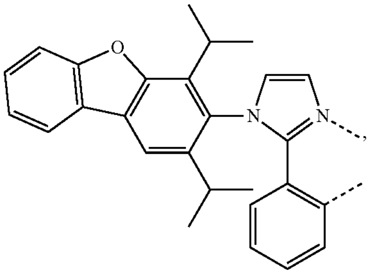
$L_{B149}$
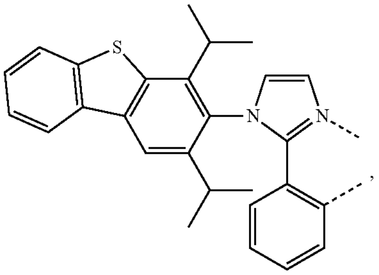
$L_{B150}$
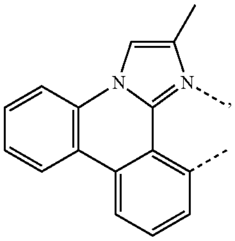
$L_{B151}$
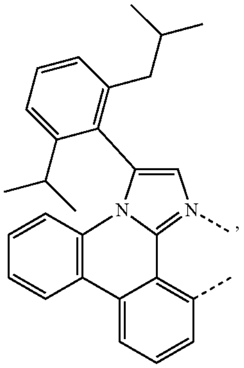
$L_{B152}$
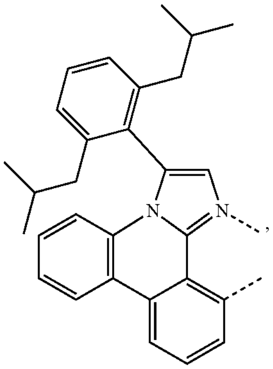

-continued
$L_{B153}$
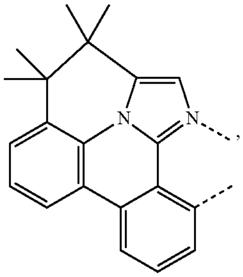
$L_{B154}$
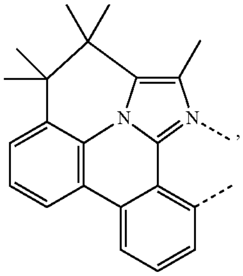
$L_{B155}$
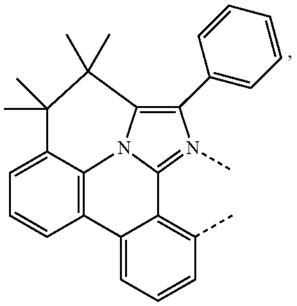
$L_{B156}$
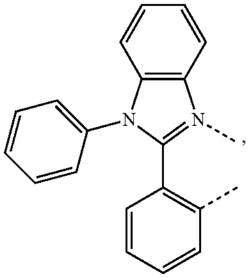
$L_{B157}$
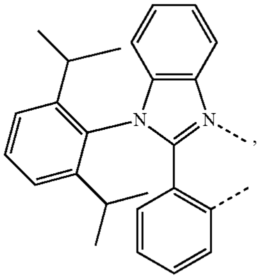
-continued
$L_{B158}$
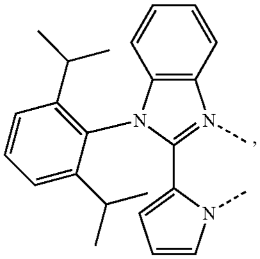
$L_{B159}$
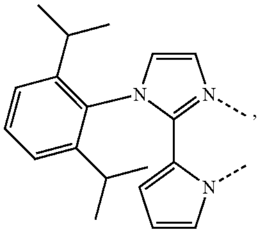
$L_{B160}$
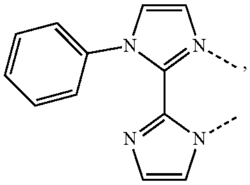
$L_{B161}$
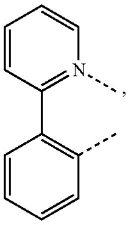
$L_{B162}$
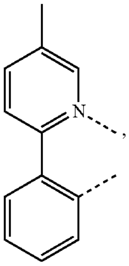
$L_{B163}$
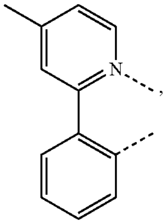

-continued
$L_{B164}$
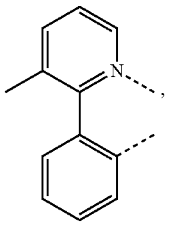
$L_{B165}$
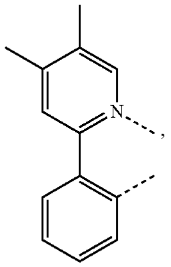
$L_{B166}$
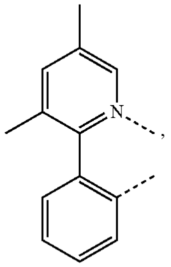
$L_{B167}$
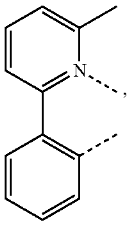
$L_{B168}$
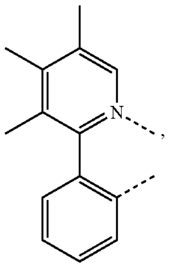
$L_{B169}$
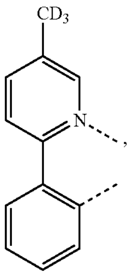
-continued
$L_{B170}$
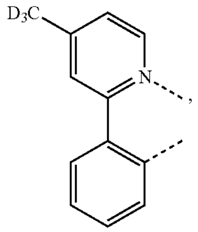
$L_{B171}$
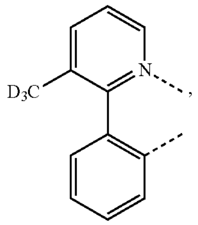
$L_{B172}$
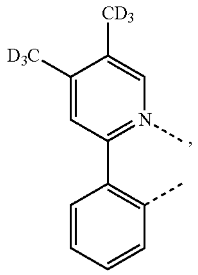
$L_{B173}$
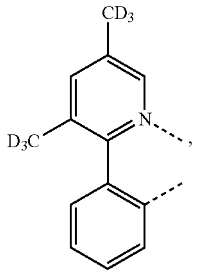
$L_{B174}$
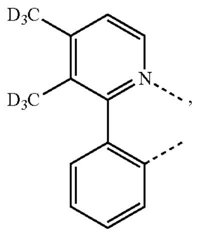
$L_{B175}$
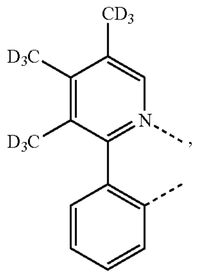

-continued
L$_{B176}$
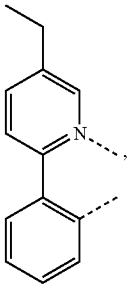
L$_{B177}$
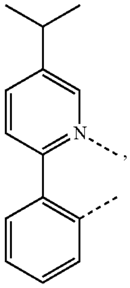
L$_{B178}$
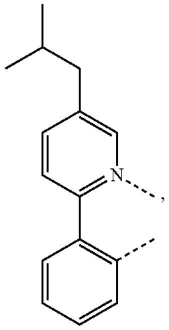
L$_{B179}$
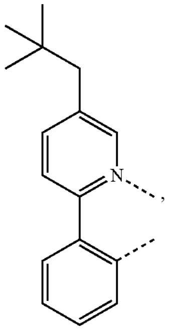
L$_{B180}$
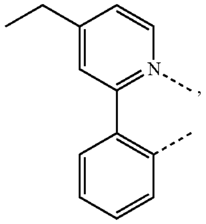
-continued
L$_{B181}$
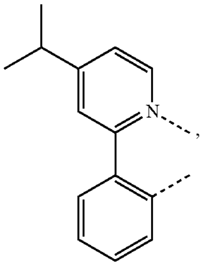
L$_{B182}$
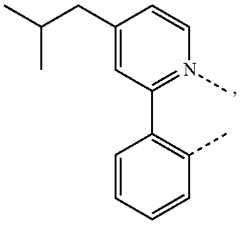
L$_{B183}$
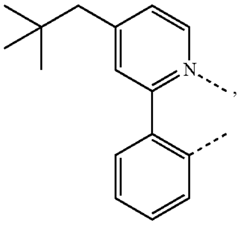
L$_{B184}$
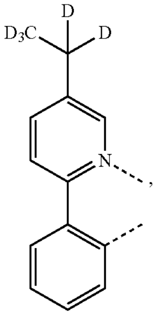
L$_{B185}$
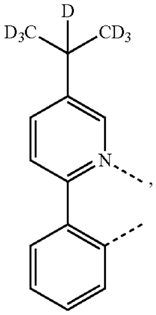

-continued
$L_{B186}$
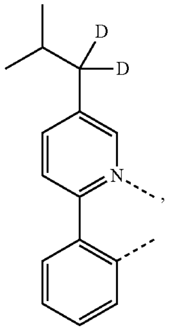
$L_{B187}$
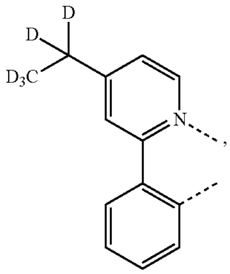
$L_{B188}$
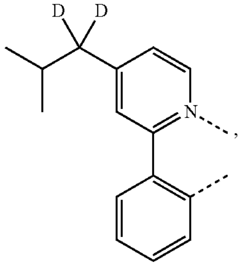
$L_{B189}$
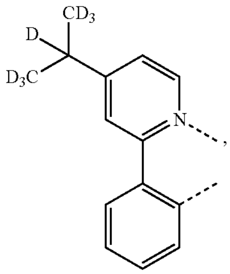
$L_{B190}$
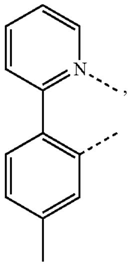
-continued
$L_{B191}$
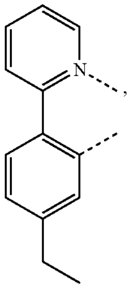
$L_{B192}$
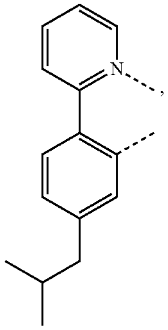
$L_{B193}$
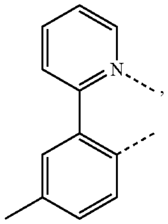
$L_{B194}$
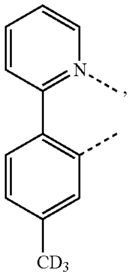
$L_{B195}$
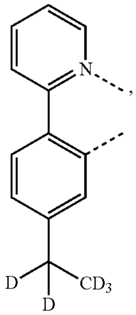

-continued
$L_{B196}$
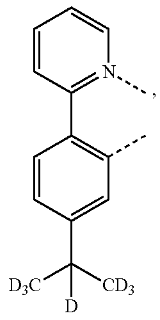
$L_{B197}$
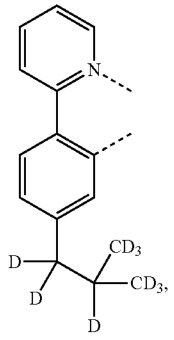
$L_{B198}$
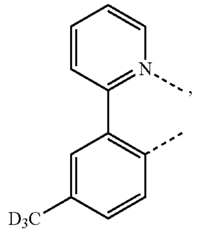
$L_{B199}$
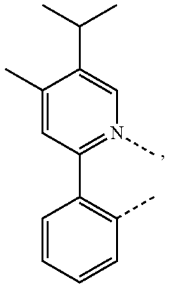
$L_{B200}$
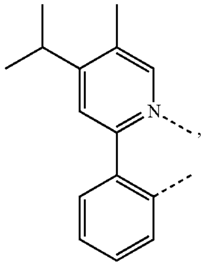
-continued
$L_{B201}$
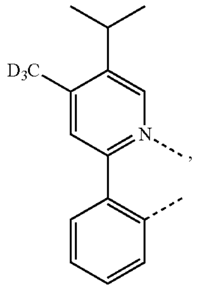
$L_{B202}$
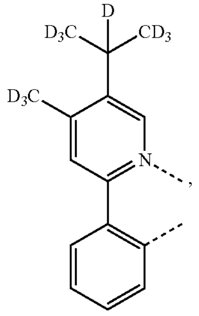
$L_{B203}$
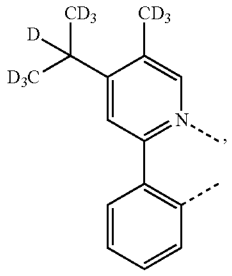
$L_{B204}$
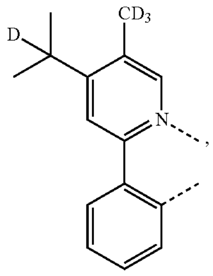
$L_{B205}$
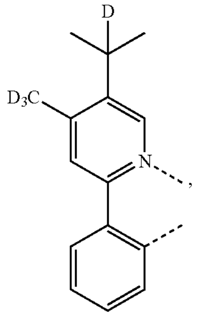

-continued
L$_{B206}$
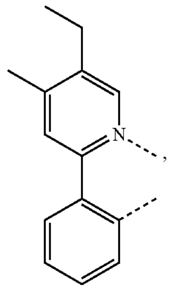
L$_{B207}$
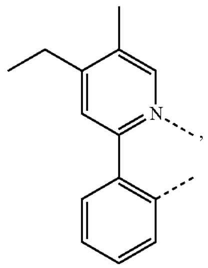
L$_{B208}$
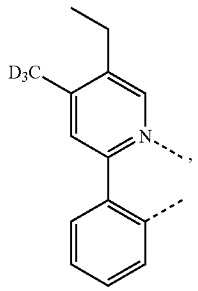
L$_{B209}$
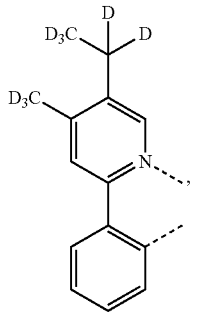
L$_{B210}$
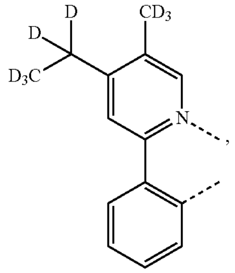
-continued
L$_{B211}$
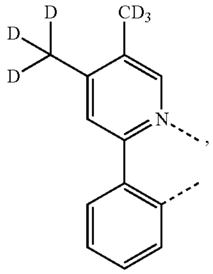
L$_{B212}$
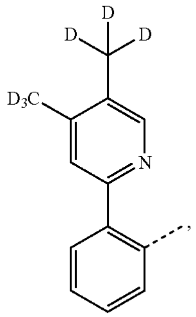
L$_{B213}$
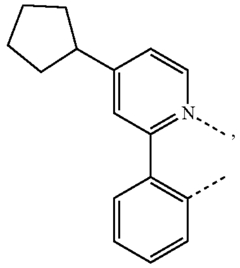
L$_{B214}$
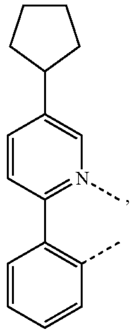
L$_{B215}$
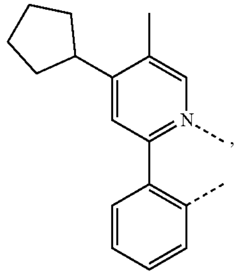

-continued
$L_{B216}$
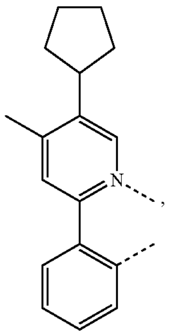
$L_{B217}$
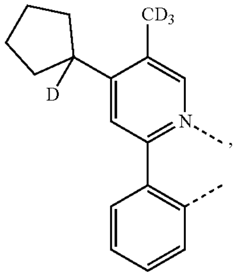
$L_{B218}$
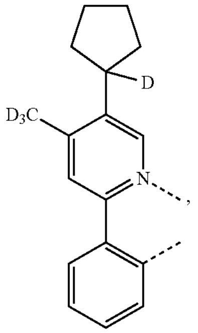
$L_{B219}$
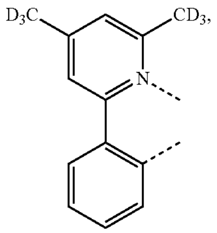
$L_{B220}$
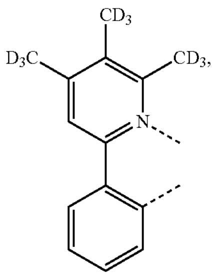
-continued
$L_{B221}$
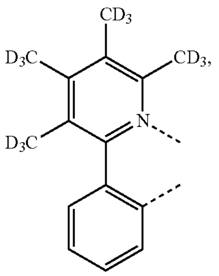
$L_{B222}$
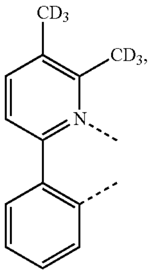
$L_{B223}$
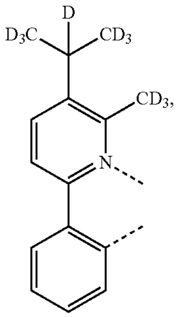
$L_{B224}$
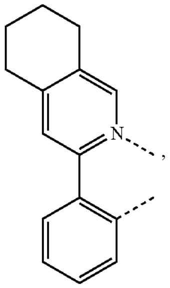
$L_{B225}$
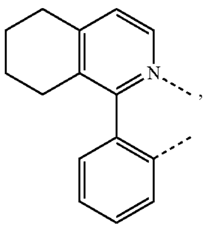

-continued
L_{B226}
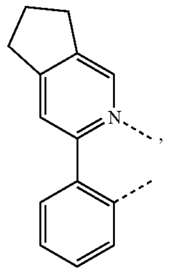
L_{B227}
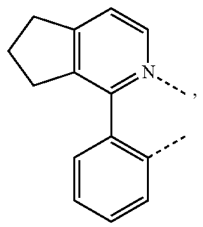
L_{B228}
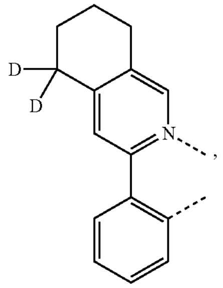
L_{B229}
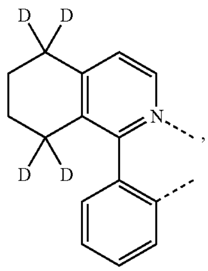
L_{B230}
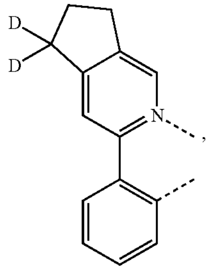
L_{B231}
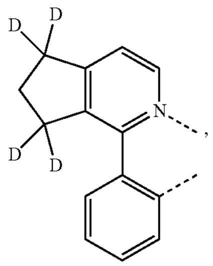
-continued
L_{B232}
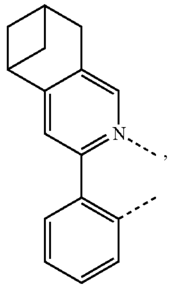
L_{B233}
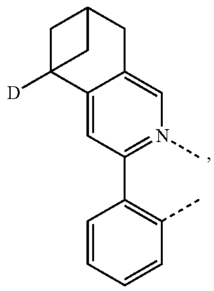
L_{B234}
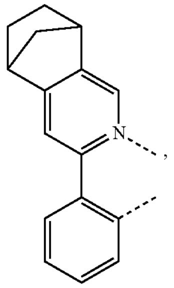
L_{B235}
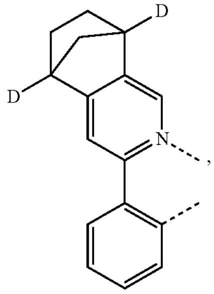
L_{B236}
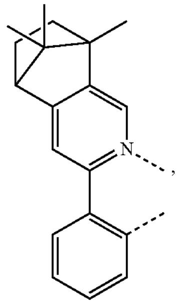

-continued
$L_{B237}$
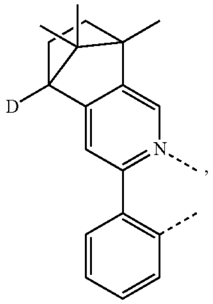
$L_{B238}$
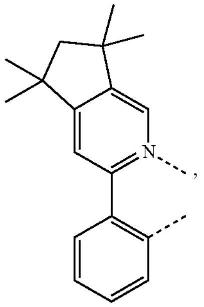
$L_{B239}$
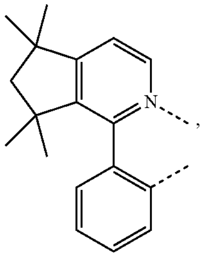
$L_{B240}$
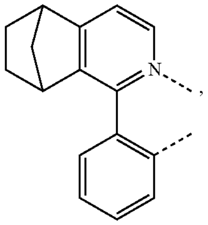
$L_{B241}$
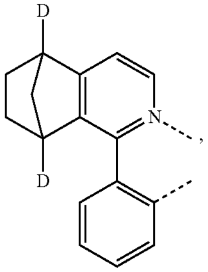
-continued
$L_{B242}$
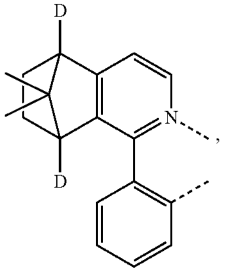
$L_{B243}$
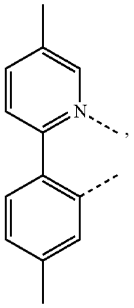
$L_{B244}$
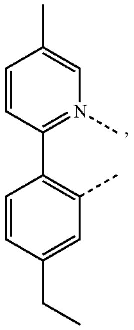
$L_{B245}$
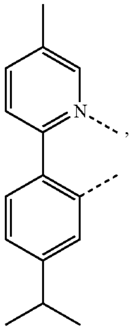
$L_{B246}$
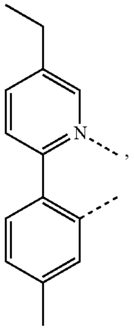

-continued
L$_{B247}$
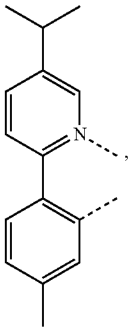
L$_{B248}$
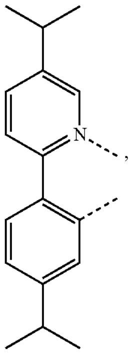
L$_{B249}$
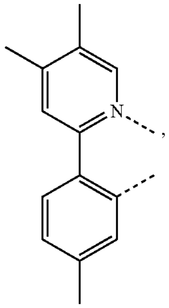
L$_{B250}$
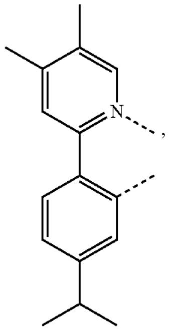
-continued
L$_{B251}$
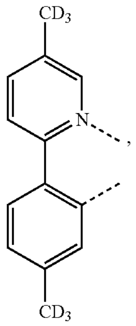
L$_{B252}$
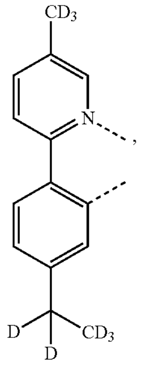
L$_{B253}$
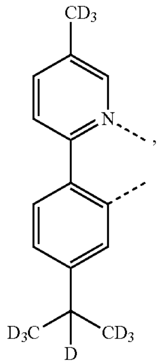
L$_{B254}$
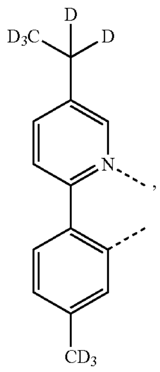

-continued
L$_{B255}$
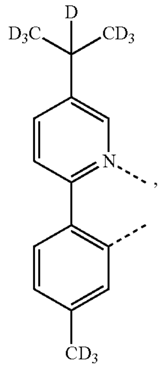
L$_{B256}$
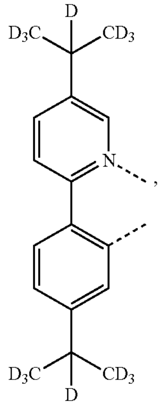
L$_{B257}$
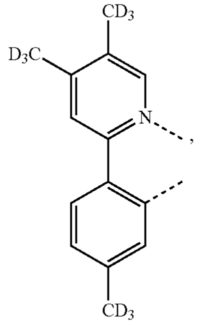
L$_{B258}$
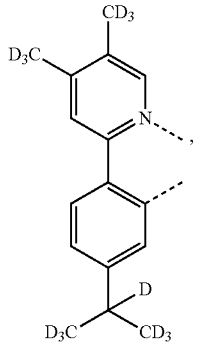
-continued
L$_{B259}$
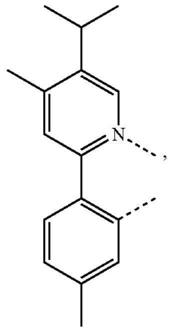
L$_{B260}$
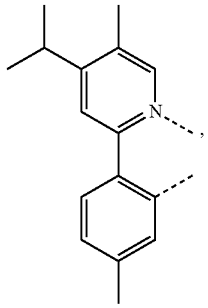
L$_{B261}$
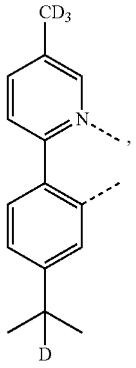
L$_{B262}$
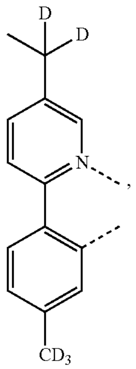

-continued
$L_{B263}$
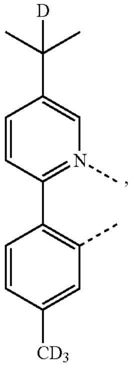
$L_{B264}$
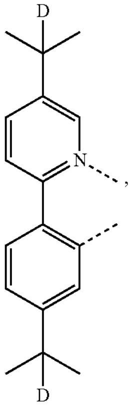
$L_{B265}$
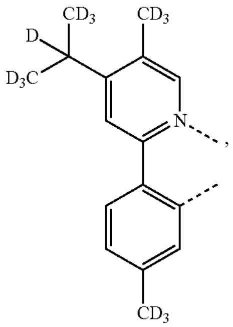
$L_{B266}$
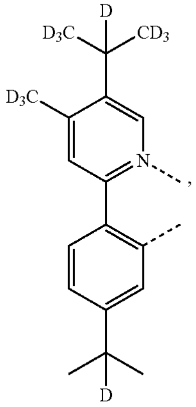
-continued
$L_{B267}$
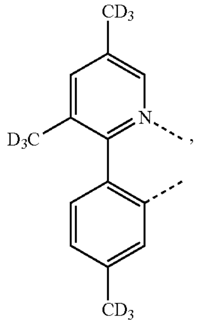
$L_{B268}$
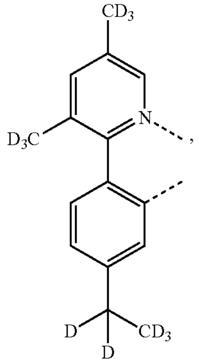
$L_{B269}$
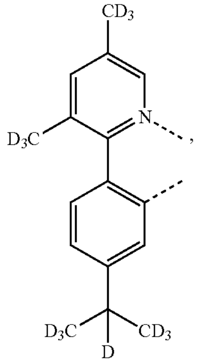
$L_{B270}$
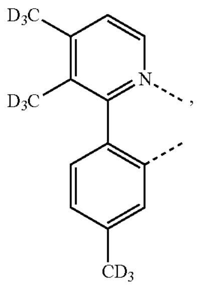

-continued
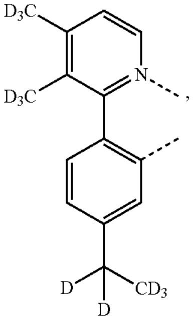
$L_{B271}$
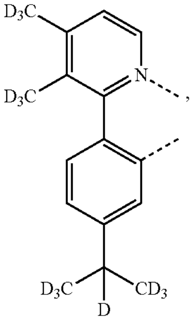
$L_{B272}$
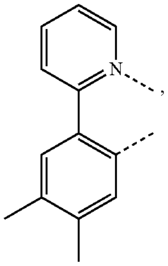
$L_{B273}$
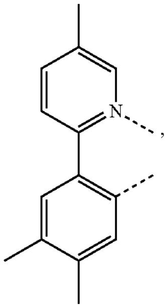
$L_{B274}$
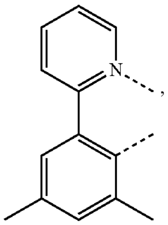
$L_{B275}$
-continued
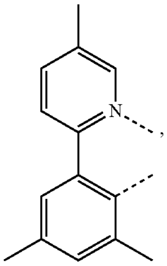
$L_{B276}$
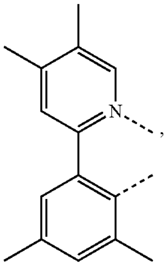
$L_{B277}$
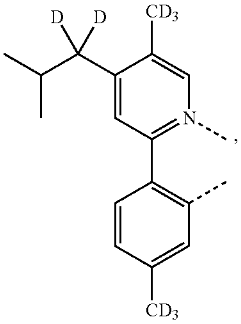
$L_{B278}$
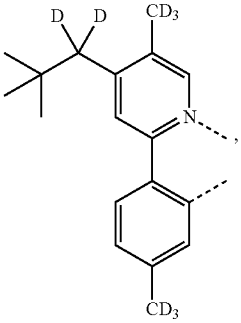
$L_{B279}$
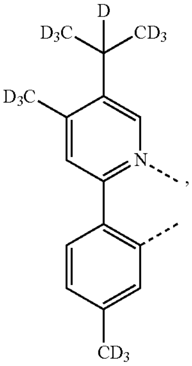
$L_{B280}$ -continued
L$_{B281}$
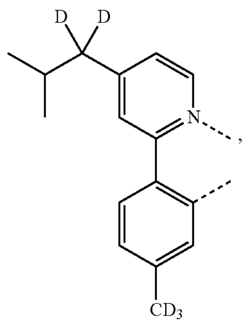
L$_{B282}$
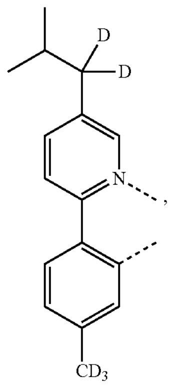
L$_{B283}$
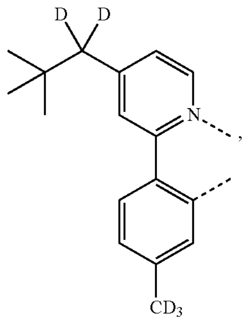
L$_{B284}$
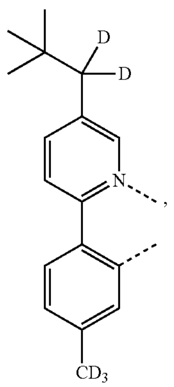
-continued
L$_{B285}$
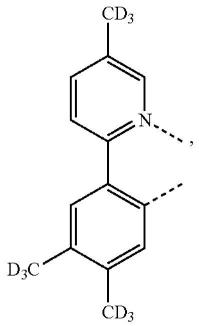
L$_{B286}$
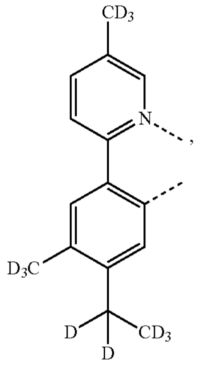
L$_{B287}$
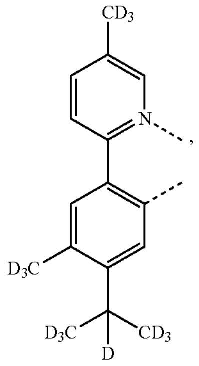
L$_{B288}$
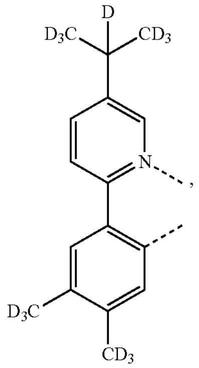

-continued
L$_{B289}$
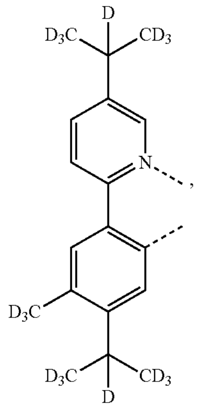
L$_{B290}$
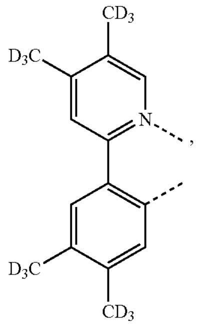
L$_{B291}$
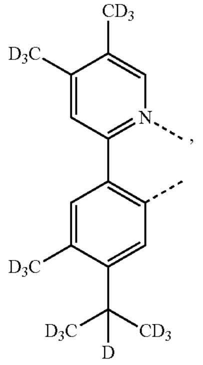
L$_{B292}$
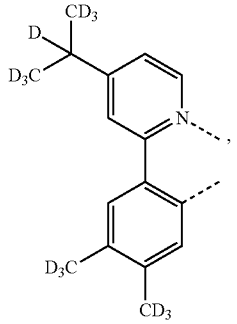
-continued
L$_{B293}$
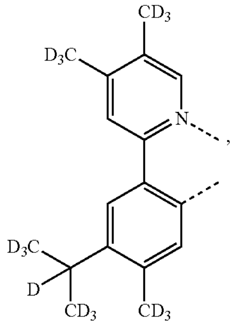
L$_{B294}$
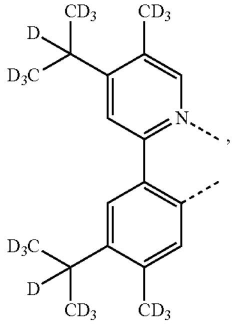
L$_{B295}$
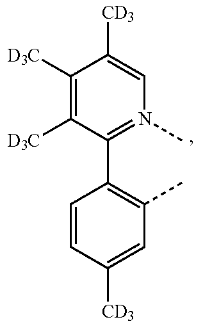
L$_{B296}$
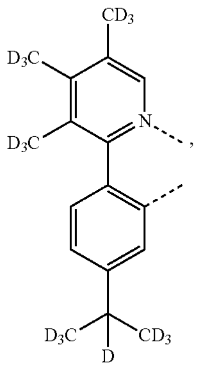

-continued
$L_{B297}$
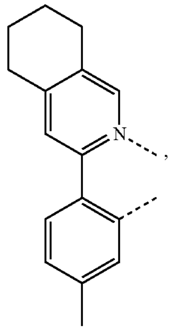
$L_{B298}$
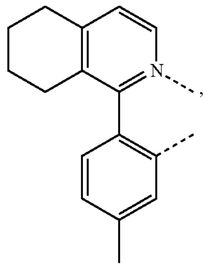
$L_{B299}$
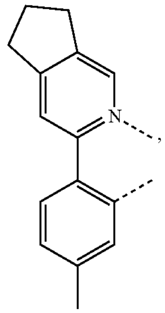
$L_{B300}$
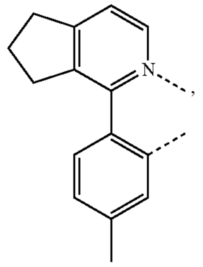
$L_{B301}$
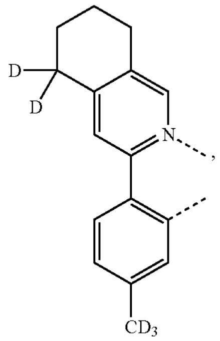
-continued
$L_{B302}$
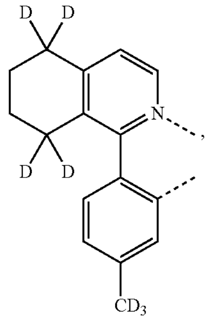
$L_{B303}$
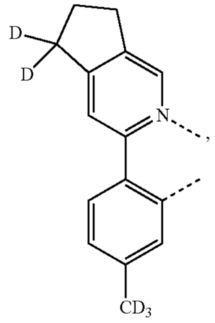
$L_{B304}$
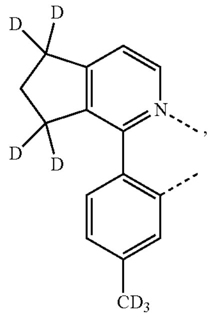
$L_{B305}$
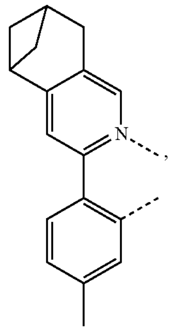

$L_{B306}$
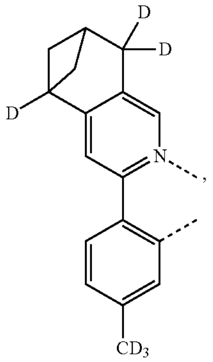
$L_{B307}$
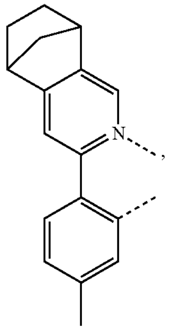
$L_{B308}$
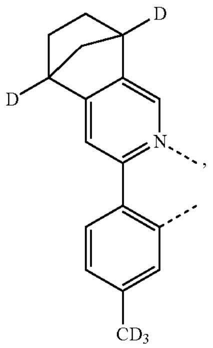
$L_{B309}$
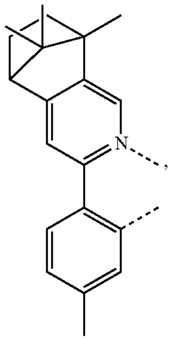
$L_{B310}$
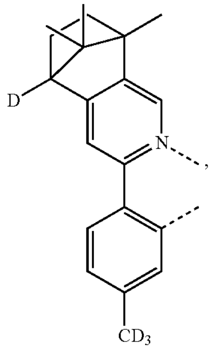
$L_{B311}$
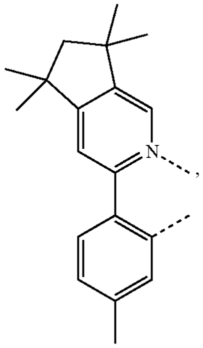
$L_{B312}$
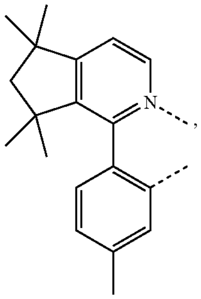
$L_{B313}$
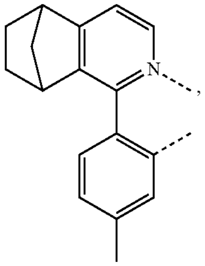
$L_{B314}$
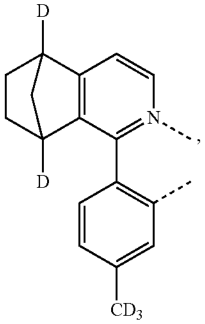

-continued
$L_{B315}$
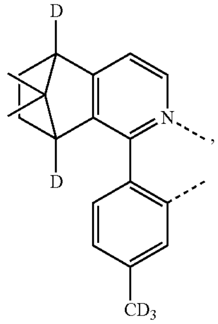
$L_{B316}$
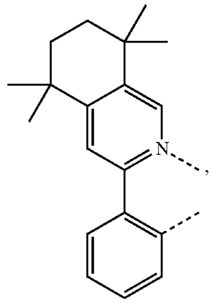
$L_{B317}$
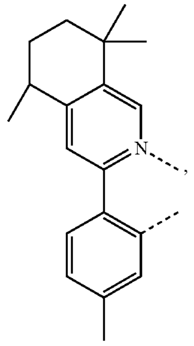
$L_{B318}$
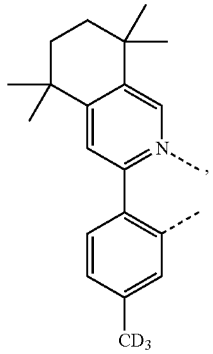
-continued
$L_{B319}$
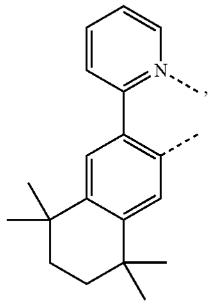
$L_{B320}$
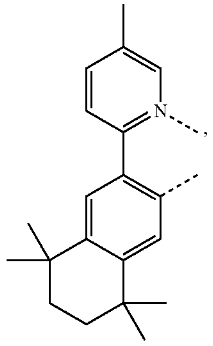
$L_{B321}$
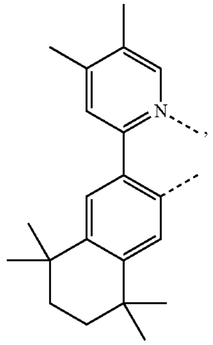
$L_{B322}$
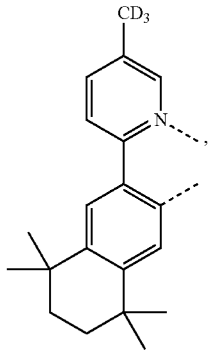

-continued
$L_{B323}$
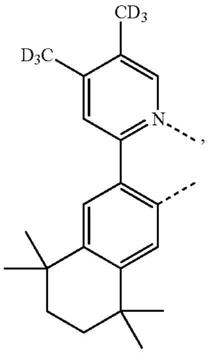
$L_{B324}$
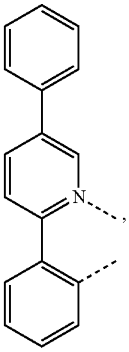
$L_{B325}$
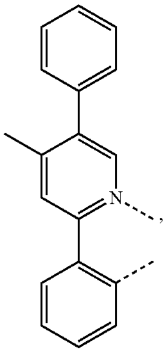
$L_{B326}$
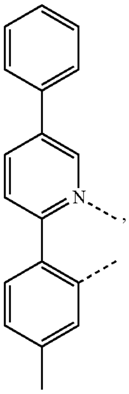
-continued
$L_{B327}$
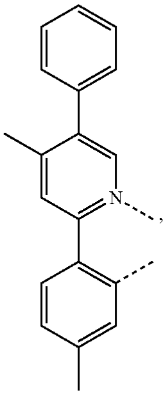
$L_{B328}$
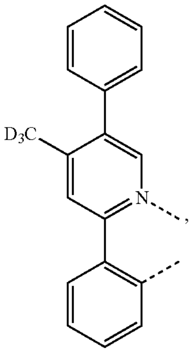
$L_{B329}$
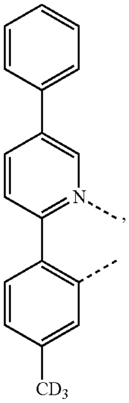
$L_{B330}$
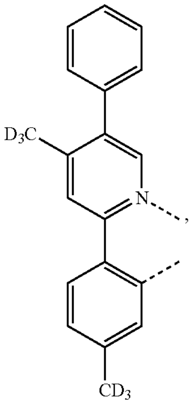

-continued
$L_{B331}$
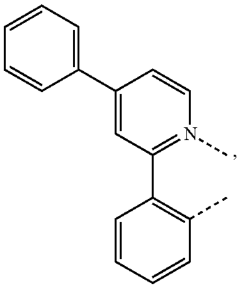
$L_{B332}$
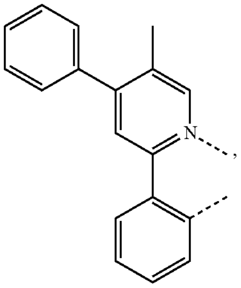
$L_{B333}$
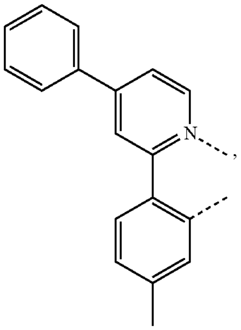
$L_{B334}$
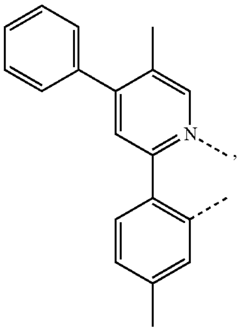
$L_{B335}$
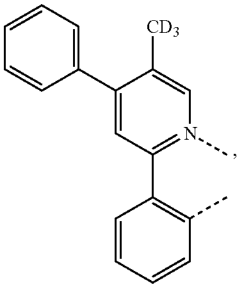
-continued
$L_{B336}$
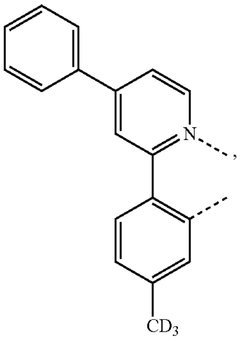
$L_{B337}$
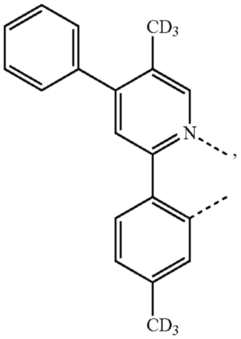
$L_{B338}$
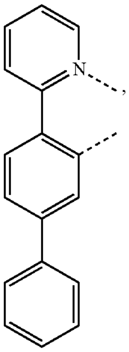
$L_{B339}$
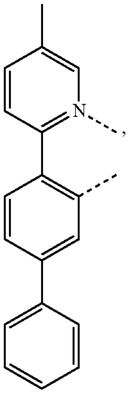

-continued
L$_{B340}$
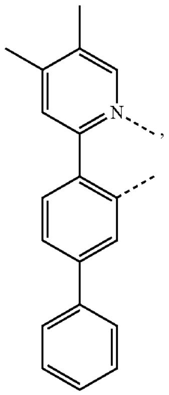
L$_{B341}$
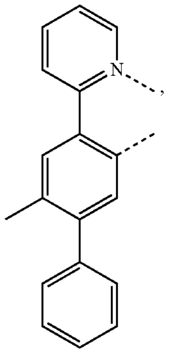
L$_{B342}$
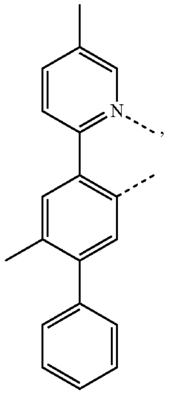
L$_{B343}$
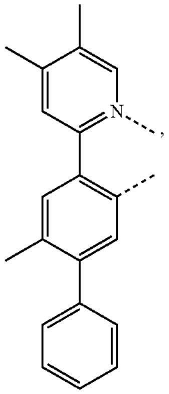
-continued
L$_{B344}$
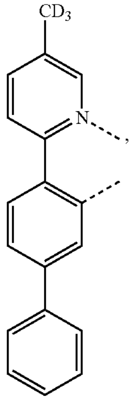
L$_{B345}$
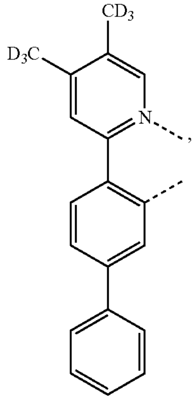
L$_{B346}$
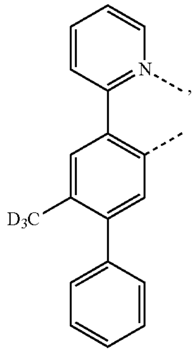
L$_{B347}$
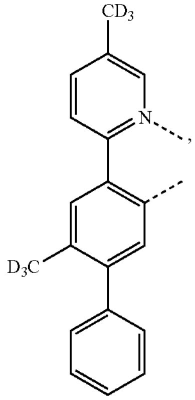

-continued
$L_{B348}$
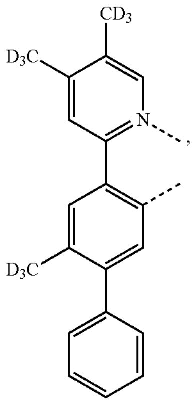
$L_{B349}$
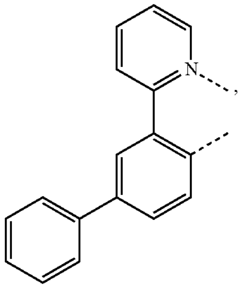
$L_{B350}$
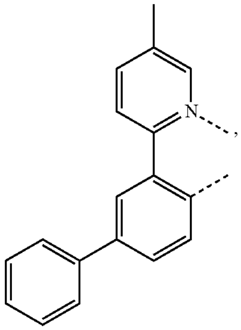
$L_{B351}$
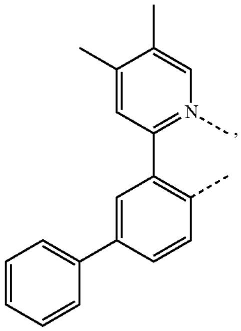
-continued
$L_{B352}$
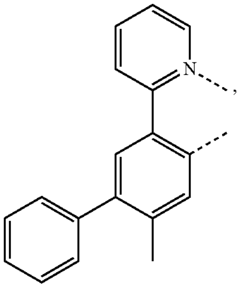
$L_{B353}$
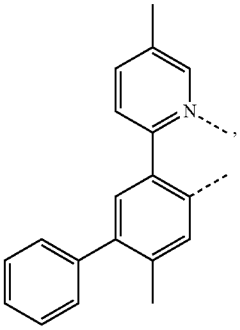
$L_{B354}$
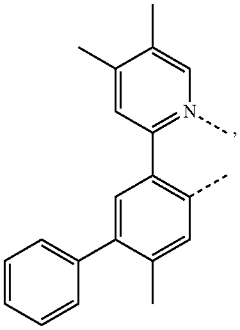
$L_{B355}$
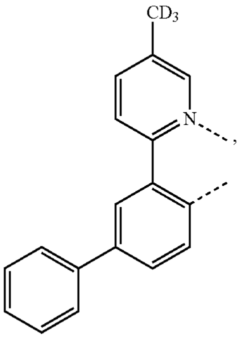

$L_{B356}$
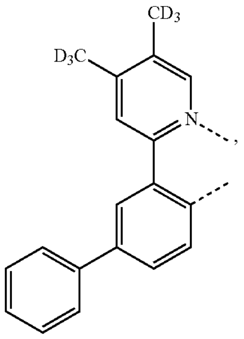
$L_{B357}$
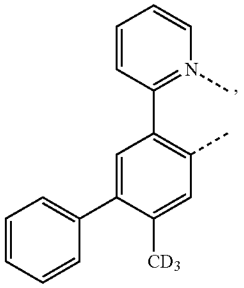
$L_{B358}$
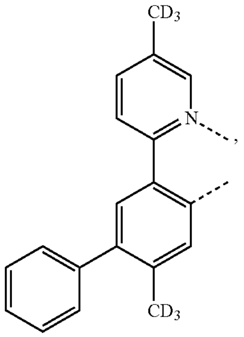
$L_{B359}$
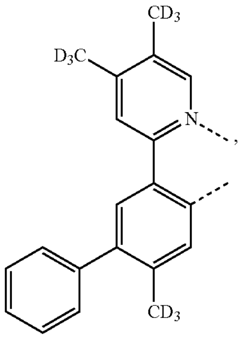
$L_{B360}$
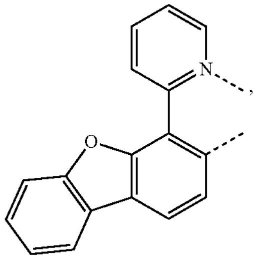
$L_{B361}$
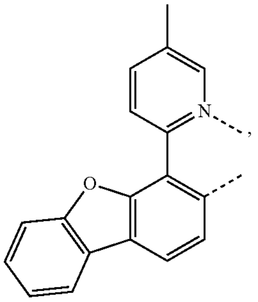
$L_{B362}$
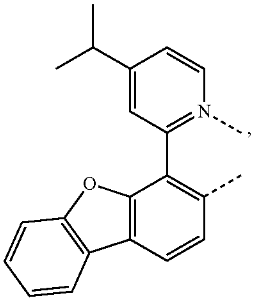
$L_{B363}$
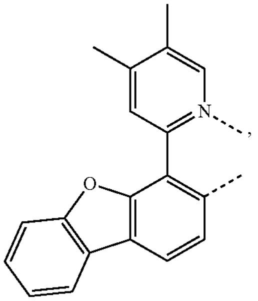
$L_{B364}$
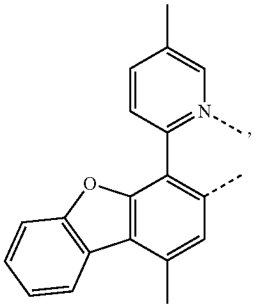
$L_{B365}$
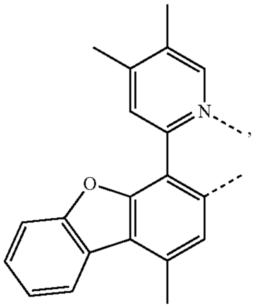

-continued
L$_{B366}$
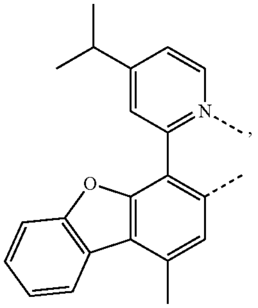
L$_{B367}$
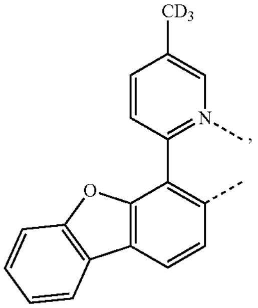
L$_{B368}$
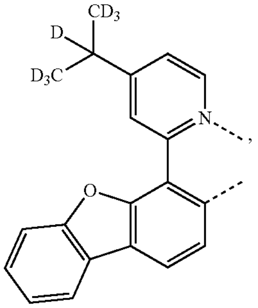
L$_{B369}$
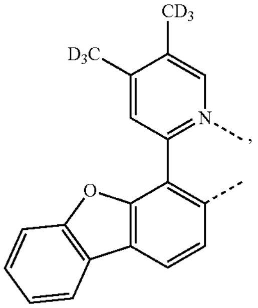
L$_{B370}$
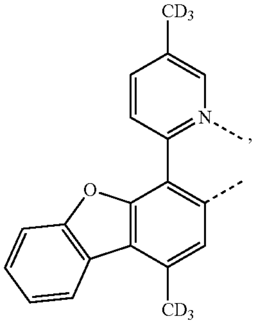
-continued
L$_{B371}$
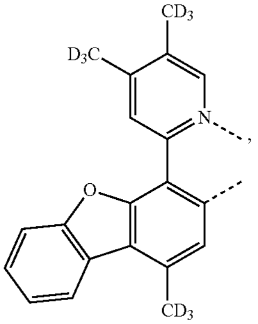
L$_{B372}$
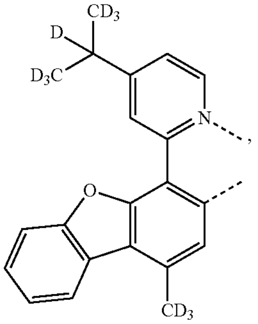
L$_{B373}$
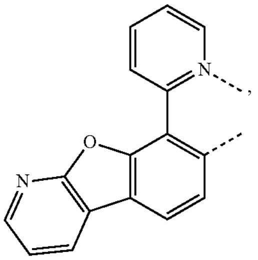
L$_{B374}$
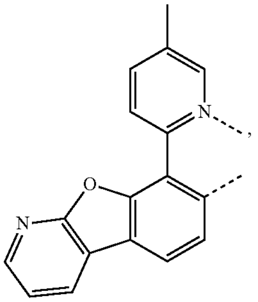
L$_{B375}$
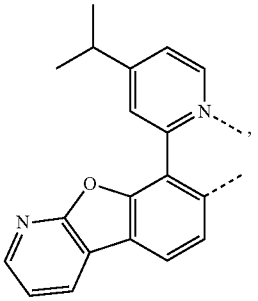

LB376
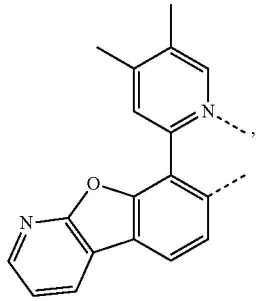
LB377
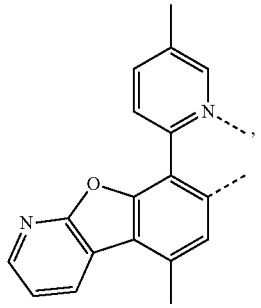
LB378
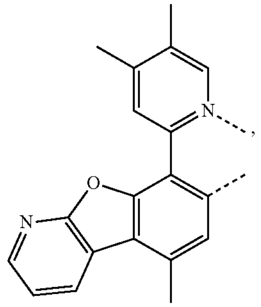
LB379
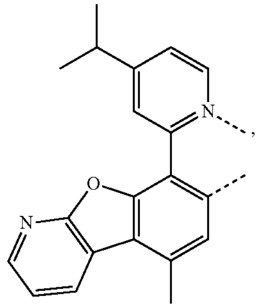
LB380
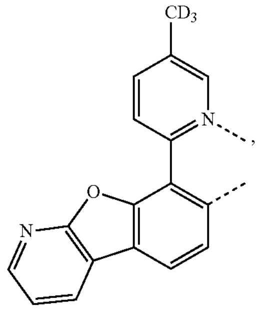
LB381
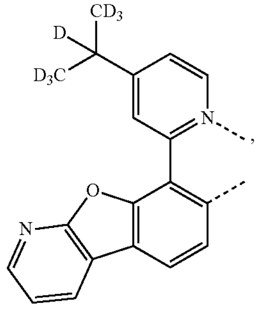
LB382
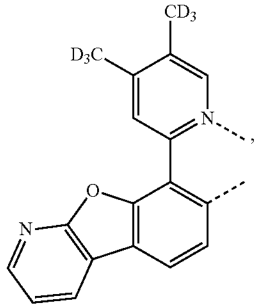
LB383
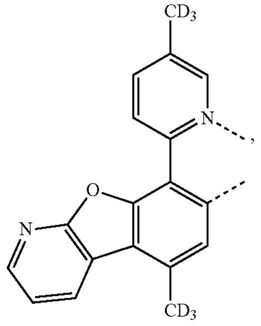
LB384
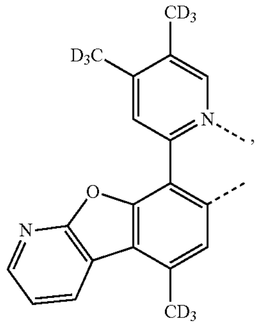
LB385
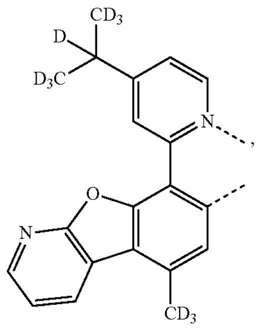

-continued
$L_{B386}$
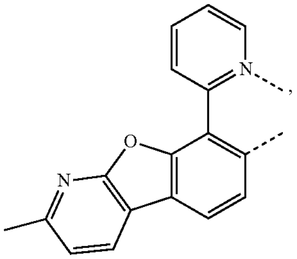
$L_{B387}$
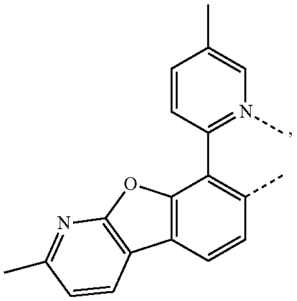
$L_{B388}$
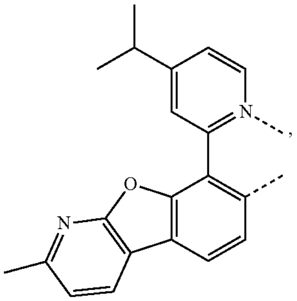
$L_{B389}$
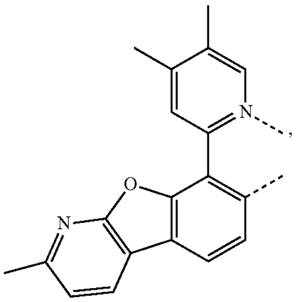
$L_{B390}$
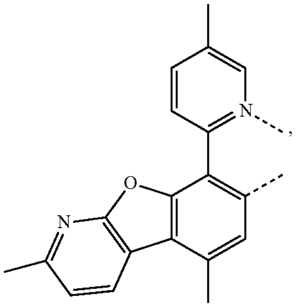
-continued
$L_{B391}$
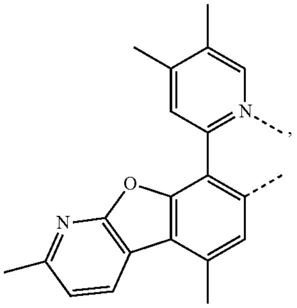
$L_{B392}$
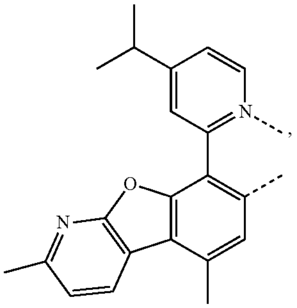
$L_{B393}$
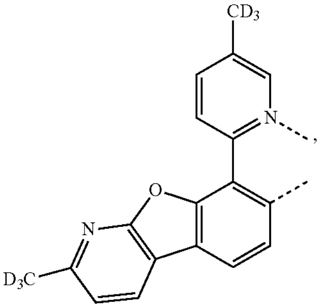
$L_{B394}$
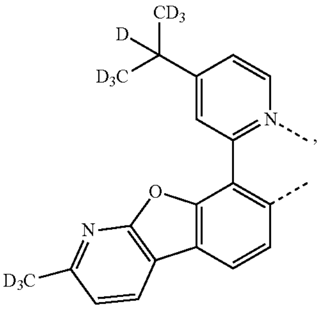
$L_{B395}$
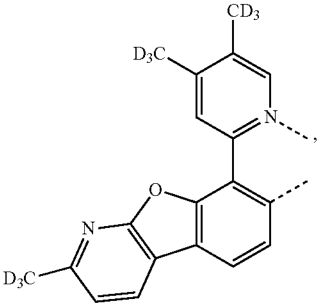

-continued
$L_{B396}$
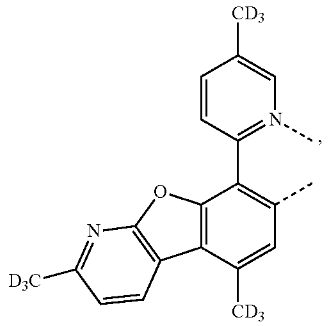
$L_{B397}$
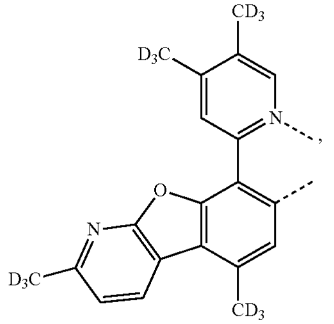
$L_{B398}$
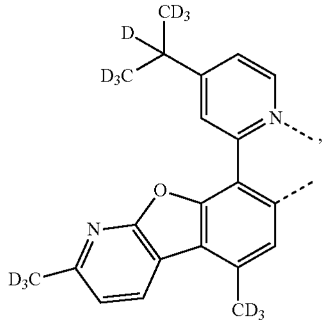
$L_{B399}$
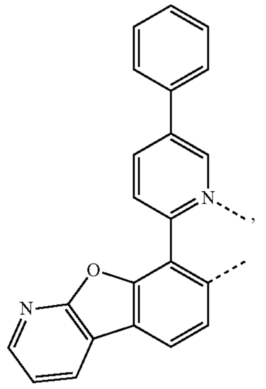
-continued
$L_{B400}$
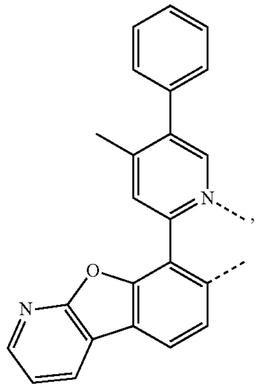
$L_{B401}$
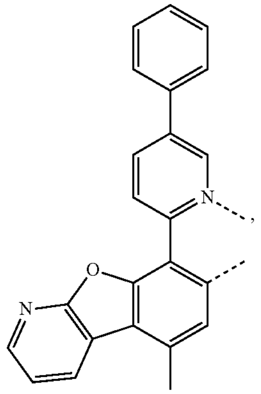
$L_{B402}$
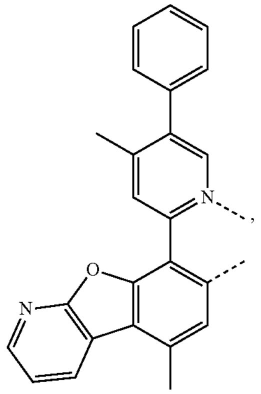
$L_{B403}$
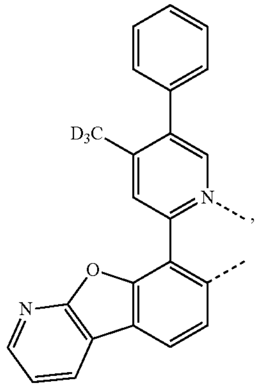

-continued
$L_{B404}$
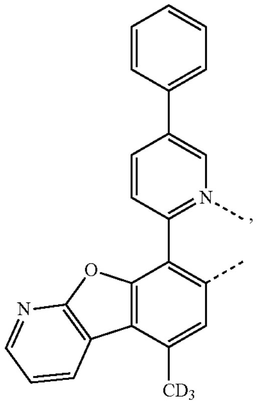
$L_{B405}$
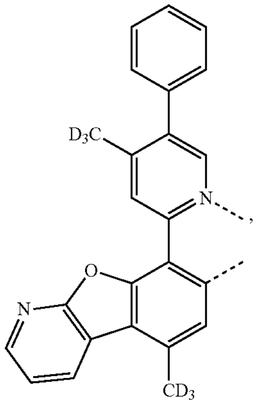
$L_{B406}$
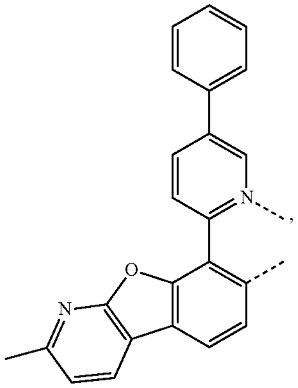
$L_{B407}$
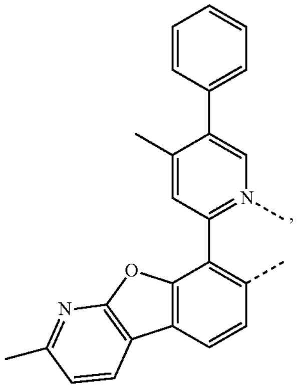
-continued
$L_{B408}$
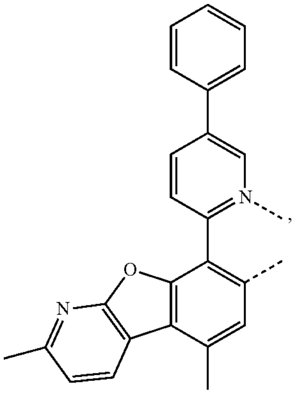
$L_{B409}$
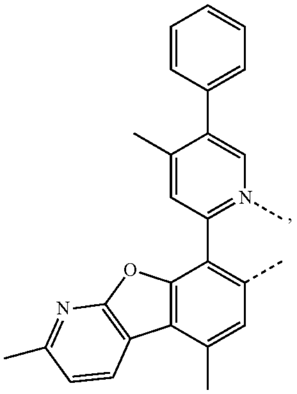
$L_{B410}$
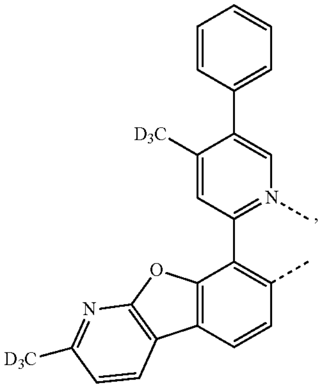
$L_{B411}$
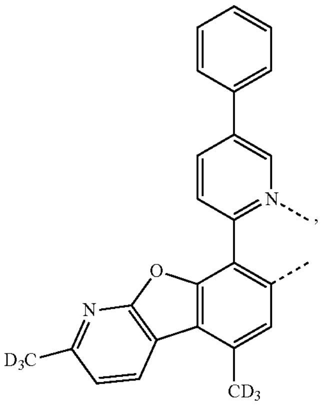

-continued
$L_{B412}$
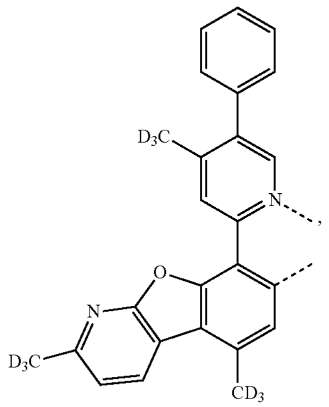
$L_{B413}$
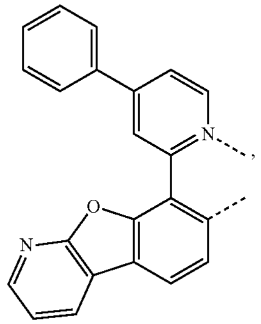
$L_{B414}$
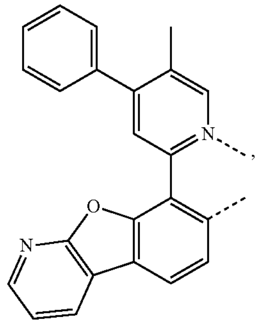
$L_{B415}$
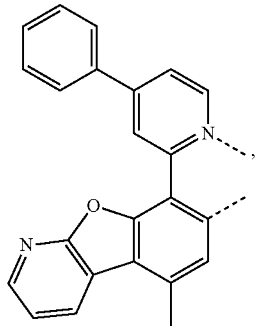
-continued
$L_{B416}$
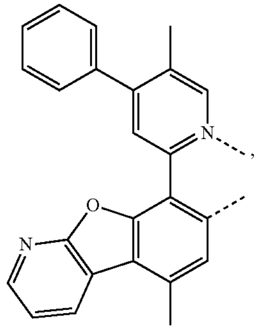
$L_{B417}$
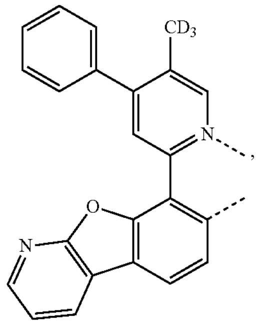
$L_{B418}$
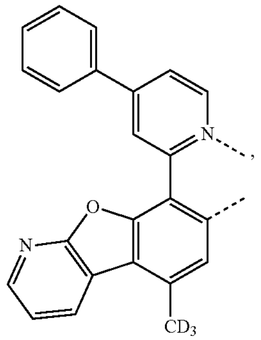
$L_{B419}$
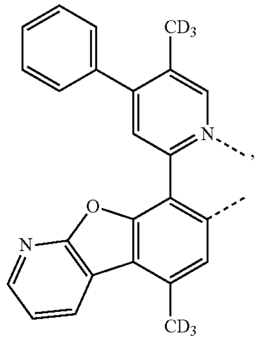

-continued
$L_{B420}$
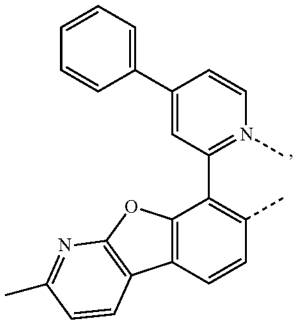
$L_{B421}$
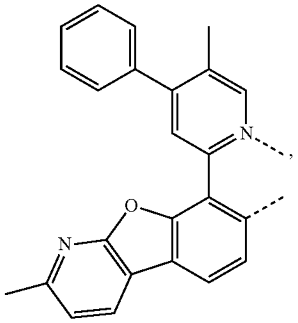
$L_{B422}$
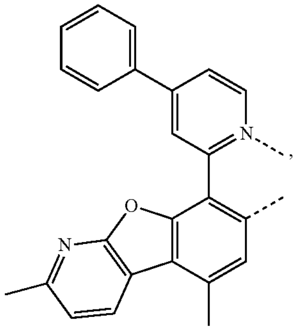
$L_{B423}$
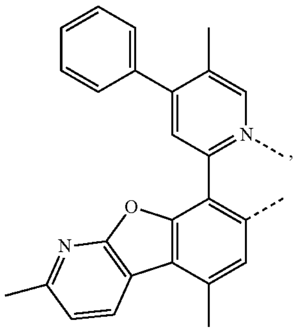
-continued
$L_{B424}$
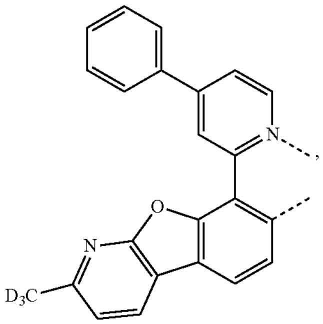
$L_{B425}$
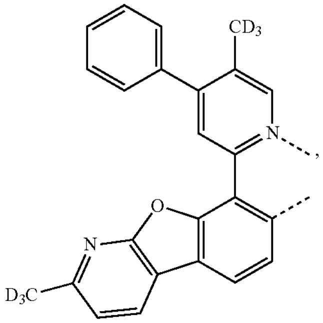
$L_{B426}$
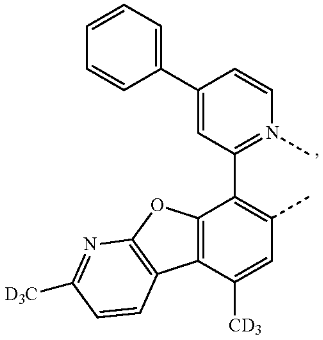
$L_{B427}$
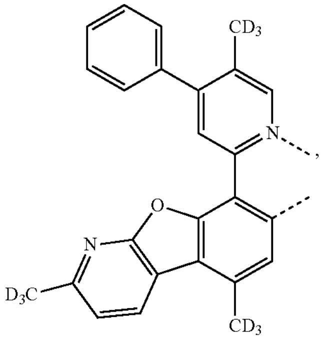
$L_{B428}$
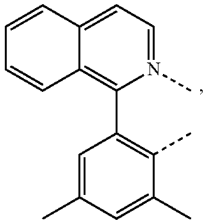

-continued
$L_{B429}$
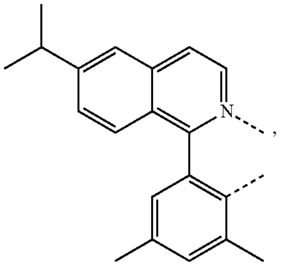
$L_{B430}$
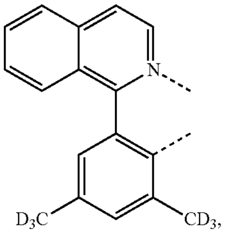
$L_{B431}$
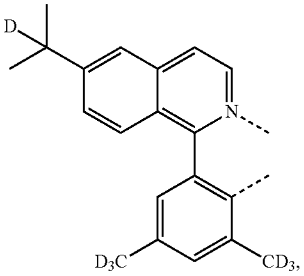
$L_{B432}$
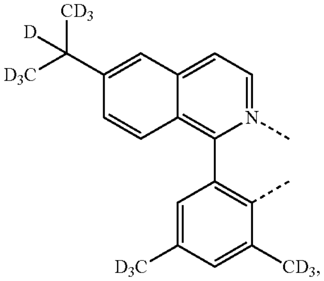
$L_{B433}$
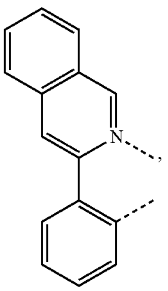
-continued
$L_{B434}$
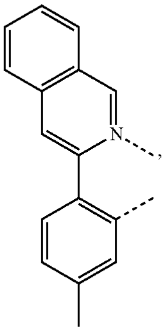
$L_{B435}$
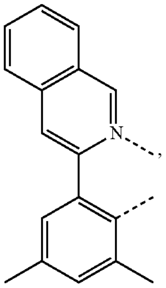
$L_{B436}$
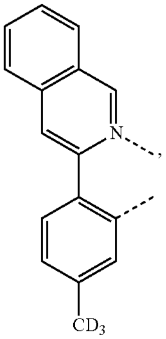
$L_{B437}$
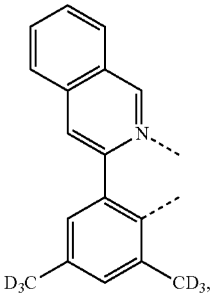
$L_{B438}$
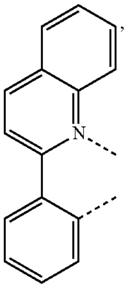

-continued
$L_{B439}$
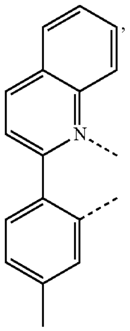
$L_{B440}$
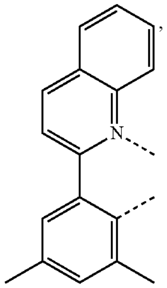
$L_{B441}$
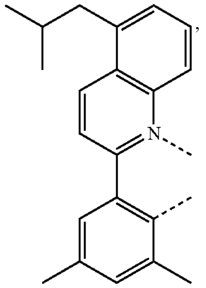
$L_{B442}$
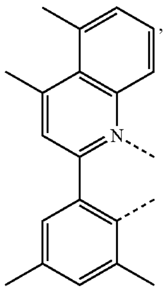
$L_{B443}$
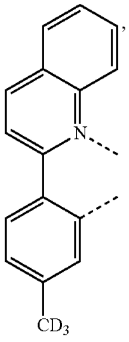
-continued
$L_{B444}$
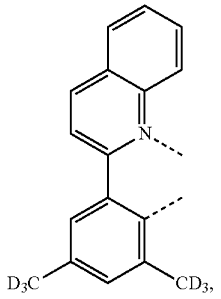
$L_{B445}$
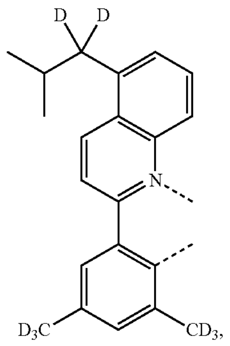
$L_{B446}$
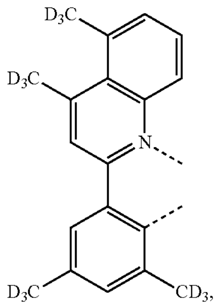
$L_{B447}$
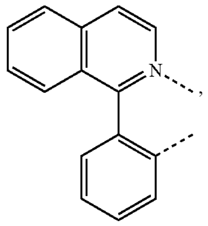
$L_{B448}$
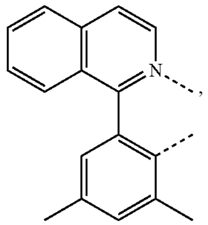

-continued
$L_{B449}$
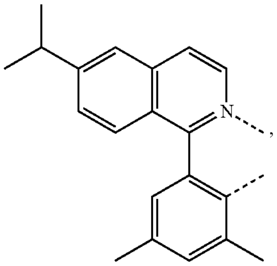
$L_{B450}$
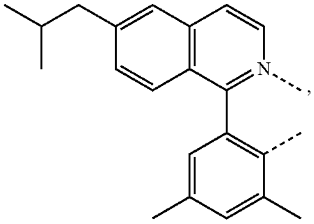
$L_{B451}$
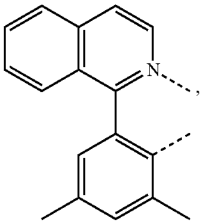
$L_{B452}$
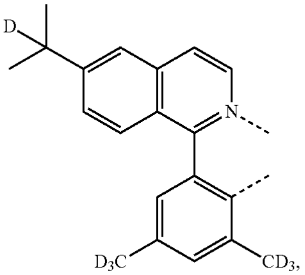
$L_{B453}$
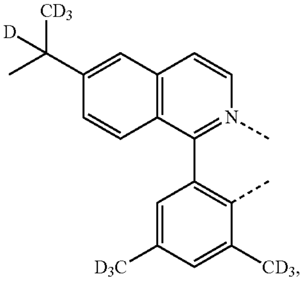
$L_{B454}$
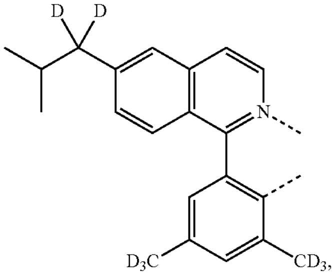
-continued
$L_{B455}$
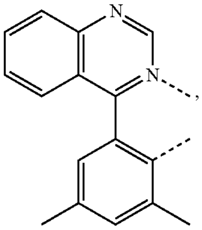
$L_{B456}$
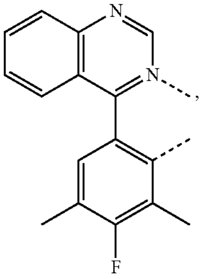
$L_{B457}$
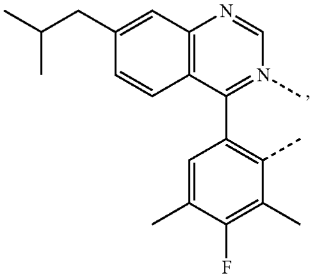
$L_{B458}$
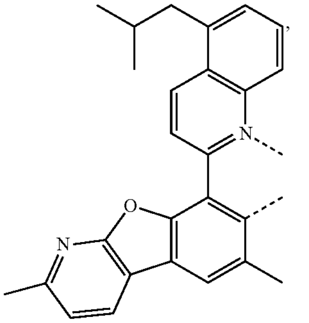
$L_{B459}$
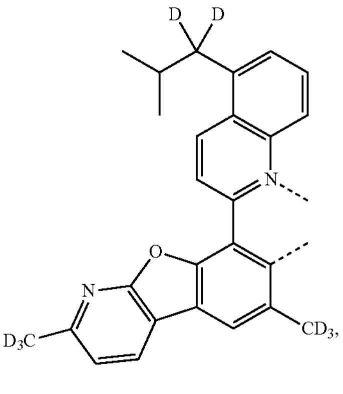

-continued
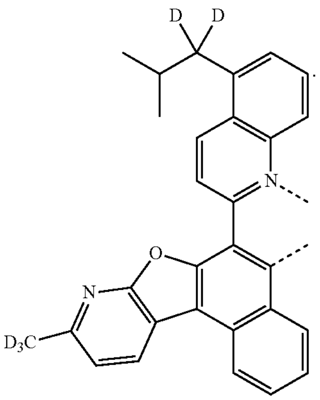
$L_{B460}$
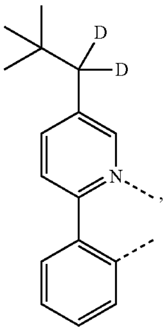
$L_{B461}$
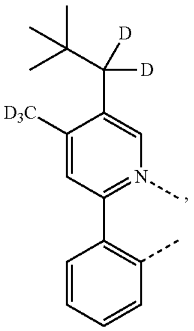
$L_{B462}$
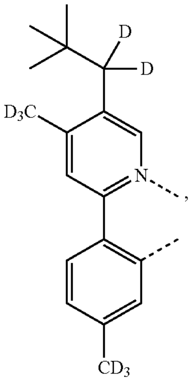
$L_{B463}$
-continued
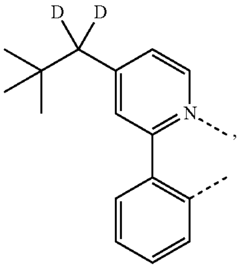
$L_{B464}$
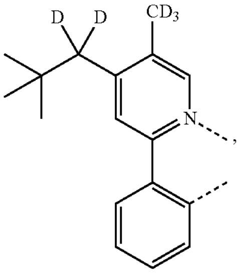
$L_{B465}$
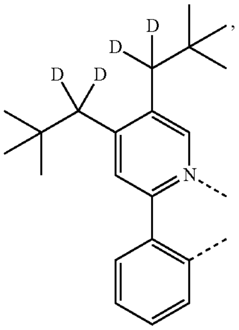
$L_{B466}$
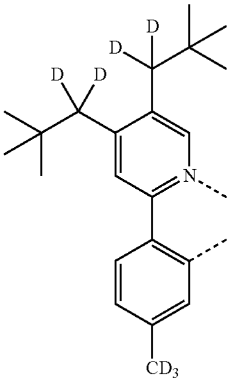
$L_{B467}$
and -continued $L_{B468}$

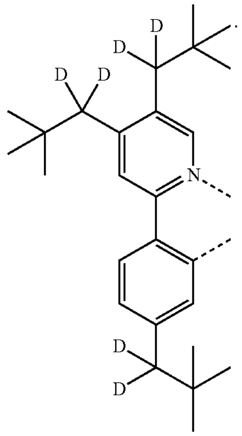

In some embodiments of the compound having a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$, where $L_B$ and $L_C$ are each a bidentate ligand, and $L_A$, $L_B$, and $L_C$ are different from each other, $L_C$ can be selected from the group consisting of $L_{C1}$ through $L_{C1260}$ based on a structure of Formula X,

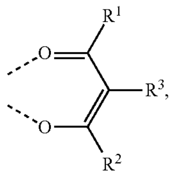

in which $R^1$, $R^2$, and $R^3$ are defined as:

| Ligand | $R^1$ | $R^2$ | $R^3$ |
|---|---|---|---|
| $L_{C1}$ | $R^{D1}$ | $R^{D1}$ | H |
| $L_{C2}$ | $R^{D2}$ | $R^{D2}$ | H |
| $L_{C3}$ | $R^{D3}$ | $R^{D3}$ | H |
| $L_{C4}$ | $R^{D4}$ | $R^{D4}$ | H |
| $L_{C5}$ | $R^{D5}$ | $R^{D5}$ | H |
| $L_{C6}$ | $R^{D6}$ | $R^{D6}$ | H |
| $L_{C7}$ | $R^{D7}$ | $R^{D7}$ | H |
| $L_{C8}$ | $R^{D8}$ | $R^{D8}$ | H |
| $L_{C9}$ | $R^{D9}$ | $R^{D9}$ | H |
| $L_{C10}$ | $R^{D10}$ | $R^{D10}$ | H |
| $L_{C11}$ | $R^{D11}$ | $R^{D11}$ | H |
| $L_{C12}$ | $R^{D12}$ | $R^{D12}$ | H |
| $L_{C13}$ | $R^{D13}$ | $R^{D13}$ | H |
| $L_{C14}$ | $R^{D14}$ | $R^{D14}$ | H |
| $L_{C15}$ | $R^{D15}$ | $R^{D15}$ | H |
| $L_{C16}$ | $R^{D16}$ | $R^{D16}$ | H |
| $L_{C17}$ | $R^{D17}$ | $R^{D17}$ | H |
| $L_{C18}$ | $R^{D18}$ | $R^{D18}$ | H |
| $L_{C19}$ | $R^{D19}$ | $R^{D19}$ | H |
| $L_{C20}$ | $R^{D20}$ | $R^{D20}$ | H |
| $L_{C21}$ | $R^{D21}$ | $R^{D21}$ | H |
| $L_{C22}$ | $R^{D22}$ | $R^{D22}$ | H |
| $L_{C23}$ | $R^{D23}$ | $R^{D23}$ | H |
| $L_{C24}$ | $R^{D24}$ | $R^{D24}$ | H |
| $L_{C25}$ | $R^{D25}$ | $R^{D25}$ | H |
| $L_{C26}$ | $R^{D26}$ | $R^{D26}$ | H |
| $L_{C27}$ | $R^{D27}$ | $R^{D27}$ | H |
| $L_{C28}$ | $R^{D28}$ | $R^{D28}$ | H |
| $L_{C29}$ | $R^{D29}$ | $R^{D29}$ | H |
| $L_{C30}$ | $R^{D30}$ | $R^{D30}$ | H |
| $L_{C31}$ | $R^{D31}$ | $R^{D31}$ | H |

-continued

| Ligand | $R^1$ | $R^2$ | $R^3$ |
|---|---|---|---|
| $L_{C32}$ | $R^{D32}$ | $R^{D32}$ | H |
| $L_{C33}$ | $R^{D33}$ | $R^{D33}$ | H |
| $L_{C34}$ | $R^{D34}$ | $R^{D34}$ | H |
| $L_{C35}$ | $R^{D35}$ | $R^{D35}$ | H |
| $L_{C36}$ | $R^{D40}$ | $R^{D40}$ | H |
| $L_{C37}$ | $R^{D41}$ | $R^{D41}$ | H |
| $L_{C38}$ | $R^{D42}$ | $R^{D42}$ | H |
| $L_{C39}$ | $R^{D64}$ | $R^{D64}$ | H |
| $L_{C40}$ | $R^{D66}$ | $R^{D66}$ | H |
| $L_{C41}$ | $R^{D68}$ | $R^{D68}$ | H |
| $L_{C42}$ | $R^{D76}$ | $R^{D76}$ | H |
| $L_{C43}$ | $R^{D1}$ | $R^{D2}$ | H |
| $L_{C44}$ | $R^{D1}$ | $R^{D3}$ | H |
| $L_{C45}$ | $R^{D1}$ | $R^{D4}$ | H |
| $L_{C46}$ | $R^{D1}$ | $R^{D5}$ | H |
| $L_{C47}$ | $R^{D1}$ | $R^{D6}$ | H |
| $L_{C48}$ | $R^{D1}$ | $R^{D7}$ | H |
| $L_{C49}$ | $R^{D1}$ | $R^{D8}$ | H |
| $L_{C50}$ | $R^{D1}$ | $R^{D9}$ | H |
| $L_{C51}$ | $R^{D1}$ | $R^{D10}$ | H |
| $L_{C52}$ | $R^{D1}$ | $R^{D11}$ | H |
| $L_{C53}$ | $R^{D1}$ | $R^{D12}$ | H |
| $L_{C54}$ | $R^{D1}$ | $R^{D13}$ | H |
| $L_{C55}$ | $R^{D1}$ | $R^{D14}$ | H |
| $L_{C56}$ | $R^{D1}$ | $R^{D15}$ | H |
| $L_{C57}$ | $R^{D1}$ | $R^{D16}$ | H |
| $L_{C58}$ | $R^{D1}$ | $R^{D17}$ | H |
| $L_{C59}$ | $R^{D1}$ | $R^{D18}$ | H |
| $L_{C60}$ | $R^{D1}$ | $R^{D19}$ | H |
| $L_{C61}$ | $R^{D1}$ | $R^{D20}$ | H |
| $L_{C62}$ | $R^{D1}$ | $R^{D21}$ | H |
| $L_{C63}$ | $R^{D1}$ | $R^{D22}$ | H |
| $L_{C64}$ | $R^{D1}$ | $R^{D23}$ | H |
| $L_{C65}$ | $R^{D1}$ | $R^{D24}$ | H |
| $L_{C66}$ | $R^{D1}$ | $R^{D25}$ | H |
| $L_{C67}$ | $R^{D1}$ | $R^{D26}$ | H |
| $L_{C68}$ | $R^{D1}$ | $R^{D27}$ | H |
| $L_{C69}$ | $R^{D1}$ | $R^{D28}$ | H |
| $L_{C70}$ | $R^{D1}$ | $R^{D29}$ | H |
| $L_{C71}$ | $R^{D1}$ | $R^{D30}$ | H |
| $L_{C72}$ | $R^{D1}$ | $R^{D31}$ | H |
| $L_{C73}$ | $R^{D1}$ | $R^{D32}$ | H |
| $L_{C74}$ | $R^{D1}$ | $R^{D33}$ | H |
| $L_{C75}$ | $R^{D1}$ | $R^{D34}$ | H |
| $L_{C76}$ | $R^{D1}$ | $R^{D35}$ | H |
| $L_{C77}$ | $R^{D1}$ | $R^{D40}$ | H |
| $L_{C78}$ | $R^{D1}$ | $R^{D41}$ | H |
| $L_{C79}$ | $R^{D1}$ | $R^{D42}$ | H |
| $L_{C80}$ | $R^{D1}$ | $R^{D64}$ | H |
| $L_{C81}$ | $R^{D1}$ | $R^{D66}$ | H |
| $L_{C82}$ | $R^{D1}$ | $R^{D68}$ | H |
| $L_{C83}$ | $R^{D1}$ | $R^{D76}$ | H |
| $L_{C84}$ | $R^{D2}$ | $R^{D1}$ | H |
| $L_{C85}$ | $R^{D2}$ | $R^{D3}$ | H |
| $L_{C86}$ | $R^{D2}$ | $R^{D4}$ | H |
| $L_{C87}$ | $R^{D2}$ | $R^{D5}$ | H |
| $L_{C88}$ | $R^{D2}$ | $R^{D6}$ | H |
| $L_{C89}$ | $R^{D2}$ | $R^{D7}$ | H |
| $L_{C90}$ | $R^{D2}$ | $R^{D8}$ | H |
| $L_{C91}$ | $R^{D2}$ | $R^{D9}$ | H |
| $L_{C92}$ | $R^{D2}$ | $R^{D10}$ | H |
| $L_{C93}$ | $R^{D2}$ | $R^{D11}$ | H |
| $L_{C94}$ | $R^{D2}$ | $R^{D12}$ | H |
| $L_{C95}$ | $R^{D2}$ | $R^{D13}$ | H |
| $L_{C96}$ | $R^{D2}$ | $R^{D14}$ | H |
| $L_{C97}$ | $R^{D2}$ | $R^{D15}$ | H |
| $L_{C98}$ | $R^{D2}$ | $R^{D16}$ | H |
| $L_{C99}$ | $R^{D2}$ | $R^{D17}$ | H |
| $L_{C100}$ | $R^{D2}$ | $R^{D18}$ | H |
| $L_{C101}$ | $R^{D2}$ | $R^{D19}$ | H |
| $L_{C102}$ | $R^{D2}$ | $R^{D20}$ | H |
| $L_{C103}$ | $R^{D2}$ | $R^{D21}$ | H |
| $L_{C104}$ | $R^{D2}$ | $R^{D22}$ | H |
| $L_{C105}$ | $R^{D2}$ | $R^{D23}$ | H |
| $L_{C106}$ | $R^{D2}$ | $R^{D24}$ | H |
| $L_{C107}$ | $R^{D2}$ | $R^{D25}$ | H |
| $L_{C108}$ | $R^{D2}$ | $R^{D26}$ | H |

-continued

| Ligand | $R^1$ | $R^2$ | $R^3$ |
|---|---|---|---|
| $L_{C109}$ | $R^{D2}$ | $R^{D27}$ | H |
| $L_{C110}$ | $R^{D2}$ | $R^{D28}$ | H |
| $L_{C111}$ | $R^{D2}$ | $R^{D29}$ | H |
| $L_{C112}$ | $R^{D2}$ | $R^{D30}$ | H |
| $L_{C113}$ | $R^{D2}$ | $R^{D31}$ | H |
| $L_{C114}$ | $R^{D2}$ | $R^{D32}$ | H |
| $L_{C115}$ | $R^{D2}$ | $R^{D33}$ | H |
| $L_{C116}$ | $R^{D2}$ | $R^{D34}$ | H |
| $L_{C117}$ | $R^{D2}$ | $R^{D35}$ | H |
| $L_{C118}$ | $R^{D2}$ | $R^{D40}$ | H |
| $L_{C119}$ | $R^{D2}$ | $R^{D41}$ | H |
| $L_{C120}$ | $R^{D2}$ | $R^{D42}$ | H |
| $L_{C121}$ | $R^{D2}$ | $R^{D64}$ | H |
| $L_{C122}$ | $R^{D2}$ | $R^{D66}$ | H |
| $L_{C123}$ | $R^{D2}$ | $R^{D68}$ | H |
| $L_{C124}$ | $R^{D2}$ | $R^{D76}$ | H |
| $L_{C125}$ | $R^{D3}$ | $R^{D4}$ | H |
| $L_{C126}$ | $R^{D3}$ | $R^{D5}$ | H |
| $L_{C127}$ | $R^{D3}$ | $R^{D6}$ | H |
| $L_{C128}$ | $R^{D3}$ | $R^{D7}$ | H |
| $L_{C129}$ | $R^{D3}$ | $R^{D8}$ | H |
| $L_{C130}$ | $R^{D3}$ | $R^{D9}$ | H |
| $L_{C131}$ | $R^{D3}$ | $R^{D10}$ | H |
| $L_{C132}$ | $R^{D3}$ | $R^{D11}$ | H |
| $L_{C133}$ | $R^{D3}$ | $R^{D12}$ | H |
| $L_{C134}$ | $R^{D3}$ | $R^{D13}$ | H |
| $L_{C135}$ | $R^{D3}$ | $R^{D14}$ | H |
| $L_{C136}$ | $R^{D3}$ | $R^{D15}$ | H |
| $L_{C137}$ | $R^{D3}$ | $R^{D16}$ | H |
| $L_{C138}$ | $R^{D3}$ | $R^{D17}$ | H |
| $L_{C139}$ | $R^{D3}$ | $R^{D18}$ | H |
| $L_{C140}$ | $R^{D3}$ | $R^{D19}$ | H |
| $L_{C141}$ | $R^{D3}$ | $R^{D20}$ | H |
| $L_{C142}$ | $R^{D3}$ | $R^{D21}$ | H |
| $L_{C143}$ | $R^{D3}$ | $R^{D22}$ | H |
| $L_{C144}$ | $R^{D3}$ | $R^{D23}$ | H |
| $L_{C145}$ | $R^{D3}$ | $R^{D24}$ | H |
| $L_{C146}$ | $R^{D3}$ | $R^{D25}$ | H |
| $L_{C147}$ | $R^{D3}$ | $R^{D26}$ | H |
| $L_{C148}$ | $R^{D3}$ | $R^{D27}$ | H |
| $L_{C149}$ | $R^{D3}$ | $R^{D28}$ | H |
| $L_{C150}$ | $R^{D3}$ | $R^{D29}$ | H |
| $L_{C151}$ | $R^{D3}$ | $R^{D30}$ | H |
| $L_{C152}$ | $R^{D3}$ | $R^{D31}$ | H |
| $L_{C153}$ | $R^{D3}$ | $R^{D32}$ | H |
| $L_{C154}$ | $R^{D3}$ | $R^{D33}$ | H |
| $L_{C155}$ | $R^{D3}$ | $R^{D34}$ | H |
| $L_{C156}$ | $R^{D3}$ | $R^{D35}$ | H |
| $L_{C157}$ | $R^{D3}$ | $R^{D40}$ | H |
| $L_{C158}$ | $R^{D3}$ | $R^{D41}$ | H |
| $L_{C159}$ | $R^{D3}$ | $R^{D42}$ | H |
| $L_{C160}$ | $R^{D3}$ | $R^{D64}$ | H |
| $L_{C161}$ | $R^{D3}$ | $R^{D66}$ | H |
| $L_{C162}$ | $R^{D3}$ | $R^{D68}$ | H |
| $L_{C163}$ | $R^{D3}$ | $R^{D76}$ | H |
| $L_{C164}$ | $R^{D4}$ | $R^{D5}$ | H |
| $L_{C165}$ | $R^{D4}$ | $R^{D6}$ | H |
| $L_{C166}$ | $R^{D4}$ | $R^{D7}$ | H |
| $L_{C167}$ | $R^{D4}$ | $R^{D8}$ | H |
| $L_{C168}$ | $R^{D4}$ | $R^{D9}$ | H |
| $L_{C169}$ | $R^{D4}$ | $R^{D10}$ | H |
| $L_{C170}$ | $R^{D4}$ | $R^{D11}$ | H |
| $L_{C171}$ | $R^{D4}$ | $R^{D12}$ | H |
| $L_{C172}$ | $R^{D4}$ | $R^{D13}$ | H |
| $L_{C173}$ | $R^{D4}$ | $R^{D14}$ | H |
| $L_{C174}$ | $R^{D4}$ | $R^{D15}$ | H |
| $L_{C175}$ | $R^{D4}$ | $R^{D16}$ | H |
| $L_{C176}$ | $R^{D4}$ | $R^{D17}$ | H |
| $L_{C177}$ | $R^{D4}$ | $R^{D18}$ | H |
| $L_{C178}$ | $R^{D4}$ | $R^{D19}$ | H |
| $L_{C179}$ | $R^{D4}$ | $R^{D20}$ | H |
| $L_{C180}$ | $R^{D4}$ | $R^{D21}$ | H |
| $L_{C181}$ | $R^{D4}$ | $R^{D22}$ | H |
| $L_{C182}$ | $R^{D4}$ | $R^{D23}$ | H |
| $L_{C183}$ | $R^{D4}$ | $R^{D24}$ | H |
| $L_{C184}$ | $R^{D4}$ | $R^{D25}$ | H |
| $L_{C185}$ | $R^{D4}$ | $R^{D26}$ | H |

-continued

| Ligand | $R^1$ | $R^2$ | $R^3$ |
|---|---|---|---|
| $L_{C186}$ | $R^{D4}$ | $R^{D27}$ | H |
| $L_{C187}$ | $R^{D4}$ | $R^{D28}$ | H |
| $L_{C188}$ | $R^{D4}$ | $R^{D29}$ | H |
| $L_{C189}$ | $R^{D4}$ | $R^{D30}$ | H |
| $L_{C190}$ | $R^{D4}$ | $R^{D31}$ | H |
| $L_{C191}$ | $R^{D4}$ | $R^{D32}$ | H |
| $L_{C192}$ | $R^{D4}$ | $R^{D33}$ | H |
| $L_{C193}$ | $R^{D4}$ | $R^{D34}$ | H |
| $L_{C194}$ | $R^{D4}$ | $R^{D35}$ | H |
| $L_{C195}$ | $R^{D4}$ | $R^{D40}$ | H |
| $L_{C196}$ | $R^{D4}$ | $R^{D41}$ | H |
| $L_{C197}$ | $R^{D4}$ | $R^{D42}$ | H |
| $L_{C198}$ | $R^{D4}$ | $R^{D64}$ | H |
| $L_{C199}$ | $R^{D4}$ | $R^{D66}$ | H |
| $L_{C200}$ | $R^{D4}$ | $R^{D68}$ | H |
| $L_{C201}$ | $R^{D4}$ | $R^{D76}$ | H |
| $L_{C202}$ | $R^{D4}$ | $R^{D1}$ | H |
| $L_{C203}$ | $R^{D7}$ | $R^{D5}$ | H |
| $L_{C204}$ | $R^{D7}$ | $R^{D6}$ | H |
| $L_{C205}$ | $R^{D7}$ | $R^{D8}$ | H |
| $L_{C206}$ | $R^{D7}$ | $R^{D9}$ | H |
| $L_{C207}$ | $R^{D7}$ | $R^{D10}$ | H |
| $L_{C208}$ | $R^{D7}$ | $R^{D11}$ | H |
| $L_{C209}$ | $R^{D7}$ | $R^{D12}$ | H |
| $L_{C210}$ | $R^{D7}$ | $R^{D13}$ | H |
| $L_{C211}$ | $R^{D7}$ | $R^{D14}$ | H |
| $L_{C212}$ | $R^{D7}$ | $R^{D15}$ | H |
| $L_{C213}$ | $R^{D7}$ | $R^{D16}$ | H |
| $L_{C214}$ | $R^{D7}$ | $R^{D17}$ | H |
| $L_{C215}$ | $R^{D7}$ | $R^{D18}$ | H |
| $L_{C216}$ | $R^{D7}$ | $R^{D19}$ | H |
| $L_{C217}$ | $R^{D7}$ | $R^{D20}$ | H |
| $L_{C218}$ | $R^{D7}$ | $R^{D21}$ | H |
| $L_{C219}$ | $R^{D7}$ | $R^{D22}$ | H |
| $L_{C220}$ | $R^{D7}$ | $R^{D23}$ | H |
| $L_{C221}$ | $R^{D7}$ | $R^{D24}$ | H |
| $L_{C222}$ | $R^{D7}$ | $R^{D25}$ | H |
| $L_{C223}$ | $R^{D7}$ | $R^{D26}$ | H |
| $L_{C224}$ | $R^{D7}$ | $R^{D27}$ | H |
| $L_{C225}$ | $R^{D7}$ | $R^{D28}$ | H |
| $L_{C226}$ | $R^{D7}$ | $R^{D29}$ | H |
| $L_{C227}$ | $R^{D7}$ | $R^{D30}$ | H |
| $L_{C228}$ | $R^{D7}$ | $R^{D31}$ | H |
| $L_{C229}$ | $R^{D7}$ | $R^{D32}$ | H |
| $L_{C230}$ | $R^{D7}$ | $R^{D33}$ | H |
| $L_{C231}$ | $R^{D7}$ | $R^{D34}$ | H |
| $L_{C232}$ | $R^{D7}$ | $R^{D35}$ | H |
| $L_{C233}$ | $R^{D7}$ | $R^{D40}$ | H |
| $L_{C234}$ | $R^{D7}$ | $R^{D41}$ | H |
| $L_{C235}$ | $R^{D7}$ | $R^{D42}$ | H |
| $L_{C236}$ | $R^{D7}$ | $R^{D64}$ | H |
| $L_{C237}$ | $R^{D7}$ | $R^{D66}$ | H |
| $L_{C238}$ | $R^{D7}$ | $R^{D68}$ | H |
| $L_{C239}$ | $R^{D7}$ | $R^{D76}$ | H |
| $L_{C240}$ | $R^{D8}$ | $R^{D5}$ | H |
| $L_{C241}$ | $R^{D8}$ | $R^{D6}$ | H |
| $L_{C242}$ | $R^{D8}$ | $R^{D9}$ | H |
| $L_{C243}$ | $R^{D8}$ | $R^{D10}$ | H |
| $L_{C244}$ | $R^{D8}$ | $R^{D11}$ | H |
| $L_{C245}$ | $R^{D8}$ | $R^{D12}$ | H |
| $L_{C246}$ | $R^{D8}$ | $R^{D13}$ | H |
| $L_{C247}$ | $R^{D8}$ | $R^{D14}$ | H |
| $L_{C248}$ | $R^{D8}$ | $R^{D15}$ | H |
| $L_{C249}$ | $R^{D8}$ | $R^{D16}$ | H |
| $L_{C250}$ | $R^{D8}$ | $R^{D17}$ | H |
| $L_{C251}$ | $R^{D8}$ | $R^{D18}$ | H |
| $L_{C252}$ | $R^{D8}$ | $R^{D19}$ | H |
| $L_{C253}$ | $R^{D8}$ | $R^{D20}$ | H |
| $L_{C254}$ | $R^{D8}$ | $R^{D21}$ | H |
| $L_{C255}$ | $R^{D8}$ | $R^{D22}$ | H |
| $L_{C256}$ | $R^{D8}$ | $R^{D23}$ | H |
| $L_{C257}$ | $R^{D8}$ | $R^{D24}$ | H |
| $L_{C258}$ | $R^{D8}$ | $R^{D25}$ | H |
| $L_{C259}$ | $R^{D8}$ | $R^{D26}$ | H |
| $L_{C260}$ | $R^{D8}$ | $R^{D27}$ | H |
| $L_{C261}$ | $R^{D8}$ | $R^{D28}$ | H |
| $L_{C262}$ | $R^{D8}$ | $R^{D29}$ | H |

-continued

| Ligand | $R^1$ | $R^2$ | $R^3$ |
|---|---|---|---|
| $L_{C263}$ | $R^{D8}$ | $R^{D30}$ | H |
| $L_{C264}$ | $R^{D8}$ | $R^{D31}$ | H |
| $L_{C265}$ | $R^{D8}$ | $R^{D32}$ | H |
| $L_{C266}$ | $R^{D8}$ | $R^{D33}$ | H |
| $L_{C267}$ | $R^{D8}$ | $R^{D34}$ | H |
| $L_{C268}$ | $R^{D8}$ | $R^{D35}$ | H |
| $L_{C269}$ | $R^{D8}$ | $R^{D40}$ | H |
| $L_{C270}$ | $R^{D8}$ | $R^{D41}$ | H |
| $L_{C271}$ | $R^{D8}$ | $R^{D42}$ | H |
| $L_{C272}$ | $R^{D8}$ | $R^{D64}$ | H |
| $L_{C273}$ | $R^{D8}$ | $R^{D66}$ | H |
| $L_{C274}$ | $R^{D8}$ | $R^{D68}$ | H |
| $L_{C275}$ | $R^{D8}$ | $R^{D76}$ | H |
| $L_{C276}$ | $R^{D11}$ | $R^{D5}$ | H |
| $L_{C277}$ | $R^{D11}$ | $R^{D6}$ | H |
| $L_{C278}$ | $R^{D11}$ | $R^{D9}$ | H |
| $L_{C279}$ | $R^{D11}$ | $R^{D10}$ | H |
| $L_{C280}$ | $R^{D11}$ | $R^{D12}$ | H |
| $L_{C281}$ | $R^{D11}$ | $R^{D13}$ | H |
| $L_{C282}$ | $R^{D11}$ | $R^{D14}$ | H |
| $L_{C283}$ | $R^{D11}$ | $R^{D15}$ | H |
| $L_{C284}$ | $R^{D11}$ | $R^{D16}$ | H |
| $L_{C285}$ | $R^{D11}$ | $R^{D17}$ | H |
| $L_{C286}$ | $R^{D11}$ | $R^{D18}$ | H |
| $L_{C287}$ | $R^{D11}$ | $R^{D19}$ | H |
| $L_{C288}$ | $R^{D11}$ | $R^{D20}$ | H |
| $L_{C289}$ | $R^{D11}$ | $R^{D21}$ | H |
| $L_{C290}$ | $R^{D11}$ | $R^{D22}$ | H |
| $L_{C291}$ | $R^{D11}$ | $R^{D23}$ | H |
| $L_{C292}$ | $R^{D11}$ | $R^{D24}$ | H |
| $L_{C293}$ | $R^{D11}$ | $R^{D25}$ | H |
| $L_{C294}$ | $R^{D11}$ | $R^{D26}$ | H |
| $L_{C295}$ | $R^{D11}$ | $R^{D27}$ | H |
| $L_{C296}$ | $R^{D11}$ | $R^{D28}$ | H |
| $L_{C297}$ | $R^{D11}$ | $R^{D29}$ | H |
| $L_{C298}$ | $R^{D11}$ | $R^{D30}$ | H |
| $L_{C299}$ | $R^{D11}$ | $R^{D31}$ | H |
| $L_{C300}$ | $R^{D11}$ | $R^{D32}$ | H |
| $L_{C301}$ | $R^{D11}$ | $R^{D33}$ | H |
| $L_{C302}$ | $R^{D11}$ | $R^{D34}$ | H |
| $L_{C303}$ | $R^{D11}$ | $R^{D35}$ | H |
| $L_{C304}$ | $R^{D11}$ | $R^{D40}$ | H |
| $L_{C305}$ | $R^{D11}$ | $R^{D41}$ | H |
| $L_{C306}$ | $R^{D11}$ | $R^{D42}$ | H |
| $L_{C307}$ | $R^{D11}$ | $R^{D64}$ | H |
| $L_{C308}$ | $R^{D11}$ | $R^{D66}$ | H |
| $L_{C309}$ | $R^{D11}$ | $R^{D68}$ | H |
| $L_{C310}$ | $R^{D11}$ | $R^{D76}$ | H |
| $L_{C311}$ | $R^{D13}$ | $R^{D5}$ | H |
| $L_{C312}$ | $R^{D13}$ | $R^{D6}$ | H |
| $L_{C313}$ | $R^{D13}$ | $R^{D9}$ | H |
| $L_{C314}$ | $R^{D13}$ | $R^{D10}$ | H |
| $L_{C315}$ | $R^{D13}$ | $R^{D12}$ | H |
| $L_{C316}$ | $R^{D13}$ | $R^{D14}$ | H |
| $L_{C317}$ | $R^{D13}$ | $R^{D15}$ | H |
| $L_{C318}$ | $R^{D13}$ | $R^{D16}$ | H |
| $L_{C319}$ | $R^{D13}$ | $R^{D17}$ | H |
| $L_{C320}$ | $R^{D13}$ | $R^{D18}$ | H |
| $L_{C321}$ | $R^{D13}$ | $R^{D19}$ | H |
| $L_{C322}$ | $R^{D13}$ | $R^{D20}$ | H |
| $L_{C323}$ | $R^{D13}$ | $R^{D21}$ | H |
| $L_{C324}$ | $R^{D13}$ | $R^{D22}$ | H |
| $L_{C325}$ | $R^{D13}$ | $R^{D23}$ | H |
| $L_{C326}$ | $R^{D13}$ | $R^{D24}$ | H |
| $L_{C327}$ | $R^{D13}$ | $R^{D25}$ | H |
| $L_{C328}$ | $R^{D13}$ | $R^{D26}$ | H |
| $L_{C329}$ | $R^{D13}$ | $R^{D27}$ | H |
| $L_{C330}$ | $R^{D13}$ | $R^{D28}$ | H |
| $L_{C331}$ | $R^{D13}$ | $R^{D29}$ | H |
| $L_{C332}$ | $R^{D13}$ | $R^{D30}$ | H |
| $L_{C333}$ | $R^{D13}$ | $R^{D31}$ | H |
| $L_{C334}$ | $R^{D13}$ | $R^{D32}$ | H |
| $L_{C335}$ | $R^{D13}$ | $R^{D33}$ | H |
| $L_{C336}$ | $R^{D13}$ | $R^{D34}$ | H |
| $L_{C337}$ | $R^{D13}$ | $R^{D35}$ | H |
| $L_{C338}$ | $R^{D13}$ | $R^{D40}$ | H |
| $L_{C339}$ | $R^{D13}$ | $R^{D41}$ | H |

-continued

| Ligand | $R^1$ | $R^2$ | $R^3$ |
|---|---|---|---|
| $L_{C340}$ | $R^{D13}$ | $R^{D42}$ | H |
| $L_{C341}$ | $R^{D13}$ | $R^{D64}$ | H |
| $L_{C342}$ | $R^{D13}$ | $R^{D66}$ | H |
| $L_{C343}$ | $R^{D13}$ | $R^{D68}$ | H |
| $L_{C344}$ | $R^{D13}$ | $R^{D76}$ | H |
| $L_{C345}$ | $R^{D14}$ | $R^{D5}$ | H |
| $L_{C346}$ | $R^{D14}$ | $R^{D6}$ | H |
| $L_{C347}$ | $R^{D14}$ | $R^{D9}$ | H |
| $L_{C348}$ | $R^{D14}$ | $R^{D10}$ | H |
| $L_{C349}$ | $R^{D14}$ | $R^{D12}$ | H |
| $L_{C350}$ | $R^{D14}$ | $R^{D15}$ | H |
| $L_{C351}$ | $R^{D14}$ | $R^{D16}$ | H |
| $L_{C352}$ | $R^{D14}$ | $R^{D17}$ | H |
| $L_{C353}$ | $R^{D14}$ | $R^{D18}$ | H |
| $L_{C354}$ | $R^{D14}$ | $R^{D19}$ | H |
| $L_{C355}$ | $R^{D14}$ | $R^{D20}$ | H |
| $L_{C356}$ | $R^{D14}$ | $R^{D21}$ | H |
| $L_{C357}$ | $R^{D14}$ | $R^{D22}$ | H |
| $L_{C358}$ | $R^{D14}$ | $R^{D23}$ | H |
| $L_{C359}$ | $R^{D14}$ | $R^{D24}$ | H |
| $L_{C360}$ | $R^{D14}$ | $R^{D25}$ | H |
| $L_{C361}$ | $R^{D14}$ | $R^{D26}$ | H |
| $L_{C362}$ | $R^{D14}$ | $R^{D27}$ | H |
| $L_{C363}$ | $R^{D14}$ | $R^{D28}$ | H |
| $L_{C364}$ | $R^{D14}$ | $R^{D29}$ | H |
| $L_{C365}$ | $R^{D14}$ | $R^{D30}$ | H |
| $L_{C366}$ | $R^{D14}$ | $R^{D31}$ | H |
| $L_{C367}$ | $R^{D14}$ | $R^{D32}$ | H |
| $L_{C368}$ | $R^{D14}$ | $R^{D33}$ | H |
| $L_{C369}$ | $R^{D14}$ | $R^{D34}$ | H |
| $L_{C370}$ | $R^{D14}$ | $R^{D35}$ | H |
| $L_{C371}$ | $R^{D14}$ | $R^{D40}$ | H |
| $L_{C372}$ | $R^{D14}$ | $R^{D41}$ | H |
| $L_{C373}$ | $R^{D14}$ | $R^{D42}$ | H |
| $L_{C374}$ | $R^{D14}$ | $R^{D64}$ | H |
| $L_{C375}$ | $R^{D14}$ | $R^{D66}$ | H |
| $L_{C376}$ | $R^{D14}$ | $R^{D68}$ | H |
| $L_{C377}$ | $R^{D14}$ | $R^{D76}$ | H |
| $L_{C378}$ | $R^{D22}$ | $R^{D5}$ | H |
| $L_{C379}$ | $R^{D22}$ | $R^{D6}$ | H |
| $L_{C380}$ | $R^{D22}$ | $R^{D9}$ | H |
| $L_{C381}$ | $R^{D22}$ | $R^{D10}$ | H |
| $L_{C382}$ | $R^{D22}$ | $R^{D12}$ | H |
| $L_{C383}$ | $R^{D22}$ | $R^{D15}$ | H |
| $L_{C384}$ | $R^{D22}$ | $R^{D16}$ | H |
| $L_{C385}$ | $R^{D22}$ | $R^{D17}$ | H |
| $L_{C386}$ | $R^{D22}$ | $R^{D18}$ | H |
| $L_{C387}$ | $R^{D22}$ | $R^{D19}$ | H |
| $L_{C388}$ | $R^{D22}$ | $R^{D20}$ | H |
| $L_{C389}$ | $R^{D22}$ | $R^{D21}$ | H |
| $L_{C390}$ | $R^{D22}$ | $R^{D23}$ | H |
| $L_{C391}$ | $R^{D22}$ | $R^{D24}$ | H |
| $L_{C392}$ | $R^{D22}$ | $R^{D25}$ | H |
| $L_{C393}$ | $R^{D22}$ | $R^{D26}$ | H |
| $L_{C394}$ | $R^{D22}$ | $R^{D27}$ | H |
| $L_{C395}$ | $R^{D22}$ | $R^{D28}$ | H |
| $L_{C396}$ | $R^{D22}$ | $R^{D29}$ | H |
| $L_{C397}$ | $R^{D22}$ | $R^{D30}$ | H |
| $L_{C398}$ | $R^{D22}$ | $R^{D31}$ | H |
| $L_{C399}$ | $R^{D22}$ | $R^{D32}$ | H |
| $L_{C400}$ | $R^{D22}$ | $R^{D33}$ | H |
| $L_{C401}$ | $R^{D22}$ | $R^{D34}$ | H |
| $L_{C402}$ | $R^{D22}$ | $R^{D35}$ | H |
| $L_{C403}$ | $R^{D22}$ | $R^{D40}$ | H |
| $L_{C404}$ | $R^{D22}$ | $R^{D41}$ | H |
| $L_{C405}$ | $R^{D22}$ | $R^{D42}$ | H |
| $L_{C406}$ | $R^{D22}$ | $R^{D64}$ | H |
| $L_{C407}$ | $R^{D22}$ | $R^{D66}$ | H |
| $L_{C408}$ | $R^{D22}$ | $R^{D68}$ | H |
| $L_{C409}$ | $R^{D22}$ | $R^{D76}$ | H |
| $L_{C410}$ | $R^{D26}$ | $R^{D5}$ | H |
| $L_{C411}$ | $R^{D26}$ | $R^{D6}$ | H |
| $L_{C412}$ | $R^{D26}$ | $R^{D9}$ | H |
| $L_{C413}$ | $R^{D26}$ | $R^{D10}$ | H |
| $L_{C414}$ | $R^{D26}$ | $R^{D12}$ | H |
| $L_{C415}$ | $R^{D26}$ | $R^{D15}$ | H |
| $L_{C416}$ | $R^{D26}$ | $R^{D16}$ | H |

-continued

| Ligand | $R^1$ | $R^2$ | $R^3$ |
|---|---|---|---|
| $L_{C417}$ | $R^{D26}$ | $R^{D17}$ | H |
| $L_{C418}$ | $R^{D26}$ | $R^{D18}$ | H |
| $L_{C419}$ | $R^{D26}$ | $R^{D19}$ | H |
| $L_{C420}$ | $R^{D26}$ | $R^{D20}$ | H |
| $L_{C421}$ | $R^{D26}$ | $R^{D21}$ | H |
| $L_{C422}$ | $R^{D26}$ | $R^{D23}$ | H |
| $L_{C423}$ | $R^{D26}$ | $R^{D24}$ | H |
| $L_{C424}$ | $R^{D26}$ | $R^{D25}$ | H |
| $L_{C425}$ | $R^{D26}$ | $R^{D27}$ | H |
| $L_{C426}$ | $R^{D26}$ | $R^{D28}$ | H |
| $L_{C427}$ | $R^{D26}$ | $R^{D29}$ | H |
| $L_{C428}$ | $R^{D26}$ | $R^{D30}$ | H |
| $L_{C429}$ | $R^{D26}$ | $R^{D31}$ | H |
| $L_{C430}$ | $R^{D26}$ | $R^{D32}$ | H |
| $L_{C431}$ | $R^{D26}$ | $R^{D33}$ | H |
| $L_{C432}$ | $R^{D26}$ | $R^{D34}$ | H |
| $L_{C433}$ | $R^{D26}$ | $R^{D35}$ | H |
| $L_{C434}$ | $R^{D26}$ | $R^{D40}$ | H |
| $L_{C435}$ | $R^{D26}$ | $R^{D41}$ | H |
| $L_{C436}$ | $R^{D26}$ | $R^{D42}$ | H |
| $L_{C437}$ | $R^{D26}$ | $R^{D64}$ | H |
| $L_{C438}$ | $R^{D26}$ | $R^{D66}$ | H |
| $L_{C439}$ | $R^{D26}$ | $R^{D68}$ | H |
| $L_{C440}$ | $R^{D26}$ | $R^{D76}$ | H |
| $L_{C441}$ | $R^{D35}$ | $R^{D5}$ | H |
| $L_{C442}$ | $R^{D35}$ | $R^{D6}$ | H |
| $L_{C443}$ | $R^{D35}$ | $R^{D9}$ | H |
| $L_{C444}$ | $R^{D35}$ | $R^{D10}$ | H |
| $L_{C445}$ | $R^{D35}$ | $R^{D12}$ | H |
| $L_{C446}$ | $R^{D35}$ | $R^{D15}$ | H |
| $L_{C447}$ | $R^{D35}$ | $R^{D16}$ | H |
| $L_{C448}$ | $R^{D35}$ | $R^{D17}$ | H |
| $L_{C449}$ | $R^{D35}$ | $R^{D18}$ | H |
| $L_{C450}$ | $R^{D35}$ | $R^{D19}$ | H |
| $L_{C451}$ | $R^{D35}$ | $R^{D20}$ | H |
| $L_{C452}$ | $R^{D35}$ | $R^{D21}$ | H |
| $L_{C453}$ | $R^{D35}$ | $R^{D23}$ | H |
| $L_{C454}$ | $R^{D35}$ | $R^{D24}$ | H |
| $L_{C455}$ | $R^{D35}$ | $R^{D25}$ | H |
| $L_{C456}$ | $R^{D35}$ | $R^{D27}$ | H |
| $L_{C457}$ | $R^{D35}$ | $R^{D28}$ | H |
| $L_{C458}$ | $R^{D35}$ | $R^{D29}$ | H |
| $L_{C459}$ | $R^{D35}$ | $R^{D30}$ | H |
| $L_{C460}$ | $R^{D35}$ | $R^{D31}$ | H |
| $L_{C461}$ | $R^{D35}$ | $R^{D32}$ | H |
| $L_{C462}$ | $R^{D35}$ | $R^{D33}$ | H |
| $L_{C463}$ | $R^{D35}$ | $R^{D34}$ | H |
| $L_{C464}$ | $R^{D35}$ | $R^{D40}$ | H |
| $L_{C465}$ | $R^{D35}$ | $R^{D41}$ | H |
| $L_{C466}$ | $R^{D35}$ | $R^{D42}$ | H |
| $L_{C467}$ | $R^{D35}$ | $R^{D64}$ | H |
| $L_{C468}$ | $R^{D35}$ | $R^{D66}$ | H |
| $L_{C469}$ | $R^{D35}$ | $R^{D68}$ | H |
| $L_{C470}$ | $R^{D35}$ | $R^{D76}$ | H |
| $L_{C471}$ | $R^{D40}$ | $R^{D5}$ | H |
| $L_{C472}$ | $R^{D40}$ | $R^{D6}$ | H |
| $L_{C473}$ | $R^{D40}$ | $R^{D9}$ | H |
| $L_{C474}$ | $R^{D40}$ | $R^{D10}$ | H |
| $L_{C475}$ | $R^{D40}$ | $R^{D12}$ | H |
| $L_{C476}$ | $R^{D40}$ | $R^{D15}$ | H |
| $L_{C477}$ | $R^{D40}$ | $R^{D16}$ | H |
| $L_{C478}$ | $R^{D40}$ | $R^{D17}$ | H |
| $L_{C479}$ | $R^{D40}$ | $R^{D18}$ | H |
| $L_{C480}$ | $R^{D40}$ | $R^{D19}$ | H |
| $L_{C481}$ | $R^{D40}$ | $R^{D20}$ | H |
| $L_{C482}$ | $R^{D40}$ | $R^{D21}$ | H |
| $L_{C483}$ | $R^{D40}$ | $R^{D23}$ | H |
| $L_{C484}$ | $R^{D40}$ | $R^{D24}$ | H |
| $L_{C485}$ | $R^{D40}$ | $R^{D25}$ | H |
| $L_{C486}$ | $R^{D40}$ | $R^{D27}$ | H |
| $L_{C487}$ | $R^{D40}$ | $R^{D28}$ | H |
| $L_{C488}$ | $R^{D40}$ | $R^{D29}$ | H |
| $L_{C489}$ | $R^{D40}$ | $R^{D30}$ | H |
| $L_{C490}$ | $R^{D40}$ | $R^{D31}$ | H |
| $L_{C491}$ | $R^{D40}$ | $R^{D32}$ | H |
| $L_{C492}$ | $R^{D40}$ | $R^{D33}$ | H |
| $L_{C493}$ | $R^{D40}$ | $R^{D34}$ | H |

-continued

| Ligand | $R^1$ | $R^2$ | $R^3$ |
|---|---|---|---|
| $L_{C494}$ | $R^{D40}$ | $R^{D41}$ | H |
| $L_{C495}$ | $R^{D40}$ | $R^{D42}$ | H |
| $L_{C496}$ | $R^{D40}$ | $R^{D64}$ | H |
| $L_{C497}$ | $R^{D40}$ | $R^{D66}$ | H |
| $L_{C498}$ | $R^{D40}$ | $R^{D68}$ | H |
| $L_{C499}$ | $R^{D40}$ | $R^{D76}$ | H |
| $L_{C500}$ | $R^{D41}$ | $R^{D5}$ | H |
| $L_{C501}$ | $R^{D41}$ | $R^{D6}$ | H |
| $L_{C502}$ | $R^{D41}$ | $R^{D9}$ | H |
| $L_{C503}$ | $R^{D41}$ | $R^{D10}$ | H |
| $L_{C504}$ | $R^{D41}$ | $R^{D12}$ | H |
| $L_{C505}$ | $R^{D41}$ | $R^{D15}$ | H |
| $L_{C506}$ | $R^{D41}$ | $R^{D16}$ | H |
| $L_{C507}$ | $R^{D41}$ | $R^{D17}$ | H |
| $L_{C508}$ | $R^{D41}$ | $R^{D18}$ | H |
| $L_{C509}$ | $R^{D41}$ | $R^{D19}$ | H |
| $L_{C510}$ | $R^{D41}$ | $R^{D20}$ | H |
| $L_{C511}$ | $R^{D41}$ | $R^{D21}$ | H |
| $L_{C512}$ | $R^{D41}$ | $R^{D23}$ | H |
| $L_{C513}$ | $R^{D41}$ | $R^{D24}$ | H |
| $L_{C514}$ | $R^{D41}$ | $R^{D25}$ | H |
| $L_{C515}$ | $R^{D41}$ | $R^{D27}$ | H |
| $L_{C516}$ | $R^{D41}$ | $R^{D28}$ | H |
| $L_{C517}$ | $R^{D41}$ | $R^{D29}$ | H |
| $L_{C518}$ | $R^{D41}$ | $R^{D30}$ | H |
| $L_{C519}$ | $R^{D41}$ | $R^{D31}$ | H |
| $L_{C520}$ | $R^{D41}$ | $R^{D32}$ | H |
| $L_{C521}$ | $R^{D41}$ | $R^{D33}$ | H |
| $L_{C522}$ | $R^{D41}$ | $R^{D34}$ | H |
| $L_{C523}$ | $R^{D41}$ | $R^{D42}$ | H |
| $L_{C524}$ | $R^{D41}$ | $R^{D64}$ | H |
| $L_{C525}$ | $R^{D41}$ | $R^{D66}$ | H |
| $L_{C526}$ | $R^{D41}$ | $R^{D68}$ | H |
| $L_{C527}$ | $R^{D41}$ | $R^{D76}$ | H |
| $L_{C528}$ | $R^{D64}$ | $R^{D5}$ | H |
| $L_{C529}$ | $R^{D64}$ | $R^{D6}$ | H |
| $L_{C530}$ | $R^{D64}$ | $R^{D9}$ | H |
| $L_{C531}$ | $R^{D64}$ | $R^{D10}$ | H |
| $L_{C532}$ | $R^{D64}$ | $R^{D12}$ | H |
| $L_{C533}$ | $R^{D64}$ | $R^{D15}$ | H |
| $L_{C534}$ | $R^{D64}$ | $R^{D16}$ | H |
| $L_{C535}$ | $R^{D64}$ | $R^{D17}$ | H |
| $L_{C536}$ | $R^{D64}$ | $R^{D18}$ | H |
| $L_{C537}$ | $R^{D64}$ | $R^{D19}$ | H |
| $L_{C538}$ | $R^{D64}$ | $R^{D20}$ | H |
| $L_{C539}$ | $R^{D64}$ | $R^{D21}$ | H |
| $L_{C540}$ | $R^{D64}$ | $R^{D23}$ | H |
| $L_{C541}$ | $R^{D64}$ | $R^{D24}$ | H |
| $L_{C542}$ | $R^{D64}$ | $R^{D25}$ | H |
| $L_{C543}$ | $R^{D64}$ | $R^{D27}$ | H |
| $L_{C544}$ | $R^{D64}$ | $R^{D28}$ | H |
| $L_{C545}$ | $R^{D64}$ | $R^{D29}$ | H |
| $L_{C546}$ | $R^{D64}$ | $R^{D30}$ | H |
| $L_{C547}$ | $R^{D64}$ | $R^{D31}$ | H |
| $L_{C548}$ | $R^{D64}$ | $R^{D32}$ | H |
| $L_{C549}$ | $R^{D64}$ | $R^{D33}$ | H |
| $L_{C550}$ | $R^{D64}$ | $R^{D34}$ | H |
| $L_{C551}$ | $R^{D64}$ | $R^{D42}$ | H |
| $L_{C552}$ | $R^{D64}$ | $R^{D64}$ | H |
| $L_{C553}$ | $R^{D64}$ | $R^{D66}$ | H |
| $L_{C554}$ | $R^{D64}$ | $R^{D68}$ | H |
| $L_{C555}$ | $R^{D64}$ | $R^{D76}$ | H |
| $L_{C556}$ | $R^{D66}$ | $R^{D5}$ | H |
| $L_{C557}$ | $R^{D66}$ | $R^{D6}$ | H |
| $L_{C558}$ | $R^{D66}$ | $R^{D9}$ | H |
| $L_{C559}$ | $R^{D66}$ | $R^{D10}$ | H |
| $L_{C560}$ | $R^{D66}$ | $R^{D12}$ | H |
| $L_{C561}$ | $R^{D66}$ | $R^{D15}$ | H |
| $L_{C562}$ | $R^{D66}$ | $R^{D16}$ | H |
| $L_{C563}$ | $R^{D66}$ | $R^{D17}$ | H |
| $L_{C564}$ | $R^{D66}$ | $R^{D18}$ | H |
| $L_{C565}$ | $R^{D66}$ | $R^{D19}$ | H |
| $L_{C566}$ | $R^{D66}$ | $R^{D20}$ | H |
| $L_{C567}$ | $R^{D66}$ | $R^{D21}$ | H |
| $L_{C568}$ | $R^{D66}$ | $R^{D23}$ | H |
| $L_{C569}$ | $R^{D66}$ | $R^{D24}$ | H |
| $L_{C570}$ | $R^{D66}$ | $R^{D25}$ | H |

-continued

| Ligand | $R^1$ | $R^2$ | $R^3$ |
|---|---|---|---|
| $L_{C571}$ | $R^{D66}$ | $R^{D27}$ | H |
| $L_{C572}$ | $R^{D66}$ | $R^{D28}$ | H |
| $L_{C573}$ | $R^{D66}$ | $R^{D29}$ | H |
| $L_{C574}$ | $R^{D66}$ | $R^{D30}$ | H |
| $L_{C575}$ | $R^{D66}$ | $R^{D31}$ | H |
| $L_{C576}$ | $R^{D66}$ | $R^{D32}$ | H |
| $L_{C577}$ | $R^{D66}$ | $R^{D33}$ | H |
| $L_{C578}$ | $R^{D66}$ | $R^{D34}$ | H |
| $L_{C579}$ | $R^{D66}$ | $R^{D42}$ | H |
| $L_{C580}$ | $R^{D66}$ | $R^{D68}$ | H |
| $L_{C581}$ | $R^{D66}$ | $R^{D76}$ | H |
| $L_{C582}$ | $R^{D68}$ | $R^{D5}$ | H |
| $L_{C583}$ | $R^{D68}$ | $R^{D6}$ | H |
| $L_{C584}$ | $R^{D68}$ | $R^{D9}$ | H |
| $L_{C585}$ | $R^{D68}$ | $R^{D10}$ | H |
| $L_{C586}$ | $R^{D68}$ | $R^{D12}$ | H |
| $L_{C587}$ | $R^{D68}$ | $R^{D15}$ | H |
| $L_{C588}$ | $R^{D68}$ | $R^{D16}$ | H |
| $L_{C589}$ | $R^{D68}$ | $R^{D17}$ | H |
| $L_{C590}$ | $R^{D68}$ | $R^{D18}$ | H |
| $L_{C591}$ | $R^{D68}$ | $R^{D19}$ | H |
| $L_{C592}$ | $R^{D68}$ | $R^{D20}$ | H |
| $L_{C593}$ | $R^{D68}$ | $R^{D21}$ | H |
| $L_{C594}$ | $R^{D68}$ | $R^{D23}$ | H |
| $L_{C595}$ | $R^{D68}$ | $R^{D24}$ | H |
| $L_{C596}$ | $R^{D68}$ | $R^{D25}$ | H |
| $L_{C597}$ | $R^{D68}$ | $R^{D27}$ | H |
| $L_{C598}$ | $R^{D68}$ | $R^{D28}$ | H |
| $L_{C599}$ | $R^{D68}$ | $R^{D29}$ | H |
| $L_{C600}$ | $R^{D68}$ | $R^{D30}$ | H |
| $L_{C601}$ | $R^{D68}$ | $R^{D31}$ | H |
| $L_{C602}$ | $R^{D68}$ | $R^{D32}$ | H |
| $L_{C603}$ | $R^{D68}$ | $R^{D33}$ | H |
| $L_{C604}$ | $R^{D68}$ | $R^{D34}$ | H |
| $L_{C605}$ | $R^{D68}$ | $R^{D42}$ | H |
| $L_{C606}$ | $R^{D68}$ | $R^{D76}$ | H |
| $L_{C607}$ | $R^{D76}$ | $R^{D5}$ | H |
| $L_{C608}$ | $R^{D76}$ | $R^{D6}$ | H |
| $L_{C609}$ | $R^{D76}$ | $R^{D9}$ | H |
| $L_{C610}$ | $R^{D76}$ | $R^{D10}$ | H |
| $L_{C611}$ | $R^{D76}$ | $R^{D12}$ | H |
| $L_{C612}$ | $R^{D76}$ | $R^{D15}$ | H |
| $L_{C613}$ | $R^{D76}$ | $R^{D16}$ | H |
| $L_{C614}$ | $R^{D76}$ | $R^{D17}$ | H |
| $L_{C615}$ | $R^{D76}$ | $R^{D18}$ | H |
| $L_{C616}$ | $R^{D76}$ | $R^{D19}$ | H |
| $L_{C617}$ | $R^{D76}$ | $R^{D20}$ | H |
| $L_{C618}$ | $R^{D76}$ | $R^{D21}$ | H |
| $L_{C619}$ | $R^{D76}$ | $R^{D23}$ | H |
| $L_{C620}$ | $R^{D76}$ | $R^{D24}$ | H |
| $L_{C621}$ | $R^{D76}$ | $R^{D25}$ | H |
| $L_{C622}$ | $R^{D76}$ | $R^{D27}$ | H |
| $L_{C623}$ | $R^{D76}$ | $R^{D28}$ | H |
| $L_{C624}$ | $R^{D76}$ | $R^{D29}$ | H |
| $L_{C625}$ | $R^{D76}$ | $R^{D30}$ | H |
| $L_{C626}$ | $R^{D76}$ | $R^{D31}$ | H |
| $L_{C627}$ | $R^{D76}$ | $R^{D32}$ | H |
| $L_{C628}$ | $R^{D76}$ | $R^{D33}$ | H |
| $L_{C629}$ | $R^{D76}$ | $R^{D34}$ | H |
| $L_{C630}$ | $R^{D76}$ | $R^{D42}$ | H |
| $L_{C631}$ | $R^{D1}$ | $R^{D1}$ | $R^{D1}$ |
| $L_{C632}$ | $R^{D2}$ | $R^{D2}$ | $R^{D1}$ |
| $L_{C633}$ | $R^{D3}$ | $R^{D3}$ | $R^{D1}$ |
| $L_{C634}$ | $R^{D4}$ | $R^{D4}$ | $R^{D1}$ |
| $L_{C635}$ | $R^{D5}$ | $R^{D5}$ | $R^{D1}$ |
| $L_{C636}$ | $R^{D6}$ | $R^{D6}$ | $R^{D1}$ |
| $L_{C637}$ | $R^{D7}$ | $R^{D7}$ | $R^{D1}$ |
| $L_{C638}$ | $R^{D8}$ | $R^{D8}$ | $R^{D1}$ |
| $L_{C639}$ | $R^{D9}$ | $R^{D9}$ | $R^{D1}$ |
| $L_{C640}$ | $R^{D10}$ | $R^{D10}$ | $R^{D1}$ |
| $L_{C641}$ | $R^{D11}$ | $R^{D11}$ | $R^{D1}$ |
| $L_{C642}$ | $R^{D12}$ | $R^{D12}$ | $R^{D1}$ |
| $L_{C643}$ | $R^{D13}$ | $R^{D13}$ | $R^{D1}$ |
| $L_{C644}$ | $R^{D14}$ | $R^{D14}$ | $R^{D1}$ |
| $L_{C645}$ | $R^{D15}$ | $R^{D15}$ | $R^{D1}$ |
| $L_{C646}$ | $R^{D16}$ | $R^{D16}$ | $R^{D1}$ |
| $L_{C647}$ | $R^{D17}$ | $R^{D17}$ | $R^{D1}$ |

-continued

| Ligand | $R^1$ | $R^2$ | $R^3$ |
|---|---|---|---|
| $L_{C648}$ | $R^{D18}$ | $R^{D18}$ | $R^{D1}$ |
| $L_{C649}$ | $R^{D19}$ | $R^{D19}$ | $R^{D1}$ |
| $L_{C650}$ | $R^{D20}$ | $R^{D20}$ | $R^{D1}$ |
| $L_{C651}$ | $R^{D21}$ | $R^{D21}$ | $R^{D1}$ |
| $L_{C652}$ | $R^{D22}$ | $R^{D22}$ | $R^{D1}$ |
| $L_{C653}$ | $R^{D23}$ | $R^{D23}$ | $R^{D1}$ |
| $L_{C654}$ | $R^{D24}$ | $R^{D24}$ | $R^{D1}$ |
| $L_{C655}$ | $R^{D25}$ | $R^{D25}$ | $R^{D1}$ |
| $L_{C656}$ | $R^{D26}$ | $R^{D26}$ | $R^{D1}$ |
| $L_{C657}$ | $R^{D27}$ | $R^{D27}$ | $R^{D1}$ |
| $L_{C658}$ | $R^{D28}$ | $R^{D28}$ | $R^{D1}$ |
| $L_{C659}$ | $R^{D29}$ | $R^{D29}$ | $R^{D1}$ |
| $L_{C660}$ | $R^{D30}$ | $R^{D30}$ | $R^{D1}$ |
| $L_{C661}$ | $R^{D31}$ | $R^{D31}$ | $R^{D1}$ |
| $L_{C662}$ | $R^{D32}$ | $R^{D32}$ | $R^{D1}$ |
| $L_{C663}$ | $R^{D33}$ | $R^{D33}$ | $R^{D1}$ |
| $L_{C664}$ | $R^{D34}$ | $R^{D34}$ | $R^{D1}$ |
| $L_{C665}$ | $R^{D35}$ | $R^{D35}$ | $R^{D1}$ |
| $L_{C666}$ | $R^{D40}$ | $R^{D40}$ | $R^{D1}$ |
| $L_{C667}$ | $R^{D41}$ | $R^{D41}$ | $R^{D1}$ |
| $L_{C668}$ | $R^{D42}$ | $R^{D42}$ | $R^{D1}$ |
| $L_{C669}$ | $R^{D64}$ | $R^{D64}$ | $R^{D1}$ |
| $L_{C670}$ | $R^{D66}$ | $R^{D66}$ | $R^{D1}$ |
| $L_{C671}$ | $R^{D68}$ | $R^{D68}$ | $R^{D1}$ |
| $L_{C672}$ | $R^{D76}$ | $R^{D76}$ | $R^{D1}$ |
| $L_{C673}$ | $R^{D1}$ | $R^{D2}$ | $R^{D1}$ |
| $L_{C674}$ | $R^{D1}$ | $R^{D3}$ | $R^{D1}$ |
| $L_{C675}$ | $R^{D1}$ | $R^{D4}$ | $R^{D1}$ |
| $L_{C676}$ | $R^{D1}$ | $R^{D5}$ | $R^{D1}$ |
| $L_{C677}$ | $R^{D1}$ | $R^{D6}$ | $R^{D1}$ |
| $L_{C678}$ | $R^{D1}$ | $R^{D7}$ | $R^{D1}$ |
| $L_{C679}$ | $R^{D1}$ | $R^{D8}$ | $R^{D1}$ |
| $L_{C680}$ | $R^{D1}$ | $R^{D9}$ | $R^{D1}$ |
| $L_{C681}$ | $R^{D1}$ | $R^{D10}$ | $R^{D1}$ |
| $L_{C682}$ | $R^{D1}$ | $R^{D11}$ | $R^{D1}$ |
| $L_{C683}$ | $R^{D1}$ | $R^{D12}$ | $R^{D1}$ |
| $L_{C684}$ | $R^{D1}$ | $R^{D13}$ | $R^{D1}$ |
| $L_{C685}$ | $R^{D1}$ | $R^{D14}$ | $R^{D1}$ |
| $L_{C686}$ | $R^{D1}$ | $R^{D15}$ | $R^{D1}$ |
| $L_{C687}$ | $R^{D1}$ | $R^{D16}$ | $R^{D1}$ |
| $L_{C688}$ | $R^{D1}$ | $R^{D17}$ | $R^{D1}$ |
| $L_{C689}$ | $R^{D1}$ | $R^{D18}$ | $R^{D1}$ |
| $L_{C690}$ | $R^{D1}$ | $R^{D19}$ | $R^{D1}$ |
| $L_{C691}$ | $R^{D1}$ | $R^{D20}$ | $R^{D1}$ |
| $L_{C692}$ | $R^{D1}$ | $R^{D21}$ | $R^{D1}$ |
| $L_{C693}$ | $R^{D1}$ | $R^{D22}$ | $R^{D1}$ |
| $L_{C694}$ | $R^{D1}$ | $R^{D23}$ | $R^{D1}$ |
| $L_{C695}$ | $R^{D1}$ | $R^{D24}$ | $R^{D1}$ |
| $L_{C696}$ | $R^{D1}$ | $R^{D25}$ | $R^{D1}$ |
| $L_{C697}$ | $R^{D1}$ | $R^{D26}$ | $R^{D1}$ |
| $L_{C698}$ | $R^{D1}$ | $R^{D27}$ | $R^{D1}$ |
| $L_{C699}$ | $R^{D1}$ | $R^{D28}$ | $R^{D1}$ |
| $L_{C700}$ | $R^{D1}$ | $R^{D29}$ | $R^{D1}$ |
| $L_{C701}$ | $R^{D1}$ | $R^{D30}$ | $R^{D1}$ |
| $L_{C702}$ | $R^{D1}$ | $R^{D31}$ | $R^{D1}$ |
| $L_{C703}$ | $R^{D1}$ | $R^{D32}$ | $R^{D1}$ |
| $L_{C704}$ | $R^{D1}$ | $R^{D33}$ | $R^{D1}$ |
| $L_{C705}$ | $R^{D1}$ | $R^{D34}$ | $R^{D1}$ |
| $L_{C706}$ | $R^{D1}$ | $R^{D35}$ | $R^{D1}$ |
| $L_{C707}$ | $R^{D1}$ | $R^{D40}$ | $R^{D1}$ |
| $L_{C708}$ | $R^{D1}$ | $R^{D41}$ | $R^{D1}$ |
| $L_{C709}$ | $R^{D1}$ | $R^{D42}$ | $R^{D1}$ |
| $L_{C710}$ | $R^{D1}$ | $R^{D64}$ | $R^{D1}$ |
| $L_{C711}$ | $R^{D1}$ | $R^{D66}$ | $R^{D1}$ |
| $L_{C712}$ | $R^{D1}$ | $R^{D68}$ | $R^{D1}$ |
| $L_{C713}$ | $R^{D1}$ | $R^{D76}$ | $R^{D1}$ |
| $L_{C714}$ | $R^{D2}$ | $R^{D1}$ | $R^{D1}$ |
| $L_{C715}$ | $R^{D2}$ | $R^{D3}$ | $R^{D1}$ |
| $L_{C716}$ | $R^{D2}$ | $R^{D4}$ | $R^{D1}$ |
| $L_{C717}$ | $R^{D2}$ | $R^{D5}$ | $R^{D1}$ |
| $L_{C718}$ | $R^{D2}$ | $R^{D6}$ | $R^{D1}$ |
| $L_{C719}$ | $R^{D2}$ | $R^{D7}$ | $R^{D1}$ |
| $L_{C720}$ | $R^{D2}$ | $R^{D8}$ | $R^{D1}$ |
| $L_{C721}$ | $R^{D2}$ | $R^{D9}$ | $R^{D1}$ |
| $L_{C722}$ | $R^{D2}$ | $R^{D10}$ | $R^{D1}$ |
| $L_{C723}$ | $R^{D2}$ | $R^{D11}$ | $R^{D1}$ |
| $L_{C724}$ | $R^{D2}$ | $R^{D12}$ | $R^{D1}$ |

-continued

| Ligand | $R^1$ | $R^2$ | $R^3$ |
|---|---|---|---|
| $L_{C725}$ | $R^{D2}$ | $R^{D13}$ | $R^{D1}$ |
| $L_{C726}$ | $R^{D2}$ | $R^{D14}$ | $R^{D1}$ |
| $L_{C727}$ | $R^{D2}$ | $R^{D15}$ | $R^{D1}$ |
| $L_{C728}$ | $R^{D2}$ | $R^{D16}$ | $R^{D1}$ |
| $L_{C729}$ | $R^{D2}$ | $R^{D17}$ | $R^{D1}$ |
| $L_{C730}$ | $R^{D2}$ | $R^{D18}$ | $R^{D1}$ |
| $L_{C731}$ | $R^{D2}$ | $R^{D19}$ | $R^{D1}$ |
| $L_{C732}$ | $R^{D2}$ | $R^{D20}$ | $R^{D1}$ |
| $L_{C733}$ | $R^{D2}$ | $R^{D21}$ | $R^{D1}$ |
| $L_{C734}$ | $R^{D2}$ | $R^{D22}$ | $R^{D1}$ |
| $L_{C735}$ | $R^{D2}$ | $R^{D23}$ | $R^{D1}$ |
| $L_{C736}$ | $R^{D2}$ | $R^{D24}$ | $R^{D1}$ |
| $L_{C737}$ | $R^{D2}$ | $R^{D25}$ | $R^{D1}$ |
| $L_{C738}$ | $R^{D2}$ | $R^{D26}$ | $R^{D1}$ |
| $L_{C739}$ | $R^{D2}$ | $R^{D27}$ | $R^{D1}$ |
| $L_{C740}$ | $R^{D2}$ | $R^{D28}$ | $R^{D1}$ |
| $L_{C741}$ | $R^{D2}$ | $R^{D29}$ | $R^{D1}$ |
| $L_{C742}$ | $R^{D2}$ | $R^{D30}$ | $R^{D1}$ |
| $L_{C743}$ | $R^{D2}$ | $R^{D31}$ | $R^{D1}$ |
| $L_{C744}$ | $R^{D2}$ | $R^{D32}$ | $R^{D1}$ |
| $L_{C745}$ | $R^{D2}$ | $R^{D33}$ | $R^{D1}$ |
| $L_{C746}$ | $R^{D2}$ | $R^{D34}$ | $R^{D1}$ |
| $L_{C747}$ | $R^{D2}$ | $R^{D35}$ | $R^{D1}$ |
| $L_{C748}$ | $R^{D2}$ | $R^{D40}$ | $R^{D1}$ |
| $L_{C749}$ | $R^{D2}$ | $R^{D41}$ | $R^{D1}$ |
| $L_{C750}$ | $R^{D2}$ | $R^{D42}$ | $R^{D1}$ |
| $L_{C751}$ | $R^{D2}$ | $R^{D64}$ | $R^{D1}$ |
| $L_{C752}$ | $R^{D2}$ | $R^{D66}$ | $R^{D1}$ |
| $L_{C753}$ | $R^{D2}$ | $R^{D68}$ | $R^{D1}$ |
| $L_{C754}$ | $R^{D2}$ | $R^{D76}$ | $R^{D1}$ |
| $L_{C755}$ | $R^{D3}$ | $R^{D4}$ | $R^{D1}$ |
| $L_{C756}$ | $R^{D3}$ | $R^{D5}$ | $R^{D1}$ |
| $L_{C757}$ | $R^{D3}$ | $R^{D6}$ | $R^{D1}$ |
| $L_{C758}$ | $R^{D3}$ | $R^{D7}$ | $R^{D1}$ |
| $L_{C759}$ | $R^{D3}$ | $R^{D8}$ | $R^{D1}$ |
| $L_{C760}$ | $R^{D3}$ | $R^{D9}$ | $R^{D1}$ |
| $L_{C761}$ | $R^{D3}$ | $R^{D10}$ | $R^{D1}$ |
| $L_{C762}$ | $R^{D3}$ | $R^{D11}$ | $R^{D1}$ |
| $L_{C763}$ | $R^{D3}$ | $R^{D12}$ | $R^{D1}$ |
| $L_{C764}$ | $R^{D3}$ | $R^{D13}$ | $R^{D1}$ |
| $L_{C765}$ | $R^{D3}$ | $R^{D14}$ | $R^{D1}$ |
| $L_{C766}$ | $R^{D3}$ | $R^{D15}$ | $R^{D1}$ |
| $L_{C767}$ | $R^{D3}$ | $R^{D16}$ | $R^{D1}$ |
| $L_{C768}$ | $R^{D3}$ | $R^{D17}$ | $R^{D1}$ |
| $L_{C769}$ | $R^{D3}$ | $R^{D18}$ | $R^{D1}$ |
| $L_{C770}$ | $R^{D3}$ | $R^{D19}$ | $R^{D1}$ |
| $L_{C771}$ | $R^{D3}$ | $R^{D20}$ | $R^{D1}$ |
| $L_{C772}$ | $R^{D3}$ | $R^{D21}$ | $R^{D1}$ |
| $L_{C773}$ | $R^{D3}$ | $R^{D22}$ | $R^{D1}$ |
| $L_{C774}$ | $R^{D3}$ | $R^{D23}$ | $R^{D1}$ |
| $L_{C775}$ | $R^{D3}$ | $R^{D24}$ | $R^{D1}$ |
| $L_{C776}$ | $R^{D3}$ | $R^{D25}$ | $R^{D1}$ |
| $L_{C777}$ | $R^{D3}$ | $R^{D26}$ | $R^{D1}$ |
| $L_{C778}$ | $R^{D3}$ | $R^{D27}$ | $R^{D1}$ |
| $L_{C779}$ | $R^{D3}$ | $R^{D28}$ | $R^{D1}$ |
| $L_{C780}$ | $R^{D3}$ | $R^{D29}$ | $R^{D1}$ |
| $L_{C781}$ | $R^{D3}$ | $R^{D30}$ | $R^{D1}$ |
| $L_{C782}$ | $R^{D3}$ | $R^{D31}$ | $R^{D1}$ |
| $L_{C783}$ | $R^{D3}$ | $R^{D32}$ | $R^{D1}$ |
| $L_{C784}$ | $R^{D3}$ | $R^{D33}$ | $R^{D1}$ |
| $L_{C785}$ | $R^{D3}$ | $R^{D34}$ | $R^{D1}$ |
| $L_{C786}$ | $R^{D3}$ | $R^{D35}$ | $R^{D1}$ |
| $L_{C787}$ | $R^{D3}$ | $R^{D40}$ | $R^{D1}$ |
| $L_{C788}$ | $R^{D3}$ | $R^{D41}$ | $R^{D1}$ |
| $L_{C789}$ | $R^{D3}$ | $R^{D42}$ | $R^{D1}$ |
| $L_{C790}$ | $R^{D3}$ | $R^{D64}$ | $R^{D1}$ |
| $L_{C791}$ | $R^{D3}$ | $R^{D66}$ | $R^{D1}$ |
| $L_{C792}$ | $R^{D3}$ | $R^{D68}$ | $R^{D1}$ |
| $L_{C793}$ | $R^{D3}$ | $R^{D76}$ | $R^{D1}$ |
| $L_{C794}$ | $R^{D4}$ | $R^{D5}$ | $R^{D1}$ |
| $L_{C795}$ | $R^{D4}$ | $R^{D6}$ | $R^{D1}$ |
| $L_{C796}$ | $R^{D4}$ | $R^{D7}$ | $R^{D1}$ |
| $L_{C797}$ | $R^{D4}$ | $R^{D8}$ | $R^{D1}$ |
| $L_{C798}$ | $R^{D4}$ | $R^{D9}$ | $R^{D1}$ |
| $L_{C799}$ | $R^{D4}$ | $R^{D10}$ | $R^{D1}$ |
| $L_{C800}$ | $R^{D4}$ | $R^{D11}$ | $R^{D1}$ |
| $L_{C801}$ | $R^{D4}$ | $R^{D12}$ | $R^{D1}$ |

-continued

| Ligand | $R^1$ | $R^2$ | $R^3$ |
|---|---|---|---|
| $L_{C802}$ | $R^{D4}$ | $R^{D13}$ | $R^{D1}$ |
| $L_{C803}$ | $R^{D4}$ | $R^{D14}$ | $R^{D1}$ |
| $L_{C804}$ | $R^{D4}$ | $R^{D15}$ | $R^{D1}$ |
| $L_{C805}$ | $R^{D4}$ | $R^{D16}$ | $R^{D1}$ |
| $L_{C806}$ | $R^{D4}$ | $R^{D17}$ | $R^{D1}$ |
| $L_{C807}$ | $R^{D4}$ | $R^{D18}$ | $R^{D1}$ |
| $L_{C808}$ | $R^{D4}$ | $R^{D19}$ | $R^{D1}$ |
| $L_{C809}$ | $R^{D4}$ | $R^{D20}$ | $R^{D1}$ |
| $L_{C810}$ | $R^{D4}$ | $R^{D21}$ | $R^{D1}$ |
| $L_{C811}$ | $R^{D4}$ | $R^{D22}$ | $R^{D1}$ |
| $L_{C812}$ | $R^{D4}$ | $R^{D23}$ | $R^{D1}$ |
| $L_{C813}$ | $R^{D4}$ | $R^{D24}$ | $R^{D1}$ |
| $L_{C814}$ | $R^{D4}$ | $R^{D25}$ | $R^{D1}$ |
| $L_{C815}$ | $R^{D4}$ | $R^{D26}$ | $R^{D1}$ |
| $L_{C816}$ | $R^{D4}$ | $R^{D27}$ | $R^{D1}$ |
| $L_{C817}$ | $R^{D4}$ | $R^{D28}$ | $R^{D1}$ |
| $L_{C818}$ | $R^{D4}$ | $R^{D29}$ | $R^{D1}$ |
| $L_{C819}$ | $R^{D4}$ | $R^{D30}$ | $R^{D1}$ |
| $L_{C820}$ | $R^{D4}$ | $R^{D31}$ | $R^{D1}$ |
| $L_{C821}$ | $R^{D4}$ | $R^{D32}$ | $R^{D1}$ |
| $L_{C822}$ | $R^{D4}$ | $R^{D33}$ | $R^{D1}$ |
| $L_{C823}$ | $R^{D4}$ | $R^{D34}$ | $R^{D1}$ |
| $L_{C824}$ | $R^{D4}$ | $R^{D35}$ | $R^{D1}$ |
| $L_{C825}$ | $R^{D4}$ | $R^{D40}$ | $R^{D1}$ |
| $L_{C826}$ | $R^{D4}$ | $R^{D41}$ | $R^{D1}$ |
| $L_{C827}$ | $R^{D4}$ | $R^{D42}$ | $R^{D1}$ |
| $L_{C828}$ | $R^{D4}$ | $R^{D64}$ | $R^{D1}$ |
| $L_{C829}$ | $R^{D4}$ | $R^{D66}$ | $R^{D1}$ |
| $L_{C830}$ | $R^{D4}$ | $R^{D68}$ | $R^{D1}$ |
| $L_{C831}$ | $R^{D4}$ | $R^{D76}$ | $R^{D1}$ |
| $L_{C832}$ | $R^{D4}$ | $R^{D1}$ | $R^{D1}$ |
| $L_{C833}$ | $R^{D7}$ | $R^{D5}$ | $R^{D1}$ |
| $L_{C834}$ | $R^{D7}$ | $R^{D6}$ | $R^{D1}$ |
| $L_{C835}$ | $R^{D7}$ | $R^{D8}$ | $R^{D1}$ |
| $L_{C836}$ | $R^{D7}$ | $R^{D9}$ | $R^{D1}$ |
| $L_{C837}$ | $R^{D7}$ | $R^{D10}$ | $R^{D1}$ |
| $L_{C838}$ | $R^{D7}$ | $R^{D11}$ | $R^{D1}$ |
| $L_{C839}$ | $R^{D7}$ | $R^{D12}$ | $R^{D1}$ |
| $L_{C840}$ | $R^{D7}$ | $R^{D13}$ | $R^{D1}$ |
| $L_{C841}$ | $R^{D7}$ | $R^{D14}$ | $R^{D1}$ |
| $L_{C842}$ | $R^{D7}$ | $R^{D15}$ | $R^{D1}$ |
| $L_{C843}$ | $R^{D7}$ | $R^{D16}$ | $R^{D1}$ |
| $L_{C844}$ | $R^{D7}$ | $R^{D17}$ | $R^{D1}$ |
| $L_{C845}$ | $R^{D7}$ | $R^{D18}$ | $R^{D1}$ |
| $L_{C846}$ | $R^{D7}$ | $R^{D19}$ | $R^{D1}$ |
| $L_{C847}$ | $R^{D7}$ | $R^{D20}$ | $R^{D1}$ |
| $L_{C848}$ | $R^{D7}$ | $R^{D21}$ | $R^{D1}$ |
| $L_{C849}$ | $R^{D7}$ | $R^{D22}$ | $R^{D1}$ |
| $L_{C850}$ | $R^{D7}$ | $R^{D23}$ | $R^{D1}$ |
| $L_{C851}$ | $R^{D7}$ | $R^{D24}$ | $R^{D1}$ |
| $L_{C852}$ | $R^{D7}$ | $R^{D25}$ | $R^{D1}$ |
| $L_{C853}$ | $R^{D7}$ | $R^{D26}$ | $R^{D1}$ |
| $L_{C854}$ | $R^{D7}$ | $R^{D27}$ | $R^{D1}$ |
| $L_{C855}$ | $R^{D7}$ | $R^{D28}$ | $R^{D1}$ |
| $L_{C856}$ | $R^{D7}$ | $R^{D29}$ | $R^{D1}$ |
| $L_{C857}$ | $R^{D7}$ | $R^{D30}$ | $R^{D1}$ |
| $L_{C858}$ | $R^{D7}$ | $R^{D31}$ | $R^{D1}$ |
| $L_{C859}$ | $R^{D7}$ | $R^{D32}$ | $R^{D1}$ |
| $L_{C860}$ | $R^{D7}$ | $R^{D33}$ | $R^{D1}$ |
| $L_{C861}$ | $R^{D7}$ | $R^{D34}$ | $R^{D1}$ |
| $L_{C862}$ | $R^{D7}$ | $R^{D35}$ | $R^{D1}$ |
| $L_{C863}$ | $R^{D7}$ | $R^{D40}$ | $R^{D1}$ |
| $L_{C864}$ | $R^{D7}$ | $R^{D41}$ | $R^{D1}$ |
| $L_{C865}$ | $R^{D7}$ | $R^{D42}$ | $R^{D1}$ |
| $L_{C866}$ | $R^{D7}$ | $R^{D64}$ | $R^{D1}$ |
| $L_{C867}$ | $R^{D7}$ | $R^{D66}$ | $R^{D1}$ |
| $L_{C868}$ | $R^{D7}$ | $R^{D68}$ | $R^{D1}$ |
| $L_{C869}$ | $R^{D7}$ | $R^{D76}$ | $R^{D1}$ |
| $L_{C870}$ | $R^{D8}$ | $R^{D5}$ | $R^{D1}$ |
| $L_{C871}$ | $R^{D8}$ | $R^{D6}$ | $R^{D1}$ |
| $L_{C872}$ | $R^{D8}$ | $R^{D9}$ | $R^{D1}$ |
| $L_{C873}$ | $R^{D8}$ | $R^{D10}$ | $R^{D1}$ |
| $L_{C874}$ | $R^{D8}$ | $R^{D11}$ | $R^{D1}$ |
| $L_{C875}$ | $R^{D8}$ | $R^{D12}$ | $R^{D1}$ |
| $L_{C876}$ | $R^{D8}$ | $R^{D13}$ | $R^{D1}$ |
| $L_{C877}$ | $R^{D8}$ | $R^{D14}$ | $R^{D1}$ |
| $L_{C878}$ | $R^{D8}$ | $R^{D15}$ | $R^{D1}$ |

-continued

| Ligand | $R^1$ | $R^2$ | $R^3$ |
|---|---|---|---|
| $L_{C879}$ | $R^{D8}$ | $R^{D16}$ | $R^{D1}$ |
| $L_{C880}$ | $R^{D8}$ | $R^{D17}$ | $R^{D1}$ |
| $L_{C881}$ | $R^{D8}$ | $R^{D18}$ | $R^{D1}$ |
| $L_{C882}$ | $R^{D8}$ | $R^{D19}$ | $R^{D1}$ |
| $L_{C883}$ | $R^{D8}$ | $R^{D20}$ | $R^{D1}$ |
| $L_{C884}$ | $R^{D8}$ | $R^{D21}$ | $R^{D1}$ |
| $L_{C885}$ | $R^{D8}$ | $R^{D22}$ | $R^{D1}$ |
| $L_{C886}$ | $R^{D8}$ | $R^{D23}$ | $R^{D1}$ |
| $L_{C887}$ | $R^{D8}$ | $R^{D24}$ | $R^{D1}$ |
| $L_{C888}$ | $R^{D8}$ | $R^{D25}$ | $R^{D1}$ |
| $L_{C889}$ | $R^{D8}$ | $R^{D26}$ | $R^{D1}$ |
| $L_{C890}$ | $R^{D8}$ | $R^{D27}$ | $R^{D1}$ |
| $L_{C891}$ | $R^{D8}$ | $R^{D28}$ | $R^{D1}$ |
| $L_{C892}$ | $R^{D8}$ | $R^{D29}$ | $R^{D1}$ |
| $L_{C893}$ | $R^{D8}$ | $R^{D30}$ | $R^{D1}$ |
| $L_{C894}$ | $R^{D8}$ | $R^{D31}$ | $R^{D1}$ |
| $L_{C895}$ | $R^{D8}$ | $R^{D32}$ | $R^{D1}$ |
| $L_{C896}$ | $R^{D8}$ | $R^{D33}$ | $R^{D1}$ |
| $L_{C897}$ | $R^{D8}$ | $R^{D34}$ | $R^{D1}$ |
| $L_{C898}$ | $R^{D8}$ | $R^{D35}$ | $R^{D1}$ |
| $L_{C899}$ | $R^{D8}$ | $R^{D40}$ | $R^{D1}$ |
| $L_{C900}$ | $R^{D8}$ | $R^{D41}$ | $R^{D1}$ |
| $L_{C901}$ | $R^{D8}$ | $R^{D42}$ | $R^{D1}$ |
| $L_{C902}$ | $R^{D8}$ | $R^{D64}$ | $R^{D1}$ |
| $L_{C903}$ | $R^{D8}$ | $R^{D66}$ | $R^{D1}$ |
| $L_{C904}$ | $R^{D8}$ | $R^{D68}$ | $R^{D1}$ |
| $L_{C905}$ | $R^{D8}$ | $R^{D76}$ | $R^{D1}$ |
| $L_{C906}$ | $R^{D11}$ | $R^{D5}$ | $R^{D1}$ |
| $L_{C907}$ | $R^{D11}$ | $R^{D6}$ | $R^{D1}$ |
| $L_{C908}$ | $R^{D11}$ | $R^{D9}$ | $R^{D1}$ |
| $L_{C909}$ | $R^{D11}$ | $R^{D10}$ | $R^{D1}$ |
| $L_{C910}$ | $R^{D11}$ | $R^{D12}$ | $R^{D1}$ |
| $L_{C911}$ | $R^{D11}$ | $R^{D13}$ | $R^{D1}$ |
| $L_{C912}$ | $R^{D11}$ | $R^{D14}$ | $R^{D1}$ |
| $L_{C913}$ | $R^{D11}$ | $R^{D15}$ | $R^{D1}$ |
| $L_{C914}$ | $R^{D11}$ | $R^{D16}$ | $R^{D1}$ |
| $L_{C915}$ | $R^{D11}$ | $R^{D17}$ | $R^{D1}$ |
| $L_{C916}$ | $R^{D11}$ | $R^{D18}$ | $R^{D1}$ |
| $L_{C917}$ | $R^{D11}$ | $R^{D19}$ | $R^{D1}$ |
| $L_{C918}$ | $R^{D11}$ | $R^{D20}$ | $R^{D1}$ |
| $L_{C919}$ | $R^{D11}$ | $R^{D21}$ | $R^{D1}$ |
| $L_{C920}$ | $R^{D11}$ | $R^{D22}$ | $R^{D1}$ |
| $L_{C921}$ | $R^{D11}$ | $R^{D23}$ | $R^{D1}$ |
| $L_{C922}$ | $R^{D11}$ | $R^{D24}$ | $R^{D1}$ |
| $L_{C923}$ | $R^{D11}$ | $R^{D25}$ | $R^{D1}$ |
| $L_{C924}$ | $R^{D11}$ | $R^{D26}$ | $R^{D1}$ |
| $L_{C925}$ | $R^{D11}$ | $R^{D27}$ | $R^{D1}$ |
| $L_{C926}$ | $R^{D11}$ | $R^{D28}$ | $R^{D1}$ |
| $L_{C927}$ | $R^{D11}$ | $R^{D29}$ | $R^{D1}$ |
| $L_{C928}$ | $R^{D11}$ | $R^{D30}$ | $R^{D1}$ |
| $L_{C929}$ | $R^{D11}$ | $R^{D31}$ | $R^{D1}$ |
| $L_{C930}$ | $R^{D11}$ | $R^{D32}$ | $R^{D1}$ |
| $L_{C931}$ | $R^{D11}$ | $R^{D33}$ | $R^{D1}$ |
| $L_{C932}$ | $R^{D11}$ | $R^{D34}$ | $R^{D1}$ |
| $L_{C933}$ | $R^{D11}$ | $R^{D35}$ | $R^{D1}$ |
| $L_{C934}$ | $R^{D11}$ | $R^{D40}$ | $R^{D1}$ |
| $L_{C935}$ | $R^{D11}$ | $R^{D41}$ | $R^{D1}$ |
| $L_{C936}$ | $R^{D11}$ | $R^{D42}$ | $R^{D1}$ |
| $L_{C937}$ | $R^{D11}$ | $R^{D64}$ | $R^{D1}$ |
| $L_{C938}$ | $R^{D11}$ | $R^{D66}$ | $R^{D1}$ |
| $L_{C939}$ | $R^{D11}$ | $R^{D68}$ | $R^{D1}$ |
| $L_{C940}$ | $R^{D11}$ | $R^{D76}$ | $R^{D1}$ |
| $L_{C941}$ | $R^{D13}$ | $R^{D5}$ | $R^{D1}$ |
| $L_{C942}$ | $R^{D13}$ | $R^{D6}$ | $R^{D1}$ |
| $L_{C943}$ | $R^{D13}$ | $R^{D9}$ | $R^{D1}$ |
| $L_{C944}$ | $R^{D13}$ | $R^{D10}$ | $R^{D1}$ |
| $L_{C945}$ | $R^{D13}$ | $R^{D12}$ | $R^{D1}$ |
| $L_{C946}$ | $R^{D13}$ | $R^{D14}$ | $R^{D1}$ |
| $L_{C947}$ | $R^{D13}$ | $R^{D15}$ | $R^{D1}$ |
| $L_{C948}$ | $R^{D13}$ | $R^{D16}$ | $R^{D1}$ |
| $L_{C949}$ | $R^{D13}$ | $R^{D17}$ | $R^{D1}$ |
| $L_{C950}$ | $R^{D13}$ | $R^{D18}$ | $R^{D1}$ |
| $L_{C951}$ | $R^{D13}$ | $R^{D19}$ | $R^{D1}$ |
| $L_{C952}$ | $R^{D13}$ | $R^{D20}$ | $R^{D1}$ |
| $L_{C953}$ | $R^{D13}$ | $R^{D21}$ | $R^{D1}$ |
| $L_{C954}$ | $R^{D13}$ | $R^{D22}$ | $R^{D1}$ |
| $L_{C955}$ | $R^{D13}$ | $R^{D23}$ | $R^{D1}$ |
| $L_{C956}$ | $R^{D13}$ | $R^{D24}$ | $R^{D1}$ |
| $L_{C957}$ | $R^{D13}$ | $R^{D25}$ | $R^{D1}$ |
| $L_{C958}$ | $R^{D13}$ | $R^{D26}$ | $R^{D1}$ |
| $L_{C959}$ | $R^{D13}$ | $R^{D27}$ | $R^{D1}$ |
| $L_{C960}$ | $R^{D13}$ | $R^{D28}$ | $R^{D1}$ |
| $L_{C961}$ | $R^{D13}$ | $R^{D29}$ | $R^{D1}$ |
| $L_{C962}$ | $R^{D13}$ | $R^{D30}$ | $R^{D1}$ |
| $L_{C963}$ | $R^{D13}$ | $R^{D31}$ | $R^{D1}$ |
| $L_{C964}$ | $R^{D13}$ | $R^{D32}$ | $R^{D1}$ |
| $L_{C965}$ | $R^{D13}$ | $R^{D33}$ | $R^{D1}$ |
| $L_{C966}$ | $R^{D13}$ | $R^{D34}$ | $R^{D1}$ |
| $L_{C967}$ | $R^{D13}$ | $R^{D35}$ | $R^{D1}$ |
| $L_{C968}$ | $R^{D13}$ | $R^{D40}$ | $R^{D1}$ |
| $L_{C969}$ | $R^{D13}$ | $R^{D41}$ | $R^{D1}$ |
| $L_{C970}$ | $R^{D13}$ | $R^{D42}$ | $R^{D1}$ |
| $L_{C971}$ | $R^{D13}$ | $R^{D64}$ | $R^{D1}$ |
| $L_{C972}$ | $R^{D13}$ | $R^{D66}$ | $R^{D1}$ |
| $L_{C973}$ | $R^{D13}$ | $R^{D68}$ | $R^{D1}$ |
| $L_{C974}$ | $R^{D13}$ | $R^{D76}$ | $R^{D1}$ |
| $L_{C975}$ | $R^{D14}$ | $R^{D5}$ | $R^{D1}$ |
| $L_{C976}$ | $R^{D14}$ | $R^{D6}$ | $R^{D1}$ |
| $L_{C977}$ | $R^{D14}$ | $R^{D9}$ | $R^{D1}$ |
| $L_{C978}$ | $R^{D14}$ | $R^{D10}$ | $R^{D1}$ |
| $L_{C979}$ | $R^{D14}$ | $R^{D12}$ | $R^{D1}$ |
| $L_{C980}$ | $R^{D14}$ | $R^{D15}$ | $R^{D1}$ |
| $L_{C981}$ | $R^{D14}$ | $R^{D16}$ | $R^{D1}$ |
| $L_{C982}$ | $R^{D14}$ | $R^{D17}$ | $R^{D1}$ |
| $L_{C983}$ | $R^{D14}$ | $R^{D18}$ | $R^{D1}$ |
| $L_{C984}$ | $R^{D14}$ | $R^{D19}$ | $R^{D1}$ |
| $L_{C985}$ | $R^{D14}$ | $R^{D20}$ | $R^{D1}$ |
| $L_{C986}$ | $R^{D14}$ | $R^{D21}$ | $R^{D1}$ |
| $L_{C987}$ | $R^{D14}$ | $R^{D22}$ | $R^{D1}$ |
| $L_{C988}$ | $R^{D14}$ | $R^{D23}$ | $R^{D1}$ |
| $L_{C989}$ | $R^{D14}$ | $R^{D24}$ | $R^{D1}$ |
| $L_{C990}$ | $R^{D14}$ | $R^{D25}$ | $R^{D1}$ |
| $L_{C991}$ | $R^{D14}$ | $R^{D26}$ | $R^{D1}$ |
| $L_{C992}$ | $R^{D14}$ | $R^{D27}$ | $R^{D1}$ |
| $L_{C993}$ | $R^{D14}$ | $R^{D28}$ | $R^{D1}$ |
| $L_{C994}$ | $R^{D14}$ | $R^{D29}$ | $R^{D1}$ |
| $L_{C995}$ | $R^{D14}$ | $R^{D30}$ | $R^{D1}$ |
| $L_{C996}$ | $R^{D14}$ | $R^{D31}$ | $R^{D1}$ |
| $L_{C997}$ | $R^{D14}$ | $R^{D32}$ | $R^{D1}$ |
| $L_{C998}$ | $R^{D14}$ | $R^{D33}$ | $R^{D1}$ |
| $L_{C999}$ | $R^{D14}$ | $R^{D34}$ | $R^{D1}$ |
| $L_{C1000}$ | $R^{D14}$ | $R^{D35}$ | $R^{D1}$ |
| $L_{C1001}$ | $R^{D14}$ | $R^{D40}$ | $R^{D1}$ |
| $L_{C1002}$ | $R^{D14}$ | $R^{D41}$ | $R^{D1}$ |
| $L_{C1003}$ | $R^{D14}$ | $R^{D42}$ | $R^{D1}$ |
| $L_{C1004}$ | $R^{D14}$ | $R^{D64}$ | $R^{D1}$ |
| $L_{C1005}$ | $R^{D14}$ | $R^{D66}$ | $R^{D1}$ |
| $L_{C1006}$ | $R^{D14}$ | $R^{D68}$ | $R^{D1}$ |
| $L_{C1007}$ | $R^{D14}$ | $R^{D76}$ | $R^{D1}$ |
| $L_{C1008}$ | $R^{D22}$ | $R^{D5}$ | $R^{D1}$ |
| $L_{C1009}$ | $R^{D22}$ | $R^{D6}$ | $R^{D1}$ |
| $L_{C1010}$ | $R^{D22}$ | $R^{D9}$ | $R^{D1}$ |
| $L_{C1011}$ | $R^{D22}$ | $R^{D10}$ | $R^{D1}$ |
| $L_{C1012}$ | $R^{D22}$ | $R^{D12}$ | $R^{D1}$ |
| $L_{C1013}$ | $R^{D22}$ | $R^{D15}$ | $R^{D1}$ |
| $L_{C1014}$ | $R^{D22}$ | $R^{D16}$ | $R^{D1}$ |
| $L_{C1015}$ | $R^{D22}$ | $R^{D17}$ | $R^{D1}$ |
| $L_{C1016}$ | $R^{D22}$ | $R^{D18}$ | $R^{D1}$ |
| $L_{C1017}$ | $R^{D22}$ | $R^{D19}$ | $R^{D1}$ |
| $L_{C1018}$ | $R^{D22}$ | $R^{D20}$ | $R^{D1}$ |
| $L_{C1019}$ | $R^{D22}$ | $R^{D21}$ | $R^{D1}$ |
| $L_{C1020}$ | $R^{D22}$ | $R^{D23}$ | $R^{D1}$ |
| $L_{C1021}$ | $R^{D22}$ | $R^{D24}$ | $R^{D1}$ |
| $L_{C1022}$ | $R^{D22}$ | $R^{D25}$ | $R^{D1}$ |
| $L_{C1023}$ | $R^{D22}$ | $R^{D26}$ | $R^{D1}$ |
| $L_{C1024}$ | $R^{D22}$ | $R^{D27}$ | $R^{D1}$ |
| $L_{C1025}$ | $R^{D22}$ | $R^{D28}$ | $R^{D1}$ |
| $L_{C1026}$ | $R^{D22}$ | $R^{D29}$ | $R^{D1}$ |
| $L_{C1027}$ | $R^{D22}$ | $R^{D30}$ | $R^{D1}$ |
| $L_{C1028}$ | $R^{D22}$ | $R^{D31}$ | $R^{D1}$ |
| $L_{C1029}$ | $R^{D22}$ | $R^{D32}$ | $R^{D1}$ |
| $L_{C1030}$ | $R^{D22}$ | $R^{D33}$ | $R^{D1}$ |
| $L_{C1031}$ | $R^{D22}$ | $R^{D34}$ | $R^{D1}$ |
| $L_{C1032}$ | $R^{D22}$ | $R^{D35}$ | $R^{D1}$ |

-continued

| Ligand | $R^1$ | $R^2$ | $R^3$ |
|---|---|---|---|
| $L_{C1033}$ | $R^{D22}$ | $R^{D40}$ | $R^{D1}$ |
| $L_{C1034}$ | $R^{D22}$ | $R^{D41}$ | $R^{D1}$ |
| $L_{C1035}$ | $R^{D22}$ | $R^{D42}$ | $R^{D1}$ |
| $L_{C1036}$ | $R^{D22}$ | $R^{D64}$ | $R^{D1}$ |
| $L_{C1037}$ | $R^{D22}$ | $R^{D66}$ | $R^{D1}$ |
| $L_{C1038}$ | $R^{D22}$ | $R^{D68}$ | $R^{D1}$ |
| $L_{C1039}$ | $R^{D22}$ | $R^{D76}$ | $R^{D1}$ |
| $L_{C1040}$ | $R^{D26}$ | $R^{D5}$ | $R^{D1}$ |
| $L_{C1041}$ | $R^{D26}$ | $R^{D6}$ | $R^{D1}$ |
| $L_{C1042}$ | $R^{D26}$ | $R^{D9}$ | $R^{D1}$ |
| $L_{C1043}$ | $R^{D26}$ | $R^{D10}$ | $R^{D1}$ |
| $L_{C1044}$ | $R^{D26}$ | $R^{D12}$ | $R^{D1}$ |
| $L_{C1045}$ | $R^{D26}$ | $R^{D15}$ | $R^{D1}$ |
| $L_{C1046}$ | $R^{D26}$ | $R^{D16}$ | $R^{D1}$ |
| $L_{C1047}$ | $R^{D26}$ | $R^{D17}$ | $R^{D1}$ |
| $L_{C1048}$ | $R^{D26}$ | $R^{D18}$ | $R^{D1}$ |
| $L_{C1049}$ | $R^{D26}$ | $R^{D19}$ | $R^{D1}$ |
| $L_{C1050}$ | $R^{D26}$ | $R^{D20}$ | $R^{D1}$ |
| $L_{C1051}$ | $R^{D26}$ | $R^{D21}$ | $R^{D1}$ |
| $L_{C1052}$ | $R^{D26}$ | $R^{D23}$ | $R^{D1}$ |
| $L_{C1053}$ | $R^{D26}$ | $R^{D24}$ | $R^{D1}$ |
| $L_{C1054}$ | $R^{D26}$ | $R^{D25}$ | $R^{D1}$ |
| $L_{C1055}$ | $R^{D26}$ | $R^{D27}$ | $R^{D1}$ |
| $L_{C1056}$ | $R^{D26}$ | $R^{D28}$ | $R^{D1}$ |
| $L_{C1057}$ | $R^{D26}$ | $R^{D29}$ | $R^{D1}$ |
| $L_{C1058}$ | $R^{D26}$ | $R^{D30}$ | $R^{D1}$ |
| $L_{C1059}$ | $R^{D26}$ | $R^{D31}$ | $R^{D1}$ |
| $L_{C1060}$ | $R^{D26}$ | $R^{D32}$ | $R^{D1}$ |
| $L_{C1061}$ | $R^{D26}$ | $R^{D33}$ | $R^{D1}$ |
| $L_{C1062}$ | $R^{D26}$ | $R^{D34}$ | $R^{D1}$ |
| $L_{C1063}$ | $R^{D26}$ | $R^{D35}$ | $R^{D1}$ |
| $L_{C1064}$ | $R^{D26}$ | $R^{D40}$ | $R^{D1}$ |
| $L_{C1065}$ | $R^{D26}$ | $R^{D41}$ | $R^{D1}$ |
| $L_{C1066}$ | $R^{D26}$ | $R^{D42}$ | $R^{D1}$ |
| $L_{C1067}$ | $R^{D26}$ | $R^{D64}$ | $R^{D1}$ |
| $L_{C1068}$ | $R^{D26}$ | $R^{D66}$ | $R^{D1}$ |
| $L_{C1069}$ | $R^{D26}$ | $R^{D68}$ | $R^{D1}$ |
| $L_{C1070}$ | $R^{D26}$ | $R^{D76}$ | $R^{D1}$ |
| $L_{C1071}$ | $R^{D35}$ | $R^{D5}$ | $R^{D1}$ |
| $L_{C1072}$ | $R^{D35}$ | $R^{D6}$ | $R^{D1}$ |
| $L_{C1073}$ | $R^{D35}$ | $R^{D9}$ | $R^{D1}$ |
| $L_{C1074}$ | $R^{D35}$ | $R^{D11}$ | $R^{D1}$ |
| $L_{C1075}$ | $R^{D35}$ | $R^{D12}$ | $R^{D1}$ |
| $L_{C1076}$ | $R^{D35}$ | $R^{D15}$ | $R^{D1}$ |
| $L_{C1077}$ | $R^{D35}$ | $R^{D16}$ | $R^{D1}$ |
| $L_{C1078}$ | $R^{D35}$ | $R^{D17}$ | $R^{D1}$ |
| $L_{C1079}$ | $R^{D35}$ | $R^{D18}$ | $R^{D1}$ |
| $L_{C1080}$ | $R^{D35}$ | $R^{D19}$ | $R^{D1}$ |
| $L_{C1081}$ | $R^{D35}$ | $R^{D20}$ | $R^{D1}$ |
| $L_{C1082}$ | $R^{D35}$ | $R^{D21}$ | $R^{D1}$ |
| $L_{C1083}$ | $R^{D35}$ | $R^{D23}$ | $R^{D1}$ |
| $L_{C1084}$ | $R^{D35}$ | $R^{D24}$ | $R^{D1}$ |
| $L_{C1085}$ | $R^{D35}$ | $R^{D25}$ | $R^{D1}$ |
| $L_{C1086}$ | $R^{D35}$ | $R^{D27}$ | $R^{D1}$ |
| $L_{C1087}$ | $R^{D35}$ | $R^{D28}$ | $R^{D1}$ |
| $L_{C1088}$ | $R^{D35}$ | $R^{D29}$ | $R^{D1}$ |
| $L_{C1089}$ | $R^{D35}$ | $R^{D30}$ | $R^{D1}$ |
| $L_{C1090}$ | $R^{D35}$ | $R^{D31}$ | $R^{D1}$ |
| $L_{C1091}$ | $R^{D35}$ | $R^{D32}$ | $R^{D1}$ |
| $L_{C1092}$ | $R^{D35}$ | $R^{D33}$ | $R^{D1}$ |
| $L_{C1093}$ | $R^{D35}$ | $R^{D34}$ | $R^{D1}$ |
| $L_{C1094}$ | $R^{D35}$ | $R^{D40}$ | $R^{D1}$ |
| $L_{C1095}$ | $R^{D35}$ | $R^{D41}$ | $R^{D1}$ |
| $L_{C1096}$ | $R^{D35}$ | $R^{D42}$ | $R^{D1}$ |
| $L_{C1097}$ | $R^{D35}$ | $R^{D64}$ | $R^{D1}$ |
| $L_{C1098}$ | $R^{D35}$ | $R^{D66}$ | $R^{D1}$ |
| $L_{C1099}$ | $R^{D35}$ | $R^{D68}$ | $R^{D1}$ |
| $L_{C1100}$ | $R^{D35}$ | $R^{D76}$ | $R^{D1}$ |
| $L_{C1101}$ | $R^{D40}$ | $R^{D5}$ | $R^{D1}$ |
| $L_{C1102}$ | $R^{D40}$ | $R^{D6}$ | $R^{D1}$ |
| $L_{C1103}$ | $R^{D40}$ | $R^{D9}$ | $R^{D1}$ |
| $L_{C1104}$ | $R^{D40}$ | $R^{D10}$ | $R^{D1}$ |
| $L_{C1105}$ | $R^{D40}$ | $R^{D12}$ | $R^{D1}$ |
| $L_{C1106}$ | $R^{D40}$ | $R^{D15}$ | $R^{D1}$ |
| $L_{C1107}$ | $R^{D40}$ | $R^{D16}$ | $R^{D1}$ |
| $L_{C1108}$ | $R^{D40}$ | $R^{D17}$ | $R^{D1}$ |
| $L_{C1109}$ | $R^{D40}$ | $R^{D18}$ | $R^{D1}$ |

-continued

| Ligand | $R^1$ | $R^2$ | $R^3$ |
|---|---|---|---|
| $L_{C1110}$ | $R^{D40}$ | $R^{D19}$ | $R^{D1}$ |
| $L_{C1111}$ | $R^{D40}$ | $R^{D20}$ | $R^{D1}$ |
| $L_{C1112}$ | $R^{D40}$ | $R^{D21}$ | $R^{D1}$ |
| $L_{C1113}$ | $R^{D40}$ | $R^{D23}$ | $R^{D1}$ |
| $L_{C1114}$ | $R^{D40}$ | $R^{D24}$ | $R^{D1}$ |
| $L_{C1115}$ | $R^{D40}$ | $R^{D25}$ | $R^{D1}$ |
| $L_{C1116}$ | $R^{D40}$ | $R^{D27}$ | $R^{D1}$ |
| $L_{C1117}$ | $R^{D40}$ | $R^{D28}$ | $R^{D1}$ |
| $L_{C1118}$ | $R^{D40}$ | $R^{D29}$ | $R^{D1}$ |
| $L_{C1119}$ | $R^{D40}$ | $R^{D30}$ | $R^{D1}$ |
| $L_{C1120}$ | $R^{D40}$ | $R^{D31}$ | $R^{D1}$ |
| $L_{C1121}$ | $R^{D40}$ | $R^{D32}$ | $R^{D1}$ |
| $L_{C1122}$ | $R^{D40}$ | $R^{D33}$ | $R^{D1}$ |
| $L_{C1123}$ | $R^{D40}$ | $R^{D34}$ | $R^{D1}$ |
| $L_{C1124}$ | $R^{D40}$ | $R^{D41}$ | $R^{D1}$ |
| $L_{C1125}$ | $R^{D40}$ | $R^{D42}$ | $R^{D1}$ |
| $L_{C1126}$ | $R^{D40}$ | $R^{D64}$ | $R^{D1}$ |
| $L_{C1127}$ | $R^{D40}$ | $R^{D66}$ | $R^{D1}$ |
| $L_{C1128}$ | $R^{D40}$ | $R^{D68}$ | $R^{D1}$ |
| $L_{C1129}$ | $R^{D40}$ | $R^{D76}$ | $R^{D1}$ |
| $L_{C1130}$ | $R^{D41}$ | $R^{D5}$ | $R^{D1}$ |
| $L_{C1131}$ | $R^{D41}$ | $R^{D6}$ | $R^{D1}$ |
| $L_{C1132}$ | $R^{D41}$ | $R^{D9}$ | $R^{D1}$ |
| $L_{C1133}$ | $R^{D41}$ | $R^{D10}$ | $R^{D1}$ |
| $L_{C1134}$ | $R^{D41}$ | $R^{D12}$ | $R^{D1}$ |
| $L_{C1135}$ | $R^{D41}$ | $R^{D15}$ | $R^{D1}$ |
| $L_{C1136}$ | $R^{D41}$ | $R^{D16}$ | $R^{D1}$ |
| $L_{C1137}$ | $R^{D41}$ | $R^{D17}$ | $R^{D1}$ |
| $L_{C1138}$ | $R^{D41}$ | $R^{D18}$ | $R^{D1}$ |
| $L_{C1139}$ | $R^{D41}$ | $R^{D19}$ | $R^{D1}$ |
| $L_{C1140}$ | $R^{D41}$ | $R^{D20}$ | $R^{D1}$ |
| $L_{C1141}$ | $R^{D41}$ | $R^{D21}$ | $R^{D1}$ |
| $L_{C1142}$ | $R^{D41}$ | $R^{D23}$ | $R^{D1}$ |
| $L_{C1143}$ | $R^{D41}$ | $R^{D24}$ | $R^{D1}$ |
| $L_{C1144}$ | $R^{D41}$ | $R^{D25}$ | $R^{D1}$ |
| $L_{C1145}$ | $R^{D41}$ | $R^{D27}$ | $R^{D1}$ |
| $L_{C1146}$ | $R^{D41}$ | $R^{D28}$ | $R^{D1}$ |
| $L_{C1147}$ | $R^{D41}$ | $R^{D29}$ | $R^{D1}$ |
| $L_{C1148}$ | $R^{D41}$ | $R^{D30}$ | $R^{D1}$ |
| $L_{C1149}$ | $R^{D41}$ | $R^{D31}$ | $R^{D1}$ |
| $L_{C1150}$ | $R^{D41}$ | $R^{D32}$ | $R^{D1}$ |
| $L_{C1151}$ | $R^{D41}$ | $R^{D33}$ | $R^{D1}$ |
| $L_{C1152}$ | $R^{D41}$ | $R^{D34}$ | $R^{D1}$ |
| $L_{C1153}$ | $R^{D41}$ | $R^{D42}$ | $R^{D1}$ |
| $L_{C1154}$ | $R^{D41}$ | $R^{D64}$ | $R^{D1}$ |
| $L_{C1155}$ | $R^{D41}$ | $R^{D66}$ | $R^{D1}$ |
| $L_{C1156}$ | $R^{D41}$ | $R^{D68}$ | $R^{D1}$ |
| $L_{C1157}$ | $R^{D41}$ | $R^{D76}$ | $R^{D1}$ |
| $L_{C1158}$ | $R^{D64}$ | $R^{D5}$ | $R^{D1}$ |
| $L_{C1159}$ | $R^{D64}$ | $R^{D6}$ | $R^{D1}$ |
| $L_{C1160}$ | $R^{D64}$ | $R^{D9}$ | $R^{D1}$ |
| $L_{C1161}$ | $R^{D64}$ | $R^{D10}$ | $R^{D1}$ |
| $L_{C1162}$ | $R^{D64}$ | $R^{D12}$ | $R^{D1}$ |
| $L_{C1163}$ | $R^{D64}$ | $R^{D15}$ | $R^{D1}$ |
| $L_{C1164}$ | $R^{D64}$ | $R^{D16}$ | $R^{D1}$ |
| $L_{C1165}$ | $R^{D64}$ | $R^{D17}$ | $R^{D1}$ |
| $L_{C1166}$ | $R^{D64}$ | $R^{D18}$ | $R^{D1}$ |
| $L_{C1167}$ | $R^{D64}$ | $R^{D19}$ | $R^{D1}$ |
| $L_{C1168}$ | $R^{D64}$ | $R^{D20}$ | $R^{D1}$ |
| $L_{C1169}$ | $R^{D64}$ | $R^{D21}$ | $R^{D1}$ |
| $L_{C1170}$ | $R^{D64}$ | $R^{D23}$ | $R^{D1}$ |
| $L_{C1171}$ | $R^{D64}$ | $R^{D24}$ | $R^{D1}$ |
| $L_{C1172}$ | $R^{D64}$ | $R^{D25}$ | $R^{D1}$ |
| $L_{C1173}$ | $R^{D64}$ | $R^{D27}$ | $R^{D1}$ |
| $L_{C1174}$ | $R^{D64}$ | $R^{D28}$ | $R^{D1}$ |
| $L_{C1175}$ | $R^{D64}$ | $R^{D29}$ | $R^{D1}$ |
| $L_{C1176}$ | $R^{D64}$ | $R^{D30}$ | $R^{D1}$ |
| $L_{C1177}$ | $R^{D64}$ | $R^{D31}$ | $R^{D1}$ |
| $L_{C1178}$ | $R^{D64}$ | $R^{D32}$ | $R^{D1}$ |
| $L_{C1179}$ | $R^{D64}$ | $R^{D33}$ | $R^{D1}$ |
| $L_{C1180}$ | $R^{D64}$ | $R^{D34}$ | $R^{D1}$ |
| $L_{C1181}$ | $R^{D64}$ | $R^{D42}$ | $R^{D1}$ |
| $L_{C1182}$ | $R^{D64}$ | $R^{D64}$ | $R^{D1}$ |
| $L_{C1183}$ | $R^{D64}$ | $R^{D66}$ | $R^{D1}$ |
| $L_{C1184}$ | $R^{D64}$ | $R^{D68}$ | $R^{D1}$ |
| $L_{C1185}$ | $R^{D64}$ | $R^{D76}$ | $R^{D1}$ |
| $L_{C1186}$ | $R^{D66}$ | $R^{D5}$ | $R^{D1}$ |

-continued

| Ligand | $R^1$ | $R^2$ | $R^3$ |
|---|---|---|---|
| $L_{C1187}$ | $R^{D66}$ | $R^{D6}$ | $R^{D1}$ |
| $L_{C1188}$ | $R^{D66}$ | $R^{D9}$ | $R^{D1}$ |
| $L_{C1189}$ | $R^{D66}$ | $R^{D10}$ | $R^{D1}$ |
| $L_{C1190}$ | $R^{D66}$ | $R^{D12}$ | $R^{D1}$ |
| $L_{C1191}$ | $R^{D66}$ | $R^{D15}$ | $R^{D1}$ |
| $L_{C1192}$ | $R^{D66}$ | $R^{D16}$ | $R^{D1}$ |
| $L_{C1193}$ | $R^{D66}$ | $R^{D17}$ | $R^{D1}$ |
| $L_{C1194}$ | $R^{D66}$ | $R^{D18}$ | $R^{D1}$ |
| $L_{C1195}$ | $R^{D66}$ | $R^{D19}$ | $R^{D1}$ |
| $L_{C1196}$ | $R^{D66}$ | $R^{D20}$ | $R^{D1}$ |
| $L_{C1197}$ | $R^{D66}$ | $R^{D21}$ | $R^{D1}$ |
| $L_{C1198}$ | $R^{D66}$ | $R^{D23}$ | $R^{D1}$ |
| $L_{C1199}$ | $R^{D66}$ | $R^{D24}$ | $R^{D1}$ |
| $L_{C1100}$ | $R^{D66}$ | $R^{D25}$ | $R^{D1}$ |
| $L_{C1101}$ | $R^{D66}$ | $R^{D27}$ | $R^{D1}$ |
| $L_{C1202}$ | $R^{D66}$ | $R^{D28}$ | $R^{D1}$ |
| $L_{C1203}$ | $R^{D66}$ | $R^{D29}$ | $R^{D1}$ |
| $L_{C1204}$ | $R^{D66}$ | $R^{D30}$ | $R^{D1}$ |
| $L_{C1205}$ | $R^{D66}$ | $R^{D31}$ | $R^{D1}$ |
| $L_{C1206}$ | $R^{D66}$ | $R^{D32}$ | $R^{D1}$ |
| $L_{C1207}$ | $R^{D66}$ | $R^{D33}$ | $R^{D1}$ |
| $L_{C1208}$ | $R^{D66}$ | $R^{D34}$ | $R^{D1}$ |
| $L_{C1209}$ | $R^{D66}$ | $R^{D42}$ | $R^{D1}$ |
| $L_{C1110}$ | $R^{D66}$ | $R^{D68}$ | $R^{D1}$ |
| $L_{C1211}$ | $R^{D66}$ | $R^{D76}$ | $R^{D1}$ |
| $L_{C1212}$ | $R^{D68}$ | $R^{D5}$ | $R^{D1}$ |
| $L_{C1213}$ | $R^{D68}$ | $R^{D6}$ | $R^{D1}$ |
| $L_{C1214}$ | $R^{D68}$ | $R^{D9}$ | $R^{D1}$ |
| $L_{C1215}$ | $R^{D68}$ | $R^{D10}$ | $R^{D1}$ |
| $L_{C1216}$ | $R^{D68}$ | $R^{D12}$ | $R^{D1}$ |
| $L_{C1217}$ | $R^{D68}$ | $R^{D15}$ | $R^{D1}$ |
| $L_{C1218}$ | $R^{D68}$ | $R^{D16}$ | $R^{D1}$ |
| $L_{C1219}$ | $R^{D68}$ | $R^{D17}$ | $R^{D1}$ |
| $L_{C1220}$ | $R^{D68}$ | $R^{D18}$ | $R^{D1}$ |
| $L_{C1221}$ | $R^{D68}$ | $R^{D19}$ | $R^{D1}$ |
| $L_{C1222}$ | $R^{D68}$ | $R^{D20}$ | $R^{D1}$ |
| $L_{C1223}$ | $R^{D68}$ | $R^{D21}$ | $R^{D1}$ |
| $L_{C1224}$ | $R^{D68}$ | $R^{D23}$ | $R^{D1}$ |
| $L_{C1225}$ | $R^{D68}$ | $R^{D24}$ | $R^{D1}$ |
| $L_{C1226}$ | $R^{D68}$ | $R^{D25}$ | $R^{D1}$ |
| $L_{C1227}$ | $R^{D68}$ | $R^{D27}$ | $R^{D1}$ |
| $L_{C1228}$ | $R^{D68}$ | $R^{D28}$ | $R^{D1}$ |
| $L_{C1229}$ | $R^{D68}$ | $R^{D29}$ | $R^{D1}$ |
| $L_{C1230}$ | $R^{D68}$ | $R^{D30}$ | $R^{D1}$ |
| $L_{C1231}$ | $R^{D68}$ | $R^{D31}$ | $R^{D1}$ |
| $L_{C1232}$ | $R^{D68}$ | $R^{D32}$ | $R^{D1}$ |
| $L_{C1233}$ | $R^{D68}$ | $R^{D33}$ | $R^{D1}$ |
| $L_{C1234}$ | $R^{D68}$ | $R^{D34}$ | $R^{D1}$ |
| $L_{C1235}$ | $R^{D68}$ | $R^{D42}$ | $R^{D1}$ |
| $L_{C1236}$ | $R^{D68}$ | $R^{D76}$ | $R^{D1}$ |
| $L_{C1237}$ | $R^{D76}$ | $R^{D5}$ | $R^{D1}$ |
| $L_{C1238}$ | $R^{D76}$ | $R^{D6}$ | $R^{D1}$ |
| $L_{C1239}$ | $R^{D76}$ | $R^{D9}$ | $R^{D1}$ |
| $L_{C1240}$ | $R^{D76}$ | $R^{D10}$ | $R^{D1}$ |
| $L_{C1241}$ | $R^{D76}$ | $R^{D12}$ | $R^{D1}$ |
| $L_{C1242}$ | $R^{D76}$ | $R^{D15}$ | $R^{D1}$ |
| $L_{C1243}$ | $R^{D76}$ | $R^{D16}$ | $R^{D1}$ |
| $L_{C1244}$ | $R^{D76}$ | $R^{D17}$ | $R^{D1}$ |
| $L_{C1245}$ | $R^{D76}$ | $R^{D18}$ | $R^{D1}$ |
| $L_{C1246}$ | $R^{D76}$ | $R^{D19}$ | $R^{D1}$ |
| $L_{C1247}$ | $R^{D76}$ | $R^{D20}$ | $R^{D1}$ |
| $L_{C1248}$ | $R^{D76}$ | $R^{D21}$ | $R^{D1}$ |
| $L_{C1249}$ | $R^{D76}$ | $R^{D23}$ | $R^{D1}$ |
| $L_{C1250}$ | $R^{D76}$ | $R^{D24}$ | $R^{D1}$ |
| $L_{C1251}$ | $R^{D76}$ | $R^{D25}$ | $R^{D1}$ |
| $L_{C1252}$ | $R^{D76}$ | $R^{D27}$ | $R^{D1}$ |
| $L_{C1253}$ | $R^{D76}$ | $R^{D28}$ | $R^{D1}$ |
| $L_{C1254}$ | $R^{D76}$ | $R^{D29}$ | $R^{D1}$ |
| $L_{C1255}$ | $R^{D76}$ | $R^{D30}$ | $R^{D1}$ |
| $L_{C1256}$ | $R^{D76}$ | $R^{D31}$ | $R^{D1}$ |
| $L_{C1257}$ | $R^{D76}$ | $R^{D32}$ | $R^{D1}$ |
| $L_{C1258}$ | $R^{D76}$ | $R^{D33}$ | $R^{D1}$ |
| $L_{C1259}$ | $R^{D76}$ | $R^{D34}$ | $R^{D1}$ |
| $L_{C1260}$ | $R^{D76}$ | $R^{D42}$ | $R^{D1}$, |

wherein $R^{D1}$ to $R^{D81}$ have the following structures:

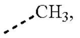

$R^{D1}$

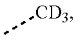

$R^{D2}$

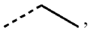

$R^{D3}$

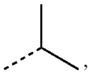

$R^{D4}$

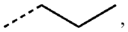

$R^{D5}$

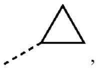

$R^{D6}$

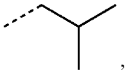

$R^{D7}$

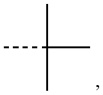

$R^{D8}$

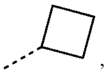

$R^{D9}$

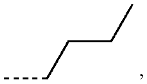

$R^{D10}$

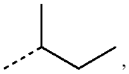

$R^{D11}$

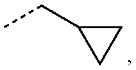

$R^{D12}$

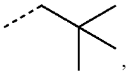

$R^{D13}$

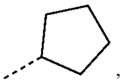

$R^{D14}$

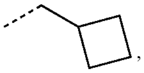

$R^{D15}$

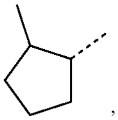

$R^{D16}$

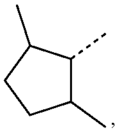

$R^{D17}$

-continued
$R^{D18}$
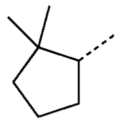,
$R^{D19}$
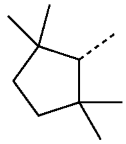,
$R^{D20}$
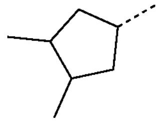,
$R^{D21}$
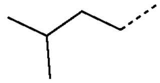,
$R^{D22}$
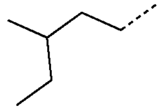,
$R^{D23}$
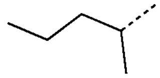,
$R^{D24}$
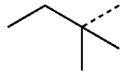,
$R^{D25}$
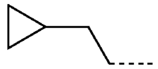,
$R^{D26}$
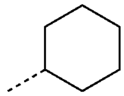,
$R^{D27}$
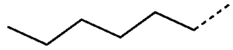,
$R^{D28}$
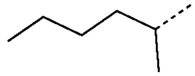,
$R^{D29}$
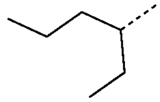,
$R^{D30}$
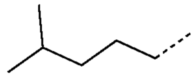,
$R^{D31}$
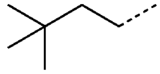,
-continued
$R^{D32}$
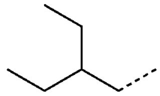,
$R^{D33}$
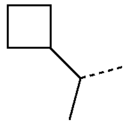,
$R^{D34}$
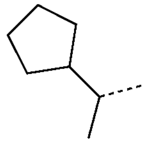,
$R^{D35}$
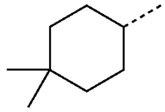,
$R^{D36}$
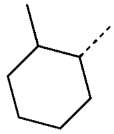,
$R^{D37}$
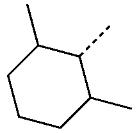,
$R^{D38}$
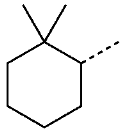,
$R^{D39}$
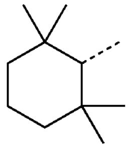,
$R^{D40}$
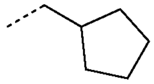,
$R^{D41}$
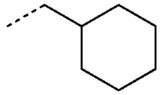,
$R^{D42}$
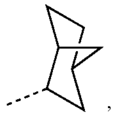, -continued
$R^{D43}$
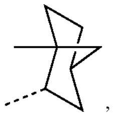,
$R^{D44}$
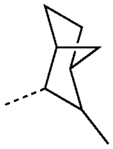,
$R^{D45}$
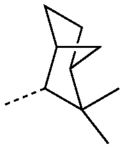,
$R^{D46}$
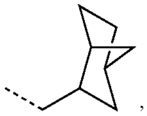,
$R^{D47}$
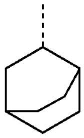,
$R^{D48}$
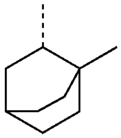,
$R^{D49}$
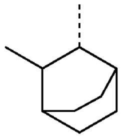,
$R^{D50}$
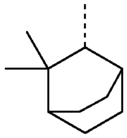,
$R^{D51}$
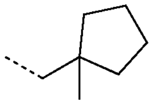,
$R^{D52}$
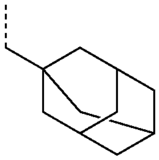,
-continued
$R^{D53}$
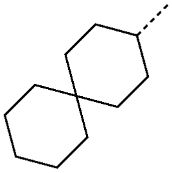,
$R^{D54}$
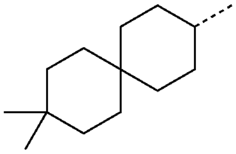,
$R^{D55}$
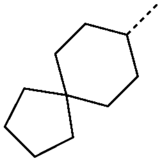,
$R^{D56}$
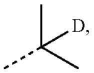
$R^{D57}$
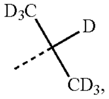
$R^{D58}$
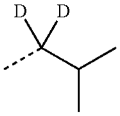,
$R^{D59}$
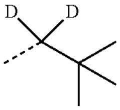,
$R^{D60}$
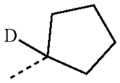,
$R^{D61}$
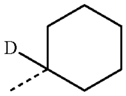,
$R^{D62}$
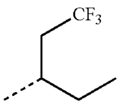,
$R^{D63}$
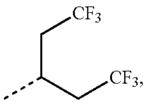
$R^{D64}$
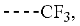
$R^{D65}$
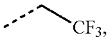
$R^{D66}$
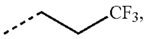

-continued $R^{D67}$

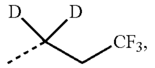

$R^{D68}$

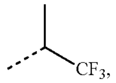

$R^{D69}$

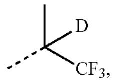

$R^{D70}$

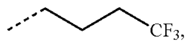

$R^{D71}$

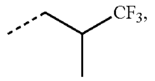

$R^{D72}$

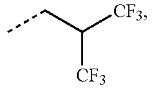

$R^{D73}$

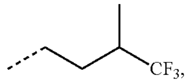

$R^{D74}$

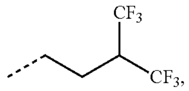

$R^{D75}$

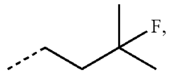

$R^{D76}$

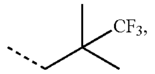

$R^{D77}$

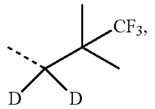

$R^{D78}$

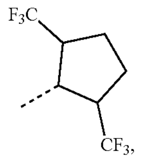

$R^{D79}$

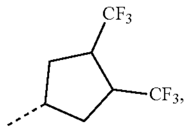

$R^{D80}$

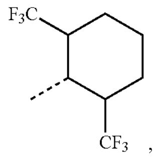

and

-continued $R^{D81}$

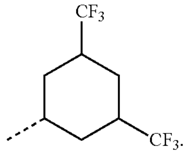

In some embodiment of the compound where the first ligand $L_A$ is selected from the group consisting of $L_{A1}$ to $L_{A1144}$ defined above, the compound is Compound Ax having the formula $Ir(L_{Ai})_3$, Compound By having the formula $Ir(L_{Ai})(L_{Bk})_2$, or Compound Cz having the formula $Ir(L_{Ai})_2(L_{Cj})$; wherein, $$x=i, y=468i+k-468, \text{ and } z=1260i+j-1260;$$

i is an integer from 1 to 1144, and k is an integer from 1 to 468, and j is an integer from 1 to 1260; wherein the corresponding $L_{Bk}$ and $L_{Cj}$ are as defined above.

According to another aspect, an OLED comprising: an anode; a cathode; and an organic layer, disposed between the anode and the cathode is disclosed. The organic layer comprises a compound comprising:

a ligand $L_A$ of Formula I

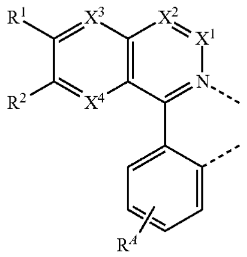

where, $R^A$ represents mono to the maximum allowable substitutions; $X^1$ to $X^4$ are each independently CR or N; $R^A$, R, $R^1$, and $R^2$ are each independently selected from the group consisting of hydrogen or a substituent selected from the general substituents defined above; at least one of $R^1$ and $R^2$ has the formula of $-L^1-G^1$; $L^1$ is an organic linker or a direct bond, $G^1$ is a substituted cycloalkyl group, or a substituted or unsubstituted multicyclic group; at least one $R^A$ is not hydrogen; $L_A$ is coordinated to Ir; Ir can be coordinated to other ligands; $L_A$ can be linked with other ligands to comprise a tridentate, tetradentate, pentadentate, or hexadentate ligand; and any two substituents can be joined or fused together to form a ring, with the proviso that $R^1$ and $R^2$ are not joined to form a ring.

In some embodiments of the OLED, the organic layer is an emissive layer and the compound is an emissive dopant or a non-emissive dopant. In some embodiments of the OLED, the organic layer further comprises a host, wherein host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In some embodiments of the OLED where the organic layer further comprises a host, the host can be selected from the group consisting of:

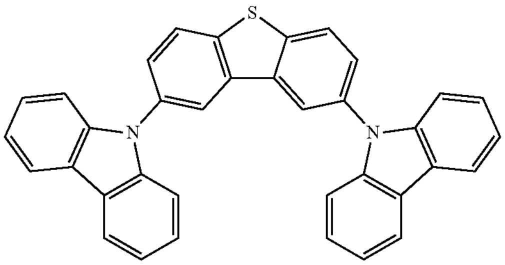
,
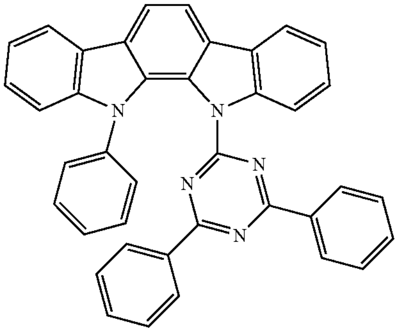
,
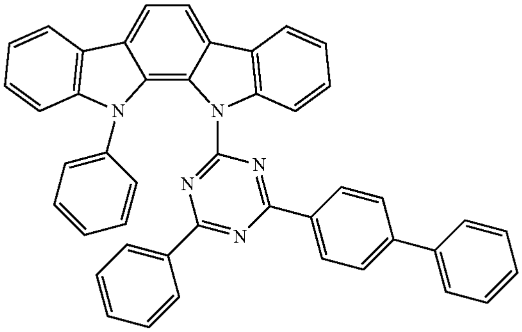
,
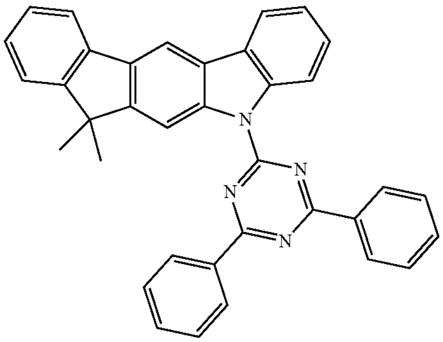
,
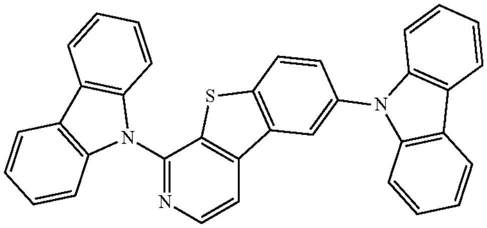
,
-continued
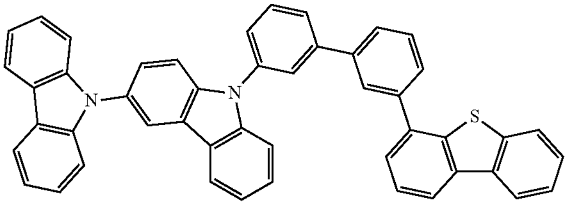
,
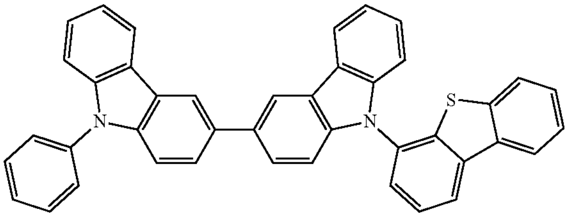
,
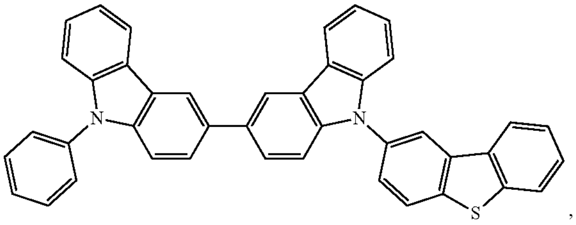
,
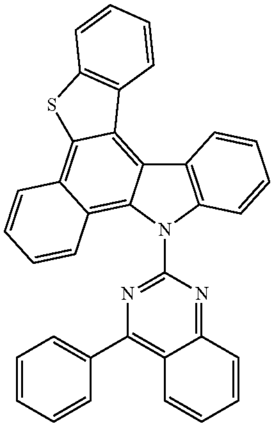
,
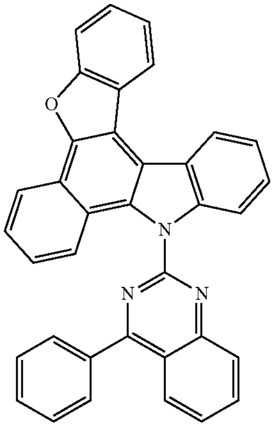
, -continued
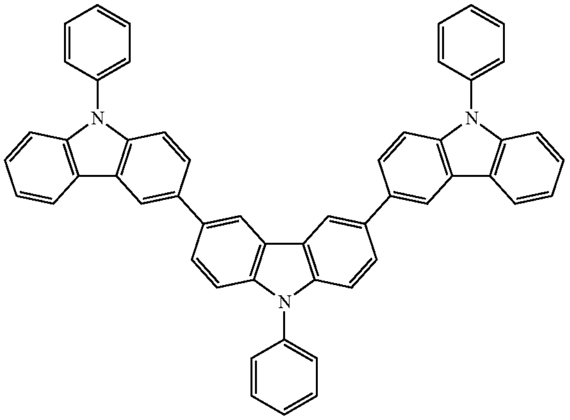
,
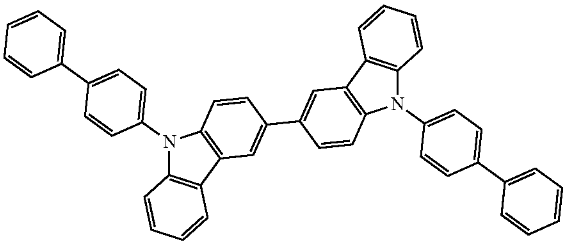
,
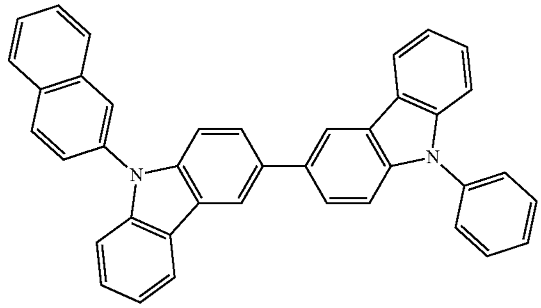
,
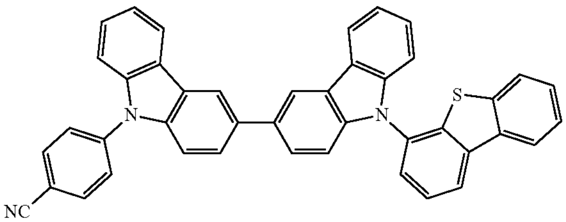
,
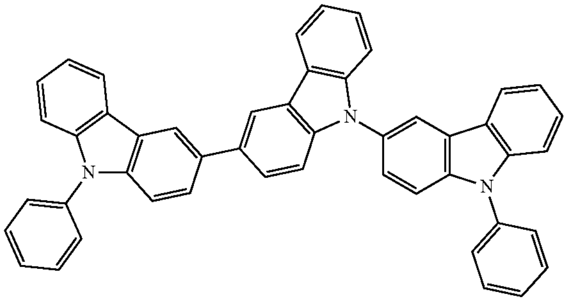
,
-continued
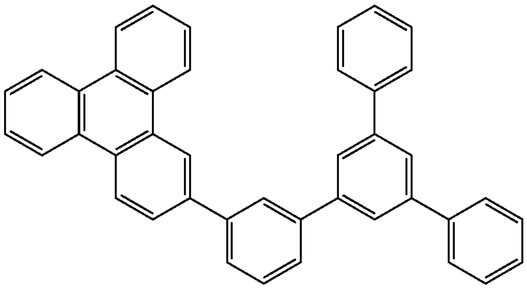
,
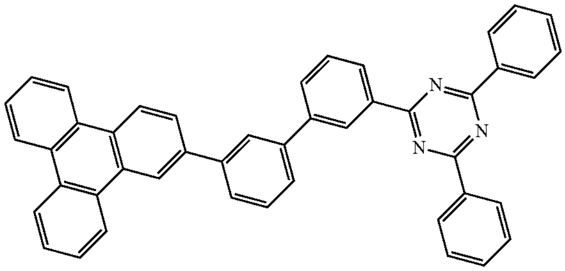
,
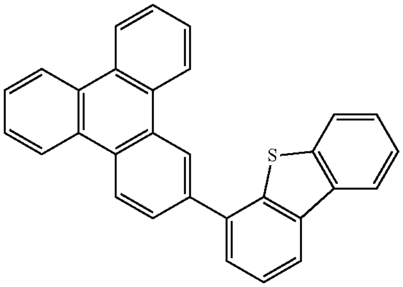
,
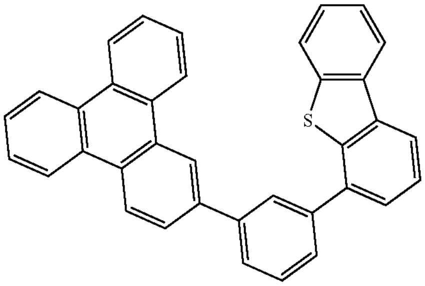
,
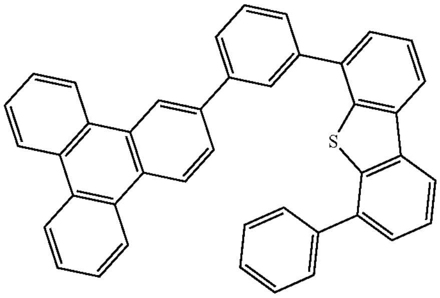
,
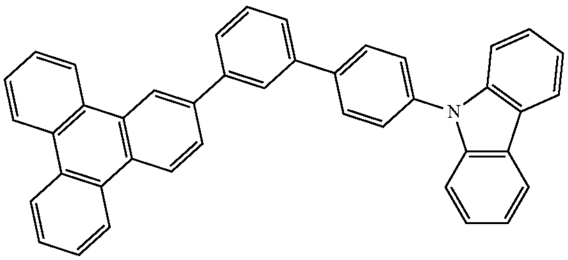
, -continued

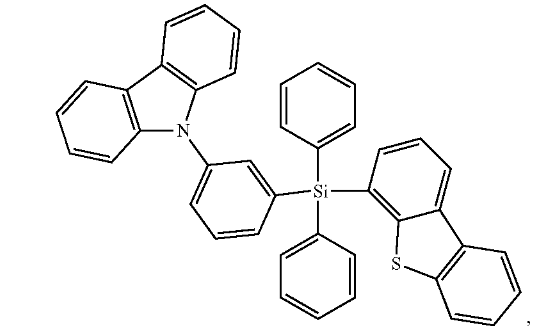

,

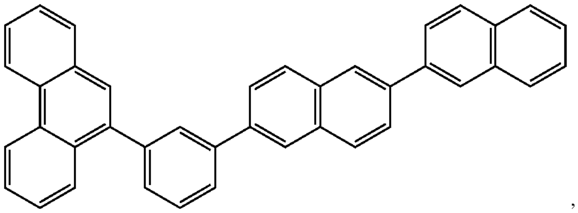

,

, and combinations thereof.

In some embodiments of the OLED where the organic layer further comprises a host, the host can comprise a metal complex.

In some embodiments of the OLED, the compound is a sensitizer and the OLED further comprises an acceptor; and wherein the acceptor is selected from the group consisting of fluorescent emitter, delayed fluorescence emitter, and combination thereof.

A consumer product comprising the OLED incorporating the novel compound of the present disclosure as defined above is also disclosed. In some embodiments, such consumer product can be selected from the group of consumer products defined above.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, published on Mar. 14, 2019 as U.S. patent application publication No. 2019/0081248, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others).

When there are more than one ligand coordinated to a metal, the ligands can all be the same in some embodiments. In some other embodiments, at least one ligand is different from the other ligand(s). In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}C{-}C_nH_{2n+1}$, $Ar_1$, $Ar_1$-$Ar_2$, and $C_nH_{2n}$-$Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example, for example, a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the Host Group consisting of:

-continued
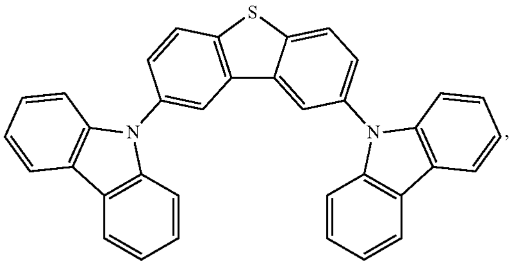,
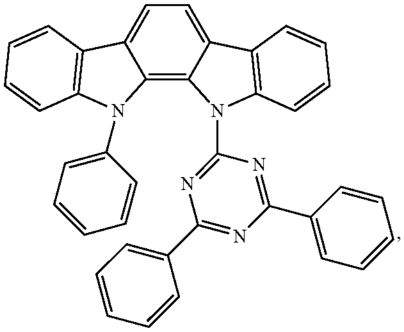,
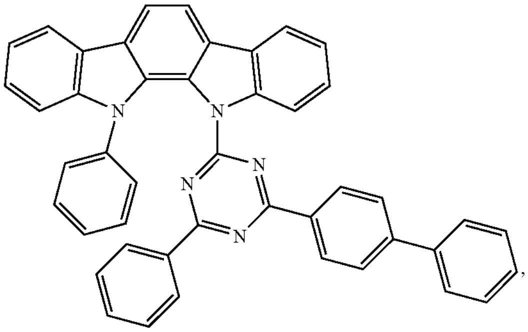,
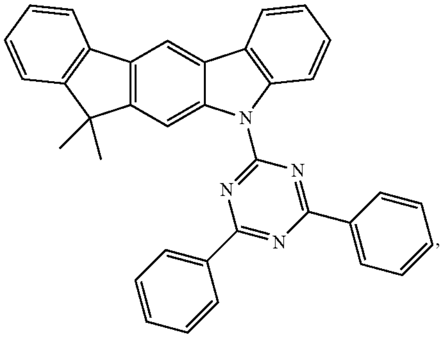,
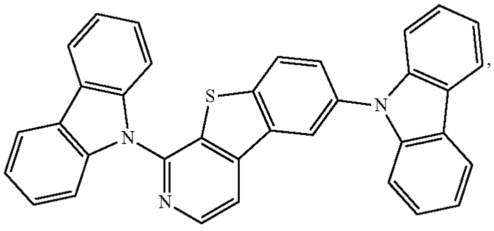,
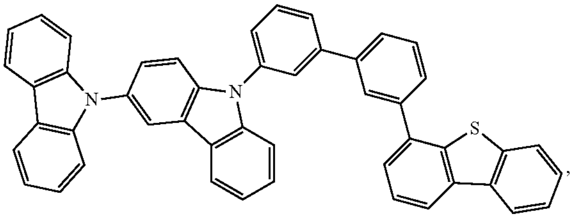,
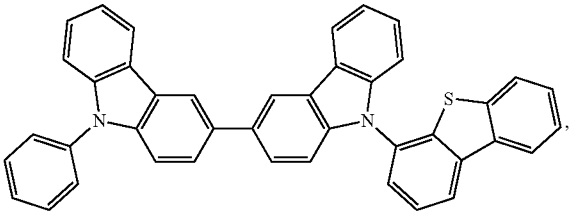,
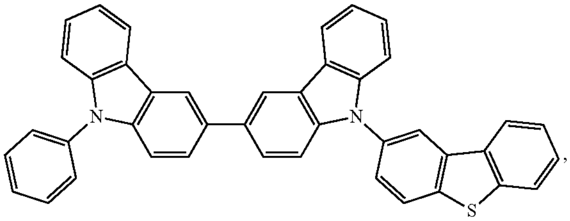,
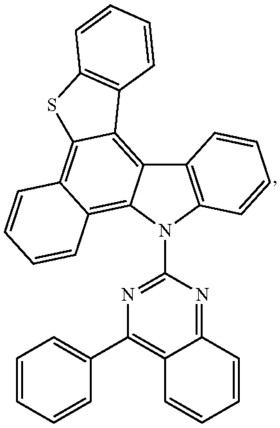,
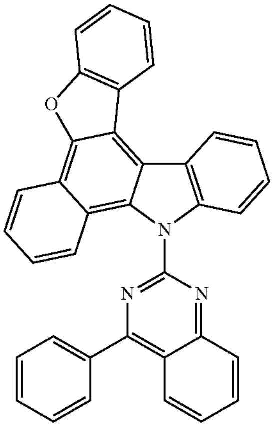,
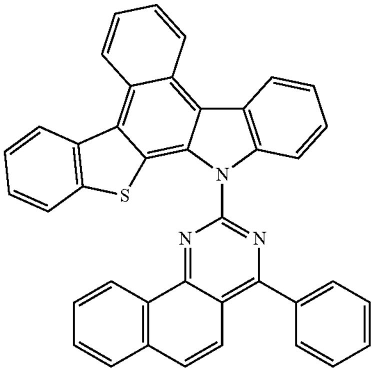, -continued
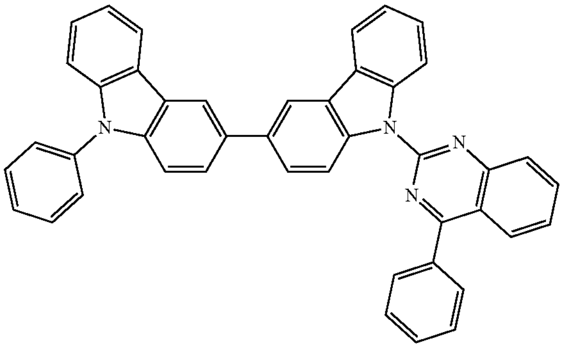
,
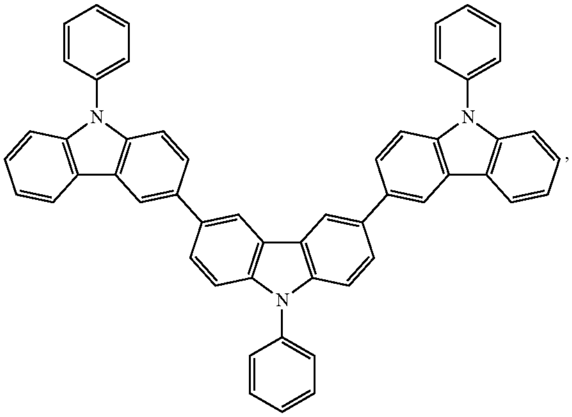
,
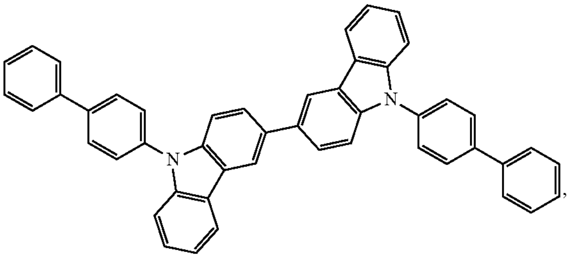
,
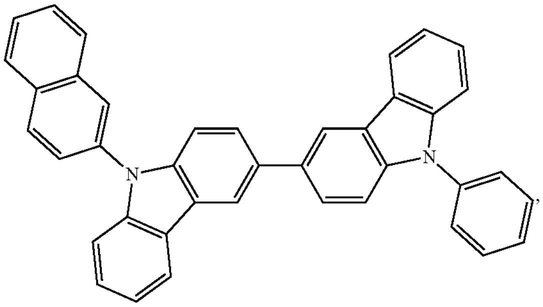
,
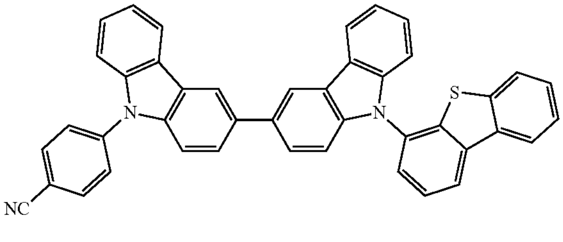
,
-continued
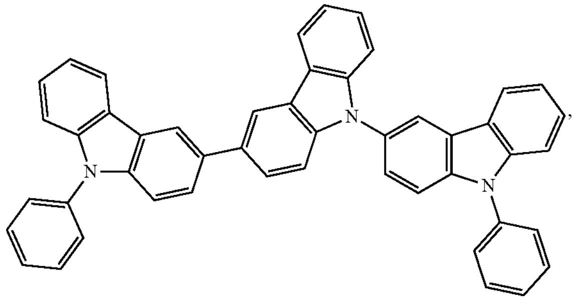
,
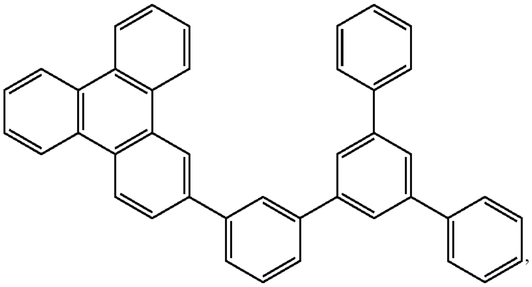
,
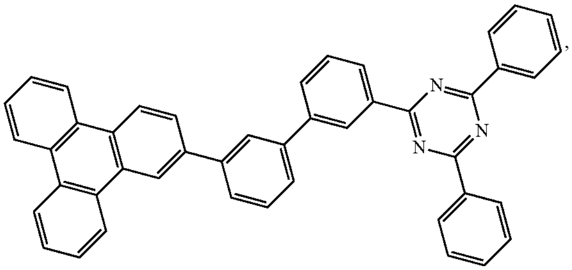
,
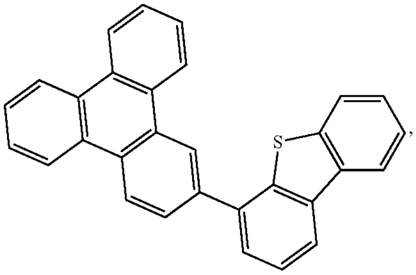
,
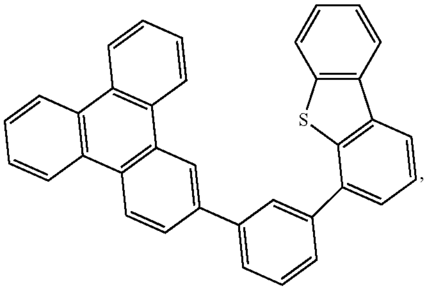
,
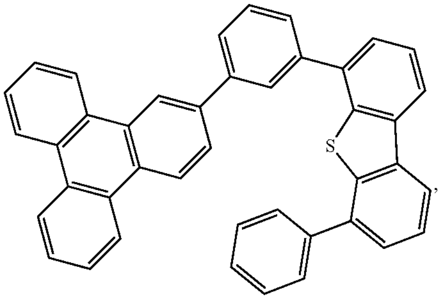
, -continued

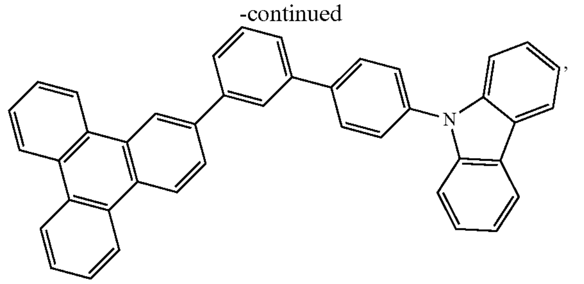

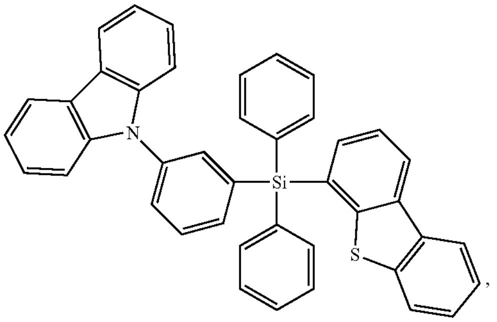

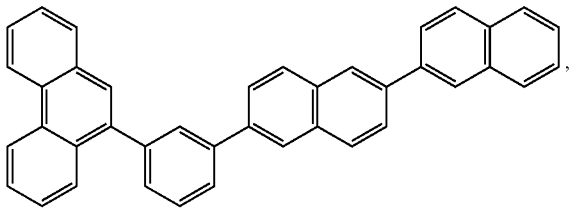

and combinations thereof.

Additional information on possible hosts is provided below.

An emissive region in an OLED is also disclosed. The emissive region comprises the compound comprising the ligand $L_A$ of Formula I

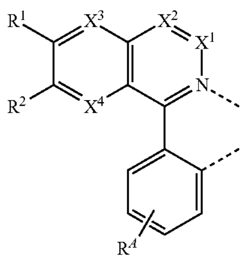

described herein.

In some embodiments of the emissive region, the compound is an emissive dopant or a non-emissive dopant. In some embodiments, the emissive region further comprises a host, wherein the host contains at least one group selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

In some embodiments, the emissive region further comprises a host, wherein the host is selected from the group consisting of:

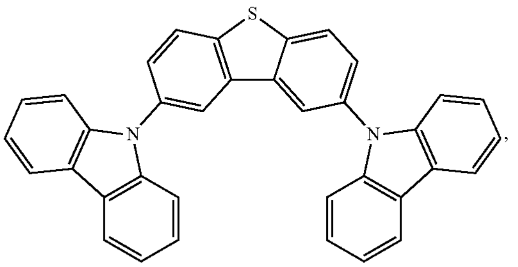

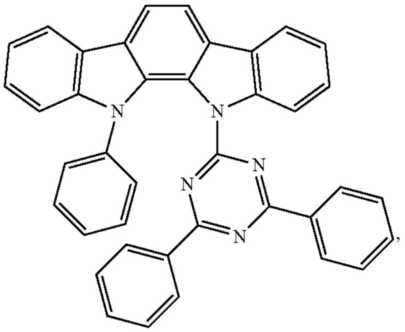

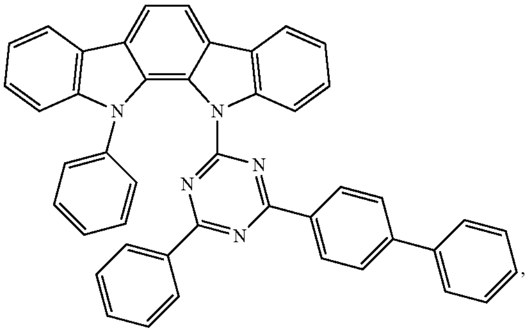

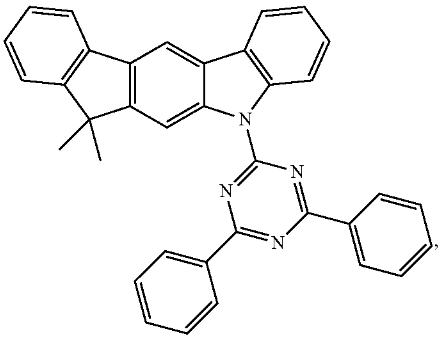

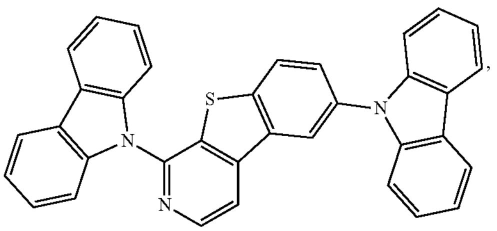

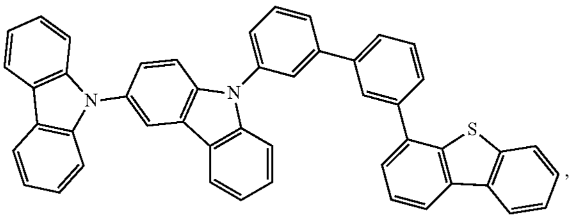

-continued
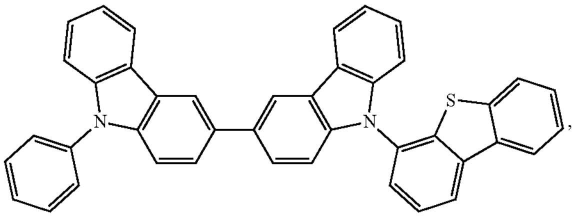,
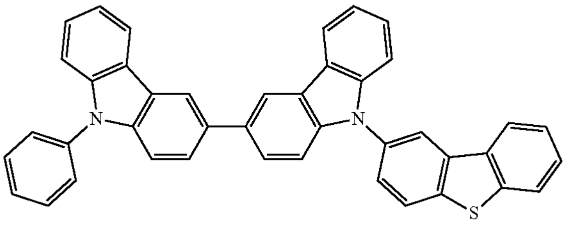,
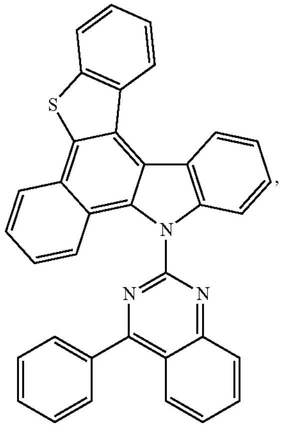,
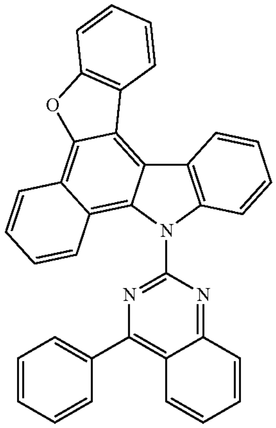,
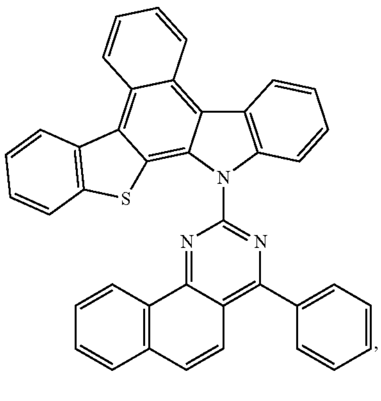,
-continued
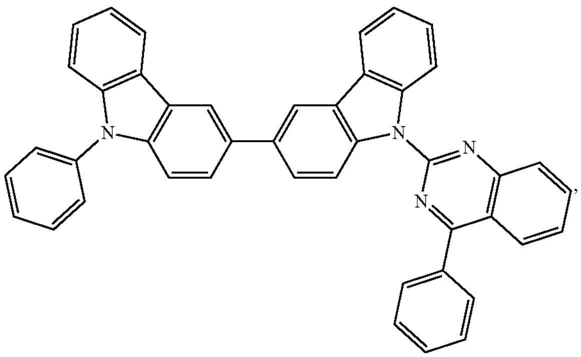,
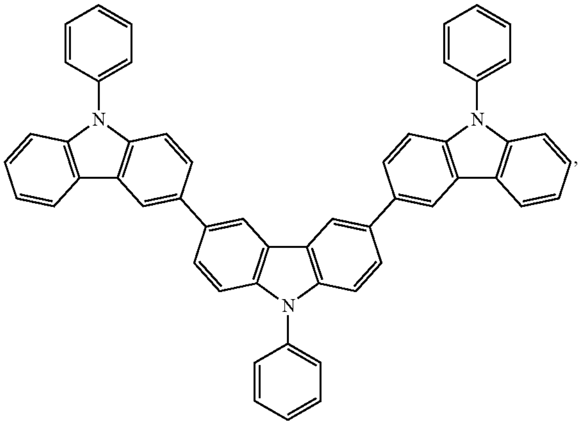,
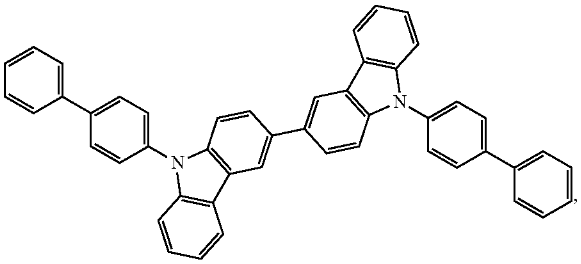,
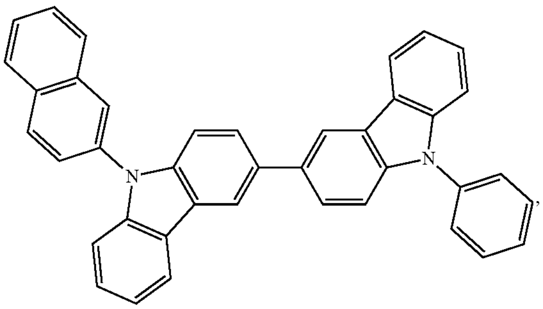,
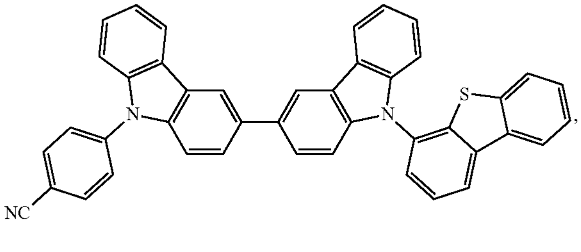, -continued

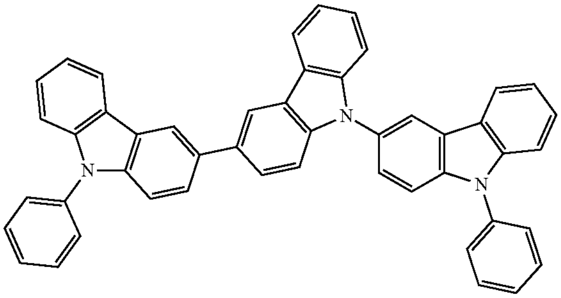
,

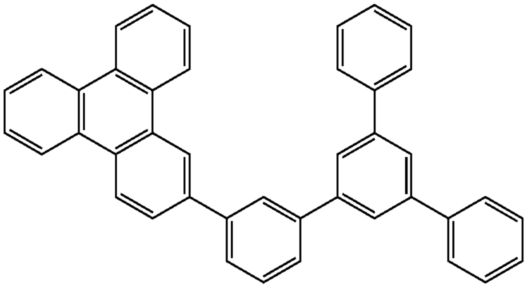
,

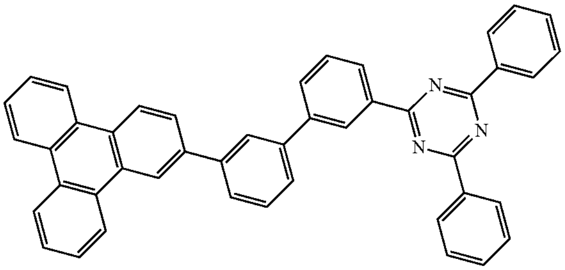
,

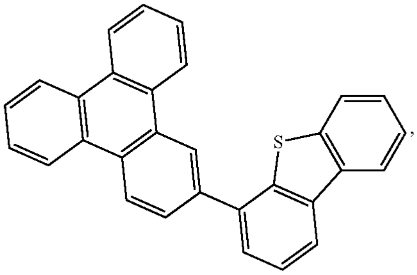
,

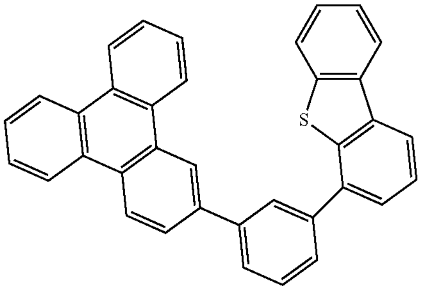
,

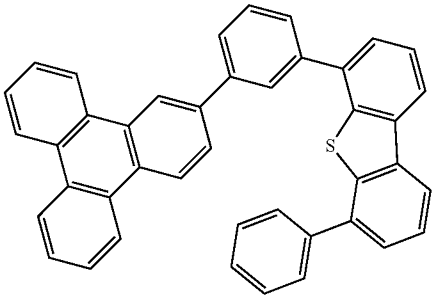
,

-continued

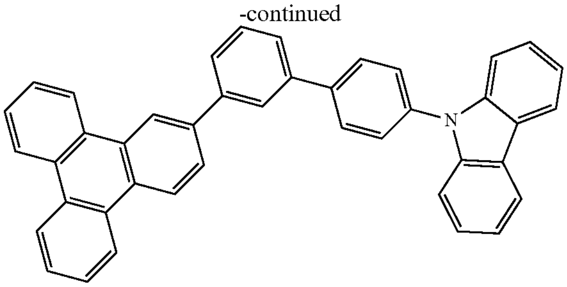
,

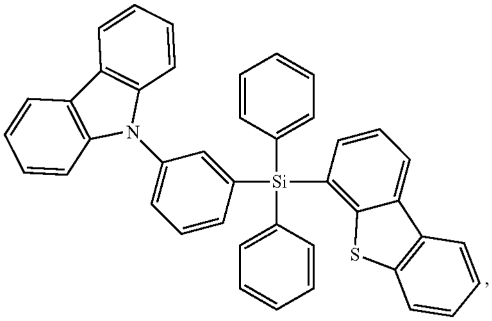
,

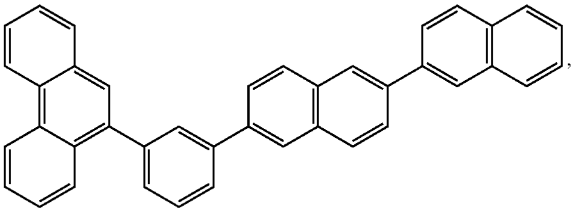
, and combinations thereof.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound is can also be incorporated into the supramolecule complex without covalent bonds.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

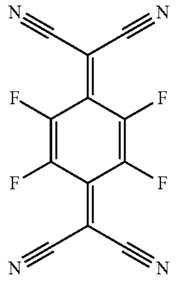

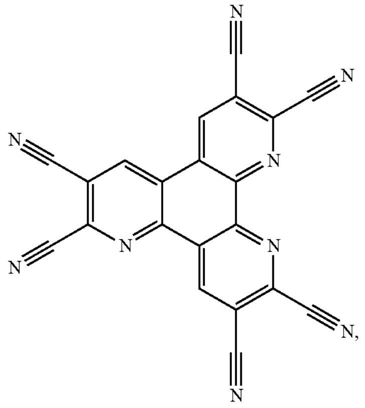

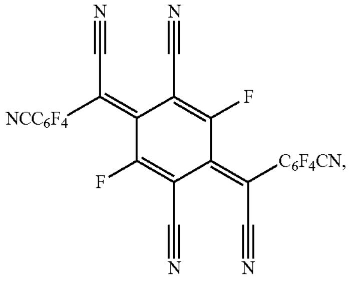

-continued

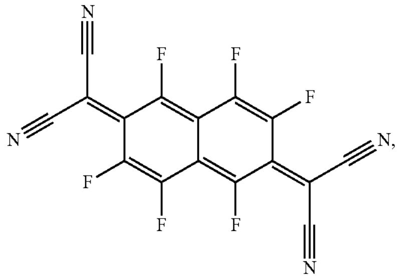

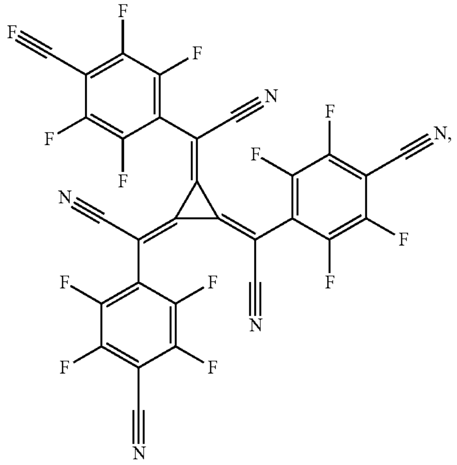

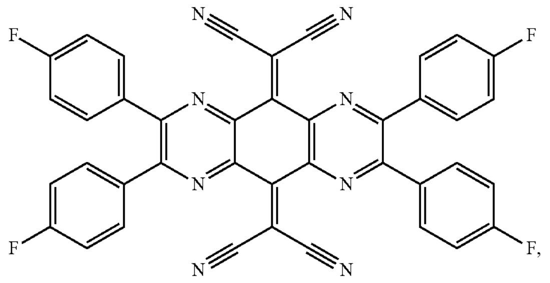

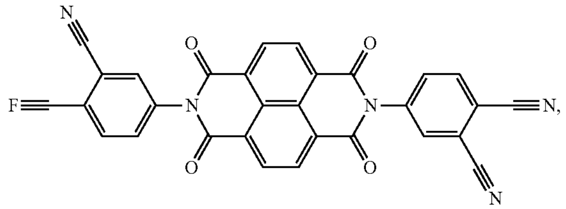

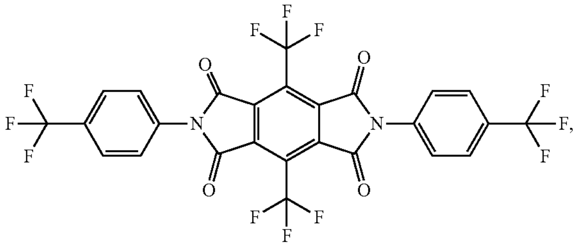

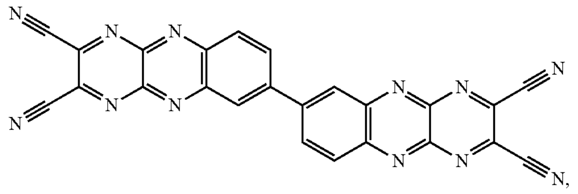

-continued

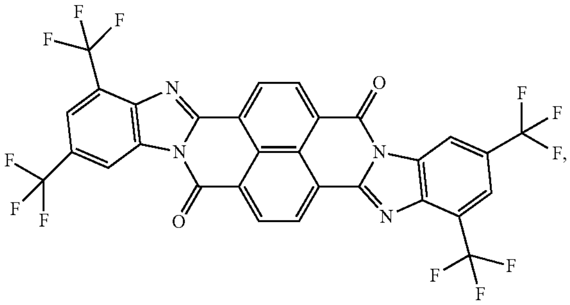

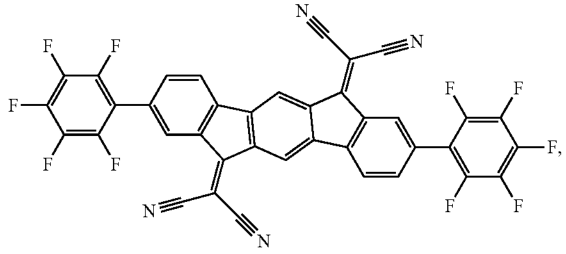

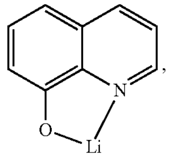

, and

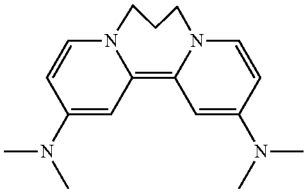

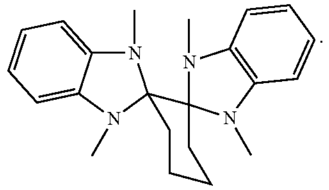

.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

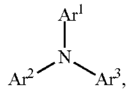

,

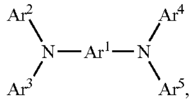

,

-continued

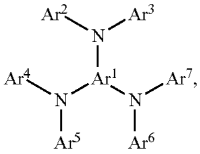

,

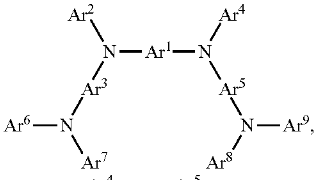

, and

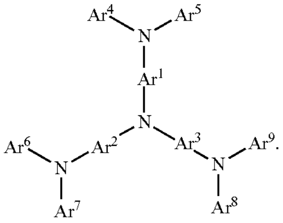

.

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

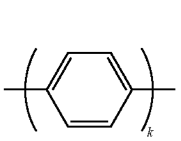

,

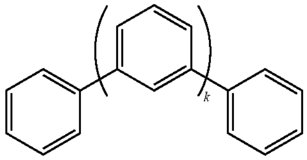

,

-continued

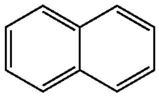, 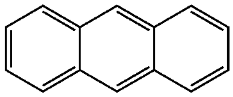,

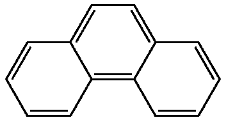, 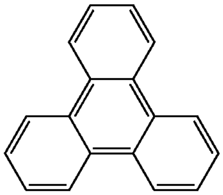,

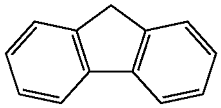, and

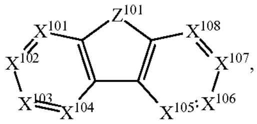

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

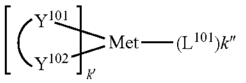

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO005075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

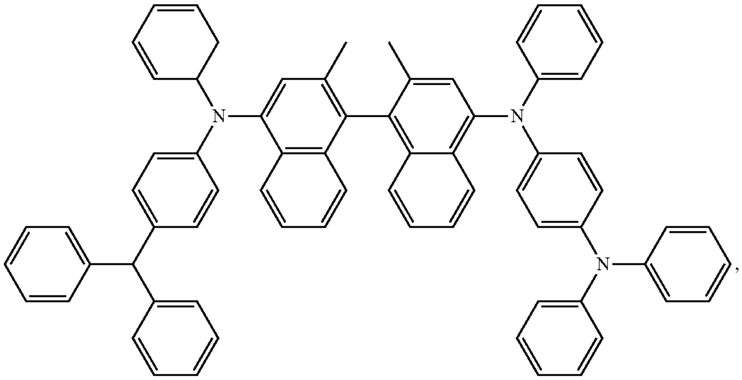,

-continued
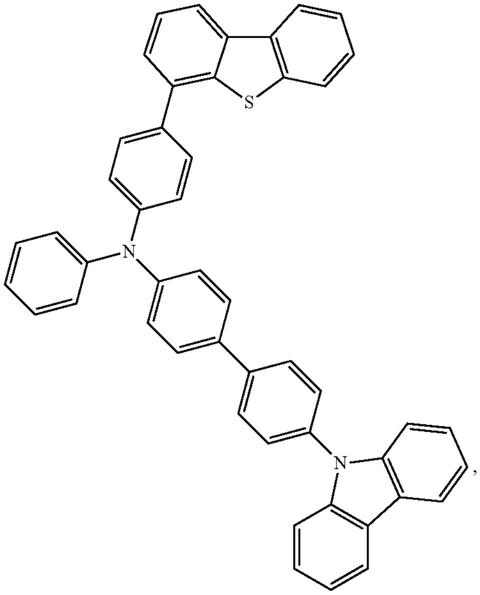
,
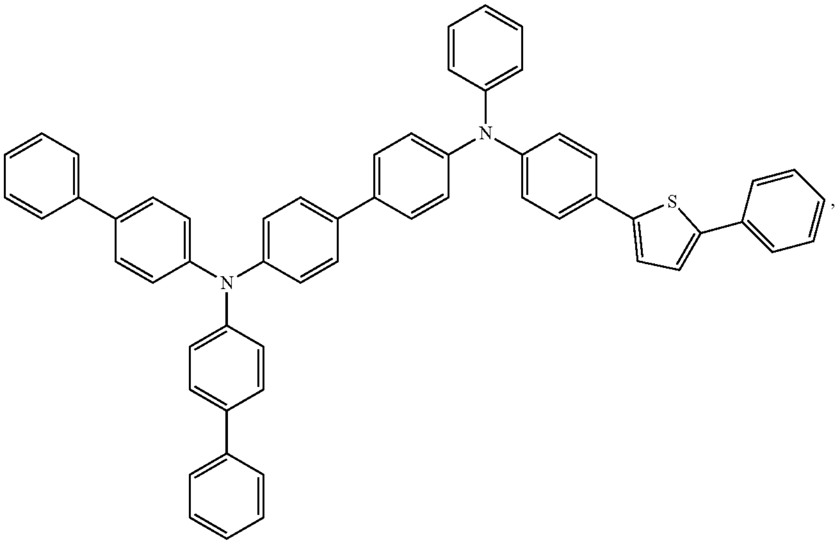
,
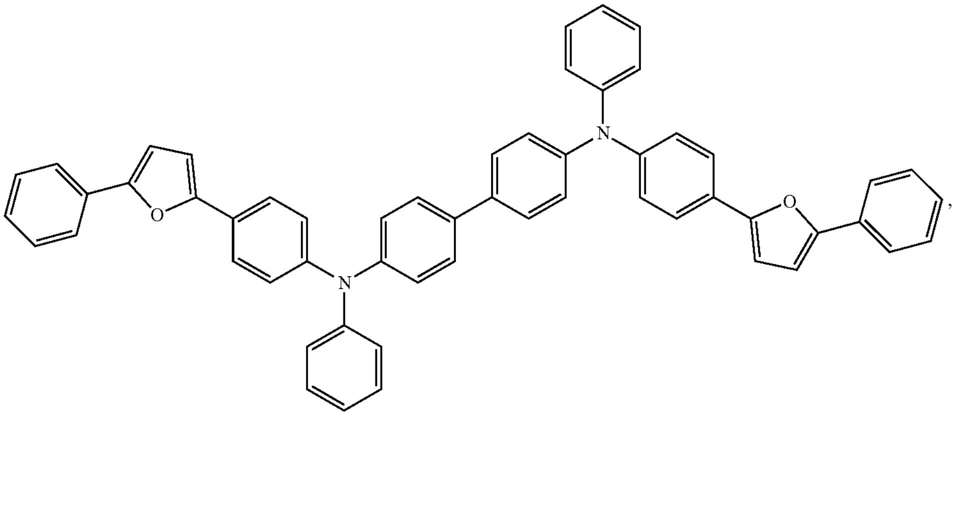
,

-continued
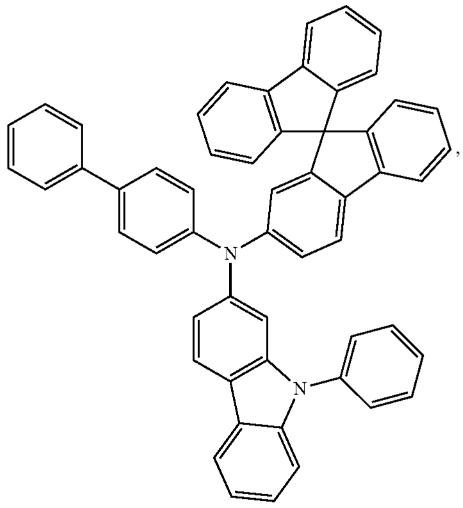
,
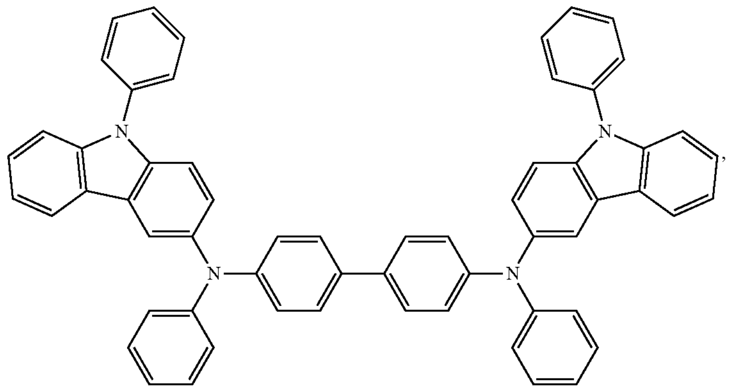
,
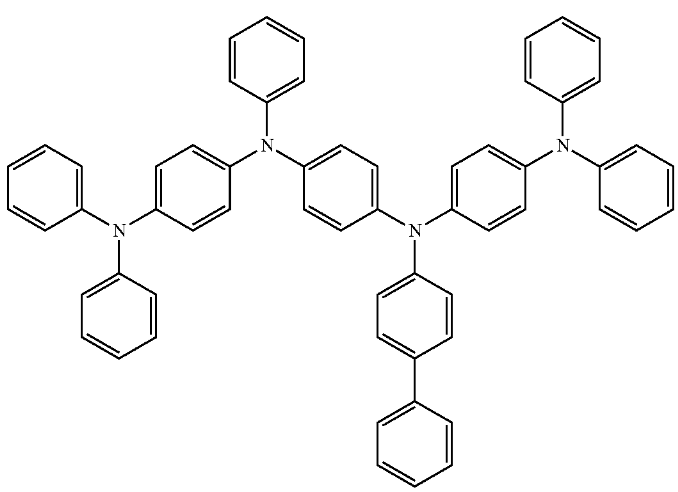
,

-continued
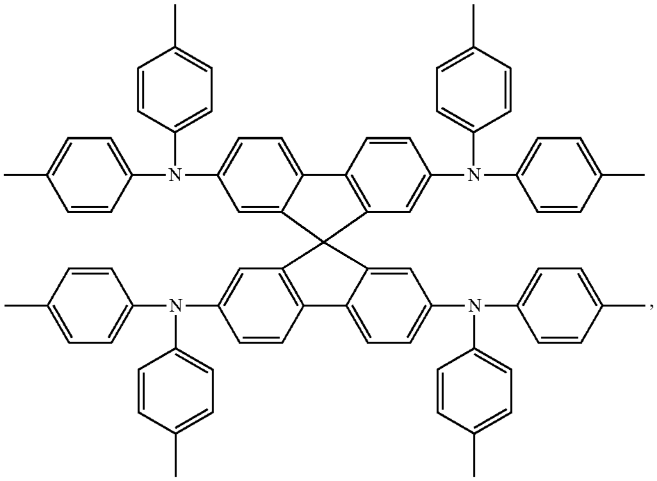
,
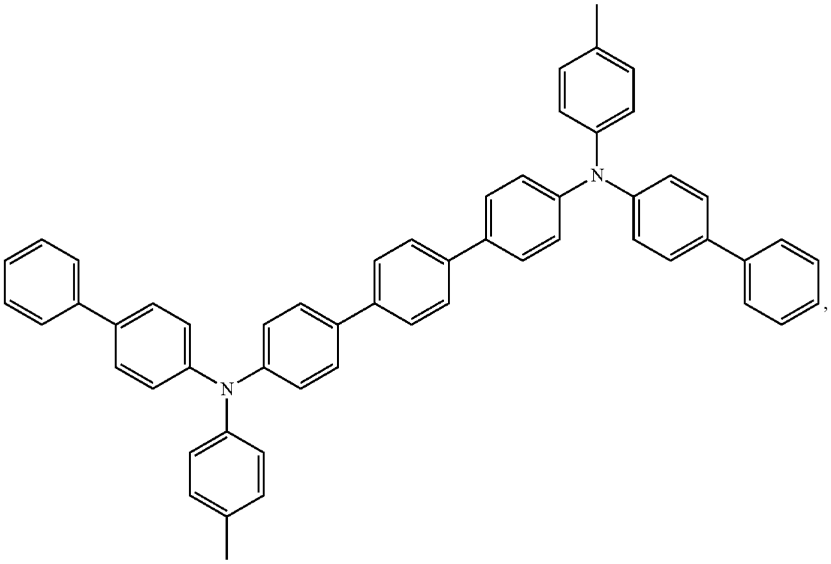
,
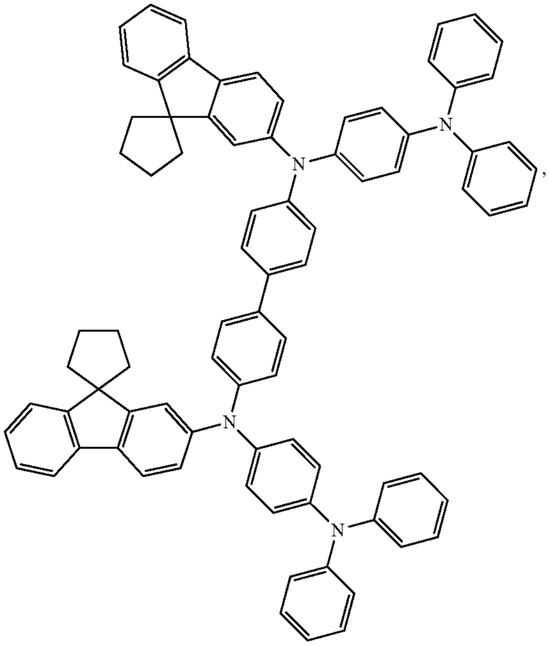
,

-continued
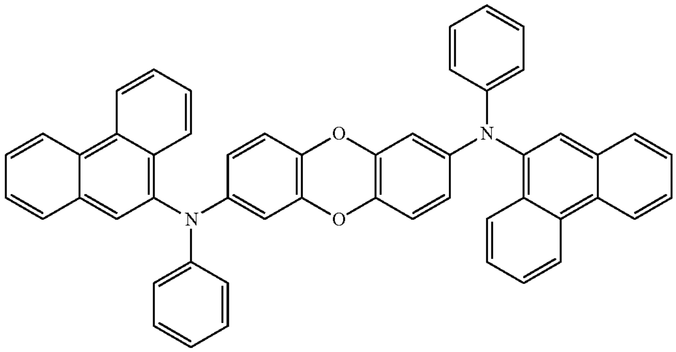
,
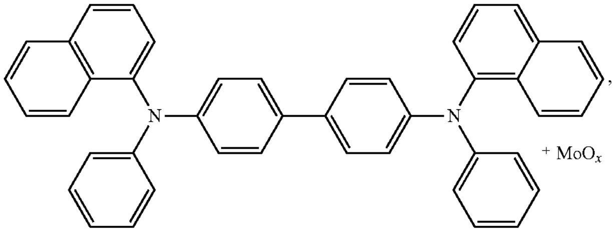
,
+ $MoO_x$
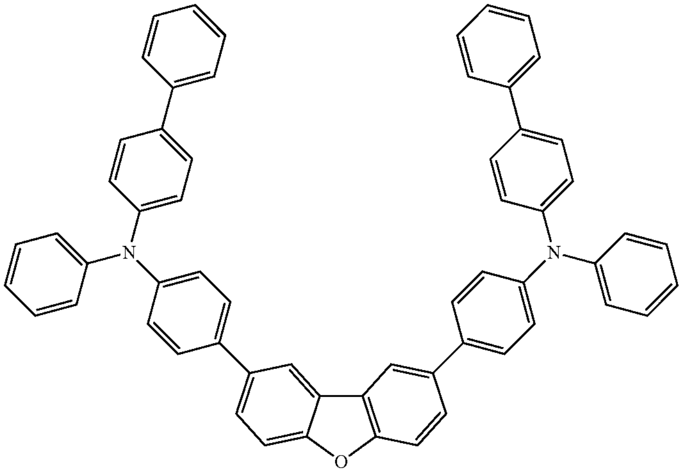
,
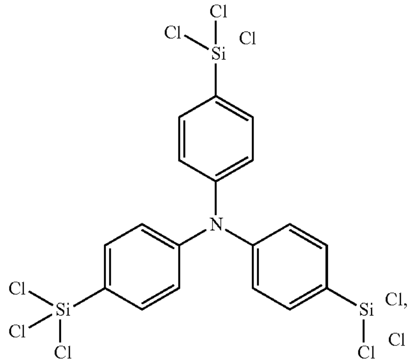
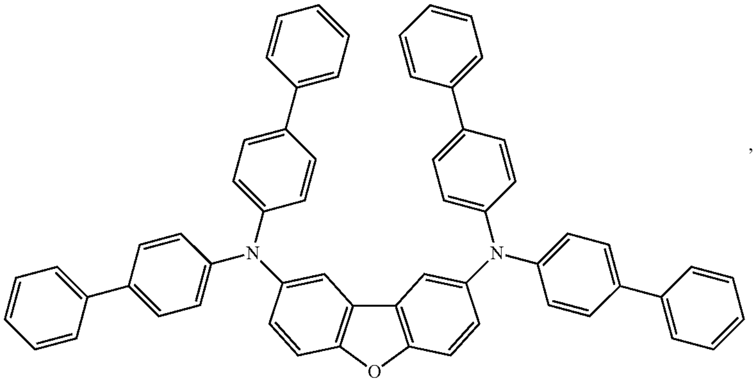
,
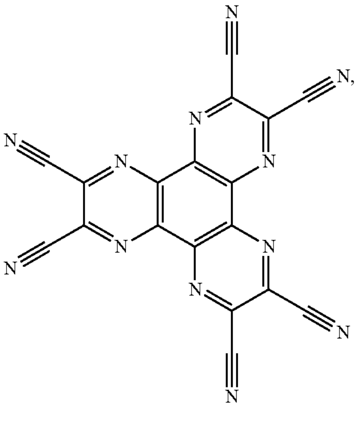

-continued
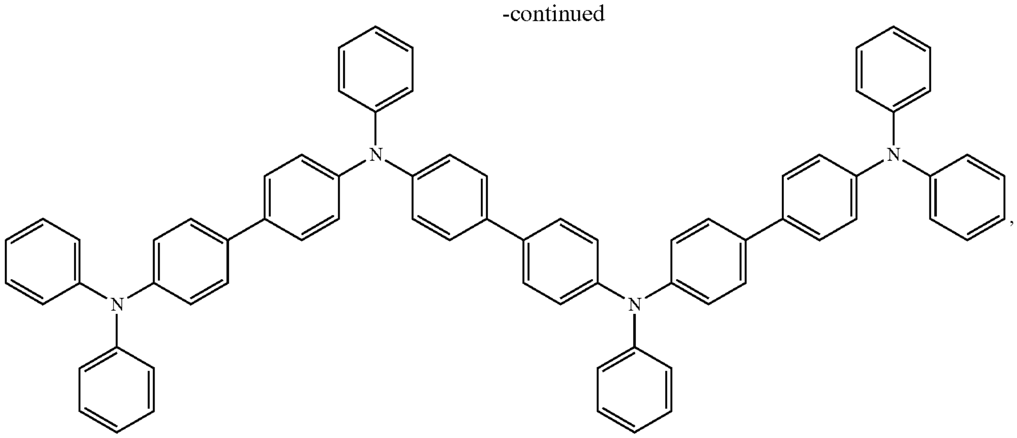
,
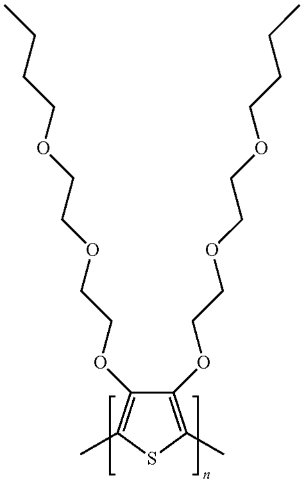
,
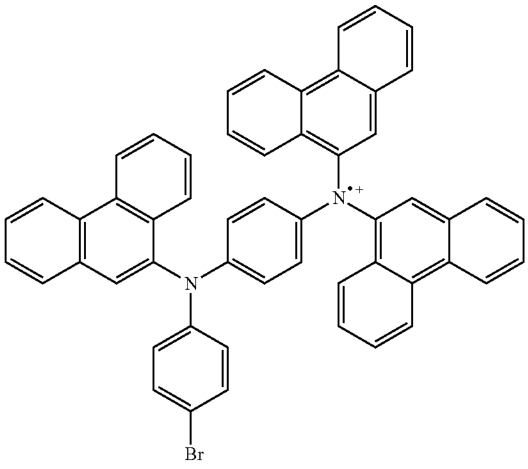
,
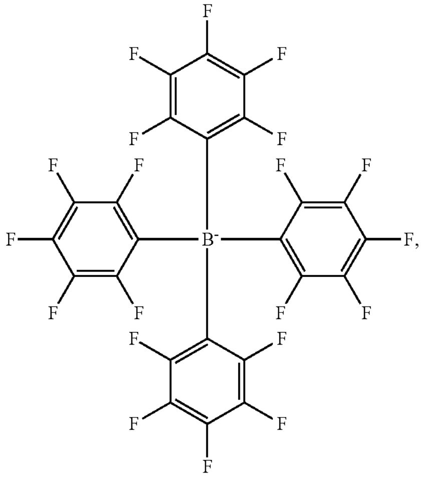
F,
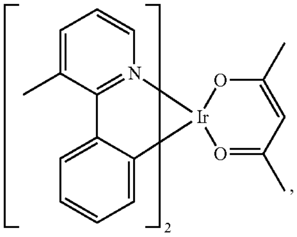
, -continued
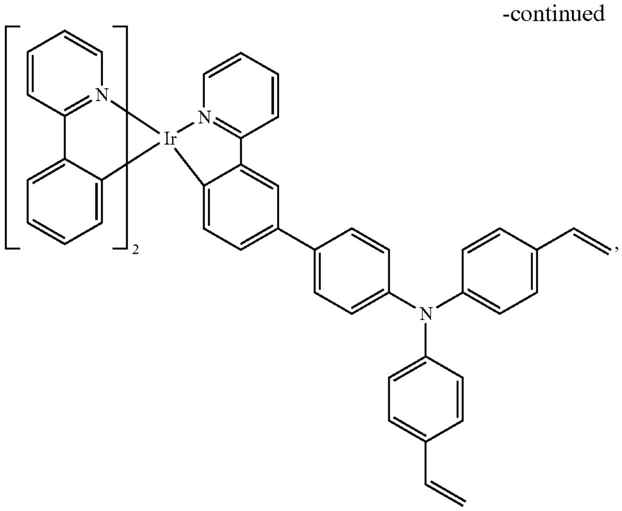
,
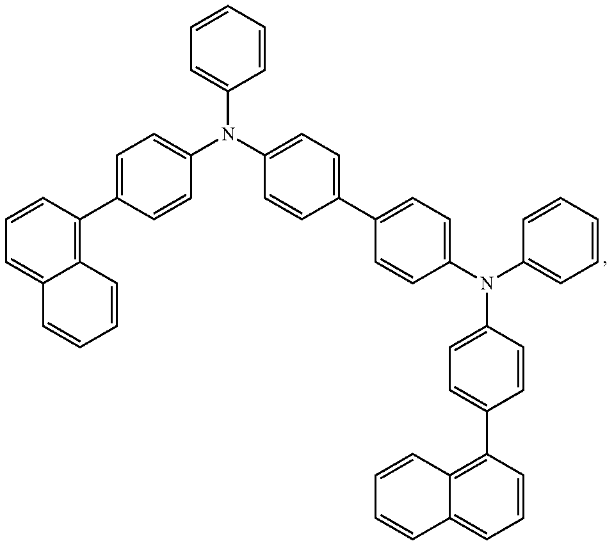
,
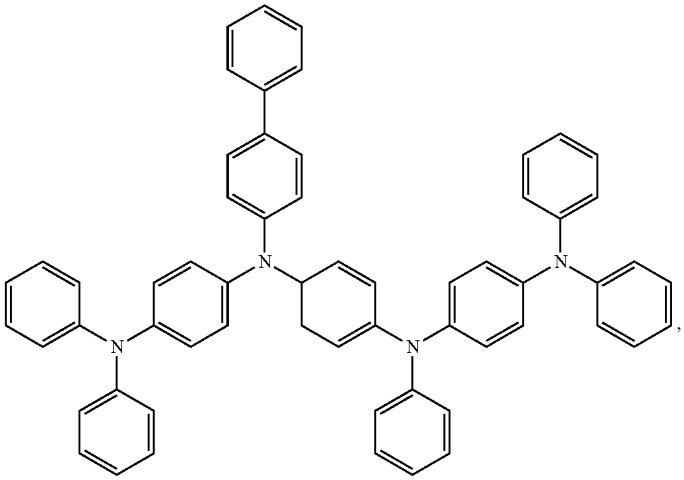
, -continued
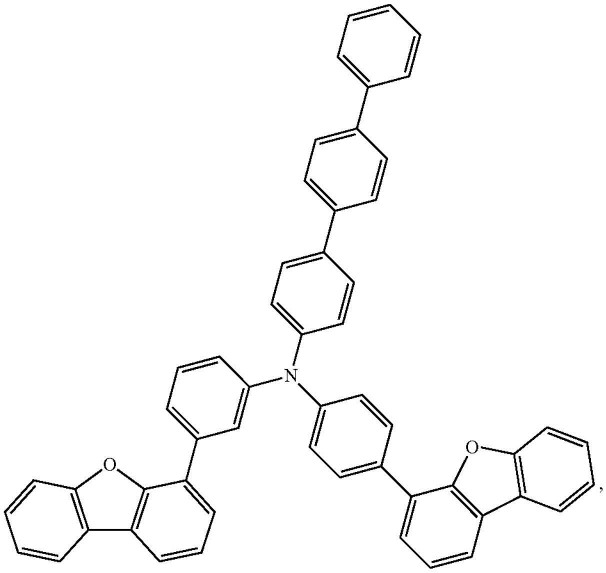
,
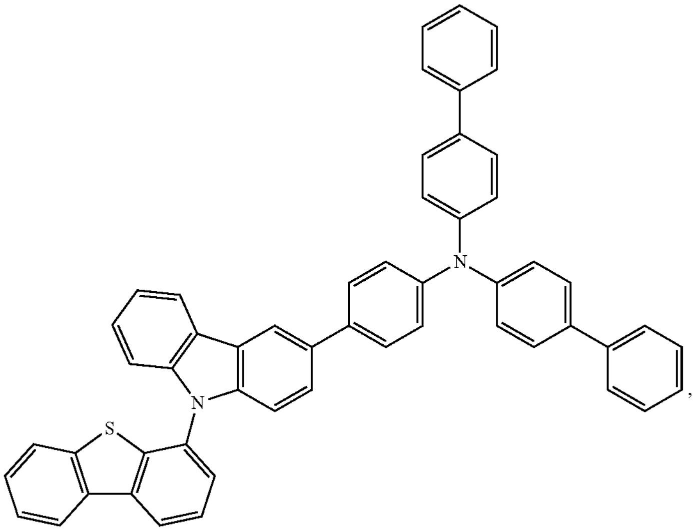
,
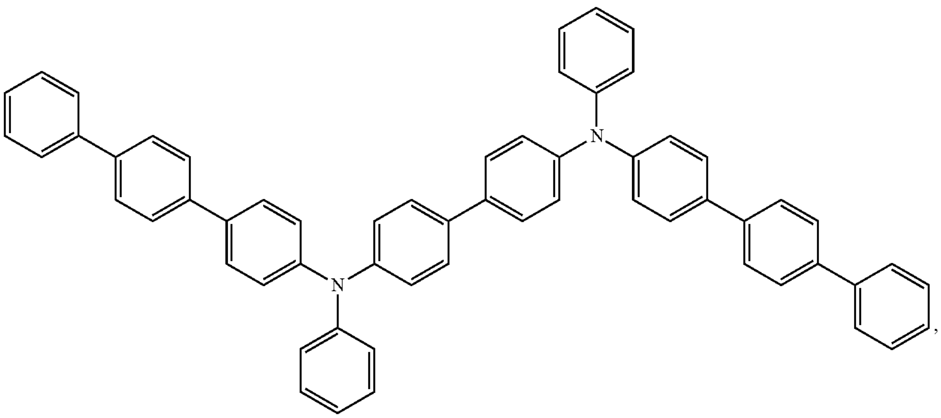
, -continued
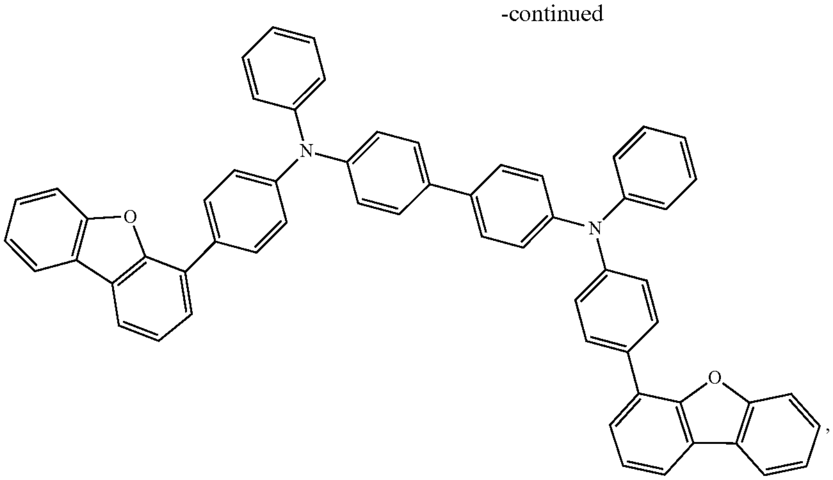
,
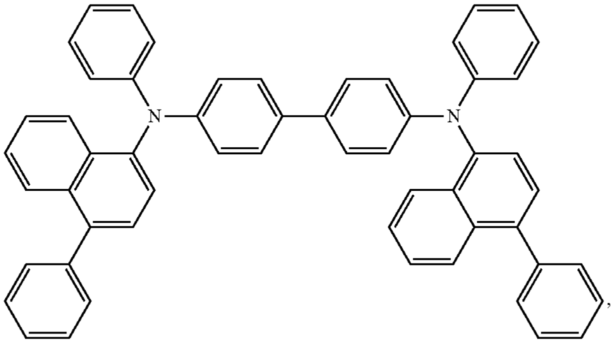
,
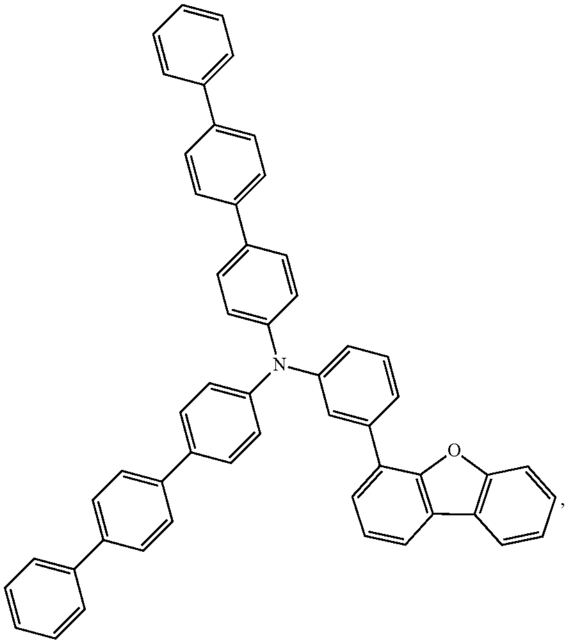
,
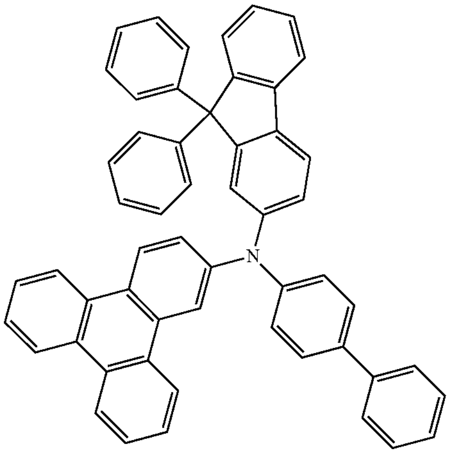
, -continued
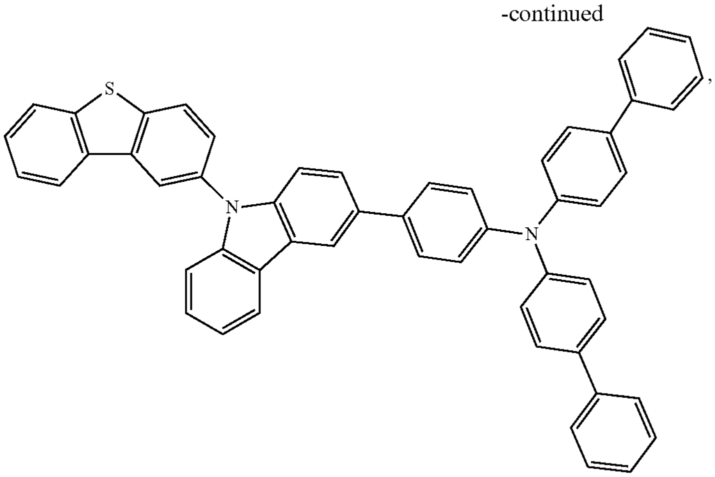
,
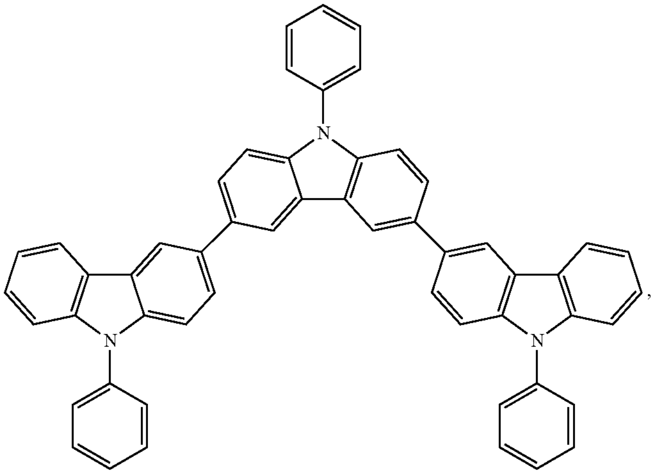
,
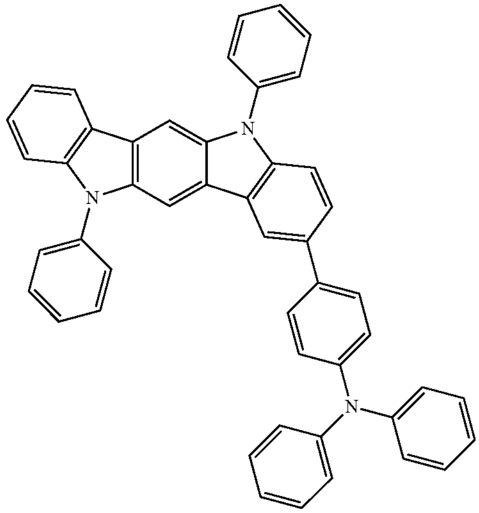
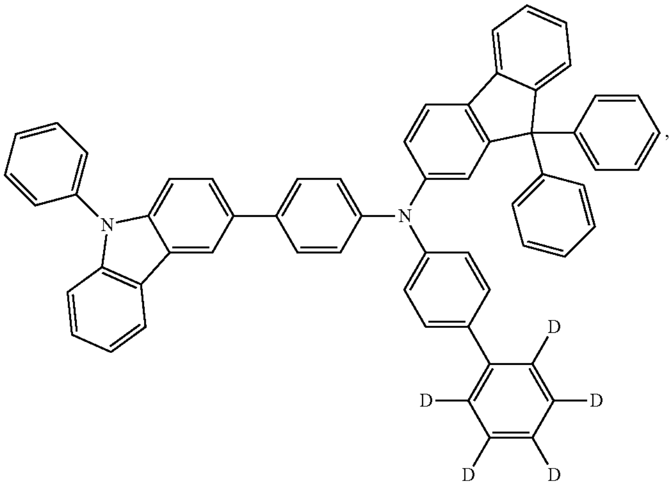
, -continued
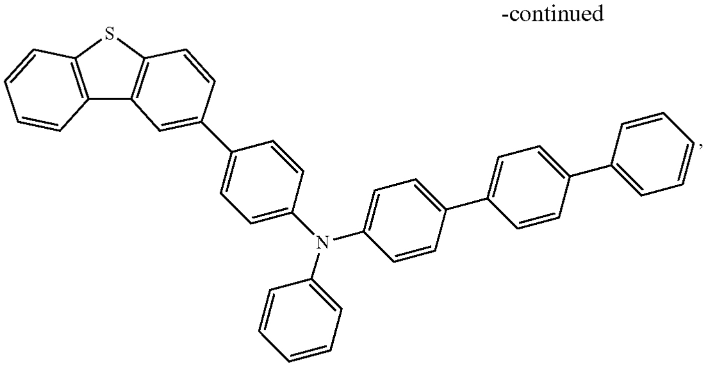
,
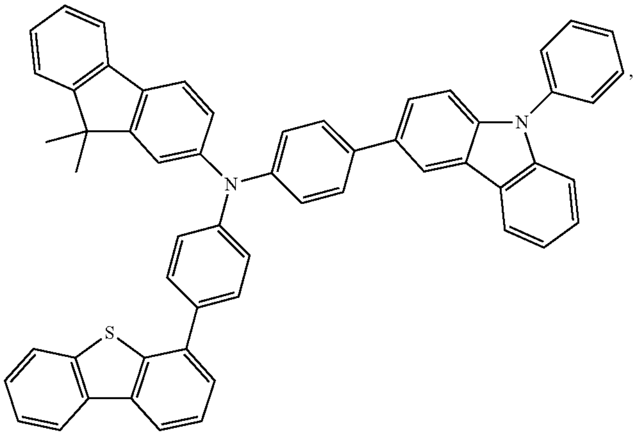
,
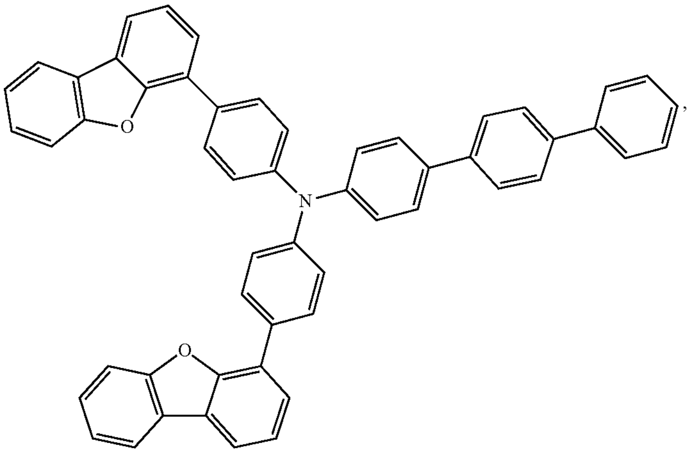
, -continued
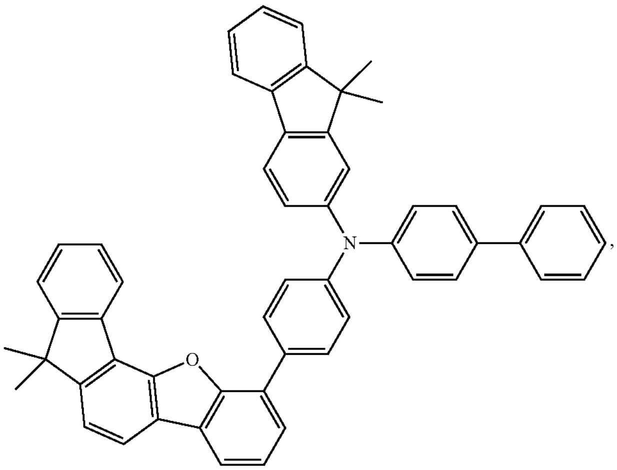
,
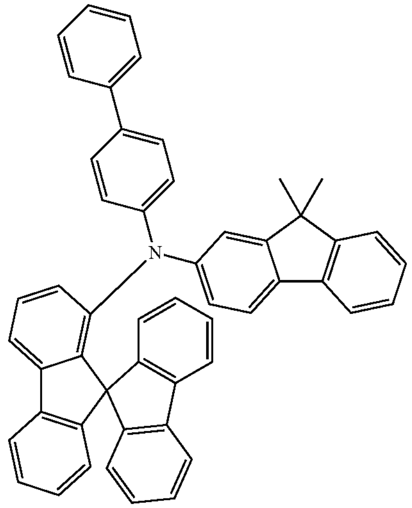
,
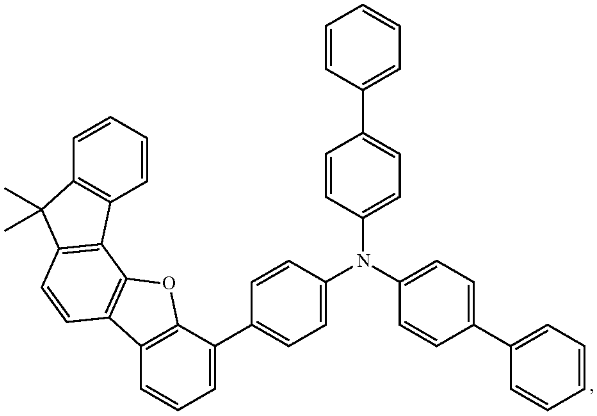
,
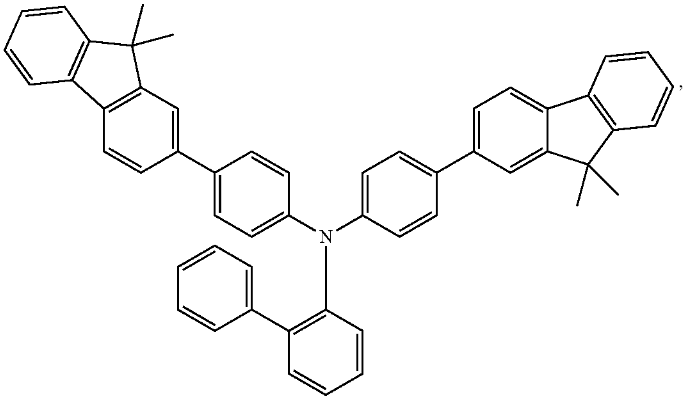
, -continued
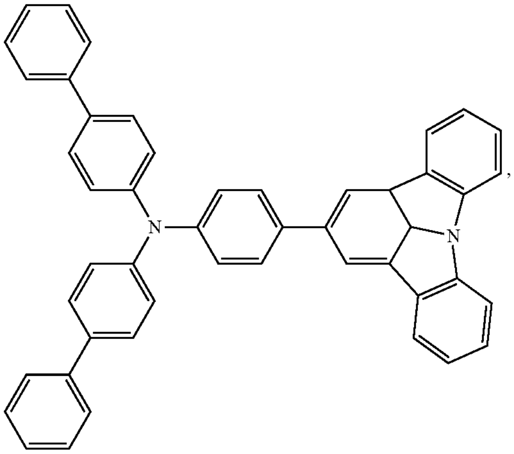
,
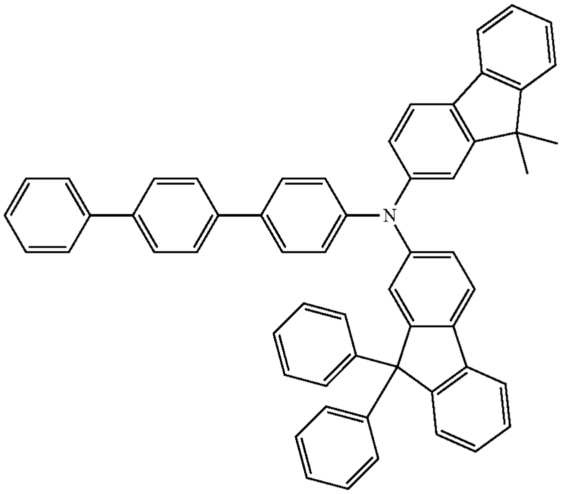
,
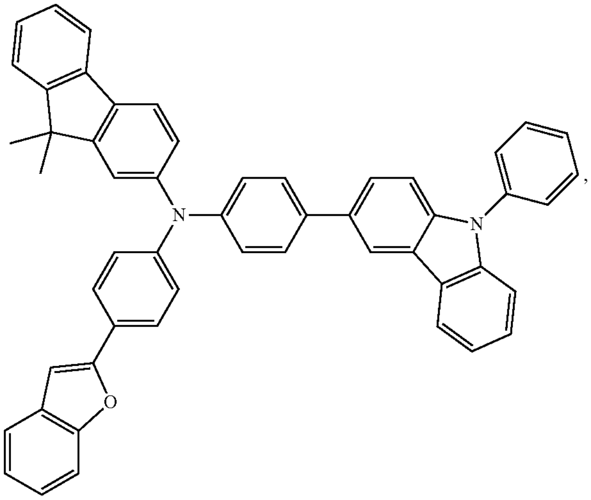
,
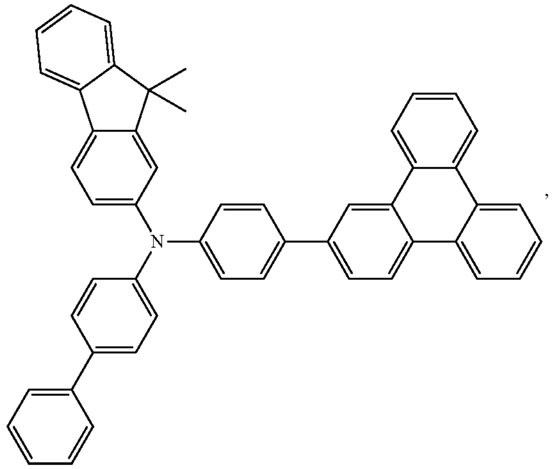
,
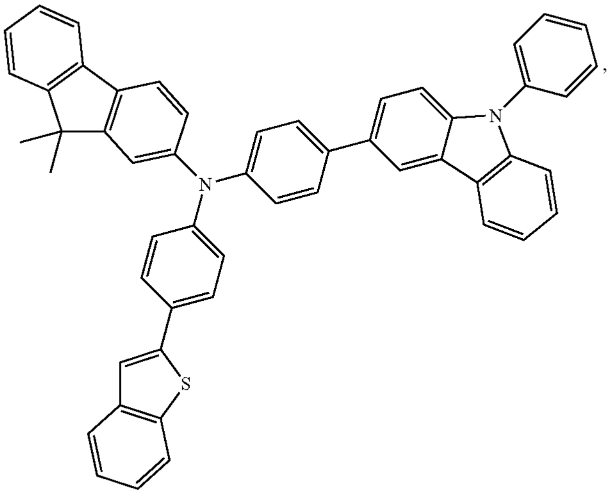
, -continued
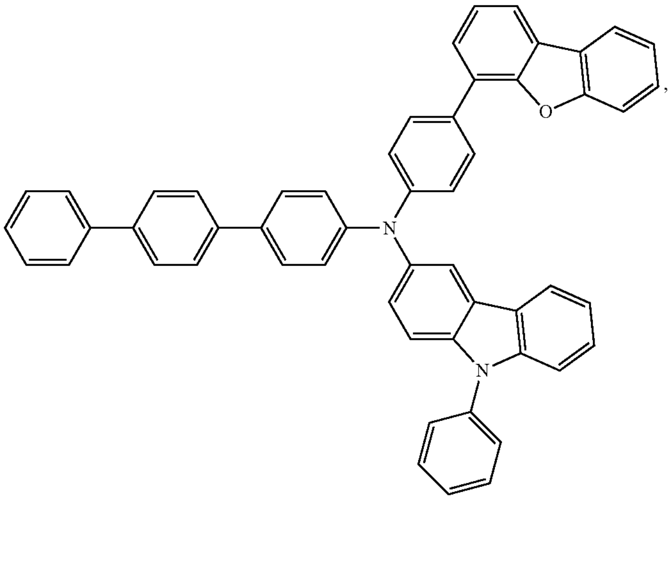
,
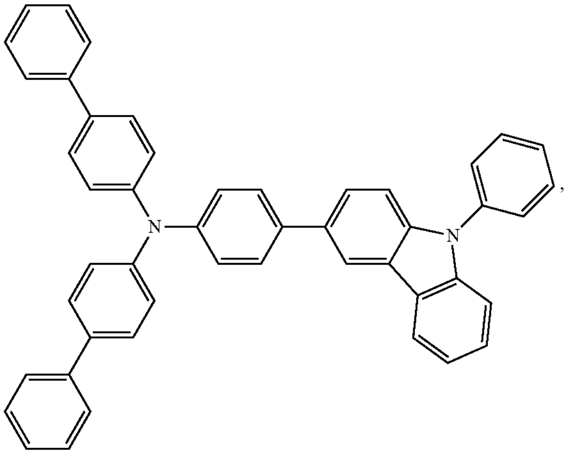
,
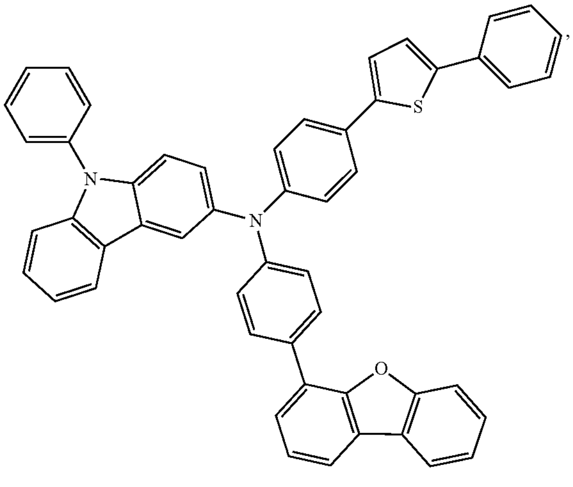
,
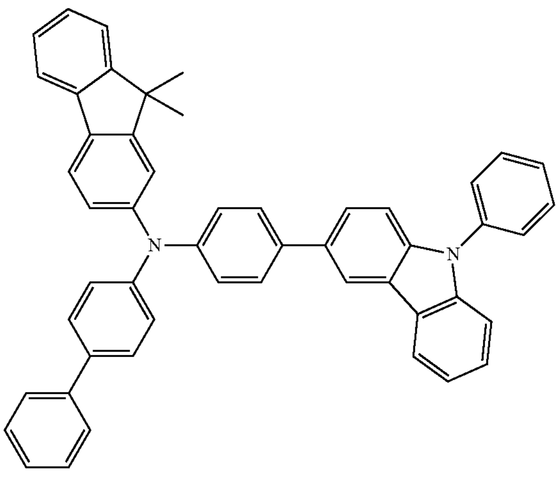
, -continued
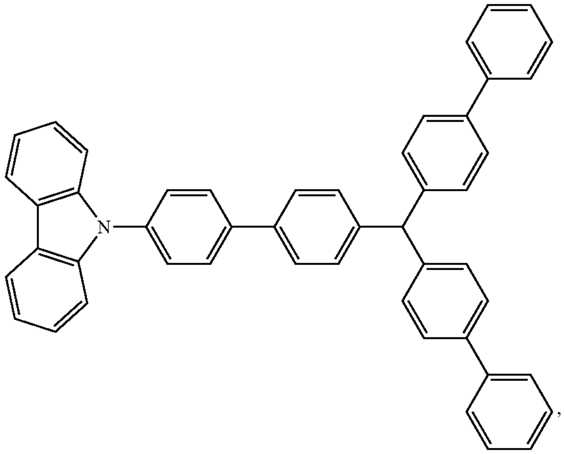
,
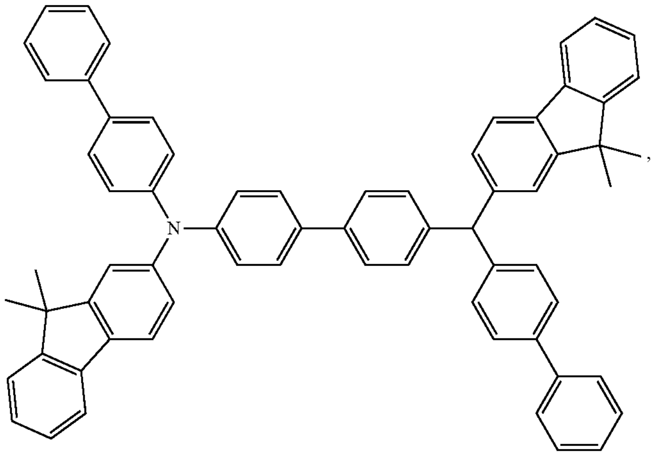
,
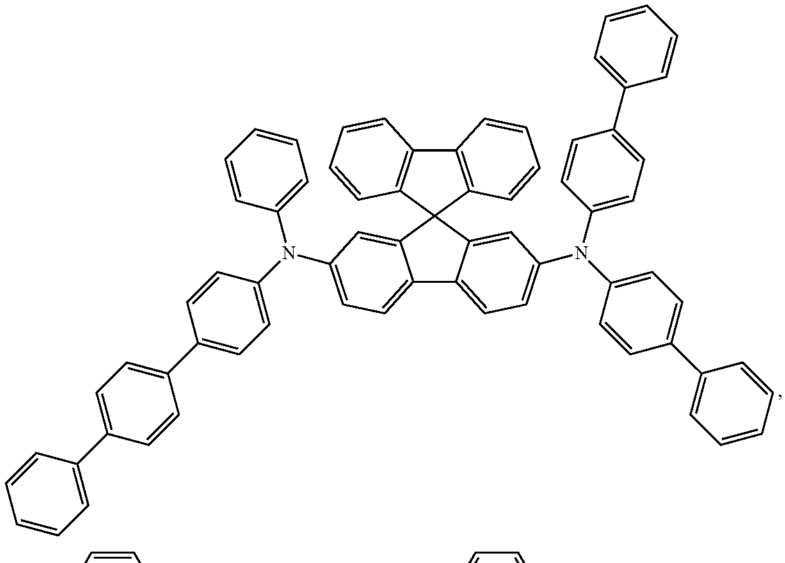
,
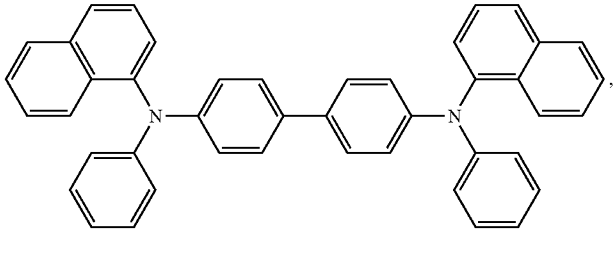
, -continued
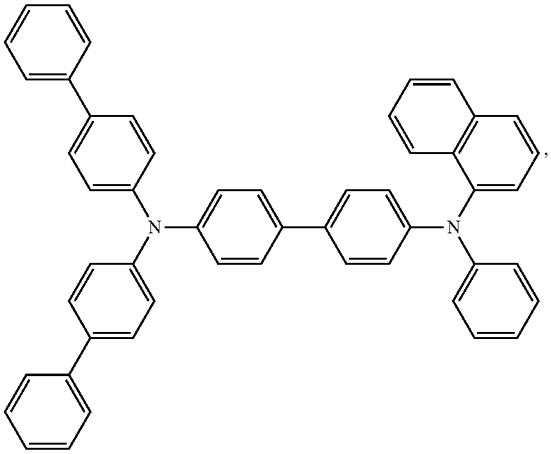
,
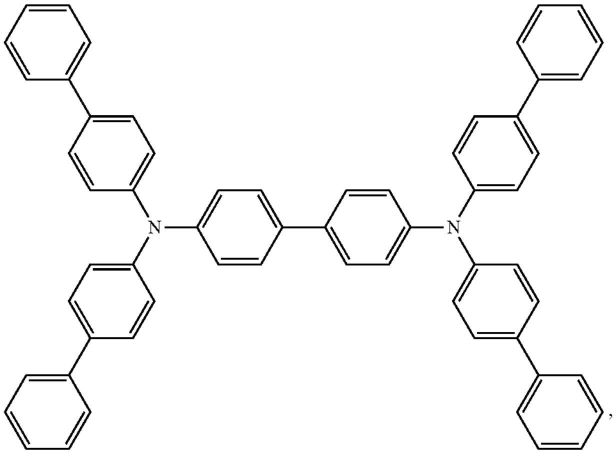
,
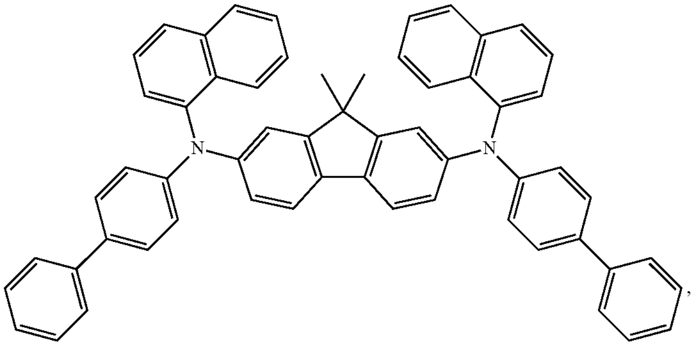
, -continued
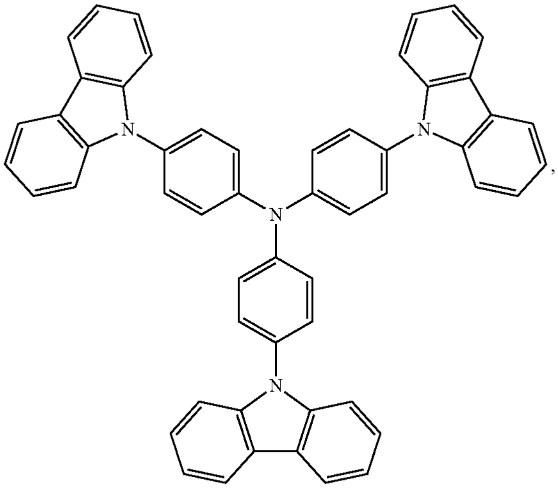,
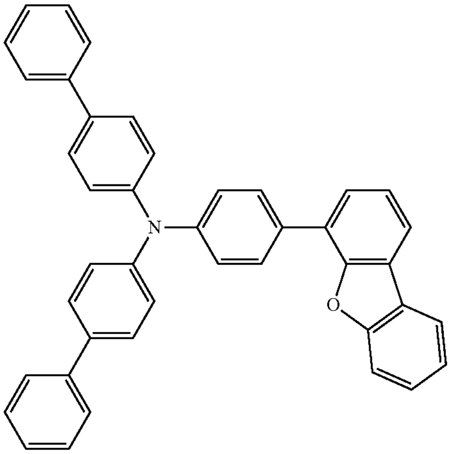,
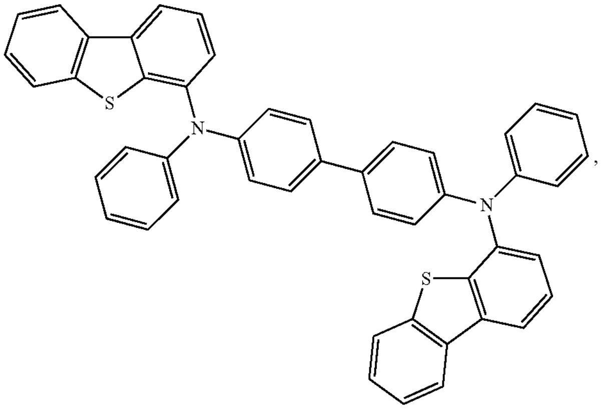,
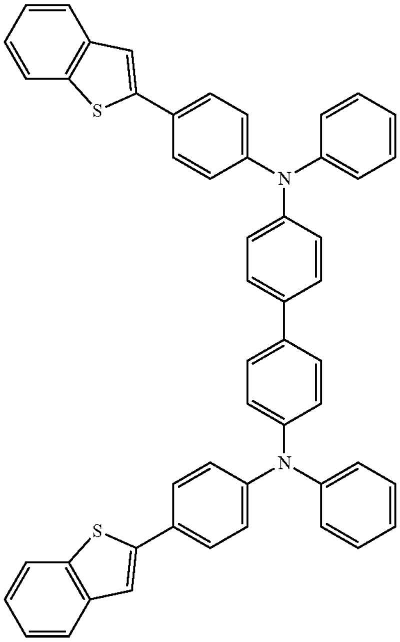, and
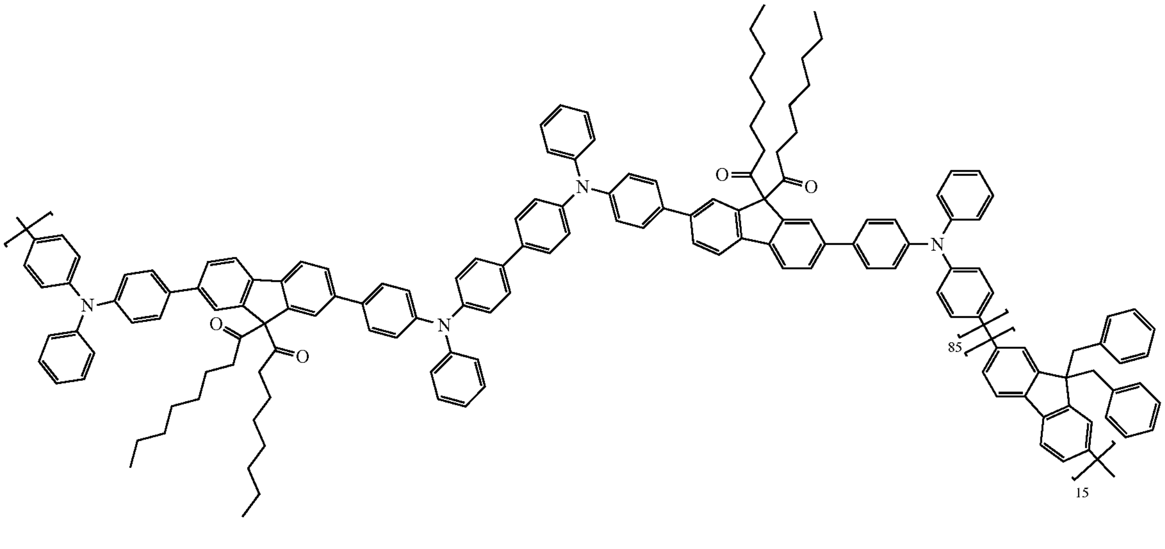

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

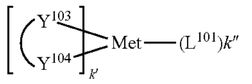

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

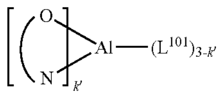 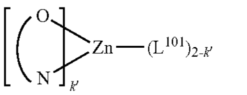

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

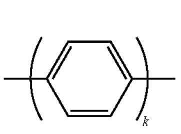, 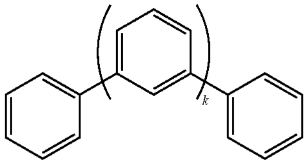,

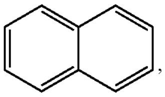, 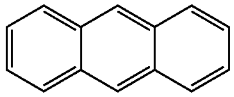,

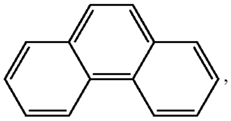,

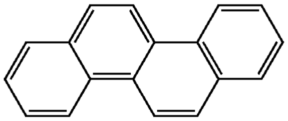,

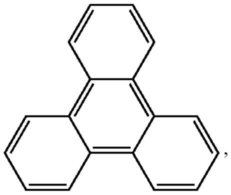,

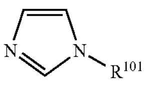, 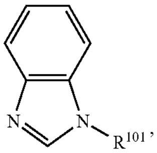,

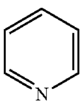, 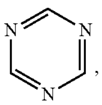, 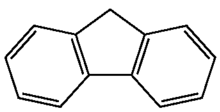,

-continued

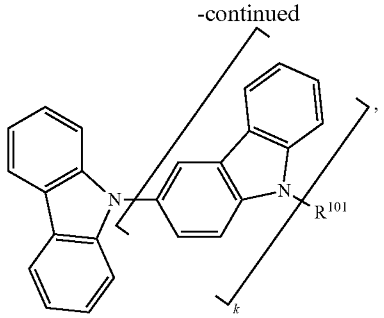

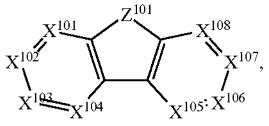

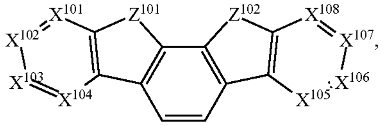

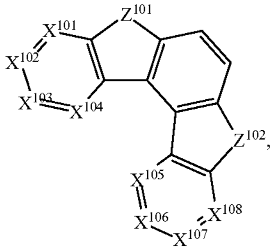

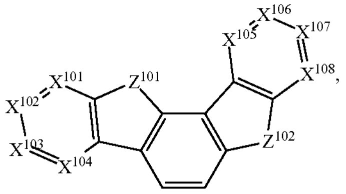

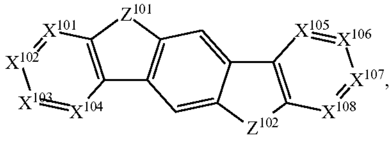

and

-continued

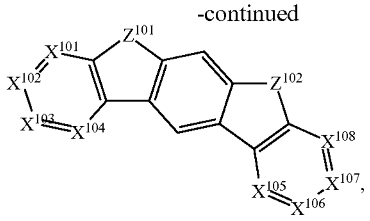

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

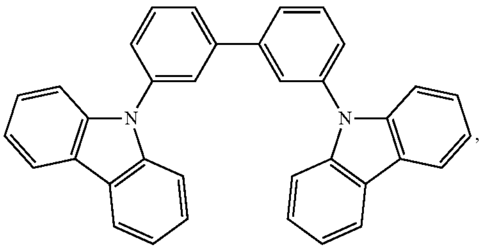

,

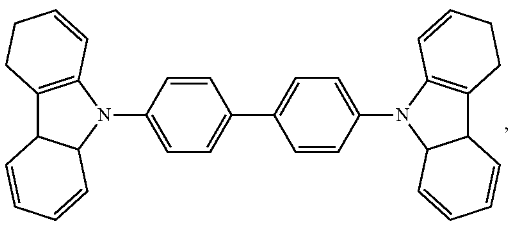

,

-continued
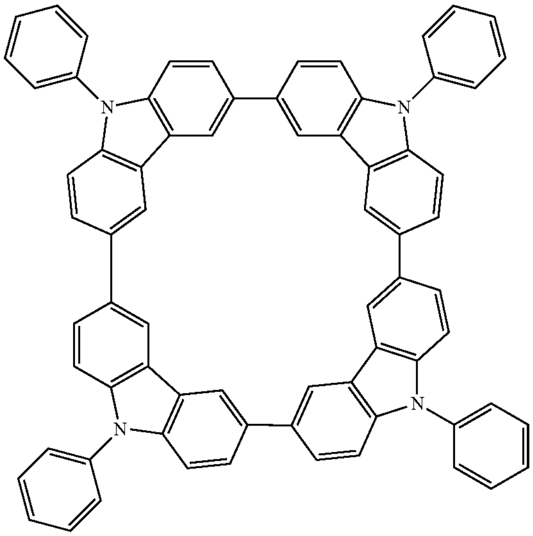
,
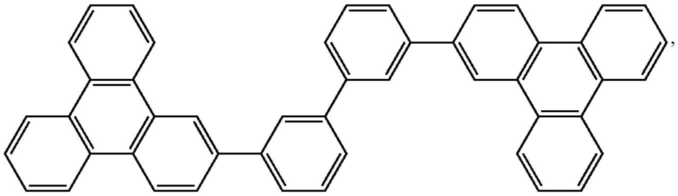
,
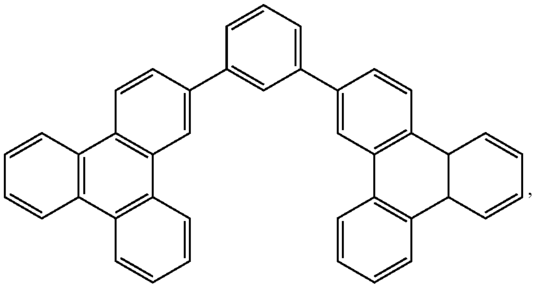
,
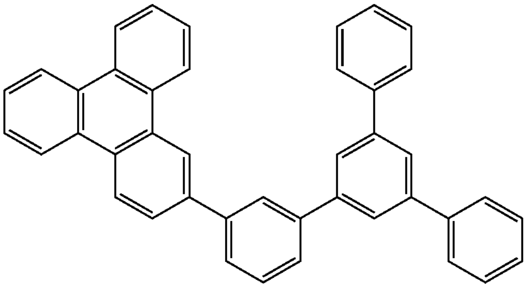
,
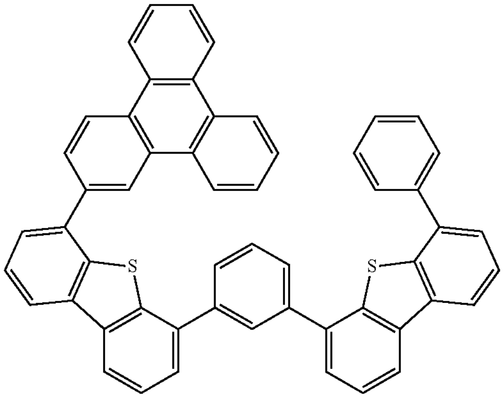
,
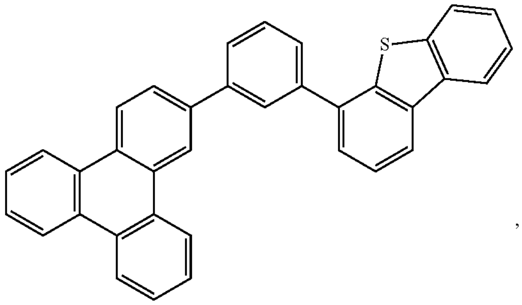
,
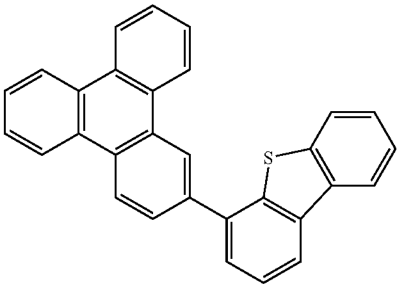
,
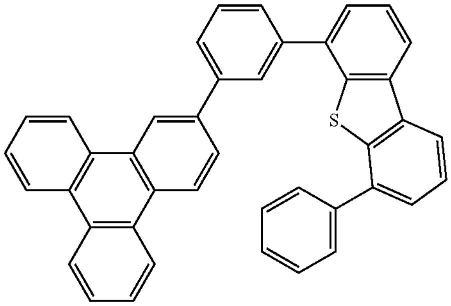
, -continued
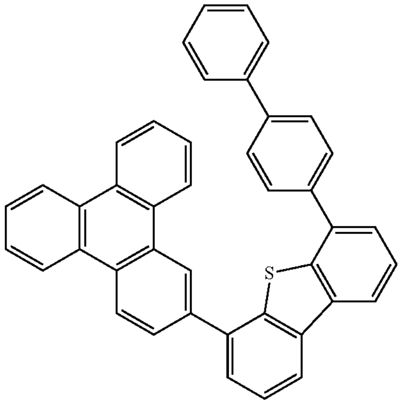
,
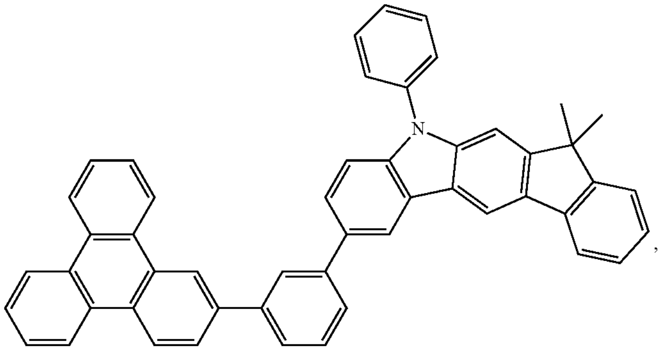
,
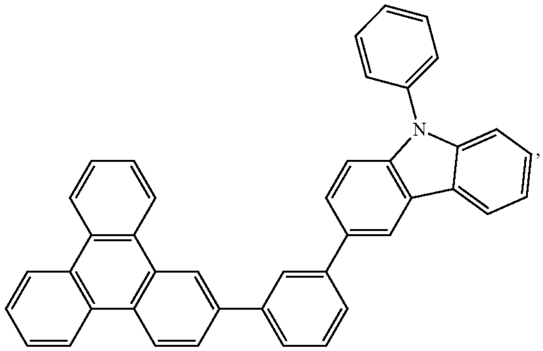
,
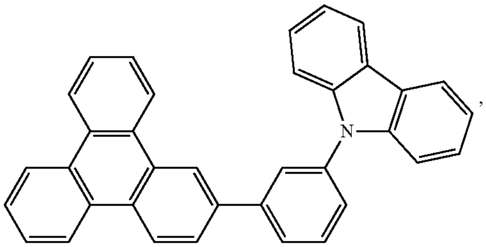
,
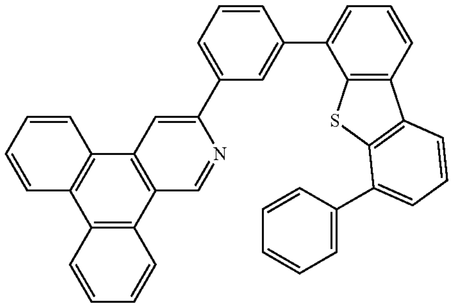
,
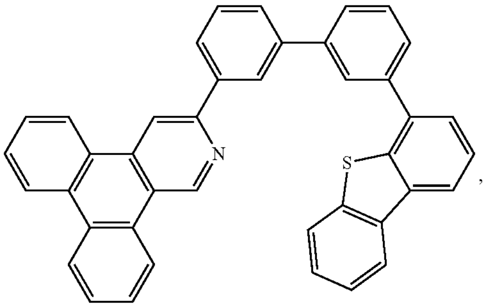
,
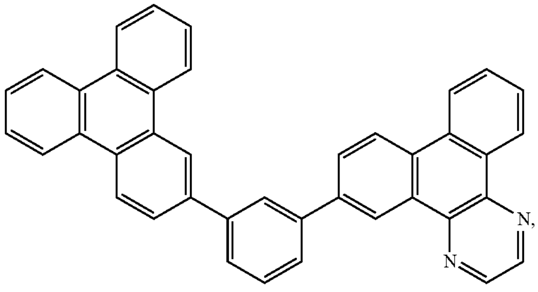
,
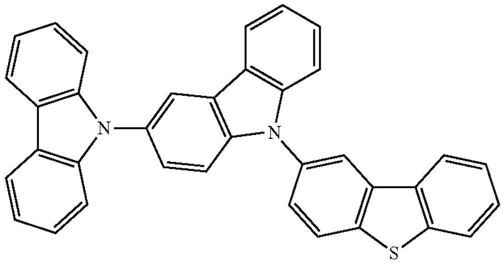
,
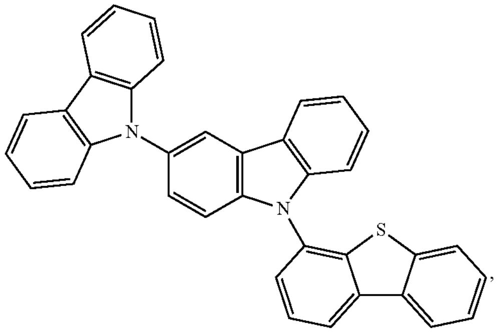
,
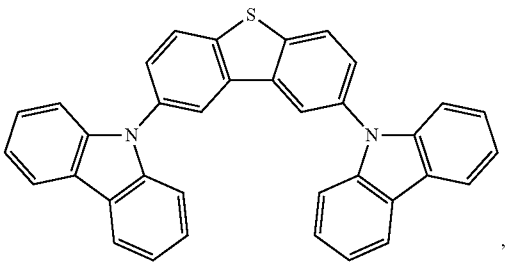
, -continued
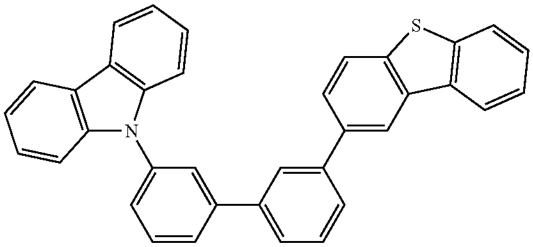
,
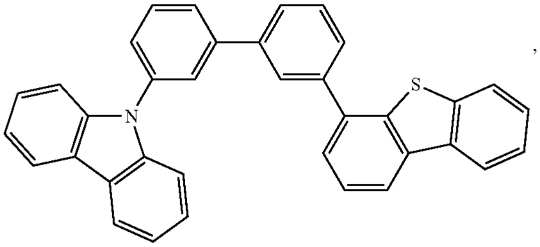
,
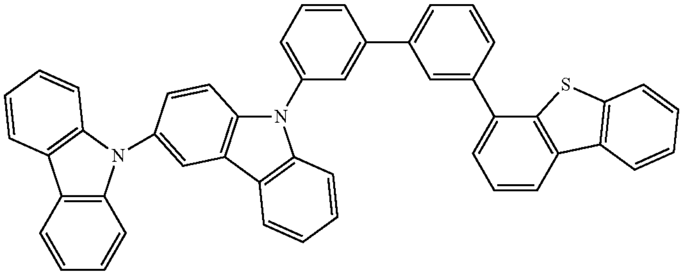
,
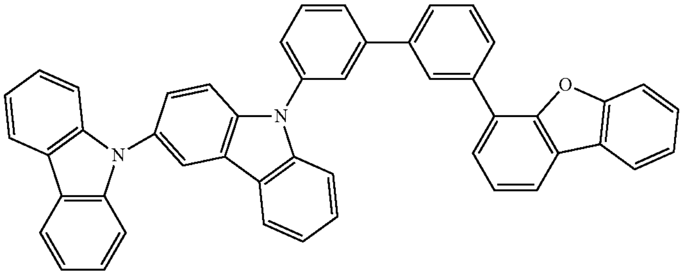
,
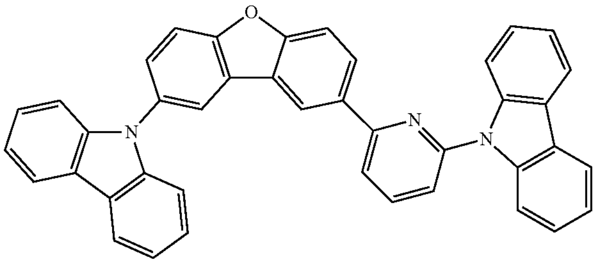
,
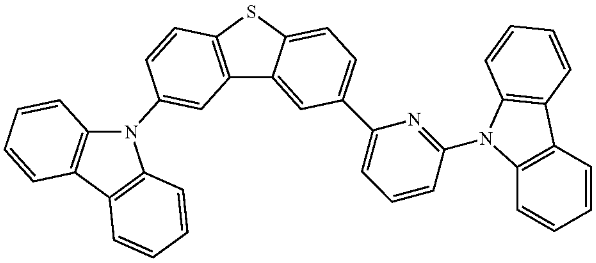
,
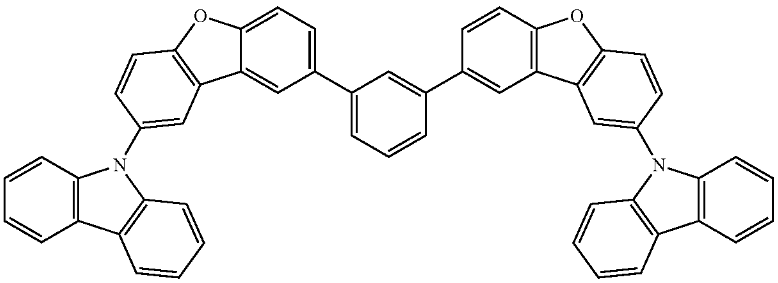
, -continued
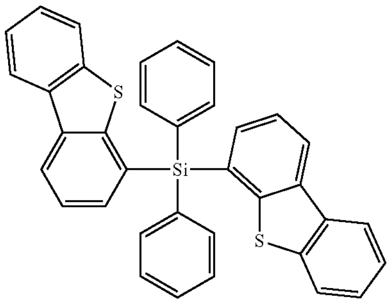
,
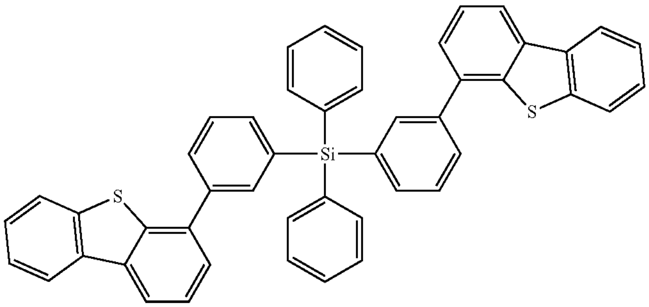
,
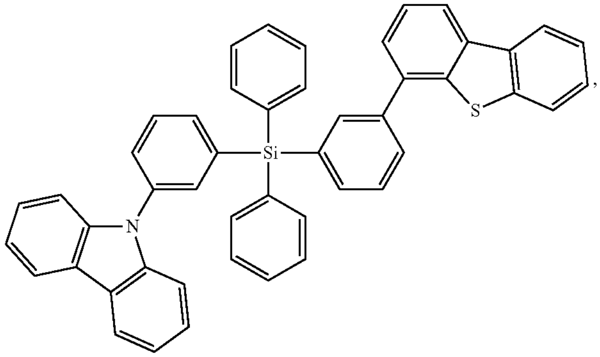
,
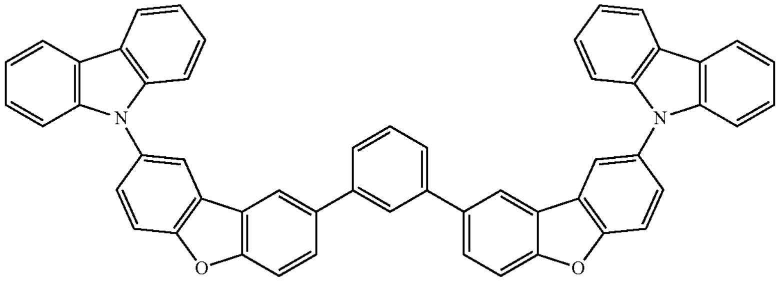
,
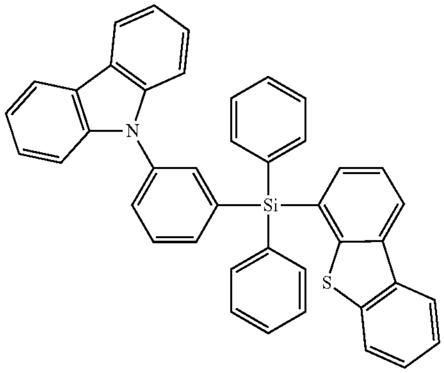
,
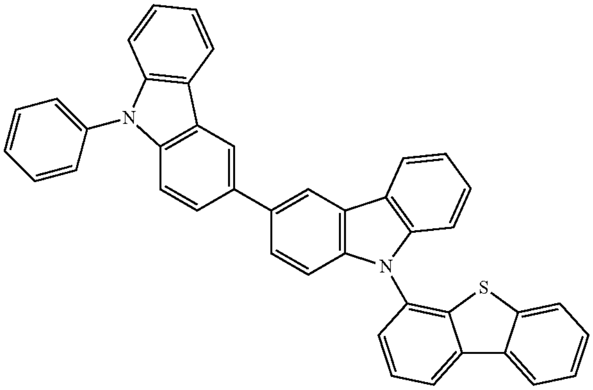
,
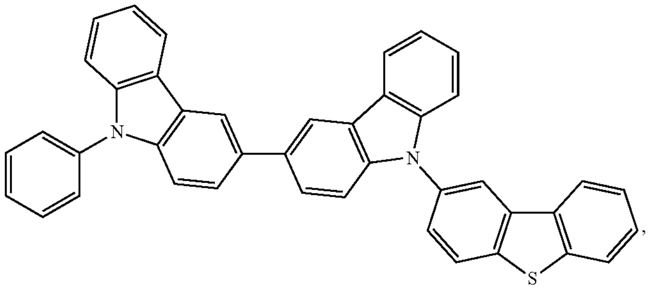
, -continued
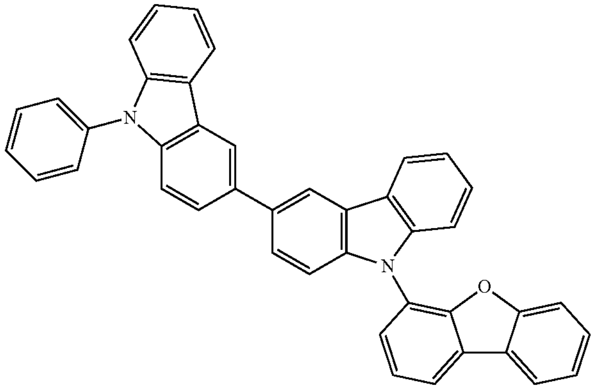
,
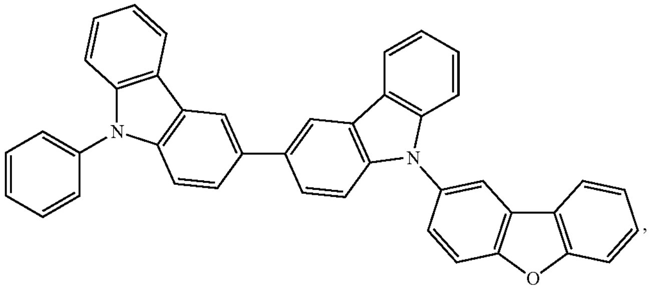
,
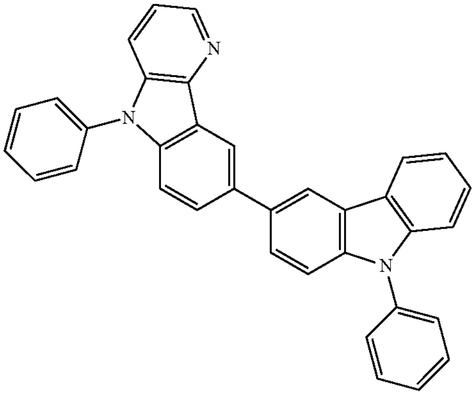
,
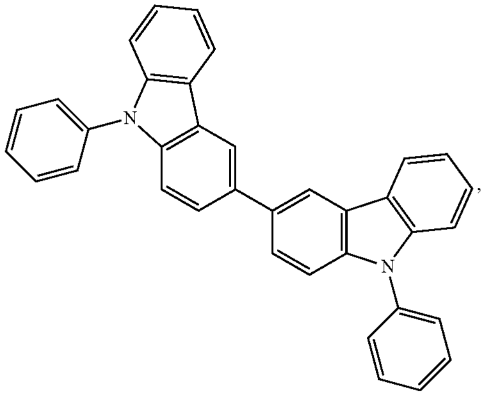
,
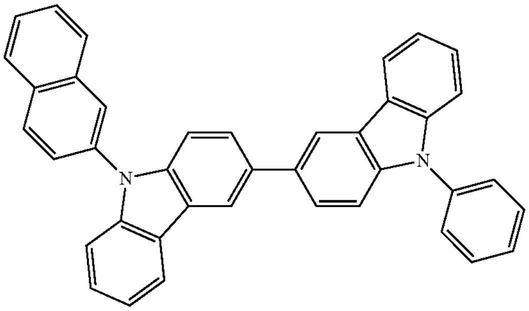
,
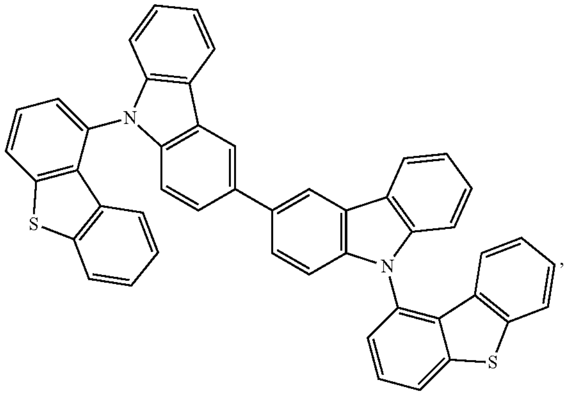
,
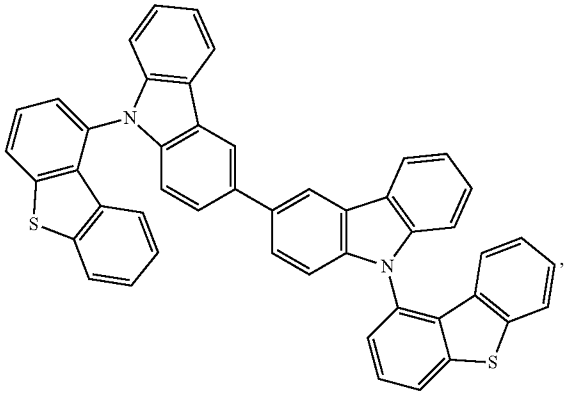
, -continued
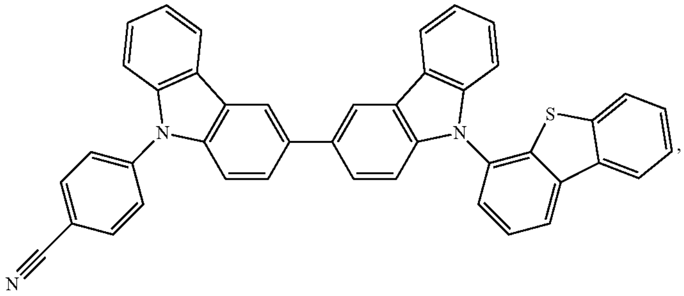
,
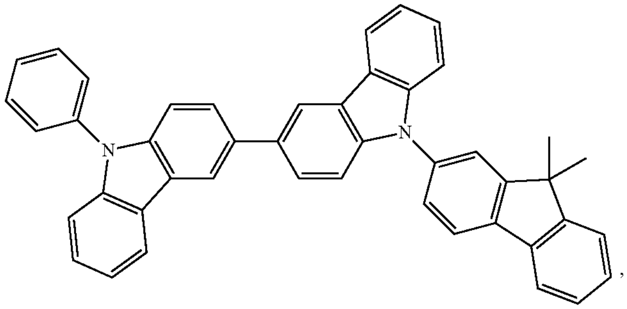
,
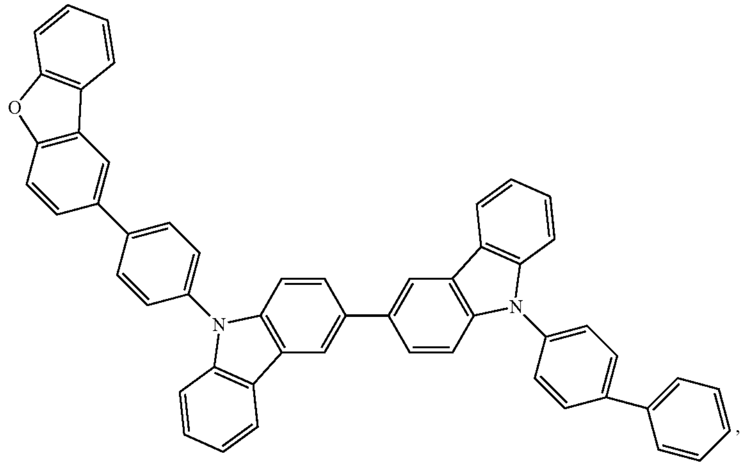
,
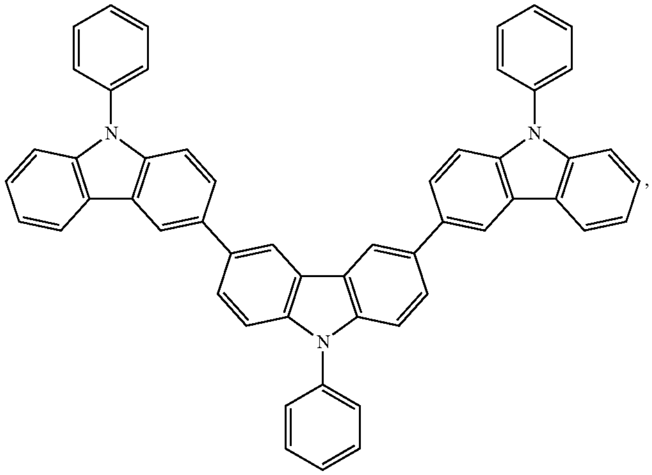
, -continued
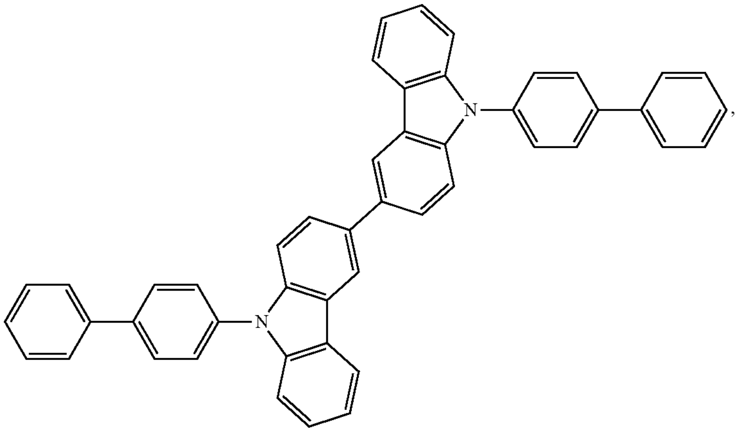
,
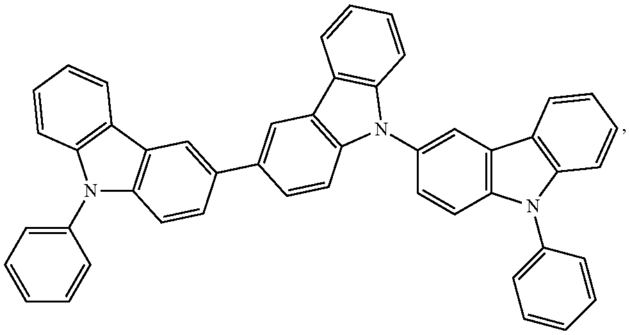
,
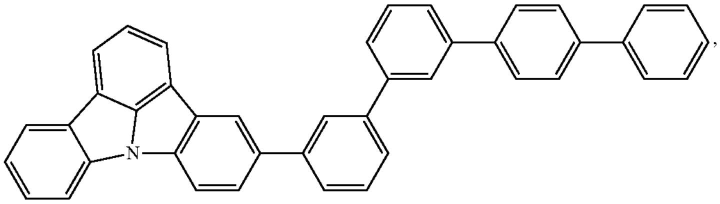
,
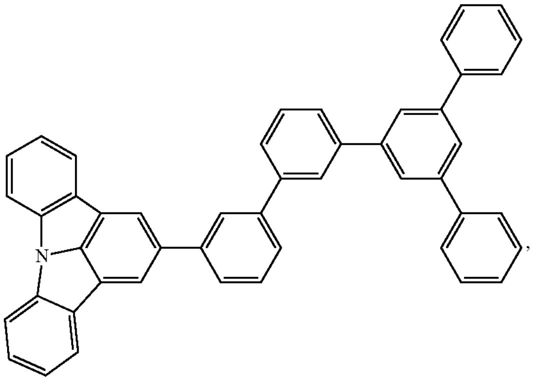
,
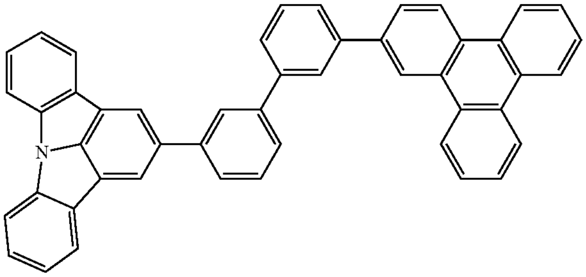
,
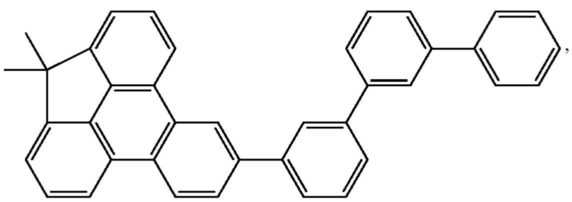
,
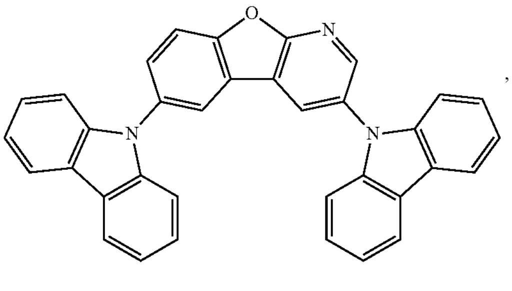
, -continued
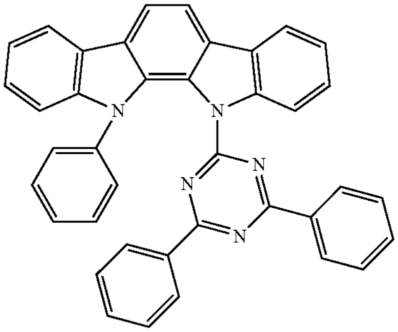,
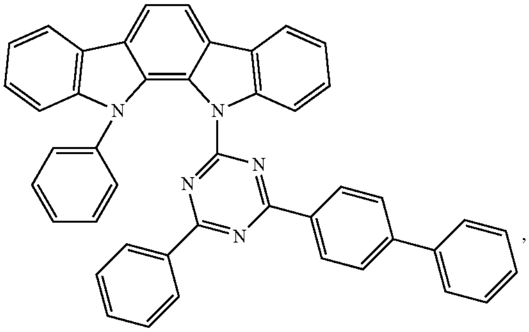,
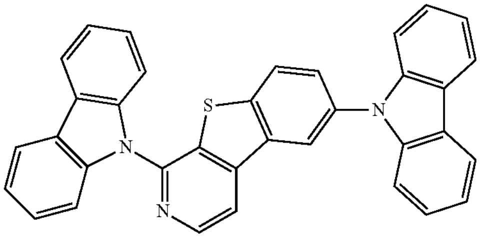,
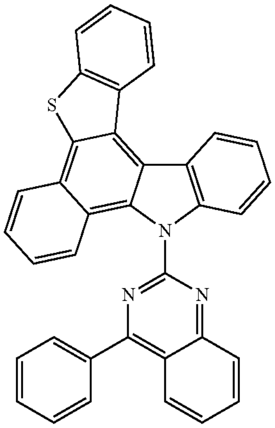,
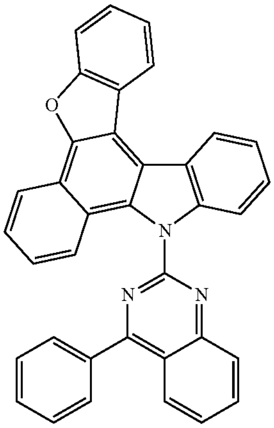,
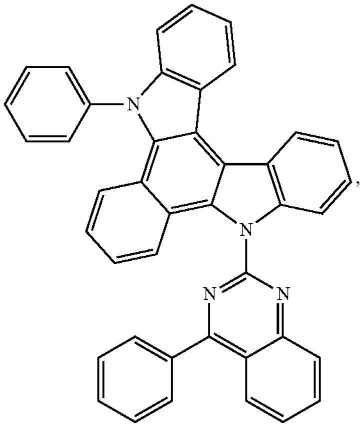,
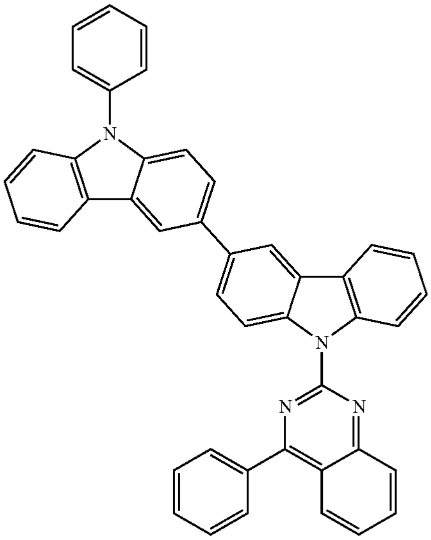,
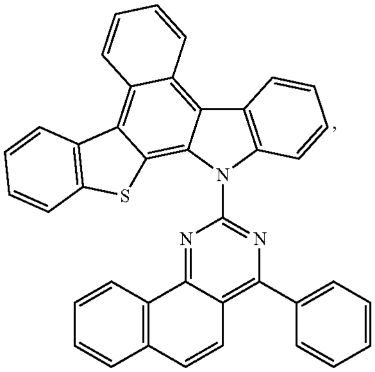,
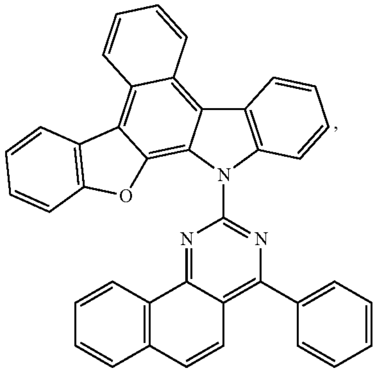, -continued
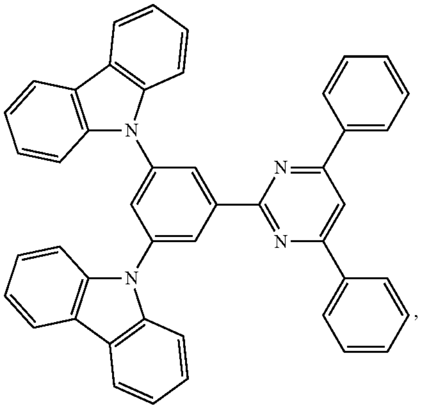
,
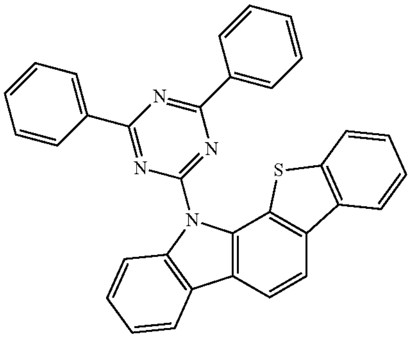
,
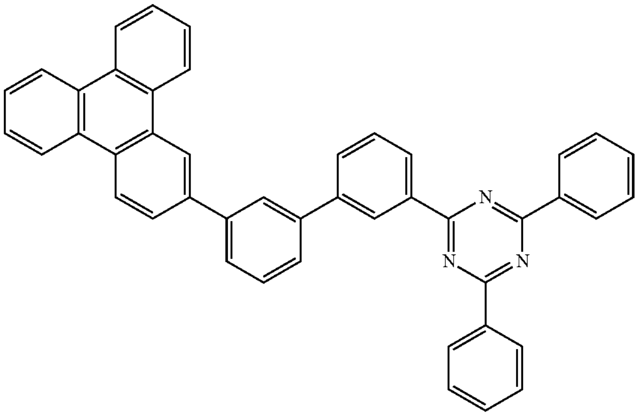
,
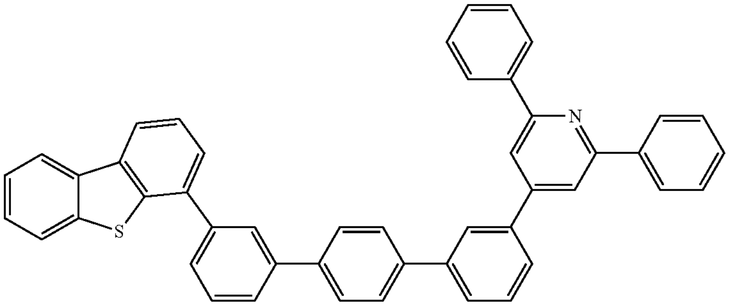
,
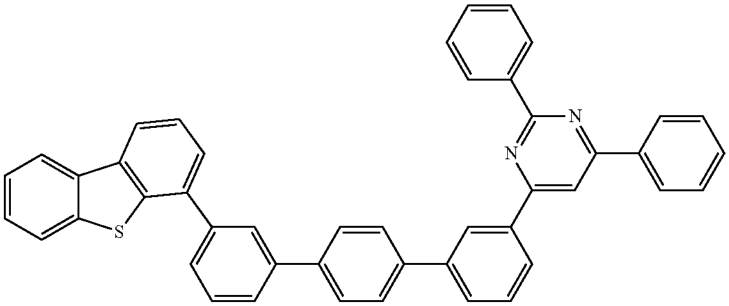
,
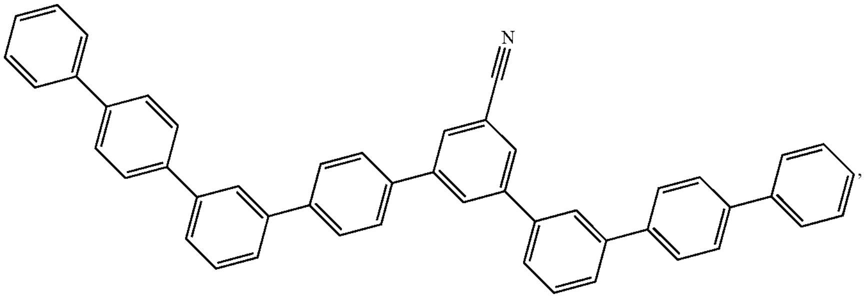
, -continued

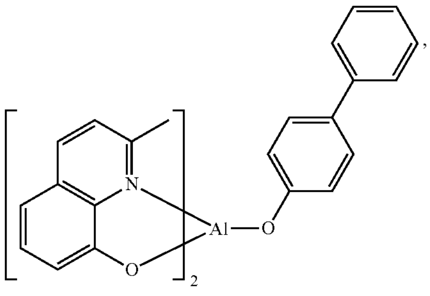

,

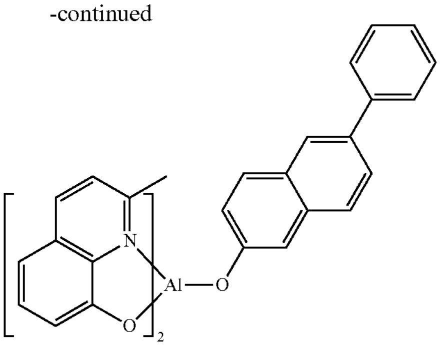

,

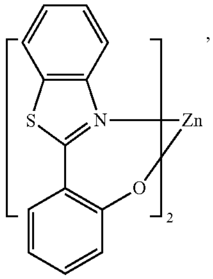

,

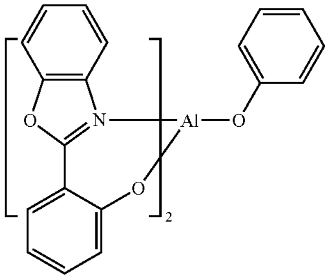

,

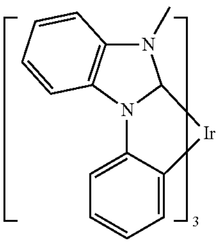

,

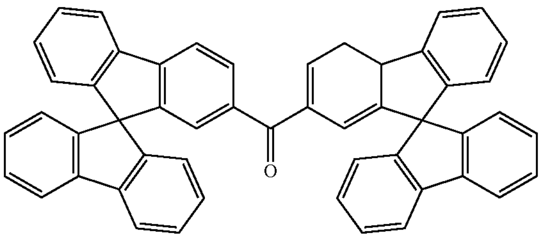

,

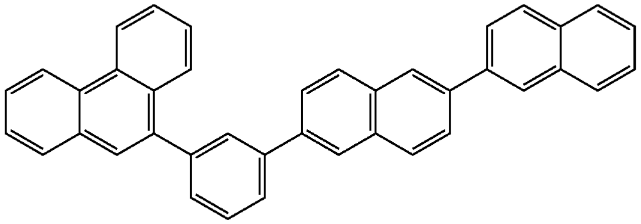

,

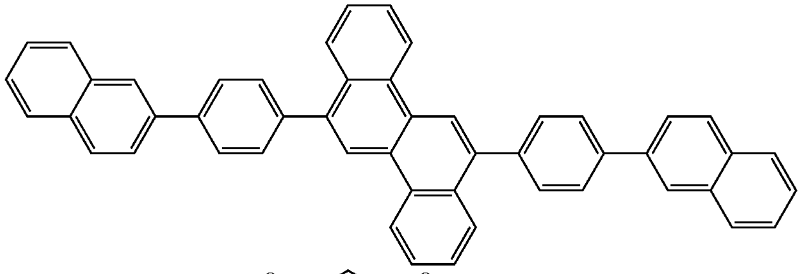

, and

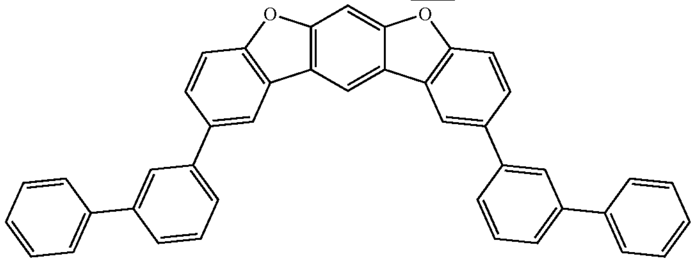

.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
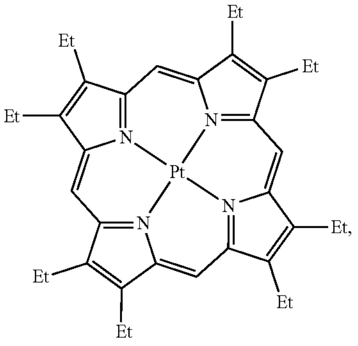
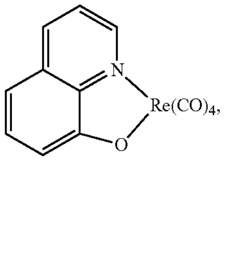
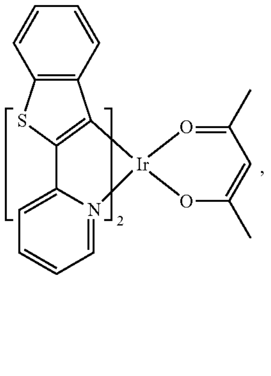
-continued
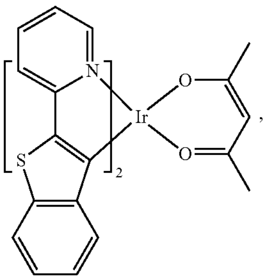
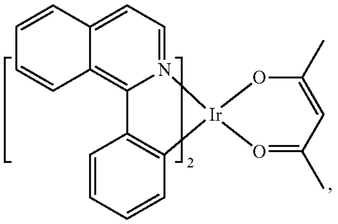
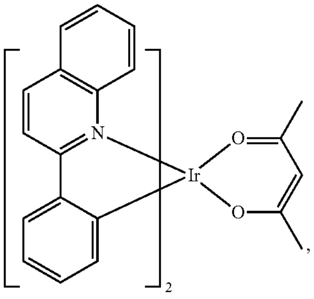
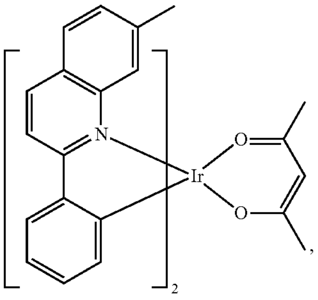
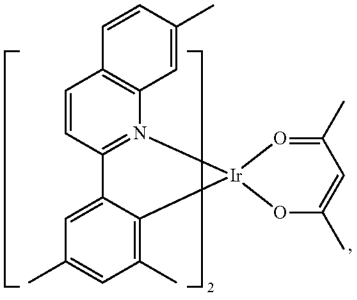
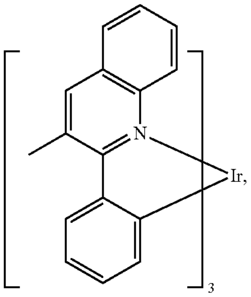

-continued
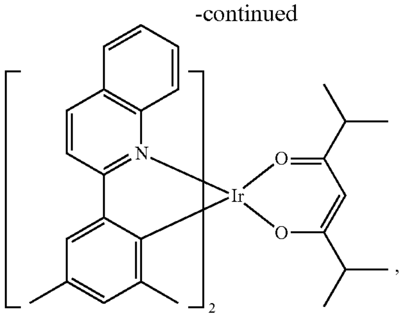
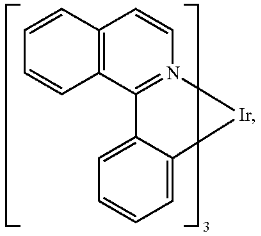
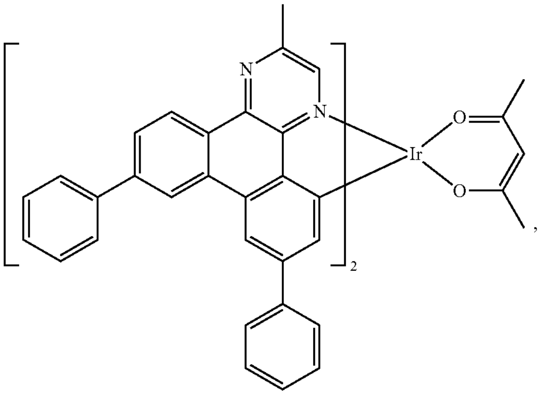
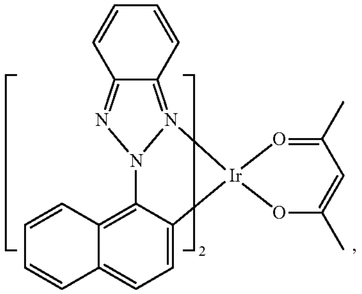
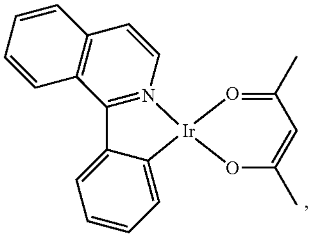
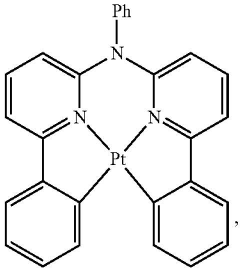
-continued
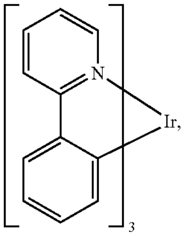
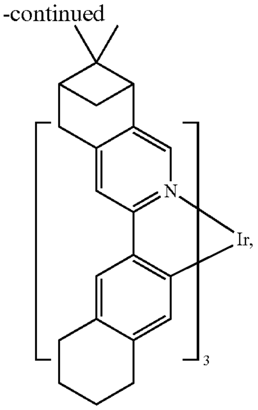
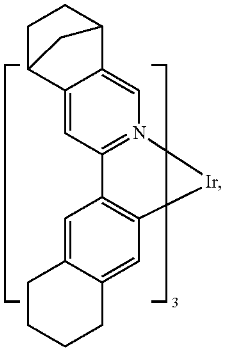
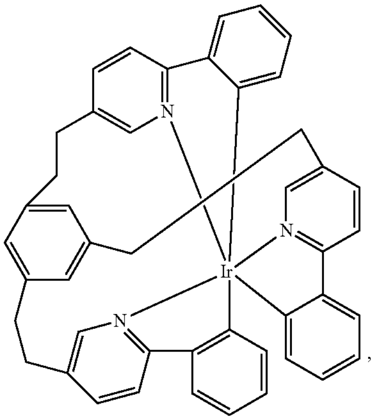
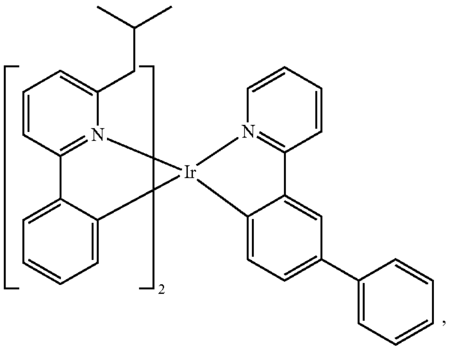

-continued
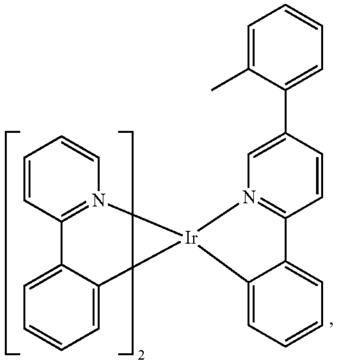
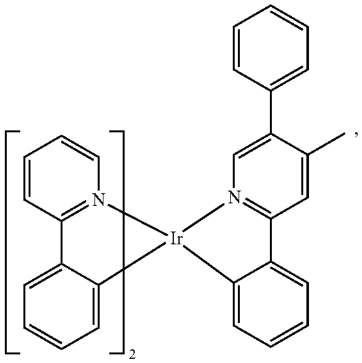
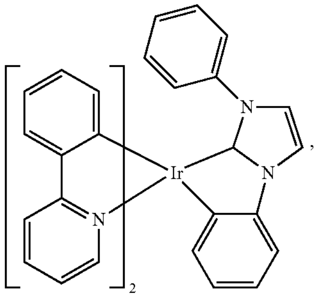
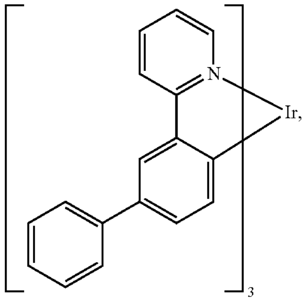
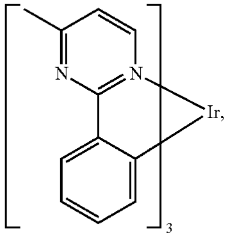
-continued
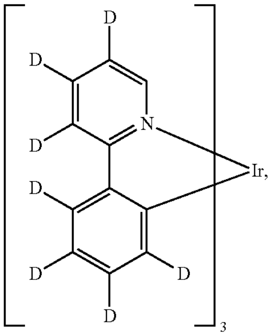
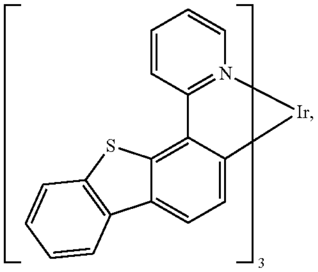
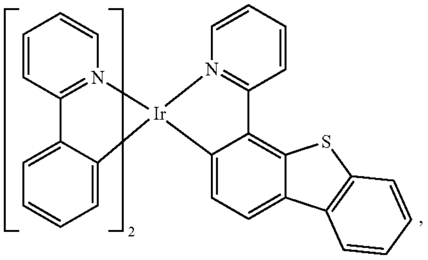
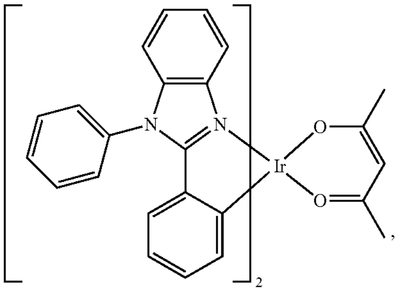
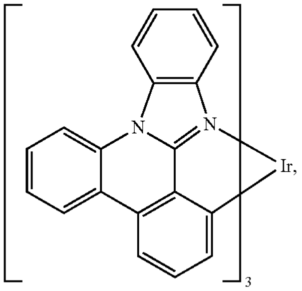

-continued
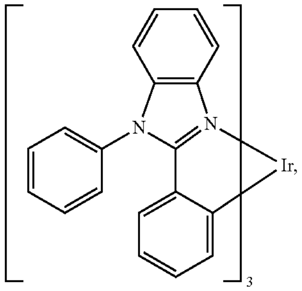
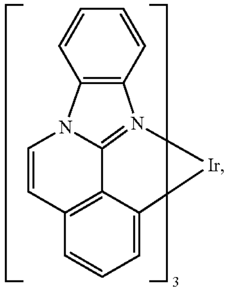
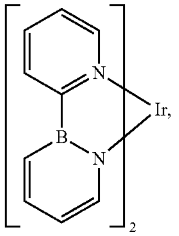
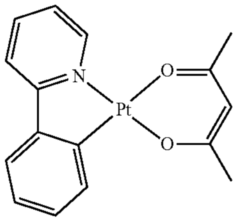
,
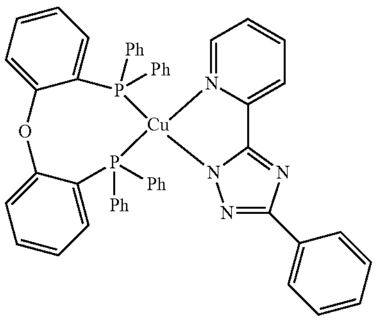
,
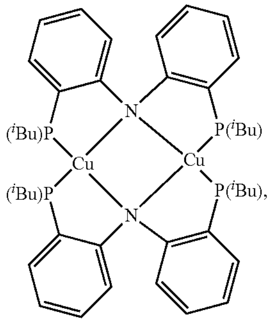
-continued
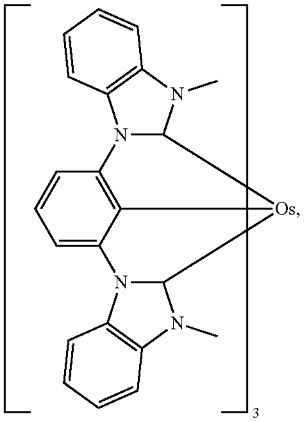
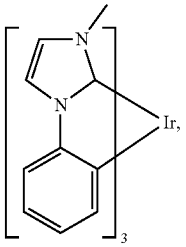
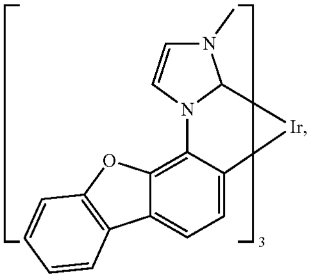
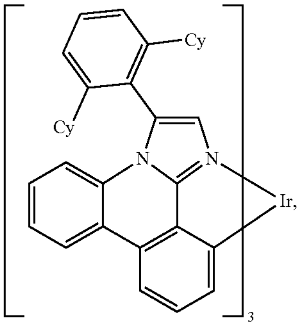
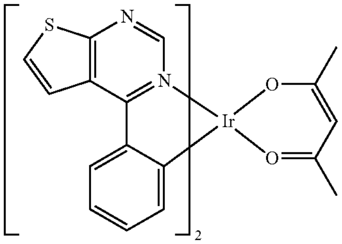
,
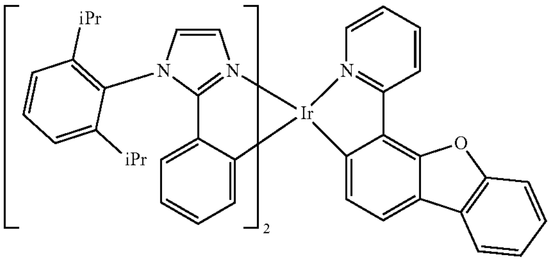
, -continued
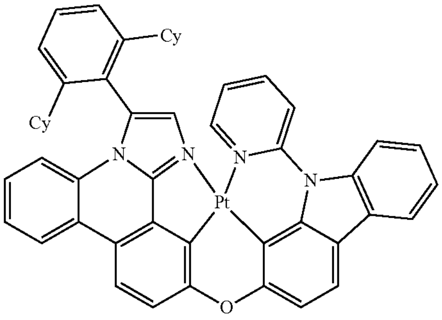
,
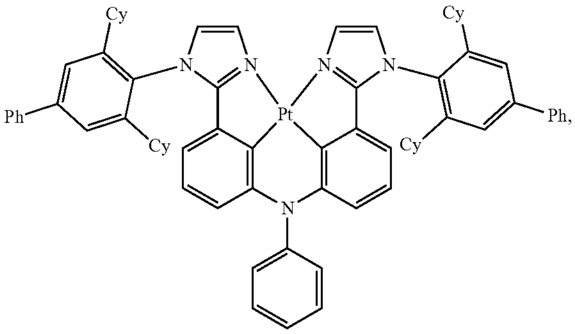
,
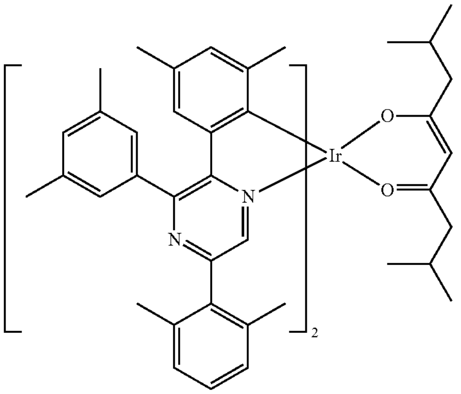
,
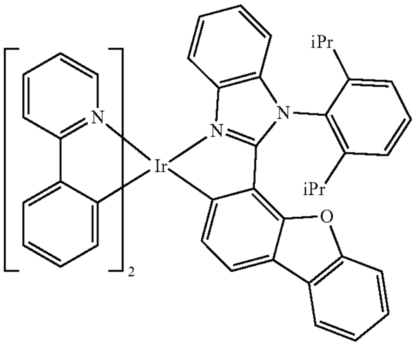
,
-continued
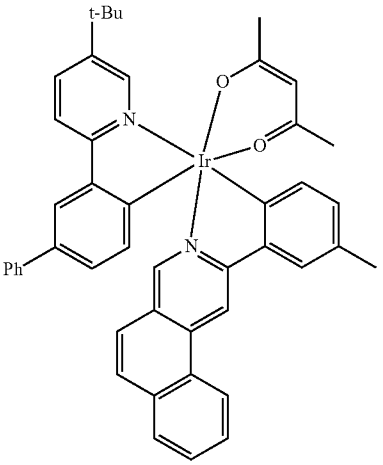
,
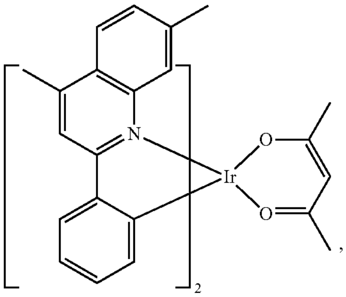
,
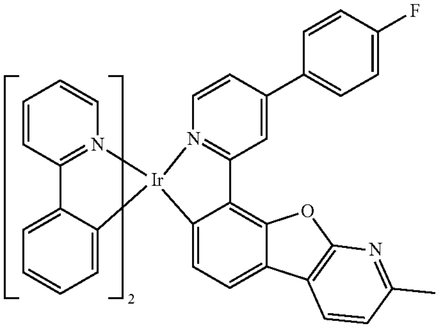
,
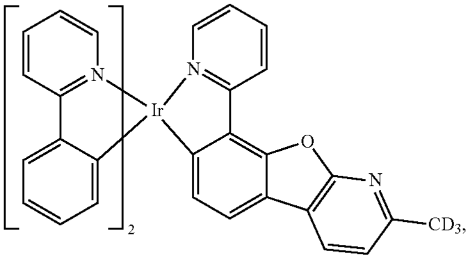
,
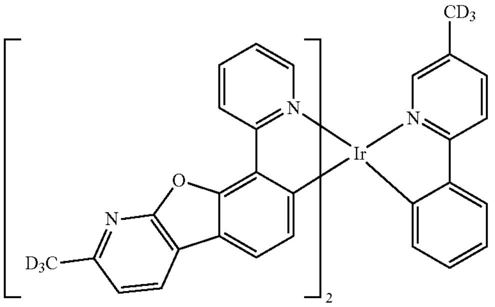
, -continued
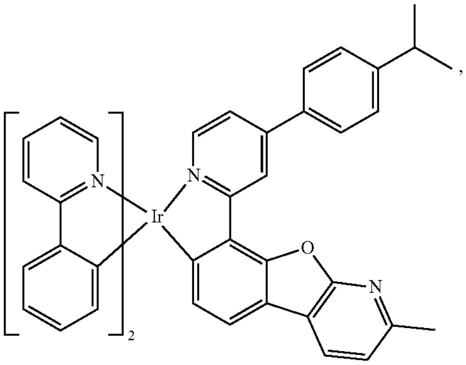,
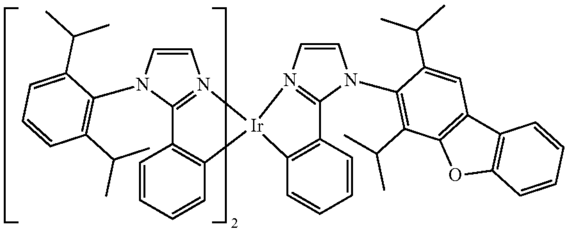,
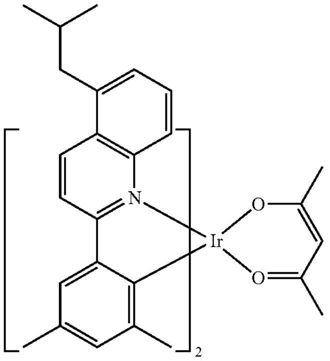,
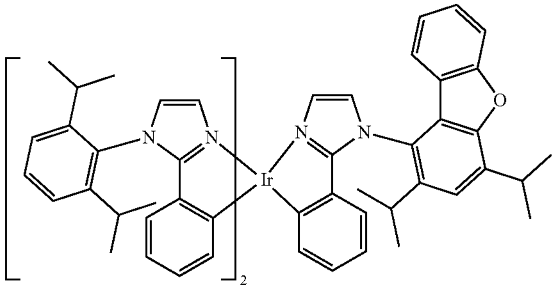,
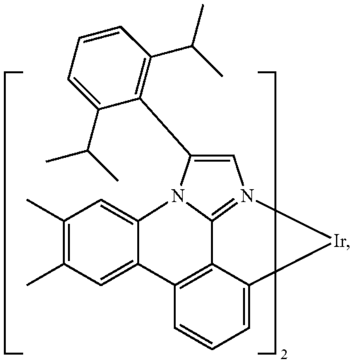
-continued
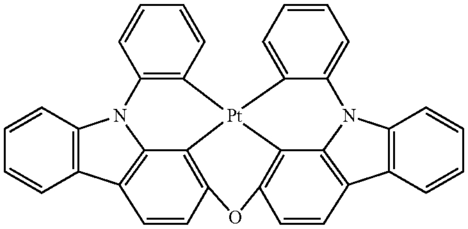,
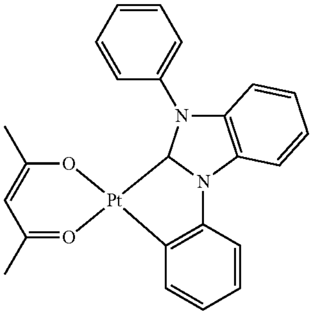,
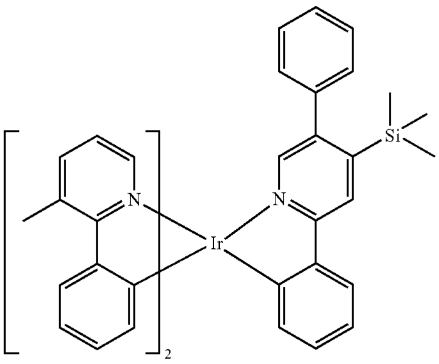,
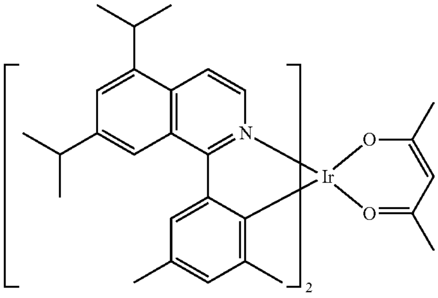,
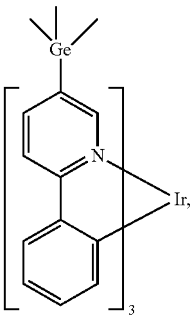

-continued
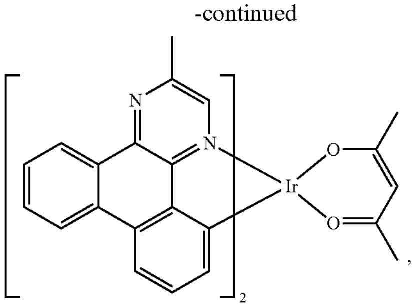
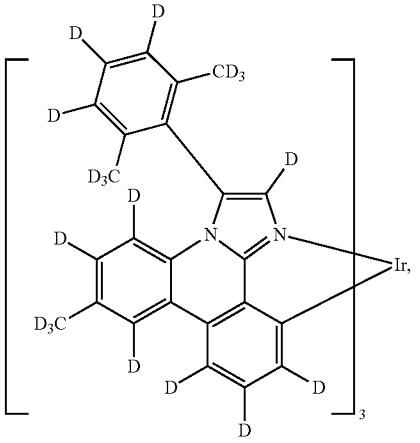
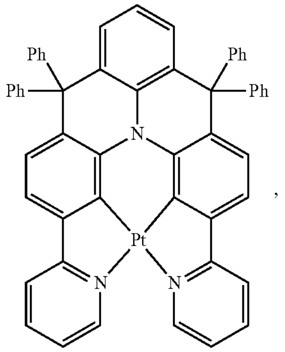
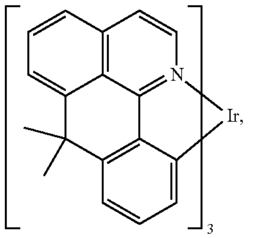
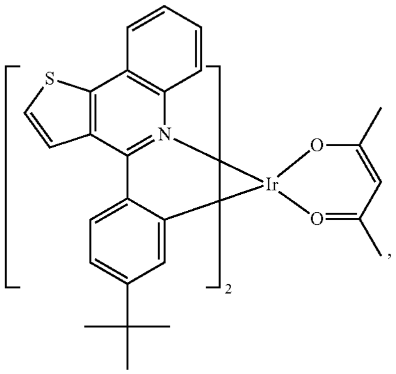
-continued
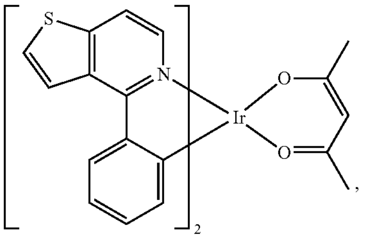
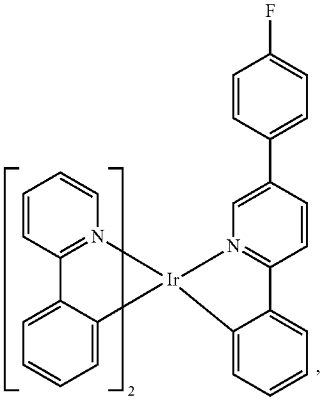
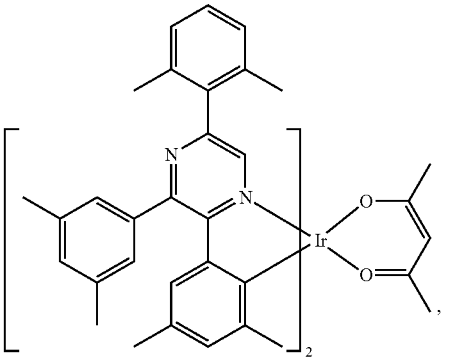
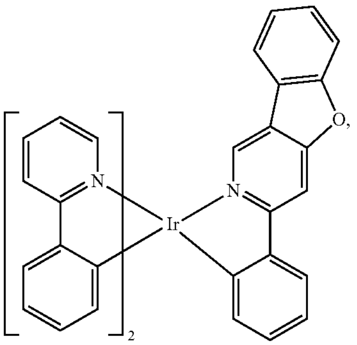

-continued
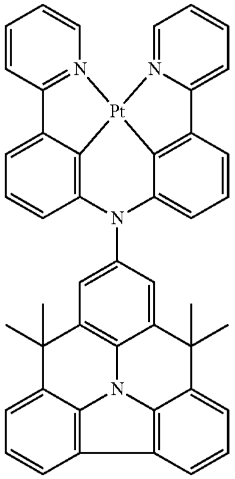
,
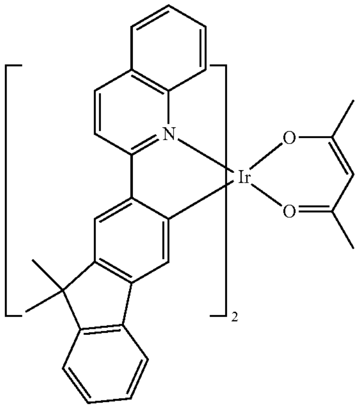
,
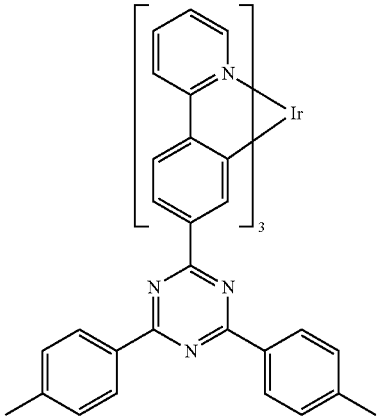
,
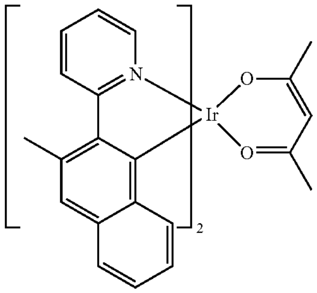
,
-continued
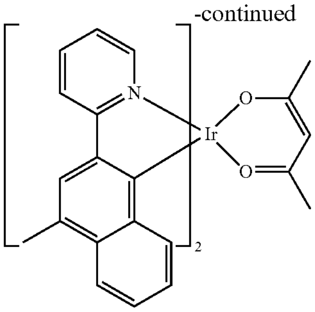
,
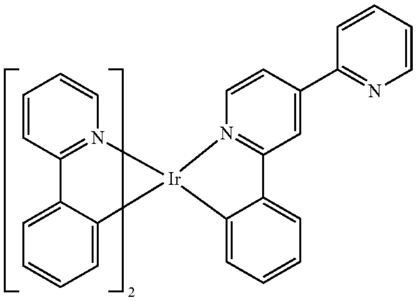
,
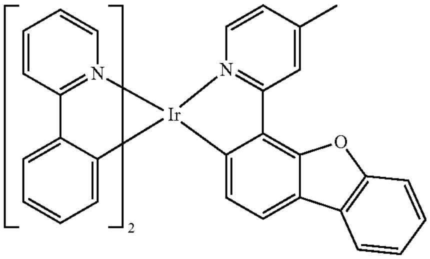
,
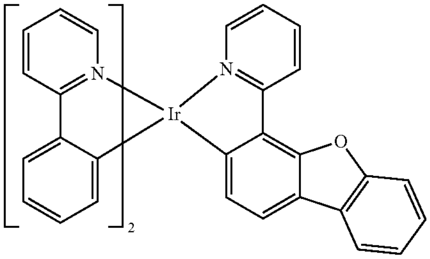
,
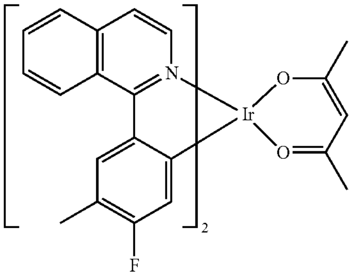
,
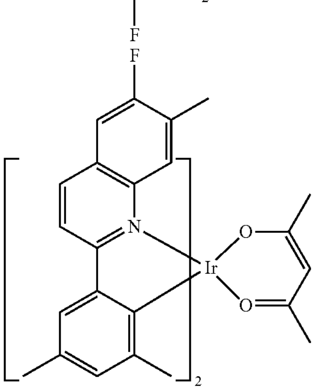
, -continued
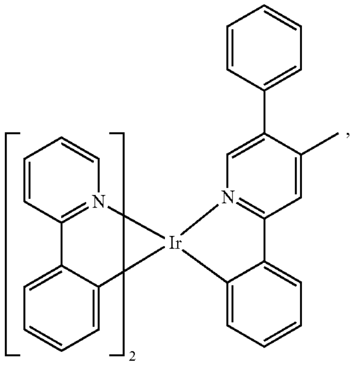
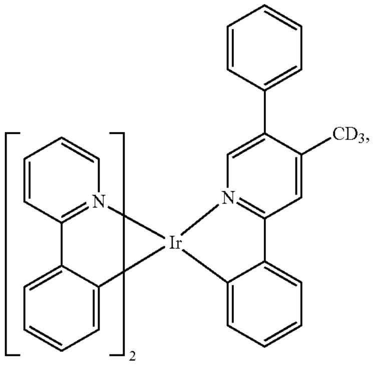
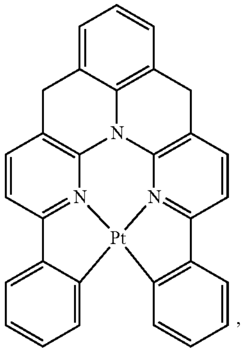
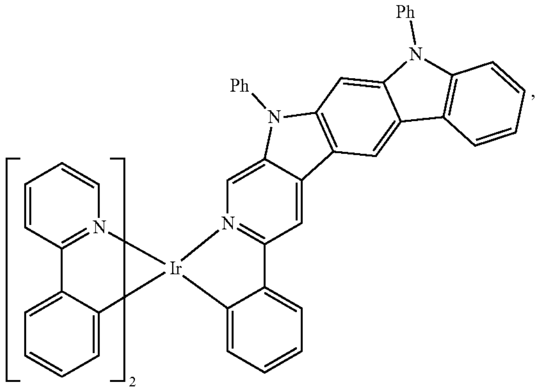
-continued
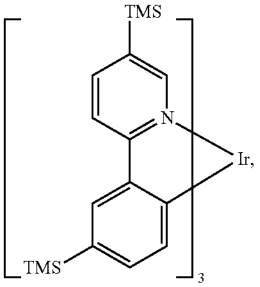
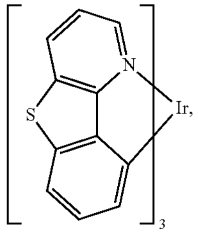
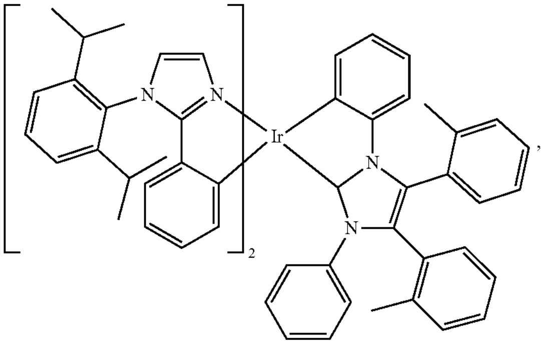
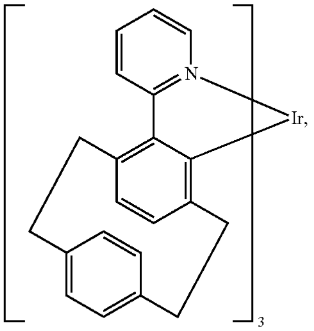
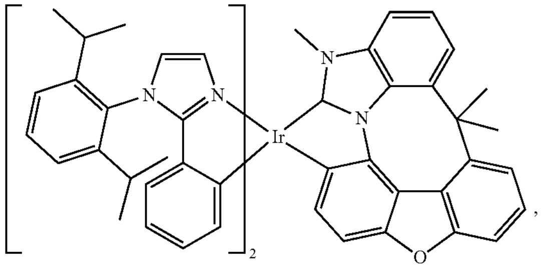
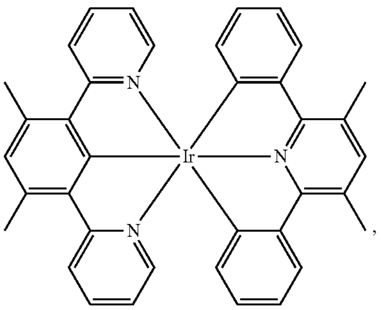

-continued
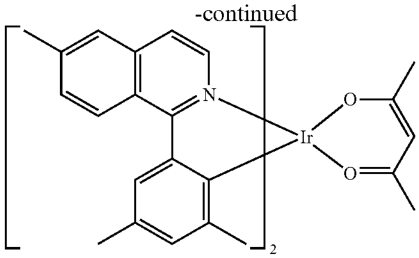
,
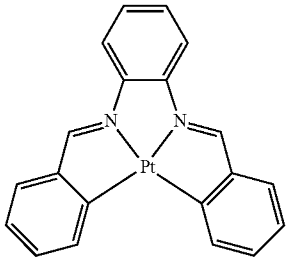
,
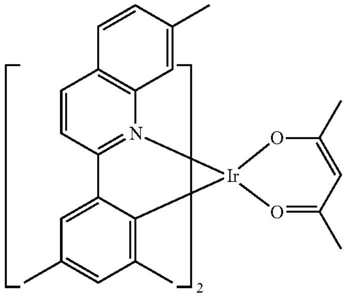
,
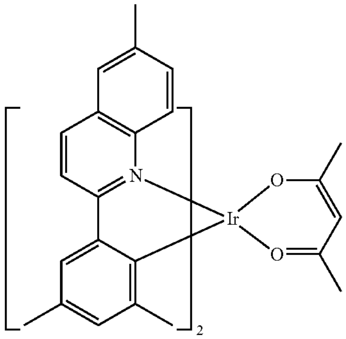
,
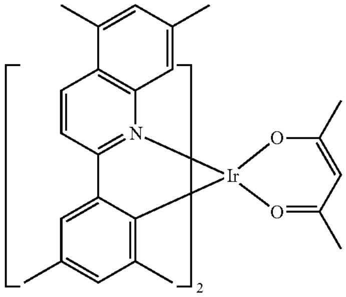
,
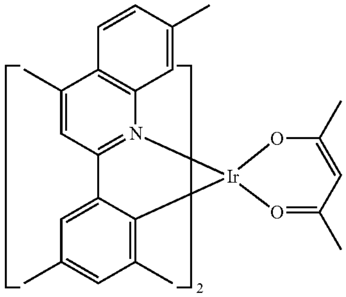
,
-continued
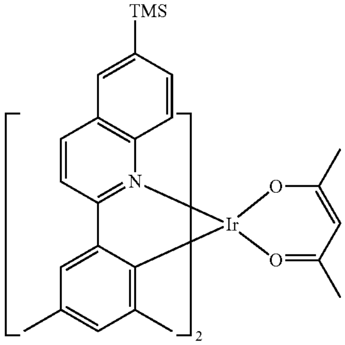
,
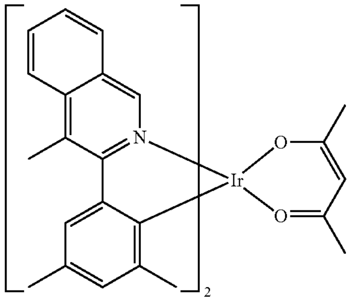
,
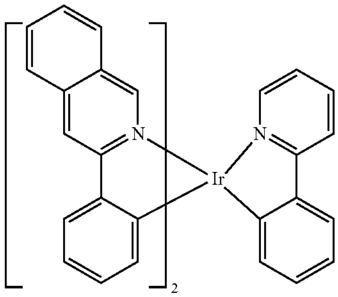
,
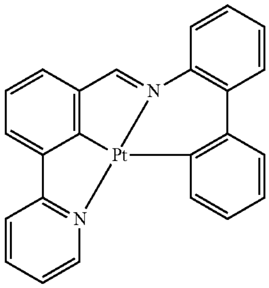
,
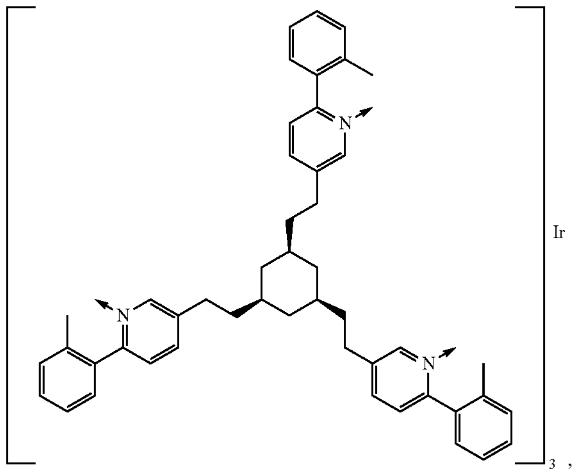
, -continued
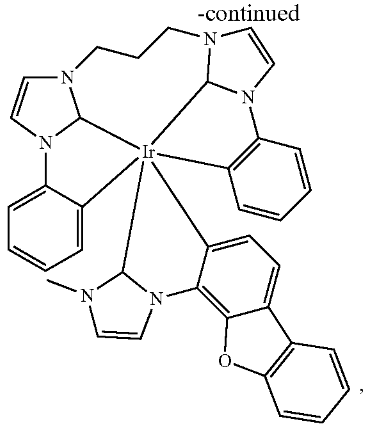
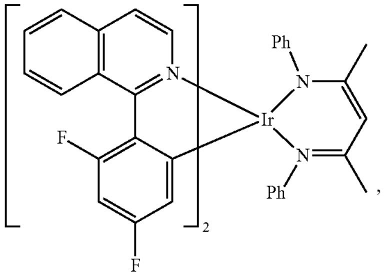
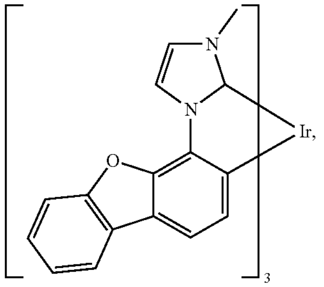
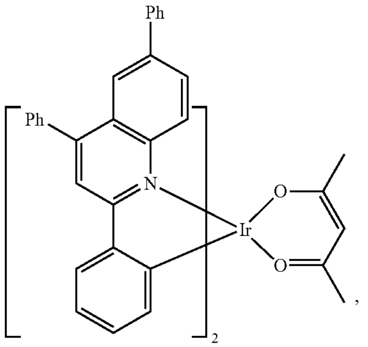
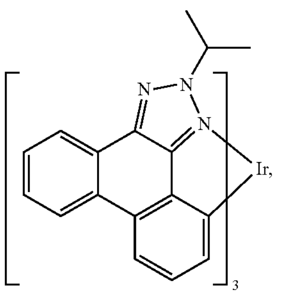
-continued
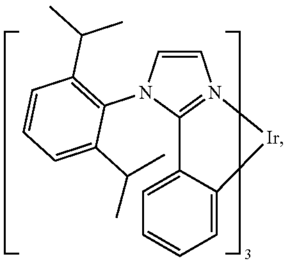
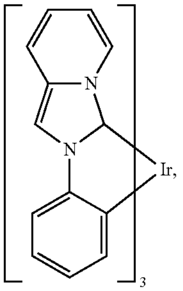
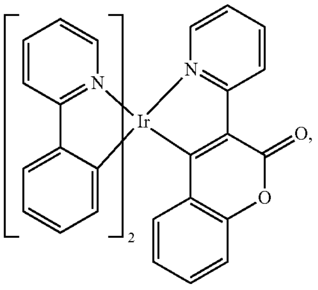
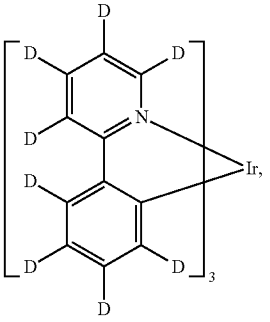
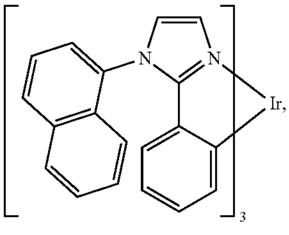
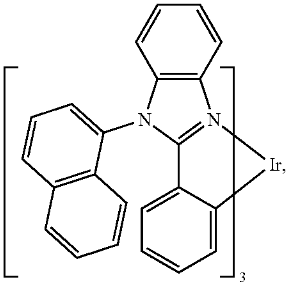

-continued

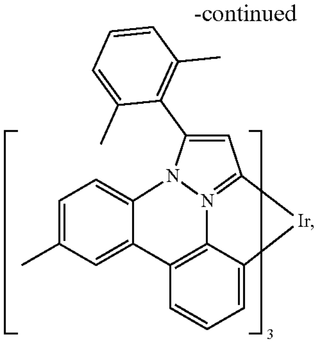

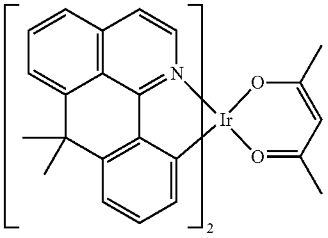

,

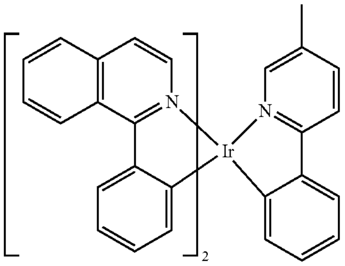

,

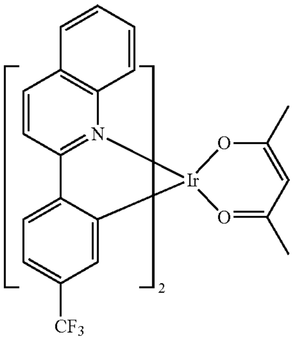

,

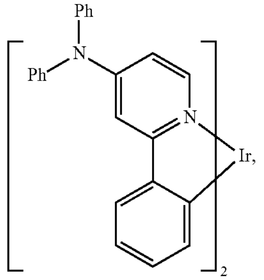

and

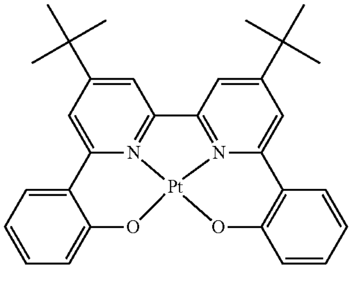

.

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

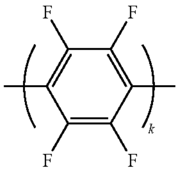

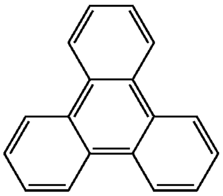

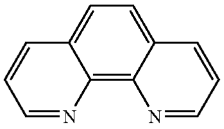

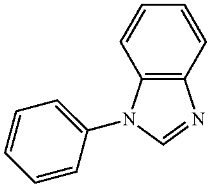

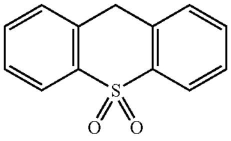

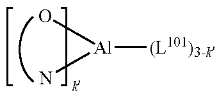

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

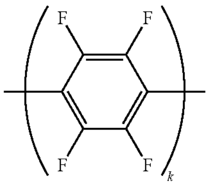

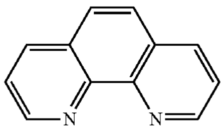

-continued

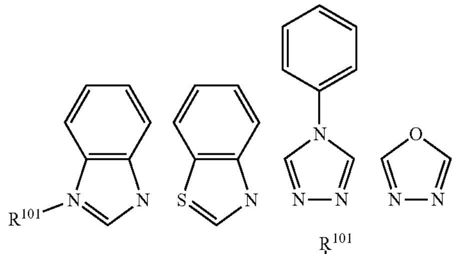

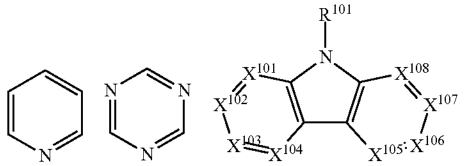

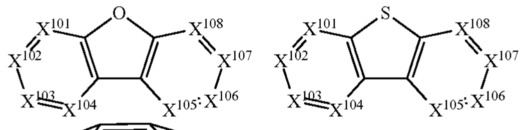

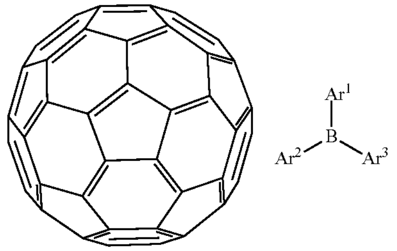

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

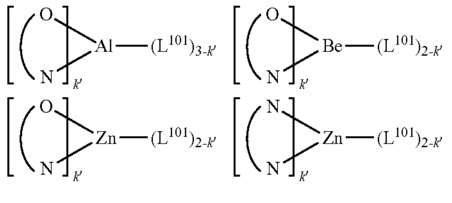

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

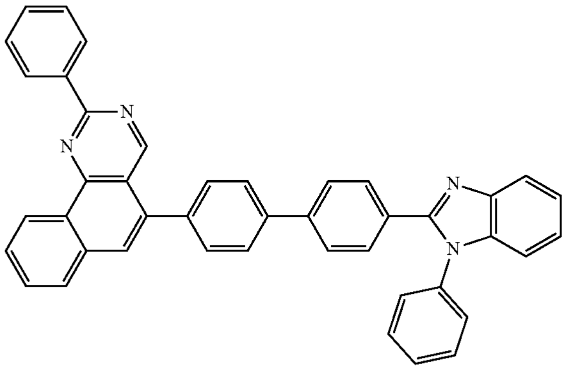

,

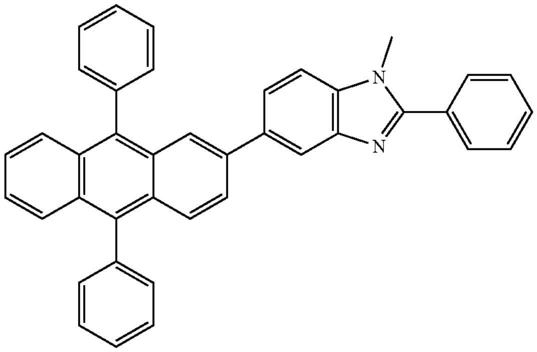

,

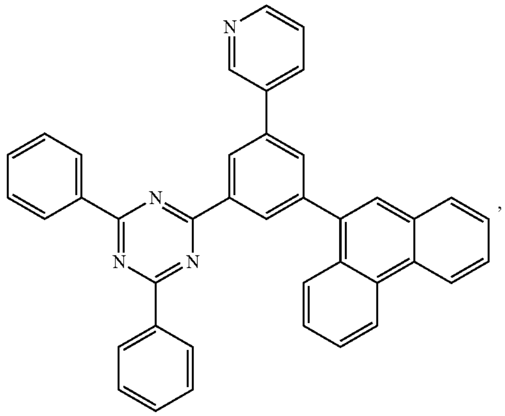

,

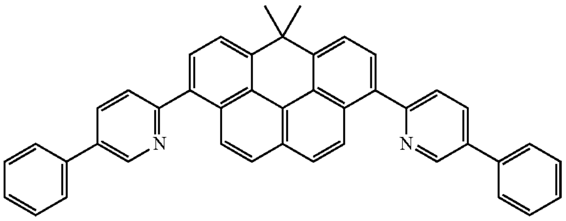

,

-continued
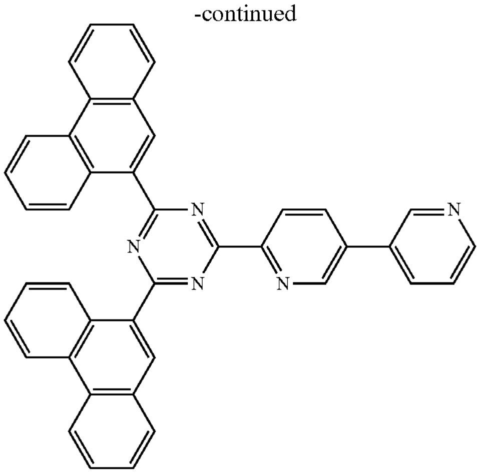
,
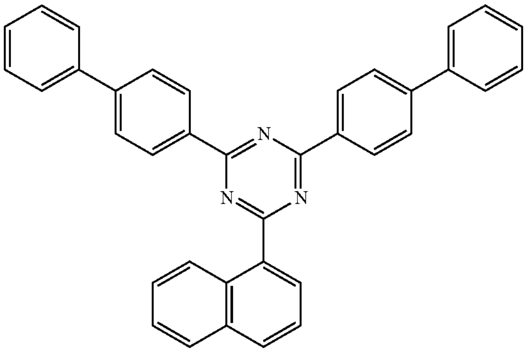
,
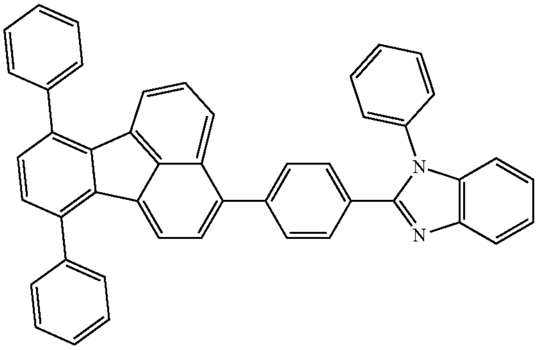
,
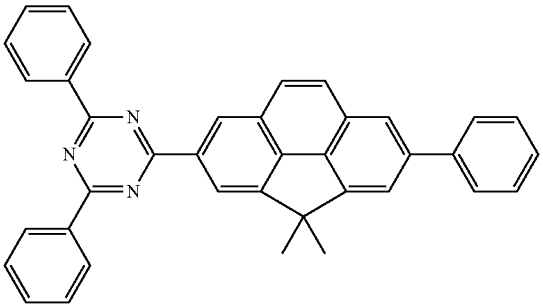
,
-continued
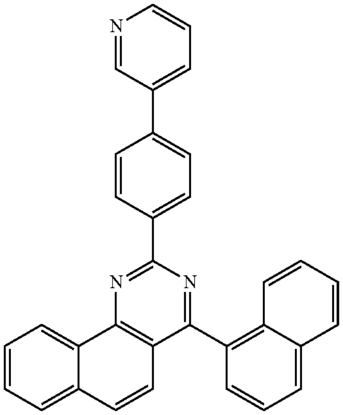
,
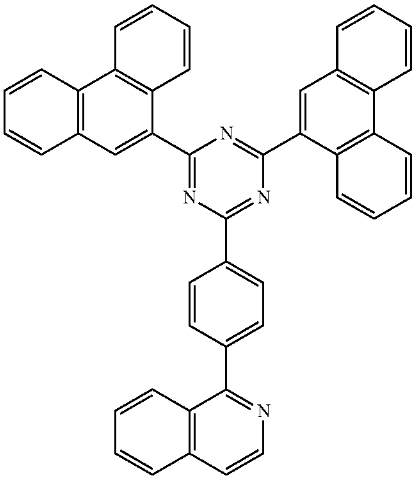
,
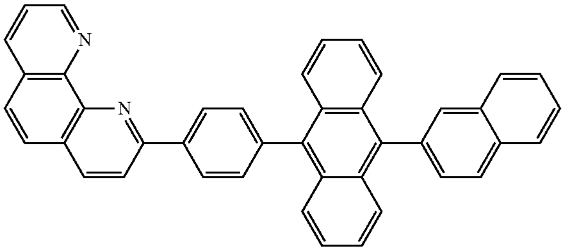
,
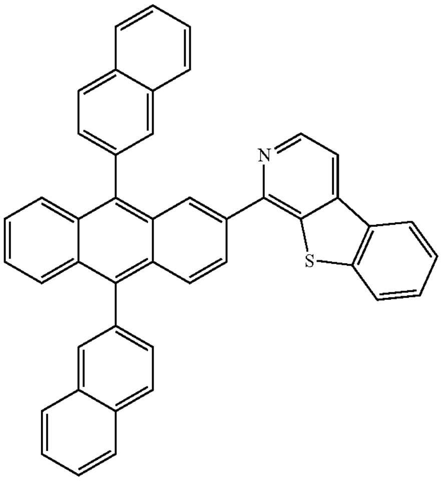
, -continued
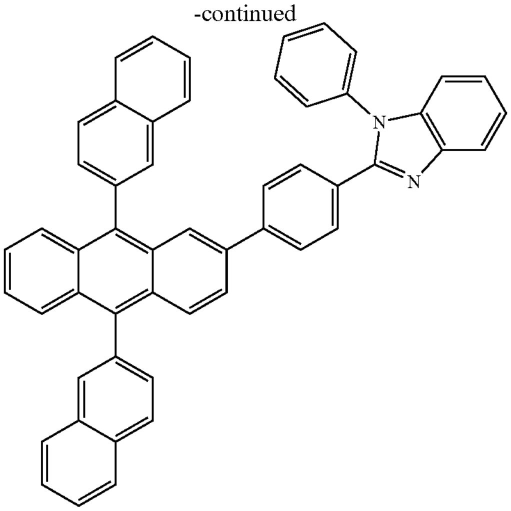
,
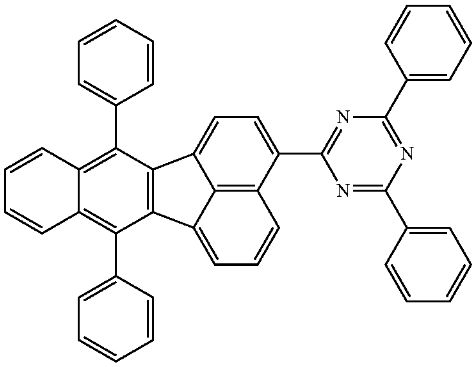
,
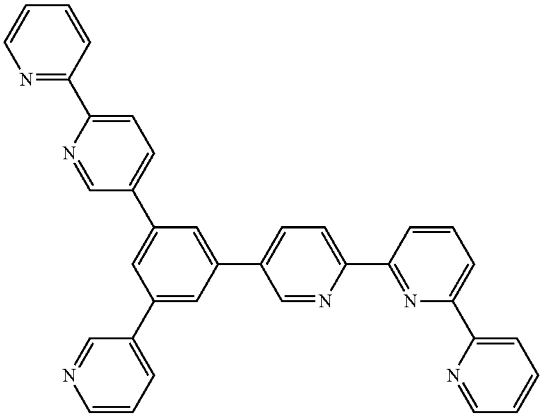
,
-continued
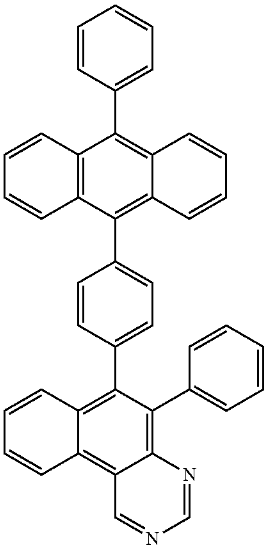
,
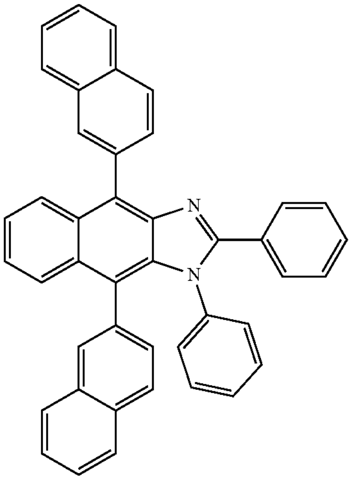
,
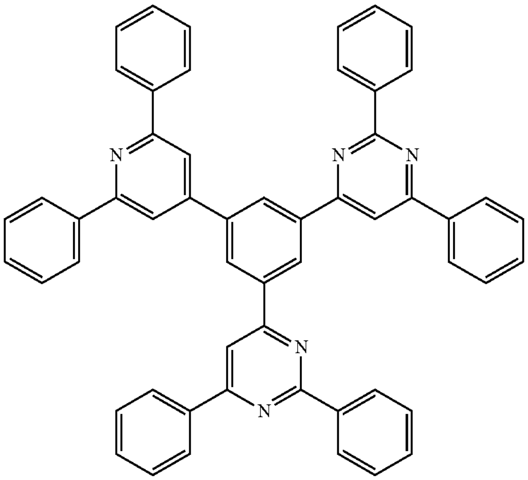
, -continued
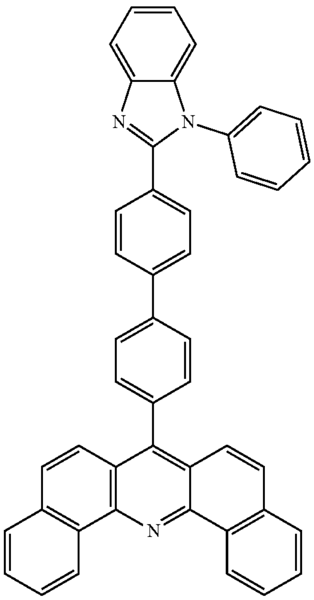
,
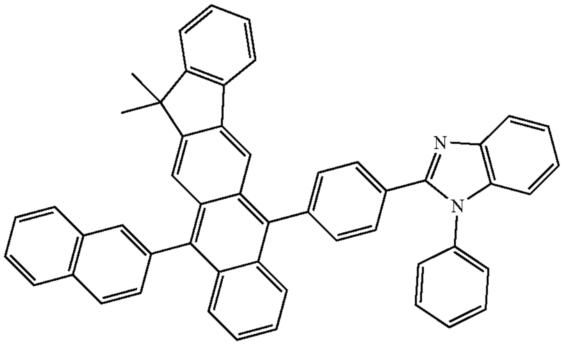
,
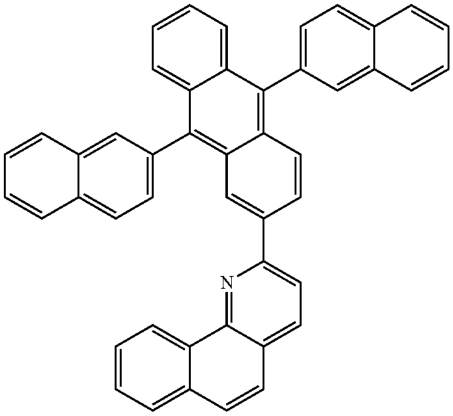
,
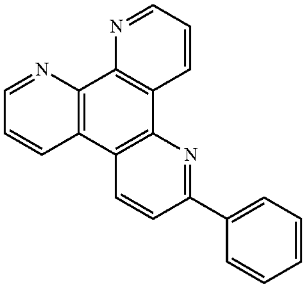
,
-continued
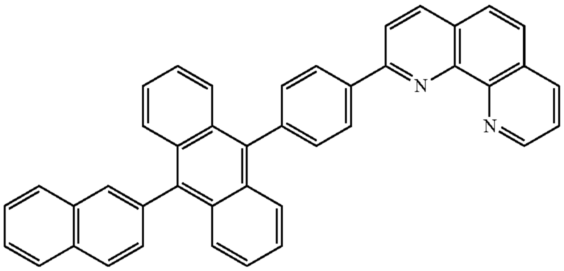
,
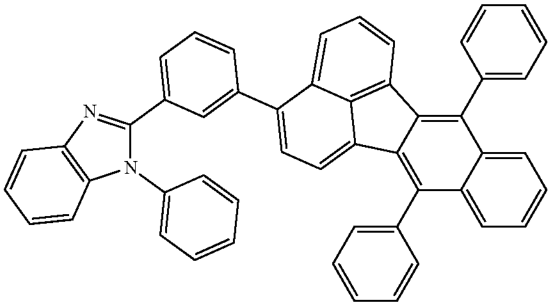
,
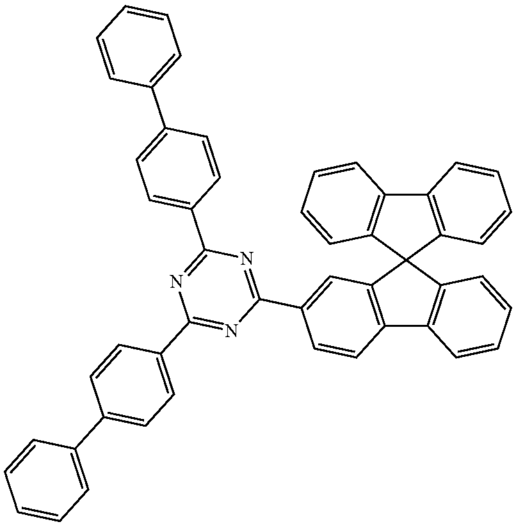
,
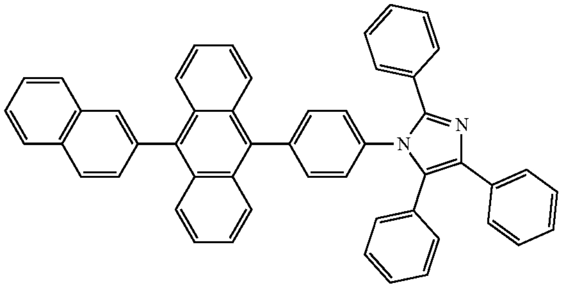
,
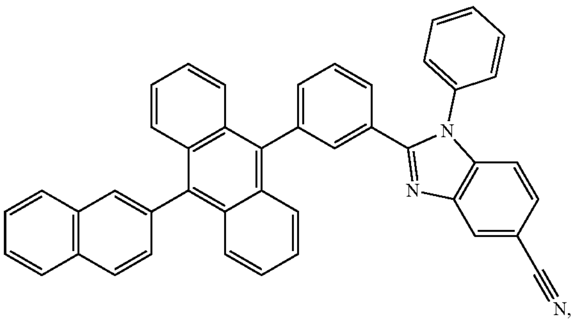
,

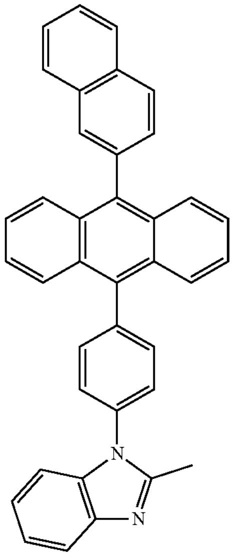

,

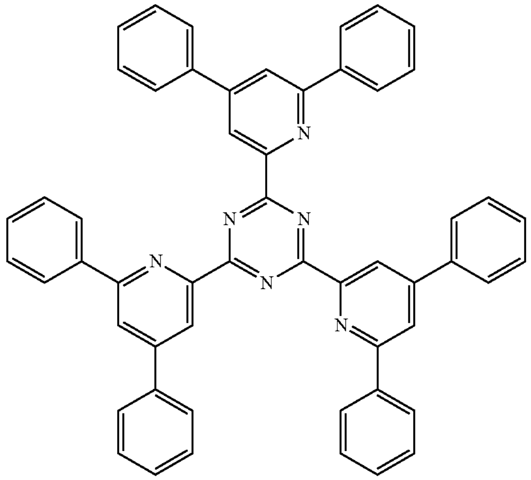

,

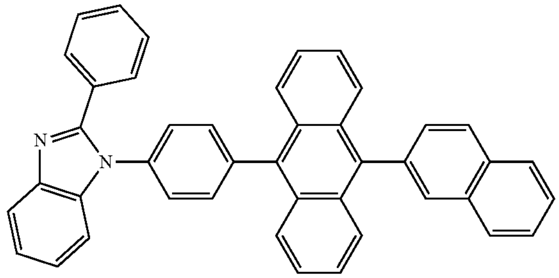

,

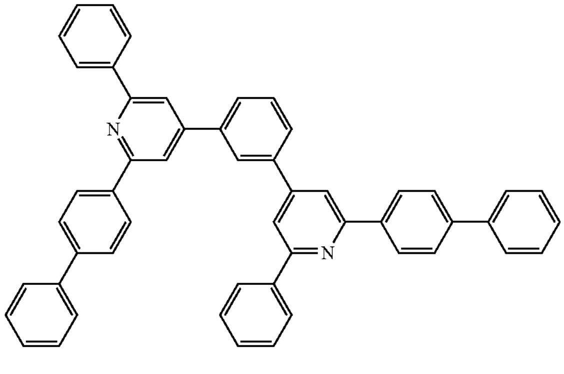

,

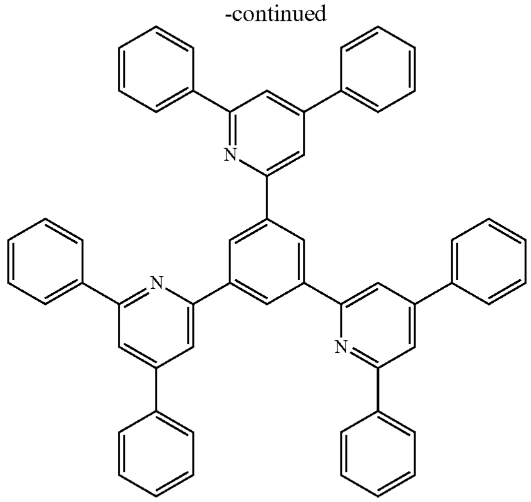

,

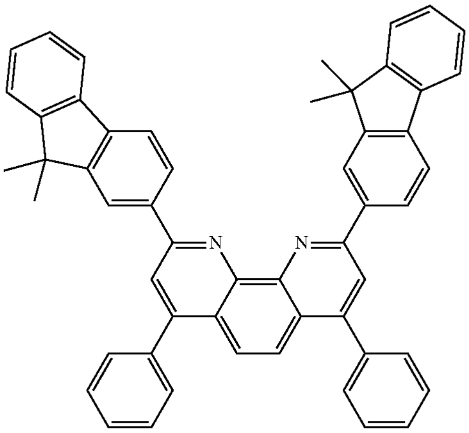

, and

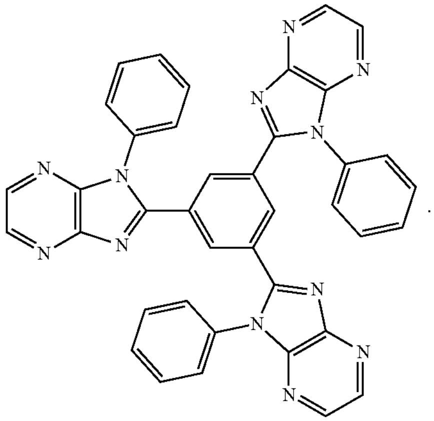 [SMILES: c1ccc(-n2c(-c3cc(-c4nc5nccnc5n4-c4ccccc4)cc(-c4nc5nccnc5n4-c4ccccc4)c3)nc3nccnc32)cc1 ; "."]

.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

All reactions were carried out under nitrogen protection unless specified otherwise. All solvents for reactions were anhydrous and used as received from the commercial sources

Synthesis of Comparative Compound 1 (CC1)

Synthesis of 6-Cyclohexyl-1-(3,5-dimethylphenyl) isoquinoline

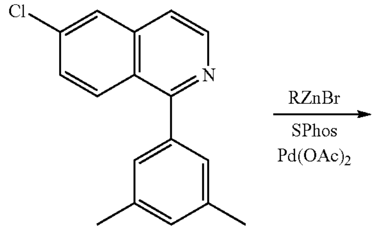

-continued

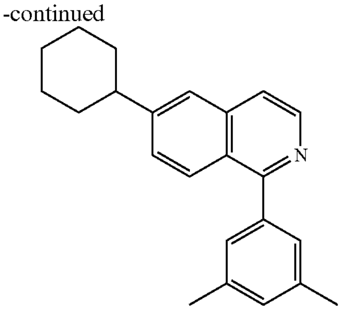

A solution of 6-chloro-1-(3,5-dimethylphenyl) isoquinoline (20.1 g, 75.0 mmol), palladium (II) acetate (0.505 g, 2.25 mmol) and 2-dicyclohexyl-phosphino-2',6'-dimethoxybiphenyl (SPhos) (1.85 g, 4.5 mmol) in anhydrous tetrahydrofuran (375 mL) was sparged with nitrogen for 10 minutes then heated at 49° C. for 10 minutes. A 0.52M cyclohexylzinc (II) bromide in tetrahydrofuran (216 mL, 112.5 mmol) was added dropwise over 40 minutes then the reaction mixture heated at 48° C. for 24 hours.

Saturated aqueous sodium sulfite and saturated aqueous sodium carbonate were added and the reaction mixture was cooled to room temperature over 30 minutes. The layers were separated and the aqueous layer was extracted with ethyl acetate. The combined organic layers were washed with saturated brine, dried over sodium sulfate and passed through a pad of silica gel topped with Celite, washing with ethyl acetate. The crude product was purified with silica gel column, eluting with a gradient of 0-5% ethyl acetate in heptanes, to give 6-cyclohexyl-1-(3,5-dimethylphenyl)-isoquinoline (12.3 g, 52% yield) as a viscous oil.

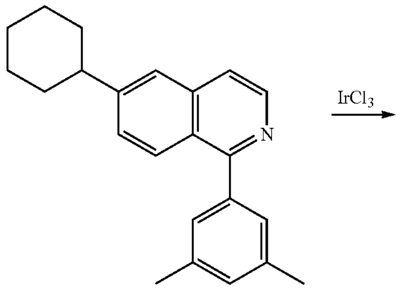

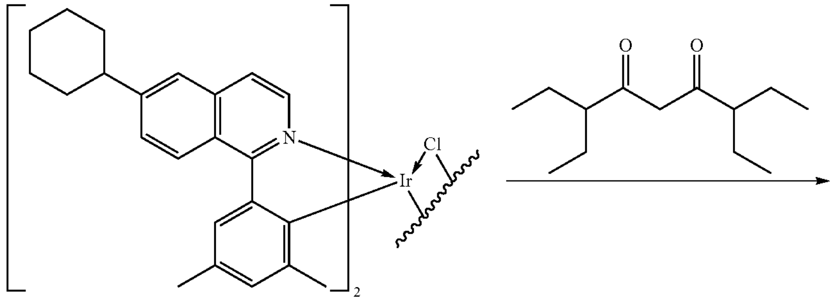

-continued

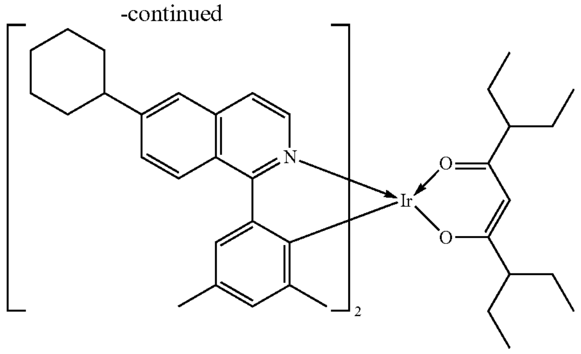

Synthesis of Comparative Compound 1 (CC1)

(A) A solution of 6-cyclohexyl-1-(3,5-dimethylphenyl)-isoquinoline (4.01 g, 12.71 mmol) in 2-ethoxyethanol (85 mL) and deionized ultra-filtered (DIUF) water (17 mL) was sparged with nitrogen for 5 minutes. Iridium (III) chloride hydrate (1.92 g, 6.05 mmol) was added, sparging continued for 5 minutes then the reaction mixture was heated at 70° C. for 24 hours. The reaction mixture was cooled to ~50° C., filtered and the solid air-dried for 30 minutes to give crude di-u-chloro-tetrakis [(6-cyclohexyl-1-(3,5-dimethylphenyl) isoquinoline-2-yl)]diiridium (III) (2.57 g) as a reddish solid which contained some residual solvent.

(B) A solution of crude di-u-chloro-tetrakis[6-cyclohexyl-1-(3,5-dimethylphenyl) isoquinoline-2-yl]diirid-ium (III) (2.57 g, 3.0 mmol) and 3,7-diethylnonane-4,6-dione (1.27 g, 6.0 mmol) in 2-ethoxyethanol (60 mL) was sparged with nitrogen for 5 minutes. Powdered potassium carbonate (0.829 g, 6.0 mmol) was added and sparging continued for 3 minutes. The reaction mixture was stirred at room temperature overnight in a flask wrapped in aluminum foil to exclude light. DIUF water was added, the suspension stirred for 30 minutes, the solid filtered and washed with water. The sticky solid was slurried in methanol for 10 minutes, filtered and the solid was washed with methanol. The red solid was dissolved/suspended in dichloromethane (20 mL) and loaded directly onto a column of silica gel topped with basic alumina. The column was eluted with 30% dichloromethane in hexanes. Product fractions were concentrated under reduced pressure and the solid was dried at 50° C. for 4 hours under high vacuum to give bis[(6-cyclohexyl-1-(3,5-dimethylphenyl)-isoquinolin-2-yl)]-(3,7-diethyl-4,6-nonanedionato-$k_2$O,O') iridium (III) (2.2 g, 35% overall yield) as a red solid.

Synthesis of Compound $C_{25,222}$

Synthesis of (1,1-Dimethyl)-4-iodocyclohexane

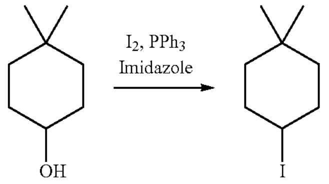

Iodine (218 g, 858 mmol) was added in portions over ~30 minutes to an ice cooled solution of triphenylphosphine (225 g, 858 mmol) and imidazole (117 g, 1716 mmol) in dichloromethane (1.32 L) at a rate in which the temperature remained below 5° C. After stirring for ~15 minutes, a solution of 4,4-dimethyl-cyclohexanol (100 g, 780 mmol) in dichloromethane (20 mL) was added dropwise, keeping the temperature below 15° C. The solution was warmed gradually to room temperature and stirred overnight. The solvent was removed under reduced pressure and the residue poured in portions into a flask containing heptanes (3.0 L) with vigorous stirring. Stirring was continued over 2 days at which point the gum had partially solidified. The heptanes layer was decanted and passed through a pad of silica gel. The residue in the flask was extracted a second time with heptanes. The heptanes layer was decanted and passed through the silica gel pad, flushing with heptanes. The filtrate was concentrated under reduced pressure (bath temperature ~30° C.) to give (1,1-dimethyl)-4-iodocyclohexane (130 g, 70% yield) as a colorless liquid.

Synthesis of (4,4-Dimethylcyclohexyl)zinc(II) iodide

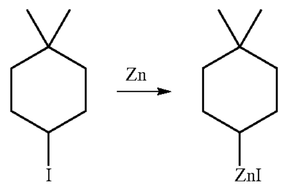

A mixture of zinc (228 g, 3.49 mol) and anhydrous lithium chloride (74 g, 1.74 mol) in anhydrous tetrahydrofuran (1.6 L) was heated at reflux for 30 minutes under nitrogen. The mixture was cooled to room temperature, 1,2-dibromoethane (10.11 g, 0.058 mol) and chlorotrimethyl-silane (6.32 g, 0.058 mol) were added successively and mixture heated at reflux for 10 minutes. The mixture was cooled to ~27° C. and a solution of 4-iodo-1,1-dimethylcyclohexane (277 g, 1.16 mol) in anhydrous tetrahydrofuran (0.52 L) added, keeping the temperature below 30° C. during the addition. The mixture was stirred at room temperature overnight. The solids were allowed to settle and the solution decanted into nitrogen flushed bottles and stored until needed.

Synthesis of 6-(4,4-dimethylcyclohexyl)-1-(3,5-dimethylphenyl)isoquinoline

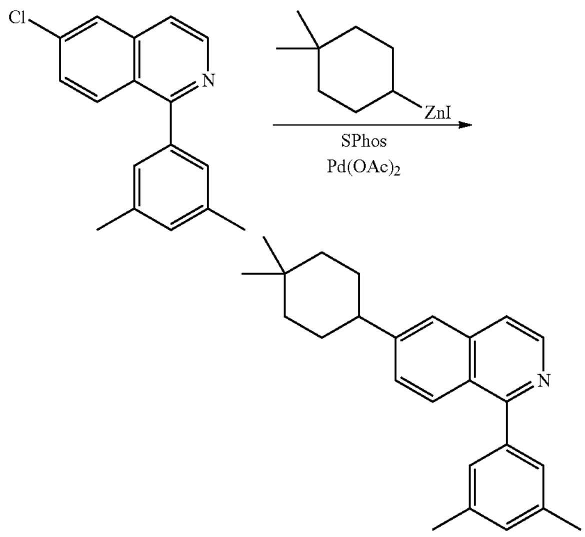

An ice cooled mixture of 6-chloro-1-(3,5-dimethylphenyl)isoquinoline (50 g, 187 mmol), palladium(II) acetate (1.26 g, 5.60 mmol) and 2-dicyclohexylphosphino-2',6'-dimethoxy-biphenyl (SPhos) (4.60 g, 11.20 mmol) in anhydrous tetrahydrofuran (346 mL) was sparged with nitrogen for 20 minutes. 0.5M 4,4-Dimethylcyclohexylzinc(II) iodide solution (549 mL, 187 mmol) was added dropwise to the mixture over ~30 minutes, keeping the temperature below 5° C. The mixture was stirred at room temperature overnight then diluted with ethyl acetate (100 mL) and saturated aqueous sodium carbonate. The layers were separated and the organic layer was washed with brine, dried over sodium sulfate, filtered and concentrated under reduced pressure. The crude product was purified with silica gel column, eluting with 100% heptanes for 10 minutes followed by a gradient of 0-20% ethyl acetate in heptanes for 40 minutes, 20-50% ethyl acetate in heptanes for 5 minutes, then 100% ethyl acetate for 5 minutes, to afford 1-(3,5-dimethylphenyl)-6-(4,4-dimethylcyclohexyl)-isoquinoline (36 g, 72% yield) as a pale yellow oil.

Synthesis of Compound $C_{25,222}$

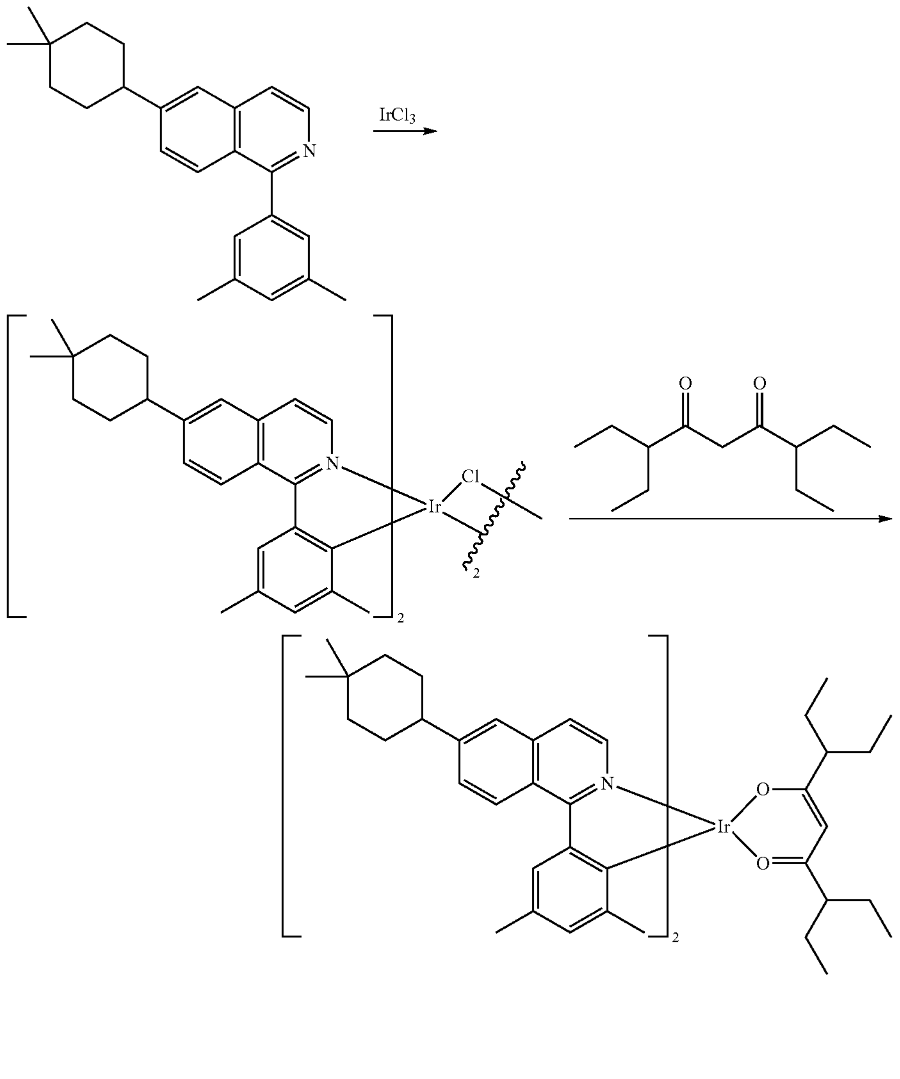

(A) To a solution of 1-(3,5-dimethylphenyl)-6-(4,4-dimethylcyclohexyl)isoquinoline (70 g, 204 mmol) in 2-ethoxyethanol (773 mL) and DIUF water (258 mL), iridium(III) chloride tetrahydrate (34 g, 92 mmol) was added and the reaction mixture was heated at 85° C. for 52 hours. The reaction mixture was cooled, filtered and the solid washed with hot methanol. The red solid was air-dried for 30 minutes to give di-g-chloro-tetrakis[((1-(3,5-dimethylphenyl-2'-yl)-6-(4,4-(di-methyl)cyclohexyl)isoquinolin-2-yl)]diiridium(III) (48 g, 57.3% yield) as a red solid.

(B) To a suspension of di-g-chloro-tetrakis[((1-(3,5-dimethylphenyl-2'-yl)-6-(4,4-(di-methyl)cyclohexyl)isoquinolin-2-yl)]diiridium(III) (48 g, 26.3 mmol) and 3,7-diethylnonane-4,6-dione (22.33 g, 105 mmol) in 2-ethoxyethanol (730 mL), powdered potassium carbonate (14.54 g, 105 mmol) was added. The reaction mixture was stirred at room temperature in the dark for 72 hours. DIUF water (730 mL) was added and the slurry was stirred for 1 hour. The suspension was filtered, the solid was washed with water then returned to the reaction flask. Methanol was added and the mixture was stirred for 45 minutes. The suspension was filtered, the solid washed with methanol and air-dried. The red solid (52 g) was dissolved in 1:1 heptanes:dichloromethane (500 mL) and basic alumina was added. The suspension was loaded directly unto a silica gel column, eluting with 50% dichloro-methane in heptanes. Product fractions were concentrated and air-dried overnight to give bis[((1-(3,5-dimethylphenyl-2'-yl)-6-(4,4-(dimethyl)cyclohexyl)-isoquinolin-2-yl)]-(3,7-diethyl-4,6-nonanedionato $k_2$O,O')iridium(III) (24 g, 42% yield) as a red solid.

Device Examples

All example devices were fabricated by high vacuum (<$10^{-7}$ Torr) thermal evaporation. The anode electrode was 1150 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package. The organic stack of the device examples consisted of sequentially, from the ITO surface, 100 Å of LG101 (from LG chem) as the hole injection layer (HIL); 400 Å of a hole transporting material (HTM) as a hole transporting layer (HTL); 300 Å of an emissive layer (EML) containing Compound H as a host, a stability dopant (SD) (18%), and Comparative Compound 1 or Compound $C_{25,222}$ as the emitter (3%); 100 Å of Compound H as a blocking layer; and 350 Å of Liq (8-hydroxyquinoline lithium) doped with 40% of ETM as the ETL. The emitter was selected to provide the desired color, efficiency and lifetime. The stability dopant (SD) was added to the electron-transporting host to help transport positive charge in the emissive layer. The Comparative Example devices were fabricated similarly to the device examples except that Comparative Compounds were used as the emitters in the EML. Table 1 below provides the materials used for the device layers and the layer thicknesses.

TABLE 1

Device layer materials and thicknesses

| Layer | Material | Thickness [Å] |
|---|---|---|
| Anode | ITO | 1150 |
| HIL | HATCN | 100 |
| HTL | HTM | 450 |
| EML | Compound H: SD 18%:Emitter 3% | 400 |
| ETL | Liq: ETM 40% | 350 |
| EIL | Liq | 10 |
| Cathode | Al | 1000 |

The device performance data are normalized to comparative compound and summarized in Table 2 below. The maximum wavelength of emission ($\lambda_{max}$) is similar for Comparative Compound 1 and Compound $C_{25,222}$ at 625 nm the emission line shape is also the same (FWHM). The inventive compound (Compound $C_{25,222}$) shows improved external quantum efficiency (EQE) compared to Comparative Compound 1 (1.03 vs. 1.00). The luminous efficacy (LE) is also better for Compound $C_{25,222}$ (1.08 vs. 1.00). This data shows that the current invention of adding substitution on cycloalkyl side chains is beneficial to the overall performance of the metal complexes.

TABLE 2

Performance of the devices made with Comparative Compounds and Inventive Compounds.

| Device Example | Emitter | 1931 CIE x | 1931 CIE y | λ max [nm] | FWHM [nm] | At 10 mA/cm² Voltage [au] | EQE [au] | LE [au] |
|---|---|---|---|---|---|---|---|---|
| Example 1 | Compound $C_{25,222}$ | 0.67 | 0.33 | 625 | 1.00 | 1.00 | 1.03 | 1.08 |
| CE1 | Comparative Compound 1 | 0.68 | 0.32 | 625 | 1.00 | 1.00 | 1.00 | 1.00 |

The chemical structures for the materials used in the experimental OLED devices are shown below:

COMPOUND H

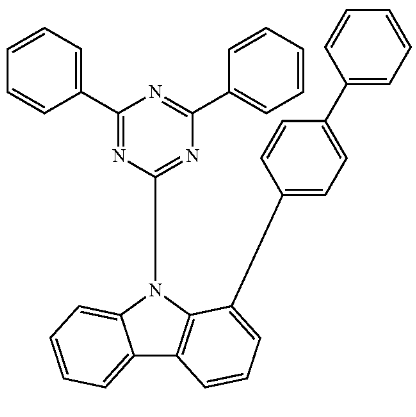

,

-continued

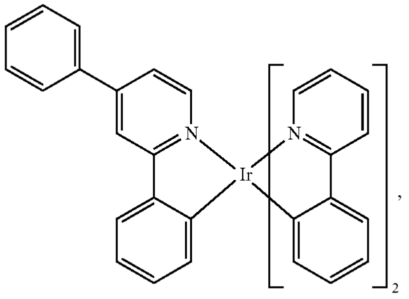

SD

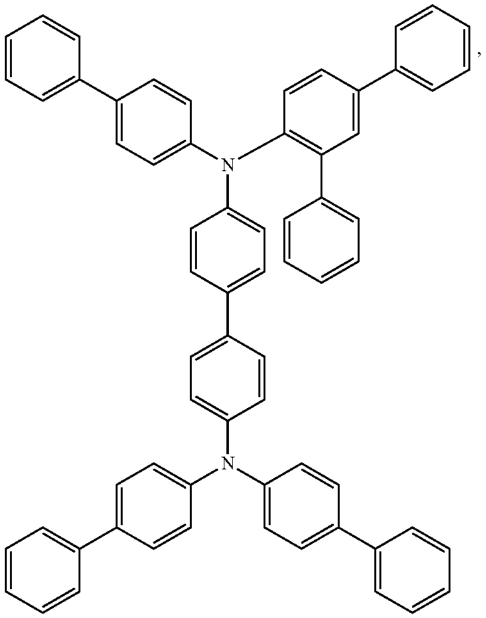

HTM

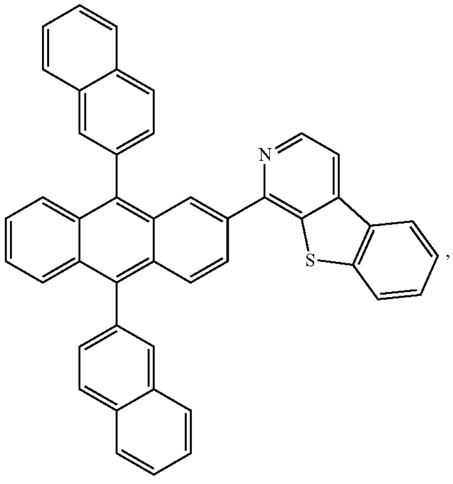

ETM

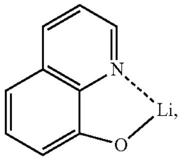

Liq

-continued

Compound $C_{25,222}$

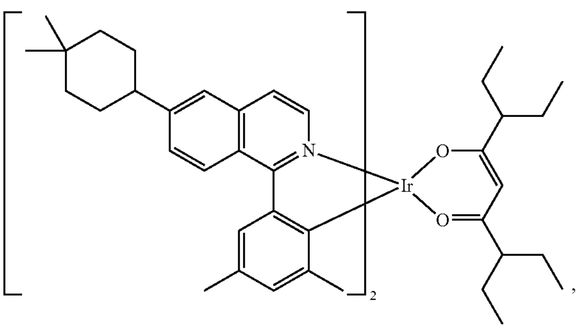

Comparative Compound 1

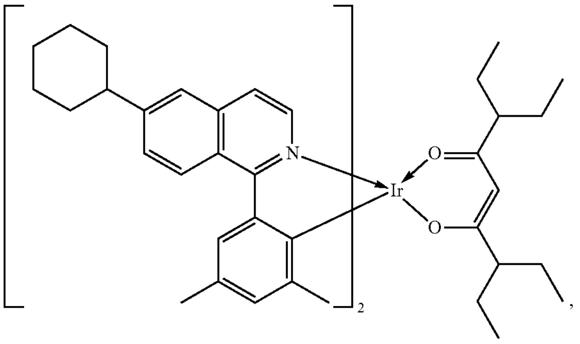

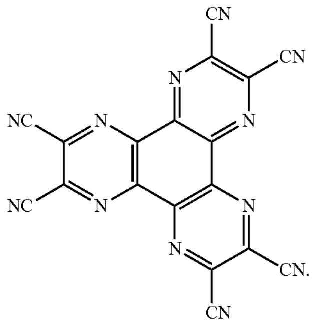

HATCN

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; wherein $L_B$ and $L_C$ are each a bidentate ligand, and wherein $L_A$, $L_B$, and $L_C$ are different from each other, wherein $L_A$ has the structure of Formula I

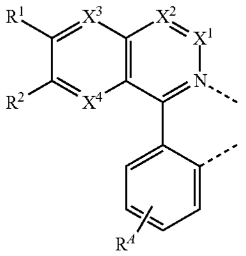

wherein, $R^A$ represents mono to the maximum allowable substitutions;

$X^1$ to $X^4$ are each independently CR or N;

$R^A$, R, $R^1$, and $R^2$ are each independently selected from the group consisting of hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

at least one $R^A$ is not hydrogen;

at least one of $R^1$ and $R^2$ has the formula of $-L^1-G^1$;

$L^1$ is an organic linker or a direct bond, $G^1$ is a substituted cycloalkyl group or a substituted or unsubstituted spirocycle;

wherein when $G^1$ is a substituted cycloalkyl group, the substituted cycloalkyl group is selected from the group consisting of alkyl substituted cycloalkyl, a partially or fully fluorinated cycloalkyl or alkyl substituted cycloalkyl;

$L_A$ is coordinated to Ir;

Ir can be coordinated to other ligands;

$L_A$ can be linked with other ligands to comprise a tridentate, tetradentate, pentadentate, or hexadentate ligand;

two substituents $R^A$ are joined or fused together to form an aryl group, wherein $R^A$ or said aryl group further comprises a branched alkyl, a cycloalkyl, or a silyl;

$R^1$ and $R^2$ are not joined to form a ring;

wherein $L_B$ and $L_C$ are each independently selected from the group consisting of:

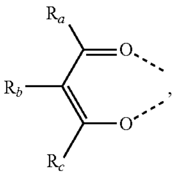

,

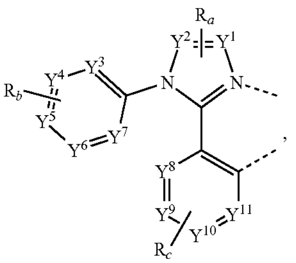

,

-continued

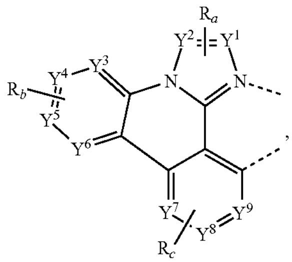

,

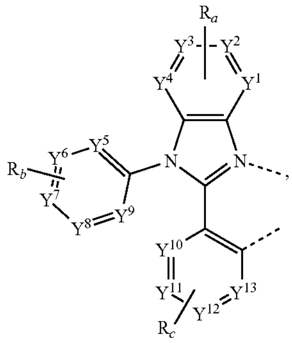

,

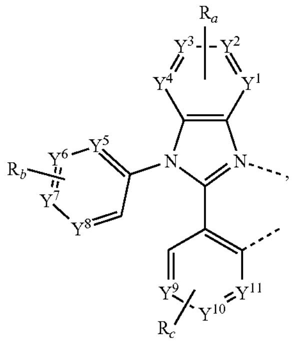

,

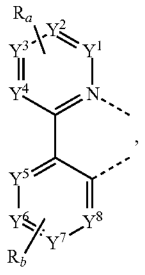

,

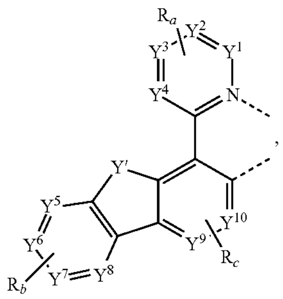

,

-continued

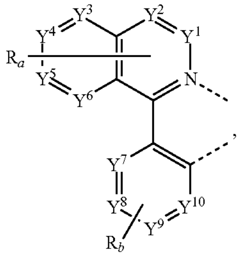

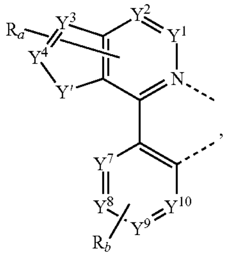

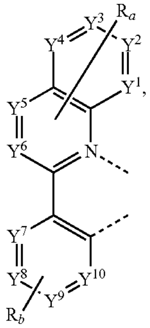

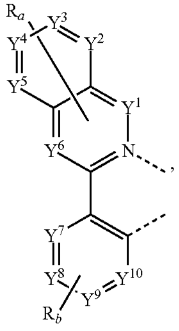

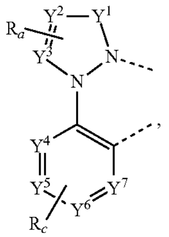

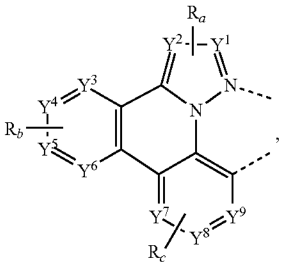

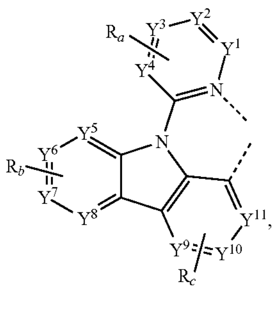

-continued

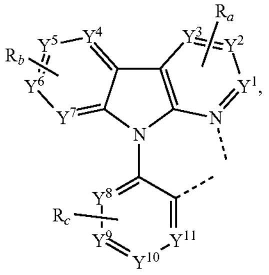

and

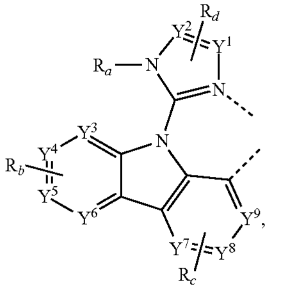

wherein, $Y^1$ to $Y^{13}$ are each independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ are optionally fused or joined to form a ring;

each $R_a$, $R_b$, $R_c$, and $R_d$ can independently represent from mono substitution to the maximum possible number of substitutions, or no substitution;

$R_a$, $R_b$, $R_c$, $R_d$, $R_e$ and $R_f$ are each independently selected from the group consisting of hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two adjacent substituents of $R_a$, $R_b$, $R_c$, and $R_d$ are optionally fused or joined to form a ring or form a multidentate ligand.

2. The compound of claim 1, wherein $R^A$, R, $R^1$, and $R^2$ are each independently selected from the group consisting of hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

3. The compound of claim 1, wherein $L^1$ is a direct bond.

4. The compound of claim 1, wherein $L^1$ is alkyl.

5. The compound of claim 1, wherein $R^1$ comprises more C atoms than $R^2$.

6. The compound of claim 1, wherein $R^2$ comprises more C atoms than $R^1$.

7. The compound of claim 1, wherein $G^1$ is a substituted cycloalkyl, wherein the substituted cycloalkyl is selected from the group consisting of alkyl substituted cycloalkyl, a partially or fully fluorinated cycloalkyl or alkyl substituted cycloalkyl, and combinations thereof.

8. The compound of claim 1, wherein $X^1$ to $X^4$ are each CH.

9. The compound of claim 1, wherein one of $X^1$ to $X^4$ is N, and the remainder are CH.

10. The compound of claim 1, wherein the ligand $L_A$ is selected from the group consisting of:

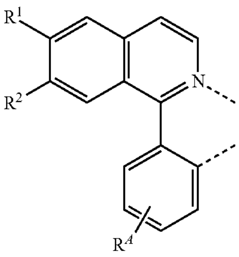

,

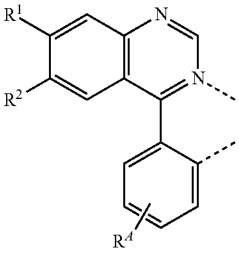

,

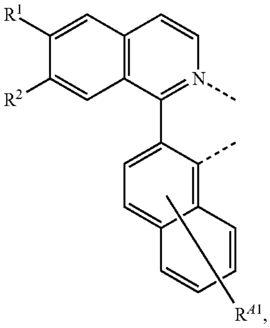

,

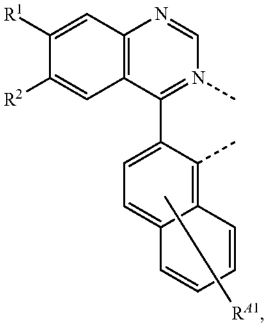

,

-continued

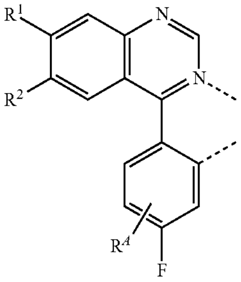

,

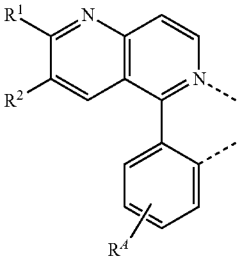

,

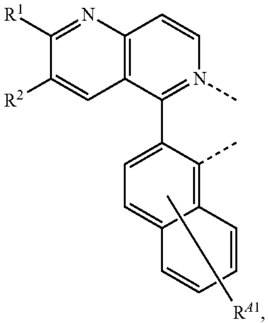

,

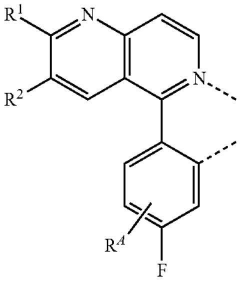

,

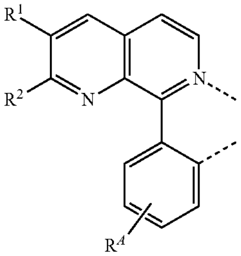

,

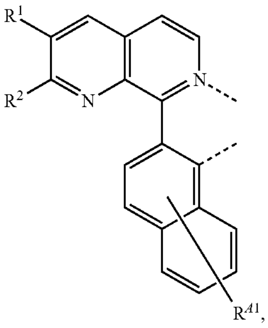

, and

-continued

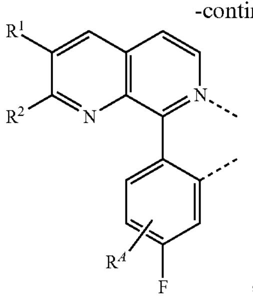

;

and wherein $R^{A1}$ has the same definition as $R^{A}$.

11. A compound having a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; wherein $L_B$ and $L_C$ are each a bidentate ligand, and wherein $L_A$, $L_B$, and $L_C$ are different from each other, wherein the ligand $L_A$ is selected from the group consisting of:

$L_{A40}$ through $L_{A44}$, $L_{A46}$ through $L_{A51}$, $L_{A53}$ through $L_{A57}$, $L_{A59}$ through $L_{A64}$, $L_{A79}$ through $L_{A83}$, $L_{A85}$ through $L_{A90}$, $L_{A92}$ through $L_{A96}$, $L_{A98}$ through $L_{A103}$, $L_{A144}$ through $L_{A148}$, $L_{A150}$ through $L_{A155}$, $L_{A157}$ through $L_{A161}$, $L_{A163}$ through $L_{A168}$, $L_{A183}$ through $L_{A187}$, $L_{A189}$ through $L_{A194}$, $L_{A196}$ through $L_{A200}$, $L_{A202}$ through $L_{A207}$, $L_{A248}$ through $L_{A252}$, $L_{A254}$ through $L_{A259}$, $L_{A261}$ through $L_{A265}$, $L_{A267}$ through $L_{A271}$, $L_{A287}$ through $L_{A291}$, $L_{A293}$ through $L_{A298}$, $L_{A300}$ through $L_{A304}$, $L_{A306}$ through $L_{A311}$, $L_{A352}$ through $L_{A356}$, $L_{A358}$ through $L_{A363}$, $L_{A365}$ through $L_{A369}$, $L_{A371}$ through $L_{A376}$, $L_{A391}$ through $L_{A395}$, $L_{A397}$ through $L_{A402}$, $L_{A404}$ through $L_{A407}$, and $L_{A409}$ through $L_{A415}$ based on a structure of Formula II,

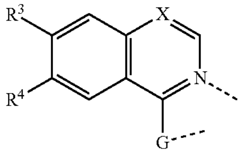

, in which $R^3$, $R^4$, G, and X are defined as:

| Ligand | $R^3$ | $R^4$ | G | X | Ligand | $R^3$ | $R^4$ | G | X |
|---|---|---|---|---|---|---|---|---|---|
| $L_{A40}$ | $R^{C11}$ | H | $R^{D8}$ | C | $L_{A248}$ | $R^{C11}$ | H | $R^{D8}$ | N |
| $L_{A41}$ | $R^{C14}$ | H | $R^{D8}$ | C | $L_{A249}$ | $R^{C14}$ | H | $R^{D8}$ | N |
| $L_{A42}$ | $R^{C18}$ | H | $R^{D8}$ | C | $L_{A250}$ | $R^{C18}$ | H | $R^{D8}$ | N |
| $L_{A43}$ | $R^{C19}$ | H | $R^{D8}$ | C | $L_{A251}$ | $R^{C19}$ | H | $R^{D8}$ | N |
| $L_{A44}$ | $R^{C23}$ | H | $R^{D8}$ | C | $L_{A252}$ | $R^{C23}$ | H | $R^{D8}$ | N |
| $L_{A46}$ | $R^{C38}$ | H | $R^{D8}$ | C | $L_{A254}$ | $R^{C38}$ | H | $R^{D8}$ | N |
| $L_{A47}$ | $R^{C40}$ | H | $R^{D8}$ | C | $L_{A255}$ | $R^{C40}$ | H | $R^{D8}$ | N |
| $L_{A48}$ | $R^{C41}$ | H | $R^{D8}$ | C | $L_{A256}$ | $R^{C41}$ | H | $R^{D8}$ | N |
| $L_{A49}$ | $R^{C48}$ | H | $R^{D8}$ | C | $L_{A257}$ | $R^{C48}$ | H | $R^{D8}$ | N |
| $L_{A50}$ | $R^{C54}$ | H | $R^{D8}$ | C | $L_{A258}$ | $R^{C54}$ | H | $R^{D8}$ | N |
| $L_{A51}$ | $R^{C55}$ | H | $R^{D8}$ | C | $L_{A259}$ | $R^{C55}$ | H | $R^{D8}$ | N |
| $L_{A53}$ | $R^{C11}$ | H | $R^{D9}$ | C | $L_{A261}$ | $R^{C11}$ | H | $R^{D9}$ | N |
| $L_{A54}$ | $R^{C14}$ | H | $R^{D9}$ | C | $L_{A262}$ | $R^{C14}$ | H | $R^{D9}$ | N |
| $L_{A55}$ | $R^{C18}$ | H | $R^{D9}$ | C | $L_{A263}$ | $R^{C18}$ | H | $R^{D9}$ | N |
| $L_{A56}$ | $R^{C19}$ | H | $R^{D9}$ | C | $L_{A264}$ | $R^{C19}$ | H | $R^{D9}$ | N |
| $L_{A57}$ | $R^{C23}$ | H | $R^{D9}$ | C | $L_{A265}$ | $R^{C23}$ | H | $R^{D9}$ | N |
| $L_{A59}$ | $R^{C38}$ | H | $R^{D9}$ | C | $L_{A267}$ | $R^{C38}$ | H | $R^{D9}$ | N |
| $L_{A60}$ | $R^{C40}$ | H | $R^{D9}$ | C | $L_{A268}$ | $R^{C40}$ | H | $R^{D9}$ | N |
| $L_{A61}$ | $R^{C41}$ | H | $R^{D9}$ | C | $L_{A269}$ | $R^{C41}$ | H | $R^{D9}$ | N |
| $L_{A62}$ | $R^{C48}$ | H | $R^{D9}$ | C | $L_{A270}$ | $R^{C48}$ | H | $R^{D9}$ | N |
| $L_{A63}$ | $R^{C54}$ | H | $R^{D9}$ | C | $L_{A271}$ | $R^{C54}$ | H | $R^{D9}$ | N |
| $L_{A64}$ | $R^{C55}$ | H | $R^{D9}$ | C | $L_{A287}$ | $R^{C11}$ | H | $R^{D22}$ | N |

-continued

| Ligand | $R^3$ | $R^4$ | G | X | Ligand | $R^3$ | $R^4$ | G | X |
|---|---|---|---|---|---|---|---|---|---|
| $L_{A79}$ | $R^{C11}$ | H | $R^{D22}$ | C | $L_{A288}$ | $R^{C14}$ | H | $R^{D22}$ | N |
| $L_{A80}$ | $R^{C14}$ | H | $R^{D22}$ | C | $L_{A289}$ | $R^{C18}$ | H | $R^{D22}$ | N |
| $L_{A81}$ | $R^{C18}$ | H | $R^{D22}$ | C | $L_{A290}$ | $R^{C19}$ | H | $R^{D22}$ | N |
| $L_{A82}$ | $R^{C19}$ | H | $R^{D22}$ | C | $L_{A291}$ | $R^{C23}$ | H | $R^{D22}$ | N |
| $L_{A83}$ | $R^{C23}$ | H | $R^{D22}$ | C | $L_{A293}$ | $R^{C38}$ | H | $R^{D22}$ | N |
| $L_{A85}$ | $R^{C38}$ | H | $R^{D22}$ | C | $L_{A294}$ | $R^{C40}$ | H | $R^{D22}$ | N |
| $L_{A86}$ | $R^{C40}$ | H | $R^{D22}$ | C | $L_{A295}$ | $R^{C41}$ | H | $R^{D22}$ | N |
| $L_{A87}$ | $R^{C41}$ | H | $R^{D22}$ | C | $L_{A296}$ | $R^{C48}$ | H | $R^{D22}$ | N |
| $L_{A88}$ | $R^{C48}$ | H | $R^{D22}$ | C | $L_{A297}$ | $R^{C54}$ | H | $R^{D22}$ | N |
| $L_{A89}$ | $R^{C54}$ | H | $R^{D22}$ | C | $L_{A298}$ | $R^{C55}$ | H | $R^{D22}$ | N |
| $L_{A90}$ | $R^{C55}$ | H | $R^{D22}$ | C | $L_{A300}$ | $R^{C11}$ | H | $R^{D28}$ | N |
| $L_{A92}$ | $R^{C11}$ | H | $R^{D28}$ | C | $L_{A301}$ | $R^{C14}$ | H | $R^{D28}$ | N |
| $L_{A93}$ | $R^{C14}$ | H | $R^{D28}$ | C | $L_{A302}$ | $R^{C18}$ | H | $R^{D28}$ | N |
| $L_{A94}$ | $R^{C18}$ | H | $R^{D28}$ | C | $L_{A303}$ | $R^{C19}$ | H | $R^{D28}$ | N |
| $L_{A95}$ | $R^{C19}$ | H | $R^{D28}$ | C | $L_{A304}$ | $R^{C23}$ | H | $R^{D28}$ | N |
| $L_{A96}$ | $R^{C23}$ | H | $R^{D28}$ | C | $L_{A306}$ | $R^{C38}$ | H | $R^{D28}$ | N |
| $L_{A98}$ | $R^{C38}$ | H | $R^{D28}$ | C | $L_{A307}$ | $R^{C40}$ | H | $R^{D28}$ | N |
| $L_{A99}$ | $R^{C40}$ | H | $R^{D28}$ | C | $L_{A308}$ | $R^{C41}$ | H | $R^{D28}$ | N |
| $L_{A100}$ | $R^{C41}$ | H | $R^{D28}$ | C | $L_{A309}$ | $R^{C48}$ | H | $R^{D28}$ | N |
| $L_{A101}$ | $R^{C48}$ | H | $R^{D28}$ | C | $L_{A310}$ | $R^{C54}$ | H | $R^{D28}$ | N |
| $L_{A102}$ | $R^{C54}$ | H | $R^{D28}$ | C | $L_{A311}$ | $R^{C55}$ | H | $R^{D28}$ | N |
| $L_{A103}$ | $R^{C55}$ | H | $R^{D28}$ | C | $L_{A352}$ | H | $R^{C11}$ | $R^{D8}$ | N |
| $L_{A144}$ | H | $R^{C11}$ | $R^{D8}$ | C | $L_{A353}$ | H | $R^{C14}$ | $R^{D8}$ | N |
| $L_{A145}$ | H | $R^{C14}$ | $R^{D8}$ | C | $L_{A354}$ | H | $R^{C18}$ | $R^{D8}$ | N |
| $L_{A146}$ | H | $R^{C18}$ | $R^{D8}$ | C | $L_{A355}$ | H | $R^{C19}$ | $R^{D8}$ | N |
| $L_{A147}$ | H | $R^{C19}$ | $R^{D8}$ | C | $L_{A356}$ | H | $R^{C23}$ | $R^{D8}$ | N |
| $L_{A148}$ | H | $R^{C23}$ | $R^{D8}$ | C | $L_{A358}$ | H | $R^{C38}$ | $R^{D8}$ | N |
| $L_{A150}$ | H | $R^{C38}$ | $R^{D8}$ | C | $L_{A359}$ | H | $R^{C40}$ | $R^{D8}$ | N |
| $L_{A151}$ | H | $R^{C40}$ | $R^{D8}$ | C | $L_{A360}$ | H | $R^{C41}$ | $R^{D8}$ | N |
| $L_{A152}$ | H | $R^{C41}$ | $R^{D8}$ | C | $L_{A361}$ | H | $R^{C48}$ | $R^{D8}$ | N |
| $L_{A153}$ | H | $R^{C48}$ | $R^{D8}$ | C | $L_{A362}$ | H | $R^{C54}$ | $R^{D8}$ | N |
| $L_{A154}$ | H | $R^{C54}$ | $R^{D8}$ | C | $L_{A363}$ | H | $R^{C55}$ | $R^{D8}$ | N |
| $L_{A155}$ | H | $R^{C55}$ | $R^{D8}$ | C | $L_{A365}$ | H | $R^{C11}$ | $R^{D9}$ | N |
| $L_{A157}$ | H | $R^{C11}$ | $R^{D9}$ | C | $L_{A366}$ | H | $R^{C14}$ | $R^{D9}$ | N |
| $L_{A158}$ | H | $R^{C14}$ | $R^{D9}$ | C | $L_{A367}$ | H | $R^{C18}$ | $R^{D9}$ | N |
| $L_{A159}$ | H | $R^{C18}$ | $R^{D9}$ | C | $L_{A368}$ | H | $R^{C19}$ | $R^{D9}$ | N |
| $L_{A160}$ | H | $R^{C19}$ | $R^{D9}$ | C | $L_{A369}$ | H | $R^{C23}$ | $R^{D9}$ | N |
| $L_{A161}$ | H | $R^{C23}$ | $R^{D9}$ | C | $L_{A371}$ | H | $R^{C38}$ | $R^{D9}$ | N |
| $L_{A163}$ | H | $R^{C38}$ | $R^{D9}$ | C | $L_{A372}$ | H | $R^{C40}$ | $R^{D9}$ | N |
| $L_{A164}$ | H | $R^{C40}$ | $R^{D9}$ | C | $L_{A373}$ | H | $R^{C41}$ | $R^{D9}$ | N |
| $L_{A165}$ | H | $R^{C41}$ | $R^{D9}$ | C | $L_{A374}$ | H | $R^{C48}$ | $R^{D9}$ | N |
| $L_{A166}$ | H | $R^{C48}$ | $R^{D9}$ | C | $L_{A375}$ | H | $R^{C54}$ | $R^{D9}$ | N |
| $L_{A167}$ | H | $R^{C54}$ | $R^{D9}$ | C | $L_{A376}$ | H | $R^{C55}$ | $R^{D9}$ | N |
| $L_{A168}$ | H | $R^{C55}$ | $R^{D9}$ | C | $L_{A391}$ | H | $R^{C11}$ | $R^{D22}$ | N |
| $L_{A183}$ | H | $R^{C11}$ | $R^{D22}$ | C | $L_{A392}$ | H | $R^{C14}$ | $R^{D22}$ | N |
| $L_{A184}$ | H | $R^{C14}$ | $R^{D22}$ | C | $L_{A393}$ | H | $R^{C18}$ | $R^{D22}$ | N |
| $L_{A185}$ | H | $R^{C18}$ | $R^{D22}$ | C | $L_{A394}$ | H | $R^{C19}$ | $R^{D22}$ | N |
| $L_{A186}$ | H | $R^{C19}$ | $R^{D22}$ | C | $L_{A395}$ | H | $R^{C23}$ | $R^{D22}$ | N |
| $L_{A187}$ | H | $R^{C23}$ | $R^{D22}$ | C | $L_{A397}$ | H | $R^{C38}$ | $R^{D22}$ | N |
| $L_{A189}$ | H | $R^{C38}$ | $R^{D22}$ | C | $L_{A398}$ | H | $R^{C40}$ | $R^{D22}$ | N |
| $L_{A190}$ | H | $R^{C40}$ | $R^{D22}$ | C | $L_{A399}$ | H | $R^{C41}$ | $R^{D22}$ | N |
| $L_{A191}$ | H | $R^{C41}$ | $R^{D22}$ | C | $L_{A400}$ | H | $R^{C48}$ | $R^{D22}$ | N |
| $L_{A192}$ | H | $R^{C48}$ | $R^{D22}$ | C | $L_{A401}$ | H | $R^{C54}$ | $R^{D22}$ | N |
| $L_{A193}$ | H | $R^{C54}$ | $R^{D22}$ | C | $L_{A402}$ | H | $R^{C55}$ | $R^{D22}$ | N |
| $L_{A194}$ | H | $R^{C55}$ | $R^{D22}$ | C | $L_{A401}$ | H | $R^{C54}$ | $R^{D22}$ | N |
| $L_{A196}$ | H | $R^{C11}$ | $R^{D28}$ | C | $L_{A402}$ | H | $R^{C55}$ | $R^{D22}$ | N |
| $L_{A197}$ | H | $R^{C14}$ | $R^{D28}$ | C | $L_{A398}$ | H | $R^{C40}$ | $R^{D22}$ | N |
| $L_{A198}$ | H | $R^{C18}$ | $R^{D28}$ | C | $L_{A399}$ | H | $R^{C41}$ | $R^{D22}$ | N |
| $L_{A199}$ | H | $R^{C19}$ | $R^{D28}$ | C | $L_{A400}$ | H | $R^{C48}$ | $R^{D22}$ | N |
| $L_{A200}$ | H | $R^{C23}$ | $R^{D28}$ | C | $L_{A401}$ | H | $R^{C54}$ | $R^{D22}$ | N |
| $L_{A202}$ | H | $R^{C38}$ | $R^{D28}$ | C | $L_{A402}$ | H | $R^{C55}$ | $R^{D22}$ | N |
| $L_{A203}$ | H | $R^{C40}$ | $R^{D28}$ | C | $L_{A401}$ | H | $R^{C54}$ | $R^{D22}$ | N |
| $L_{A204}$ | H | $R^{C41}$ | $R^{D28}$ | C | $L_{A402}$ | H | $R^{C55}$ | $R^{D22}$ | N |
| $L_{A205}$ | H | $R^{C48}$ | $R^{D28}$ | C | | | | | |
| $L_{A206}$ | H | $R^{C54}$ | $R^{D28}$ | C | | | | | |
| $L_{A207}$ | H | $R^{C55}$ | $R^{D28}$ | C | | | | | |
| $L_{A404}$ | H | $R^{C11}$ | $R^{D28}$ | N | | | | | |
| $L_{A405}$ | H | $R^{C14}$ | $R^{D28}$ | N | | | | | |
| $L_{A406}$ | H | $R^{C18}$ | $R^{D28}$ | N | | | | | |
| $L_{A407}$ | H | $R^{C19}$ | $R^{D28}$ | N | | | | | |
| $L_{A409}$ | H | $R^{C33}$ | $R^{D28}$ | N | | | | | |
| $L_{A410}$ | H | $R^{C38}$ | $R^{D28}$ | N | | | | | |
| $L_{A411}$ | H | $R^{C40}$ | $R^{D28}$ | N | | | | | |

-continued

| Ligand | $R^3$ | $R^4$ | G | X | Ligand | $R^3$ | $R^4$ | G | X |
|---|---|---|---|---|---|---|---|---|---|
| $L_{A412}$ | H | $R^{C41}$ | $R^{D28}$ | N | | | | | |
| $L_{A413}$ | H | $R^{C48}$ | $R^{D28}$ | N | | | | | |
| $L_{A414}$ | H | $R^{C54}$ | $R^{D28}$ | N | | | | | |
| $L_{A415}$ | H | $R^{C55}$ | $R^{D28}$ | N | | | | | |

$L_{A573}$ through $L_{A577}$, $L_{A579}$ through $L_{A584}$, $L_{A587}$ through $L_{A590}$, $L_{A592}$ through $L_{A597}$, $L_{A599}$ through $L_{A603}$, $L_{A605}$ through $L_{A610}$, $L_{A612}$ through $L_{A616}$, $L_{A618}$ through $L_{A623}$, $L_{A625}$ through $L_{A629}$, $L_{A631}$ through $L_{A635}$, $L_{A636}$ through $L_{A642}$, $L_{A644}$ through $L_{A649}$, $L_{A651}$ through $L_{A655}$, $L_{A657}$ through $L_{A662}$, $L_{A665}$ through $L_{A668}$, $L_{A670}$ through $L_{A675}$, $L_{A729}$ through $L_{A733}$, $L_{A735}$ through $L_{A740}$, $L_{A742}$ through $L_{A746}$, $L_{A748}$ through $L_{A753}$, $L_{A755}$ through $L_{A759}$, $L_{A761}$ through $L_{A766}$, $L_{A768}$ through $L_{A772}$, $L_{A774}$ through $L_{A779}$, $L_{A781}$ through $L_{A785}$, $L_{A787}$ through $L_{A792}$, $L_{A794}$ through $L_{A798}$, $L_{A800}$ through $L_{A805}$, $L_{A808}$ through $L_{A811}$, $L_{A813}$ through $L_{A818}$, $L_{A820}$ through $L_{A824}$, and $L_{A826}$ through $L_{A831}$ based on a structure of Formula III,

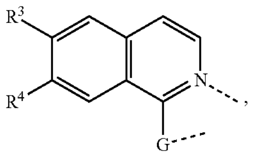

in which $R^3$, $R^4$, and G are defined as:

| Ligand | $R^3$ | $R^4$ | G |
|---|---|---|---|
| $L_{A573}$ | $R^{C11}$ | $R^{C11}$ | $R^{D8}$ |
| $L_{A574}$ | $R^{C14}$ | $R^{C14}$ | $R^{D8}$ |
| $L_{A575}$ | $R^{C18}$ | $R^{C18}$ | $R^{D8}$ |
| $L_{A576}$ | $R^{C19}$ | $R^{C19}$ | $R^{D8}$ |
| $L_{A577}$ | $R^{C23}$ | $R^{C23}$ | $R^{D8}$ |
| $L_{A579}$ | $R^{C38}$ | $R^{C38}$ | $R^{D8}$ |
| $L_{A580}$ | $R^{C40}$ | $R^{C40}$ | $R^{D8}$ |
| $L_{A581}$ | $R^{C41}$ | $R^{C41}$ | $R^{D8}$ |
| $L_{A582}$ | $R^{C48}$ | $R^{C48}$ | $R^{D8}$ |
| $L_{A583}$ | $R^{C54}$ | $R^{C54}$ | $R^{D8}$ |
| $L_{A584}$ | $R^{C55}$ | $R^{C55}$ | $R^{D8}$ |
| $L_{A586}$ | $R^{C11}$ | $R^{B1}$ | $R^{D8}$ |
| $L_{A587}$ | $R^{C14}$ | $R^{B1}$ | $R^{D8}$ |
| $L_{A588}$ | $R^{C18}$ | $R^{B1}$ | $R^{D8}$ |
| $L_{A589}$ | $R^{C19}$ | $R^{B1}$ | $R^{D8}$ |
| $L_{A590}$ | $R^{C23}$ | $R^{B1}$ | $R^{D8}$ |
| $L_{A592}$ | $R^{C38}$ | $R^{B1}$ | $R^{D8}$ |
| $L_{A593}$ | $R^{C40}$ | $R^{B1}$ | $R^{D8}$ |
| $L_{A594}$ | $R^{C41}$ | $R^{B1}$ | $R^{D8}$ |
| $L_{A595}$ | $R^{C48}$ | $R^{B1}$ | $R^{D8}$ |
| $L_{A596}$ | $R^{C54}$ | $R^{B1}$ | $R^{D8}$ |
| $L_{A597}$ | $R^{C55}$ | $R^{B1}$ | $R^{D8}$ |
| $L_{A599}$ | $R^{C11}$ | $R^{B3}$ | $R^{D8}$ |
| $L_{A600}$ | $R^{C14}$ | $R^{B3}$ | $R^{D8}$ |
| $L_{A601}$ | $R^{C18}$ | $R^{B3}$ | $R^{D8}$ |
| $L_{A602}$ | $R^{C19}$ | $R^{B3}$ | $R^{D8}$ |
| $L_{A603}$ | $R^{C23}$ | $R^{B3}$ | $R^{D8}$ |
| $L_{A605}$ | $R^{C38}$ | $R^{B3}$ | $R^{D8}$ |
| $L_{A606}$ | $R^{C40}$ | $R^{B3}$ | $R^{D8}$ |
| $L_{A607}$ | $R^{C41}$ | $R^{B3}$ | $R^{D8}$ |
| $L_{A608}$ | $R^{C48}$ | $R^{B3}$ | $R^{D8}$ |
| $L_{A609}$ | $R^{C54}$ | $R^{B3}$ | $R^{D8}$ |
| $L_{A610}$ | $R^{C55}$ | $R^{B3}$ | $R^{D8}$ |
| $L_{A612}$ | $R^{C11}$ | $R^{B4}$ | $R^{D8}$ |
| $L_{A613}$ | $R^{C14}$ | $R^{B4}$ | $R^{D8}$ |
| $L_{A614}$ | $R^{C18}$ | $R^{B4}$ | $R^{D8}$ |
| $L_{A615}$ | $R^{C19}$ | $R^{B4}$ | $R^{D8}$ |

-continued

| Ligand | $R^3$ | $R^4$ | G |
|---|---|---|---|
| $L_{A616}$ | $R^{C23}$ | $R^{B4}$ | $R^{D8}$ |
| $L_{A618}$ | $R^{C38}$ | $R^{B4}$ | $R^{D8}$ |
| $L_{A619}$ | $R^{C40}$ | $R^{B4}$ | $R^{D8}$ |
| $L_{A620}$ | $R^{C41}$ | $R^{B4}$ | $R^{D8}$ |
| $L_{A621}$ | $R^{C48}$ | $R^{B4}$ | $R^{D8}$ |
| $L_{A622}$ | $R^{C54}$ | $R^{B4}$ | $R^{D8}$ |
| $L_{A623}$ | $R^{C55}$ | $R^{B4}$ | $R^{D8}$ |
| $L_{A625}$ | $R^{C11}$ | $R^{C11}$ | $R^{D9}$ |
| $L_{A626}$ | $R^{C14}$ | $R^{C14}$ | $R^{D9}$ |
| $L_{A627}$ | $R^{C18}$ | $R^{C18}$ | $R^{D9}$ |
| $L_{A628}$ | $R^{C19}$ | $R^{C19}$ | $R^{D9}$ |
| $L_{A629}$ | $R^{C23}$ | $R^{C23}$ | $R^{D9}$ |
| $L_{A631}$ | $R^{C38}$ | $R^{C38}$ | $R^{D9}$ |
| $L_{A632}$ | $R^{C40}$ | $R^{C40}$ | $R^{D9}$ |
| $L_{A633}$ | $R^{C41}$ | $R^{C41}$ | $R^{D9}$ |
| $L_{A634}$ | $R^{C48}$ | $R^{C48}$ | $R^{D9}$ |
| $L_{A635}$ | $R^{C54}$ | $R^{C54}$ | $R^{D9}$ |
| $L_{A636}$ | $R^{C55}$ | $R^{C55}$ | $R^{D9}$ |
| $L_{A638}$ | $R^{C11}$ | $R^{B1}$ | $R^{D9}$ |
| $L_{A639}$ | $R^{C14}$ | $R^{B1}$ | $R^{D9}$ |
| $L_{A640}$ | $R^{C18}$ | $R^{B1}$ | $R^{D9}$ |
| $L_{A641}$ | $R^{C19}$ | $R^{B1}$ | $R^{D9}$ |
| $L_{A642}$ | $R^{C23}$ | $R^{B1}$ | $R^{D9}$ |
| $L_{A644}$ | $R^{C38}$ | $R^{B1}$ | $R^{D9}$ |
| $L_{A645}$ | $R^{C40}$ | $R^{B1}$ | $R^{D9}$ |
| $L_{A646}$ | $R^{C41}$ | $R^{B1}$ | $R^{D9}$ |
| $L_{A647}$ | $R^{C48}$ | $R^{B1}$ | $R^{D9}$ |
| $L_{A648}$ | $R^{C54}$ | $R^{B1}$ | $R^{D9}$ |
| $L_{A649}$ | $R^{C55}$ | $R^{B1}$ | $R^{D9}$ |
| $L_{A651}$ | $R^{C11}$ | $R^{B3}$ | $R^{D9}$ |
| $L_{A652}$ | $R^{C14}$ | $R^{B3}$ | $R^{D9}$ |
| $L_{A653}$ | $R^{C18}$ | $R^{B3}$ | $R^{D9}$ |
| $L_{A654}$ | $R^{C19}$ | $R^{B3}$ | $R^{D9}$ |
| $L_{A655}$ | $R^{C23}$ | $R^{B3}$ | $R^{D9}$ |
| $L_{A657}$ | $R^{C38}$ | $R^{B3}$ | $R^{D9}$ |
| $L_{A658}$ | $R^{C40}$ | $R^{B3}$ | $R^{D9}$ |
| $L_{A659}$ | $R^{C41}$ | $R^{B3}$ | $R^{D9}$ |
| $L_{A660}$ | $R^{C48}$ | $R^{B3}$ | $R^{D9}$ |
| $L_{A661}$ | $R^{C54}$ | $R^{B3}$ | $R^{D9}$ |
| $L_{A662}$ | $R^{C55}$ | $R^{B3}$ | $R^{D9}$ |
| $L_{A664}$ | $R^{C11}$ | $R^{B4}$ | $R^{D9}$ |
| $L_{A665}$ | $R^{C14}$ | $R^{B4}$ | $R^{D9}$ |
| $L_{A666}$ | $R^{C18}$ | $R^{B4}$ | $R^{D9}$ |
| $L_{A667}$ | $R^{C19}$ | $R^{B4}$ | $R^{D9}$ |
| $L_{A668}$ | $R^{C23}$ | $R^{B4}$ | $R^{D9}$ |
| $L_{A670}$ | $R^{C38}$ | $R^{B4}$ | $R^{D9}$ |
| $L_{A671}$ | $R^{C40}$ | $R^{B4}$ | $R^{D9}$ |
| $L_{A672}$ | $R^{C41}$ | $R^{B4}$ | $R^{D9}$ |
| $L_{A673}$ | $R^{C48}$ | $R^{B4}$ | $R^{D9}$ |
| $L_{A674}$ | $R^{C54}$ | $R^{B4}$ | $R^{D9}$ |
| $L_{A729}$ | $R^{C11}$ | $R^{C11}$ | $R^{D22}$ |
| $L_{A730}$ | $R^{C14}$ | $R^{C14}$ | $R^{D22}$ |
| $L_{A731}$ | $R^{C18}$ | $R^{C18}$ | $R^{D22}$ |
| $L_{A732}$ | $R^{C19}$ | $R^{C19}$ | $R^{D22}$ |
| $L_{A733}$ | $R^{C23}$ | $R^{C23}$ | $R^{D22}$ |
| $L_{A735}$ | $R^{C38}$ | $R^{C38}$ | $R^{D22}$ |
| $L_{A736}$ | $R^{C40}$ | $R^{C40}$ | $R^{D22}$ |
| $L_{A737}$ | $R^{C41}$ | $R^{C41}$ | $R^{D22}$ |
| $L_{A738}$ | $R^{C48}$ | $R^{C48}$ | $R^{D22}$ |
| $L_{A739}$ | $R^{C54}$ | $R^{C54}$ | $R^{D22}$ |
| $L_{A740}$ | $R^{C55}$ | $R^{C55}$ | $R^{D22}$ |
| $L_{A742}$ | $R^{C11}$ | $R^{B1}$ | $R^{D22}$ |
| $L_{A743}$ | $R^{C14}$ | $R^{B1}$ | $R^{D22}$ |
| $L_{A744}$ | $R^{C18}$ | $R^{B1}$ | $R^{D22}$ |
| $L_{A745}$ | $R^{C19}$ | $R^{B1}$ | $R^{D22}$ |
| $L_{A746}$ | $R^{C23}$ | $R^{B1}$ | $R^{D22}$ |
| $L_{A748}$ | $R^{C38}$ | $R^{B1}$ | $R^{D22}$ |
| $L_{A749}$ | $R^{C40}$ | $R^{B1}$ | $R^{D22}$ |
| $L_{A750}$ | $R^{C41}$ | $R^{B1}$ | $R^{D22}$ |
| $L_{A751}$ | $R^{C48}$ | $R^{B1}$ | $R^{D22}$ |
| $L_{A752}$ | $R^{C54}$ | $R^{B1}$ | $R^{D22}$ |
| $L_{A753}$ | $R^{C55}$ | $R^{B1}$ | $R^{D22}$ |
| $L_{A755}$ | $R^{C11}$ | $R^{B3}$ | $R^{D22}$ |
| $L_{A756}$ | $R^{C14}$ | $R^{B3}$ | $R^{D22}$ |
| $L_{A757}$ | $R^{C18}$ | $R^{B3}$ | $R^{D22}$ |
| $L_{A758}$ | $R^{C19}$ | $R^{B3}$ | $R^{D22}$ |
| $L_{A759}$ | $R^{C23}$ | $R^{B3}$ | $R^{D22}$ |

-continued

| Ligand | $R^3$ | $R^4$ | G |
|---|---|---|---|
| $L_{A4761}$ | $R^{C38}$ | $R^{B3}$ | $R^{D22}$ |
| $L_{A4762}$ | $R^{C40}$ | $R^{B3}$ | $R^{D22}$ |
| $L_{A4763}$ | $R^{C41}$ | $R^{B3}$ | $R^{D22}$ |
| $L_{A4764}$ | $R^{C48}$ | $R^{B3}$ | $R^{D22}$ |
| $L_{A4765}$ | $R^{C54}$ | $R^{B3}$ | $R^{D22}$ |
| $L_{A4766}$ | $R^{C55}$ | $R^{B3}$ | $R^{D22}$ |
| $L_{A4768}$ | $R^{C11}$ | $R^{B4}$ | $R^{D22}$ |
| $L_{A4769}$ | $R^{C14}$ | $R^{B4}$ | $R^{D22}$ |
| $L_{A4770}$ | $R^{C18}$ | $R^{B4}$ | $R^{D22}$ |
| $L_{A4771}$ | $R^{C19}$ | $R^{B4}$ | $R^{D22}$ |
| $L_{A4772}$ | $R^{C23}$ | $R^{B4}$ | $R^{D22}$ |
| $L_{A4774}$ | $R^{C38}$ | $R^{B4}$ | $R^{D22}$ |
| $L_{A4775}$ | $R^{C40}$ | $R^{B4}$ | $R^{D22}$ |
| $L_{A4776}$ | $R^{C41}$ | $R^{B4}$ | $R^{D22}$ |
| $L_{A4777}$ | $R^{C48}$ | $R^{B4}$ | $R^{D22}$ |
| $L_{A4778}$ | $R^{C54}$ | $R^{B4}$ | $R^{D22}$ |
| $L_{A4779}$ | $R^{C55}$ | $R^{B4}$ | $R^{D22}$ |
| $L_{A4781}$ | $R^{C11}$ | $R^{C11}$ | $R^{D28}$ |
| $L_{A4782}$ | $R^{C14}$ | $R^{C14}$ | $R^{D28}$ |
| $L_{A4783}$ | $R^{C18}$ | $R^{C18}$ | $R^{D28}$ |
| $L_{A4784}$ | $R^{C19}$ | $R^{C19}$ | $R^{D28}$ |
| $L_{A4785}$ | $R^{C23}$ | $R^{C23}$ | $R^{D28}$ |
| $L_{A4787}$ | $R^{C38}$ | $R^{C38}$ | $R^{D28}$ |
| $L_{A4788}$ | $R^{C40}$ | $R^{C40}$ | $R^{D28}$ |
| $L_{A4789}$ | $R^{C41}$ | $R^{C41}$ | $R^{D28}$ |
| $L_{A4790}$ | $R^{C48}$ | $R^{C48}$ | $R^{D28}$ |
| $L_{A4791}$ | $R^{C54}$ | $R^{C54}$ | $R^{D28}$ |
| $L_{A4792}$ | $R^{C55}$ | $R^{C55}$ | $R^{D28}$ |
| $L_{A4794}$ | $R^{C11}$ | $R^{B1}$ | $R^{D28}$ |
| $L_{A4795}$ | $R^{C14}$ | $R^{B1}$ | $R^{D28}$ |
| $L_{A4796}$ | $R^{C18}$ | $R^{B1}$ | $R^{D28}$ |
| $L_{A4797}$ | $R^{C19}$ | $R^{B1}$ | $R^{D28}$ |
| $L_{A4798}$ | $R^{C23}$ | $R^{B1}$ | $R^{D28}$ |
| $L_{A4800}$ | $R^{C38}$ | $R^{B1}$ | $R^{D28}$ |
| $L_{A4801}$ | $R^{C40}$ | $R^{B1}$ | $R^{D28}$ |
| $L_{A4802}$ | $R^{C41}$ | $R^{B1}$ | $R^{D28}$ |
| $L_{A4803}$ | $R^{C48}$ | $R^{B1}$ | $R^{D28}$ |
| $L_{A4804}$ | $R^{C54}$ | $R^{B1}$ | $R^{D28}$ |
| $L_{A4805}$ | $R^{C55}$ | $R^{B1}$ | $R^{D28}$ |
| $L_{A4807}$ | $R^{C11}$ | $R^{B3}$ | $R^{D28}$ |
| $L_{A4808}$ | $R^{C14}$ | $R^{B3}$ | $R^{D28}$ |
| $L_{A4809}$ | $R^{C18}$ | $R^{B3}$ | $R^{D28}$ |
| $L_{A4810}$ | $R^{C19}$ | $R^{B3}$ | $R^{D28}$ |
| $L_{A4811}$ | $R^{C23}$ | $R^{B3}$ | $R^{D28}$ |
| $L_{A4813}$ | $R^{C38}$ | $R^{B3}$ | $R^{D28}$ |
| $L_{A4814}$ | $R^{C40}$ | $R^{B3}$ | $R^{D28}$ |
| $L_{A4815}$ | $R^{C41}$ | $R^{B3}$ | $R^{D28}$ |
| $L_{A4816}$ | $R^{C48}$ | $R^{B3}$ | $R^{D28}$ |
| $L_{A4817}$ | $R^{C54}$ | $R^{B3}$ | $R^{D28}$ |
| $L_{A4818}$ | $R^{C55}$ | $R^{B3}$ | $R^{D28}$ |
| $L_{A4820}$ | $R^{C11}$ | $R^{B4}$ | $R^{D28}$ |
| $L_{A4821}$ | $R^{C14}$ | $R^{B4}$ | $R^{D28}$ |
| $L_{A4822}$ | $R^{C18}$ | $R^{B4}$ | $R^{D28}$ |
| $L_{A4823}$ | $R^{C19}$ | $R^{B4}$ | $R^{D28}$ |
| $L_{A4824}$ | $R^{C23}$ | $R^{B4}$ | $R^{D28}$ |
| $L_{A4826}$ | $R^{C38}$ | $R^{B4}$ | $R^{D28}$ |
| $L_{A4827}$ | $R^{C40}$ | $R^{B4}$ | $R^{D28}$ |
| $L_{A4828}$ | $R^{C41}$ | $R^{B4}$ | $R^{D28}$ |
| $L_{A4829}$ | $R^{C48}$ | $R^{B4}$ | $R^{D28}$ |
| $L_{A4830}$ | $R^{C54}$ | $R^{B4}$ | $R^{D28}$ |
| $L_{A4831}$ | $R^{C55}$ | $R^{B4}$ | $R^{D28}$ |

$L_{A950}$ through $L_{A954}$, $L_{A956}$ through $L_{A961}$, $L_{A963}$ through $L_{A967}$, $L_{A969}$ through $L_{A974}$, $L_{A976}$ through $L_{A980}$, $L_{A982}$ through $L_{A987}$, $L_{A989}$ through $L_{A993}$, $L_{A995}$ through $L_{A1000}$, $L_{A1002}$ through $L_{A1006}$, $L_{A1008}$ through $L_{A1013}$, $L_{A1015}$ through $L_{A1019}$, $L_{A1021}$ through $L_{A1026}$, $L_{A1028}$, $L_{A1067}$ through $L_{A1071}$, $L_{A1073}$ through $L_{A1078}$, $L_{A1080}$ through $L_{A1084}$, $L_{A1086}$ through $L_{A1091}$, $L_{A1093}$ through $L_{A1097}$, $L_{A1099}$ through $L_{A1104}$, $L_{A1106}$ through $L_{A1110}$, $L_{A1112}$ through $L_{A1117}$, $L_{A1119}$ through $L_{A1123}$, $L_{A1125}$ through $L_{A1130}$, $L_{A1132}$ through $L_{A1136}$, and $L_{A1138}$ through $L_{A1143}$ based on a structure of Formula III,

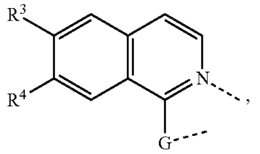

in which $R^3$, $R^4$, and G are defined as:

| Ligand | $R^3$ | $R^4$ | G | Ligand | $R^3$ | $R^4$ | G |
|---|---|---|---|---|---|---|---|
| $L_{A4950}$ | $R^{C11}$ | $R^{B1}$ | $R^{D8}$ | $L_{A1067}$ | $R^{C11}$ | $R^{B1}$ | $R^{D22}$ |
| $L_{A4951}$ | $R^{C14}$ | $R^{B1}$ | $R^{D8}$ | $L_{A1068}$ | $R^{C14}$ | $R^{B1}$ | $R^{D22}$ |
| $L_{A4952}$ | $R^{C18}$ | $R^{B1}$ | $R^{D8}$ | $L_{A1069}$ | $R^{C18}$ | $R^{B1}$ | $R^{D22}$ |
| $L_{A4953}$ | $R^{C19}$ | $R^{B1}$ | $R^{D8}$ | $L_{A1070}$ | $R^{C19}$ | $R^{B1}$ | $R^{D22}$ |
| $L_{A4954}$ | $R^{C23}$ | $R^{B1}$ | $R^{D8}$ | $L_{A1071}$ | $R^{C23}$ | $R^{B1}$ | $R^{D22}$ |
| $L_{A4956}$ | $R^{C38}$ | $R^{B1}$ | $R^{D8}$ | $L_{A1073}$ | $R^{C38}$ | $R^{B1}$ | $R^{D22}$ |
| $L_{A4957}$ | $R^{C40}$ | $R^{B1}$ | $R^{D8}$ | $L_{A1074}$ | $R^{C40}$ | $R^{B1}$ | $R^{D22}$ |
| $L_{A4958}$ | $R^{C41}$ | $R^{B1}$ | $R^{D8}$ | $L_{A1075}$ | $R^{C41}$ | $R^{B1}$ | $R^{D22}$ |
| $L_{A4959}$ | $R^{C48}$ | $R^{B1}$ | $R^{D8}$ | $L_{A1076}$ | $R^{C48}$ | $R^{B1}$ | $R^{D22}$ |
| $L_{A4960}$ | $R^{C54}$ | $R^{B1}$ | $R^{D8}$ | $L_{A1077}$ | $R^{C54}$ | $R^{B1}$ | $R^{D22}$ |
| $L_{A4961}$ | $R^{C55}$ | $R^{B1}$ | $R^{D8}$ | $L_{A1078}$ | $R^{C55}$ | $R^{B1}$ | $R^{D22}$ |
| $L_{A4963}$ | $R^{C11}$ | $R^{B3}$ | $R^{D8}$ | $L_{A1080}$ | $R^{C11}$ | $R^{B3}$ | $R^{D22}$ |
| $L_{A4964}$ | $R^{C14}$ | $R^{B3}$ | $R^{D8}$ | $L_{A1081}$ | $R^{C14}$ | $R^{B3}$ | $R^{D22}$ |
| $L_{A4965}$ | $R^{C18}$ | $R^{B3}$ | $R^{D8}$ | $L_{A1082}$ | $R^{C18}$ | $R^{B3}$ | $R^{D22}$ |
| $L_{A4966}$ | $R^{C19}$ | $R^{B3}$ | $R^{D8}$ | $L_{A1083}$ | $R^{C19}$ | $R^{B3}$ | $R^{D22}$ |
| $L_{A4967}$ | $R^{C23}$ | $R^{B3}$ | $R^{D8}$ | $L_{A1084}$ | $R^{C23}$ | $R^{B3}$ | $R^{D22}$ |
| $L_{A4969}$ | $R^{C38}$ | $R^{B3}$ | $R^{D8}$ | $L_{A1086}$ | $R^{C38}$ | $R^{B3}$ | $R^{D22}$ |
| $L_{A4970}$ | $R^{C40}$ | $R^{B3}$ | $R^{D8}$ | $L_{A1087}$ | $R^{C40}$ | $R^{B3}$ | $R^{D22}$ |
| $L_{A4971}$ | $R^{C41}$ | $R^{B3}$ | $R^{D8}$ | $L_{A1088}$ | $R^{C41}$ | $R^{B3}$ | $R^{D22}$ |
| $L_{A4972}$ | $R^{C48}$ | $R^{B3}$ | $R^{D8}$ | $L_{A1089}$ | $R^{C48}$ | $R^{B3}$ | $R^{D22}$ |
| $L_{A4973}$ | $R^{C54}$ | $R^{B3}$ | $R^{D8}$ | $L_{A1090}$ | $R^{C54}$ | $R^{B3}$ | $R^{D22}$ |
| $L_{A4974}$ | $R^{C55}$ | $R^{B3}$ | $R^{D8}$ | $L_{A1091}$ | $R^{C55}$ | $R^{B3}$ | $R^{D22}$ |
| $L_{A4976}$ | $R^{C11}$ | $R^{B4}$ | $R^{D8}$ | $L_{A1093}$ | $R^{C11}$ | $R^{B4}$ | $R^{D22}$ |
| $L_{A4977}$ | $R^{C14}$ | $R^{B4}$ | $R^{D8}$ | $L_{A1094}$ | $R^{C14}$ | $R^{B4}$ | $R^{D22}$ |
| $L_{A4978}$ | $R^{C18}$ | $R^{B4}$ | $R^{D8}$ | $L_{A1095}$ | $R^{C18}$ | $R^{B4}$ | $R^{D22}$ |
| $L_{A4979}$ | $R^{C19}$ | $R^{B4}$ | $R^{D8}$ | $L_{A1096}$ | $R^{C19}$ | $R^{B4}$ | $R^{D22}$ |
| $L_{A4980}$ | $R^{C23}$ | $R^{B4}$ | $R^{D8}$ | $L_{A1097}$ | $R^{C23}$ | $R^{B4}$ | $R^{D22}$ |
| $L_{A4982}$ | $R^{C38}$ | $R^{B4}$ | $R^{D8}$ | $L_{A1099}$ | $R^{C38}$ | $R^{B4}$ | $R^{D22}$ |
| $L_{A4983}$ | $R^{C40}$ | $R^{B4}$ | $R^{D8}$ | $L_{A1100}$ | $R^{C40}$ | $R^{B4}$ | $R^{D22}$ |
| $L_{A4984}$ | $R^{C41}$ | $R^{B4}$ | $R^{D8}$ | $L_{A1101}$ | $R^{C41}$ | $R^{B4}$ | $R^{D22}$ |
| $L_{A4985}$ | $R^{C48}$ | $R^{B4}$ | $R^{D8}$ | $L_{A1102}$ | $R^{C48}$ | $R^{B4}$ | $R^{D22}$ |
| $L_{A4986}$ | $R^{C54}$ | $R^{B4}$ | $R^{D8}$ | $L_{A1103}$ | $R^{C54}$ | $R^{B4}$ | $R^{D22}$ |
| $L_{A4987}$ | $R^{C55}$ | $R^{B4}$ | $R^{D8}$ | $L_{A1104}$ | $R^{C55}$ | $R^{B4}$ | $R^{D22}$ |
| $L_{A4989}$ | $R^{C11}$ | $R^{B1}$ | $R^{D9}$ | $L_{A1106}$ | $R^{C11}$ | $R^{B1}$ | $R^{D28}$ |
| $L_{A4990}$ | $R^{C14}$ | $R^{B1}$ | $R^{D9}$ | $L_{A1107}$ | $R^{C14}$ | $R^{B1}$ | $R^{D28}$ |
| $L_{A4991}$ | $R^{C18}$ | $R^{B1}$ | $R^{D9}$ | $L_{A1108}$ | $R^{C18}$ | $R^{B1}$ | $R^{D28}$ |
| $L_{A4992}$ | $R^{C19}$ | $R^{B1}$ | $R^{D9}$ | $L_{A1109}$ | $R^{C19}$ | $R^{B1}$ | $R^{D28}$ |
| $L_{A4993}$ | $R^{C23}$ | $R^{B1}$ | $R^{D9}$ | $L_{A1110}$ | $R^{C23}$ | $R^{B1}$ | $R^{D28}$ |
| $L_{A4995}$ | $R^{C38}$ | $R^{B1}$ | $R^{D9}$ | $L_{A1112}$ | $R^{C38}$ | $R^{B1}$ | $R^{D28}$ |
| $L_{A4996}$ | $R^{C40}$ | $R^{B1}$ | $R^{D9}$ | $L_{A1113}$ | $R^{C40}$ | $R^{B1}$ | $R^{D28}$ |
| $L_{A4997}$ | $R^{C41}$ | $R^{B1}$ | $R^{D9}$ | $L_{A1114}$ | $R^{C41}$ | $R^{B1}$ | $R^{D28}$ |
| $L_{A4998}$ | $R^{C48}$ | $R^{B1}$ | $R^{D9}$ | $L_{A1115}$ | $R^{C48}$ | $R^{B1}$ | $R^{D28}$ |
| $L_{A4999}$ | $R^{C54}$ | $R^{B1}$ | $R^{D9}$ | $L_{A1116}$ | $R^{C54}$ | $R^{B1}$ | $R^{D28}$ |
| $L_{A1000}$ | $R^{C55}$ | $R^{B1}$ | $R^{D9}$ | $L_{A1117}$ | $R^{C55}$ | $R^{B1}$ | $R^{D28}$ |
| $L_{A1002}$ | $R^{C11}$ | $R^{B3}$ | $R^{D9}$ | $L_{A1119}$ | $R^{C11}$ | $R^{B3}$ | $R^{D28}$ |
| $L_{A1003}$ | $R^{C14}$ | $R^{B3}$ | $R^{D9}$ | $L_{A1120}$ | $R^{C14}$ | $R^{B3}$ | $R^{D28}$ |
| $L_{A1004}$ | $R^{C18}$ | $R^{B3}$ | $R^{D9}$ | $L_{A1121}$ | $R^{C18}$ | $R^{B3}$ | $R^{D28}$ |
| $L_{A1005}$ | $R^{C19}$ | $R^{B3}$ | $R^{D9}$ | $L_{A1122}$ | $R^{C19}$ | $R^{B3}$ | $R^{D28}$ |
| $L_{A1006}$ | $R^{C23}$ | $R^{B3}$ | $R^{D9}$ | $L_{A1123}$ | $R^{C23}$ | $R^{B3}$ | $R^{D28}$ |
| $L_{A1008}$ | $R^{C38}$ | $R^{B3}$ | $R^{D9}$ | $L_{A1125}$ | $R^{C38}$ | $R^{B3}$ | $R^{D28}$ |
| $L_{A1009}$ | $R^{C40}$ | $R^{B3}$ | $R^{D9}$ | $L_{A1126}$ | $R^{C40}$ | $R^{B3}$ | $R^{D28}$ |
| $L_{A1010}$ | $R^{C41}$ | $R^{B3}$ | $R^{D9}$ | $L_{A1127}$ | $R^{C41}$ | $R^{B3}$ | $R^{D28}$ |
| $L_{A1011}$ | $R^{C48}$ | $R^{B3}$ | $R^{D9}$ | $L_{A1128}$ | $R^{C48}$ | $R^{B3}$ | $R^{D28}$ |
| $L_{A1012}$ | $R^{C54}$ | $R^{B3}$ | $R^{D9}$ | $L_{A1129}$ | $R^{C54}$ | $R^{B3}$ | $R^{D28}$ |
| $L_{A1013}$ | $R^{C55}$ | $R^{B3}$ | $R^{D9}$ | $L_{A1130}$ | $R^{C55}$ | $R^{B3}$ | $R^{D28}$ |
| $L_{A1015}$ | $R^{C11}$ | $R^{B4}$ | $R^{D9}$ | $L_{A1109}$ | $R^{C19}$ | $R^{B1}$ | $R^{D28}$ |
| $L_{A1016}$ | $R^{C14}$ | $R^{B4}$ | $R^{D9}$ | $L_{A1110}$ | $R^{C23}$ | $R^{B1}$ | $R^{D28}$ |
| $L_{A1017}$ | $R^{C18}$ | $R^{B4}$ | $R^{D9}$ | $L_{A1112}$ | $R^{C38}$ | $R^{B1}$ | $R^{D28}$ |
| $L_{A1018}$ | $R^{C19}$ | $R^{B4}$ | $R^{D9}$ | $L_{A1113}$ | $R^{C40}$ | $R^{B1}$ | $R^{D28}$ |
| $L_{A1019}$ | $R^{C23}$ | $R^{B4}$ | $R^{D9}$ | $L_{A1114}$ | $R^{C41}$ | $R^{B1}$ | $R^{D28}$ |
| $L_{A1021}$ | $R^{C38}$ | $R^{B4}$ | $R^{D9}$ | $L_{A1115}$ | $R^{C48}$ | $R^{B1}$ | $R^{D28}$ |
| $L_{A1022}$ | $R^{C40}$ | $R^{B4}$ | $R^{D9}$ | $L_{A1116}$ | $R^{C54}$ | $R^{B1}$ | $R^{D28}$ |
| $L_{A1023}$ | $R^{C41}$ | $R^{B4}$ | $R^{D9}$ | $L_{A1117}$ | $R^{C55}$ | $R^{B1}$ | $R^{D28}$ |
| $L_{A1024}$ | $R^{C48}$ | $R^{B4}$ | $R^{D9}$ | $L_{A1119}$ | $R^{C11}$ | $R^{B3}$ | $R^{D28}$ |
| $L_{A1025}$ | $R^{C54}$ | $R^{B4}$ | $R^{D9}$ | $L_{A1120}$ | $R^{C14}$ | $R^{B3}$ | $R^{D28}$ |
| $L_{A1132}$ | $R^{C11}$ | $R^{B4}$ | $R^{D28}$ | | | | |

-continued

| Ligand | $R^3$ | $R^4$ | G | Ligand | $R^3$ | $R^4$ | G |
|---|---|---|---|---|---|---|---|
| $L_{A1133}$ | $R^{C14}$ | $R^{B4}$ | $R^{D28}$ | | | | |
| $L_{A1134}$ | $R^{C18}$ | $R^{B4}$ | $R^{D28}$ | | | | |
| $L_{A1135}$ | $R^{C19}$ | $R^{B4}$ | $R^{D28}$ | | | | |
| $L_{A1136}$ | $R^{C23}$ | $R^{B4}$ | $R^{D28}$ | | | | |
| $L_{A1138}$ | $R^{C38}$ | $R^{B4}$ | $R^{D28}$ | | | | |
| $L_{A1139}$ | $R^{C40}$ | $R^{B4}$ | $R^{D28}$ | | | | |
| $L_{A1140}$ | $R^{C41}$ | $R^{B4}$ | $R^{D28}$ | | | | |
| $L_{A1141}$ | $R^{C48}$ | $R^{B4}$ | $R^{D28}$ | | | | |
| $L_{A1142}$ | $R^{C54}$ | $R^{B4}$ | $R^{D28}$ | | | | |
| $L_{A1143}$ | $R^{C55}$ | $R^{B4}$ | $R^{D28}$ | | | | |

wherein $R^{B1}$, $R^{B3}$, and $R^{B4}$ have the following structures:

$R^{B1}$

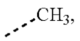

$R^{B3}$

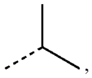

, and $R^{B4}$

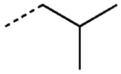

wherein $R^{C11}$, $R^{C14}$, $R^{C18}$, $R^{C19}$, $R^{C23}$, $R^{C38}$, $R^{C40}$, $R^{C41}$, $R^{C48}$, $R^{C54}$, and $R^{C55}$ have the following structures:

$R^{C11}$

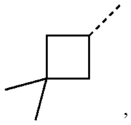

, $R^{C14}$

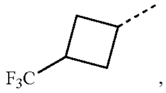

, $R^{C18}$

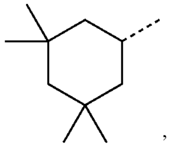

, $R^{C19}$

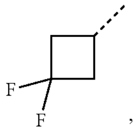

, $R^{C23}$

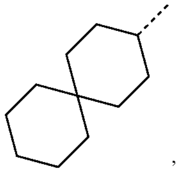

,

-continued $R^{C38}$

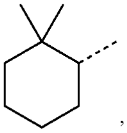

, $R^{C40}$

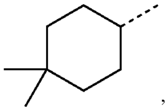

, $R^{C41}$

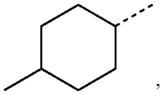

, $R^{C48}$

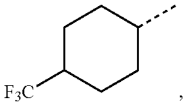

, $R^{C54}$

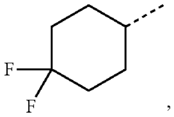

, and $R^{C55}$

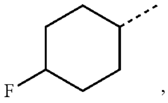

, wherein $R^{D8}$, $R^{D9}$, $R^{D22}$, and $R^{D28}$ have the following structures:

$R^{D8}$

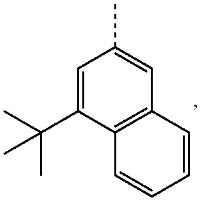

, $R^{D9}$

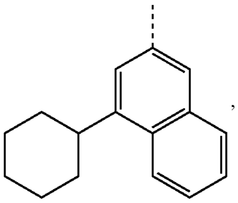

, $R^{D22}$

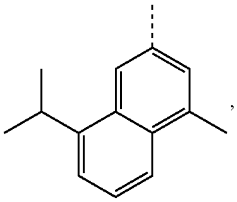

, and

-continued
$R^{D28}$
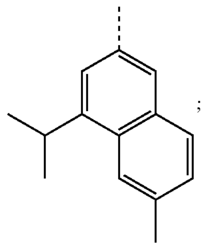
;
wherein $L_B$ and $L_C$ are each independently selected from the group consisting of:
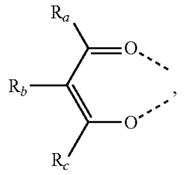
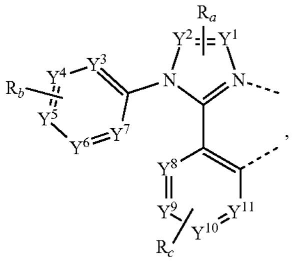
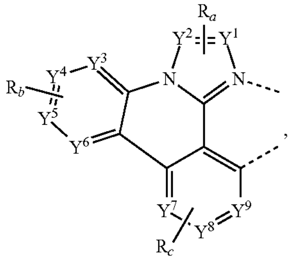
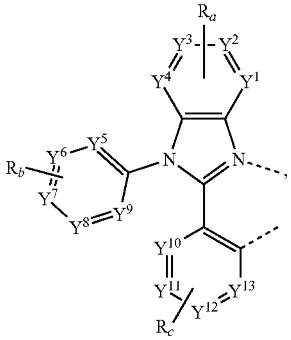
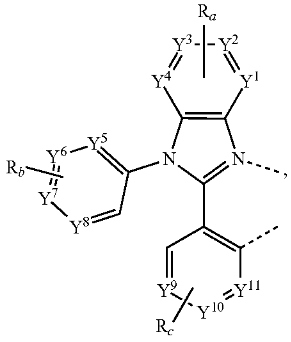
-continued
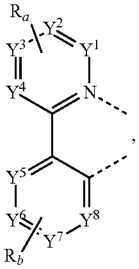
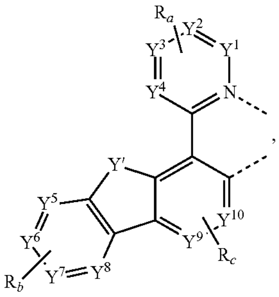
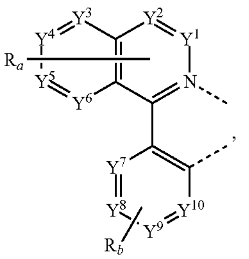
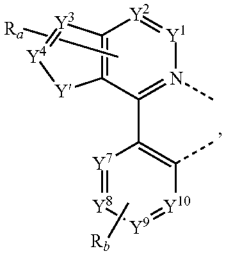
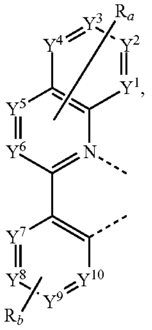

-continued

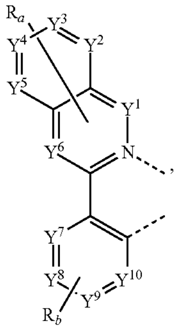

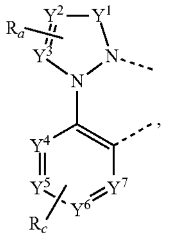

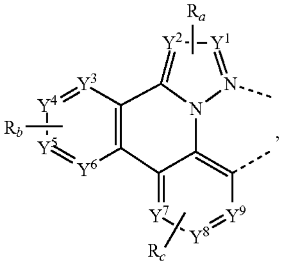

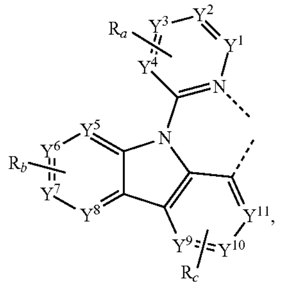

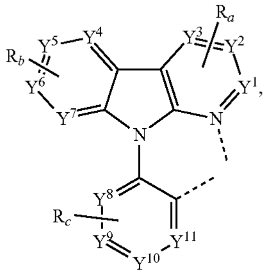

and

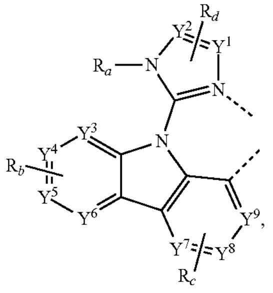

wherein, $Y^1$ to $Y^{13}$ are each independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ are optionally fused or joined to form a ring;

each $R_a$, $R_b$, $R_c$, and $R_d$ can independently represent from mono substitution to the maximum possible number of substitutions, or no substitution;

$R_a$, $R_b$, $R_c$, $R_d$, $R_e$ and $R_f$ are each independently selected from the group consisting of hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two adjacent substituents of $R_a$, $R_b$, $R_c$, and $R_d$ are optionally fused or joined to form a ring or form a multidentate ligand.

12. An organic light emitting device (OLED) comprising:

an anode;

a cathode; and an organic layer, disposed between the anode and the cathode, comprising a compound having a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; wherein $L_B$ and $L_C$ are each a bidentate ligand, and wherein $L_A$, $L_B$, and $L_C$ are different from each other, wherein $L_A$ has the structure of Formula I

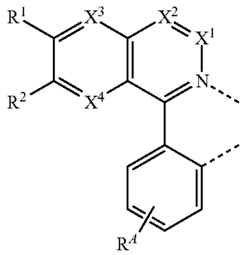

wherein, $R^A$ represents mono to the maximum allowable substitutions;

$X^1$ to $X^4$ are each independently CR or N;

$R^A$, R, $R^1$, and $R^2$ are each independently selected from the group consisting of hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

at least one $R^A$ is not hydrogen;

at least one of $R^1$ and $R^2$ has the formula of $-L^1-G^1$;

$L^1$ is an organic linker or a direct bond, $G^1$ is a substituted cycloalkyl group or a substituted or unsubstituted spirocycle;

wherein when $G^1$ is a substituted cycloalkyl group, the substituted cycloalkyl group is substituted with a substituent selected from the group consisting of fluorine, methyl, and combinations thereof;

$L_A$ is coordinated to Ir;

Ir can be coordinated to other ligands;

$L_A$ can be linked with other ligands to comprise a tridentate, tetradentate, pentadentate, or hexadentate ligand;

two substituents $R^A$ are joined or fused together to form an aryl group, wherein $R^A$ or said aryl group further comprises a branched alkyl, cycloalkyl, or a silyl;

$R^1$ and $R^2$ are not joined to form a ring;
wherein $L_B$ and $L_C$ are each independently selected from the group consisting of:
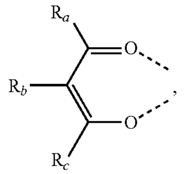
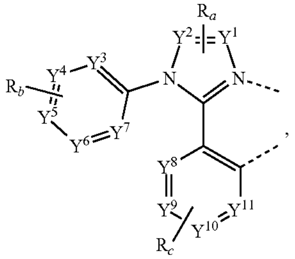
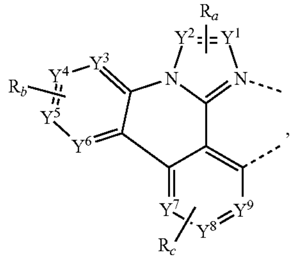
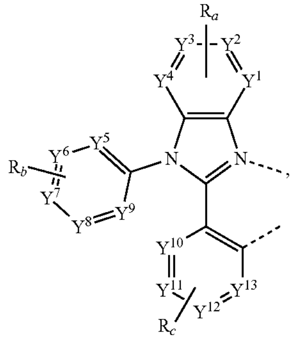
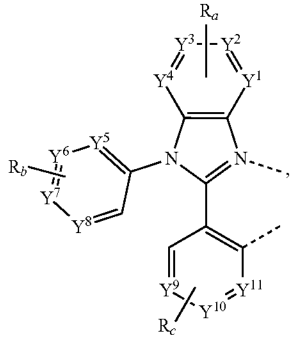
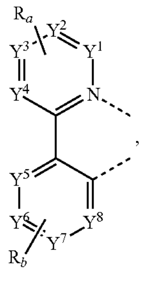
-continued
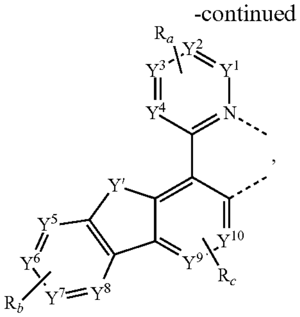
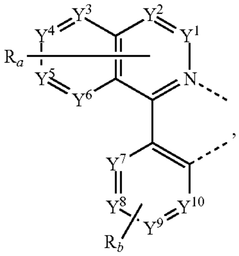
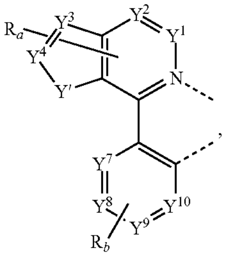
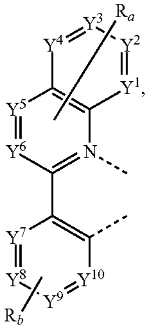
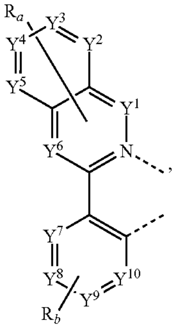
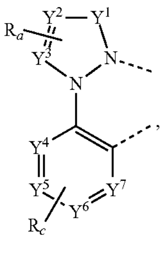
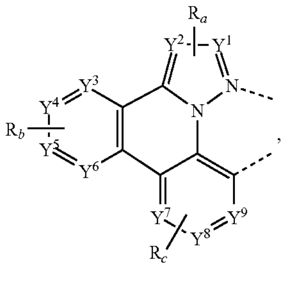

-continued

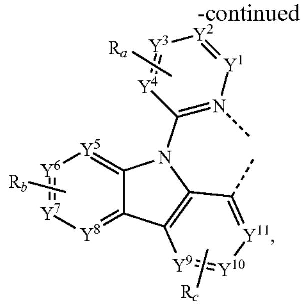

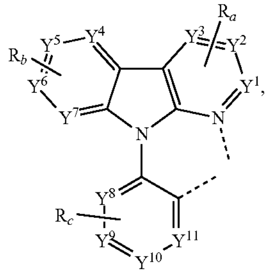

and

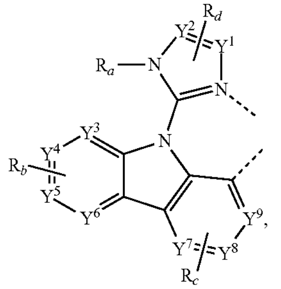

wherein, $Y^1$ to $Y^{13}$ are each independently selected from the group consisting of carbon and nitrogen;

$Y'$ is selected from the group consisting of $BR_e$, $NR_e$, $PR_e$, O, S, Se, C=O, S=O, $SO_2$, $CR_eR_f$, $SiR_eR_f$, and $GeR_eR_f$;

$R_e$ and $R_f$ are optionally fused or joined to form a ring;

each $R_a$, $R_b$, $R_c$, and $R_d$ can independently represent from mono substitution to the maximum possible number of substitutions, or no substitution;

$R_a$, $R_b$, $R_c$, $R_d$, $R_e$ and $R_f$ are each independently selected from the group consisting of hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two adjacent substituents of $R_a$, $R_b$, $R_c$, and $R_d$ are optionally fused or joined to form a ring or form a multidentate ligand.

13. The OLED of claim 12, wherein the organic layer is an emissive layer and the compound is an emissive dopant or a non-emissive dopant.

14. The OLED of claim 12, wherein the organic layer further comprises a host, wherein host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

15. The OLED of claim 14, wherein the host is selected from the group consisting of:

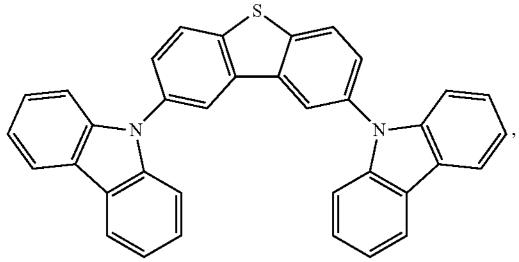

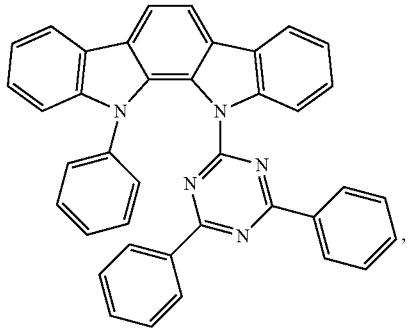

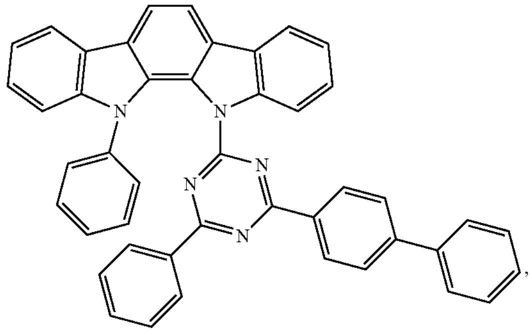

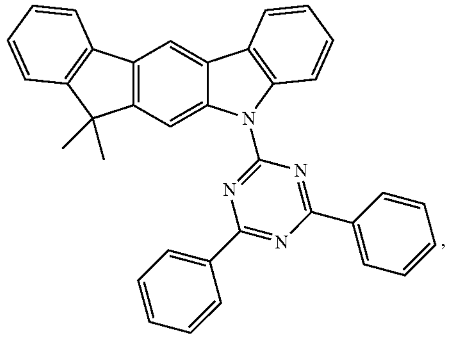

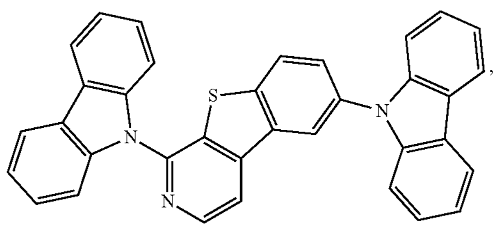

-continued
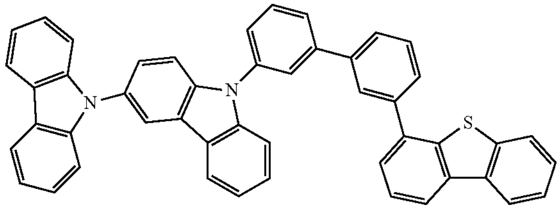
,
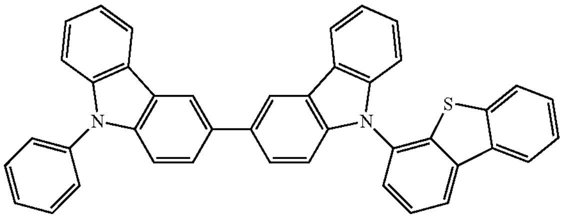
,
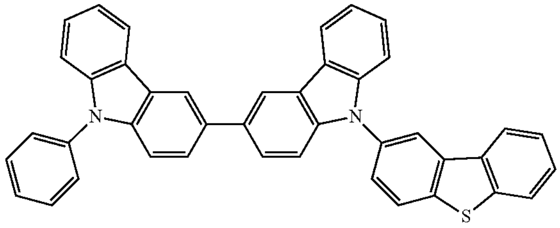
,
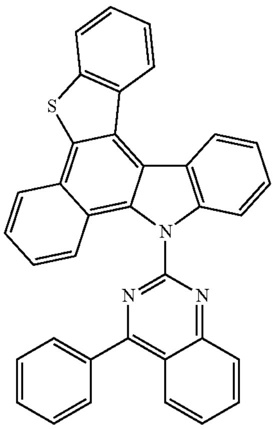
,
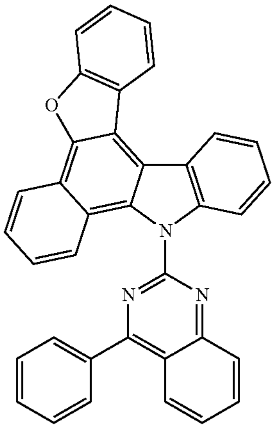
,
-continued
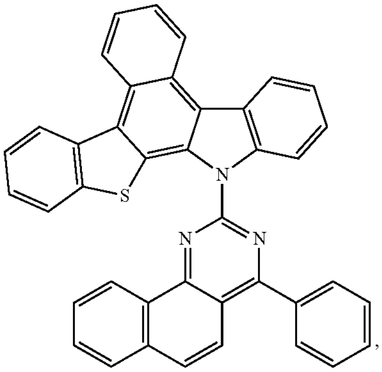
,
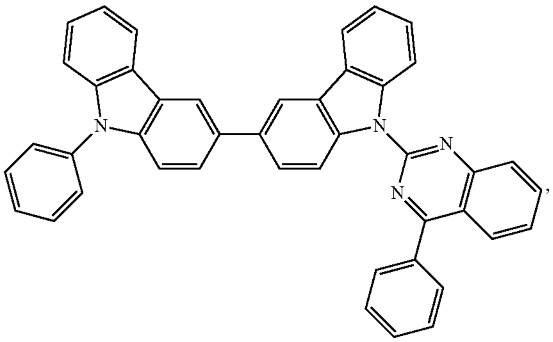
,
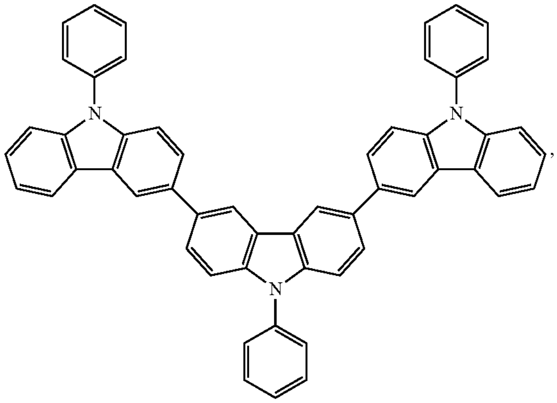
,
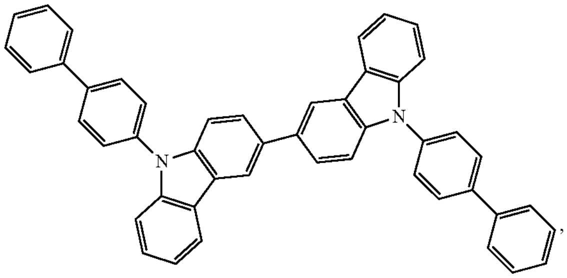
,
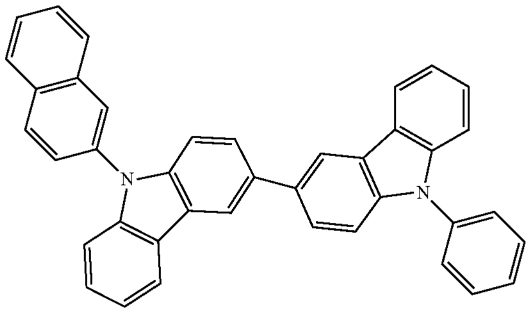
, -continued

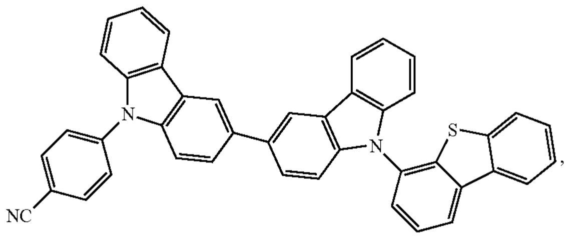

,

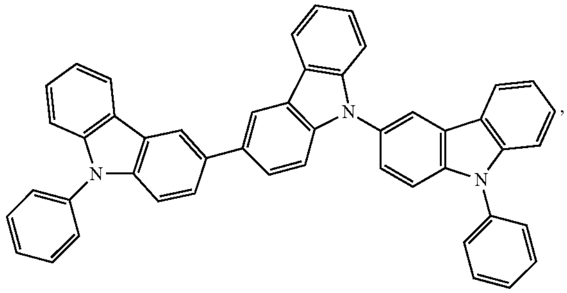

,

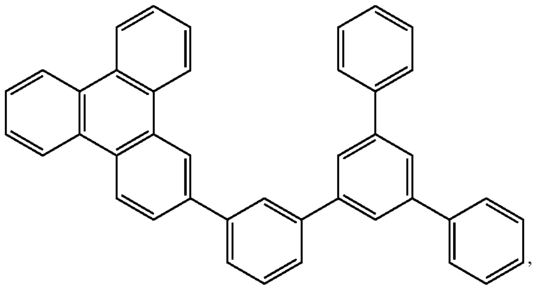

,

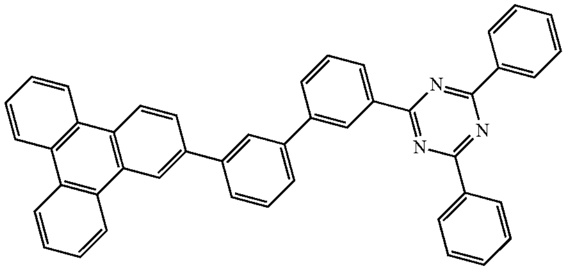

,

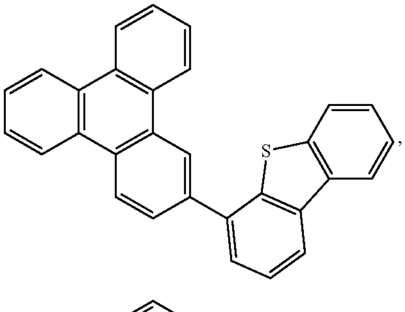

,

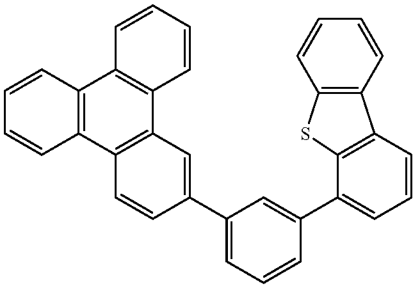

,

-continued

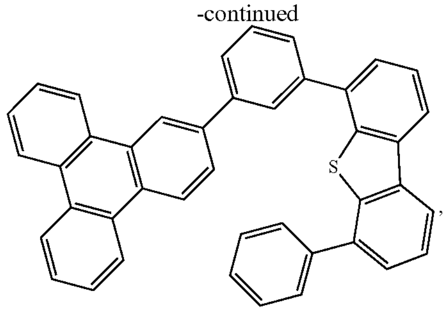

,

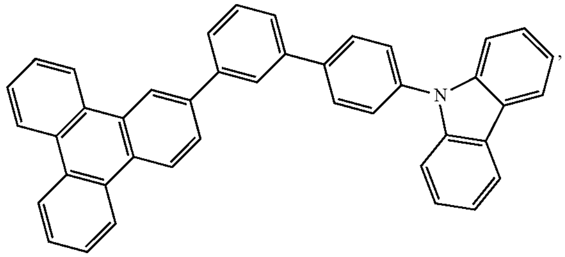

,

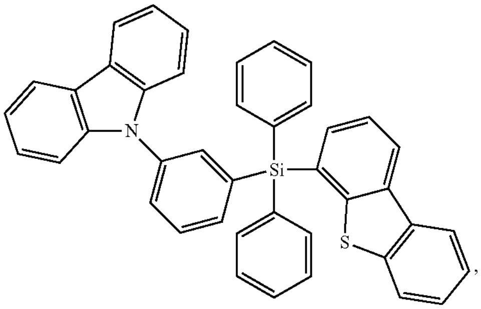

,

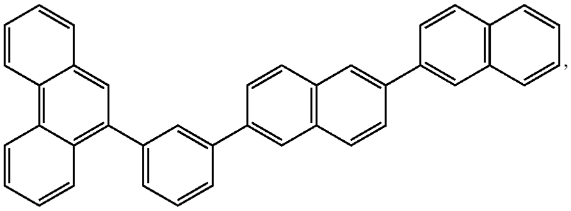

, and combinations thereof.

16. A consumer product comprising an organic light-emitting device (OLED) comprising:

an anode;

a cathode; and an organic layer, disposed between the anode and the cathode, comprising the compound of claim 1.

17. A formulation comprising a compound according to claim 1.

18. An organic light emitting device (OLED) comprising:

an anode;

a cathode; and an organic layer, disposed between the anode and the cathode, comprising the compound of claim 11.

19. The compound of claim 1, wherein $R^A$ or the aryl group formed by two $R^A$ further comprises a substituent selected from the group consisting of a branched alkyl and a cycloalkyl.

20. The compound of claim 11, wherein the compound is the Compound Ax having the formula $Ir(L_{Ai})_3$, the Compound By having the formula $Ir(L_{Ai})(L_{Bk})_2$, or the Compound Cz having the formula $Ir(L_{Ai})_2(L_{Cj})$;

wherein, $$x=i, y=333i+k-333, \text{ and } z=1260i+j-1260;$$

i is an integer from 40 to 44, 46 to 51, 53 to 57, 59 to 64, 79 to 83, 85 to 90, 92 to 96, 98 to 103, 144 to 148, 150 to 155, 157 to 161, 163 to 168, 183 to 187, 189 to 194, 196 to 200, 202 to 207, 248 to 252, 254 to 259, 261 to 265, 267 to 271, 287 to 291, 293 to 298, 300 to 304, 306 to 311, 352 to 356, 358 to 363, 365 to 369, 371 to 376, 391 to 395, 397 to 402, 404 to 407, 409 to 415, 573 to 577, 579 to 584, 587 to 590, 592 to 597, 599 to 603, 605 to 610, 612 to 616, 618 to 623, 625 to 629, 631 to 635, 636 to 642, 644 to 649, 651 to 655, 657 to 662, 665 to 668, 670 to 675, 729 to 733, 735 to 740, 742 to 746, 478, 753, 755 to 759, 761 to 766, 768 to 772, 774 to 779, 781 to 785, 787 to 792, 794 to 798, 800 to 805, 808 to 811, 813 to 818, 820 to 824, 826 to 831, 950 to 954, 956 to 961, 963 to 967, 969 to 974, 976 to 980, 982 to 987, 989 to 993, 995 to 1000, 1002 to 1006, 1008 to 1013, 1015 to 1019, 1021 to 1026, 1028, 1067 to 1071, 1073 to 1078, 1080 to 1084, 1086 to 1091, 1093 to 1097, 1099 to 1104, 1106 to 1110, 1112 to 1117, 1119 to 1123, 1125 to 1130, 1132 to 1136, and 1138 to 1143 and k is an integer from 136 to 468, and j is an integer from 1 to 1260;

$L_{Bk}$ is selected from the group consisting of the following structures:

$L_{B136}$

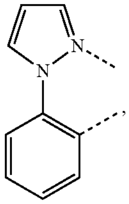

, $L_{B137}$

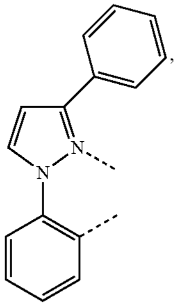

, $L_{B138}$

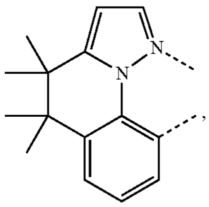

,

-continued $L_{B139}$

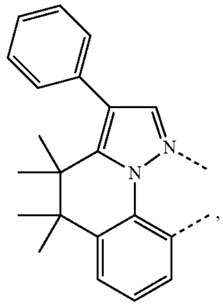

, $L_{B140}$

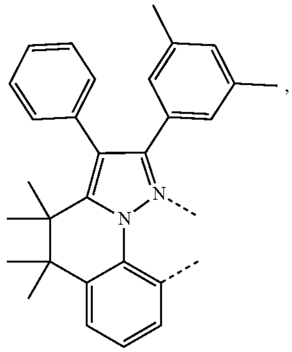

, $L_{B141}$

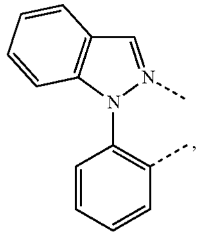

, $L_{B142}$

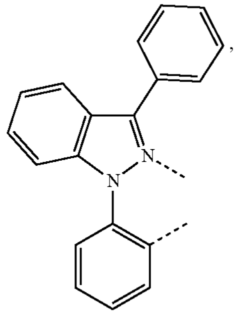

, $L_{B143}$

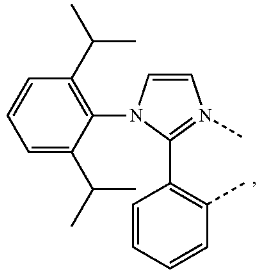

,

-continued
L_B144
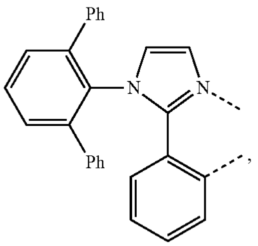
L_B145
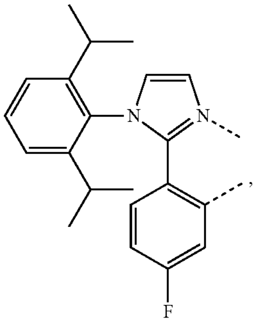
L_B146
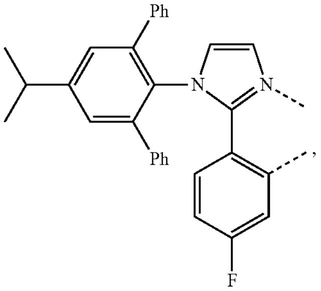
L_B147
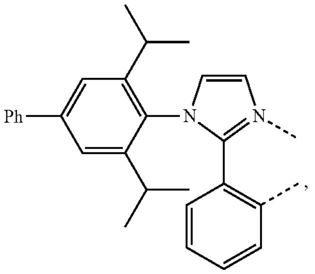
L_B148
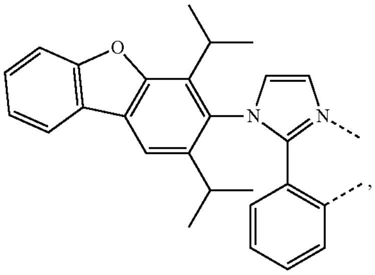
-continued
L_B149
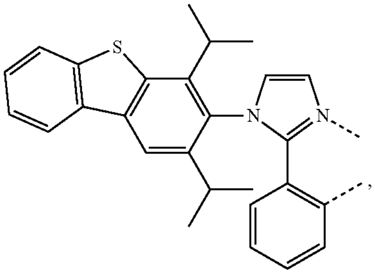
L_B150
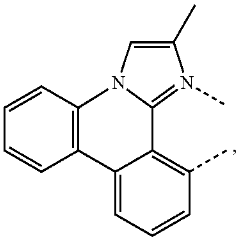
L_B151
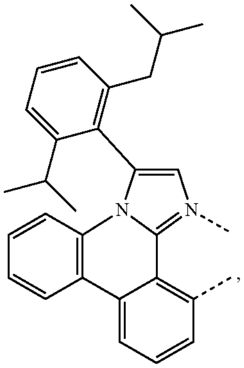
L_B152
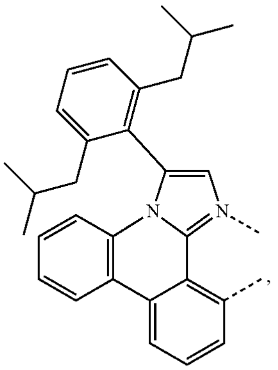
L_B153
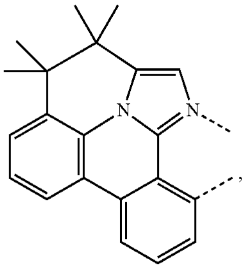

-continued
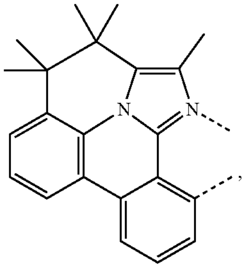
$L_{B154}$
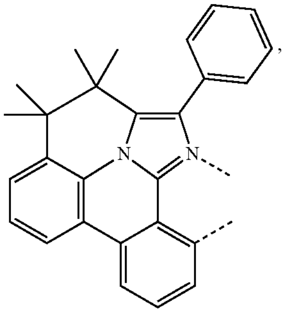
$L_{B155}$
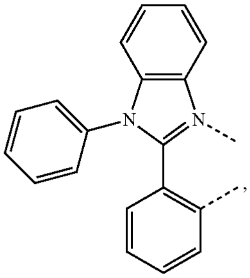
$L_{B156}$
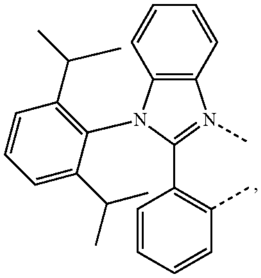
$L_{B157}$
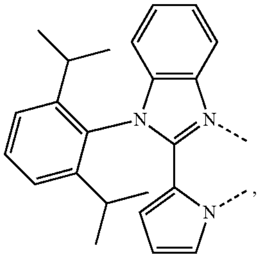
$L_{B158}$
-continued
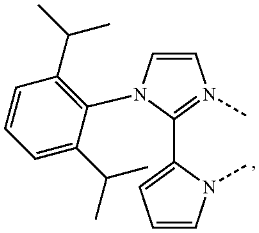
$L_{B159}$
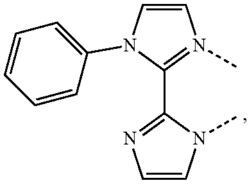
$L_{B160}$
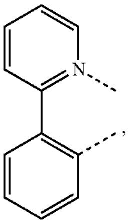
$L_{B161}$
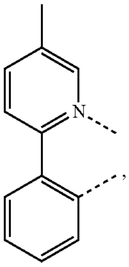
$L_{B162}$
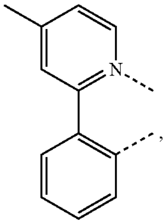
$L_{B163}$
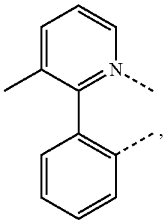
$L_{B164}$ -continued
$L_{B165}$
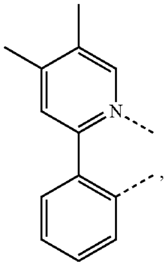
$L_{B166}$
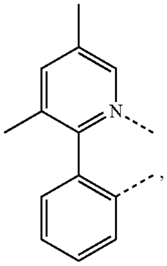
$L_{B167}$
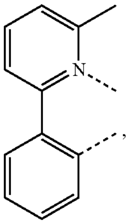
$L_{B168}$
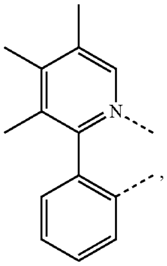
$L_{B169}$
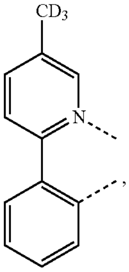
$L_{B170}$
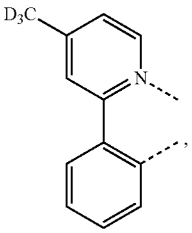
-continued
$L_{B171}$
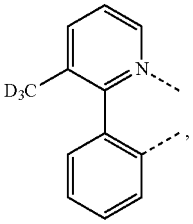
$L_{B172}$
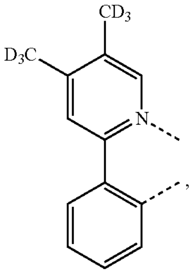
$L_{B173}$
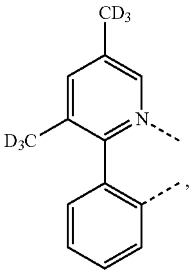
$L_{B174}$
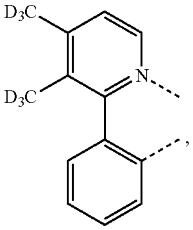
$L_{B175}$
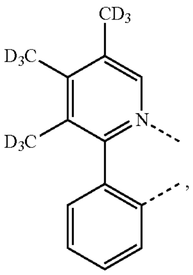
$L_{B176}$
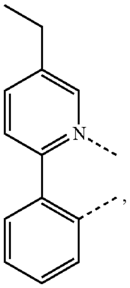

-continued
$L_{B177}$
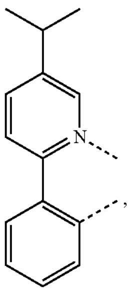
$L_{B178}$
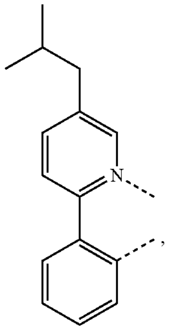
$L_{B179}$
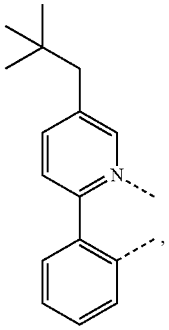
$L_{B180}$
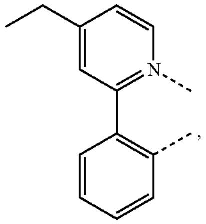
$L_{B181}$
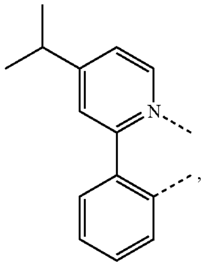
-continued
$L_{B182}$
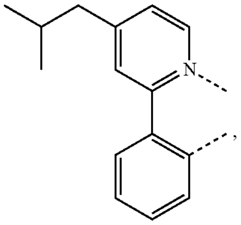
$L_{B183}$
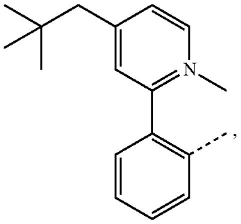
$L_{B184}$
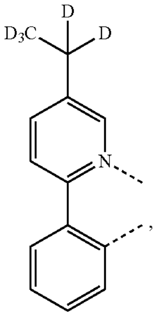
$L_{B185}$
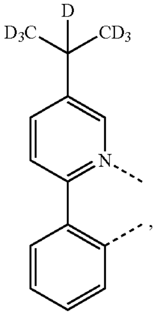
$L_{B186}$
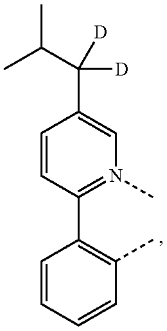

-continued
L$_{B187}$
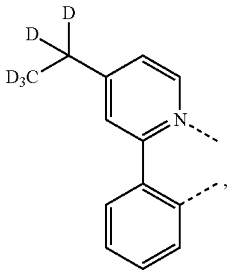
L$_{B188}$
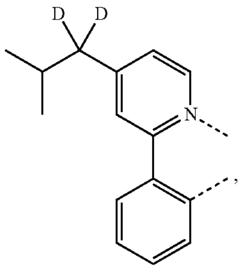
L$_{B189}$
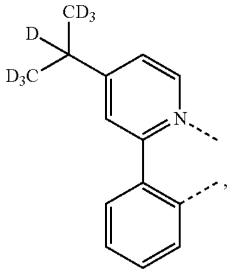
L$_{B190}$
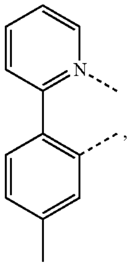
L$_{B191}$
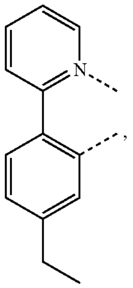
-continued
L$_{B192}$
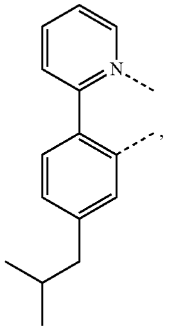
L$_{B193}$
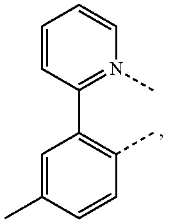
L$_{B194}$
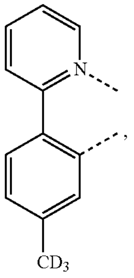
L$_{B195}$
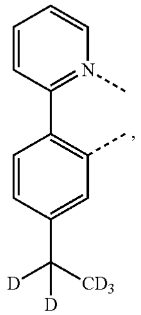
L$_{B196}$
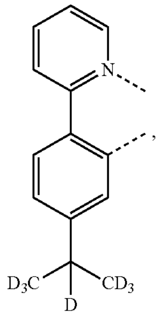

-continued
$L_{B197}$
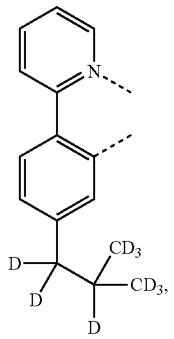
$L_{B198}$
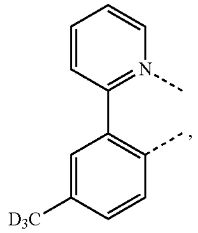
$L_{B199}$
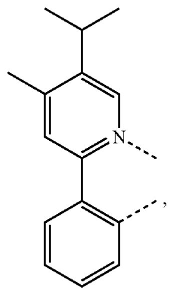
$L_{B200}$
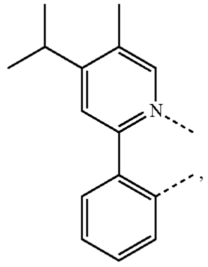
$L_{B201}$
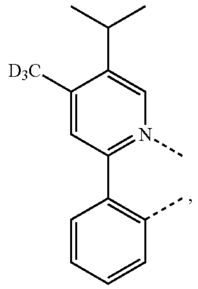
-continued
$L_{B202}$
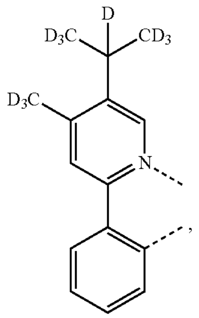
$L_{B203}$
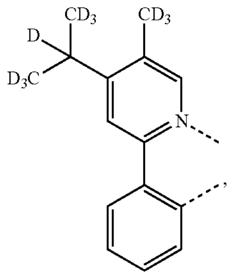
$L_{B204}$
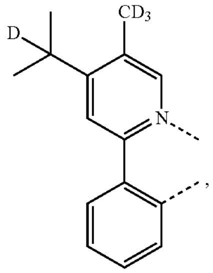
$L_{B205}$
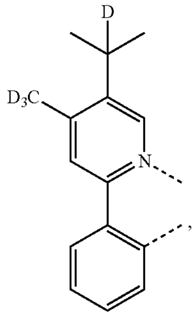
$L_{B206}$
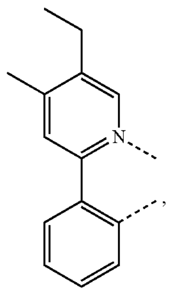

$L_{B207}$
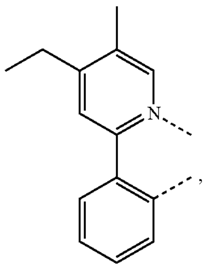
$L_{B208}$
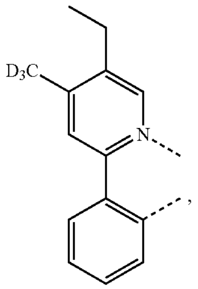
$L_{B209}$
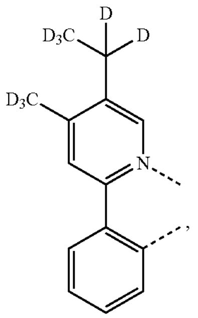
$L_{B210}$
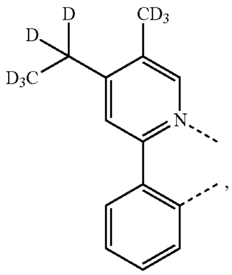
$L_{B211}$
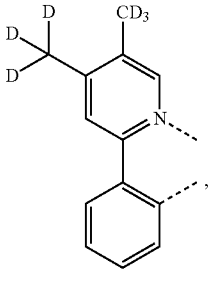
$L_{B212}$
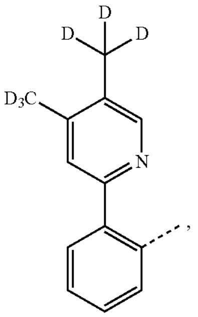
$L_{B213}$
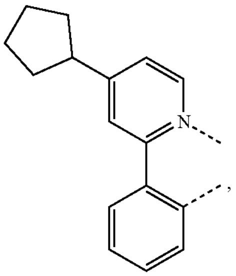
$L_{B214}$
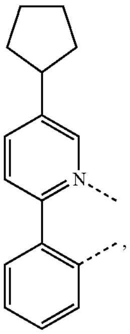
$L_{B215}$
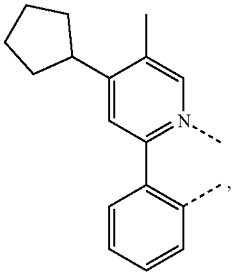
$L_{B216}$
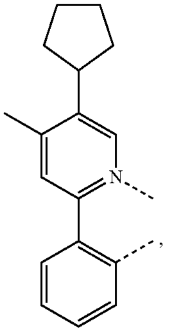

-continued
$L_{B217}$
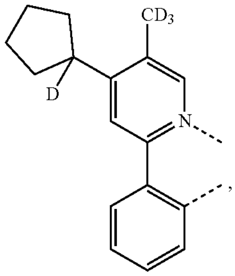
$L_{B218}$
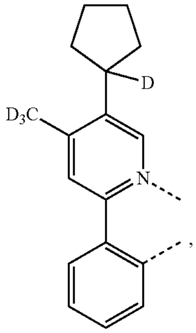
$L_{B219}$
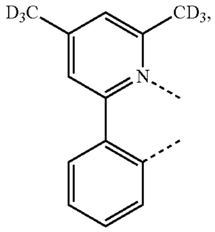
$L_{B220}$
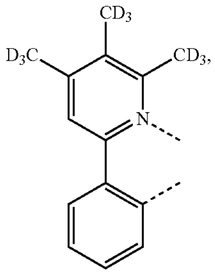
$L_{B221}$
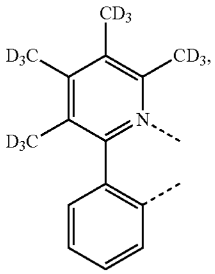
-continued
$L_{B222}$
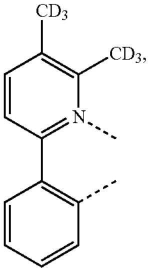
$L_{B223}$
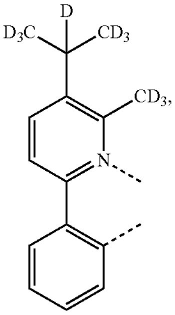
$L_{B224}$
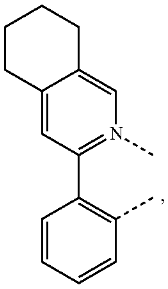
$L_{B225}$
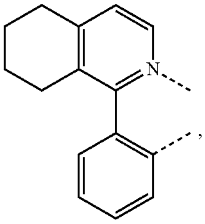
$L_{B226}$
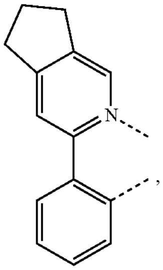

-continued
$L_{B227}$
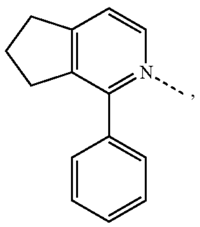
$L_{B228}$
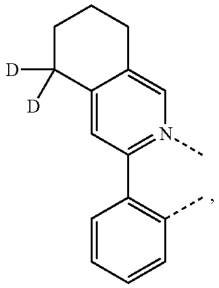
$L_{B229}$
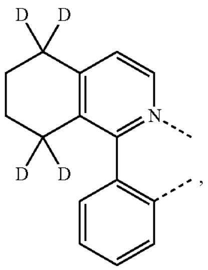
$L_{B230}$
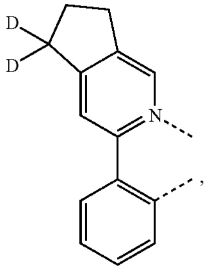
$L_{B231}$
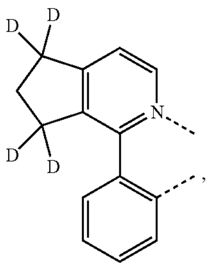
-continued
$L_{B232}$
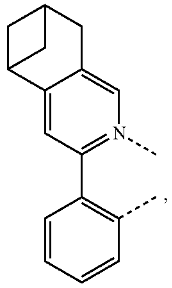
$L_{B233}$
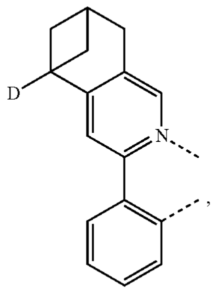
$L_{B234}$
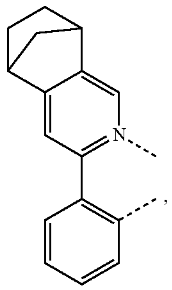
$L_{B235}$
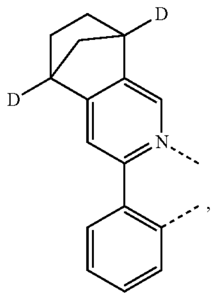
$L_{B236}$
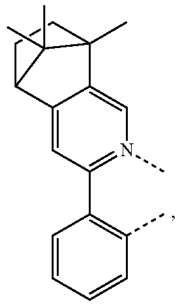

-continued
$L_{B237}$
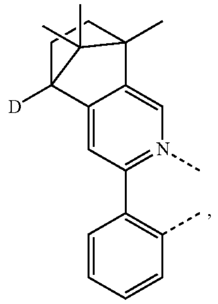
$L_{B238}$
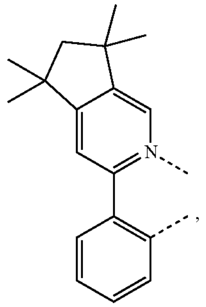
$L_{B239}$
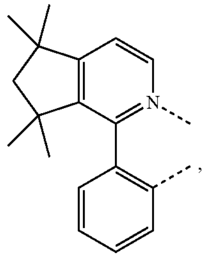
$L_{B240}$
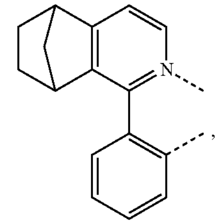
$L_{B241}$
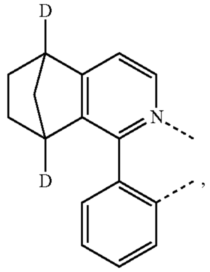
-continued
$L_{B242}$
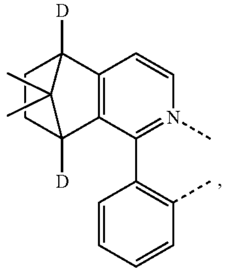
$L_{B243}$
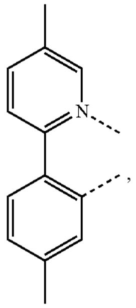
$L_{B244}$
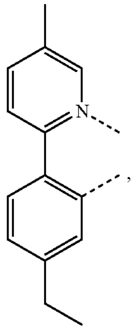
$L_{B245}$
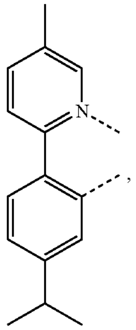
$L_{B246}$
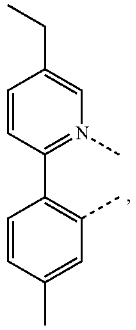

-continued
$L_{B247}$
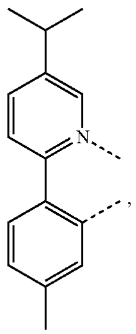
$L_{B248}$
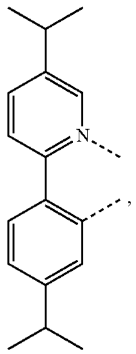
$L_{B249}$
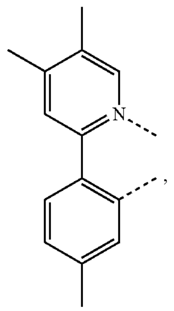
$L_{B250}$
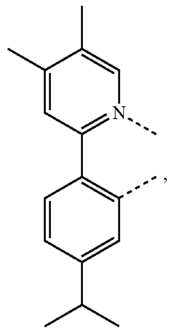
-continued
$L_{B251}$
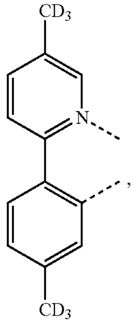
$L_{B252}$
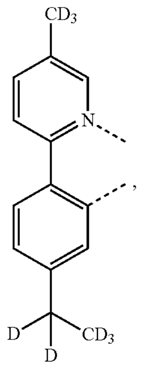
$L_{B253}$
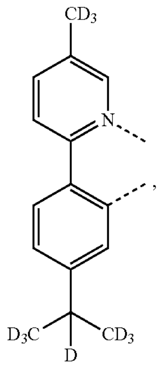
$L_{B254}$
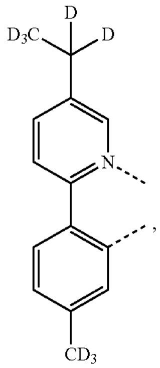

-continued
$L_{B255}$
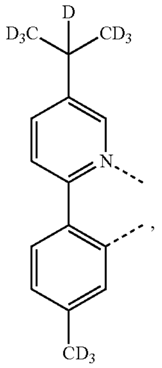
$L_{B256}$
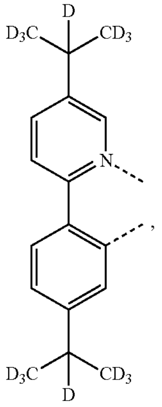
$L_{B257}$
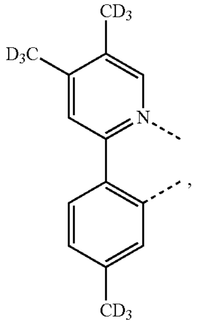
$L_{B258}$
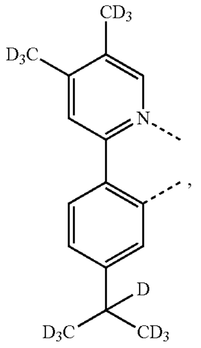
-continued
$L_{B259}$
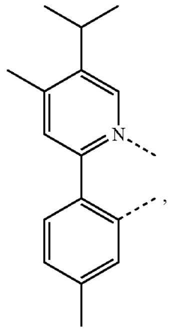
$L_{B260}$
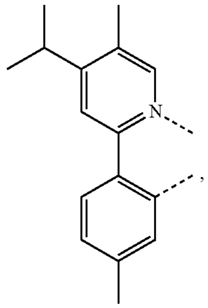
$L_{B261}$
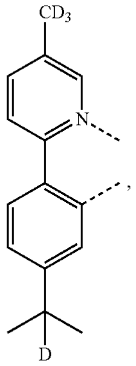
$L_{B262}$
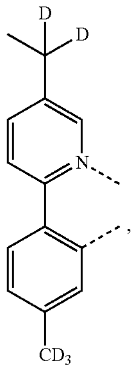

-continued
L_{B263}
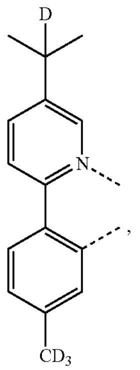
L_{B264}
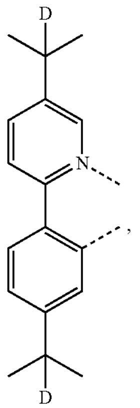
L_{B265}
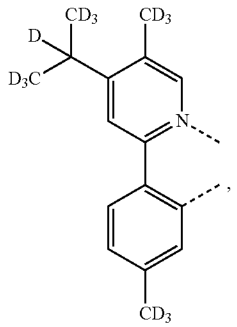
L_{B266}
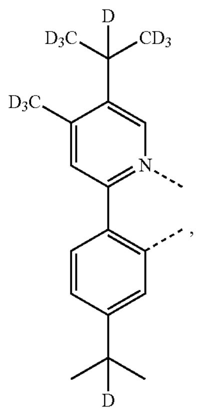
-continued
L_{B267}
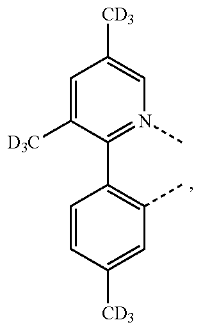
L_{B268}
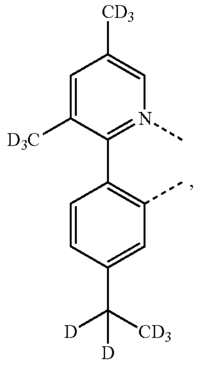
L_{B269}
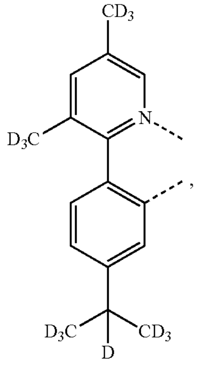
L_{B270}
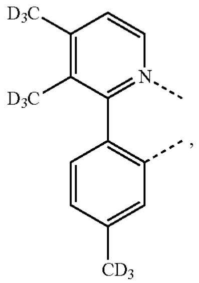

-continued
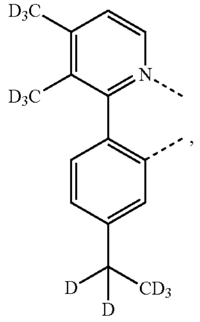
$L_{B271}$
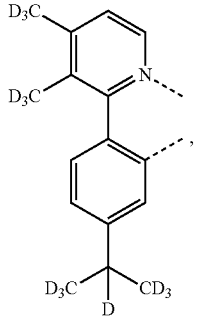
$L_{B272}$
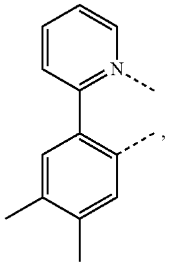
$L_{B273}$
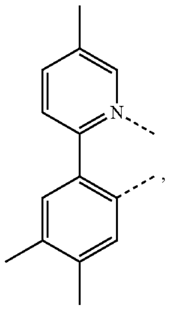
$L_{B274}$
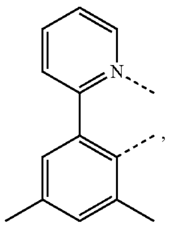
$L_{B275}$
-continued
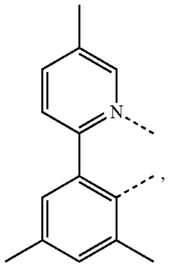
$L_{B276}$
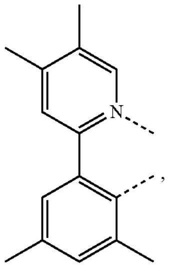
$L_{B277}$
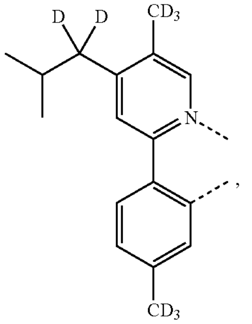
$L_{B278}$
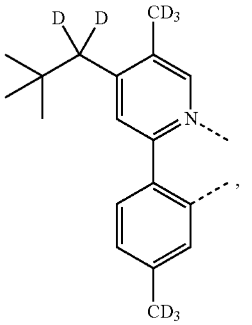
$L_{B279}$
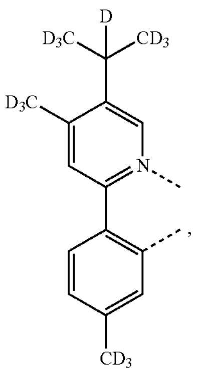
$L_{B280}$ -continued
$L_{B281}$
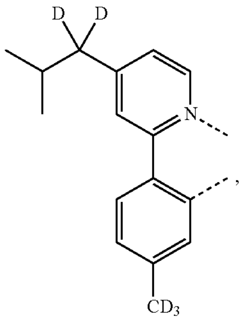
$L_{B282}$
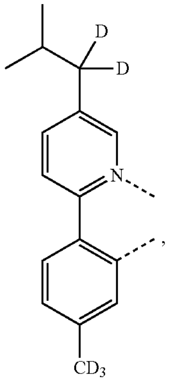
$L_{B283}$
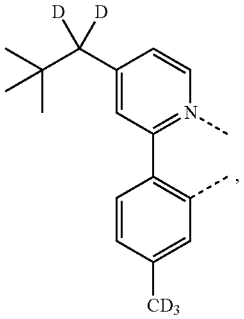
$L_{B284}$
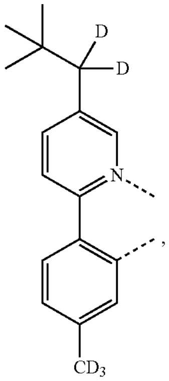
-continued
$L_{B285}$
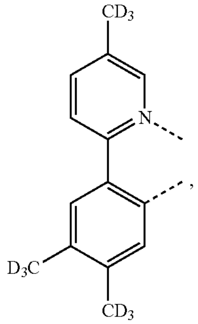
$L_{B286}$
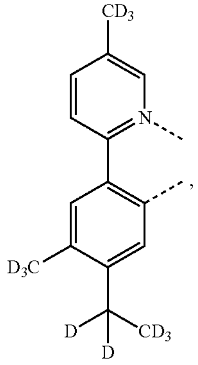
$L_{B287}$
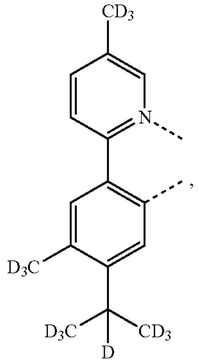
$L_{B288}$
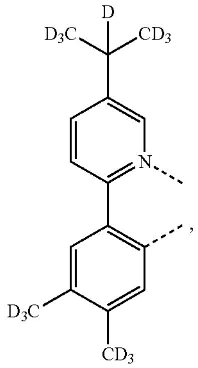

-continued
$L_{B289}$
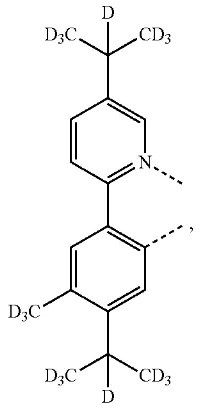
$L_{B290}$
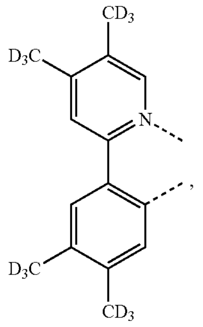
$L_{B291}$
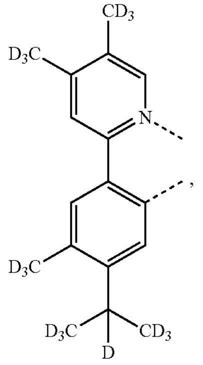
$L_{B292}$
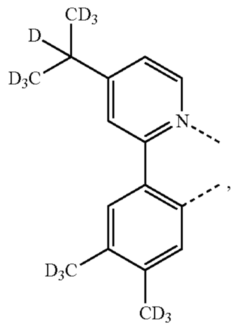
-continued
$L_{B293}$
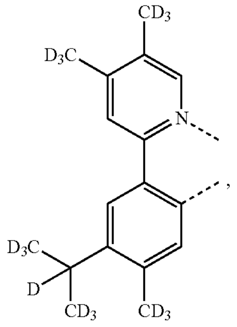
$L_{B294}$
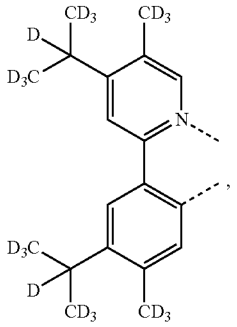
$L_{B295}$
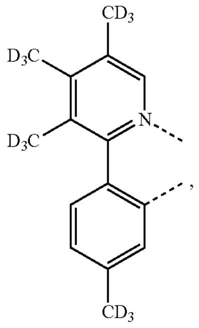
$L_{B296}$
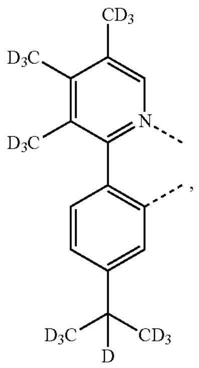

-continued
$L_{B297}$
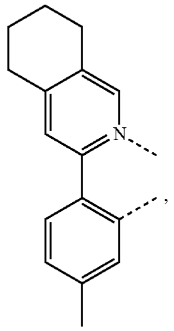
$L_{B298}$
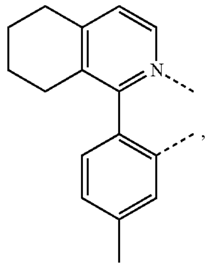
$L_{B299}$
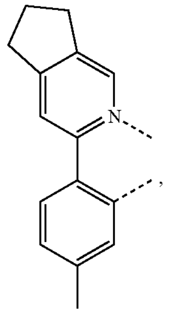
$L_{B300}$
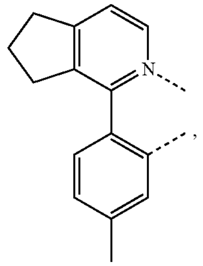
$L_{B301}$
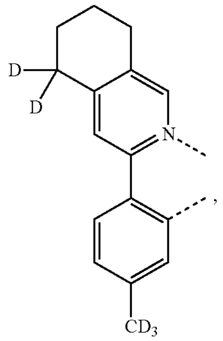
-continued
$L_{B302}$
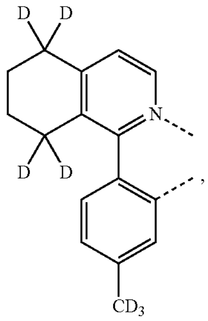
$L_{B303}$
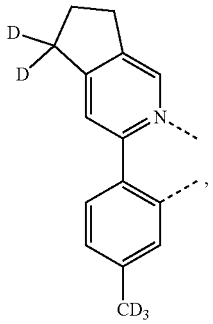
$L_{B304}$
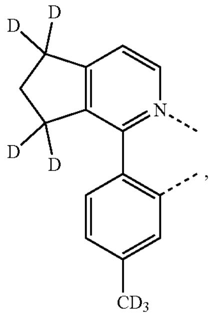
$L_{B305}$
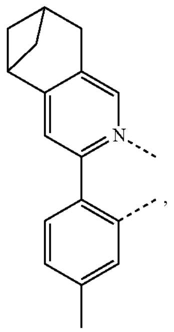

-continued
$L_{B306}$
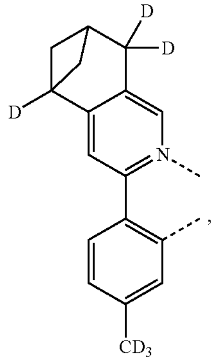
$L_{B307}$
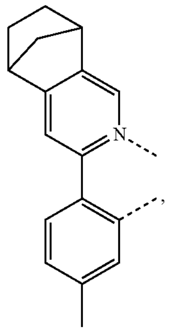
$L_{B308}$
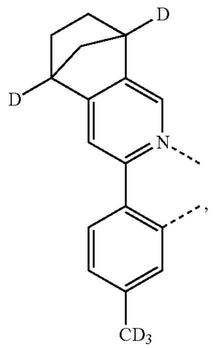
$L_{B309}$
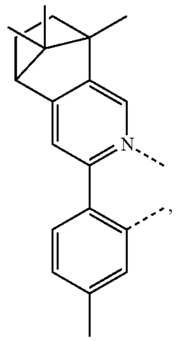
-continued
$L_{B310}$
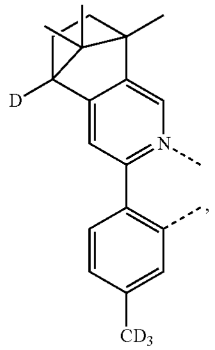
$L_{B311}$
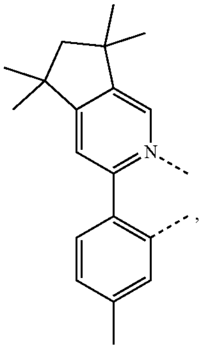
$L_{B312}$
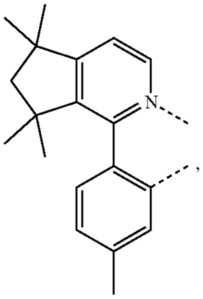
$L_{B313}$
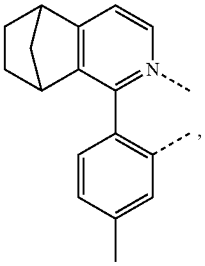
$L_{B314}$
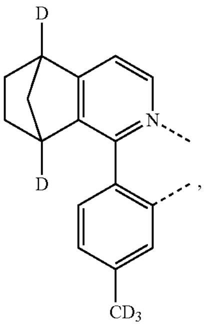

-continued
$L_{B315}$
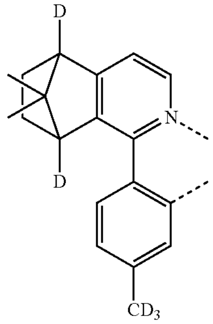
,
$L_{B316}$
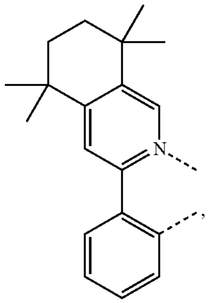
,
$L_{B298}$
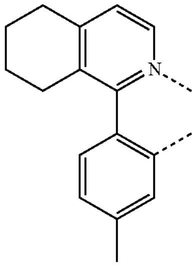
,
$L_{B299}$
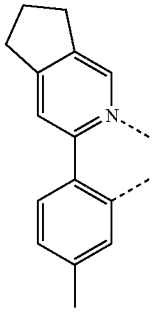
,
$L_{B300}$
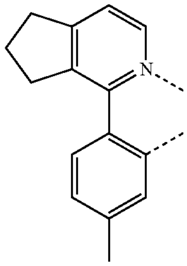
,
-continued
$L_{B301}$
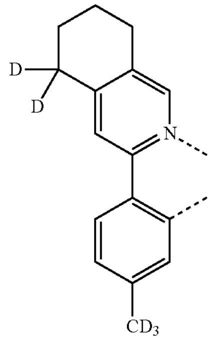
,
$L_{B302}$
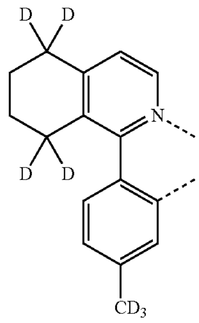
,
$L_{B303}$
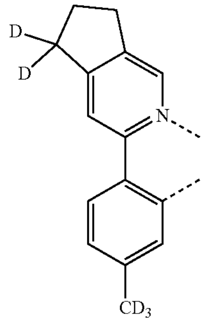
,
$L_{B304}$
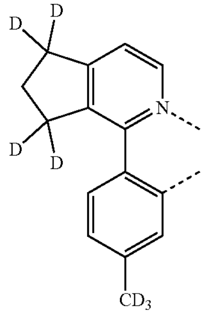
, -continued
$L_{B305}$
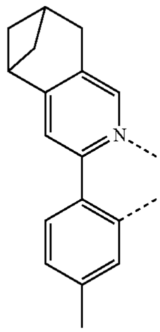
,
$L_{B306}$
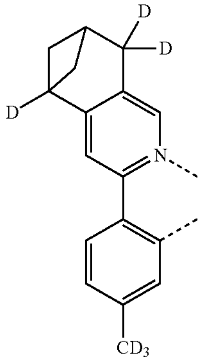
,
$L_{B307}$
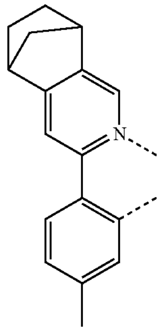
,
$L_{B308}$
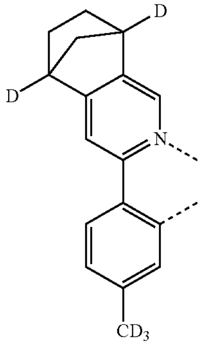
,
-continued
$L_{B309}$
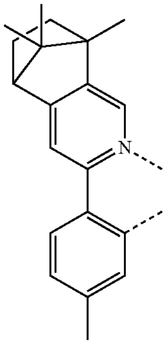
,
$L_{B310}$
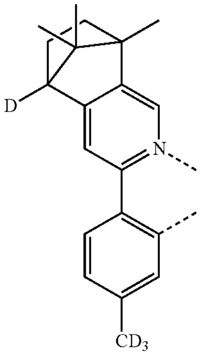
,
$L_{B311}$
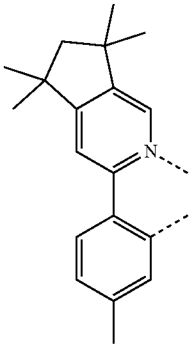
,
$L_{B312}$
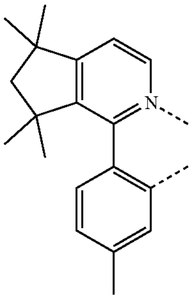
, -continued
$L_{B313}$
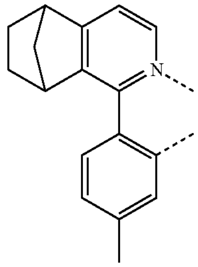
,
$L_{B314}$
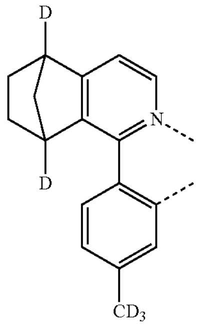
,
$L_{B315}$
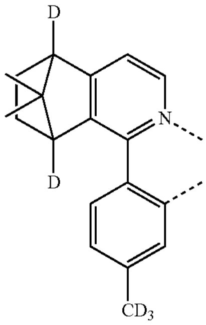
,
$L_{B316}$
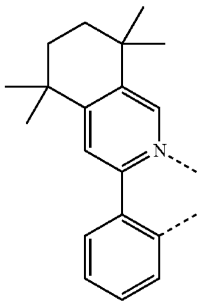
,
$L_{B317}$
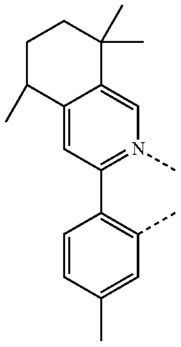
,
-continued
$L_{B318}$
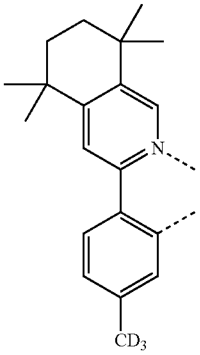
,
$L_{B319}$
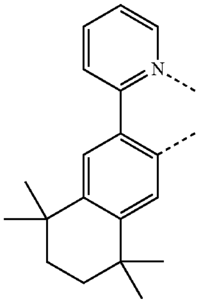
,
$L_{B320}$
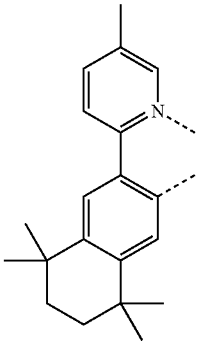
,
$L_{B321}$
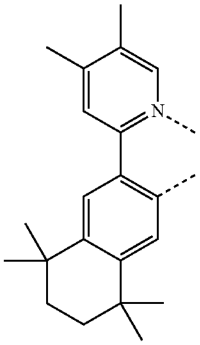
, -continued
$L_{B322}$
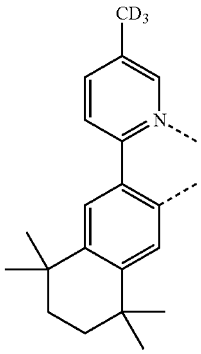
,
$L_{B323}$
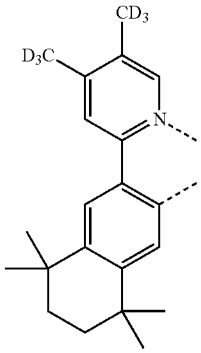
,
$L_{B324}$
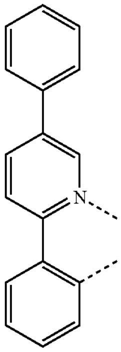
,
$L_{B325}$
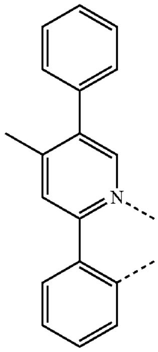
,
-continued
$L_{B326}$
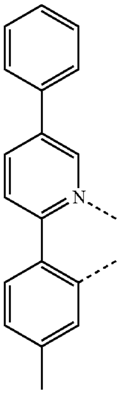
,
$L_{B327}$
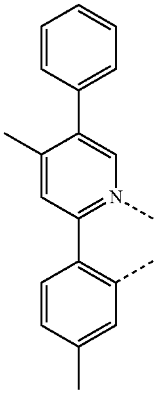
,
$L_{B328}$
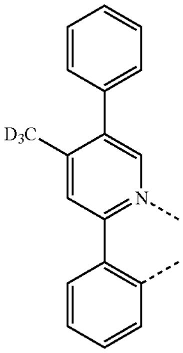
,
$L_{B329}$
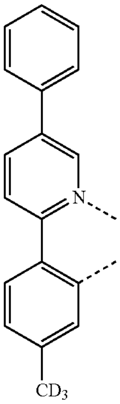
, -continued
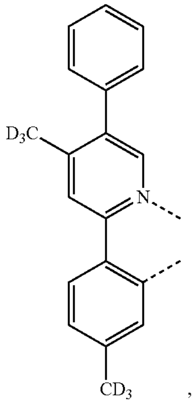
$L_{B330}$
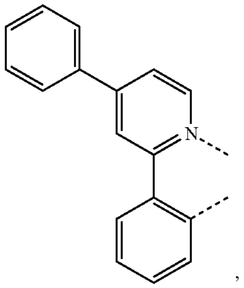
$L_{B331}$
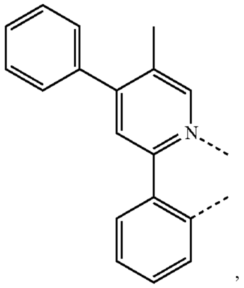
$L_{B332}$
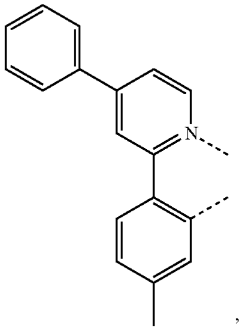
$L_{B333}$
-continued
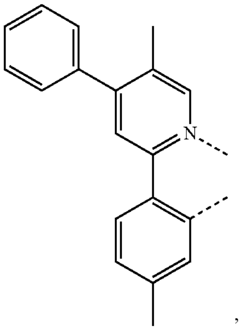
$L_{B334}$
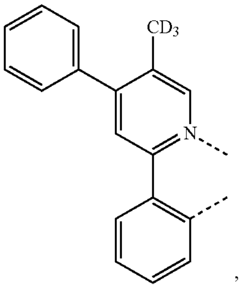
$L_{B335}$
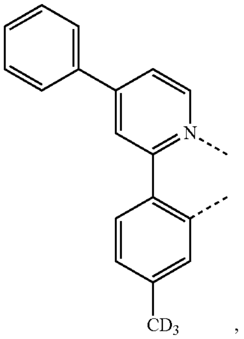
$L_{B336}$
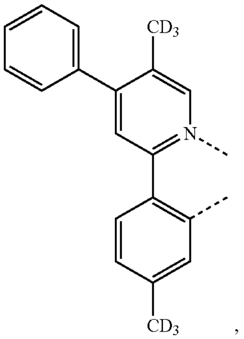
$L_{B337}$ -continued
$L_{B338}$
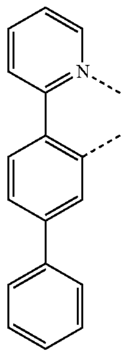
,
$L_{B339}$
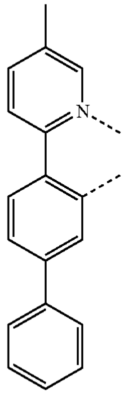
,
$L_{B340}$
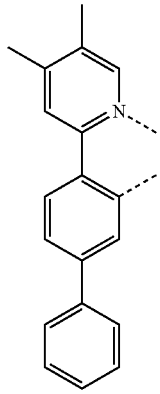
,
$L_{B341}$
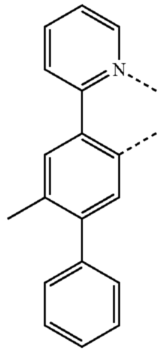
,
-continued
$L_{B342}$
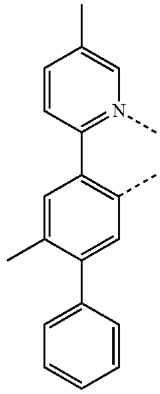
,
$L_{B343}$
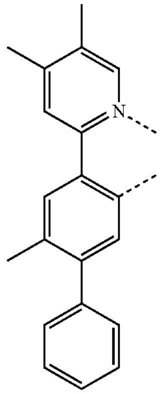
,
$L_{B344}$
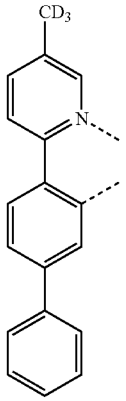
,
$L_{B345}$
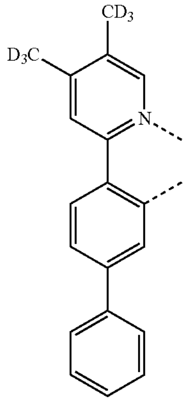
, -continued
$L_{B346}$
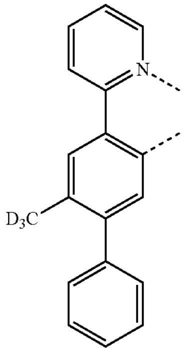
,
$L_{B347}$
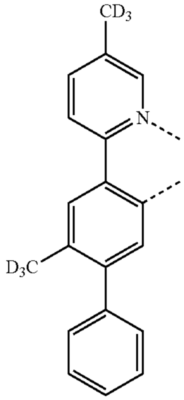
,
$L_{B348}$
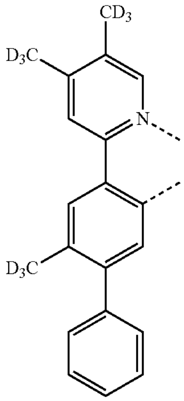
,
$L_{B349}$
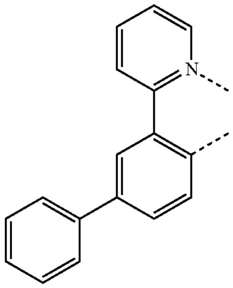
,
-continued
$L_{B350}$
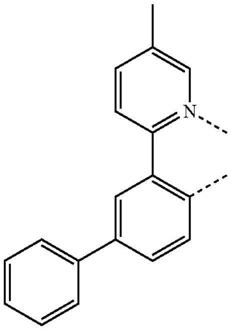
,
$L_{B351}$
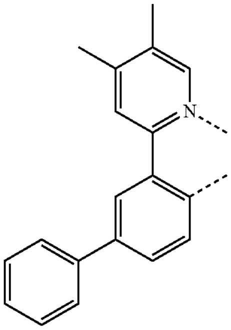
,
$L_{B352}$
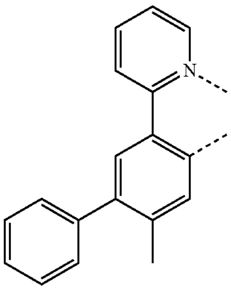
,
$L_{B353}$
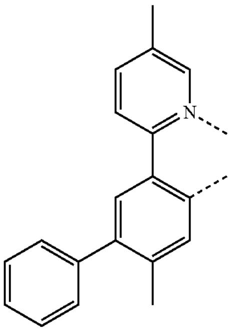
,
$L_{B354}$
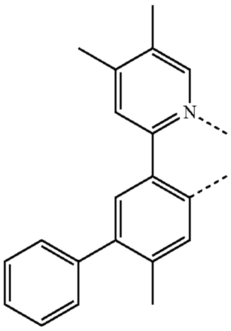
, L$_{B355}$
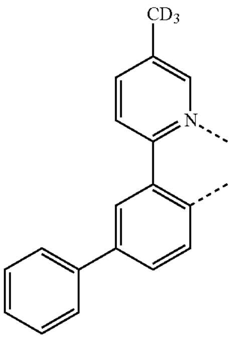
,
L$_{B356}$
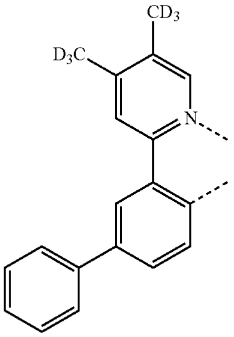
,
L$_{B357}$
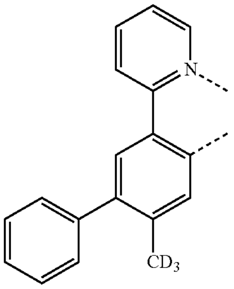
,
L$_{B358}$
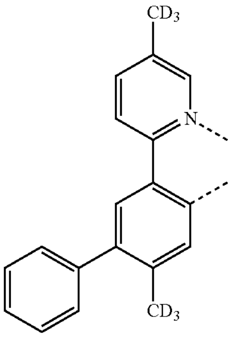
,
L$_{B359}$
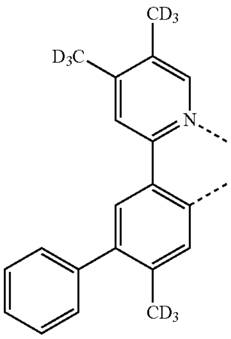
,
L$_{B360}$
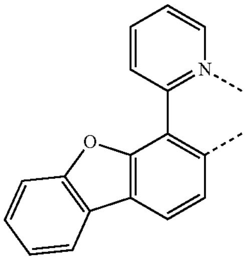
,
L$_{B361}$
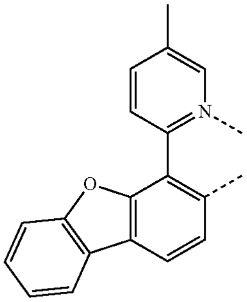
,
L$_{B362}$
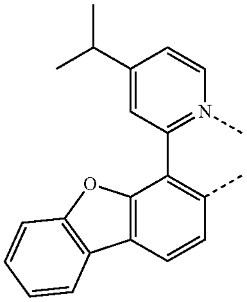
,
L$_{B363}$
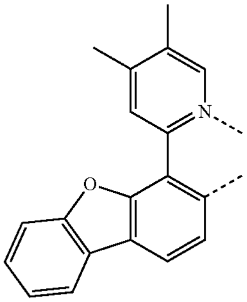
, -continued
$L_{B364}$
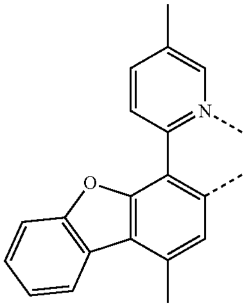
,
$L_{B365}$
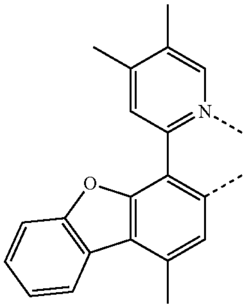
,
$L_{B366}$
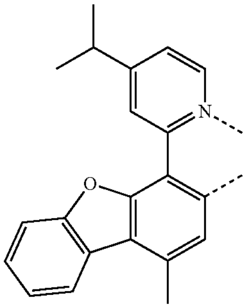
,
$L_{B367}$
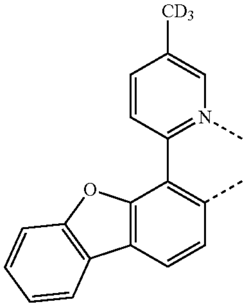
,
$L_{B368}$
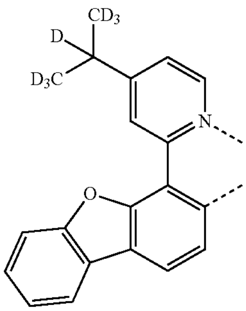
,
-continued
$L_{B369}$
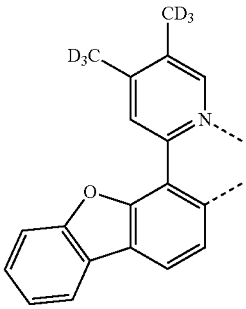
,
$L_{B370}$
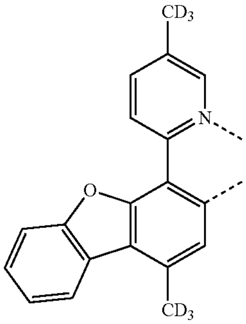
,
$L_{B371}$
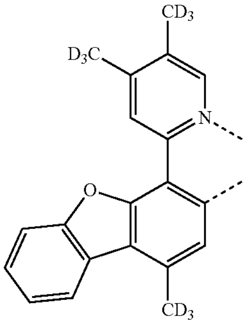
,
$L_{B372}$
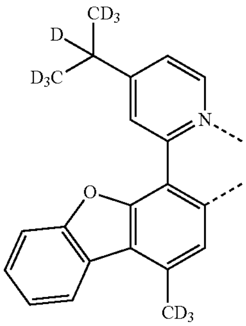
,
$L_{B373}$
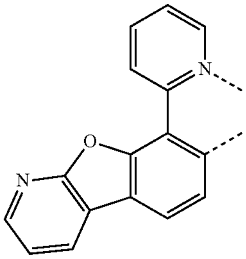
, -continued
$L_{B374}$
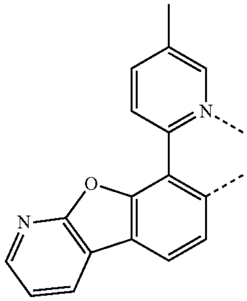
,
$L_{B375}$
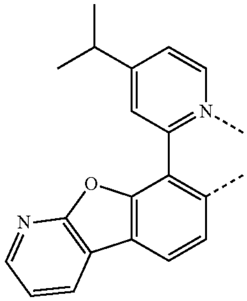
,
$L_{B376}$
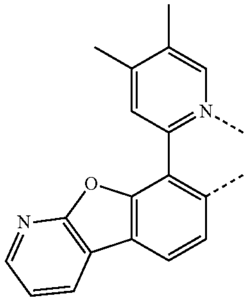
,
$L_{B377}$
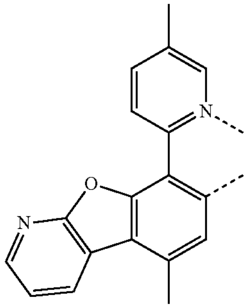
,
$L_{B378}$
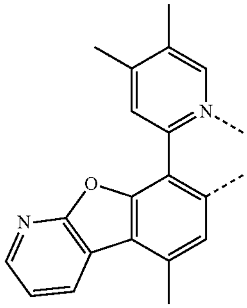
,
-continued
$L_{B379}$
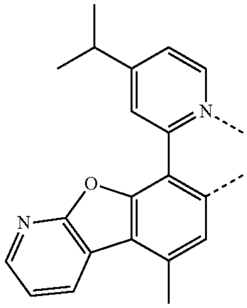
,
$L_{B380}$
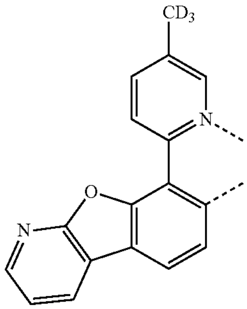
,
$L_{B381}$
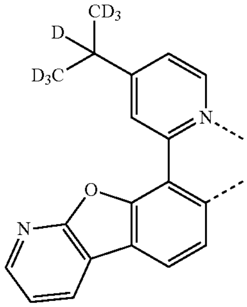
,
$L_{B382}$
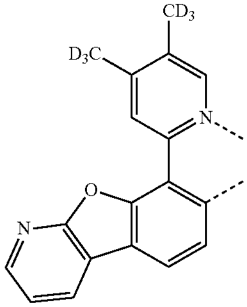
,
$L_{B383}$
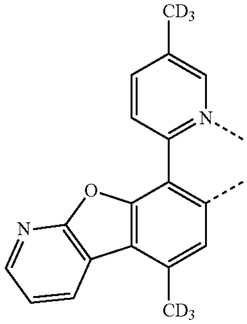
, -continued
$L_{B384}$
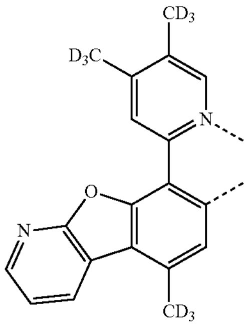
,
$L_{B385}$
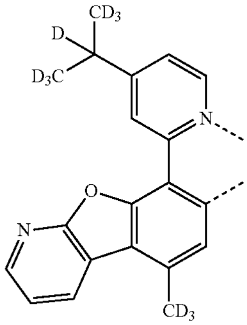
,
$L_{B386}$
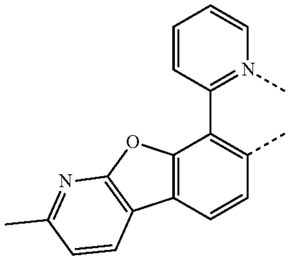
,
$L_{B387}$
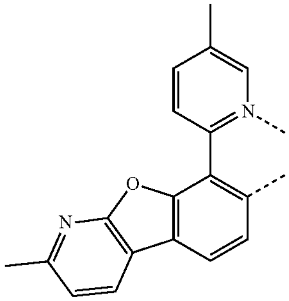
,
$L_{B388}$
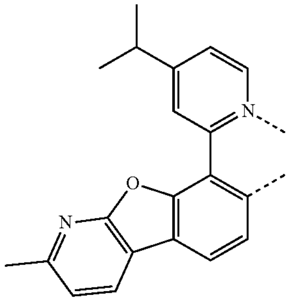
,
-continued
$L_{B389}$
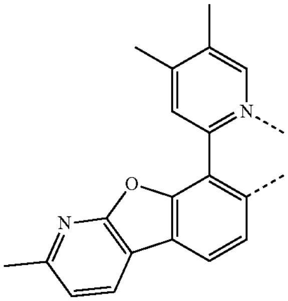
,
$L_{B390}$
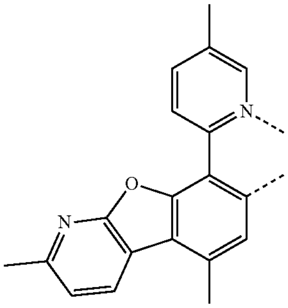
,
$L_{B391}$
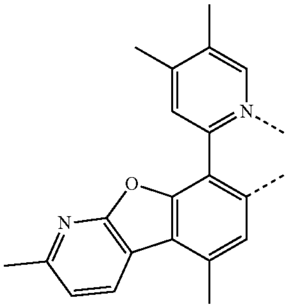
,
$L_{B392}$
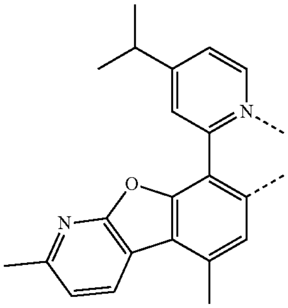
,
$L_{B393}$
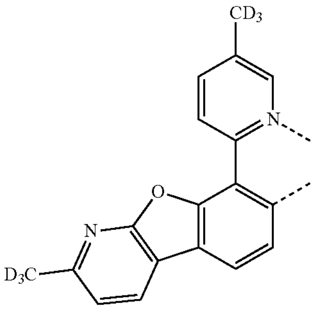
, -continued
$L_{B394}$
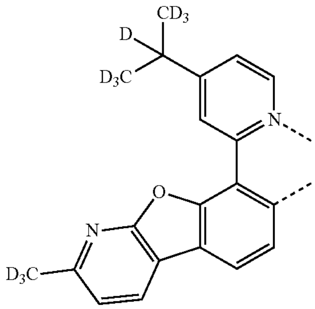
,
$L_{B395}$
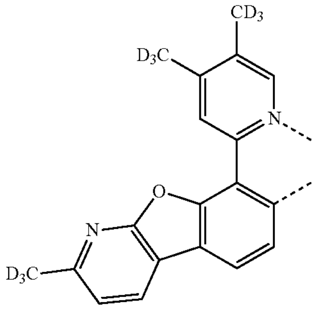
,
$L_{B396}$
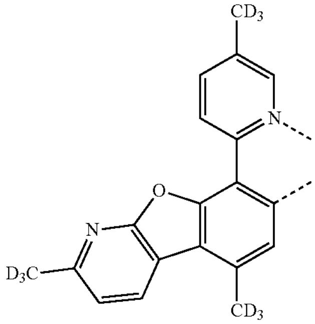
,
$L_{B397}$
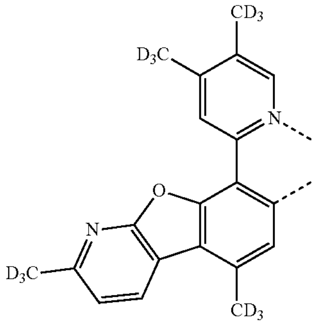
,
$L_{B398}$
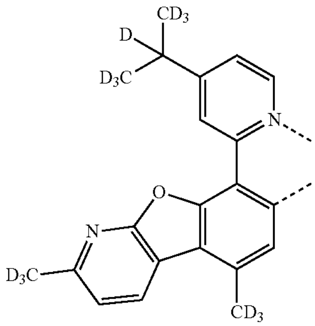
,
-continued
$L_{B399}$
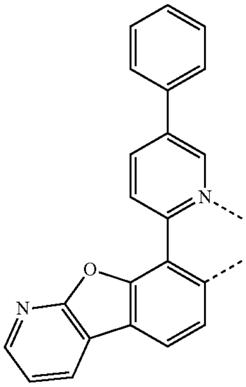
,
$L_{B400}$
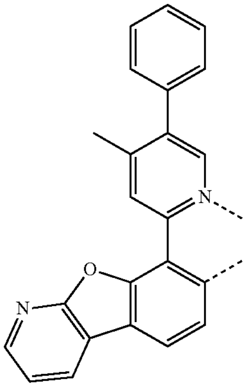
,
$L_{B401}$
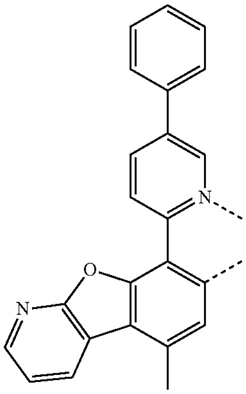
,
$L_{B402}$
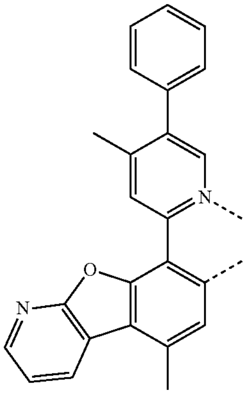
, -continued
$L_{B403}$
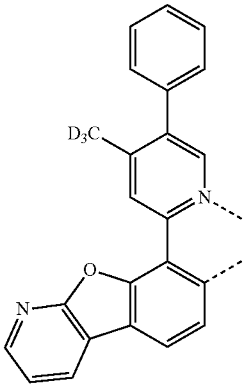
,
$L_{B404}$
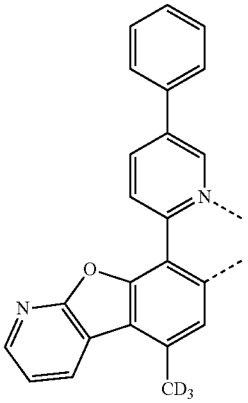
,
$L_{B405}$
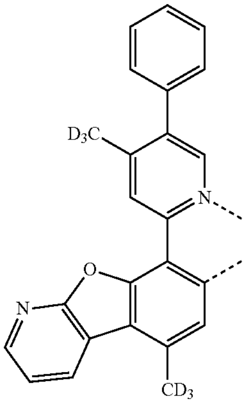
,
$L_{B406}$
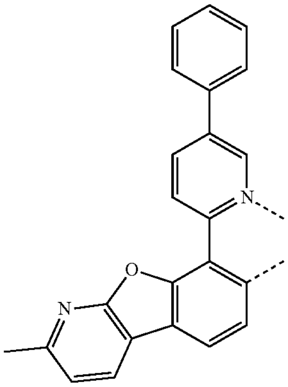
,
-continued
$L_{B407}$
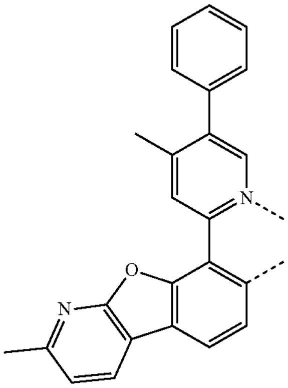
,
$L_{B408}$
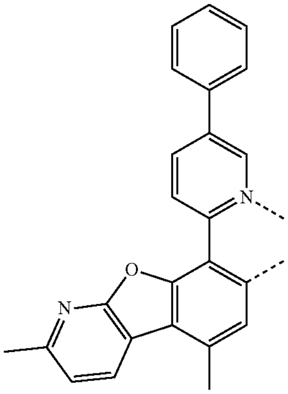
,
$L_{B409}$
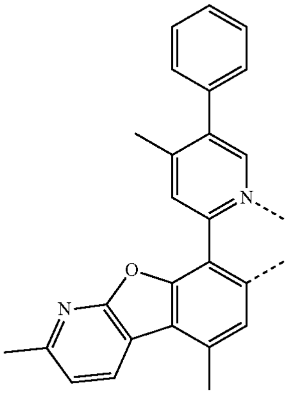
,
$L_{B410}$
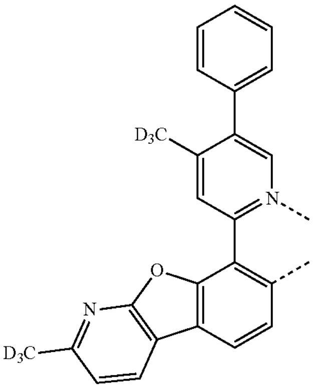
, -continued
$L_{B411}$
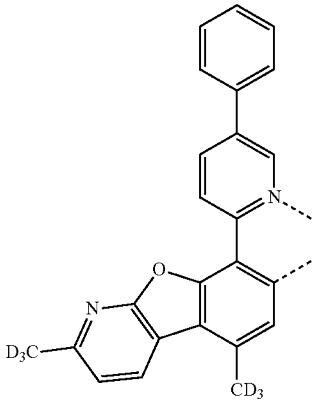
,
$L_{B412}$
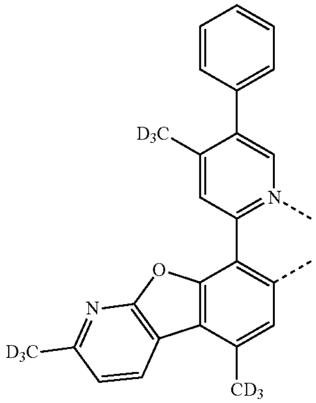
,
$L_{B413}$
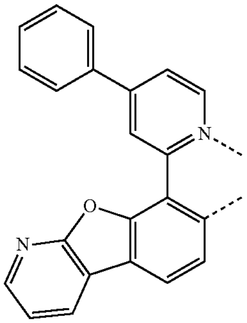
,
$L_{B414}$
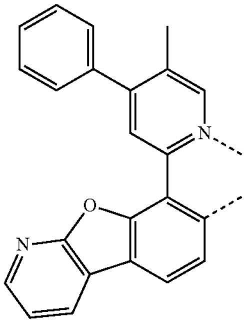
,
-continued
$L_{B415}$
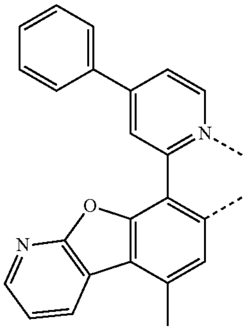
,
$L_{B416}$
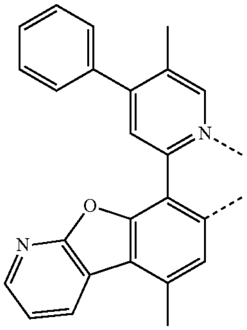
,
$L_{B417}$
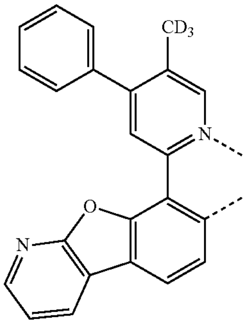
,
$L_{B418}$
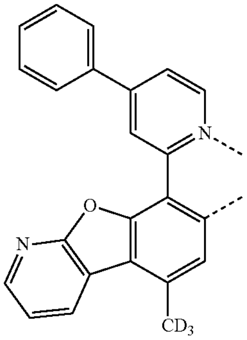
, -continued
$L_{B419}$
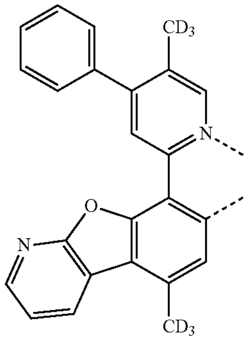
,
$L_{B420}$
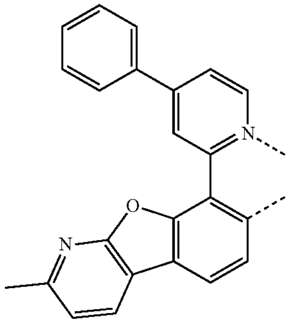
,
$L_{B421}$
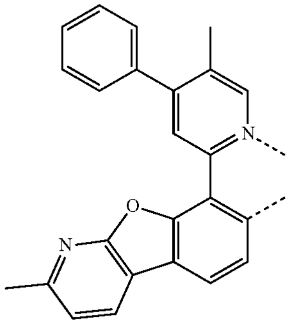
,
$L_{B422}$
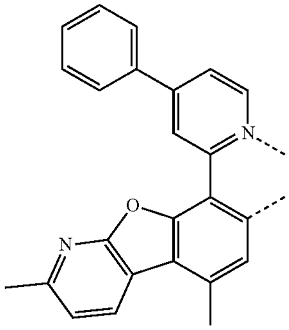
,
-continued
$L_{B423}$
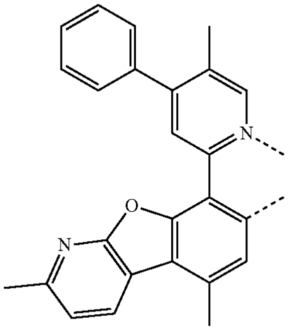
,
$L_{B424}$
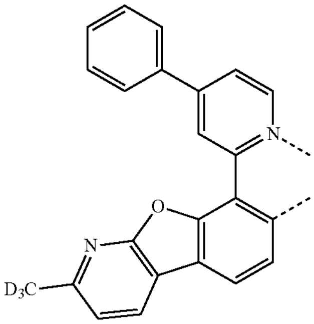
,
$L_{B425}$
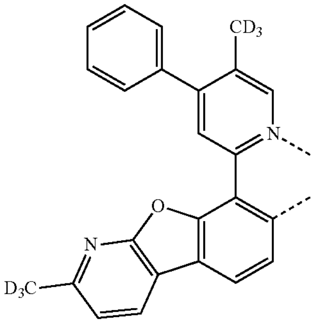
,
$L_{B426}$
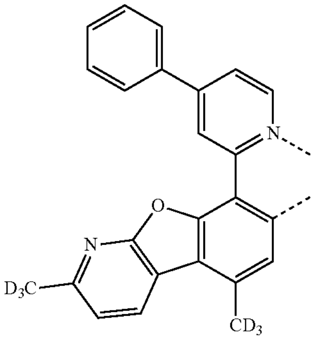
, -continued
$L_{B427}$
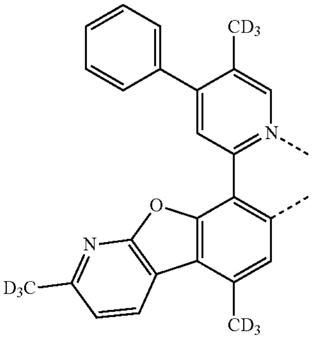
,
$L_{B428}$
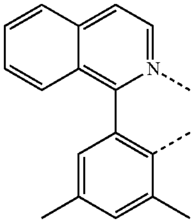
,
$L_{B429}$
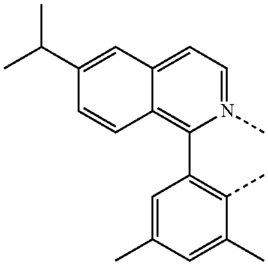
,
$L_{B430}$
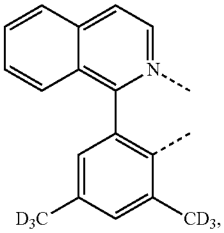
$L_{B431}$
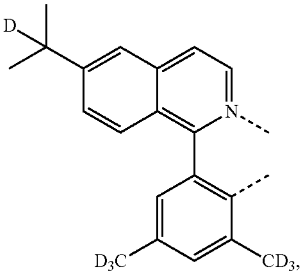
-continued
$L_{B432}$
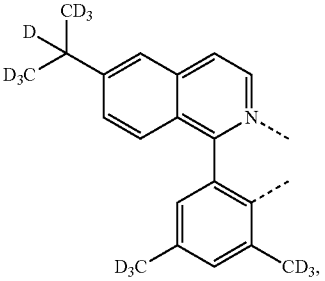
$L_{B433}$
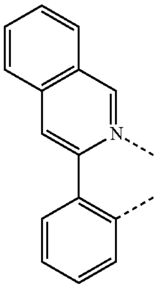
,
$L_{B434}$
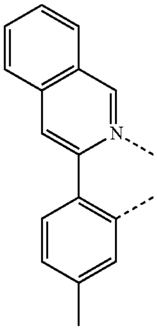
,
$L_{B435}$
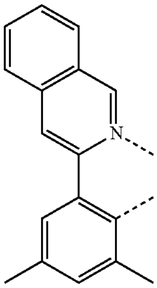
,
$L_{B436}$
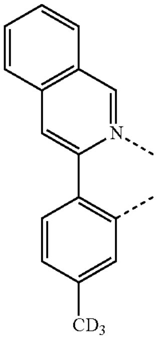
, -continued
$L_{B437}$
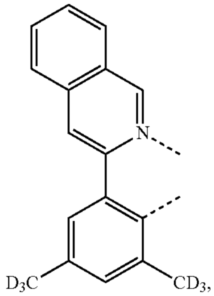
,
$L_{B438}$
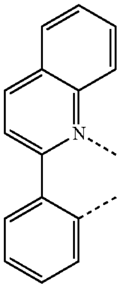
,
$L_{B439}$
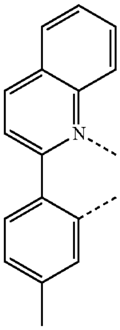
,
$L_{B440}$
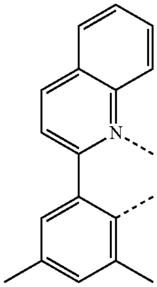
,
$L_{B441}$
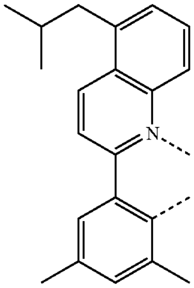
,
-continued
$L_{B442}$
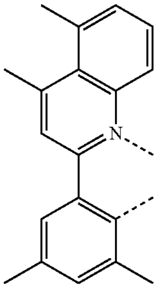
,
$L_{B443}$
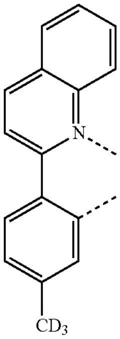
,
$L_{B444}$
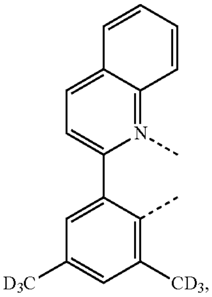
,
$L_{B445}$
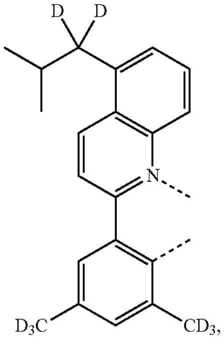
,
$L_{B446}$
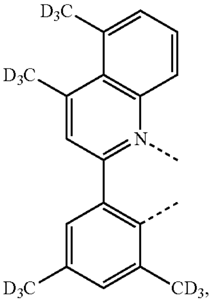
, -continued
$L_{B447}$
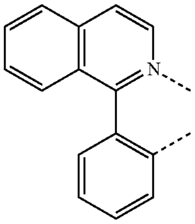
,
$L_{B448}$
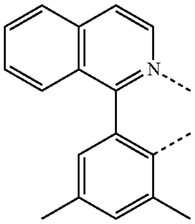
,
$L_{B449}$
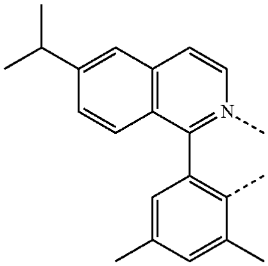
,
$L_{B450}$
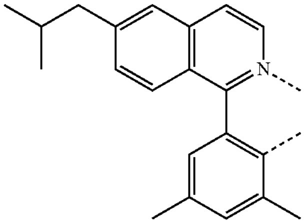
,
$L_{B451}$
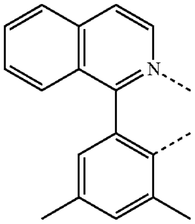
,
$L_{B452}$
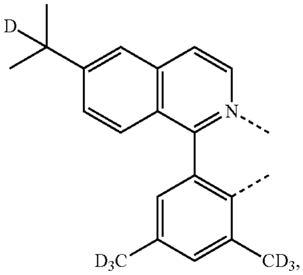
,
-continued
$L_{B453}$
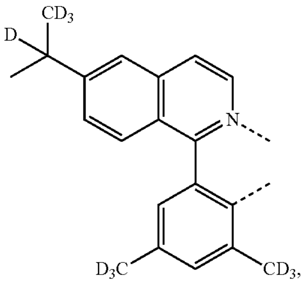
,
$L_{B454}$
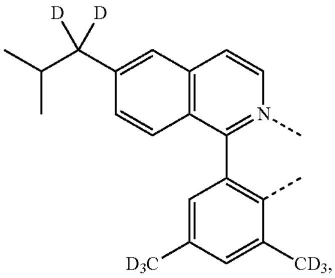
,
$L_{B455}$
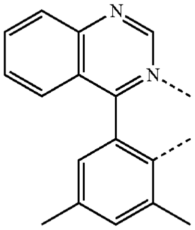
,
$L_{B456}$
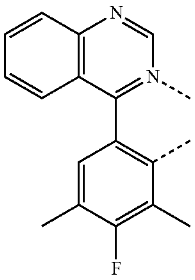
,
$L_{B457}$
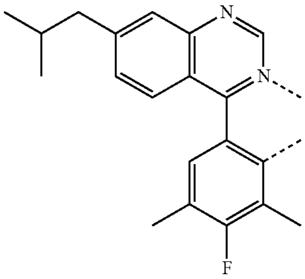
, -continued
$L_{B458}$
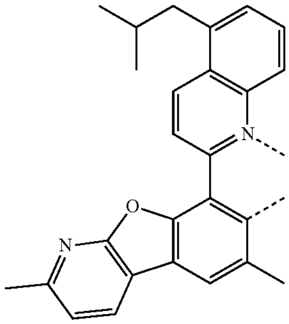
,
$L_{B459}$
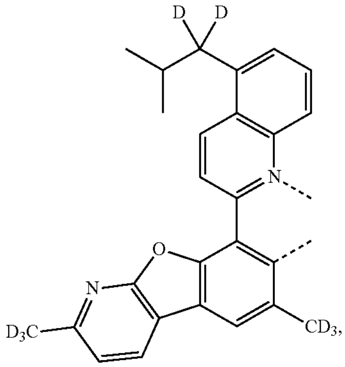
,
$L_{B460}$
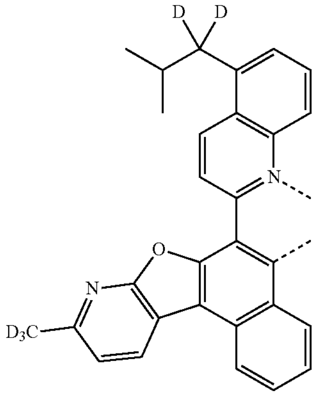
,
$L_{B461}$
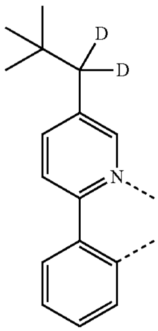
,
-continued
$L_{B462}$
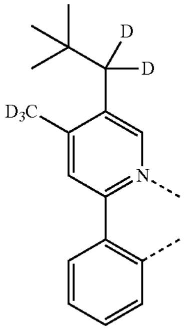
,
$L_{B463}$
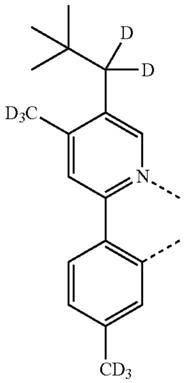
,
$L_{B464}$
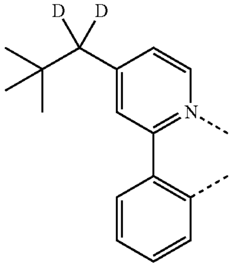
,
$L_{B465}$
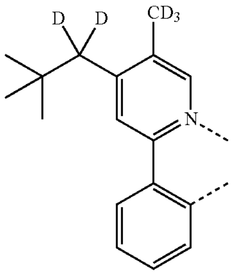
,
$L_{B466}$
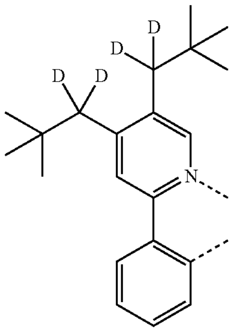
, -continued $L_{B467}$

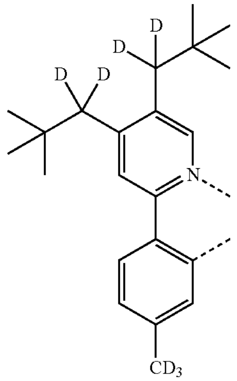

and $L_{B468}$

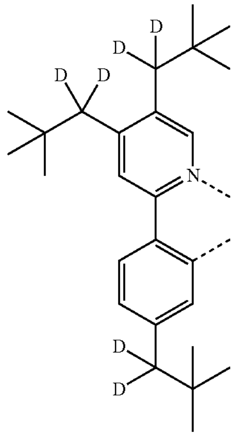

;

and $L_C$ is selected from the group consisting of the following structures:

$L^{C1}$ through $L^{C1260}$ based on a structure of Formula X,

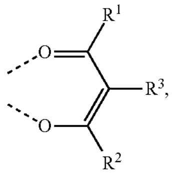

in which $R^1$, $R^2$, and $R^3$ are defined as:

| Ligand | $R^1$ | $R^2$ | $R^3$ |
|---|---|---|---|
| $L_{C1}$ | $R^{D1}$ | $R^{D1}$ | H |
| $L_{C2}$ | $R^{D2}$ | $R^{D2}$ | H |
| $L_{C3}$ | $R^{D3}$ | $R^{D3}$ | H |
| $L_{C4}$ | $R^{D4}$ | $R^{D4}$ | H |
| $L_{C5}$ | $R^{D5}$ | $R^{D5}$ | H |
| $L_{C6}$ | $R^{D6}$ | $R^{D6}$ | H |
| $L_{C7}$ | $R^{D7}$ | $R^{D7}$ | H |
| $L_{C8}$ | $R^{D8}$ | $R^{D8}$ | H |
| $L_{C9}$ | $R^{D9}$ | $R^{D9}$ | H |
| $L_{C10}$ | $R^{D10}$ | $R^{D10}$ | H |
| $L_{C11}$ | $R^{D11}$ | $R^{D11}$ | H |
| $L_{C12}$ | $R^{D12}$ | $R^{D12}$ | H |
| $L_{C13}$ | $R^{D13}$ | $R^{D13}$ | H |
| $L_{C14}$ | $R^{D14}$ | $R^{D14}$ | H |
| $L_{C15}$ | $R^{D15}$ | $R^{D15}$ | H |

-continued

| Ligand | $R^1$ | $R^2$ | $R^3$ |
|---|---|---|---|
| $L_{C16}$ | $R^{D16}$ | $R^{D16}$ | H |
| $L_{C17}$ | $R^{D17}$ | $R^{D17}$ | H |
| $L_{C18}$ | $R^{D18}$ | $R^{D18}$ | H |
| $L_{C19}$ | $R^{D19}$ | $R^{D19}$ | H |
| $L_{C20}$ | $R^{D20}$ | $R^{D20}$ | H |
| $L_{C21}$ | $R^{D21}$ | $R^{D21}$ | H |
| $L_{C22}$ | $R^{D22}$ | $R^{D22}$ | H |
| $L_{C23}$ | $R^{D23}$ | $R^{D23}$ | H |
| $L_{C24}$ | $R^{D24}$ | $R^{D24}$ | H |
| $L_{C25}$ | $R^{D25}$ | $R^{D25}$ | H |
| $L_{C26}$ | $R^{D26}$ | $R^{D26}$ | H |
| $L_{C27}$ | $R^{D27}$ | $R^{D27}$ | H |
| $L_{C28}$ | $R^{D28}$ | $R^{D28}$ | H |
| $L_{C29}$ | $R^{D29}$ | $R^{D29}$ | H |
| $L_{C30}$ | $R^{D30}$ | $R^{D30}$ | H |
| $L_{C31}$ | $R^{D31}$ | $R^{D31}$ | H |
| $L_{C32}$ | $R^{D32}$ | $R^{D32}$ | H |
| $L_{C33}$ | $R^{D33}$ | $R^{D33}$ | H |
| $L_{C34}$ | $R^{D34}$ | $R^{D34}$ | H |
| $L_{C35}$ | $R^{D35}$ | $R^{D35}$ | H |
| $L_{C36}$ | $R^{D40}$ | $R^{D40}$ | H |
| $L_{C37}$ | $R^{D41}$ | $R^{D41}$ | H |
| $L_{C38}$ | $R^{D42}$ | $R^{D42}$ | H |
| $L_{C39}$ | $R^{D64}$ | $R^{D64}$ | H |
| $L_{C40}$ | $R^{D66}$ | $R^{D66}$ | H |
| $L_{C41}$ | $R^{D68}$ | $R^{D68}$ | H |
| $L_{C42}$ | $R^{D76}$ | $R^{D76}$ | H |
| $L_{C43}$ | $R^{D1}$ | $R^{D2}$ | H |
| $L_{C44}$ | $R^{D1}$ | $R^{D3}$ | H |
| $L_{C45}$ | $R^{D1}$ | $R^{D4}$ | H |
| $L_{C46}$ | $R^{D1}$ | $R^{D5}$ | H |
| $L_{C47}$ | $R^{D1}$ | $R^{D6}$ | H |
| $L_{C48}$ | $R^{D1}$ | $R^{D7}$ | H |
| $L_{C49}$ | $R^{D1}$ | $R^{D8}$ | H |
| $L_{C50}$ | $R^{D1}$ | $R^{D9}$ | H |
| $L_{C51}$ | $R^{D1}$ | $R^{D10}$ | H |
| $L_{C52}$ | $R^{D1}$ | $R^{D11}$ | H |
| $L_{C53}$ | $R^{D1}$ | $R^{D12}$ | H |
| $L_{C54}$ | $R^{D1}$ | $R^{D13}$ | H |
| $L_{C55}$ | $R^{D1}$ | $R^{D14}$ | H |
| $L_{C56}$ | $R^{D1}$ | $R^{D15}$ | H |
| $L_{C57}$ | $R^{D1}$ | $R^{D16}$ | H |
| $L_{C58}$ | $R^{D1}$ | $R^{D17}$ | H |
| $L_{C59}$ | $R^{D1}$ | $R^{D18}$ | H |
| $L_{C60}$ | $R^{D1}$ | $R^{D19}$ | H |
| $L_{C61}$ | $R^{D1}$ | $R^{D20}$ | H |
| $L_{C62}$ | $R^{D1}$ | $R^{D21}$ | H |
| $L_{C63}$ | $R^{D1}$ | $R^{D22}$ | H |
| $L_{C64}$ | $R^{D1}$ | $R^{D23}$ | H |
| $L_{C65}$ | $R^{D1}$ | $R^{D24}$ | H |
| $L_{C66}$ | $R^{D1}$ | $R^{D25}$ | H |
| $L_{C67}$ | $R^{D1}$ | $R^{D26}$ | H |
| $L_{C68}$ | $R^{D1}$ | $R^{D27}$ | H |
| $L_{C69}$ | $R^{D1}$ | $R^{D28}$ | H |
| $L_{C70}$ | $R^{D1}$ | $R^{D29}$ | H |
| $L_{C71}$ | $R^{D1}$ | $R^{D30}$ | H |
| $L_{C72}$ | $R^{D1}$ | $R^{D31}$ | H |
| $L_{C73}$ | $R^{D1}$ | $R^{D32}$ | H |
| $L_{C74}$ | $R^{D1}$ | $R^{D33}$ | H |
| $L_{C75}$ | $R^{D1}$ | $R^{D34}$ | H |
| $L_{C76}$ | $R^{D1}$ | $R^{D35}$ | H |
| $L_{C77}$ | $R^{D1}$ | $R^{D40}$ | H |
| $L_{C78}$ | $R^{D1}$ | $R^{D41}$ | H |
| $L_{C79}$ | $R^{D1}$ | $R^{D42}$ | H |
| $L_{C80}$ | $R^{D1}$ | $R^{D64}$ | H |
| $L_{C81}$ | $R^{D1}$ | $R^{D66}$ | H |
| $L_{C82}$ | $R^{D1}$ | $R^{D68}$ | H |
| $L_{C83}$ | $R^{D1}$ | $R^{D76}$ | H |
| $L_{C84}$ | $R^{D2}$ | $R^{D1}$ | H |
| $L_{C85}$ | $R^{D2}$ | $R^{D3}$ | H |
| $L_{C86}$ | $R^{D2}$ | $R^{D4}$ | H |
| $L_{C87}$ | $R^{D2}$ | $R^{D5}$ | H |
| $L_{C88}$ | $R^{D2}$ | $R^{D6}$ | H |
| $L_{C89}$ | $R^{D2}$ | $R^{D7}$ | H |
| $L_{C90}$ | $R^{D2}$ | $R^{D8}$ | H |
| $L_{C91}$ | $R^{D2}$ | $R^{D9}$ | H |
| $L_{C92}$ | $R^{D2}$ | $R^{D10}$ | H |

-continued

| Ligand | $R^1$ | $R^2$ | $R^3$ |
|---|---|---|---|
| $L_{C93}$ | $R^{D2}$ | $R^{D11}$ | H |
| $L_{C94}$ | $R^{D2}$ | $R^{D12}$ | H |
| $L_{C95}$ | $R^{D2}$ | $R^{D13}$ | H |
| $L_{C96}$ | $R^{D2}$ | $R^{D14}$ | H |
| $L_{C97}$ | $R^{D2}$ | $R^{D15}$ | H |
| $L_{C98}$ | $R^{D2}$ | $R^{D16}$ | H |
| $L_{C99}$ | $R^{D2}$ | $R^{D17}$ | H |
| $L_{C100}$ | $R^{D2}$ | $R^{D18}$ | H |
| $L_{C101}$ | $R^{D2}$ | $R^{D19}$ | H |
| $L_{C102}$ | $R^{D2}$ | $R^{D20}$ | H |
| $L_{C103}$ | $R^{D2}$ | $R^{D21}$ | H |
| $L_{C104}$ | $R^{D2}$ | $R^{D22}$ | H |
| $L_{C105}$ | $R^{D2}$ | $R^{D23}$ | H |
| $L_{C106}$ | $R^{D2}$ | $R^{D24}$ | H |
| $L_{C107}$ | $R^{D2}$ | $R^{D25}$ | H |
| $L_{C108}$ | $R^{D2}$ | $R^{D26}$ | H |
| $L_{C109}$ | $R^{D2}$ | $R^{D27}$ | H |
| $L_{C110}$ | $R^{D2}$ | $R^{D28}$ | H |
| $L_{C111}$ | $R^{D2}$ | $R^{D29}$ | H |
| $L_{C112}$ | $R^{D2}$ | $R^{D30}$ | H |
| $L_{C113}$ | $R^{D2}$ | $R^{D31}$ | H |
| $L_{C114}$ | $R^{D2}$ | $R^{D32}$ | H |
| $L_{C115}$ | $R^{D2}$ | $R^{D33}$ | H |
| $L_{C116}$ | $R^{D2}$ | $R^{D34}$ | H |
| $L_{C117}$ | $R^{D2}$ | $R^{D35}$ | H |
| $L_{C118}$ | $R^{D2}$ | $R^{D40}$ | H |
| $L_{C119}$ | $R^{D2}$ | $R^{D41}$ | H |
| $L_{C120}$ | $R^{D2}$ | $R^{D42}$ | H |
| $L_{C121}$ | $R^{D2}$ | $R^{D64}$ | H |
| $L_{C122}$ | $R^{D2}$ | $R^{D66}$ | H |
| $L_{C123}$ | $R^{D2}$ | $R^{D68}$ | H |
| $L_{C124}$ | $R^{D2}$ | $R^{D76}$ | H |
| $L_{C125}$ | $R^{D3}$ | $R^{D4}$ | H |
| $L_{C126}$ | $R^{D3}$ | $R^{D5}$ | H |
| $L_{C127}$ | $R^{D3}$ | $R^{D6}$ | H |
| $L_{C128}$ | $R^{D3}$ | $R^{D7}$ | H |
| $L_{C129}$ | $R^{D3}$ | $R^{D8}$ | H |
| $L_{C130}$ | $R^{D3}$ | $R^{D9}$ | H |
| $L_{C131}$ | $R^{D3}$ | $R^{D10}$ | H |
| $L_{C132}$ | $R^{D3}$ | $R^{D11}$ | H |
| $L_{C133}$ | $R^{D3}$ | $R^{D12}$ | H |
| $L_{C134}$ | $R^{D3}$ | $R^{D13}$ | H |
| $L_{C135}$ | $R^{D3}$ | $R^{D14}$ | H |
| $L_{C136}$ | $R^{D3}$ | $R^{D15}$ | H |
| $L_{C137}$ | $R^{D3}$ | $R^{D16}$ | H |
| $L_{C138}$ | $R^{D3}$ | $R^{D17}$ | H |
| $L_{C139}$ | $R^{D3}$ | $R^{D18}$ | H |
| $L_{C140}$ | $R^{D3}$ | $R^{D19}$ | H |
| $L_{C141}$ | $R^{D3}$ | $R^{D20}$ | H |
| $L_{C142}$ | $R^{D3}$ | $R^{D21}$ | H |
| $L_{C143}$ | $R^{D3}$ | $R^{D22}$ | H |
| $L_{C144}$ | $R^{D3}$ | $R^{D23}$ | H |
| $L_{C145}$ | $R^{D3}$ | $R^{D24}$ | H |
| $L_{C146}$ | $R^{D3}$ | $R^{D25}$ | H |
| $L_{C147}$ | $R^{D3}$ | $R^{D26}$ | H |
| $L_{C148}$ | $R^{D3}$ | $R^{D27}$ | H |
| $L_{C149}$ | $R^{D3}$ | $R^{D28}$ | H |
| $L_{C150}$ | $R^{D3}$ | $R^{D29}$ | H |
| $L_{C151}$ | $R^{D3}$ | $R^{D30}$ | H |
| $L_{C152}$ | $R^{D3}$ | $R^{D31}$ | H |
| $L_{C153}$ | $R^{D3}$ | $R^{D32}$ | H |
| $L_{C154}$ | $R^{D3}$ | $R^{D33}$ | H |
| $L_{C155}$ | $R^{D3}$ | $R^{D34}$ | H |
| $L_{C156}$ | $R^{D3}$ | $R^{D35}$ | H |
| $L_{C157}$ | $R^{D3}$ | $R^{D40}$ | H |
| $L_{C158}$ | $R^{D3}$ | $R^{D41}$ | H |
| $L_{C159}$ | $R^{D3}$ | $R^{D42}$ | H |
| $L_{C160}$ | $R^{D3}$ | $R^{D64}$ | H |
| $L_{C161}$ | $R^{D3}$ | $R^{D66}$ | H |
| $L_{C162}$ | $R^{D3}$ | $R^{D68}$ | H |
| $L_{C163}$ | $R^{D3}$ | $R^{D76}$ | H |
| $L_{C164}$ | $R^{D4}$ | $R^{D5}$ | H |
| $L_{C165}$ | $R^{D4}$ | $R^{D6}$ | H |
| $L_{C166}$ | $R^{D4}$ | $R^{D7}$ | H |
| $L_{C167}$ | $R^{D4}$ | $R^{D8}$ | H |
| $L_{C168}$ | $R^{D4}$ | $R^{D9}$ | H |
| $L_{C169}$ | $R^{D4}$ | $R^{D10}$ | H |

-continued

| Ligand | $R^1$ | $R^2$ | $R^3$ |
|---|---|---|---|
| $L_{C170}$ | $R^{D4}$ | $R^{D11}$ | H |
| $L_{C171}$ | $R^{D4}$ | $R^{D12}$ | H |
| $L_{C172}$ | $R^{D4}$ | $R^{D13}$ | H |
| $L_{C173}$ | $R^{D4}$ | $R^{D14}$ | H |
| $L_{C174}$ | $R^{D4}$ | $R^{D15}$ | H |
| $L_{C175}$ | $R^{D4}$ | $R^{D16}$ | H |
| $L_{C176}$ | $R^{D4}$ | $R^{D17}$ | H |
| $L_{C177}$ | $R^{D4}$ | $R^{D18}$ | H |
| $L_{C178}$ | $R^{D4}$ | $R^{D19}$ | H |
| $L_{C179}$ | $R^{D4}$ | $R^{D20}$ | H |
| $L_{C180}$ | $R^{D4}$ | $R^{D21}$ | H |
| $L_{C181}$ | $R^{D4}$ | $R^{D22}$ | H |
| $L_{C182}$ | $R^{D4}$ | $R^{D23}$ | H |
| $L_{C183}$ | $R^{D4}$ | $R^{D24}$ | H |
| $L_{C184}$ | $R^{D4}$ | $R^{D25}$ | H |
| $L_{C185}$ | $R^{D4}$ | $R^{D26}$ | H |
| $L_{C186}$ | $R^{D4}$ | $R^{D27}$ | H |
| $L_{C187}$ | $R^{D4}$ | $R^{D28}$ | H |
| $L_{C188}$ | $R^{D4}$ | $R^{D29}$ | H |
| $L_{C189}$ | $R^{D4}$ | $R^{D30}$ | H |
| $L_{C190}$ | $R^{D4}$ | $R^{D31}$ | H |
| $L_{C191}$ | $R^{D4}$ | $R^{D32}$ | H |
| $L_{C192}$ | $R^{D4}$ | $R^{D33}$ | H |
| $L_{C193}$ | $R^{D4}$ | $R^{D34}$ | H |
| $L_{C194}$ | $R^{D4}$ | $R^{D35}$ | H |
| $L_{C195}$ | $R^{D4}$ | $R^{D40}$ | H |
| $L_{C196}$ | $R^{D4}$ | $R^{D41}$ | H |
| $L_{C197}$ | $R^{D4}$ | $R^{D42}$ | H |
| $L_{C198}$ | $R^{D4}$ | $R^{D64}$ | H |
| $L_{C199}$ | $R^{D4}$ | $R^{D66}$ | H |
| $L_{C200}$ | $R^{D4}$ | $R^{D68}$ | H |
| $L_{C201}$ | $R^{D4}$ | $R^{D76}$ | H |
| $L_{C202}$ | $R^{D4}$ | $R^{D1}$ | H |
| $L_{C203}$ | $R^{D7}$ | $R^{D5}$ | H |
| $L_{C204}$ | $R^{D7}$ | $R^{D6}$ | H |
| $L_{C205}$ | $R^{D7}$ | $R^{D8}$ | H |
| $L_{C206}$ | $R^{D7}$ | $R^{D9}$ | H |
| $L_{C207}$ | $R^{D7}$ | $R^{D10}$ | H |
| $L_{C208}$ | $R^{D7}$ | $R^{D11}$ | H |
| $L_{C209}$ | $R^{D7}$ | $R^{D12}$ | H |
| $L_{C210}$ | $R^{D7}$ | $R^{D13}$ | H |
| $L_{C211}$ | $R^{D7}$ | $R^{D14}$ | H |
| $L_{C212}$ | $R^{D7}$ | $R^{D15}$ | H |
| $L_{C213}$ | $R^{D7}$ | $R^{D16}$ | H |
| $L_{C214}$ | $R^{D7}$ | $R^{D17}$ | H |
| $L_{C215}$ | $R^{D7}$ | $R^{D18}$ | H |
| $L_{C216}$ | $R^{D7}$ | $R^{D19}$ | H |
| $L_{C217}$ | $R^{D7}$ | $R^{D20}$ | H |
| $L_{C218}$ | $R^{D7}$ | $R^{D21}$ | H |
| $L_{C219}$ | $R^{D7}$ | $R^{D22}$ | H |
| $L_{C220}$ | $R^{D7}$ | $R^{D23}$ | H |
| $L_{C221}$ | $R^{D7}$ | $R^{D24}$ | H |
| $L_{C222}$ | $R^{D7}$ | $R^{D25}$ | H |
| $L_{C223}$ | $R^{D7}$ | $R^{D26}$ | H |
| $L_{C224}$ | $R^{D7}$ | $R^{D27}$ | H |
| $L_{C225}$ | $R^{D7}$ | $R^{D28}$ | H |
| $L_{C226}$ | $R^{D7}$ | $R^{D29}$ | H |
| $L_{C227}$ | $R^{D7}$ | $R^{D30}$ | H |
| $L_{C228}$ | $R^{D7}$ | $R^{D31}$ | H |
| $L_{C229}$ | $R^{D7}$ | $R^{D32}$ | H |
| $L_{C230}$ | $R^{D7}$ | $R^{D33}$ | H |
| $L_{C231}$ | $R^{D7}$ | $R^{D34}$ | H |
| $L_{C232}$ | $R^{D7}$ | $R^{D35}$ | H |
| $L_{C233}$ | $R^{D7}$ | $R^{D40}$ | H |
| $L_{C234}$ | $R^{D7}$ | $R^{D41}$ | H |
| $L_{C235}$ | $R^{D7}$ | $R^{D42}$ | H |
| $L_{C236}$ | $R^{D7}$ | $R^{D64}$ | H |
| $L_{C237}$ | $R^{D7}$ | $R^{D66}$ | H |
| $L_{C238}$ | $R^{D7}$ | $R^{D68}$ | H |
| $L_{C239}$ | $R^{D7}$ | $R^{D76}$ | H |
| $L_{C240}$ | $R^{D8}$ | $R^{D5}$ | H |
| $L_{C241}$ | $R^{D8}$ | $R^{D6}$ | H |
| $L_{C242}$ | $R^{D8}$ | $R^{D9}$ | H |
| $L_{C243}$ | $R^{D8}$ | $R^{D10}$ | H |
| $L_{C244}$ | $R^{D8}$ | $R^{D11}$ | H |
| $L_{C245}$ | $R^{D8}$ | $R^{D12}$ | H |
| $L_{C246}$ | $R^{D8}$ | $R^{D13}$ | H |

-continued

| Ligand | $R^1$ | $R^2$ | $R^3$ |
|---|---|---|---|
| $L_{C247}$ | $R^{D8}$ | $R^{D14}$ | H |
| $L_{C248}$ | $R^{D8}$ | $R^{D15}$ | H |
| $L_{C249}$ | $R^{D8}$ | $R^{D16}$ | H |
| $L_{C250}$ | $R^{D8}$ | $R^{D17}$ | H |
| $L_{C251}$ | $R^{D8}$ | $R^{D18}$ | H |
| $L_{C252}$ | $R^{D8}$ | $R^{D19}$ | H |
| $L_{C253}$ | $R^{D8}$ | $R^{D20}$ | H |
| $L_{C254}$ | $R^{D8}$ | $R^{D21}$ | H |
| $L_{C255}$ | $R^{D8}$ | $R^{D22}$ | H |
| $L_{C256}$ | $R^{D8}$ | $R^{D23}$ | H |
| $L_{C257}$ | $R^{D8}$ | $R^{D24}$ | H |
| $L_{C258}$ | $R^{D8}$ | $R^{D25}$ | H |
| $L_{C259}$ | $R^{D8}$ | $R^{D26}$ | H |
| $L_{C260}$ | $R^{D8}$ | $R^{D27}$ | H |
| $L_{C261}$ | $R^{D8}$ | $R^{D28}$ | H |
| $L_{C262}$ | $R^{D8}$ | $R^{D29}$ | H |
| $L_{C263}$ | $R^{D8}$ | $R^{D30}$ | H |
| $L_{C264}$ | $R^{D8}$ | $R^{D31}$ | H |
| $L_{C265}$ | $R^{D8}$ | $R^{D32}$ | H |
| $L_{C266}$ | $R^{D8}$ | $R^{D33}$ | H |
| $L_{C267}$ | $R^{D8}$ | $R^{D34}$ | H |
| $L_{C268}$ | $R^{D8}$ | $R^{D35}$ | H |
| $L_{C269}$ | $R^{D8}$ | $R^{D40}$ | H |
| $L_{C270}$ | $R^{D8}$ | $R^{D41}$ | H |
| $L_{C271}$ | $R^{D8}$ | $R^{D42}$ | H |
| $L_{C272}$ | $R^{D8}$ | $R^{D64}$ | H |
| $L_{C273}$ | $R^{D8}$ | $R^{D66}$ | H |
| $L_{C274}$ | $R^{D8}$ | $R^{D68}$ | H |
| $L_{C275}$ | $R^{D8}$ | $R^{D76}$ | H |
| $L_{C276}$ | $R^{D11}$ | $R^{D5}$ | H |
| $L_{C277}$ | $R^{D11}$ | $R^{D6}$ | H |
| $L_{C278}$ | $R^{D11}$ | $R^{D9}$ | H |
| $L_{C279}$ | $R^{D11}$ | $R^{D10}$ | H |
| $L_{C280}$ | $R^{D11}$ | $R^{D12}$ | H |
| $L_{C281}$ | $R^{D11}$ | $R^{D13}$ | H |
| $L_{C282}$ | $R^{D11}$ | $R^{D14}$ | H |
| $L_{C283}$ | $R^{D11}$ | $R^{D15}$ | H |
| $L_{C284}$ | $R^{D11}$ | $R^{D16}$ | H |
| $L_{C285}$ | $R^{D11}$ | $R^{D17}$ | H |
| $L_{C286}$ | $R^{D11}$ | $R^{D18}$ | H |
| $L_{C287}$ | $R^{D11}$ | $R^{D19}$ | H |
| $L_{C288}$ | $R^{D11}$ | $R^{D20}$ | H |
| $L_{C289}$ | $R^{D11}$ | $R^{D21}$ | H |
| $L_{C290}$ | $R^{D11}$ | $R^{D22}$ | H |
| $L_{C291}$ | $R^{D11}$ | $R^{D23}$ | H |
| $L_{C292}$ | $R^{D11}$ | $R^{D24}$ | H |
| $L_{C293}$ | $R^{D11}$ | $R^{D25}$ | H |
| $L_{C294}$ | $R^{D11}$ | $R^{D26}$ | H |
| $L_{C295}$ | $R^{D11}$ | $R^{D27}$ | H |
| $L_{C296}$ | $R^{D11}$ | $R^{D28}$ | H |
| $L_{C297}$ | $R^{D11}$ | $R^{D29}$ | H |
| $L_{C298}$ | $R^{D11}$ | $R^{D30}$ | H |
| $L_{C299}$ | $R^{D11}$ | $R^{D31}$ | H |
| $L_{C300}$ | $R^{D11}$ | $R^{D32}$ | H |
| $L_{C301}$ | $R^{D11}$ | $R^{D33}$ | H |
| $L_{C302}$ | $R^{D11}$ | $R^{D34}$ | H |
| $L_{C303}$ | $R^{D11}$ | $R^{D35}$ | H |
| $L_{C304}$ | $R^{D11}$ | $R^{D40}$ | H |
| $L_{C305}$ | $R^{D11}$ | $R^{D41}$ | H |
| $L_{C306}$ | $R^{D11}$ | $R^{D42}$ | H |
| $L_{C307}$ | $R^{D11}$ | $R^{D64}$ | H |
| $L_{C308}$ | $R^{D11}$ | $R^{D66}$ | H |
| $L_{C309}$ | $R^{D11}$ | $R^{D68}$ | H |
| $L_{C310}$ | $R^{D11}$ | $R^{D76}$ | H |
| $L_{C311}$ | $R^{D13}$ | $R^{D5}$ | H |
| $L_{C312}$ | $R^{D13}$ | $R^{D6}$ | H |
| $L_{C313}$ | $R^{D13}$ | $R^{D9}$ | H |
| $L_{C314}$ | $R^{D13}$ | $R^{D10}$ | H |
| $L_{C315}$ | $R^{D13}$ | $R^{D12}$ | H |
| $L_{C316}$ | $R^{D13}$ | $R^{D14}$ | H |
| $L_{C317}$ | $R^{D13}$ | $R^{D15}$ | H |
| $L_{C318}$ | $R^{D13}$ | $R^{D16}$ | H |
| $L_{C319}$ | $R^{D13}$ | $R^{D17}$ | H |
| $L_{C320}$ | $R^{D13}$ | $R^{D18}$ | H |
| $L_{C321}$ | $R^{D13}$ | $R^{D19}$ | H |
| $L_{C322}$ | $R^{D13}$ | $R^{D20}$ | H |
| $L_{C323}$ | $R^{D13}$ | $R^{D21}$ | H |

-continued

| Ligand | $R^1$ | $R^2$ | $R^3$ |
|---|---|---|---|
| $L_{C324}$ | $R^{D13}$ | $R^{D22}$ | H |
| $L_{C325}$ | $R^{D13}$ | $R^{D23}$ | H |
| $L_{C326}$ | $R^{D13}$ | $R^{D24}$ | H |
| $L_{C327}$ | $R^{D13}$ | $R^{D25}$ | H |
| $L_{C328}$ | $R^{D13}$ | $R^{D26}$ | H |
| $L_{C329}$ | $R^{D13}$ | $R^{D27}$ | H |
| $L_{C330}$ | $R^{D13}$ | $R^{D28}$ | H |
| $L_{C331}$ | $R^{D13}$ | $R^{D29}$ | H |
| $L_{C332}$ | $R^{D13}$ | $R^{D30}$ | H |
| $L_{C333}$ | $R^{D13}$ | $R^{D31}$ | H |
| $L_{C334}$ | $R^{D13}$ | $R^{D32}$ | H |
| $L_{C335}$ | $R^{D13}$ | $R^{D33}$ | H |
| $L_{C336}$ | $R^{D13}$ | $R^{D34}$ | H |
| $L_{C337}$ | $R^{D13}$ | $R^{D35}$ | H |
| $L_{C338}$ | $R^{D13}$ | $R^{D40}$ | H |
| $L_{C339}$ | $R^{D13}$ | $R^{D41}$ | H |
| $L_{C340}$ | $R^{D13}$ | $R^{D42}$ | H |
| $L_{C341}$ | $R^{D13}$ | $R^{D64}$ | H |
| $L_{C342}$ | $R^{D13}$ | $R^{D66}$ | H |
| $L_{C343}$ | $R^{D13}$ | $R^{D68}$ | H |
| $L_{C344}$ | $R^{D13}$ | $R^{D76}$ | H |
| $L_{C345}$ | $R^{D14}$ | $R^{D5}$ | H |
| $L_{C346}$ | $R^{D14}$ | $R^{D6}$ | H |
| $L_{C347}$ | $R^{D14}$ | $R^{D9}$ | H |
| $L_{C348}$ | $R^{D14}$ | $R^{D10}$ | H |
| $L_{C349}$ | $R^{D14}$ | $R^{D12}$ | H |
| $L_{C350}$ | $R^{D14}$ | $R^{D15}$ | H |
| $L_{C351}$ | $R^{D14}$ | $R^{D16}$ | H |
| $L_{C352}$ | $R^{D14}$ | $R^{D17}$ | H |
| $L_{C353}$ | $R^{D14}$ | $R^{D18}$ | H |
| $L_{C354}$ | $R^{D14}$ | $R^{D19}$ | H |
| $L_{C355}$ | $R^{D14}$ | $R^{D20}$ | H |
| $L_{C356}$ | $R^{D14}$ | $R^{D21}$ | H |
| $L_{C357}$ | $R^{D14}$ | $R^{D22}$ | H |
| $L_{C358}$ | $R^{D14}$ | $R^{D23}$ | H |
| $L_{C359}$ | $R^{D14}$ | $R^{D24}$ | H |
| $L_{C360}$ | $R^{D14}$ | $R^{D25}$ | H |
| $L_{C361}$ | $R^{D14}$ | $R^{D26}$ | H |
| $L_{C362}$ | $R^{D14}$ | $R^{D27}$ | H |
| $L_{C363}$ | $R^{D14}$ | $R^{D28}$ | F |
| $L_{C364}$ | $R^{D14}$ | $R^{D29}$ | H |
| $L_{C365}$ | $R^{D14}$ | $R^{D30}$ | H |
| $L_{C366}$ | $R^{D14}$ | $R^{D31}$ | H |
| $L_{C367}$ | $R^{D14}$ | $R^{D32}$ | H |
| $L_{C368}$ | $R^{D14}$ | $R^{D33}$ | H |
| $L_{C369}$ | $R^{D14}$ | $R^{D34}$ | H |
| $L_{C370}$ | $R^{D14}$ | $R^{D35}$ | H |
| $L_{C371}$ | $R^{D14}$ | $R^{D40}$ | H |
| $L_{C372}$ | $R^{D14}$ | $R^{D41}$ | H |
| $L_{C373}$ | $R^{D14}$ | $R^{D42}$ | H |
| $L_{C374}$ | $R^{D14}$ | $R^{D64}$ | H |
| $L_{C375}$ | $R^{D14}$ | $R^{D66}$ | H |
| $L_{C376}$ | $R^{D14}$ | $R^{D68}$ | H |
| $L_{C377}$ | $R^{D14}$ | $R^{D76}$ | H |
| $L_{C378}$ | $R^{D22}$ | $R^{D5}$ | H |
| $L_{C379}$ | $R^{D22}$ | $R^{D6}$ | H |
| $L_{C380}$ | $R^{D22}$ | $R^{D9}$ | H |
| $L_{C381}$ | $R^{D22}$ | $R^{D10}$ | H |
| $L_{C382}$ | $R^{D22}$ | $R^{D12}$ | H |
| $L_{C383}$ | $R^{D22}$ | $R^{D15}$ | H |
| $L_{C384}$ | $R^{D22}$ | $R^{D16}$ | H |
| $L_{C385}$ | $R^{D22}$ | $R^{D17}$ | H |
| $L_{C386}$ | $R^{D22}$ | $R^{D18}$ | H |
| $L_{C387}$ | $R^{D22}$ | $R^{D19}$ | H |
| $L_{C388}$ | $R^{D22}$ | $R^{D20}$ | H |
| $L_{C389}$ | $R^{D22}$ | $R^{D21}$ | H |
| $L_{C390}$ | $R^{D22}$ | $R^{D23}$ | H |
| $L_{C391}$ | $R^{D22}$ | $R^{D24}$ | H |
| $L_{C392}$ | $R^{D22}$ | $R^{D25}$ | H |
| $L_{C393}$ | $R^{D22}$ | $R^{D26}$ | H |
| $L_{C394}$ | $R^{D22}$ | $R^{D27}$ | H |
| $L_{C395}$ | $R^{D22}$ | $R^{D28}$ | H |
| $L_{C396}$ | $R^{D22}$ | $R^{D29}$ | H |
| $L_{C397}$ | $R^{D22}$ | $R^{D30}$ | H |
| $L_{C398}$ | $R^{D22}$ | $R^{D31}$ | H |
| $L_{C399}$ | $R^{D22}$ | $R^{D32}$ | H |
| $L_{C400}$ | $R^{D22}$ | $R^{D33}$ | H |

-continued

| Ligand | $R^1$ | $R^2$ | $R^3$ |
|---|---|---|---|
| $L_{C401}$ | $R^{D22}$ | $R^{D34}$ | H |
| $L_{C402}$ | $R^{D22}$ | $R^{D35}$ | H |
| $L_{C403}$ | $R^{D22}$ | $R^{D40}$ | H |
| $L_{C404}$ | $R^{D22}$ | $R^{D41}$ | H |
| $L_{C405}$ | $R^{D22}$ | $R^{D42}$ | H |
| $L_{C406}$ | $R^{D22}$ | $R^{D64}$ | H |
| $L_{C407}$ | $R^{D22}$ | $R^{D66}$ | H |
| $L_{C408}$ | $R^{D22}$ | $R^{D68}$ | H |
| $L_{C409}$ | $R^{D22}$ | $R^{D76}$ | H |
| $L_{C410}$ | $R^{D26}$ | $R^{D5}$ | H |
| $L_{C411}$ | $R^{D26}$ | $R^{D6}$ | H |
| $L_{C412}$ | $R^{D26}$ | $R^{D9}$ | H |
| $L_{C413}$ | $R^{D26}$ | $R^{D10}$ | H |
| $L_{C414}$ | $R^{D26}$ | $R^{D12}$ | H |
| $L_{C415}$ | $R^{D26}$ | $R^{D15}$ | H |
| $L_{C416}$ | $R^{D26}$ | $R^{D16}$ | H |
| $L_{C417}$ | $R^{D26}$ | $R^{D17}$ | H |
| $L_{C418}$ | $R^{D26}$ | $R^{D18}$ | H |
| $L_{C419}$ | $R^{D26}$ | $R^{D19}$ | H |
| $L_{C420}$ | $R^{D26}$ | $R^{D20}$ | H |
| $L_{C421}$ | $R^{D26}$ | $R^{D21}$ | H |
| $L_{C422}$ | $R^{D26}$ | $R^{D23}$ | H |
| $L_{C423}$ | $R^{D26}$ | $R^{D24}$ | H |
| $L_{C424}$ | $R^{D26}$ | $R^{D25}$ | H |
| $L_{C425}$ | $R^{D26}$ | $R^{D27}$ | H |
| $L_{C426}$ | $R^{D26}$ | $R^{D28}$ | H |
| $L_{C427}$ | $R^{D26}$ | $R^{D29}$ | H |
| $L_{C428}$ | $R^{D26}$ | $R^{D30}$ | H |
| $L_{C429}$ | $R^{D26}$ | $R^{D31}$ | H |
| $L_{C430}$ | $R^{D26}$ | $R^{D32}$ | H |
| $L_{C431}$ | $R^{D26}$ | $R^{D33}$ | H |
| $L_{C432}$ | $R^{D26}$ | $R^{D34}$ | H |
| $L_{C433}$ | $R^{D26}$ | $R^{D35}$ | H |
| $L_{C434}$ | $R^{D26}$ | $R^{D40}$ | H |
| $L_{C435}$ | $R^{D26}$ | $R^{D41}$ | H |
| $L_{C436}$ | $R^{D26}$ | $R^{D42}$ | H |
| $L_{C437}$ | $R^{D26}$ | $R^{D64}$ | H |
| $L_{C438}$ | $R^{D26}$ | $R^{D66}$ | H |
| $L_{C439}$ | $R^{D26}$ | $R^{D68}$ | H |
| $L_{C440}$ | $R^{D26}$ | $R^{D76}$ | H |
| $L_{C441}$ | $R^{D35}$ | $R^{D5}$ | H |
| $L_{C442}$ | $R^{D35}$ | $R^{D6}$ | H |
| $L_{C443}$ | $R^{D35}$ | $R^{D9}$ | H |
| $L_{C444}$ | $R^{D35}$ | $R^{D10}$ | H |
| $L_{C445}$ | $R^{D35}$ | $R^{D12}$ | H |
| $L_{C446}$ | $R^{D35}$ | $R^{D15}$ | H |
| $L_{C447}$ | $R^{D35}$ | $R^{D16}$ | H |
| $L_{C448}$ | $R^{D35}$ | $R^{D17}$ | H |
| $L_{C449}$ | $R^{D35}$ | $R^{D18}$ | H |
| $L_{C450}$ | $R^{D35}$ | $R^{D19}$ | H |
| $L_{C451}$ | $R^{D35}$ | $R^{D20}$ | H |
| $L_{C452}$ | $R^{D35}$ | $R^{D21}$ | H |
| $L_{C453}$ | $R^{D35}$ | $R^{D23}$ | H |
| $L_{C454}$ | $R^{D35}$ | $R^{D24}$ | H |
| $L_{C455}$ | $R^{D35}$ | $R^{D25}$ | H |
| $L_{C456}$ | $R^{D35}$ | $R^{D27}$ | H |
| $L_{C457}$ | $R^{D35}$ | $R^{D28}$ | H |
| $L_{C458}$ | $R^{D35}$ | $R^{D29}$ | H |
| $L_{C459}$ | $R^{D35}$ | $R^{D30}$ | H |
| $L_{C460}$ | $R^{D35}$ | $R^{D31}$ | H |
| $L_{C461}$ | $R^{D35}$ | $R^{D32}$ | H |
| $L_{C462}$ | $R^{D35}$ | $R^{D33}$ | H |
| $L_{C463}$ | $R^{D35}$ | $R^{D34}$ | H |
| $L_{C464}$ | $R^{D35}$ | $R^{D40}$ | H |
| $L_{C465}$ | $R^{D35}$ | $R^{D41}$ | H |
| $L_{C466}$ | $R^{D35}$ | $R^{D42}$ | H |
| $L_{C467}$ | $R^{D35}$ | $R^{D64}$ | H |
| $L_{C468}$ | $R^{D35}$ | $R^{D66}$ | H |
| $L_{C469}$ | $R^{D35}$ | $R^{D68}$ | H |
| $L_{C470}$ | $R^{D35}$ | $R^{D76}$ | H |
| $L_{C471}$ | $R^{D40}$ | $R^{D5}$ | H |
| $L_{C472}$ | $R^{D40}$ | $R^{D6}$ | H |
| $L_{C473}$ | $R^{D40}$ | $R^{D9}$ | H |
| $L_{C474}$ | $R^{D40}$ | $R^{D10}$ | H |
| $L_{C475}$ | $R^{D40}$ | $R^{D12}$ | H |
| $L_{C476}$ | $R^{D40}$ | $R^{D13}$ | H |
| $L_{C477}$ | $R^{D40}$ | $R^{D16}$ | H |

-continued

| Ligand | $R^1$ | $R^2$ | $R^3$ |
|---|---|---|---|
| $L_{C478}$ | $R^{D40}$ | $R^{D17}$ | H |
| $L_{C479}$ | $R^{D40}$ | $R^{D18}$ | H |
| $L_{C480}$ | $R^{D40}$ | $R^{D19}$ | H |
| $L_{C481}$ | $R^{D40}$ | $R^{D20}$ | H |
| $L_{C482}$ | $R^{D40}$ | $R^{D21}$ | H |
| $L_{C483}$ | $R^{D40}$ | $R^{D23}$ | H |
| $L_{C484}$ | $R^{D40}$ | $R^{D24}$ | H |
| $L_{C485}$ | $R^{D40}$ | $R^{D25}$ | H |
| $L_{C486}$ | $R^{D40}$ | $R^{D27}$ | H |
| $L_{C487}$ | $R^{D40}$ | $R^{D28}$ | H |
| $L_{C488}$ | $R^{D40}$ | $R^{D29}$ | H |
| $L_{C489}$ | $R^{D40}$ | $R^{D30}$ | H |
| $L_{C490}$ | $R^{D40}$ | $R^{D31}$ | H |
| $L_{C491}$ | $R^{D40}$ | $R^{D32}$ | H |
| $L_{C492}$ | $R^{D40}$ | $R^{D33}$ | H |
| $L_{C493}$ | $R^{D40}$ | $R^{D34}$ | H |
| $L_{C494}$ | $R^{D40}$ | $R^{D41}$ | H |
| $L_{C495}$ | $R^{D40}$ | $R^{D42}$ | H |
| $L_{C496}$ | $R^{D40}$ | $R^{D64}$ | H |
| $L_{C497}$ | $R^{D40}$ | $R^{D66}$ | H |
| $L_{C498}$ | $R^{D40}$ | $R^{D68}$ | H |
| $L_{C499}$ | $R^{D40}$ | $R^{D76}$ | H |
| $L_{C500}$ | $R^{D41}$ | $R^{D5}$ | H |
| $L_{C501}$ | $R^{D41}$ | $R^{D6}$ | H |
| $L_{C502}$ | $R^{D41}$ | $R^{D9}$ | H |
| $L_{C503}$ | $R^{D41}$ | $R^{D10}$ | H |
| $L_{C504}$ | $R^{D41}$ | $R^{D12}$ | H |
| $L_{C505}$ | $R^{D41}$ | $R^{D15}$ | H |
| $L_{C506}$ | $R^{D41}$ | $R^{D16}$ | H |
| $L_{C507}$ | $R^{D41}$ | $R^{D17}$ | H |
| $L_{C508}$ | $R^{D41}$ | $R^{D18}$ | H |
| $L_{C509}$ | $R^{D41}$ | $R^{D19}$ | H |
| $L_{C510}$ | $R^{D41}$ | $R^{D20}$ | H |
| $L_{C511}$ | $R^{D41}$ | $R^{D21}$ | H |
| $L_{C512}$ | $R^{D41}$ | $R^{D23}$ | H |
| $L_{C513}$ | $R^{D41}$ | $R^{D24}$ | H |
| $L_{C514}$ | $R^{D41}$ | $R^{D25}$ | H |
| $L_{C515}$ | $R^{D41}$ | $R^{D27}$ | H |
| $L_{C516}$ | $R^{D41}$ | $R^{D28}$ | H |
| $L_{C517}$ | $R^{D41}$ | $R^{D29}$ | H |
| $L_{C518}$ | $R^{D41}$ | $R^{D30}$ | H |
| $L_{C519}$ | $R^{D41}$ | $R^{D31}$ | H |
| $L_{C520}$ | $R^{D41}$ | $R^{D32}$ | H |
| $L_{C521}$ | $R^{D41}$ | $R^{D33}$ | H |
| $L_{C522}$ | $R^{D41}$ | $R^{D34}$ | H |
| $L_{C523}$ | $R^{D41}$ | $R^{D42}$ | H |
| $L_{C524}$ | $R^{D41}$ | $R^{D64}$ | H |
| $L_{C525}$ | $R^{D41}$ | $R^{D66}$ | H |
| $L_{C526}$ | $R^{D41}$ | $R^{D68}$ | H |
| $L_{C527}$ | $R^{D41}$ | $R^{D76}$ | H |
| $L_{C528}$ | $R^{D64}$ | $R^{D5}$ | H |
| $L_{C529}$ | $R^{D64}$ | $R^{D6}$ | H |
| $L_{C530}$ | $R^{D64}$ | $R^{D9}$ | H |
| $L_{C531}$ | $R^{D64}$ | $R^{D10}$ | H |
| $L_{C532}$ | $R^{D64}$ | $R^{D12}$ | H |
| $L_{C533}$ | $R^{D64}$ | $R^{D15}$ | H |
| $L_{C534}$ | $R^{D64}$ | $R^{D16}$ | H |
| $L_{C535}$ | $R^{D64}$ | $R^{D17}$ | H |
| $L_{C536}$ | $R^{D64}$ | $R^{D18}$ | H |
| $L_{C537}$ | $R^{D64}$ | $R^{D19}$ | H |
| $L_{C538}$ | $R^{D64}$ | $R^{D20}$ | H |
| $L_{C539}$ | $R^{D64}$ | $R^{D21}$ | H |
| $L_{C540}$ | $R^{D64}$ | $R^{D23}$ | H |
| $L_{C541}$ | $R^{D64}$ | $R^{D24}$ | H |
| $L_{C542}$ | $R^{D64}$ | $R^{D25}$ | H |
| $L_{C543}$ | $R^{D64}$ | $R^{D27}$ | H |
| $L_{C544}$ | $R^{D64}$ | $R^{D28}$ | H |
| $L_{C545}$ | $R^{D64}$ | $R^{D29}$ | H |
| $L_{C546}$ | $R^{D64}$ | $R^{D30}$ | H |
| $L_{C547}$ | $R^{D64}$ | $R^{D31}$ | H |
| $L_{C548}$ | $R^{D64}$ | $R^{D32}$ | H |
| $L_{C549}$ | $R^{D64}$ | $R^{D33}$ | H |
| $L_{C550}$ | $R^{D64}$ | $R^{D34}$ | H |
| $L_{C551}$ | $R^{D64}$ | $R^{D42}$ | H |
| $L_{C552}$ | $R^{D64}$ | $R^{D64}$ | H |
| $L_{C553}$ | $R^{D64}$ | $R^{D66}$ | H |
| $L_{C554}$ | $R^{D64}$ | $R^{D68}$ | H |

-continued

| Ligand | $R^1$ | $R^2$ | $R^3$ |
|---|---|---|---|
| $L_{C555}$ | $R^{D64}$ | $R^{D76}$ | H |
| $L_{C556}$ | $R^{D66}$ | $R^{D5}$ | H |
| $L_{C557}$ | $R^{D66}$ | $R^{D6}$ | H |
| $L_{C558}$ | $R^{D66}$ | $R^{D9}$ | H |
| $L_{C559}$ | $R^{D66}$ | $R^{D10}$ | H |
| $L_{C560}$ | $R^{D66}$ | $R^{D12}$ | H |
| $L_{C561}$ | $R^{D66}$ | $R^{D15}$ | H |
| $L_{C562}$ | $R^{D66}$ | $R^{D16}$ | H |
| $L_{C563}$ | $R^{D66}$ | $R^{D17}$ | H |
| $L_{C564}$ | $R^{D66}$ | $R^{D18}$ | H |
| $L_{C565}$ | $R^{D66}$ | $R^{D19}$ | H |
| $L_{C566}$ | $R^{D66}$ | $R^{D20}$ | H |
| $L_{C567}$ | $R^{D66}$ | $R^{D21}$ | H |
| $L_{C568}$ | $R^{D66}$ | $R^{D23}$ | H |
| $L_{C569}$ | $R^{D66}$ | $R^{D24}$ | H |
| $L_{C570}$ | $R^{D66}$ | $R^{D25}$ | H |
| $L_{C571}$ | $R^{D66}$ | $R^{D27}$ | H |
| $L_{C572}$ | $R^{D66}$ | $R^{D28}$ | H |
| $L_{C573}$ | $R^{D66}$ | $R^{D29}$ | H |
| $L_{C574}$ | $R^{D66}$ | $R^{D30}$ | H |
| $L_{C575}$ | $R^{D66}$ | $R^{D31}$ | H |
| $L_{C576}$ | $R^{D66}$ | $R^{D32}$ | H |
| $L_{C577}$ | $R^{D66}$ | $R^{D33}$ | H |
| $L_{C578}$ | $R^{D66}$ | $R^{D34}$ | H |
| $L_{C579}$ | $R^{D66}$ | $R^{D42}$ | H |
| $L_{C580}$ | $R^{D66}$ | $R^{D68}$ | H |
| $L_{C581}$ | $R^{D66}$ | $R^{D76}$ | H |
| $L_{C582}$ | $R^{D68}$ | $R^{D5}$ | H |
| $L_{C583}$ | $R^{D68}$ | $R^{D6}$ | H |
| $L_{C584}$ | $R^{D68}$ | $R^{D9}$ | H |
| $L_{C585}$ | $R^{D68}$ | $R^{D10}$ | H |
| $L_{C586}$ | $R^{D68}$ | $R^{D12}$ | H |
| $L_{C587}$ | $R^{D68}$ | $R^{D15}$ | H |
| $L_{C588}$ | $R^{D68}$ | $R^{D16}$ | H |
| $L_{C589}$ | $R^{D68}$ | $R^{D17}$ | H |
| $L_{C590}$ | $R^{D68}$ | $R^{D18}$ | H |
| $L_{C591}$ | $R^{D68}$ | $R^{D19}$ | H |
| $L_{C592}$ | $R^{D68}$ | $R^{D20}$ | H |
| $L_{C593}$ | $R^{D68}$ | $R^{D21}$ | H |
| $L_{C594}$ | $R^{D68}$ | $R^{D23}$ | H |
| $L_{C595}$ | $R^{D68}$ | $R^{D24}$ | H |
| $L_{C596}$ | $R^{D68}$ | $R^{D25}$ | H |
| $L_{C597}$ | $R^{D68}$ | $R^{D27}$ | H |
| $L_{C598}$ | $R^{D68}$ | $R^{D28}$ | H |
| $L_{C599}$ | $R^{D68}$ | $R^{D29}$ | H |
| $L_{C600}$ | $R^{D68}$ | $R^{D30}$ | H |
| $L_{C601}$ | $R^{D68}$ | $R^{D31}$ | H |
| $L_{C602}$ | $R^{D68}$ | $R^{D32}$ | H |
| $L_{C603}$ | $R^{D68}$ | $R^{D33}$ | H |
| $L_{C604}$ | $R^{D68}$ | $R^{D34}$ | H |
| $L_{C605}$ | $R^{D68}$ | $R^{D42}$ | H |
| $L_{C606}$ | $R^{D68}$ | $R^{D76}$ | H |
| $L_{C607}$ | $R^{D76}$ | $R^{D5}$ | H |
| $L_{C608}$ | $R^{D76}$ | $R^{D6}$ | H |
| $L_{C609}$ | $R^{D76}$ | $R^{D9}$ | H |
| $L_{C610}$ | $R^{D76}$ | $R^{D10}$ | H |
| $L_{C611}$ | $R^{D76}$ | $R^{D12}$ | H |
| $L_{C612}$ | $R^{D76}$ | $R^{D15}$ | H |
| $L_{C613}$ | $R^{D76}$ | $R^{D16}$ | H |
| $L_{C614}$ | $R^{D76}$ | $R^{D17}$ | H |
| $L_{C615}$ | $R^{D76}$ | $R^{D18}$ | H |
| $L_{C616}$ | $R^{D76}$ | $R^{D19}$ | H |
| $L_{C617}$ | $R^{D76}$ | $R^{D20}$ | H |
| $L_{C618}$ | $R^{D76}$ | $R^{D21}$ | H |
| $L_{C619}$ | $R^{D76}$ | $R^{D23}$ | H |
| $L_{C620}$ | $R^{D76}$ | $R^{D24}$ | H |
| $L_{C621}$ | $R^{D76}$ | $R^{D25}$ | H |
| $L_{C622}$ | $R^{D76}$ | $R^{D27}$ | H |
| $L_{C623}$ | $R^{D76}$ | $R^{D28}$ | H |
| $L_{C624}$ | $R^{D76}$ | $R^{D29}$ | H |
| $L_{C625}$ | $R^{D76}$ | $R^{D30}$ | H |
| $L_{C626}$ | $R^{D76}$ | $R^{D31}$ | H |
| $L_{C627}$ | $R^{D76}$ | $R^{D32}$ | H |
| $L_{C628}$ | $R^{D76}$ | $R^{D33}$ | H |
| $L_{C629}$ | $R^{D76}$ | $R^{D34}$ | H |
| $L_{C630}$ | $R^{D76}$ | $R^{D42}$ | H |
| $L_{C631}$ | $R^{D1}$ | $R^{D1}$ | $R^{D1}$ |

-continued

| Ligand | $R^1$ | $R^2$ | $R^3$ |
|---|---|---|---|
| $L_{C632}$ | $R^{D2}$ | $R^{D2}$ | $R^{D1}$ |
| $L_{C633}$ | $R^{D3}$ | $R^{D3}$ | $R^{D1}$ |
| $L_{C634}$ | $R^{D4}$ | $R^{D4}$ | $R^{D1}$ |
| $L_{C635}$ | $R^{D5}$ | $R^{D5}$ | $R^{D1}$ |
| $L_{C636}$ | $R^{D6}$ | $R^{D6}$ | $R^{D1}$ |
| $L_{C637}$ | $R^{D7}$ | $R^{D7}$ | $R^{D1}$ |
| $L_{C638}$ | $R^{D8}$ | $R^{D8}$ | $R^{D1}$ |
| $L_{C639}$ | $R^{D9}$ | $R^{D9}$ | $R^{D1}$ |
| $L_{C640}$ | $R^{D10}$ | $R^{D10}$ | $R^{D1}$ |
| $L_{C641}$ | $R^{D11}$ | $R^{D11}$ | $R^{D1}$ |
| $L_{C642}$ | $R^{D12}$ | $R^{D12}$ | $R^{D1}$ |
| $L_{C643}$ | $R^{D13}$ | $R^{D13}$ | $R^{D1}$ |
| $L_{C644}$ | $R^{D14}$ | $R^{D14}$ | $R^{D1}$ |
| $L_{C645}$ | $R^{D15}$ | $R^{D15}$ | $R^{D1}$ |
| $L_{C646}$ | $R^{D16}$ | $R^{D16}$ | $R^{D1}$ |
| $L_{C647}$ | $R^{D17}$ | $R^{D17}$ | $R^{D1}$ |
| $L_{C648}$ | $R^{D18}$ | $R^{D18}$ | $R^{D1}$ |
| $L_{C649}$ | $R^{D19}$ | $R^{D19}$ | $R^{D1}$ |
| $L_{C650}$ | $R^{D20}$ | $R^{D20}$ | $R^{D1}$ |
| $L_{C651}$ | $R^{D21}$ | $R^{D21}$ | $R^{D1}$ |
| $L_{C652}$ | $R^{D22}$ | $R^{D22}$ | $R^{D1}$ |
| $L_{C653}$ | $R^{D23}$ | $R^{D23}$ | $R^{D1}$ |
| $L_{C654}$ | $R^{D24}$ | $R^{D24}$ | $R^{D1}$ |
| $L_{C655}$ | $R^{D25}$ | $R^{D25}$ | $R^{D1}$ |
| $L_{C656}$ | $R^{D26}$ | $R^{D26}$ | $R^{D1}$ |
| $L_{C657}$ | $R^{D27}$ | $R^{D27}$ | $R^{D1}$ |
| $L_{C658}$ | $R^{D28}$ | $R^{D28}$ | $R^{D1}$ |
| $L_{C659}$ | $R^{D29}$ | $R^{D29}$ | $R^{D1}$ |
| $L_{C660}$ | $R^{D30}$ | $R^{D30}$ | $R^{D1}$ |
| $L_{C661}$ | $R^{D31}$ | $R^{D31}$ | $R^{D1}$ |
| $L_{C662}$ | $R^{D32}$ | $R^{D32}$ | $R^{D1}$ |
| $L_{C663}$ | $R^{D33}$ | $R^{D33}$ | $R^{D1}$ |
| $L_{C664}$ | $R^{D34}$ | $R^{D34}$ | $R^{D1}$ |
| $L_{C665}$ | $R^{D35}$ | $R^{D35}$ | $R^{D1}$ |
| $L_{C666}$ | $R^{D40}$ | $R^{D40}$ | $R^{D1}$ |
| $L_{C667}$ | $R^{D41}$ | $R^{D41}$ | $R^{D1}$ |
| $L_{C668}$ | $R^{D42}$ | $R^{D42}$ | $R^{D1}$ |
| $L_{C669}$ | $R^{D64}$ | $R^{D64}$ | $R^{D1}$ |
| $L_{C670}$ | $R^{D66}$ | $R^{D66}$ | $R^{D1}$ |
| $L_{C671}$ | $R^{D68}$ | $R^{D68}$ | $R^{D1}$ |
| $L_{C672}$ | $R^{D76}$ | $R^{D76}$ | $R^{D1}$ |
| $L_{C673}$ | $R^{D1}$ | $R^{D2}$ | $R^{D1}$ |
| $L_{C674}$ | $R^{D1}$ | $R^{D3}$ | $R^{D1}$ |
| $L_{C675}$ | $R^{D1}$ | $R^{D4}$ | $R^{D1}$ |
| $L_{C676}$ | $R^{D1}$ | $R^{D5}$ | $R^{D1}$ |
| $L_{C677}$ | $R^{D1}$ | $R^{D6}$ | $R^{D1}$ |
| $L_{C678}$ | $R^{D1}$ | $R^{D7}$ | $R^{D1}$ |
| $L_{C679}$ | $R^{D1}$ | $R^{D8}$ | $R^{D1}$ |
| $L_{C680}$ | $R^{D1}$ | $R^{D9}$ | $R^{D1}$ |
| $L_{C681}$ | $R^{D1}$ | $R^{D10}$ | $R^{D1}$ |
| $L_{C682}$ | $R^{D1}$ | $R^{D11}$ | $R^{D1}$ |
| $L_{C683}$ | $R^{D1}$ | $R^{D12}$ | $R^{D1}$ |
| $L_{C684}$ | $R^{D1}$ | $R^{D13}$ | $R^{D1}$ |
| $L_{C685}$ | $R^{D1}$ | $R^{D14}$ | $R^{D1}$ |
| $L_{C686}$ | $R^{D1}$ | $R^{D15}$ | $R^{D1}$ |
| $L_{C687}$ | $R^{D1}$ | $R^{D16}$ | $R^{D1}$ |
| $L_{C688}$ | $R^{D1}$ | $R^{D17}$ | $R^{D1}$ |
| $L_{C689}$ | $R^{D1}$ | $R^{D18}$ | $R^{D1}$ |
| $L_{C690}$ | $R^{D1}$ | $R^{D19}$ | $R^{D1}$ |
| $L_{C691}$ | $R^{D1}$ | $R^{D20}$ | $R^{D1}$ |
| $L_{C692}$ | $R^{D1}$ | $R^{D21}$ | $R^{D1}$ |
| $L_{C693}$ | $R^{D1}$ | $R^{D22}$ | $R^{D1}$ |
| $L_{C694}$ | $R^{D1}$ | $R^{D23}$ | $R^{D1}$ |
| $L_{C695}$ | $R^{D1}$ | $R^{D24}$ | $R^{D1}$ |
| $L_{C696}$ | $R^{D1}$ | $R^{D25}$ | $R^{D1}$ |
| $L_{C697}$ | $R^{D1}$ | $R^{D26}$ | $R^{D1}$ |
| $L_{C698}$ | $R^{D1}$ | $R^{D27}$ | $R^{D1}$ |
| $L_{C699}$ | $R^{D1}$ | $R^{D28}$ | $R^{D1}$ |
| $L_{C700}$ | $R^{D1}$ | $R^{D29}$ | $R^{D1}$ |
| $L_{C701}$ | $R^{D1}$ | $R^{D30}$ | $R^{D1}$ |
| $L_{C702}$ | $R^{D1}$ | $R^{D31}$ | $R^{D1}$ |
| $L_{C703}$ | $R^{D1}$ | $R^{D32}$ | $R^{D1}$ |
| $L_{C704}$ | $R^{D1}$ | $R^{D33}$ | $R^{D1}$ |
| $L_{C705}$ | $R^{D1}$ | $R^{D34}$ | $R^{D1}$ |
| $L_{C706}$ | $R^{D1}$ | $R^{D35}$ | $R^{D1}$ |
| $L_{C707}$ | $R^{D1}$ | $R^{D40}$ | $R^{D1}$ |
| $L_{C708}$ | $R^{D1}$ | $R^{D41}$ | $R^{D1}$ |

-continued

| Ligand | $R^1$ | $R^2$ | $R^3$ |
|---|---|---|---|
| $L_{C709}$ | $R^{D1}$ | $R^{D42}$ | $R^{D1}$ |
| $L_{C710}$ | $R^{D1}$ | $R^{D64}$ | $R^{D1}$ |
| $L_{C711}$ | $R^{D1}$ | $R^{D66}$ | $R^{D1}$ |
| $L_{C712}$ | $R^{D1}$ | $R^{D68}$ | $R^{D1}$ |
| $L_{C713}$ | $R^{D1}$ | $R^{D76}$ | $R^{D1}$ |
| $L_{C714}$ | $R^{D2}$ | $R^{D1}$ | $R^{D1}$ |
| $L_{C715}$ | $R^{D2}$ | $R^{D3}$ | $R^{D1}$ |
| $L_{C716}$ | $R^{D2}$ | $R^{D4}$ | $R^{D1}$ |
| $L_{C717}$ | $R^{D2}$ | $R^{D5}$ | $R^{D1}$ |
| $L_{C718}$ | $R^{D2}$ | $R^{D6}$ | $R^{D1}$ |
| $L_{C719}$ | $R^{D2}$ | $R^{D7}$ | $R^{D1}$ |
| $L_{C720}$ | $R^{D2}$ | $R^{D8}$ | $R^{D1}$ |
| $L_{C721}$ | $R^{D2}$ | $R^{D9}$ | $R^{D1}$ |
| $L_{C722}$ | $R^{D2}$ | $R^{D10}$ | $R^{D1}$ |
| $L_{C723}$ | $R^{D2}$ | $R^{D11}$ | $R^{D1}$ |
| $L_{C724}$ | $R^{D2}$ | $R^{D12}$ | $R^{D1}$ |
| $L_{C725}$ | $R^{D2}$ | $R^{D13}$ | $R^{D1}$ |
| $L_{C726}$ | $R^{D2}$ | $R^{D14}$ | $R^{D1}$ |
| $L_{C727}$ | $R^{D2}$ | $R^{D15}$ | $R^{D1}$ |
| $L_{C728}$ | $R^{D2}$ | $R^{D16}$ | $R^{D1}$ |
| $L_{C729}$ | $R^{D2}$ | $R^{D17}$ | $R^{D1}$ |
| $L_{C730}$ | $R^{D2}$ | $R^{D18}$ | $R^{D1}$ |
| $L_{C731}$ | $R^{D2}$ | $R^{D19}$ | $R^{D1}$ |
| $L_{C732}$ | $R^{D2}$ | $R^{D20}$ | $R^{D1}$ |
| $L_{C733}$ | $R^{D2}$ | $R^{D21}$ | $R^{D1}$ |
| $L_{C734}$ | $R^{D2}$ | $R^{D22}$ | $R^{D1}$ |
| $L_{C735}$ | $R^{D2}$ | $R^{D23}$ | $R^{D1}$ |
| $L_{C736}$ | $R^{D2}$ | $R^{D24}$ | $R^{D1}$ |
| $L_{C737}$ | $R^{D2}$ | $R^{D25}$ | $R^{D1}$ |
| $L_{C738}$ | $R^{D2}$ | $R^{D26}$ | $R^{D1}$ |
| $L_{C739}$ | $R^{D2}$ | $R^{D27}$ | $R^{D1}$ |
| $L_{C740}$ | $R^{D2}$ | $R^{D28}$ | $R^{D1}$ |
| $L_{C741}$ | $R^{D2}$ | $R^{D29}$ | $R^{D1}$ |
| $L_{C742}$ | $R^{D2}$ | $R^{D30}$ | $R^{D1}$ |
| $L_{C743}$ | $R^{D2}$ | $R^{D31}$ | $R^{D1}$ |
| $L_{C744}$ | $R^{D2}$ | $R^{D32}$ | $R^{D1}$ |
| $L_{C745}$ | $R^{D2}$ | $R^{D33}$ | $R^{D1}$ |
| $L_{C746}$ | $R^{D2}$ | $R^{D34}$ | $R^{D1}$ |
| $L_{C747}$ | $R^{D2}$ | $R^{D35}$ | $R^{D1}$ |
| $L_{C748}$ | $R^{D2}$ | $R^{D40}$ | $R^{D1}$ |
| $L_{C749}$ | $R^{D2}$ | $R^{D41}$ | $R^{D1}$ |
| $L_{C750}$ | $R^{D2}$ | $R^{D42}$ | $R^{D1}$ |
| $L_{C751}$ | $R^{D2}$ | $R^{D64}$ | $R^{D1}$ |
| $L_{C752}$ | $R^{D2}$ | $R^{D66}$ | $R^{D1}$ |
| $L_{C753}$ | $R^{D2}$ | $R^{D68}$ | $R^{D1}$ |
| $L_{C754}$ | $R^{D2}$ | $R^{D76}$ | $R^{D1}$ |
| $L_{C755}$ | $R^{D3}$ | $R^{D4}$ | $R^{D1}$ |
| $L_{C756}$ | $R^{D3}$ | $R^{D5}$ | $R^{D1}$ |
| $L_{C757}$ | $R^{D3}$ | $R^{D6}$ | $R^{D1}$ |
| $L_{C758}$ | $R^{D3}$ | $R^{D7}$ | $R^{D1}$ |
| $L_{C759}$ | $R^{D3}$ | $R^{D8}$ | $R^{D1}$ |
| $L_{C760}$ | $R^{D3}$ | $R^{D9}$ | $R^{D1}$ |
| $L_{C761}$ | $R^{D3}$ | $R^{D10}$ | $R^{D1}$ |
| $L_{C762}$ | $R^{D3}$ | $R^{D11}$ | $R^{D1}$ |
| $L_{C763}$ | $R^{D3}$ | $R^{D12}$ | $R^{D1}$ |
| $L_{C764}$ | $R^{D3}$ | $R^{D13}$ | $R^{D1}$ |
| $L_{C765}$ | $R^{D3}$ | $R^{D14}$ | $R^{D1}$ |
| $L_{C766}$ | $R^{D3}$ | $R^{D15}$ | $R^{D1}$ |
| $L_{C767}$ | $R^{D3}$ | $R^{D16}$ | $R^{D1}$ |
| $L_{C768}$ | $R^{D3}$ | $R^{D17}$ | $R^{D1}$ |
| $L_{C769}$ | $R^{D3}$ | $R^{D18}$ | $R^{D1}$ |
| $L_{C770}$ | $R^{D3}$ | $R^{D19}$ | $R^{D1}$ |
| $L_{C771}$ | $R^{D3}$ | $R^{D20}$ | $R^{D1}$ |
| $L_{C772}$ | $R^{D3}$ | $R^{D21}$ | $R^{D1}$ |
| $L_{C773}$ | $R^{D3}$ | $R^{D22}$ | $R^{D1}$ |
| $L_{C774}$ | $R^{D3}$ | $R^{D23}$ | $R^{D1}$ |
| $L_{C775}$ | $R^{D3}$ | $R^{D24}$ | $R^{D1}$ |
| $L_{C776}$ | $R^{D3}$ | $R^{D25}$ | $R^{D1}$ |
| $L_{C777}$ | $R^{D3}$ | $R^{D26}$ | $R^{D1}$ |
| $L_{C778}$ | $R^{D3}$ | $R^{D27}$ | $R^{D1}$ |
| $L_{C779}$ | $R^{D3}$ | $R^{D28}$ | $R^{D1}$ |
| $L_{C780}$ | $R^{D3}$ | $R^{D29}$ | $R^{D1}$ |
| $L_{C781}$ | $R^{D3}$ | $R^{D30}$ | $R^{D1}$ |
| $L_{C782}$ | $R^{D3}$ | $R^{D31}$ | $R^{D1}$ |
| $L_{C783}$ | $R^{D3}$ | $R^{D32}$ | $R^{D1}$ |
| $L_{C784}$ | $R^{D3}$ | $R^{D33}$ | $R^{D1}$ |
| $L_{C785}$ | $R^{D3}$ | $R^{D34}$ | $R^{D1}$ |

-continued

| Ligand | $R^1$ | $R^2$ | $R^3$ |
|---|---|---|---|
| $L_{C786}$ | $R^{D3}$ | $R^{D35}$ | $R^{D1}$ |
| $L_{C787}$ | $R^{D3}$ | $R^{D40}$ | $R^{D1}$ |
| $L_{C788}$ | $R^{D3}$ | $R^{D41}$ | $R^{D1}$ |
| $L_{C789}$ | $R^{D3}$ | $R^{D42}$ | $R^{D1}$ |
| $L_{C790}$ | $R^{D3}$ | $R^{D64}$ | $R^{D1}$ |
| $L_{C791}$ | $R^{D3}$ | $R^{D66}$ | $R^{D1}$ |
| $L_{C792}$ | $R^{D3}$ | $R^{D68}$ | $R^{D1}$ |
| $L_{C793}$ | $R^{D3}$ | $R^{D76}$ | $R^{D1}$ |
| $L_{C794}$ | $R^{D4}$ | $R^{D5}$ | $R^{D1}$ |
| $L_{C795}$ | $R^{D4}$ | $R^{D6}$ | $R^{D1}$ |
| $L_{C796}$ | $R^{D4}$ | $R^{D7}$ | $R^{D1}$ |
| $L_{C797}$ | $R^{D4}$ | $R^{D8}$ | $R^{D1}$ |
| $L_{C798}$ | $R^{D4}$ | $R^{D9}$ | $R^{D1}$ |
| $L_{C799}$ | $R^{D4}$ | $R^{D10}$ | $R^{D1}$ |
| $L_{C800}$ | $R^{D4}$ | $R^{D11}$ | $R^{D1}$ |
| $L_{C801}$ | $R^{D4}$ | $R^{D12}$ | $R^{D1}$ |
| $L_{C802}$ | $R^{D4}$ | $R^{D13}$ | $R^{D1}$ |
| $L_{C803}$ | $R^{D4}$ | $R^{D14}$ | $R^{D1}$ |
| $L_{C804}$ | $R^{D4}$ | $R^{D15}$ | $R^{D1}$ |
| $L_{C805}$ | $R^{D4}$ | $R^{D16}$ | $R^{D1}$ |
| $L_{C806}$ | $R^{D4}$ | $R^{D17}$ | $R^{D1}$ |
| $L_{C807}$ | $R^{D4}$ | $R^{D18}$ | $R^{D1}$ |
| $L_{C808}$ | $R^{D4}$ | $R^{D19}$ | $R^{D1}$ |
| $L_{C809}$ | $R^{D4}$ | $R^{D20}$ | $R^{D1}$ |
| $L_{C810}$ | $R^{D4}$ | $R^{D21}$ | $R^{D1}$ |
| $L_{C811}$ | $R^{D4}$ | $R^{D22}$ | $R^{D1}$ |
| $L_{C812}$ | $R^{D4}$ | $R^{D23}$ | $R^{D1}$ |
| $L_{C813}$ | $R^{D4}$ | $R^{D24}$ | $R^{D1}$ |
| $L_{C814}$ | $R^{D4}$ | $R^{D25}$ | $R^{D1}$ |
| $L_{C815}$ | $R^{D4}$ | $R^{D26}$ | $R^{D1}$ |
| $L_{C816}$ | $R^{D4}$ | $R^{D27}$ | $R^{D1}$ |
| $L_{C817}$ | $R^{D4}$ | $R^{D28}$ | $R^{D1}$ |
| $L_{C818}$ | $R^{D4}$ | $R^{D29}$ | $R^{D1}$ |
| $L_{C819}$ | $R^{D4}$ | $R^{D30}$ | $R^{D1}$ |
| $L_{C820}$ | $R^{D4}$ | $R^{D31}$ | $R^{D1}$ |
| $L_{C821}$ | $R^{D4}$ | $R^{D32}$ | $R^{D1}$ |
| $L_{C822}$ | $R^{D4}$ | $R^{D33}$ | $R^{D1}$ |
| $L_{C823}$ | $R^{D4}$ | $R^{D34}$ | $R^{D1}$ |
| $L_{C824}$ | $R^{D4}$ | $R^{D35}$ | $R^{D1}$ |
| $L_{C825}$ | $R^{D4}$ | $R^{D40}$ | $R^{D1}$ |
| $L_{C826}$ | $R^{D4}$ | $R^{D41}$ | $R^{D1}$ |
| $L_{C827}$ | $R^{D4}$ | $R^{D42}$ | $R^{D1}$ |
| $L_{C828}$ | $R^{D4}$ | $R^{D64}$ | $R^{D1}$ |
| $L_{C829}$ | $R^{D4}$ | $R^{D66}$ | $R^{D1}$ |
| $L_{C830}$ | $R^{D4}$ | $R^{D68}$ | $R^{D1}$ |
| $L_{C831}$ | $R^{D4}$ | $R^{D76}$ | $R^{D1}$ |
| $L_{C832}$ | $R^{D4}$ | $R^{D1}$ | $R^{D1}$ |
| $L_{C833}$ | $R^{D7}$ | $R^{D5}$ | $R^{D1}$ |
| $L_{C834}$ | $R^{D7}$ | $R^{D6}$ | $R^{D1}$ |
| $L_{C835}$ | $R^{D7}$ | $R^{D8}$ | $R^{D1}$ |
| $L_{C836}$ | $R^{D7}$ | $R^{D9}$ | $R^{D1}$ |
| $L_{C837}$ | $R^{D7}$ | $R^{D10}$ | $R^{D1}$ |
| $L_{C838}$ | $R^{D7}$ | $R^{D11}$ | $R^{D1}$ |
| $L_{C839}$ | $R^{D7}$ | $R^{D12}$ | $R^{D1}$ |
| $L_{C840}$ | $R^{D7}$ | $R^{D13}$ | $R^{D1}$ |
| $L_{C841}$ | $R^{D7}$ | $R^{D14}$ | $R^{D1}$ |
| $L_{C842}$ | $R^{D7}$ | $R^{D15}$ | $R^{D1}$ |
| $L_{C843}$ | $R^{D7}$ | $R^{D16}$ | $R^{D1}$ |
| $L_{C844}$ | $R^{D7}$ | $R^{D17}$ | $R^{D1}$ |
| $L_{C845}$ | $R^{D7}$ | $R^{D18}$ | $R^{D1}$ |
| $L_{C846}$ | $R^{D7}$ | $R^{D19}$ | $R^{D1}$ |
| $L_{C847}$ | $R^{D7}$ | $R^{D20}$ | $R^{D1}$ |
| $L_{C848}$ | $R^{D7}$ | $R^{D21}$ | $R^{D1}$ |
| $L_{C849}$ | $R^{D7}$ | $R^{D22}$ | $R^{D1}$ |
| $L_{C850}$ | $R^{D7}$ | $R^{D23}$ | $R^{D1}$ |
| $L_{C851}$ | $R^{D7}$ | $R^{D24}$ | $R^{D1}$ |
| $L_{C852}$ | $R^{D7}$ | $R^{D25}$ | $R^{D1}$ |
| $L_{C853}$ | $R^{D7}$ | $R^{D26}$ | $R^{D1}$ |
| $L_{C854}$ | $R^{D7}$ | $R^{D27}$ | $R^{D1}$ |
| $L_{C855}$ | $R^{D7}$ | $R^{D28}$ | $R^{D1}$ |
| $L_{C856}$ | $R^{D7}$ | $R^{D29}$ | $R^{D1}$ |
| $L_{C857}$ | $R^{D7}$ | $R^{D30}$ | $R^{D1}$ |
| $L_{C858}$ | $R^{D7}$ | $R^{D31}$ | $R^{D1}$ |
| $L_{C859}$ | $R^{D7}$ | $R^{D32}$ | $R^{D1}$ |
| $L_{C860}$ | $R^{D7}$ | $R^{D33}$ | $R^{D1}$ |
| $L_{C861}$ | $R^{D7}$ | $R^{D34}$ | $R^{D1}$ |
| $L_{C862}$ | $R^{D7}$ | $R^{D35}$ | $R^{D1}$ |

-continued

| Ligand | $R^1$ | $R^2$ | $R^3$ |
|---|---|---|---|
| $L_{C863}$ | $R^{D7}$ | $R^{D40}$ | $R^{D1}$ |
| $L_{C864}$ | $R^{D7}$ | $R^{D41}$ | $R^{D1}$ |
| $L_{C865}$ | $R^{D7}$ | $R^{D42}$ | $R^{D1}$ |
| $L_{C866}$ | $R^{D7}$ | $R^{D64}$ | $R^{D1}$ |
| $L_{C867}$ | $R^{D7}$ | $R^{D66}$ | $R^{D1}$ |
| $L_{C868}$ | $R^{D7}$ | $R^{D68}$ | $R^{D1}$ |
| $L_{C869}$ | $R^{D7}$ | $R^{D76}$ | $R^{D1}$ |
| $L_{C870}$ | $R^{D8}$ | $R^{D5}$ | $R^{D1}$ |
| $L_{C871}$ | $R^{D8}$ | $R^{D6}$ | $R^{D1}$ |
| $L_{C872}$ | $R^{D8}$ | $R^{D9}$ | $R^{D1}$ |
| $L_{C873}$ | $R^{D8}$ | $R^{D10}$ | $R^{D1}$ |
| $L_{C874}$ | $R^{D8}$ | $R^{D11}$ | $R^{D1}$ |
| $L_{C875}$ | $R^{D8}$ | $R^{D12}$ | $R^{D1}$ |
| $L_{C876}$ | $R^{D8}$ | $R^{D13}$ | $R^{D1}$ |
| $L_{C877}$ | $R^{D8}$ | $R^{D14}$ | $R^{D1}$ |
| $L_{C878}$ | $R^{D8}$ | $R^{D15}$ | $R^{D1}$ |
| $L_{C879}$ | $R^{D8}$ | $R^{D16}$ | $R^{D1}$ |
| $L_{C880}$ | $R^{D8}$ | $R^{D17}$ | $R^{D1}$ |
| $L_{C881}$ | $R^{D8}$ | $R^{D18}$ | $R^{D1}$ |
| $L_{C882}$ | $R^{D8}$ | $R^{D19}$ | $R^{D1}$ |
| $L_{C883}$ | $R^{D8}$ | $R^{D20}$ | $R^{D1}$ |
| $L_{C884}$ | $R^{D8}$ | $R^{D21}$ | $R^{D1}$ |
| $L_{C885}$ | $R^{D8}$ | $R^{D22}$ | $R^{D1}$ |
| $L_{C886}$ | $R^{D8}$ | $R^{D23}$ | $R^{D1}$ |
| $L_{C887}$ | $R^{D8}$ | $R^{D24}$ | $R^{D1}$ |
| $L_{C888}$ | $R^{D8}$ | $R^{D25}$ | $R^{D1}$ |
| $L_{C889}$ | $R^{D8}$ | $R^{D26}$ | $R^{D1}$ |
| $L_{C890}$ | $R^{D8}$ | $R^{D27}$ | $R^{D1}$ |
| $L_{C891}$ | $R^{D8}$ | $R^{D28}$ | $R^{D1}$ |
| $L_{C892}$ | $R^{D8}$ | $R^{D29}$ | $R^{D1}$ |
| $L_{C893}$ | $R^{D8}$ | $R^{D30}$ | $R^{D1}$ |
| $L_{C894}$ | $R^{D8}$ | $R^{D31}$ | $R^{D1}$ |
| $L_{C895}$ | $R^{D8}$ | $R^{D32}$ | $R^{D1}$ |
| $L_{C896}$ | $R^{D8}$ | $R^{D33}$ | $R^{D1}$ |
| $L_{C897}$ | $R^{D8}$ | $R^{D34}$ | $R^{D1}$ |
| $L_{C898}$ | $R^{D8}$ | $R^{D35}$ | $R^{D1}$ |
| $L_{C899}$ | $R^{D8}$ | $R^{D40}$ | $R^{D1}$ |
| $L_{C900}$ | $R^{D8}$ | $R^{D41}$ | $R^{D1}$ |
| $L_{C901}$ | $R^{D8}$ | $R^{D42}$ | $R^{D1}$ |
| $L_{C902}$ | $R^{D8}$ | $R^{D64}$ | $R^{D1}$ |
| $L_{C903}$ | $R^{D8}$ | $R^{D66}$ | $R^{D1}$ |
| $L_{C904}$ | $R^{D8}$ | $R^{D68}$ | $R^{D1}$ |
| $L_{C905}$ | $R^{D8}$ | $R^{D76}$ | $R^{D1}$ |
| $L_{C906}$ | $R^{D11}$ | $R^{D5}$ | $R^{D1}$ |
| $L_{C907}$ | $R^{D11}$ | $R^{D6}$ | $R^{D1}$ |
| $L_{C908}$ | $R^{D11}$ | $R^{D9}$ | $R^{D1}$ |
| $L_{C909}$ | $R^{D11}$ | $R^{D10}$ | $R^{D1}$ |
| $L_{C910}$ | $R^{D11}$ | $R^{D12}$ | $R^{D1}$ |
| $L_{C911}$ | $R^{D11}$ | $R^{D13}$ | $R^{D1}$ |
| $L_{C912}$ | $R^{D11}$ | $R^{D14}$ | $R^{D1}$ |
| $L_{C913}$ | $R^{D11}$ | $R^{D15}$ | $R^{D1}$ |
| $L_{C914}$ | $R^{D11}$ | $R^{D16}$ | $R^{D1}$ |
| $L_{C915}$ | $R^{D11}$ | $R^{D17}$ | $R^{D1}$ |
| $L_{C916}$ | $R^{D11}$ | $R^{D18}$ | $R^{D1}$ |
| $L_{C917}$ | $R^{D11}$ | $R^{D19}$ | $R^{D1}$ |
| $L_{C918}$ | $R^{D11}$ | $R^{D20}$ | $R^{D1}$ |
| $L_{C919}$ | $R^{D11}$ | $R^{D21}$ | $R^{D1}$ |
| $L_{C920}$ | $R^{D11}$ | $R^{D22}$ | $R^{D1}$ |
| $L_{C921}$ | $R^{D11}$ | $R^{D23}$ | $R^{D1}$ |
| $L_{C922}$ | $R^{D11}$ | $R^{D24}$ | $R^{D1}$ |
| $L_{C923}$ | $R^{D11}$ | $R^{D25}$ | $R^{D1}$ |
| $L_{C924}$ | $R^{D11}$ | $R^{D26}$ | $R^{D1}$ |
| $L_{C925}$ | $R^{D11}$ | $R^{D27}$ | $R^{D1}$ |
| $L_{C926}$ | $R^{D11}$ | $R^{D28}$ | $R^{D1}$ |
| $L_{C927}$ | $R^{D11}$ | $R^{D29}$ | $R^{D1}$ |
| $L_{C928}$ | $R^{D11}$ | $R^{D30}$ | $R^{D1}$ |
| $L_{C929}$ | $R^{D11}$ | $R^{D31}$ | $R^{D1}$ |
| $L_{C930}$ | $R^{D11}$ | $R^{D32}$ | $R^{D1}$ |
| $L_{C931}$ | $R^{D11}$ | $R^{D33}$ | $R^{D1}$ |
| $L_{C932}$ | $R^{D11}$ | $R^{D34}$ | $R^{D1}$ |
| $L_{C933}$ | $R^{D11}$ | $R^{D35}$ | $R^{D1}$ |
| $L_{C934}$ | $R^{D11}$ | $R^{D40}$ | $R^{D1}$ |
| $L_{C935}$ | $R^{D11}$ | $R^{D41}$ | $R^{D1}$ |
| $L_{C936}$ | $R^{D11}$ | $R^{D42}$ | $R^{D1}$ |
| $L_{C937}$ | $R^{D11}$ | $R^{D64}$ | $R^{D1}$ |
| $L_{C938}$ | $R^{D11}$ | $R^{D66}$ | $R^{D1}$ |
| $L_{C939}$ | $R^{D11}$ | $R^{D68}$ | $R^{D1}$ |

-continued

| Ligand | $R^1$ | $R^2$ | $R^3$ |
|---|---|---|---|
| $L_{C940}$ | $R^{D11}$ | $R^{D76}$ | $R^{D1}$ |
| $L_{C941}$ | $R^{D13}$ | $R^{D5}$ | $R^{D1}$ |
| $L_{C942}$ | $R^{D13}$ | $R^{D6}$ | $R^{D1}$ |
| $L_{C943}$ | $R^{D13}$ | $R^{D9}$ | $R^{D1}$ |
| $L_{C944}$ | $R^{D13}$ | $R^{D10}$ | $R^{D1}$ |
| $L_{C945}$ | $R^{D13}$ | $R^{D12}$ | $R^{D1}$ |
| $L_{C946}$ | $R^{D13}$ | $R^{D14}$ | $R^{D1}$ |
| $L_{C947}$ | $R^{D13}$ | $R^{D15}$ | $R^{D1}$ |
| $L_{C948}$ | $R^{D13}$ | $R^{D16}$ | $R^{D1}$ |
| $L_{C949}$ | $R^{D13}$ | $R^{D17}$ | $R^{D1}$ |
| $L_{C950}$ | $R^{D13}$ | $R^{D18}$ | $R^{D1}$ |
| $L_{C951}$ | $R^{D13}$ | $R^{D19}$ | $R^{D1}$ |
| $L_{C952}$ | $R^{D13}$ | $R^{D20}$ | $R^{D1}$ |
| $L_{C953}$ | $R^{D13}$ | $R^{D21}$ | $R^{D1}$ |
| $L_{C954}$ | $R^{D13}$ | $R^{D22}$ | $R^{D1}$ |
| $L_{C955}$ | $R^{D13}$ | $R^{D23}$ | $R^{D1}$ |
| $L_{C956}$ | $R^{D13}$ | $R^{D24}$ | $R^{D1}$ |
| $L_{C957}$ | $R^{D13}$ | $R^{D25}$ | $R^{D1}$ |
| $L_{C958}$ | $R^{D13}$ | $R^{D26}$ | $R^{D1}$ |
| $L_{C959}$ | $R^{D13}$ | $R^{D27}$ | $R^{D1}$ |
| $L_{C960}$ | $R^{D13}$ | $R^{D28}$ | $R^{D1}$ |
| $L_{C961}$ | $R^{D13}$ | $R^{D29}$ | $R^{D1}$ |
| $L_{C962}$ | $R^{D13}$ | $R^{D30}$ | $R^{D1}$ |
| $L_{C963}$ | $R^{D13}$ | $R^{D31}$ | $R^{D1}$ |
| $L_{C964}$ | $R^{D13}$ | $R^{D32}$ | $R^{D1}$ |
| $L_{C965}$ | $R^{D13}$ | $R^{D33}$ | $R^{D1}$ |
| $L_{C966}$ | $R^{D13}$ | $R^{D34}$ | $R^{D1}$ |
| $L_{C967}$ | $R^{D13}$ | $R^{D35}$ | $R^{D1}$ |
| $L_{C968}$ | $R^{D13}$ | $R^{D40}$ | $R^{D1}$ |
| $L_{C969}$ | $R^{D13}$ | $R^{D41}$ | $R^{D1}$ |
| $L_{C970}$ | $R^{D13}$ | $R^{D42}$ | $R^{D1}$ |
| $L_{C971}$ | $R^{D13}$ | $R^{D64}$ | $R^{D1}$ |
| $L_{C972}$ | $R^{D13}$ | $R^{D66}$ | $R^{D1}$ |
| $L_{C973}$ | $R^{D13}$ | $R^{D68}$ | $R^{D1}$ |
| $L_{C974}$ | $R^{D13}$ | $R^{D76}$ | $R^{D1}$ |
| $L_{C975}$ | $R^{D14}$ | $R^{D5}$ | $R^{D1}$ |
| $L_{C976}$ | $R^{D14}$ | $R^{D6}$ | $R^{D1}$ |
| $L_{C977}$ | $R^{D14}$ | $R^{D9}$ | $R^{D1}$ |
| $L_{C978}$ | $R^{D14}$ | $R^{D10}$ | $R^{D1}$ |
| $L_{C979}$ | $R^{D14}$ | $R^{D12}$ | $R^{D1}$ |
| $L_{C980}$ | $R^{D14}$ | $R^{D15}$ | $R^{D1}$ |
| $L_{C981}$ | $R^{D14}$ | $R^{D16}$ | $R^{D1}$ |
| $L_{C982}$ | $R^{D14}$ | $R^{D17}$ | $R^{D1}$ |
| $L_{C983}$ | $R^{D14}$ | $R^{D18}$ | $R^{D1}$ |
| $L_{C984}$ | $R^{D14}$ | $R^{D19}$ | $R^{D1}$ |
| $L_{C985}$ | $R^{D14}$ | $R^{D20}$ | $R^{D1}$ |
| $L_{C986}$ | $R^{D14}$ | $R^{D21}$ | $R^{D1}$ |
| $L_{C987}$ | $R^{D14}$ | $R^{D22}$ | $R^{D1}$ |
| $L_{C988}$ | $R^{D14}$ | $R^{D23}$ | $R^{D1}$ |
| $L_{C989}$ | $R^{D14}$ | $R^{D24}$ | $R^{D1}$ |
| $L_{C990}$ | $R^{D14}$ | $R^{D25}$ | $R^{D1}$ |
| $L_{C991}$ | $R^{D14}$ | $R^{D26}$ | $R^{D1}$ |
| $L_{C992}$ | $R^{D14}$ | $R^{D27}$ | $R^{D1}$ |
| $L_{C993}$ | $R^{D14}$ | $R^{D28}$ | $R^{D1}$ |
| $L_{C994}$ | $R^{D14}$ | $R^{D29}$ | $R^{D1}$ |
| $L_{C995}$ | $R^{D14}$ | $R^{D30}$ | $R^{D1}$ |
| $L_{C996}$ | $R^{D14}$ | $R^{D31}$ | $R^{D1}$ |
| $L_{C997}$ | $R^{D14}$ | $R^{D32}$ | $R^{D1}$ |
| $L_{C998}$ | $R^{D14}$ | $R^{D33}$ | $R^{D1}$ |
| $L_{C999}$ | $R^{D14}$ | $R^{D34}$ | $R^{D1}$ |
| $L_{C1000}$ | $R^{D14}$ | $R^{D35}$ | $R^{D1}$ |
| $L_{C1001}$ | $R^{D14}$ | $R^{D40}$ | $R^{D1}$ |
| $L_{C1002}$ | $R^{D14}$ | $R^{D41}$ | $R^{D1}$ |
| $L_{C1003}$ | $R^{D14}$ | $R^{D42}$ | $R^{D1}$ |
| $L_{C1004}$ | $R^{D14}$ | $R^{D64}$ | $R^{D1}$ |
| $L_{C1005}$ | $R^{D14}$ | $R^{D66}$ | $R^{D1}$ |
| $L_{C1006}$ | $R^{D14}$ | $R^{D68}$ | $R^{D1}$ |
| $L_{C1007}$ | $R^{D14}$ | $R^{D76}$ | $R^{D1}$ |
| $L_{C1008}$ | $R^{D22}$ | $R^{D5}$ | $R^{D1}$ |
| $L_{C1009}$ | $R^{D22}$ | $R^{D6}$ | $R^{D1}$ |
| $L_{C1010}$ | $R^{D22}$ | $R^{D9}$ | $R^{D1}$ |
| $L_{C1011}$ | $R^{D22}$ | $R^{D10}$ | $R^{D1}$ |
| $L_{C1012}$ | $R^{D22}$ | $R^{D12}$ | $R^{D1}$ |
| $L_{C1013}$ | $R^{D22}$ | $R^{D15}$ | $R^{D1}$ |
| $L_{C1014}$ | $R^{D22}$ | $R^{D16}$ | $R^{D1}$ |
| $L_{C1015}$ | $R^{D22}$ | $R^{D17}$ | $R^{D1}$ |
| $L_{C1016}$ | $R^{D22}$ | $R^{D18}$ | $R^{D1}$ |

-continued

| Ligand | $R^1$ | $R^2$ | $R^3$ |
|---|---|---|---|
| $L_{C1017}$ | $R^{D22}$ | $R^{D19}$ | $R^{D1}$ |
| $L_{C1018}$ | $R^{D22}$ | $R^{D20}$ | $R^{D1}$ |
| $L_{C1019}$ | $R^{D22}$ | $R^{D21}$ | $R^{D1}$ |
| $L_{C1020}$ | $R^{D22}$ | $R^{D23}$ | $R^{D1}$ |
| $L_{C1021}$ | $R^{D22}$ | $R^{D24}$ | $R^{D1}$ |
| $L_{C1022}$ | $R^{D22}$ | $R^{D25}$ | $R^{D1}$ |
| $L_{C1023}$ | $R^{D22}$ | $R^{D26}$ | $R^{D1}$ |
| $L_{C1024}$ | $R^{D22}$ | $R^{D27}$ | $R^{D1}$ |
| $L_{C1025}$ | $R^{D22}$ | $R^{D28}$ | $R^{D1}$ |
| $L_{C1026}$ | $R^{D22}$ | $R^{D29}$ | $R^{D1}$ |
| $L_{C1027}$ | $R^{D22}$ | $R^{D30}$ | $R^{D1}$ |
| $L_{C1028}$ | $R^{D22}$ | $R^{D31}$ | $R^{D1}$ |
| $L_{C1029}$ | $R^{D22}$ | $R^{D32}$ | $R^{D1}$ |
| $L_{C1030}$ | $R^{D22}$ | $R^{D33}$ | $R^{D1}$ |
| $L_{C1031}$ | $R^{D22}$ | $R^{D34}$ | $R^{D1}$ |
| $L_{C1032}$ | $R^{D22}$ | $R^{D35}$ | $R^{D1}$ |
| $L_{C1033}$ | $R^{D22}$ | $R^{D40}$ | $R^{D1}$ |
| $L_{C1034}$ | $R^{D22}$ | $R^{D41}$ | $R^{D1}$ |
| $L_{C1035}$ | $R^{D22}$ | $R^{D42}$ | $R^{D1}$ |
| $L_{C1036}$ | $R^{D22}$ | $R^{D64}$ | $R^{D1}$ |
| $L_{C1037}$ | $R^{D22}$ | $R^{D66}$ | $R^{D1}$ |
| $L_{C1038}$ | $R^{D22}$ | $R^{D68}$ | $R^{D1}$ |
| $L_{C1039}$ | $R^{D22}$ | $R^{D76}$ | $R^{D1}$ |
| $L_{C1040}$ | $R^{D26}$ | $R^{D5}$ | $R^{D1}$ |
| $L_{C1041}$ | $R^{D26}$ | $R^{D6}$ | $R^{D1}$ |
| $L_{C1042}$ | $R^{D26}$ | $R^{D9}$ | $R^{D1}$ |
| $L_{C1043}$ | $R^{D26}$ | $R^{D10}$ | $R^{D1}$ |
| $L_{C1044}$ | $R^{D26}$ | $R^{D12}$ | $R^{D1}$ |
| $L_{C1045}$ | $R^{D26}$ | $R^{D15}$ | $R^{D1}$ |
| $L_{C1046}$ | $R^{D26}$ | $R^{D16}$ | $R^{D1}$ |
| $L_{C1047}$ | $R^{D26}$ | $R^{D17}$ | $R^{D1}$ |
| $L_{C1048}$ | $R^{D26}$ | $R^{D18}$ | $R^{D1}$ |
| $L_{C1049}$ | $R^{D26}$ | $R^{D19}$ | $R^{D1}$ |
| $L_{C1050}$ | $R^{D26}$ | $R^{D20}$ | $R^{D1}$ |
| $L_{C1051}$ | $R^{D26}$ | $R^{D21}$ | $R^{D1}$ |
| $L_{C1052}$ | $R^{D26}$ | $R^{D23}$ | $R^{D1}$ |
| $L_{C1053}$ | $R^{D26}$ | $R^{D24}$ | $R^{D1}$ |
| $L_{C1054}$ | $R^{D26}$ | $R^{D25}$ | $R^{D1}$ |
| $L_{C1055}$ | $R^{D26}$ | $R^{D27}$ | $R^{D1}$ |
| $L_{C1056}$ | $R^{D26}$ | $R^{D28}$ | $R^{D1}$ |
| $L_{C1057}$ | $R^{D26}$ | $R^{D29}$ | $R^{D1}$ |
| $L_{C1058}$ | $R^{D26}$ | $R^{D30}$ | $R^{D1}$ |
| $L_{C1059}$ | $R^{D26}$ | $R^{D31}$ | $R^{D1}$ |
| $L_{C1060}$ | $R^{D26}$ | $R^{D32}$ | $R^{D1}$ |
| $L_{C1061}$ | $R^{D26}$ | $R^{D33}$ | $R^{D1}$ |
| $L_{C1062}$ | $R^{D26}$ | $R^{D34}$ | $R^{D1}$ |
| $L_{C1063}$ | $R^{D26}$ | $R^{D35}$ | $R^{D1}$ |
| $L_{C1064}$ | $R^{D26}$ | $R^{D40}$ | $R^{D1}$ |
| $L_{C1065}$ | $R^{D26}$ | $R^{D41}$ | $R^{D1}$ |
| $L_{C1066}$ | $R^{D26}$ | $R^{D42}$ | $R^{D1}$ |
| $L_{C1067}$ | $R^{D26}$ | $R^{D64}$ | $R^{D1}$ |
| $L_{C1068}$ | $R^{D26}$ | $R^{D66}$ | $R^{D1}$ |
| $L_{C1069}$ | $R^{D26}$ | $R^{D68}$ | $R^{D1}$ |
| $L_{C1070}$ | $R^{D26}$ | $R^{D76}$ | $R^{D1}$ |
| $L_{C1071}$ | $R^{D35}$ | $R^{D5}$ | $R^{D1}$ |
| $L_{C1072}$ | $R^{D35}$ | $R^{D6}$ | $R^{D1}$ |
| $L_{C1073}$ | $R^{D35}$ | $R^{D9}$ | $R^{D1}$ |
| $L_{C1074}$ | $R^{D35}$ | $R^{D10}$ | $R^{D1}$ |
| $L_{C1075}$ | $R^{D35}$ | $R^{D12}$ | $R^{D1}$ |
| $L_{C1076}$ | $R^{D35}$ | $R^{D15}$ | $R^{D1}$ |
| $L_{C1077}$ | $R^{D35}$ | $R^{D16}$ | $R^{D1}$ |
| $L_{C1078}$ | $R^{D35}$ | $R^{D17}$ | $R^{D1}$ |
| $L_{C1079}$ | $R^{D35}$ | $R^{D18}$ | $R^{D1}$ |
| $L_{C1080}$ | $R^{D35}$ | $R^{D19}$ | $R^{D1}$ |
| $L_{C1081}$ | $R^{D35}$ | $R^{D20}$ | $R^{D1}$ |
| $L_{C1082}$ | $R^{D35}$ | $R^{D21}$ | $R^{D1}$ |
| $L_{C1083}$ | $R^{D35}$ | $R^{D23}$ | $R^{D1}$ |
| $L_{C1084}$ | $R^{D35}$ | $R^{D24}$ | $R^{D1}$ |
| $L_{C1085}$ | $R^{D35}$ | $R^{D25}$ | $R^{D1}$ |
| $L_{C1086}$ | $R^{D35}$ | $R^{D27}$ | $R^{D1}$ |
| $L_{C1087}$ | $R^{D35}$ | $R^{D28}$ | $R^{D1}$ |
| $L_{C1088}$ | $R^{D35}$ | $R^{D29}$ | $R^{D1}$ |
| $L_{C1089}$ | $R^{D35}$ | $R^{D30}$ | $R^{D1}$ |
| $L_{C1090}$ | $R^{D35}$ | $R^{D31}$ | $R^{D1}$ |
| $L_{C1091}$ | $R^{D35}$ | $R^{D32}$ | $R^{D1}$ |
| $L_{C1092}$ | $R^{D35}$ | $R^{D33}$ | $R^{D1}$ |
| $L_{C1093}$ | $R^{D35}$ | $R^{D34}$ | $R^{D1}$ |

-continued

| Ligand | $R^1$ | $R^2$ | $R^3$ |
|---|---|---|---|
| $L_{C1094}$ | $R^{D35}$ | $R^{D40}$ | $R^{D1}$ |
| $L_{C1095}$ | $R^{D35}$ | $R^{D41}$ | $R^{D1}$ |
| $L_{C1096}$ | $R^{D35}$ | $R^{D42}$ | $R^{D1}$ |
| $L_{C1097}$ | $R^{D35}$ | $R^{D64}$ | $R^{D1}$ |
| $L_{C1098}$ | $R^{D35}$ | $R^{D66}$ | $R^{D1}$ |
| $L_{C1099}$ | $R^{D35}$ | $R^{D68}$ | $R^{D1}$ |
| $L_{C1100}$ | $R^{D35}$ | $R^{D76}$ | $R^{D1}$ |
| $L_{C1101}$ | $R^{D40}$ | $R^{D5}$ | $R^{D1}$ |
| $L_{C1102}$ | $R^{D40}$ | $R^{D6}$ | $R^{D1}$ |
| $L_{C1103}$ | $R^{D40}$ | $R^{D9}$ | $R^{D1}$ |
| $L_{C1104}$ | $R^{D40}$ | $R^{D10}$ | $R^{D1}$ |
| $L_{C1105}$ | $R^{D40}$ | $R^{D12}$ | $R^{D1}$ |
| $L_{C1106}$ | $R^{D40}$ | $R^{D15}$ | $R^{D1}$ |
| $L_{C1107}$ | $R^{D40}$ | $R^{D16}$ | $R^{D1}$ |
| $L_{C1108}$ | $R^{D40}$ | $R^{D17}$ | $R^{D1}$ |
| $L_{C1109}$ | $R^{D40}$ | $R^{D18}$ | $R^{D1}$ |
| $L_{C1110}$ | $R^{D40}$ | $R^{D19}$ | $R^{D1}$ |
| $L_{C1111}$ | $R^{D40}$ | $R^{D20}$ | $R^{D1}$ |
| $L_{C1112}$ | $R^{D40}$ | $R^{D21}$ | $R^{D1}$ |
| $L_{C1113}$ | $R^{D40}$ | $R^{D23}$ | $R^{D1}$ |
| $L_{C1114}$ | $R^{D40}$ | $R^{D24}$ | $R^{D1}$ |
| $L_{C1115}$ | $R^{D40}$ | $R^{D25}$ | $R^{D1}$ |
| $L_{C1116}$ | $R^{D40}$ | $R^{D27}$ | $R^{D1}$ |
| $L_{C1117}$ | $R^{D40}$ | $R^{D28}$ | $R^{D1}$ |
| $L_{C1118}$ | $R^{D40}$ | $R^{D29}$ | $R^{D1}$ |
| $L_{C1119}$ | $R^{D40}$ | $R^{D30}$ | $R^{D1}$ |
| $L_{C1120}$ | $R^{D40}$ | $R^{D31}$ | $R^{D1}$ |
| $L_{C1121}$ | $R^{D40}$ | $R^{D32}$ | $R^{D1}$ |
| $L_{C1122}$ | $R^{D40}$ | $R^{D33}$ | $R^{D1}$ |
| $L_{C1123}$ | $R^{D40}$ | $R^{D34}$ | $R^{D1}$ |
| $L_{C1124}$ | $R^{D40}$ | $R^{D41}$ | $R^{D1}$ |
| $L_{C1125}$ | $R^{D40}$ | $R^{D42}$ | $R^{D1}$ |
| $L_{C1126}$ | $R^{D40}$ | $R^{D64}$ | $R^{D1}$ |
| $L_{C1127}$ | $R^{D40}$ | $R^{D66}$ | $R^{D1}$ |
| $L_{C1128}$ | $R^{D40}$ | $R^{D68}$ | $R^{D1}$ |
| $L_{C1129}$ | $R^{D40}$ | $R^{D76}$ | $R^{D1}$ |
| $L_{C1130}$ | $R^{D41}$ | $R^{D5}$ | $R^{D1}$ |
| $L_{C1131}$ | $R^{D41}$ | $R^{D6}$ | $R^{D1}$ |
| $L_{C1132}$ | $R^{D41}$ | $R^{D9}$ | $R^{D1}$ |
| $L_{C1133}$ | $R^{D41}$ | $R^{D10}$ | $R^{D1}$ |
| $L_{C1134}$ | $R^{D41}$ | $R^{D12}$ | $R^{D1}$ |
| $L_{C1135}$ | $R^{D41}$ | $R^{D15}$ | $R^{D1}$ |
| $L_{C1136}$ | $R^{D41}$ | $R^{D16}$ | $R^{D1}$ |
| $L_{C1137}$ | $R^{D41}$ | $R^{D17}$ | $R^{D1}$ |
| $L_{C1138}$ | $R^{D41}$ | $R^{D18}$ | $R^{D1}$ |
| $L_{C1139}$ | $R^{D41}$ | $R^{D19}$ | $R^{D1}$ |
| $L_{C1140}$ | $R^{D41}$ | $R^{D20}$ | $R^{D1}$ |
| $L_{C1141}$ | $R^{D41}$ | $R^{D21}$ | $R^{D1}$ |
| $L_{C1142}$ | $R^{D41}$ | $R^{D23}$ | $R^{D1}$ |
| $L_{C1143}$ | $R^{D41}$ | $R^{D24}$ | $R^{D1}$ |
| $L_{C1144}$ | $R^{D41}$ | $R^{D25}$ | $R^{D1}$ |
| $L_{C1145}$ | $R^{D41}$ | $R^{D27}$ | $R^{D1}$ |
| $L_{C1146}$ | $R^{D41}$ | $R^{D28}$ | $R^{D1}$ |
| $L_{C1147}$ | $R^{D41}$ | $R^{D29}$ | $R^{D1}$ |
| $L_{C1148}$ | $R^{D41}$ | $R^{D30}$ | $R^{D1}$ |
| $L_{C1149}$ | $R^{D41}$ | $R^{D31}$ | $R^{D1}$ |
| $L_{C1150}$ | $R^{D41}$ | $R^{D32}$ | $R^{D1}$ |
| $L_{C1151}$ | $R^{D41}$ | $R^{D33}$ | $R^{D1}$ |
| $L_{C1152}$ | $R^{D41}$ | $R^{D34}$ | $R^{D1}$ |
| $L_{C1153}$ | $R^{D41}$ | $R^{D42}$ | $R^{D1}$ |
| $L_{C1154}$ | $R^{D41}$ | $R^{D64}$ | $R^{D1}$ |
| $L_{C1155}$ | $R^{D41}$ | $R^{D66}$ | $R^{D1}$ |
| $L_{C1156}$ | $R^{D41}$ | $R^{D68}$ | $R^{D1}$ |
| $L_{C1157}$ | $R^{D41}$ | $R^{D76}$ | $R^{D1}$ |
| $L_{C1158}$ | $R^{D64}$ | $R^{D5}$ | $R^{D1}$ |
| $L_{C1159}$ | $R^{D64}$ | $R^{D6}$ | $R^{D1}$ |
| $L_{C1160}$ | $R^{D64}$ | $R^{D9}$ | $R^{D1}$ |
| $L_{C1161}$ | $R^{D64}$ | $R^{D10}$ | $R^{D1}$ |
| $L_{C1162}$ | $R^{D64}$ | $R^{D12}$ | $R^{D1}$ |
| $L_{C1163}$ | $R^{D64}$ | $R^{D15}$ | $R^{D1}$ |
| $L_{C1164}$ | $R^{D64}$ | $R^{D16}$ | $R^{D1}$ |
| $L_{C1165}$ | $R^{D64}$ | $R^{D17}$ | $R^{D1}$ |
| $L_{C1166}$ | $R^{D64}$ | $R^{D18}$ | $R^{D1}$ |
| $L_{C1167}$ | $R^{D64}$ | $R^{D19}$ | $R^{D1}$ |
| $L_{C1168}$ | $R^{D64}$ | $R^{D20}$ | $R^{D1}$ |
| $L_{C1169}$ | $R^{D64}$ | $R^{D21}$ | $R^{D1}$ |
| $L_{C1170}$ | $R^{D64}$ | $R^{D23}$ | $R^{D1}$ |

-continued

| Ligand | $R^1$ | $R^2$ | $R^3$ |
|---|---|---|---|
| $L_{C1171}$ | $R^{D64}$ | $R^{D24}$ | $R^{D1}$ |
| $L_{C1172}$ | $R^{D64}$ | $R^{D25}$ | $R^{D1}$ |
| $L_{C1173}$ | $R^{D64}$ | $R^{D27}$ | $R^{D1}$ |
| $L_{C1174}$ | $R^{D64}$ | $R^{D28}$ | $R^{D1}$ |
| $L_{C1175}$ | $R^{D64}$ | $R^{D29}$ | $R^{D1}$ |
| $L_{C1176}$ | $R^{D64}$ | $R^{D30}$ | $R^{D1}$ |
| $L_{C1177}$ | $R^{D64}$ | $R^{D31}$ | $R^{D1}$ |
| $L_{C1178}$ | $R^{D64}$ | $R^{D32}$ | $R^{D1}$ |
| $L_{C1179}$ | $R^{D64}$ | $R^{D33}$ | $R^{D1}$ |
| $L_{C1180}$ | $R^{D64}$ | $R^{D34}$ | $R^{D1}$ |
| $L_{C1181}$ | $R^{D64}$ | $R^{D42}$ | $R^{D1}$ |
| $L_{C1182}$ | $R^{D64}$ | $R^{D64}$ | $R^{D1}$ |
| $L_{C1183}$ | $R^{D64}$ | $R^{D66}$ | $R^{D1}$ |
| $L_{C1184}$ | $R^{D64}$ | $R^{D68}$ | $R^{D1}$ |
| $L_{C1185}$ | $R^{D64}$ | $R^{D76}$ | $R^{D1}$ |
| $L_{C1186}$ | $R^{D66}$ | $R^{D5}$ | $R^{D1}$ |
| $L_{C1187}$ | $R^{D66}$ | $R^{D6}$ | $R^{D1}$ |
| $L_{C1188}$ | $R^{D66}$ | $R^{D9}$ | $R^{D1}$ |
| $L_{C1189}$ | $R^{D66}$ | $R^{D10}$ | $R^{D1}$ |
| $L_{C1190}$ | $R^{D66}$ | $R^{D12}$ | $R^{D1}$ |
| $L_{C1191}$ | $R^{D66}$ | $R^{D15}$ | $R^{D1}$ |
| $L_{C1192}$ | $R^{D66}$ | $R^{D16}$ | $R^{D1}$ |
| $L_{C1193}$ | $R^{D66}$ | $R^{D17}$ | $R^{D1}$ |
| $L_{C1194}$ | $R^{D66}$ | $R^{D18}$ | $R^{D1}$ |
| $L_{C1195}$ | $R^{D66}$ | $R^{D19}$ | $R^{D1}$ |
| $L_{C1196}$ | $R^{D66}$ | $R^{D20}$ | $R^{D1}$ |
| $L_{C1197}$ | $R^{D66}$ | $R^{D21}$ | $R^{D1}$ |
| $L_{C1198}$ | $R^{D66}$ | $R^{D23}$ | $R^{D1}$ |
| $L_{C1199}$ | $R^{D66}$ | $R^{D24}$ | $R^{D1}$ |
| $L_{C1200}$ | $R^{D66}$ | $R^{D25}$ | $R^{D1}$ |
| $L_{C1201}$ | $R^{D66}$ | $R^{D27}$ | $R^{D1}$ |
| $L_{C1202}$ | $R^{D66}$ | $R^{D28}$ | $R^{D1}$ |
| $L_{C1203}$ | $R^{D66}$ | $R^{D29}$ | $R^{D1}$ |
| $L_{C1204}$ | $R^{D66}$ | $R^{D30}$ | $R^{D1}$ |
| $L_{C1205}$ | $R^{D66}$ | $R^{D31}$ | $R^{D1}$ |
| $L_{C1206}$ | $R^{D66}$ | $R^{D32}$ | $R^{D1}$ |
| $L_{C1207}$ | $R^{D66}$ | $R^{D33}$ | $R^{D1}$ |
| $L_{C1208}$ | $R^{D66}$ | $R^{D34}$ | $R^{D1}$ |
| $L_{C1209}$ | $R^{D66}$ | $R^{D42}$ | $R^{D1}$ |
| $L_{C1210}$ | $R^{D66}$ | $R^{D68}$ | $R^{D1}$ |
| $L_{C1211}$ | $R^{D66}$ | $R^{D76}$ | $R^{D1}$ |
| $L_{C1212}$ | $R^{D68}$ | $R^{D5}$ | $R^{D1}$ |
| $L_{C1213}$ | $R^{D68}$ | $R^{D6}$ | $R^{D1}$ |
| $L_{C1214}$ | $R^{D68}$ | $R^{D9}$ | $R^{D1}$ |
| $L_{C1215}$ | $R^{D68}$ | $R^{D10}$ | $R^{D1}$ |
| $L_{C1216}$ | $R^{D68}$ | $R^{D12}$ | $R^{D1}$ |
| $L_{C1217}$ | $R^{D68}$ | $R^{D15}$ | $R^{D1}$ |
| $L_{C1218}$ | $R^{D68}$ | $R^{D16}$ | $R^{D1}$ |
| $L_{C1219}$ | $R^{D68}$ | $R^{D17}$ | $R^{D1}$ |
| $L_{C1220}$ | $R^{D68}$ | $R^{D18}$ | $R^{D1}$ |
| $L_{C1221}$ | $R^{D68}$ | $R^{D19}$ | $R^{D1}$ |
| $L_{C1222}$ | $R^{D68}$ | $R^{D20}$ | $R^{D1}$ |
| $L_{C1223}$ | $R^{D68}$ | $R^{D21}$ | $R^{D1}$ |
| $L_{C1224}$ | $R^{D68}$ | $R^{D23}$ | $R^{D1}$ |
| $L_{C1225}$ | $R^{D68}$ | $R^{D24}$ | $R^{D1}$ |
| $L_{C1226}$ | $R^{D68}$ | $R^{D25}$ | $R^{D1}$ |
| $L_{C1227}$ | $R^{D68}$ | $R^{D27}$ | $R^{D1}$ |
| $L_{C1228}$ | $R^{D68}$ | $R^{D28}$ | $R^{D1}$ |
| $L_{C1229}$ | $R^{D68}$ | $R^{D29}$ | $R^{D1}$ |
| $L_{C1230}$ | $R^{D68}$ | $R^{D30}$ | $R^{D1}$ |
| $L_{C1231}$ | $R^{D68}$ | $R^{D31}$ | $R^{D1}$ |
| $L_{C1232}$ | $R^{D68}$ | $R^{D32}$ | $R^{D1}$ |
| $L_{C1233}$ | $R^{D68}$ | $R^{D33}$ | $R^{D1}$ |
| $L_{C1234}$ | $R^{D68}$ | $R^{D34}$ | $R^{D1}$ |
| $L_{C1235}$ | $R^{D68}$ | $R^{D42}$ | $R^{D1}$ |
| $L_{C1236}$ | $R^{D68}$ | $R^{D76}$ | $R^{D1}$ |
| $L_{C1237}$ | $R^{D76}$ | $R^{D5}$ | $R^{D1}$ |
| $L_{C1238}$ | $R^{D76}$ | $R^{D6}$ | $R^{D1}$ |
| $L_{C1239}$ | $R^{D76}$ | $R^{D9}$ | $R^{D1}$ |
| $L_{C1240}$ | $R^{D76}$ | $R^{D10}$ | $R^{D1}$ |
| $L_{C1241}$ | $R^{D76}$ | $R^{D12}$ | $R^{D1}$ |
| $L_{C1242}$ | $R^{D76}$ | $R^{D15}$ | $R^{D1}$ |
| $L_{C1243}$ | $R^{D76}$ | $R^{D16}$ | $R^{D1}$ |
| $L_{C1244}$ | $R^{D76}$ | $R^{D17}$ | $R^{D1}$ |
| $L_{C1245}$ | $R^{D76}$ | $R^{D18}$ | $R^{D1}$ |
| $L_{C1246}$ | $R^{D76}$ | $R^{D19}$ | $R^{D1}$ |
| $L_{C1247}$ | $R^{D76}$ | $R^{D20}$ | $R^{D1}$ |
| $L_{C1248}$ | $R^{D76}$ | $R^{D21}$ | $R^{D1}$ |
| $L_{C1249}$ | $R^{D76}$ | $R^{D23}$ | $R^{D1}$ |
| $L_{C1250}$ | $R^{D76}$ | $R^{D24}$ | $R^{D1}$ |
| $L_{C1251}$ | $R^{D76}$ | $R^{D25}$ | $R^{D1}$ |
| $L_{C1252}$ | $R^{D76}$ | $R^{D27}$ | $R^{D1}$ |
| $L_{C1253}$ | $R^{D76}$ | $R^{D28}$ | $R^{D1}$ |
| $L_{C1254}$ | $R^{D76}$ | $R^{D29}$ | $R^{D1}$ |
| $L_{C1255}$ | $R^{D76}$ | $R^{D30}$ | $R^{D1}$ |
| $L_{C1256}$ | $R^{D76}$ | $R^{D31}$ | $R^{D1}$ |
| $L_{C1257}$ | $R^{D76}$ | $R^{D32}$ | $R^{D1}$ |
| $L_{C1258}$ | $R^{D76}$ | $R^{D33}$ | $R^{D1}$ |
| $L_{C1259}$ | $R^{D76}$ | $R^{D34}$ | $R^{D1}$ |
| $L_{C1260}$ | $R^{D76}$ | $R^{D42}$ | $R^{D1}$, |

wherein $R^{D1}$ to $R^{D81}$ have the following structures:

$R^{D1}$

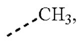

$R^{D2}$

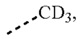

$R^{D3}$

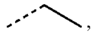

$R^{D4}$

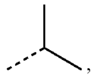

$R^{D5}$

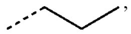

$R^{D6}$

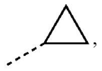

$R^{D7}$

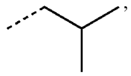

$R^{D8}$

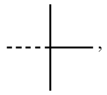

$R^{D9}$

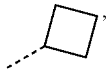

$R^{D10}$

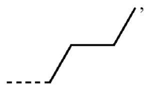

$R^{D11}$

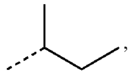

$R^{D12}$

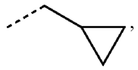

$R^{D13}$

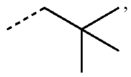

$R^{D14}$

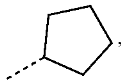

-continued
$R^{D15}$
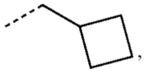
$R^{D16}$
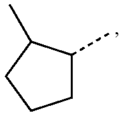
$R^{D17}$
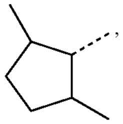
$R^{D18}$
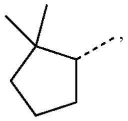
$R^{D19}$
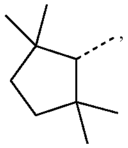
$R^{D20}$
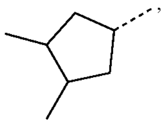
$R^{D21}$
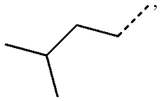
$R^{D22}$
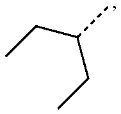
$R^{D23}$
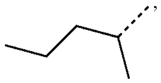
$R^{D24}$
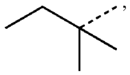
$R^{D25}$
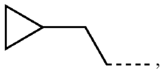
$R^{D26}$
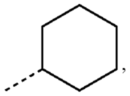
$R^{D27}$
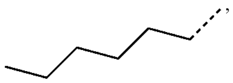
-continued
$R^{D28}$
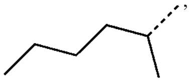
$R^{D29}$
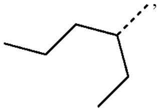
$R^{D30}$
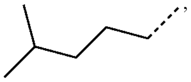
$R^{D31}$
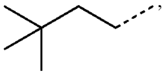
$R^{D32}$
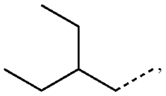
$R^{D33}$
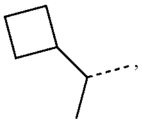
$R^{D34}$
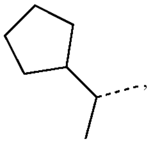
$R^{D35}$
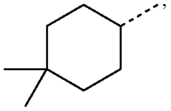
$R^{D36}$
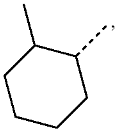
$R^{D37}$
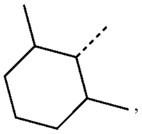
$R^{D38}$
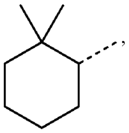
$R^{D39}$
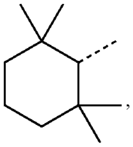

-continued
$R^{D40}$
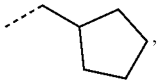
$R^{D41}$
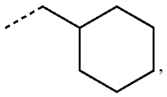
$R^{D42}$
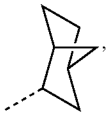
$R^{D43}$
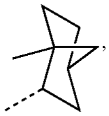
$R^{D44}$
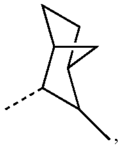
$R^{D45}$
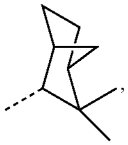
$R^{D46}$
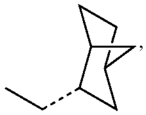
$R^{D47}$
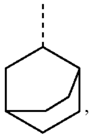
$R^{D48}$
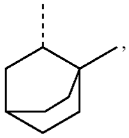
$R^{D49}$
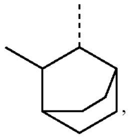
$R^{D50}$
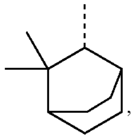
-continued
$R^{D51}$
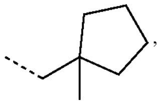
$R^{D52}$
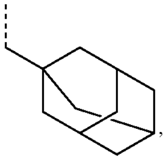
$R^{D53}$
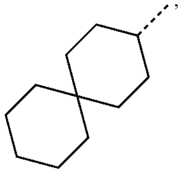
$R^{D54}$
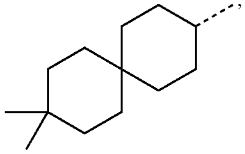
$R^{D55}$
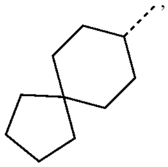
$R^{D56}$
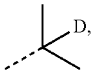
$R^{D57}$
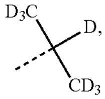
$R^{D58}$
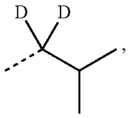
$R^{D59}$
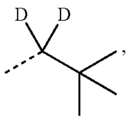
$R^{D60}$
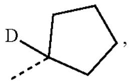
$R^{D61}$
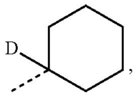

-continued
$R^{D62}$
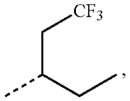
$R^{D63}$
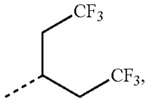
$R^{D64}$
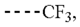
$R^{D65}$
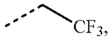
$R^{D66}$
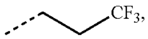
$R^{D67}$
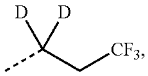
$R^{D68}$
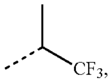
$R^{D69}$
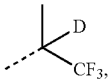
$R^{D70}$
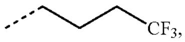
$R^{D71}$
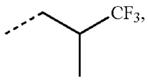
$R^{D72}$
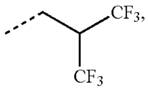
$R^{D73}$
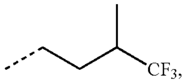
-continued
$R^{D74}$
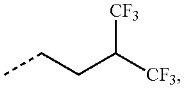
$R^{D75}$
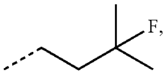
$R^{D76}$
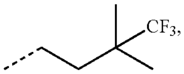
$R^{D77}$
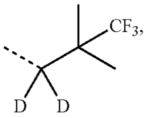
$R^{D78}$
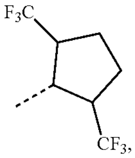
$R^{D79}$
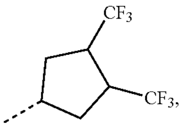
$R^{D80}$
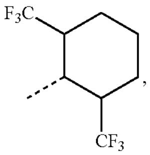
, and
$R^{D81}$
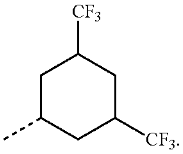
* * * * *